United States Patent
Dack et al.

(10) Patent No.: US 11,377,425 B1
(45) Date of Patent: Jul. 5, 2022

(54) SMALL MOLECULE MODULATORS OF IL-17

(71) Applicant: LEO Pharma A/S, Ballerup (DK)

(72) Inventors: Kevin Neil Dack, Ballerup (DK); Xifu Liang, Ballerup (DK); Mogens Larsen, Ballerup (DK); Mark Andrews, Ballerup (DK); Alan Stuart Jessiman, Ballerup (DK); Mia Nørreskov Burhardt, Ballerup (DK); Patrick Stephen Johnson, Ballerup (DK); Peter Andersen, Ballerup (DK); Lars Jørgensen, Ballerup (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 16/765,143

(22) PCT Filed: Dec. 19, 2019

(86) PCT No.: PCT/EP2019/086239
§ 371 (c)(1),
(2) Date: May 18, 2020

(87) PCT Pub. No.: WO2020/127685
PCT Pub. Date: Jun. 25, 2020

(30) Foreign Application Priority Data

Dec. 19, 2018 (EP) .................................. 18214002
Jul. 19, 2019 (EP) .................................. 19187352

(51) Int. Cl.
| C07D 231/12 | (2006.01) |
| C07D 403/12 | (2006.01) |
| C07D 249/06 | (2006.01) |
| C07D 271/10 | (2006.01) |
| C07D 263/32 | (2006.01) |
| C07D 413/12 | (2006.01) |
| C07D 233/64 | (2006.01) |
| C07D 231/14 | (2006.01) |
| C07D 233/68 | (2006.01) |
| C07D 233/70 | (2006.01) |
| C07D 261/08 | (2006.01) |

(52) U.S. Cl.
CPC ......... *C07D 231/12* (2013.01); *C07D 231/14* (2013.01); *C07D 233/64* (2013.01); *C07D 233/68* (2013.01); *C07D 233/70* (2013.01); *C07D 249/06* (2013.01); *C07D 261/08* (2013.01); *C07D 263/32* (2013.01); *C07D 271/10* (2013.01); *C07D 403/12* (2013.01); *C07D 413/12* (2013.01)

(58) Field of Classification Search
CPC .. C07D 231/12; C07D 233/64; C07D 249/06; C07D 261/08
See application file for complete search history.

(56) References Cited

U.S. PATENT DOCUMENTS

| 6,037,472 | A | 3/2000 | Castelhano et al. |
| 6,057,451 | A * | 5/2000 | Crute ..................... A61P 31/22 |
| | | | 548/194 |
| 6,288,091 | B1 | 9/2001 | Crute et al. |
| 2001/0044445 | A1 | 11/2001 | Bamaung et al. |
| 2003/0232868 | A1 | 12/2003 | Lehmann et al. |
| 2006/0052376 | A1 | 3/2006 | Dorsch et al. |
| 2006/0135515 | A1 | 6/2006 | Dorsch et al. |
| 2008/0076741 | A1 | 3/2008 | Glinka et al. |
| 2015/0044167 | A1 | 2/2015 | Reesink et al. |
| 2015/0087512 | A1 | 3/2015 | Wang et al. |
| 2016/0244437 | A1 | 8/2016 | Rohn et al. |
| 2020/0247785 | A1 | 8/2020 | Fatheree et al. |

FOREIGN PATENT DOCUMENTS

| CN | 103319367 | 9/2013 |
| CN | 106496071 | 3/2017 |
| CN | 107488148 | 12/2017 |
| WO | WO 95/12603 | 5/1995 |
| WO | WO 97/24343 | 7/1997 |
| WO | WO 00/29399 | 5/2000 |

(Continued)

OTHER PUBLICATIONS

Amatya N. el al. "IL-17 Signaling: The Yin and the Yang," *Trends in Immunology*, May 2017, vol. 38, No. 5, pp. 310-322.
Dakin L., "Hit Identification, binding site elucidation and structure guided design of novel macrocyclic IL-17A antagonists" *Presentation given at 12th Swiss Course on Medicinal Chemistry*, Leysin, Oct. 9-14, 2016 (10 pages).
Fan H. et al. "Oxathiazolones Selectively Inhibit the Human Immunoproteasome over the Constitutive Proteasome," *Med. Chem. Lett.* 2014, 5, pp. 405-410.
Fang X. et al. "Tetrahydroisoquinoline Derivatives As Highly Selective and Potent Rho Kinase Inhibitors" *J. Med. Chem*, 2010, 53, pp. 5727-5737.

(Continued)

*Primary Examiner* — Kamal A Saeed
(74) *Attorney, Agent, or Firm* — Finnegan, Henderson, Farabow, Garrett & Dunner, LLP

(57) ABSTRACT

The present invention relates to a compound according to formula I

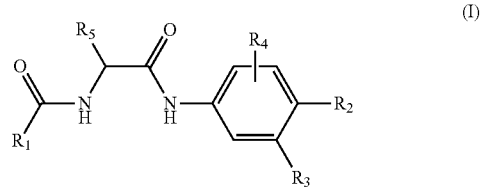

and pharmaceutically acceptable salts, hydrates, or solvates thereof. The invention further relates to said compounds for use in therapy, to pharmaceutical compositions comprising said compounds, to methods of treating diseases, e.g. dermal diseases, with said compounds, and to the use of said compounds in the manufacture of medicaments.

73 Claims, 2 Drawing Sheets

(56) References Cited

FOREIGN PATENT DOCUMENTS

Figure 1:
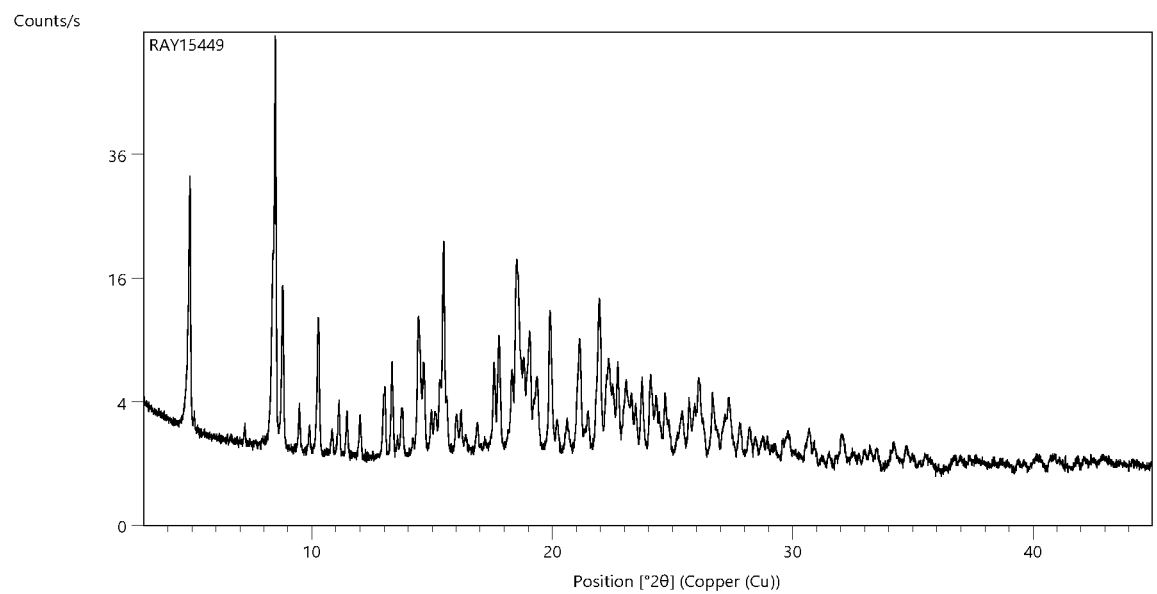

| WO | WO 01/81298 | 11/2001 |
|---|---|---|
| WO | WO 03/007945 | 1/2003 |
| WO | WO 2007/026920 | 3/2007 |
| WO | WO 2008/093236 | 8/2008 |
| WO | WO 2008/157162 | 12/2008 |
| WO | WO 2011/153588 | 12/2011 |
| WO | WO 2013/116682 | 8/2013 |
| WO | WO 2014/066726 | 5/2014 |
| WO | WO 2015/006100 | 1/2015 |
| WO | WO 2015/044167 | 4/2015 |
| WO | WO 2017/106426 | 6/2017 |
| WO | WO 2018/229079 | 12/2018 |
| WO | WO 2019/138017 | 7/2019 |
| WO | WO 2019/152437 | 8/2019 |
| WO | WO 2019/223718 | 11/2019 |
| WO | WO 2020/011731 | 1/2020 |
| WO | WO 2020/120140 | 6/2020 |
| WO | WO 2020/120141 | 6/2020 |
| WO | WO 2020/120978 A1 | 6/2020 |
| WO | WO 2020/146194 | 7/2020 |
| WO | WO 2020/163554 A1 | 8/2020 |
| WO | WO 2020/260425 A1 | 12/2020 |
| WO | WO 2020/260426 A1 | 12/2020 |
| WO | WO 2020/261141 A1 | 12/2020 |

OTHER PUBLICATIONS

Feng J. et al. "Safe and Selective Nitro Group Reductions Catalyzed by Sustainable and Recyclable Fe/ppm Pd Nanoparticles in Water at Room Temperature" *Angew. Chem. Int. Ed.* 2016, 55, pp. 8979-8983.
Fjellstrom O. et al. "Creating Novel Activated Factor XI Inhibitors through Fragment Based Lead Generation and Structure Aided Drug Design" *PLOS One*, Jan. 28, 2015, pp. 1-42.
Gaffen S. L., "The IL-23-IL-17 immune axis: from mechanisms to therapeutic testing," *Nature Reviews Immunology* vol. Sep. 14, 2014, pp. 585-600.
Kostrun S. et al. "Macrolide Inspired Macrocycles as Modulators of the IL-17A/IL-17RA Interaction," J. Med. Chem. 2021, 64, pp. 8354-8383.
Liu S. et al. "Binding site elucidation and structure guided design of macrocyclic IL-17A antagonists" *Nature Scientific Reports* 6, 30859, 2016, pp. 1-12.
Liu S. et al. "Inhibiting complex IL-17A and IL-17RA interactions with a linear peptide" *Nature Scientific Reports* 6, 30859, 2016, pp. 1-11.
Madhu C. et al. "An Efficient Synthesis of Nα-Protected Amino and Peptide Acid Aryl Amides via Iodine-Mediated Oxidative Acylation of Nα-Protected Amino and Peptide Thioacids" *Synthesis* 2013, 45, pp. 2727-2736.
Madhu C. et al. "An Efficient and Epimerization Free Synthesis of C-Terminal Arylamides Derived from a-Amino Acids and Peptide Acids via T3P Activation," *Int J Pept Res Ther* (2014) 20, pp. 353-363.
Mao L. et al. "A Convenient Synthesis of Amino Acid Arylamides Utilizing Methanesulfonyl Chloride and *N*-Methylimidazole," *Synlett* , 2011, No. 1, pp. 129-133.
Mederski W. W. K. R. et al. "Chlorothiophenecarboxamides as P1 surrogates of inhibitors of blood coagulation factor Xa" *Bioorganic & Medicinal Chemistry Letters* 14 (2004) pp. 5817-5822.
Monin L. et al. "Interleukin 17 Family Cytokines: Signaling Mechanisms, Biological Activities, and Therapeutic Implications" *Cold Spring Harb Perspect Biol*, 2018, pp. 1-8.
Moukha-chafiq O. et al. "Parallel Solution-Phase Synthesis and General Biological Activity of a Uridine Antibiotic Analog Library" *ACS Comb. Sci.* 2014, 16, pp. 232-237.
Onishi R. M. et al. "Interleukin-17 and its target genes: mechanisms of interleukin-17 function in disease," *Immunology*, 129, pp. 311-321.
Smith II L. M. et al. "Novel phenylalanine derived diamides as Factor XIa inhibitors," *Bioorganic & Medicinal Chemistry Letters* 26 (2016) pp. 472-478.
Stepanic V. et al. "Physicochemical profile of macrolides and their comparison with small molecules," European Journal of Medicinal Chemistry. 2012 (47), pp. 462-472.
SciFinder Search dated Mar. 27, 2020, (41 pages).
SciFinder Search dated Mar. 27, 2020, (30 pages).
International Search Report for International Application No. PCT/EP2019/086239, dated Feb. 28, 2020. (9 pages).
Written Opinion of the International Searching Authority for International Application No. PCT/EP2019/086239. (9 pages).
Aggerwal, Sudeepta et al., "IL-17: prototype member of an emerging cytokine family," Journal of Leukocyte Biology, 2002 vol. 71, No. 1, pp. 1-8.
Albanesi, Cristina et al., "The interplay between keratinocytes and immune cells in the pathogenesis of psoriasis." Frontiers in Immunology, 2018, vol. 9, Art. 1549 (7 pages).
Arkin, Michelle R. et al., "Small-Molecule Inhibitors of Protein—Protein Interactions: Progressing Towards the Dream," Nature Reviews Drug Discovery, 2004, vol. 3, pp. 301-317.
Arkin, Michelle R. et al., "Small-molecule inhibitors of protein-protein interactions: progressing towards the reality," Chem. Biol., 2014, vol. 1, No. 9, pp. 1102-1114.
Brembilla, Nicolo C. et al., "The IL17 family of cytokines in psoriasis: IL-17A and beyond," Frontier in Immunology, 2018, vol. 9, Art. 1682).
Doak, Bradley Croy et al., "Oral Druggable Space beyond the Rule of 5: Insights from Drugs and Clinical Candidates," Chemistry & Biology, 2014, pp. 1115-1142.
Espada, Alfonso et al., "A Binding Site on IL-17A for Inhibitory Macrocycles Revealed by Hydrogen/Deuterium Exchange Mass Spectrometry," Journal of Medicinal Chemistry, 2016, vol. 59, pp. 2255-2260.
Foulkes, Amy C. et al., "Brodalumab in psoriasis: evidence to date and clinical potential," Drugs in Context, 2019, vol. 8, p. 212570.
Gaffen, Sarah L. et al., "Structure and signalling in the IL-17 receptor superfamily," Nature Reviews Immunology, 2014, vol. 14, pp. 585-600.
Geoghegan, Kieran F. et al., "Unexpected mucin-type O-glycosylation and host-specific N-glycosylation of human recombinant interleukin-17A expressed in a human kidney cell line," Protein Expression and Purification, 2013, vol. 87, pp. 27-34.
Geopfert, Arnaud et al., "The human IL-17 A/F heterodimer: a two-faced cytokine with unique receptor recognition properties," Scientific Reports, 2017, 7:8906.
Hawkes, Jason E. et al., "Discovery of the IL-23/IL-17 Signaling Pathway and the Treatment of Psoriasis," J. Immunol., 2018, vol. 201, No. 6, pp. 1605-1613.
Jin, Wei et al., "IL-17 cytokines in immunity and inflammation," Emerging Microbes and Infections, 2013, vol. 2 No. 9, pp. 1-5.
Krueger, James G. et al., "IL-17A is essential for cell activation and inflammatory gene circuits in subjects with psoriasis," J. Allergy Clin. Immunology, 2012, vol. 130, No. 1 (18 pages).
Krueger, James G. et al., "IL-17A inhibition by secukinumab induces early clinical, histopathologic, and molecular resolution of psoriasis," J. Allergy Clin. Immunology, 2019, vol. 144, No. 3; pp. 750-763.
Lee, Hui Sun et al., "Effects of N-glycosylation on protein conformation and dynamics: Protein Data Bank analysis and molecular dynamics simulation study," Scientific Reports, vol. 5, p. 8926 (2016).
Lipinski, Christopher A. et al., "Experimental and computational approaches to estimate solubility and permeability in drug discovery and development settings," Advanced Drug Delivery Reviews, 1997, vol. 23, pp. 3-25.
Liu, Shenping et al., "Crystal structures of interleukin 17A and its complex with IL-17 receptor A," Nature Communications, 2013, vol. 4, (9 pages).
Liu, Ling et al., "Generation and characterization of ixekizumab, a humanized monoclonal antibody that neutralizes interleukin-17A," Journal of Inflammation Research, 2016, vol. 9, pp. 39-50.

(56) References Cited

OTHER PUBLICATIONS

McGonagle, Dennis G. et al., "The role of IL-17A in axial spondyloarthritis and soriatic arthritis: recent advances and controversies," Ann Rheum Dis, 2019, vol. 78, pp. 1167-1178.
Niesen, Frank H. et al., "The use of differential scanning fluorimetry to detect ligand interactions that promote protein stability," Nature Protocols, 2007, vol. 2, No. 9, pp. 2212-2221.
Pappu, Rajita et al., "The interleukin-17 cytokine family: critical players in host defence and inflammatory diseases," Immunology, 2011, vol. 134, pp. 8-16.
Reich, Kristian et al., "Evidence that a neutrophil—keratinocyte crosstalk is an early target of IL-17A inhibition in psoriasis," Experimental Dermatology, 2015, vol. 24, pp. 529-535.
Rong, Zhili et al., "IL-17RD (Sef or IL-17RLM) interacts with IL-17 receptor and mediates IL-17 signaling," Cell Res., 2009, vol. 19, No. 2, pp. 208-215.
Sawyer, Laura et al., "The comparative efficacy of brodalumab in patients with moderate-to-severe psoriasis: a systematic literature review and network meta-analysis," Journal of Dermatological Treatment, 2018, vol. 29, No. 6, pp. 557-568.
Thiel, Philipp et al., "Small-Molecule Stabilization of Protein-Protein Interactions: An Underestimated Concept in Drug Discovery," Angew. Chem. Int. Ed., 2012, vol. 51, pp. 2012-2018.
Wan, Hong et al., "Impact of Input Parameters on the Prediction of Hepatic Plasma Clearance Using the Well-Stirred Model," Current Drug Metabolism, 2010, vol. 11, pp. 583-594.
Wang, Claire Q.F. et al., "IL-17 and TNF synergistically modulate cytokine expression while suppressing melanogenesis: potential relevance to psoriasis," J. Invest. Dermatol., 2013, vol. 133, No. 12, pp. 2741-2752.

* cited by examiner

SMALL MOLECULE MODULATORS OF IL-17

This application is a national stage filing under 35 U.S.C. § 371 of International Application No. PCT/EP2019/086239, filed on Dec. 19, 2019, which claims priority of European Patent Application No. 18214002.0, filed on Dec. 19, 2018, and European Patent Application No. 19187352.0, filed Jul. 19, 2019. The contents of these applications are each incorporated herein by reference.

FIELD OF THE INVENTION

This invention relates to novel amino-acid anilides and derivatives thereof, to said compounds for use in therapy and to pharmaceutical compositions comprising said compounds.

BACKGROUND OF THE INVENTION

IL-17 (also known as IL-17A or CTLA8) is a pro-inflammatory cytokine involved in antimicrobial defense at epithelial surfaces. IL-17 is comprised of two covalently joined IL-17A subunits (IL-17AA) with an approximate mass of 32 kDa, and signals through a receptor comprising IL17RA and IL17RC subunits. This receptor is predominantly expressed in epithelial and mesenchymal cells. The IL17RA/IL17RC receptor is also used by IL-17 variants IL-17AF and IL-17FF, which both are successively weaker, partial agonists on this receptor (Monin, L., Gaffen, S. L.; 2018, Cold Spring Harb. Perspect. Biol. 10. doi:10.1101/cshperspect.a028522). Crucial for signaling is the assembly of signaling complexes containing the multifunctional protein ACT1/CIKS, which in turn can recruit TRAF and other proteins.

Via these signaling complexes IL-17 induces cytokines, chemokines, antimicrobial peptides and growth factors via activation of transcription factor NFkB or via MAP kinase-dependent pathways (e.g. IL-6, IL-8, CXCL1, CXCL2, CXCL5, CCL20, G-CSF, BD4) and stabilizes the mRNAs of certain inflammatory cytokines, such as CXCL1. This leads to amplification of their effects. Further, IL-17 acts in concert with IL-1beta, IL-22 and IFNgamma (Amatya, N. et al., Trends in Immunology, 2017, 38, 310-322. doi:10.1016/j.it.2017.01.006; Onishi, R. M., Gaffen, S. L. Immunology, 2010, 129, 311-321. doi:10.1111/j.1365-2567.2009.03240.x).

IL-17 is secreted by a variety of immune cells, such as Th17 helper cells, Tc17 cytotoxic cells, ILC3 innate cells, NKT cells, TCRbeta+ natural T cells and gamma-deltaT-cells (Monin, L., Gaffen, S. L.; 2018, Cold Spring Harb. Perspect. Biol. 10. doi:10.1101/cshperspect.a028522). Increased, disease-provoking levels of IL-17 are observed in several autoimmune diseases, such as psoriasis, ankylosing spondylitis, spondyloarthritis and psoriatic arthritis. Other diseases where deregulation of IL-17 is observed are rheumatoid arthritis, systemic lupus erythematosus, asthma, inflammatory bowel disease, autoimmune uveitis, multiple sclerosis and certain cancers (Gaffen, S. L. et al., Nat Rev Immunol., 2014, 14, 585-600. doi:10.1038/nri3707; Monin, L., Gaffen, S. L.; 2018, Cold Spring Harb. Perspect. Biol. 10. doi:10.1101/cshperspect.a028522). Hence, IL-17 is a significant therapeutic target.

Therapeutic, neutralizing antibodies against IL-17A (Secukinumab, Ixekizumab) or receptor IL17RA (Brodalumab) have shown high efficacy in the treatment of psoriasis, ankylosing spondylitis and psoriatic arthritis. These antibodies have long half-lives in the body.

Although various antibodies against IL-17A or IL-17RA are approved, only very few small molecule orally available modulators of IL-17 are known.

WO2013116682 discloses Macrocyclic Compounds for Modulating IL-17;

WO2014066726 discloses Compounds for Modulating IL-17;

WO2018229079 discloses Compounds for Modulating IL-17;

WO2019223718 discloses Compounds for Modulating IL-17;

WO2019138017 discloses Compound for Modulating IL-17;

Scientific Reports (2016) 6, 30859 discloses Macrocyclic IL-17A Antagonists.

Leslie Dakin, 12$^{th}$ Swiss Course on Medicinal Chemistry, Leysin, Oct. 9-14, 2016 discloses 'Hit Identification, binding site elucidation and structure guided design of novel macrocyclic IL-17A antagonists'.

Orally available, highly efficacious small molecule IL-17 modulators which bind to IL-17 to decrease its functional ability to activate the IL-17 receptor complex may have a number of advantages compared to monoclonal antibodies. Oral administration and flexible treatment regimen may be two significant aspects in favor of patient convenience and the compounds may exhibit improved safety due to the possibility of faster withdrawal of the drug should adverse events occur.

Therefore, there is a continuous need to develop small molecule modulators of IL-17, particularly small molecules suitable for oral administration.

In addition, some patients may be treated by topical application of small molecule modulators of IL-17. This can be particularly suitable for patients with skin lesions that are readily accessible and limited in body surface area. Topical treatment may also be prescribed for certain patients who could benefit from avoiding systemic modulation of the IL-17 pathway, for example when undergoing treatment for infections or gastrointestinal problems.

SUMMARY OF THE INVENTION

The inventors have surprisingly found that novel compounds of the present invention exhibit modulating effect on the IL-17 signalling pathway.

Compounds of the present invention may have advantageous properties such as high metabolic stability and/or membrane permeability properties that make them suitable for oral administration. Other compounds of the present invention may have advantageous properties for local topical therapy, such as high skin permeability and high metabolic instability.

Compounds of the present invention may be beneficial in preventing, treating or ameliorating a variety of diseases which involve up-regulation or de-regulation of IL-17, such as for example psoriasis, ankylosing spondylitis and psoriatic arthritis.

Accordingly, the present invention relates to a compound according to formula (I)

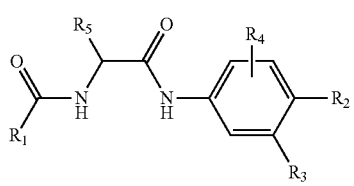
(I)

wherein $R_1$ is selected from the group consisting of 5- or 6-membered heteroaryl, 9- or 10-membered bicyclic heteroaryl, phenyl, $(C_1-C_6)$alkoxy, $(C_3-C_7)$cycloalkoxy, $(C_1-C_6)$alkyl, phenyl-$(C_1-C_4)$alkyl, $(C_3-C_7)$cycloalkyl, 4-6-membered heterocycloalkyl and —$NR_cR_d$, wherein said 5- or 6-membered heteroaryl, 9- or 10-membered bicyclic heteroaryl, phenyl, $(C_1-C_6)$alkoxy, $(C_3-C_7)$cycloalkoxy, $(C_1-C_6)$alkyl, phenyl-$(C_1-C_4)$alkyl, $(C_3-C_7)$cycloalkyl and 4-6-membered heterocycloalkyl is optionally substituted with one or more substituents independently selected from $R_a$;

$R_a$ represents deuterium, halogen, hydroxy, —$NR_cR_d$, $(C_1-C_6)$alkyl, $(C_1-C_6)$alkylcarbonyl, $(C_3-C_7)$cycloalkyl, phenyl, 5- or 6-membered heteroaryl or, 4-6-membered heterocycloalkyl, wherein said $(C_1-C_6)$alkyl, $(C_1-C_6)$alkylcarbonyl, $(C_3-C_7)$cycloalkyl, phenyl, 5- or 6-membered heteroaryl or 4-6-membered heterocycloalkyl is optionally substituted with one or more substituents independently selected from deuterium, halogen, hydroxy, cyano, $(C_1-C_4)$alkyl, $(C_3-C_7)$cycloalkyl, $(C_1-C_4)$alkoxy, —$SO_2$—$(C_1-C_4)$alkyl and —$NR_cR_d$;

$R_2$ is selected from the group consisting of 5- or 6-membered heteroaryl, wherein said 5- or 6-membered heteroaryl is optionally substituted with one or more substituents independently selected from $R_b$, wherein said 5- or 6-membered heteroaryl may optionally contain —CO— as a ring member and wherein when said 5 membered heteroaryl contains nitrogen as a ring atom said nitrogen may optionally be substituted with a substituent selected from $R_8$;

$R_b$ represents deuterium, halogen, cyano, hydroxy, —$NR_cR_d$, $(C_1-C_6)$alkyl, $(C_1-C_6)$alkoxy, $(C_1-C_6)$alkyl-CO—O—$(CH_2)_n$— or $(C_3-C_7)$cycloalkyl, wherein n is 1-4, and wherein said $(C_1-C_6)$alkyl, $(C_1-C_6)$alkoxy or $(C_3-C_7)$cycloalkyl is optionally substituted with one or more substituents independently selected from deuterium, halogen, cyano, hydroxy, —$NR_cR_d$ and $(C_1-C_4)$alkoxy;

$R_c$ and $R_d$ each independently are selected from the group consisting of hydrogen and $(C_1-C_6)$alkyl, or $R_c$ and $R_d$ together form pyrrolidinyl or piperidinyl, wherein said $(C_1-C_6)$alkyl, pyrrolidinyl or piperidinyl is optionally substituted with one or more substituents independently selected from halogen, cyano and hydroxy;

$R_8$ is selected from the group consisting of -L-PO(OH)$_2$ and

—$CHR_gO$—$(CO-A-NR_h)_m$—$CO-A-NR_hR_i$,

L is selected from the group consisting of a bond or —$CHR_gO$—, m is 0 or 1;

wherein each —$CO-A-NR_h$— independently represent an amino acid residue wherein the amino acid residue is selected from the natural amino acids either in D or L-form or as mixtures of the D and L form, and wherein said amino acid residue may be substituted on the α-amino group with a substituent $R_h$;

$R_g$, $R_h$, and $R_i$ are independently selected from hydrogen and $(C_1-C_6)$alkyl;

$R_3$ is selected from the group consisting of hydrogen, deuterium, hydroxy and halogen;

$R_4$ is selected from the group consisting of hydrogen, deuterium and halogen;

$R_5$ is selected from the group consisting of —$CHR_6R_7$, $(C_3-C_{10})$cycloalkyl and G, wherein said $(C_3-C_{10})$cycloalkyl and G are optionally substituted with one or more substituents independently selected from deuterium, halogen, cyano, hydroxy, $(C_1-C_4)$alkyl and halo$(C_1-C_4)$ alkyl;

G represents

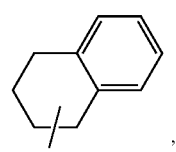
$G_1$

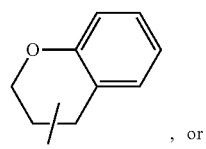
, or $G_2$

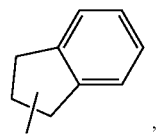
, $G_3$ $R_6$ and $R_7$ each independently represents hydrogen, phenyl, $(C_1-C_6)$alkyl, or $(C_3-C_7)$cycloalkyl, wherein said phenyl, $(C_1-C_6)$alkyl or $(C_3-C_7)$cycloalkyl is optionally substituted with one or more substituents independently selected from halogen, cyano, hydroxy and $(C_1-C_4)$alkyl; with the proviso that at least one of $R_6$ and $R_7$ are different from hydrogen;

or pharmaceutically acceptable salts, solvates, hydrates or prodrugs thereof.

In another aspect, the invention relates to a pharmaceutical composition comprising a compound of general formula (I) as defined herein together with a pharmaceutically acceptable vehicle or excipient or pharmaceutically acceptable carrier(s), optionally together with one or more other therapeutically active compound(s).

In yet another aspect, the invention relates to the use of a compound according to formula I as defined herein for use in therapy, for example for use in treatment of a disease, disorder or condition, which disease, disorder or condition is responsive of modulation of IL-17, for example for use in treatment of autoimmune diseases.

DETAILED DESCRIPTION OF THE INVENTION

Definitions

The term "$(C_a-C_b)$alkyl" is intended to indicate a hydrocarbon radical obtained when one hydrogen atom is removed from a branched or linear hydrocarbon. Said alkyl comprises (a-b) carbon atoms, such as 1-6, such as 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The terms "$(C_a-C_b)$alkyloxy" and "$(C_a-C_b)$alkoxy" are intended to indicate a radical of the formula —OR', wherein R' is $(C_a-C_b)$alkyl as indicated herein, wherein the $(C_a-C_b)$ alkyl group is appended to the parent molecular moiety through an oxygen atom, e.g. methoxy (—OCH$_3$), ethoxy (—OCH$_2$CH$_3$), n-propoxy, isopropoxy, butoxy, tert-butoxy, and the like.

The term "cyano" is intended to indicate a —CN group attached to the parent molecular moiety through the carbon atom.

The term "$(C_a-C_b)$cycloalkyl" is intended to indicate a saturated $(C_a-C_b)$cycloalkane hydrocarbon radical, including polycyclic radicals such as bicyclic or tricyclic radicals, including spirocyclic radicals, comprising a-b carbon atoms, such as 3-10 carbon atoms, such as 3-8 carbon atoms, such as 3-7 carbon atoms, such as 3-6 carbon atoms, such as 3-5 carbon atoms or such as 3-4 carbon atoms, e.g. cyclopropyl, cyclobutyl, cyclopentyl, cyclohexyl, cycloheptyl, cyclooctanyl, adamantyl, spiro[2.5]octanyl, spiro[2.3]hexanyl, bicyclo[3,1,0]hexanyl, bicyclo[4,1,0]heptanyl and bicyclo[2,2,2]octanyl.

The term "$(C_a-C_b)$cycloalkoxy" is intended to indicate a radical of the formula —OR', wherein R' is $(C_a-C_b)$cycloalkyl as indicated herein, wherein the $(C_a-C_b)$cycloalkyl group is appended to the parent molecular moiety through an oxygen atom, e.g. cyclopentyloxy or cyclobutyloxy.

The term "halo$(C_a-C_b)$alkyl" is intended to indicate an $(C_a-C_b)$alkyl group as defined herein substituted with one or more halogen atoms as defined herein, e.g. fluoro or chloro, such as difluoromethyl or trifluoromethyl.

The terms "halo$(C_a-C_b)$alkyloxy" and "halo$(C_a-C_b)$ alkoxy" are intended to indicate an halo$(C_a-C_b)$alkyl group as defined herein which is appended to the parent molecular moiety through an oxygen atom, such as difluoromethoxy or trifluoromethoxy.

The term "halogen" is intended to indicate a substituent from the 7$^{th}$ main group of the periodic table, such as fluoro, chloro and bromo.

The term "5- or 6-membered heteroaryl" is intended to indicate radicals of monocyclic heteroaromatic rings comprising 5- or 6-membered ring which contains from 1-5 carbon atoms and from 1-4 heteroatoms selected from oxygen, sulphur and nitrogen; such as 2-5 carbon atoms and 1-3 heteroatoms, such as 3-5 carbon atoms and 1-2 heteroatoms, such as 4-5 carbon atoms and 1-2 heteroatoms selected from oxygen, sulphur and nitrogen, such as furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, quinolyl, tetrazolyl, thiadiazolyl, thiazolyl and triazolyl. The term "5- or 6-membered heteroaryl" includes compounds wherein a ring member is a C(O) or carbonyl group.

The term "5-membered heteroaryl" is intended to indicate radicals of 5-membered monocyclic heteroaromatic ring which contains from 1-4 carbon atoms and from 1-4 heteroatoms selected from oxygen, sulphur and nitrogen; such as 2-4 carbon atoms and 1-3 heteroatoms, such as 3-4 carbon atoms and 1-2 heteroatoms, such as 4 carbon atoms and 1 heteroatom selected from oxygen, sulphur and nitrogen; such as furanyl, imidazolyl, isothiazolyl, isoxazolyl, oxadiazolyl, oxazolyl, pyrazolyl, pyrrolyl, quinolyl, tetrazolyl, thiadiazolyl, thiazolyl and triazolyl. The term "5-membered heteroaryl" includes compounds wherein a ring member is a C(O) or carbonyl group.

The term "9- or 10-membered bicyclic heteroaryl" is intended to indicate fused bicyclic heteroaromatic radicals comprising 9- or 10-carbon or heteroatoms, which for example contain from 3-9 carbon atoms and 1-7 heteroatoms selected from oxygen, sulphur and nitrogen, such as 1-5 heteroatoms and 5-9 carbon atoms, such as 1-3 heteroatoms and 7-9 carbon atoms, such as 1-2 heteroatoms and 8-9 carbon atoms, such as 1 heteroatom and 8 carbon atoms, such as 1 heteroatom and 9 carbon atoms, such as 2 heteroatom and 7 carbon atoms, such as 2 heteroatom and 8 carbon atoms. Said bicyclic heteroaromatic radicals comprise a 5- or 6-membered heteroaromatic ring fused to phenyl and a 5- or 6-membered heteroaromatic ring fused to another 5- or 6-membered heteroaromatic ring, as defined herein. The heteroaryl radical may be connected to the parent molecular moiety through a carbon atom or a nitrogen atom contained anywhere within the heteroaryl group. Representative examples of 9- or 10-membered bicyclic heteroaryl include, but are not limited to azaindolyl, benzofuranyl, benzothiophenyl, benzimidazolyl, benzooxazolyl, benzothiazolyl, benzothienyl, cinnolyl, imidazopyridinyl, imidazopyrimidinyl, imidazothiazolyl, indazolyl, indolyl, isobenzofuranyl, isoquinolyl, pyrrolopyrimidinyl, thienopyridinyl. pyrrolo[2,3]pyridinyl, pyrrolo[2,3]pyridinyl, pyrazolo[1,5]pyridinyl, pyrazolo[1,5]pyridazinyl, imidazo[1,2]pyrimidinyl, pyrrolo[2,3-c]pyridinyl, pyrrolo[2,3-b]pyridinyl, pyrazolo[1,5-a]pyridinyl, pyrazolo[1,5-b]pyridazinyl, imidazo[1,2-a]pyrimidinyl.

The term (5- or 6-membered heteroaryl)-$(C_a-C_b)$alkyl is intended to indicate a 5- or 6-membered heteroaryl appended to the parent molecular moiety through a $(C_a-C_b)$ alkyl group, as defined herein.

The term "(a-b) membered heterocycloalkyl" is intended to indicate a cycloalkane radical as described herein, including polycyclic radicals such as bicyclic or tricyclic radicals, including spirocyclic radicals, wherein one or more carbon atoms of said cycloalkane radical are replaced by heteroatoms, i.e. the a-b membered heterocycloalkyl comprise from a to b carbon- or hetero-atoms. Such a-b membered heterocycloalkyl could comprise for example 2-9 carbon atoms and 1-6 heteroatoms selected from O, N, or S, such as 3-8 carbon atoms and 1-4 heteroatoms, such as 3-7 carbon atoms and 1-3 heteroatoms, such as 3-6 carbon atoms and 1-2 heteroatom. The heterocycloalkyl radical may be connected to the parent molecular moiety through a carbon atom or a nitrogen atom contained anywhere within the heterocycloalkyl group. Representative examples of heterocycloalkyl groups include, but are not limited to azepanyl, azetidinyl, aziridinyl, dioxolanyl, dioxolyl, imidazolidinyl, morpholinyl, oxetanyl, piperazinyl, piperidinyl, pyrrolidinyl, tetrahydrofuranyl, tetrahydropyranyl, thietanyl, 2,6-diazaspiro[3.3] heptane, The term "(a-b membered heterocycloalkyl)-$(C_c-C_d)$alkyl" is intended to indicate a a-b membered heterocycloalkyl radical appended to the parent molecular moiety through an $(C_c-C_d)$alkyl group, as defined herein.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-6 carbon atoms, e.g. 1-5, e.g. 1-4, e.g. 1-3, e.g. 1-2 carbon atoms. The term includes alkyl and cycloalkyl as indicated herein.

The term "hydroxy($C_a$-$C_b$)alkyl" is intended to indicate an ($C_a$-$C_b$)alkyl group as defined above substituted with one or more hydroxy, e.g. hydroxymethyl, hydroxyethyl, hydroxy propyl.

The term "oxo" is intended to indicate an oxygen atom which is connected to the parent molecular moiety via a double bond (=O).

The term "phenyl-($C_a$-$C_b$)alkyl" is intended to indicate a phenyl group appended to appended to the parent molecular moiety through an ($C_a$-$C_b$)alkyl group, as defined herein.

When two or more of the above defined or similar terms are used in combination, such as cycloalkylalkyl or phenyl-($C_a$-$C_b$)alkyl and the like, it is to be understood that the first mentioned radical is a substituent on the latter mentioned radical, where the point of attachment to the parent molecular moiety is on the latter radical.

The group C(O) is intended to represent a carbonyl group (C=O).

If substituents are described as being independently selected from a group, each substituent is selected independent of the other. Each substituent may therefore be identical or different from the other substituent(s).

The term "optionally substituted" means "unsubstituted or substituted", and therefore the general formulas described herein encompasses compounds containing the specified optional substituent(s) as well as compounds that do not contain the optional substituent(s).

As used herein whenever a molecular drawing of a substituent contains an arrow—the arrow indicates the bond attaching the substituent to the rest of the molecule.

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroacetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, zinc hydroxide, barium hydroxide, ammonia or the like, or suitable non-toxic amines, such as lower alkylamines (such as diethylamine, tetraalkylammonium hydroxide), hydroxy-lower alkylamines (such as diethanolamine, 2-(diethylamino)-ethanol, ethanolamine, triethanolamine, tromethamine, deanol), cycloalkylamines, ethylene diamine, or benzylamines, (such as benethamine and benzathine), betaine, choline hydroxide, N-methyl-glucamine, hydrabamine, 1H-imidazole, 4-(2-hydroxyethyl)-morpholine, piperazine, 1-(2-hydroxyethyl)-pyrrolidine, L-arginine or L-lysine. Further examples of pharmaceutical acceptable salts are listed in Berge, S. M.; J. Pharm. Sci.; (1977), 66(1), 1-19, and Stahl, P. H. and in Wermuth, C. G, Handbook of Pharmaceutical Salts, Properties, Selection and Use, $2^{nd}$ Edition, Wiley-VCH, 2011 both of which is incorporated herein by reference For example when $R_8$ is -L-PO(OH)$_2$ the phosphoric acid group may form a salt with a monovalent cation $M^+$ or divalent cation $Q^{2+}$ to form a group selected from -L-PO(OH)O$^-$.$M^+$, -L-PO(OH)O$^-$.½$Q^{2+}$ -L-PO(O$^-$)$_2$.2$M^+$, and -L-PO(O$^-$)$_2$.$Q^{2+}$. The term 'monovalent cation' is intended to indicate monovalent cations such as alkali metal ions, such as for example sodium (Na$^+$), potassium (K$^+$) or lithium (Li$^+$), or ammonium ions, such as for example NH$_4^+$, dialkylammonium (NH$_2$(($C_1$-$C_4$)alkyl)$_2$)$^+$, trialkylammonium (NH(($C_1$-$C_4$)alkyl)$_3$)$^+$, or tetraalkylammonium (N(($C_1$-$C_4$)alkyl)$_4$)$^+$, alkylammonium (H$_3$N($C_1$-$C_4$)alkyl)$^+$ or hydroxyalkylammonium (H$_3$N-hydroxy($C_1$-$C_4$)alkyl)$^+$, the protonated forms of L-arginine, L-lysine or the protonated forms of any pharmaceutically acceptable bases such as those mentioned above.

The term 'divalent cation' is intended to indicate divalent cations such as alkaline earth metal ions such as calcium (Ca$^{2+}$), Magnesium (Mg$^{2+}$) or barium (Ba$^{2+}$), or Zinc (Zn$^{2+}$).

The term 'prodrug' is intended to indicate compounds which are drug-precursors which, upon administration, are converted to the parent drug in vivo by enzymatic and/or chemical reactions. Generally, the pro-drug is less biologically active than its parent drug. The prodrug may have improved physical-chemical properties compared to the parent drug, such as improved aqueous solubility, thereby facilitating the absorption and consequently the bioavailability of the parent compound upon administration.

The term 'parent drug' or 'parent compound' is intended to indicate the biologically active compound which is released from the prodrug via enzymatic and/or chemical processes following administration of the prodrug. The parent drug is frequently the starting material for the preparation of the corresponding prodrug.

Examples of prodrugs according to the invention are prodrugs that are attached to a nitrogen or oxygen of the parent molecule.

For example when the parent molecule contains a 5-membered heteroaryl containing nitrogen substituted with hydrogen as a ring atom said hydrogen may be replaced with a substituent selected from $R_8$ to form a prodrug.

5-membered heteroaryls such as pyrrole, imidazole, pyrazole, triazole and tetrazole when attached to the reminder of the molecule via a carbon ring atom are moieties that may contain a nitrogen ring atom substituted by hydrogen.

In one example $R_8$ is -L-PO(OH)$_2$ and in another embodiment $R_8$ is

—CHR$_g$O—(CO-A-NR$_h$)$_m$—CO-A-NR$_h$R$_i$, wherein

L is selected from the group consisting of a bond or —CHR$_g$O—, m is 0 or 1;

and each —CO-A-NR$_h$— independently represent an amino acid residue wherein the amino acid residue is selected from natural amino acid residues either in D or L-form or as mixtures of the D and L form, wherein said amino acid residue may be substituted on the α-amino group with a substituent $R_h$; and $R_g$, $R_h$, and $R_i$ are independently selected from hydrogen and ($C_1$-$C_6$)alkyl.

As used herein "natural amino acid residues" means any of the 20 natural amino acid residues (except a proline) either in D or L-form or as mixtures of the D and L form —CO-A-NR$_h$— may thus represent any of the following amino acid residues:

—CO—CH$_2$—NR$_h$—,
—CO—CH(CH$_3$)—NR$_h$—,
—CO—CH(CH$_2$OH)—NR$_h$—,
—CO—CH(CH$_2$SH)—NR$_h$—,
—CO—CH(CH(CH$_3$)(OH))—NR$_h$—,
—CO—CH(CH(CH$_3$)$_2$)—NR$_h$—,
—CO—CH(CH$_2$CH(CH$_3$)$_2$)—NR$_h$—,
—CO—CH(CH(CH$_3$)(CH$_2$CH$_3$))—NR$_h$—,
—CO—CH(CH$_2$CH$_2$—S—CH$_3$)—NR$_h$—,
—CO—CH(CH$_2$-phenyl)—NR$_h$—, —CO—CH(CH$_2$(4-hydroxyphenyl))—NR$_h$—,
—CO—CH(CH$_2$—COOH)—NR$_h$—,
—CO—CH(CH$_2$—CH$_2$—COOH)—NR$_h$—,
—CO—CH(CH$_2$—CH$_2$—CONH$_2$)—NR$_h$—,
—CO—CH(CH$_2$—CONH$_2$)—NR$_h$—,
—CO—CH((CH$_2$)$_4$—NH$_2$)—NR$_h$—,
—CO—CH((CH$_2$)$_3$—NH—C(NH)(NH$_2$))—NR$_h$—,
—CO—CH—(CH$_2$-(4-imidazolyl))—NR$_h$—, and
—CO—CH—(CH$_2$-(3-indolyl))—NR$_h$— wherein R$_h$ is defined as above.

In another example the parent molecule contains an OH group as a substituent and the hydrogen in said OH substituent is replaced with a substituent selected from R$_8$ to form a prodrug.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

All references, including publications, patent applications and patents, cited herein are hereby incorporated by reference in their entirety and to the same extent as if each reference were individually and specifically indicated to be incorporated by reference, regardless of any separately provided incorporation of particular documents made elsewhere herein.

EMBODIMENTS OF THE INVENTION

In an embodiment the invention relates to a compound of general formula (I) as defined above, wherein R$_1$ is selected from 5-membered heteroaryl, 9-membered bicyclic heteroaryl, (C$_3$-C$_7$)cycloalkyl, 4-6-membered heterocycloalkyl, (C$_1$-C$_6$)alkyl and (C$_1$-C$_6$)alkoxy, wherein said 5-membered heteroaryl, 9-membered bicyclic heteroaryl, (C$_3$-C$_7$) cycloalkyl, 4-6-membered heterocycloalkyl, (C$_1$-C$_6$)alkyl and (C$_1$-C$_6$)alkoxy is optionally substituted with one or more substituents independently selected from R$_a$.

In an embodiment the invention relates to a compound of general formula (I) as defined above, wherein R$_2$ is selected from pyrazolyl or imidazolyl, wherein said pyrazolyl or imidazolyl is optionally substituted with one or more substituents independently selected from R$_b$.

In an embodiment the invention relates to a prodrug of a compound of general formula (I) as defined above.

In an embodiment, R$_2$ in the prodrug is selected from pyrazolyl or imidazolyl, wherein said pyrazolyl or imidazolyl is optionally substituted with one or more substituents independently selected from R$_b$.

In an embodiment, R$_2$ in the prodrug is selected from pyrazolyl or imidazolyl, wherein a nitrogen ring atom of said pyrazolyl or imidazolyl is substituted by R$_8$ and other ring atoms of said pyrazolyl or imidazolyl is substituted by one or more substituents independently selected from R$_b$.

In an embodiment the invention relates to a compound of general formula (I) as defined above, wherein R$_5$ is selected from cyclohexyl, cycloheptyl, cyclooctanyl, adamantyl, spiro[2.5]octanyl, spiro[2.3]hexanyl, bicyclo[3,1,0]hexanyl, bicyclo[4,1,0]heptanyl and bicyclo[2,2,2]octanyl, wherein said cyclohexyl, cycloheptyl, cyclooctanyl, adamantyl, spiro [2.5]octanyl, spiro[2.3]hexanyl, bicyclo[3,1,0]hexanyl, bicyclo[4,1,0]heptanyl and bicyclo[2,2,2]octanyl is optionally substituted with one or more substituents independently selected from deuterium, halogen, cyano, hydroxy, (C$_1$-C$_4$) alkyl and halo(C$_1$-C$_4$)alkyl.

In an embodiment the invention relates to a compound of general formula (I) as defined above, wherein R$_5$ is selected from G, wherein G represents

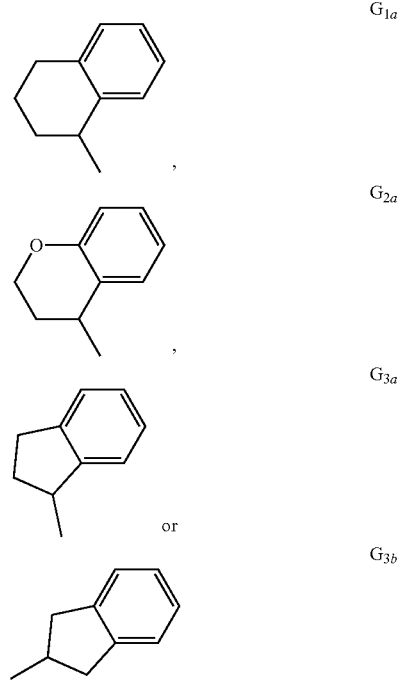

wherein said G is optionally substituted with one or more substituents independently selected from deuterium, halogen, cyano, hydroxy, (C$_1$-C$_4$)alkyl and halo(C$_1$-C$_4$)alkyl.

In an embodiment the invention relates to a compound of general formula (I) as defined above, wherein R$_5$ is selected from —CHR$_6$R$_7$, and wherein R$_6$ and R$_7$ each independently represents hydrogen, phenyl, cyclopropyl, cyclobutyl, cyclopentyl, cyclohexyl, methyl or ethyl, wherein said phenyl, cyclopropyl, cyclobutyl, cyclopentyl, cyclohexyl, methyl or ethyl, is optionally substituted with one or more substituents independently selected from halogen, cyano, (C$_1$-C$_4$)alkyl; with the proviso that at least one of R$_6$ and R$_7$ are different from hydrogen.

In a further embodiment the invention relates to a compound of general formula (I) as defined above, wherein R$_5$ is selected from —CHR$_6$R$_7$, and wherein R$_6$ and R$_7$ each independently represents C$_{3-7}$cycloalkyl, wherein said C$_{3-7}$cycloalkyl is optionally substituted with one or more substituents independently selected from halogen, cyano, (C$_1$-C$_4$)alkyl.

In a further embodiment the invention relates to a compound of general formula (I) as defined above, wherein $R_5$ is selected from —$CHR_6R_7$, and wherein $R_6$ and $R_7$ each independently represents cyclopropyl, wherein said cyclopropyl is optionally substituted with one or more substituents independently selected from halogen, cyano, ($C_1$-$C_4$) alkyl.

In one or more embodiments of the present invention, the compounds of general formula I have an ($EC_{50}$) value in IL-8 release assay of less than 1 micromolar, or of less than 100 nanomolar.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula I comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials.

Furthermore, when a double bond or a fully or partially saturated ring system is present in the molecule geometric isomers may be formed. Any geometric isomer, as separated, pure or partially purified geometric isomers or mixtures thereof are included within the scope of the invention.

In the compounds of general Formula I, the atoms may exhibit their natural isotopic abundances, or one or more of the atoms may be artificially enriched in a particular isotope having the same atomic number, but an atomic mass or mass number different from the atomic mass or mass number found in nature. The present invention includes all suitable isotopic variations of the compounds of general Formula I. For example, different isotopic forms of hydrogen include $^1H$, $^2H$ and $^3H$, different isotopic forms of carbon include $^{12}C$, $^{13}C$ and $^{14}C$ and different isotopic forms of nitrogen include $^{14}N$ and $^{15}N$. Enriching for deuterium ($^2H$) may for example increase in-vivo half-life or reduce dosage regiments, or may provide a compound useful as a standard for characterization of biological samples. Isotopically enriched compounds within general formula I can be prepared by conventional techniques well known to a person skilled in the art or by processes analogous to those described in the general procedures and examples herein using appropriate isotopically enriched reagents and/or intermediates.

Some compounds have lower aqueous solubility which may affect the absorption and consequently the bioavailability of the compounds. Such compounds may advantageously be administered in the form of prodrugs improving the aqueous solubility of the parent compound. Such prodrugs which, upon administration, are converted to their parent compounds may be less active in vitro compared to their parent compounds, but because of the improved aqueous solubility, facilitating the absorption and consequently the bioavailability of the parent compounds upon administration, such prodrugs have improved in vivo activity compared to their parent compounds.

Prodrugs of the compounds of formula (I) form part of the invention claimed.

Solvates and hydrates form part of the invention claimed.

The compounds of the present invention may be useful for preventing, treating or ameliorating any of the following diseases: psoriasis, ankylosing spondylitis, spondyloarthritis or psoriatic arthritis, lichen planus, lupus nephritis, Sjögren's syndrome, acne, vitiligo, alopecia areata, ichthyosis, acute and chronic liver diseases, gout, osteoarthritis, SLE (besides LN and DLE), multiple sclerosis, plaque psoriasis, pustular psoriasis, psoriatric arthritis, rheumatoid arthritis, *Pityriasis rubra* pilaris, pyoderma gangrenosum, hidradenitis suppurativa, discoid lupus erythematosus, Papulopustolar rosacea, atopic dermatitis, Ichthyosis, bullous pemphigoid, scleroderma, rheumatoid arthritis, tendinopathy, chronic wounds and cancer.

In an embodiment the invention relates to the use of a compound of general formula (I) as defined above, in the manufacture of a medicament for the prophylaxis, treatment or amelioration of any of the following diseases: psoriasis, ankylosing spondylitis, spondyloarthritis or psoriatic arthritis, lichen planus, lupus nephritis, Sjögren's syndrome, acne, vitiligo, alopecia areata, ichthyosis, acute and chronic liver diseases, gout, osteoarthritis, SLE (besides LN and DLE), multiple sclerosis, plaque psoriasis, pustular psoriasis, psoriatric arthritis, rheumatoid arthritis, *Pityriasis rubra* pilaris, pyoderma gangrenosum, hidradenitis suppurativa, discoid lupus erythematosus, Papulopustolar rosacea, atopic dermatitis, Ichthyosis, bullous pemphigoid, scleroderma, rheumatoid arthritis, tendinopathy, chronic wounds and cancer.

In an embodiment the invention relates to the use of a compound of general formula (I) as defined above, in the manufacture of a medicament for the prophylaxis, treatment or amelioration of autoimmune diseases, such as psoriasis, ankylosing spondylitis, spondyloarthritis or psoriatic arthritis.

In an embodiment the invention relates to a method of preventing, treating or ameliorating autoimmune diseases, such as psoriatic arthritis, lichen planus, lupus nephritis, Sjögren's syndrome, acne, vitiligo, alopecia areata, ichthyosis, acute and chronic liver diseases, gout, osteoarthritis, SLE (besides LN and DLE), multiple sclerosis, plaque psoriasis, pustular psoriasis, psoriatric arthritis, rheumatoid arthritis, *Pityriasis rubra* pilaris, pyoderma gangrenosum, hidradenitis suppurativa, discoid lupus erythematosus, Papulopustolar rosacea, atopic dermatitis, Ichthyosis, bullous pemphigoid, scleroderma, rheumatoid arthritis, tendinopathy, chronic wounds and cancer, the method comprising administering to a person suffering from at least one of said diseases an effective amount of one or more compounds according to according to general formula (I), optionally together with a pharmaceutically acceptable carrier or one or more excipients, optionally in combination with other therapeutically active compounds.

In an embodiment the invention relates to a method of preventing, treating or ameliorating autoimmune diseases, such as psoriasis, ankylosing spondylitis, spondyloarthritis or psoriatic arthritis, the method comprising administering to a person suffering from at least one of said diseases an effective amount of one or more compounds according to according to general formula (I), optionally together with a pharmaceutically acceptable carrier or one or more excipients, optionally in combination with other therapeutically active compounds.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.0001-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.01 mg and 300 mg of a compound of formula I.

A suitable dosage of the compound of the invention will depend, inter alia, on the age and condition of the patient, the severity of the disease to be treated and other factors well known to the practising physician. The compound may be administered either orally, parenterally, topically, transdermally or interdermally and other routes according to different dosing schedules, e.g. daily, weekly or with monthly intervals. In general a single dose will be in the range from 0.001 to 400 mg/kg body weight.

If the treatment involves administration of another therapeutically active compound it is recommended to consult Goodman & Gilman's *The Pharmacological Basis of Therapeutics*, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral, rectal, parenteral transdermal, intradermal, ophthalmic, topical, nasal, sublingual or buccal administration.

The formulations may conveniently be presented in dosage unit form and may be prepared by but not restricted to any of the methods well known in the art of pharmacy, e.g. as disclosed in Remington, *The Science and Practice of Pharmacy*, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient.

A tablet may be made by compressing, moulding or freeze drying the active ingredient optionally with one or more accessory ingredients. Compressed tablets may be prepared by compressing, in a suitable machine, the active ingredient(s) in a free-flowing form; for example with a lubricant; a disintegrating agent or a dispersing agent. Moulded tablets may be made by moulding, in a suitable machine, a mixture of the powdered active ingredient and suitable carrier. Freeze dried tablets may be formed in a freeze-dryer from a solution of the drug substance.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. Liposomal formulations are also suitable for parenteral administration.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients. Liposomal formulations or biodegradable polymer systems may also be used to present the active ingredient for ophthalmic administration.

Formulations suitable for topical, such as dermal, intradermal or ophthalmic administration include liquid or semisolid preparations, solutions or suspensions.

Formulations suitable for nasal or buccal administration include powder, self-propelling and spray formulations, such as aerosols and atomisers.

Methods of Preparation

The compounds of the present invention can be prepared in a number of ways well known to those skilled in the art of synthesis. The compounds of the invention could for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used.

The compounds of the present invention or any intermediate could be purified, if required, using standard methods well known to a synthetic organist chemist, e.g. methods described in "Purification of Laboratory Chemicals", 6$^{th}$ ed. 2009, W. Amarego and C. Chai, Butterworth-Heinemann.

Starting materials are either known or commercially available compounds, or may be prepared by routine synthetic methods well known to a person skilled in the art.

Unless otherwise noted, reagents and solvents were used as received from commercial suppliers. The organic solvents used were usually anhydrous. The solvent ratios indicated refer to vol:vol unless otherwise noted. Thin layer chromatography was performed using Merck 6OF254 silica-gel TLC plates. Visualisation of TLC plates was performed using UV light (254 nm) or by an appropriate staining technique.

Proton nuclear magnetic resonance spectra were obtained at the stated frequencies in the solvents indicated. Tetramethylsilane was used as an internal standard for proton spectra. The value of a multiplet, either defined doublet (d), triplet (t), quartet (q) or (m) at the approximate midpoint is given unless a range is quoted, (br) indicates a broad peak, whilst (s) indicates a singlet.

Differential scanning calorimetry (DSC): DSC experiments were carried out using a TA Instruments Q20 system. About 2 mg of sample was used for the measurements. An aluminium pan was used for the analysis and was sealed by applying pressure by hand and pushing each part of the pan together. The temperature was ramped from −10 to 250° C. at 10° C./min. Nitrogen was used as the purge gas. The melting point was determined as the onset value for the corresponding endothermic event.

X-Ray Powder Diffraction (XRPD): XRPD patterns were collected with a PANalytical X'pert PRO MPD diffractometer using an incident Cu Kα radiation and operating at 45 kV and 40 mA. The XRPD patterns were collected in the 2 theta range from 3 to 45 degrees with a step size of 0.007°, counting time of 148.93 s and in transmission geometry. In the incident beam path an elliptically graded multilayer mirror together with a 4 mm fixed mask, fixed anti-scatter slit 1° and fixed divergence slits of ½° were placed to line focus the Cu Kα X-rays through the sample and onto the detector. At the diffracted beam path, a long antiscatter extension were placed to minimize the background generated by air. Furthermore, soller slits of 0.02 rad where placed on both the incident and diffracted beam paths to minimize broadening from axial divergence.

The sample was placed on a 3 µm thick foil on a 96 high throughput well plate stage and oscillated in the X direction for better particle statistics. The diffraction patterns were collected using a Pixel RTMS detector with active length of 3.347° and located 240 mm from the sample.

Mass spectra were obtained using the following methods. LCMS Method 1 was used, unless otherwise stated.

LCMS Method 1:
Column: Acquity UPLC HSS T31.8 µm; 2.1×50 mm
Flow: 0.7 mL/min
Column temp: 30° C.
Mobile phases: A: 10 mM Ammonium acetate+0.1% formic acid
B: 100% Acetonitrile+0.1% formic acid
UV: 240-400 nm
Injection volume: 1 µl

| Gradient: | | |
|---|---|---|
| Time | A % | B % |
| 0.0 | 99% | 1% |
| 0.5 | 94% | 6% |
| 1.0 | 94% | 6% |
| 2.6 | 5% | 95% |
| 3.8 | 5% | 95% |
| 3.81 | 99% | 1% |
| 4.8 | 99% | 1% |

UPLC (inlet method): XEV Metode 1 CM
MS—method: Pos_50_1000 or Neg_50_1000
Instruments: Waters Acquity UPLC, Waters XEVO G2-XS QTof, Waters PDA (Photodiode Array)

LCMS Method 2:
Column: Acquity UPLC BEH 1.7 µm; 2.1×50 mm
Flow: 0.7 mL/min
Column temp.: 30° C.
Mobile phases: A: 10 mM Ammonium bicarbonate
B: 100% Acetonitrile
UV: 240-400 nm
Injection volume: 1 µl

| Gradient: | | |
|---|---|---|
| Time | A % | B % |
| 0.0 min. | 99% | 1% |
| 0.5 min. | 94% | 6% |
| 1.0 min. | 94% | 6% |
| 2.6 min. | 5% | 95% |
| 3.8 min. | 5% | 95% |
| 3.81 min. | 99% | 1% |
| 4.8 min. | 99% | 1% |

UPLC (inlet method): XEV Metode 1 CM_BASIC
MS—method: Pos_50_1000 or Neg_50_1000
Instruments: Waters Acquity UPLCWaters, XEVO G2-XS QTof LCMS Method 3:
Column: Waters Acquity UPLC HSS T31.8 µm, 2.1×50 mm.
Column temperature: 60° C.
UV: PDA 210-400 nm.
Injection volume: 2 µl.
Eluents: A: 10 mM Ammonium acetate with 0.1% formic acid.
B: 100% Acetonitrile with 0.1% formic acid.

| Gradient: | | | |
|---|---|---|---|
| Time | A % | B % | Flow (mL/min) |
| 0.0 | 95 | 5 | 1.2 |
| 0.9 | 5 | 95 | 1.2 |
| 0.91 | 5 | 95 | 1.3 |
| 1.2 | 5 | 95 | 1.3 |
| 1.21 | 5 | 95 | 1.2 |
| 1.4 | 95 | 5 | 1.2 |

MS: Electrospray switching between positive and negative ionisation.
Instruments: Waters ACQUITY UPLC, Waters SQD, Waters PDA (Photodiode array)

LCMS Method 4:
Column: Waters ACQUITY UPLC BEH 1.7 µm, 2.1×50 mm.
Column temperature: 60° C.

UV: PDA 210-400 nm.
Injection volume: 2 μl.
Eluents: A: 10 mM Ammonium Bicarbonate
B: 100% Acetonitrile

| Gradient: | | | |
|---|---|---|---|
| Time | % A | % B | Flow (mL/min) |
| 0.0 | 95 | 5 | 1.2 |
| 0.9 | 5 | 95 | 1.2 |
| 0.91 | 5 | 95 | 1.3 |
| 1.2 | 5 | 95 | 1.3 |
| 1.21 | 5 | 95 | 1.2 |
| 1.4 | 95 | 5 | 1.2 |

MS: Electrospray positive or negative ionisation.
Instrument: Waters ACQUITY UPLC, Waters QDa (MS detector), Waters PDA (Photodiode Array)
LCMS Method 5:
Mass spectra were obtained on a Waters Quattro micro API/Waters SQD2/Waters
Quattro Premier Spectrometer using electrospray ionization and atmospheric-pressure
chemical ionization with the column and solvents indicated.
Basic preparative HPLC conditions:
Column: XBridge Prep C18 5 μm OBD, 19×150 mm
Eluents: Ammonium formate (50 mM)/acetonitrile, 10-100% acetonitrile
Flow: 30 mL/min
Acidic preparative HPLC conditions:
Column: XTerra® RP-18 5 μm OBD, 19×150 mm
Eluents: 0.1% formic acid in water/acetonitrile, 10-100% acetonitrile
Flow: 30 mL/min
The following abbreviations have been used throughout:
ABPR automated back pressure regulator
AcOH acetic acid
Boc tert-butoxycarbonyl
BOP (Benzotriazol-1-yloxy)tris(dimethylamino)phosphonium hexafluorophosphate
CBz benzyloxycarbonyl
CDI carbonyldiimidazole
DABCO 1,4-diazabicyclo[2.2.2]octane
DAST (Diethylamino)sulfur trifluoride
DEA diethylamine
DCC Dicyclohexylcarbodiimide
DCM dichloromethane
DIPEA diisopropylethylamine
DMF N,N-dimethylformamide
DMSO dimethylsulfoxide
dppf 1,1'-bis(diphenylphosphino)ferrocene
EDC N-(3-Dimethylaminopropyl)-N'-ethylcarbodiimide
FA formic acid
EtOAc ethyl acetate
EtOH ethanol
FMOC fluorenylmethoxycarbonyl
HATU 1-[Bis(dimethylamino)methylene]-1H-1,2,3-triazolo[4,5-b]pyridinium 3-oxide hexafluorophosphate
HBTU N,N,N',N'-Tetramethyl-O-(1H-benzotriazol-1-yl)uronium hexafluorophosphate
HPLC high-performance liquid chromatography
IPA isopropyl alcohol
LCMS liquid chromatography-mass spectrometry
Me methyl
MeCN acetonitrile
MeOH methanol
MHz megahertz
NBS N-bromosuccinimide
NMP N-methyl-2-pyrrolidinone
NMR nuclear magnetic resonance
ppm parts per million
Prep. Preparation
Prep. HPLC preparative HPLC
PyBOP (Benzotriazol-1-yloxy)tripyrrolidinophosphonium hexafluorophosphate
SEM 2-(trimethylsilyl)ethoxymethyl
SFC supercritical fluid chromatography
SM starting material
TBME tert-butyl methyl ether
TFA trifluoroacetic acid
THF tetrahydrofuran
TMS trimethylsilyl
TLC thin layer chromatography
T3P propanephosphonic acid anhydride
General Methods
Compounds of the invention may be prepared according to the following non-limiting general methods and examples:
Scheme 1
Synthesis of a compound of general formula (I), wherein $R_1$, $R_2$, $R_3$, $R_4$, and $R_5$ are as previously defined and PG represents a suitable protecting group:

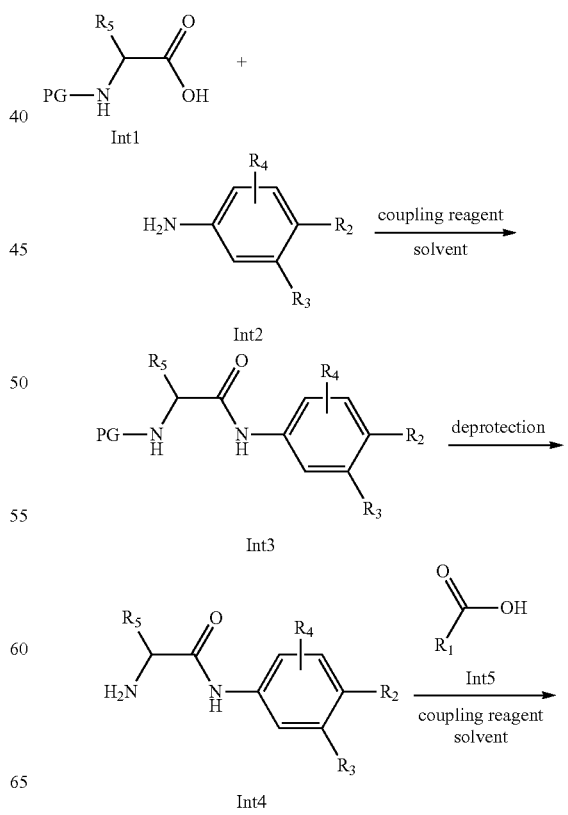

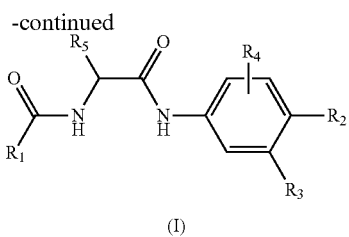

(I)

Compounds of general formula (I) can be prepared, as shown in Scheme 1. Compounds of general formula (Int1), which are either commercially available or are synthesised in a racemic form or an enantiomerically pure form, are coupled with amines of general formula (Int2), which are either commercially available or synthesised, in the presence of a coupling reagent such as HATU, HBTU, CDI, T3P, PyBOP, BOP, DCC or EDC and in most of the cases in the presence of a base, such as DIPEA or triethylamine, in a suitable solvent, such as DMF or acetonitrile to form compounds of formula (Int3). Protecting groups (PG), such as Boc, Cbz or FMOC, on compounds of general formula (Int3) can be removed or selectively removed by methods known to those skilled in the art. Compounds of general formula (Int4) are coupled with amines of general formula (Int5), which are either commercially available or synthesised, in the presence of a coupling reagent such as HATU, HBTU, CDI, T3P, PyBOP, BOP, DCC or EDC and in most of the cases in the presence of a base, such as DIPEA or triethylamine, in a suitable solvents, such as DMF or acetonitrile to form compounds of general formula (I). Where the compounds of general formula (I) contain protecting groups, those protecting groups can be removed by methods known to those skilled in the art. Racemic compounds of general formula (Int3), (Int4) or (I) can be separated by chiral SFC, to give the S-enantiomers of compounds of general formula (Int3), (Int4) or (I).

Scheme 2

Synthesis of a compound of formula (Int1), wherein $R_5$ is as previously defined and PG represents a suitable protecting group:

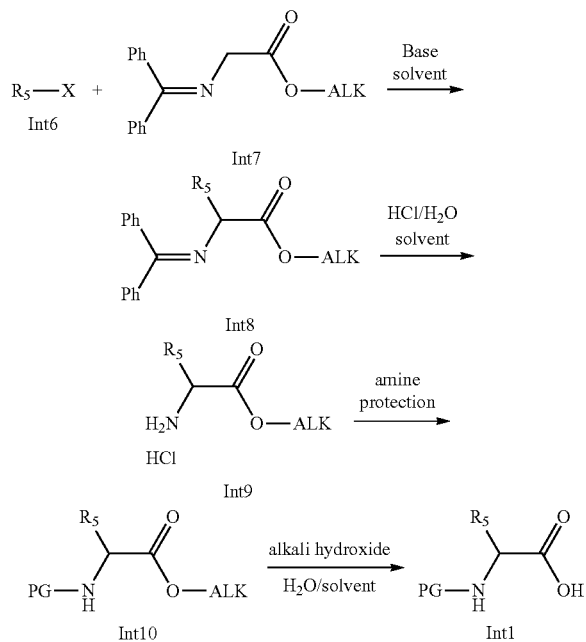

Compounds of general formula (Int1) can be prepared, as shown in Scheme 2. Compounds of formula (Int6) are reacted with a commercially available compound (Int7) in the presence of an alkali carbonate, such as sodium carbonate, potassium carbonate or caesium carbonate in a suitable solvent such as DMSO, DMF or acetontrile to form compounds of formula (Int8). Hydrolysis of compound of formula (Int8) can be performed by using aqueous HCl in a suitable solvent, such as THF, to give compounds of general formula (Int9). The amines of formula (Int9) can be protected by methods known to those skilled in the art. The esters of formula (Int10) are readily converted to Formula (Int1) in the presence of an alkali hydroxide such as sodium hydroxide, potassium hydroxide or lithium hydroxide. Racemic compounds of general formula (Int10) can be separated by chiral SFC, to give the S-enantiomers of compounds of general formula (Int10).

Scheme 3

Preparation of an enantiomerically pure compound of formula (Int1'), wherein $R_5$ is as previously defined and PG represents a suitable protecting group:

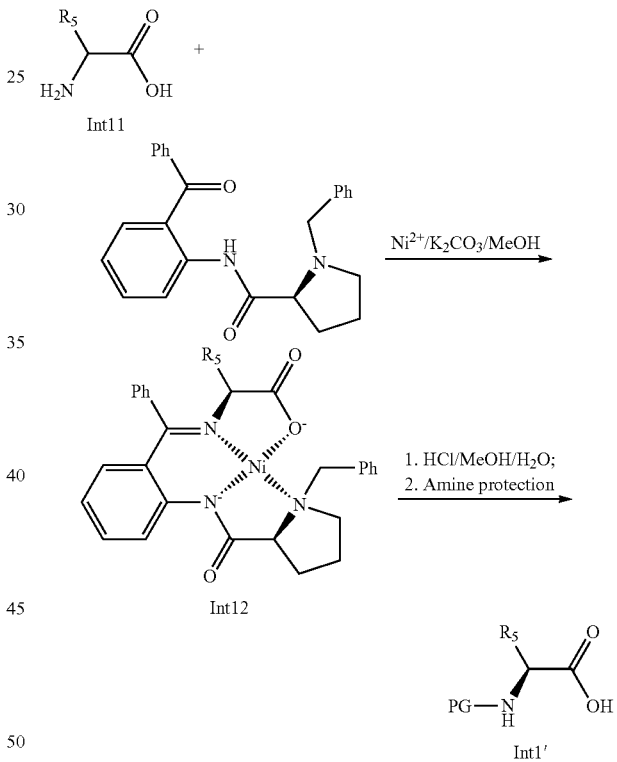

Compounds of formula (Int1') can be prepared, as shown in Scheme 3. Compounds of formula (Int11) and a commercially available ligand are mixed in the presence of $Ni^{2+}$/$K_2CO_3$ in a protic solvent, such as methanol, to form nickel complexes of formula (Int12) (for dynamic kinetic resolution of α-amino acids, see: Angew. Chem. Int. Ed. 2015, 54, 12918-12922). Compounds of formula (Int1') are prepared by hydrolysis of compounds of formula (Int12) in the presence of aq. HCl in a suitable protic solvent such as methanol and protecting amino functions by using, for example, CbzCl or Boc anhydride.

Scheme 4

Preparation of an enantiomerically pure compound of formula (Int17) where PG represents a suitable protecting group.

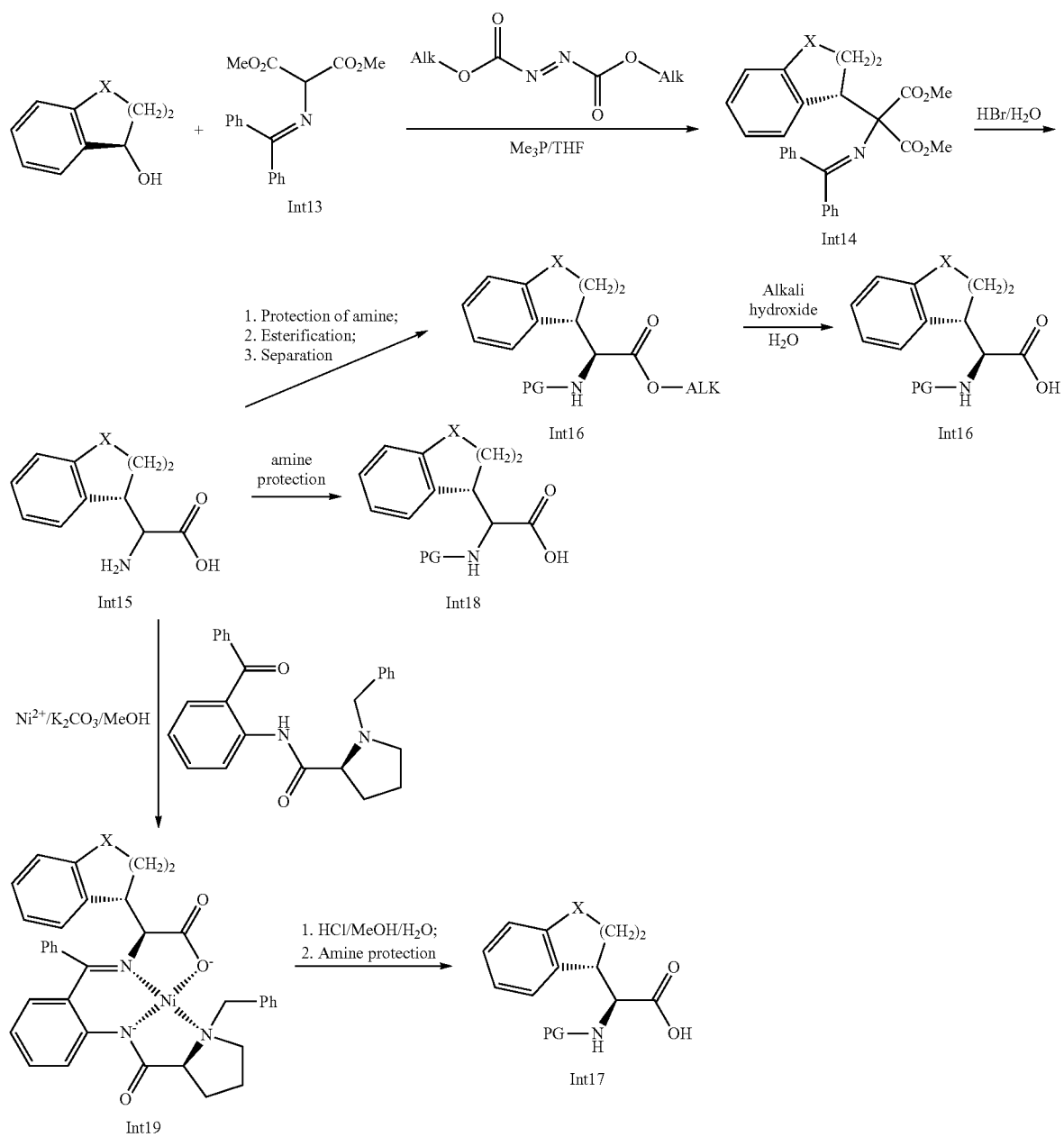

Compounds of formula (Int17) can be prepared, as shown in Scheme 4. The compound of Formula (Int13) is prepared according to a literature procedure (J. Org. Chem. 2017, 82, 12849-12856). Compounds of formula (Int14) can be formed by reaction of chiral alcohols with compounds of formula (Int13) under Mitsunobu reaction conditions (Me₃P, DEAD or DIAD) in a suitable solvent such as toluene (for a similar Mitsunobu reaction, see: Org. Lett. 2004, 6, 573-576). Compounds of formula (Int14) can be treated with aqueous HBr under reflux, giving compounds of formula (Int15). Compounds of formula (Int15) can be converted to N-protected amino acid esters which are a mixture of two diastereomers. Compounds of Formula (Int16) can be isolated by silica gel flash chromatography. Alternatively, compounds of formula (Int15) and a commercially available ligand are mixed in the presence of $Ni^{2+}/K_2CO_3$ in a protic solvent, such as methanol, to form nickel complexes of formula (Int19) (for dynamic kinetic resolution of α-amino acids, see: Angew. Chem. Int. Ed. 2015, 54, 12918-12922; see also: scheme 3). Compounds of formula (Int17) can be prepared by hydrolysis of compounds of formula (Int19) in the presence of aq. HCl in a suitable protic solvent such as methanol and subsequently protecting the amino function by using, for example, CbzCl or Boc anhydride.

Still alternatively, diastereomeric mixtures of formula (Int18) can be synthesised by protecting the amino function of compounds of formula (Int15) by using, for example, CbzCl or Boc anhydride.

Scheme 5

Preparation of compounds of formula (Int23) and compounds of formula (Int26) where PG represents a suitable protecting group.

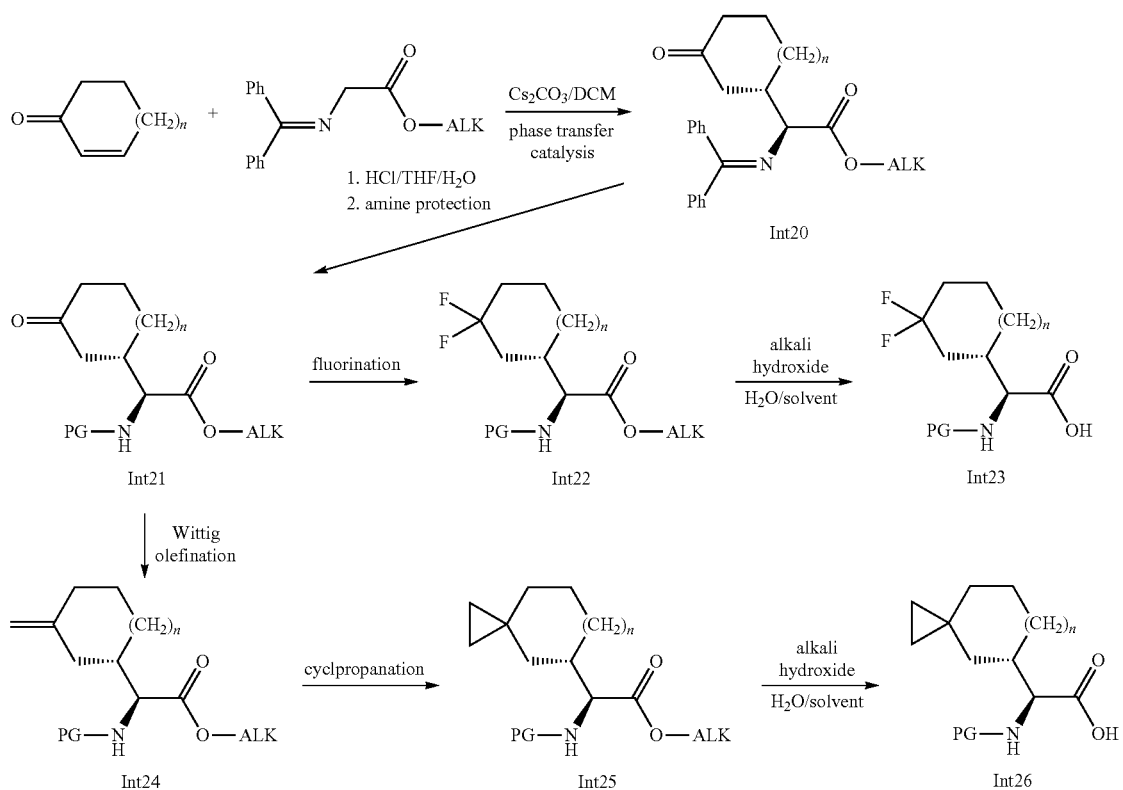

Compounds of formula (Int23) and compounds of formula (Int26) can be prepared, as shown in Scheme 5. Compounds of formula (Int20) can be prepared by using chiral phase transfer catalysts in the presence of bases such as caesium hydroxide monohydrate in a suitable solvent such as DCM (references: 1.PCT Int. Appl., 2006052722, 18 May 2006; 2. Tetrahedron Lett. 1998, 39, 5347-5350). Hydrolysis of Schiff's bases of formula (Int20) in the presence of aq. HCl in a suitable solvent, such as THF, followed by protecting amino functions can give compounds of formula (Int21) (for an alternative synthesis of compounds of formula (Int21), see: Angew. Chem. 1988, 100, 1238-1239). Compounds of formula (Int22) can be synthesised by using a fluorinating reagent such as DAST or Deoxo Fluor in a suitable solvent such as DCM. The esters of formula (Int22) can readily be converted to compounds of formula (Int23) in the presence of an alkali hydroxide such as sodium hydroxide, potassium hydroxide or lithium hydroxide.

Compounds of formula (Int24) can be synthesised by Wittig olefination, for example using methyltriphenylphosphonium bromide and a suitable base, such as potassium t-butoxide, in a suitable solvent, such as THF). Compounds of formula (Int25) can be made by the Simmons-Smith cyclopropanation reaction (for a review for Simmons-Smith cyclopropanation reactions, see: Org. Reac. 2001, 58, 1-415).

Scheme 6

Preparation of a compound of formula (Int29), wherein $R_6$ and $R_7$ are as previously defined and PG represents a suitable protecting group:

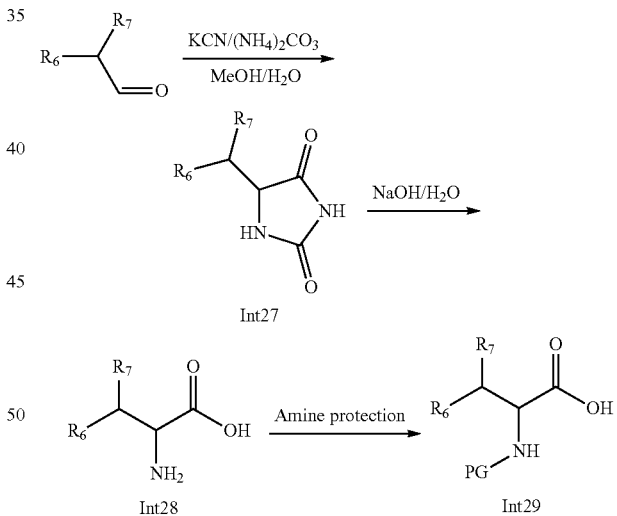

Compounds of formula (Int29) can be prepared as shown in Scheme 6. Reaction of an aldehyde with ammonium carbonate and potassium cyanide in water and methanol forms compounds of Formula (Int27) (For Bucherer Bergs reaction, see: J. Prakt. Chem. 1934, 140, 69; ibid. 291; Chemical Reviews 2017117 (23), 13757-13809). Compounds of formula (Int28) can be prepared by treatment of compounds of formula (Int27) with alkali hydroxides such as potassium hydroxide in water. Compounds of formula (Int29) can be synthesised by protecting amino functions using, for example, CbzCl or Boc anhydride.

Scheme 7

Synthesis of a compound of general formula (III), wherein $R_1$, $R_3$, $R_4$, $R_5$ and $R_b$ are as previously defined and PG' represents a suitable protecting group:

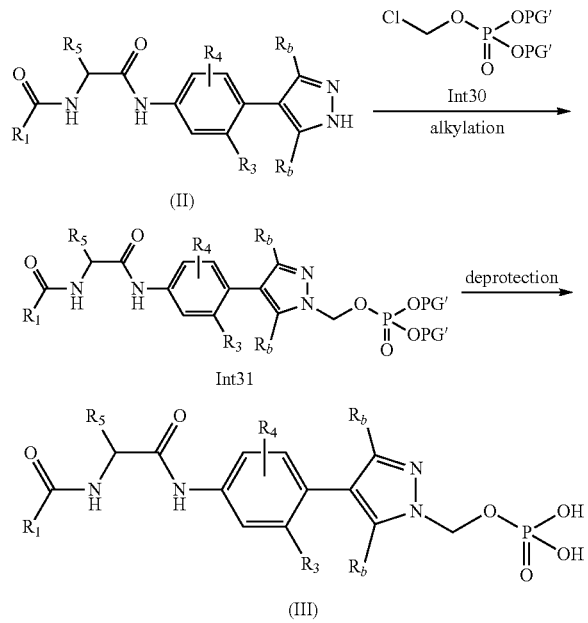

Compounds of general formula (III) can be prepared as shown in Scheme 7. Compounds of general formula (II), which can be prepared as outlined in the General Methods, Preparations and Examples, can be reacted with an alkylating agent of general formula (Int30), where PG' is a suitable protecting group such as tert-butyl or benzyl, in the presence of a suitable base, such as caesium carbonate, in a suitable solvent, such as DMF or DMSO, to give compounds of general formula (Int31). The protecting groups can then be removed, by methods known to those skilled in the art, to give compounds of general formula (III). For example, where PG' is tert-butyl the compounds can be deprotected by treatment with a suitable acid, such as TFA or HCl, in a suitable solvent or solvent mixture, such as DCM, MeOH and/or dioxane. Where PG' is benzyl the compounds of general formula (Int31) can be deprotected using catalytic hydrogenation, using a suitable catalyst, such as Pd on carbon, in a suitable solvent, such as EtOAc, MeOH or iPrOH, under a suitable pressure of hydrogen.

Scheme 8

Preparation of a compound of formula (Int36), wherein $R_3$, $R_4$, and $R_b$ are as previously defined, X is a suitable halogen and PG' represents a suitable protecting group:

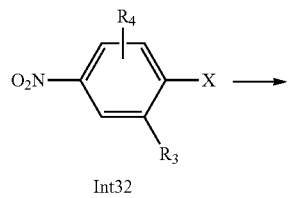

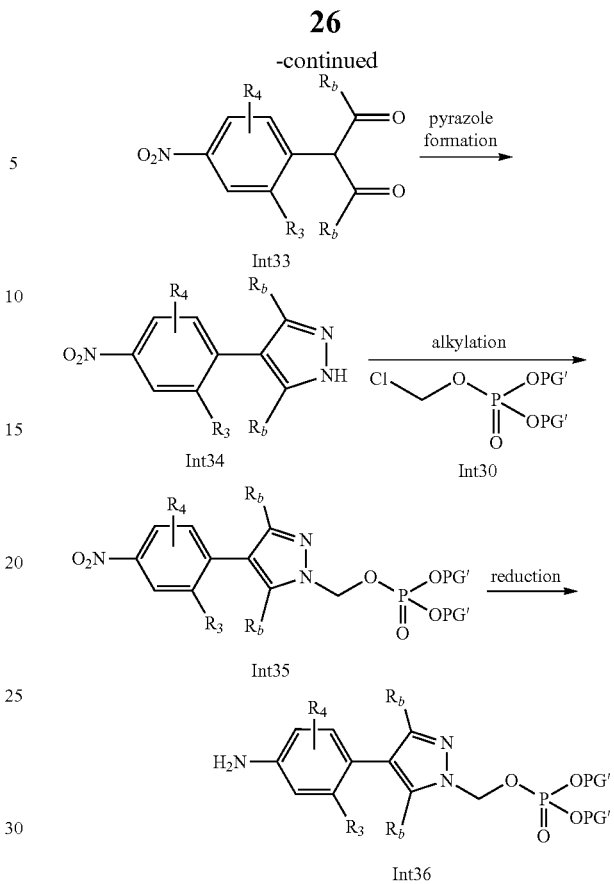

Compounds of general formula (Int36) can be synthesised as outlined in Scheme 8. Compounds of general formula (Int32), which are either commercially available or can be synthesised according to methods known to those skilled in the art, can be reacted with an appropriate 1,3-diketone to give compounds of general formula (Int33). For example, when X=Br or I a compound of general formula (Int32) can be reacted with an appropriate 1,3-diketone in the presence of CuI, proline and a suitable base, such as potassium carbonate, in an appropriate solvent, such as DMSO, at an elevated temperature, for example 70-100° C. Alternatively, when X=F, a compound of general formula (Int32) can be reacted with an appropriate 1,3-diketone in the presence of a suitable base, such as potassium or caesium carbonate, in a suitable solvent, such as DMF or DMSO, at an elevated temperature, for example 50-100° C.

Compounds of general formula (Int33) can be converted to pyrazoles of general formula (Int34) by treatment with hydrazine hydrate in a suitable solvent, such as EtOH, at an appropriate temperature, for example from room temperature to 80° C.

Compounds of general formula (Int35) can be formed by reaction of compounds of general formula (Int34) with an alkylating agent of general formula (Int30), where PG' is a suitable protecting group such as tert-butyl or benzyl, in the presence of a suitable base, such as caesium carbonate, in a suitable solvent, such as DMF or DMSO. Reduction of the nitro group in compounds of general formula (Int35) can be carried out by many methods known to those skilled in the art to give anilines of general formula (Int36). For example, by catalytic hydrogenation, using a suitable catalyst, such as Pd on carbon, in a suitable solvent, such as EtOAc, MeOH or iPrOH, under a suitable pressure of hydrogen.

Scheme 9
Synthesis of a compound of general formula (Int31), wherein $R_1$, $R_3$, $R_4$, $R_5$ and $R_b$ are as previously defined and PG and PG' represent suitable protecting groups:

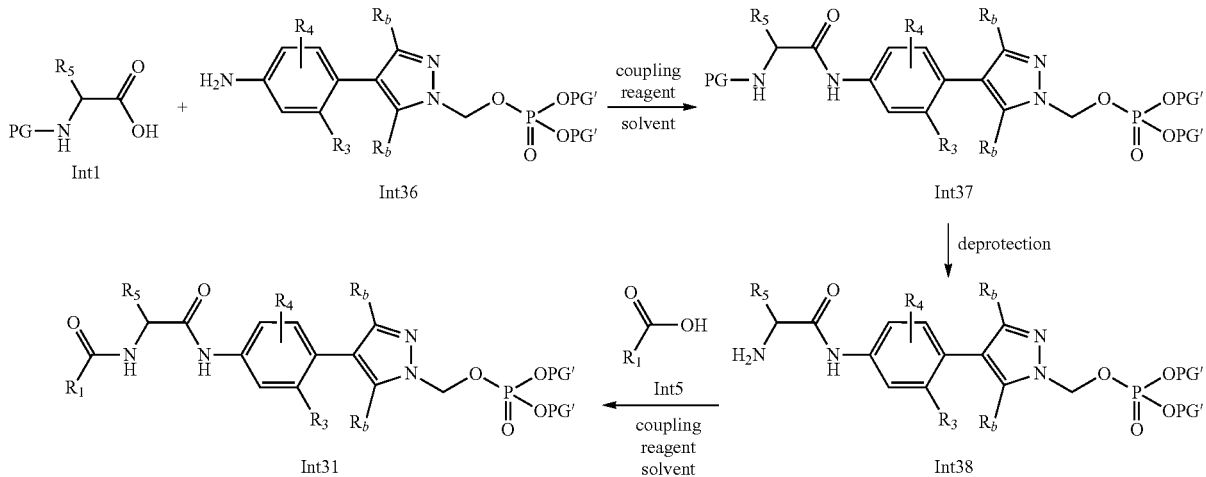

Alternatively, compounds of general formula (Int31) can be prepared, as shown in Scheme 9. Compounds of general formula (Int1), which are either commercially available or can be synthesised, are coupled with amines of general formula (Int36) in the presence of a coupling reagent, such as HATU, HBTU, CDI, T3P, PyBOP, BOP, DCC or EDC, and, in most of the cases, in the presence of a base, such as DIPEA or triethylamine, in a suitable solvent, such as DMF or acetonitrile to form compounds of formula (Int3). Protecting groups (PG), such as Boc, Cbz or FMOC, on compounds of general formula (Int37) can be removed or selectively removed by methods known to those skilled in the art to give compounds of general formula (Int38). Compounds of general formula (Int38) are coupled with amines of general formula (Int5), which are either commercially available or synthesised, in the presence of a coupling reagent such as HATU, HBTU, CDI, T3P, PyBOP, BOP, DCC or EDC and in most of the cases in the presence of a base, such as DIPEA or triethylamine, in a suitable solvents, such as DMF or acetonitrile to form compounds of general formula (Int31).

PREPARATIONS AND EXAMPLES

Preparations

Preparation 1

2-[[3,5-dimethyl-4-(4-nitrophenyl)pyrazol-1-yl]methoxy]ethyl-trimethyl-silane

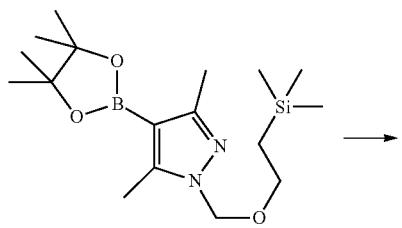

-continued

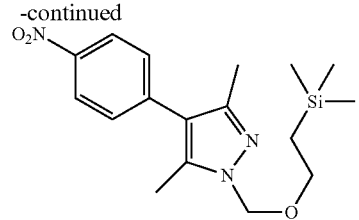

$K_2CO_3$ (2.12 g, 15.3 mmol) in water (11.5 mL) and Pd(dppf)Cl$_2$ (313 mg, 0.383 mmol) were added to a mixture of 2-[[3,5-dimethyl-4-(4,4,5,5-tetramethyl-1,3,2-dioxaborolan-2-yl)pyrazol-1-yl]methoxy]ethyl-trimethyl-silane (WO 2008001076, R. P. Alexander et al.) (2.70 g, 7.66 mmol) and 4-bromonitrobenzene (1.55 g, 7.66 mmol) in THF (23 mL) and MeOH (3.83 mL). The mixture was placed in two 20 mL microwave vials which were degassed with argon for 10 min, capped and stirred for 20 min at 90° C. in a heating block. The combined reactions were diluted with EtOAc (100 mL), washed with water (2×20 mL) and brine (20 mL), dried (MgSO$_4$) and concentrated in vacuo to give a dark oil. The crude product was purified by column chromatography (silica gel, loaded in DCM, eluting with 0-30% EtOAc in heptane) to give the title compound (1.89 g, 71%). 1H NMR (300 MHz, DMSO-d6) δ 8.39-8.19 (m, 2H), 7.69-7.40 (m, 2H), 5.39 (s, 2H), 3.64-3.53 (m, 2H), 2.33 (s, 3H), 2.21 (s, 3H), 0.92-0.76 (m, 2H), −0.03 (s, 9H); LCMS (ES): m/z 384.3 [M+H]$^+$, RT=0.95 min.

Preparation 2

4-[3,5-dimethyl-1-(2-trimethylsilylethoxymethyl)pyrazol-4-yl]aniline

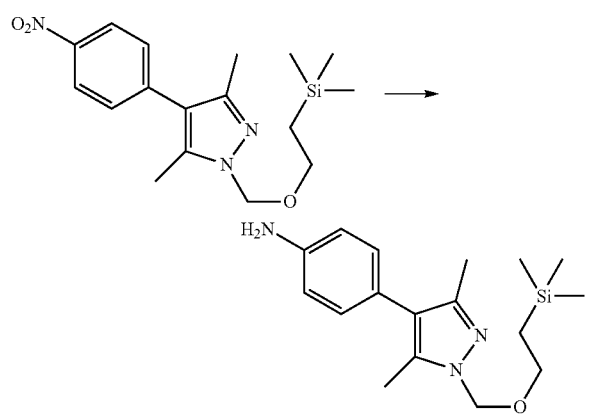

10% Pd/C (188 mg) was added to a solution of the compound of Preparation 1 (1.88 g, 5.41 mmol) in MeOH (30 mL) and placed under hydrogen at atmospheric pressure. After 1 hour the catalyst was filtered off, washing with MeOH, and the filtrate was concentrated in vacuo to give the title compound (1.67 g, 97%) as a colourless solid. 1H NMR (300 MHz, DMSO-d6) δ 6.96-6.85 (m, 2H), 6.65-6.57 (m, 2H), 5.30 (s, 2H), 5.03 (s, 2H), 3.59-3.48 (m, 2H), 2.20 (s, 3H), 2.08 (s, 3H), 0.83 (dd, J=8.4, 7.4 Hz, 2H), −0.04 (s, 9H); LCMS (ES): m/z 318.4 [M+H]$^+$, RT=0.80 min.

Preparation 3 tert-butyl N-[(1S)-1-cyclohexyl-2-[4-[3,5-dimethyl-1-(2-trimethylsilylethoxymethyl)pyrazol-4-yl]anilino]-2-oxo-ethyl]carbamate

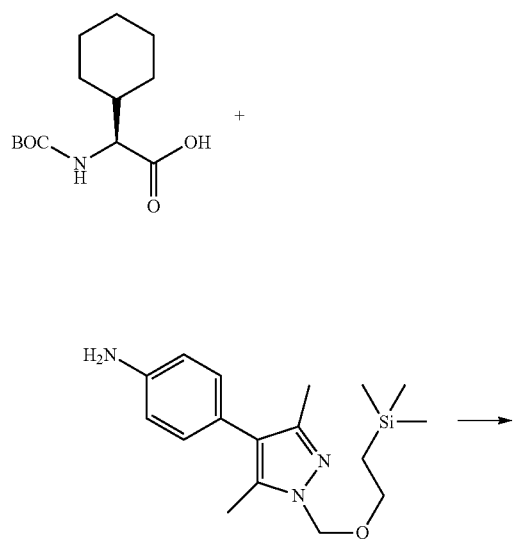

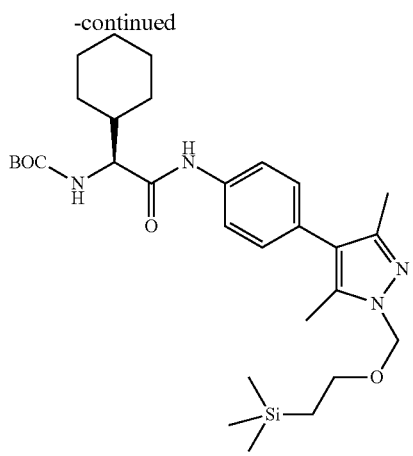

DIPEA (3.07 mL, 2.28 g, 17.6 mmol) was added to a stirred solution of (2S)-2-(tert-butoxycarbonylamino)-2-cyclohexyl-acetic acid (1.51 g, 5.87 mmol) in DMF (25 mL) followed by the amine of Preparation 2 (1.86 g, 5.87 mmol). The mixture was stirred for 5 minutes to ensure complete dissolution and HATU (2.45 g, 6.46 mmol) was then added. After 5 minutes the temperature had risen from 22° C. to 28° C. After 75 min the reaction was concentrated to approximately 5 mL in vacuo and the residue was diluted with EtOAc (50 mL), washed with water (50 mL), 10% aq. K$_2$CO$_3$ (50 mL) and brine (50 mL), dried (MgSO$_4$) and evaporated. The crude product was purified by column chromatography (silica gel, eluting with 0-50% EtOAc in heptane) to give the title compound as a yellow foam (3.03 g, 89%). 1H NMR (300 MHz, Chloroform-d) δ 8.11 (s, 1H), 7.69-7.49 (m, 2H), 7.23-7.17 (m, 2H), 5.39 (s, 2H), 5.17 (d, J=8.7 Hz, 1H), 4.09-3.98 (m, 1H), 3.69-3.56 (m, 2H), 2.29 (s, 3H), 2.23 (s, 3H), 2.00-1.62 (m, 6H), 1.48 (s, 9H), 1.37-1.01 (m, 5H), 0.97-0.87 (m, 2H), 0.00 (s, 9H)); LCMS (ES): m/z 557.7 [M+H]$^+$, RT=1.02 min.

Preparation 4

(2S)-2-amino-2-cyclohexyl-N-[4-[3,5-dimethyl-1-(2-trimethylsilylethoxymethyl)pyrazol-4-yl]phenyl]acetamide hydrochloride

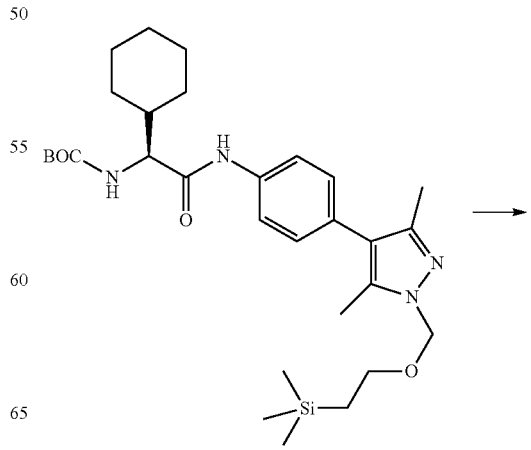

-continued

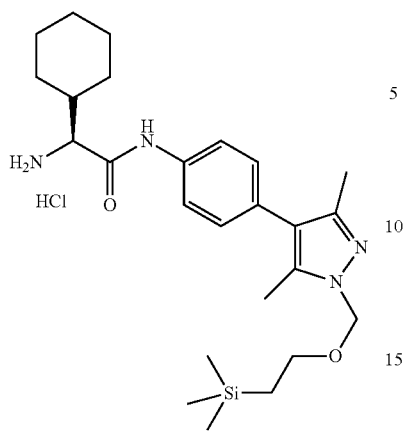

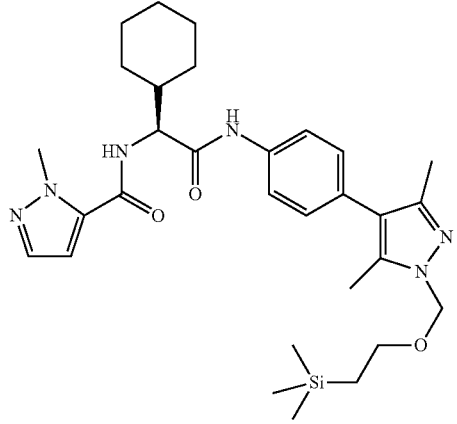

Tert-butyl N-[(1S)-1-cyclohexyl-2-[4-[3,5-dimethyl-1-(2-trimethylsilylethoxymethyl)-pyrazol-4-yl]anilino]-2-oxo-ethyl]carbamate from Preparation 3 (2.25 g, 4.04 mmol) was dissolved in MeOH (10 mL) and 4M HCl in dioxane (20 mL, 80 mmol) was added. After 90 minutes the reaction was diluted with MeOH (10 mL) and concentrated in vacuo. The residue was treated with DCM (30 mL) and concentrated in vacuo (twice), then dried in vacuo to give the target compound as a pale yellow foam that was used without further purification. LCMS (ES): m/z 457.6 [M+H]$^+$, RT=0.73 min.

Preparation 5

N-[(1S)-1-cyclohexyl-2-[4-[3,5-dimethyl-1-(2-trimethylsilylethoxymethyl) pyrazol-4-yl]anilino]-2-oxo-ethyl]-2-methyl-pyrazole-3-carboxamide

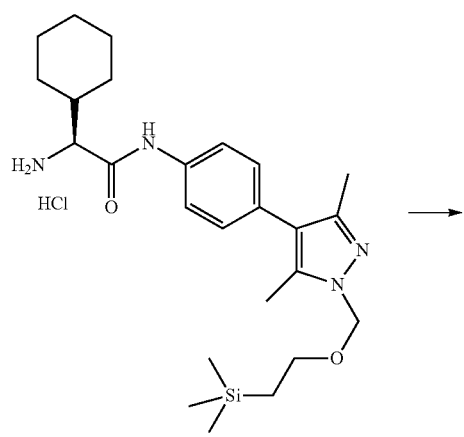

DIPEA (4.14 mL, 3.13 g, 24.2 mmol) was added to a solution of the compound of Preparation 4 (4.04 mmol) in DMF (20 mL). The yellow solution was cooled in an ice bath and 2-methylpyrazole-3-carboxylic acid (612 mg, 4.85 mmol) was added followed by HATU (2.0 g, 5.25 mmol). After the initial exothermic reaction had ended the ice bath was removed. The yellow solution was stirred at room temperature for 1 hour then poured into a mixture of sat. aq. sodium bicarbonate solution (25 mL) and water (200 mL). This was extracted with EtOAc (2×150 mL) and the combined organic phases were washed with brine (200 mL), dried (Na$_2$SO$_4$) and evaporated. The crude product was purified by column chromatography (silica gel, eluting with DCM/MeOH 99:1 to DCM/MeOH 98:2) to give the title compound (2.06 g, 86%) as a pale red solid. 1H NMR (300 MHz, Chloroform-d) δ 8.06 (s, 1H), 7.66-7.53 (m, 2H), 7.46 (d, J=2.1 Hz, 1H), 7.26-7.19 (m, 2H), 6.84 (d, J=8.6 Hz, 1H), 6.64 (d, J=2.1 Hz, 1H), 5.39 (s, 2H), 4.51 (t, J=8.1 Hz, 1H), 4.17 (s, 3H), 3.70-3.58 (m, 2H), 2.30 (s, 3H), 2.23 (s, 3H), 2.12-1.63 (m, 6H), 1.42-1.06 (m, 5H), 0.99-0.86 (m, 2H), 0.00 (s, 9H); LCMS (METHOD 3) (ES): m/z 565.7 [M+H]$^+$, RT=0.93 min.

Preparation 6

(4,4-difluorocyclohexyl) 4-methylbenzenesulfonate

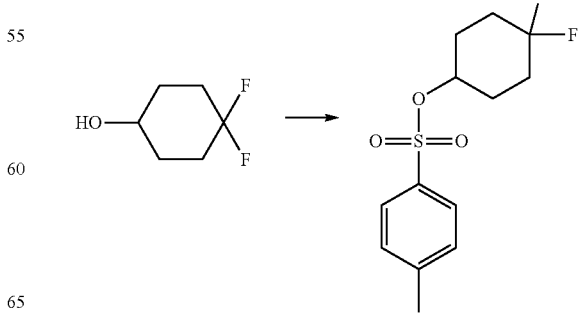

4,4-Difluorocyclohexanol (300 mg 2.20 mmol) was dissolved in DCM (5 mL) and tosyl chloride (840 mg, 4.41 mmol) and pyridine (0.71 mL, 700 mg, 8.81 mmol) were added. The reaction was stirred at room temperature over the weekend then quenched by the addition of 1N HCl and extracted with DCM (×2). The combined organic phases were washed with water and brine and then dried, Na$_2$SO$_4$), filtered and evaporated on dicalite. Purification by column chromatography (silica gel, eluting with 0-25% EtOAc in heptane) gave the title compound (508 mg, 79%). 1H NMR (300 MHz, DMSO-d6) δ 7.97-7.67 (m, 2H), 7.63-7.34 (m, 2H), 4.94-4.53 (m, 1H), 2.43 (s, 3H), 2.04-1.84 (m, 4H), 1.83-1.64 (m, 4H).

Preparation 7 ethyl 2-(benzhydrylideneamino)-2-(4,4-difluorocyclohexyl)acetate

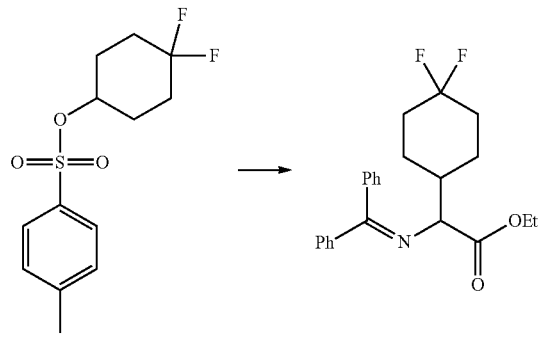 [SMILES: Cc1ccc(S(=O)(=O)OC2CCC(F)(F)CC2)cc1 ; CCOC(=O)C(N=C(c1ccccc1)c1ccccc1)C1CCC(F)(F)CC1]

The compound of Preparation 6 (500 mg, 1.72 mmol) and ethyl 2-(benzhydrylideneamino)acetate (460 mg, 1.72 mmol,) were dissolved in toluene (4 mL) and the mixture was degassed with argon for 2 minutes. LiHMDS (2.1 mL 2.1 mmol) was added slowly, the vial was capped and the reaction was stirred at 100° C. for 16 h. After cooling to room temperature water was added and the mixture was extracted with EtOAc (×2). The combined organic phases were washed with brine, dried (Na$_2$SO$_4$), filtered and evaporated onto silica. Purification by column chromatography (silica gel, eluting with 0-25% EtOAc in heptane) gave the title compound (528 mg, 80%). 1H NMR (300 MHz, DMSO-d6) δ 7.63-7.31 (m, 8H), 7.22-7.03 (m, 2H), 4.09 (q, J=7.1 Hz, 2H), 3.77 (d, J=6.1 Hz, 1H), 2.22-1.62 (m, 6H), 1.62-1.32 (m, 2H), 1.26-1.16 (m, 1H), 1.16 (t, J=7.1 Hz, 3H); LCMS (METHOD 3) (ES): m/z 386.5 [M+H]$^+$, RT=0.97 min Preparation 8

Nickelous (2S)-2-[(E)-[[2-[(2S)-1-benzylpyrrolidine-2-carbonyl]azanidylphenyl]-phenyl-methylene]amino]-2-(4,4-difluorocyclohexyl)acetate

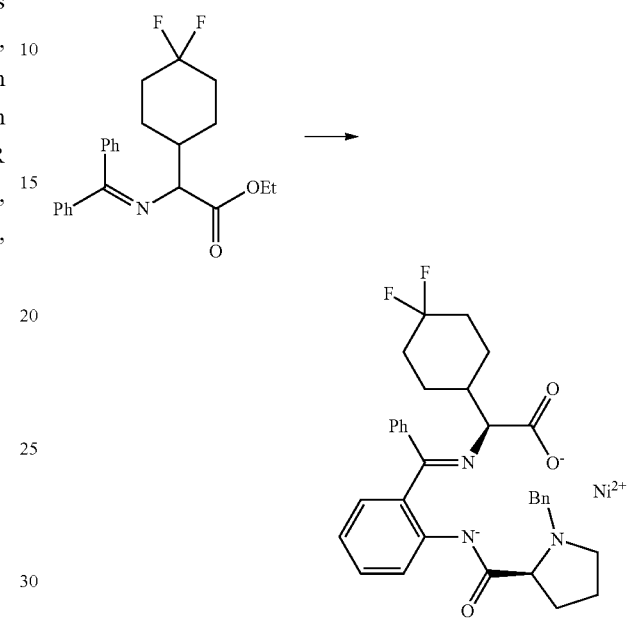

The compound of Preparation 7 (500 mg, 1.30 mmol) was dissolved in diethyl ether (5 mL) and 1N HCl (5 mL) was added. The reaction mixture was stirred at room temperature for 16 hours and then 4N NaOH was added until the pH was 12-13. The reaction mixture was stirred at 50° C. for 3 h then allowed to cool to room temperature and stirred for 16 hours. 4N HCl was added to the reaction mixture until the pH reached 5-6 and a precipitate started to appear. After 10 minutes the reaction mixture was filtered, washed with water and freeze dried over the weekend to give the amino acid (184 mg) as a solid. The crude amino acid was combined with (2S)—N-(2-benzoylphenyl)-1-benzyl-pyrrolidine-2-carboxamide (537 mg, 1.40 mmol), nickel (II) acetate hydrate (236 mg, 1.21 mmol), K$_2$CO$_3$ (515 mg, 3.73 mmol) and MeOH (6 mL) in a 20 mL microwave vial. The vial was capped and the reaction mixture was stirred for 16 hours at 55° C. The reaction mixture was then stirred at 60° C. for a further 24 hours. After cooling, water was added to the reaction and the mixture was extracted with DCM (×3). The combined organic phases were evaporated to dryness and taken up in MTBE (20 mL). Precipitation of an orange solid was seen. The mixture was stirred for 10 minutes, the precipitate was filtered off, washed with MTBE and freeze dried for 16 hours to give the title compound (460 mg, 58%) as an orange solid. 1H NMR (300 MHz, DMSO-d6) δ 8.43-8.30 (m, 2H), 8.10 (dd, J=8.8, 1.1 Hz, 1H), 7.68-7.43 (m, 4H), 7.41-7.26 (m, 3H), 7.17-7.04 (m, 2H), 6.67 (ddd, J=8.1, 6.8, 1.2 Hz, 1H), 6.58 (dd, J=8.2, 1.7 Hz, 1H), 4.06 (d, J=12.3 Hz, 1H), 3.76 (br s, 1H), 3.65-3.51 (m, 2H), 3.48 (d, J=1.7 Hz, 1H), 3.23-3.09 (m, 1H), 2.50-2.40 (m, 3H, partially obscured by DMSO signal), 2.36-1.76 (m, 5H), 1.74-1.22 (m, 4H), 0.63 (br d, J=9.7 Hz, 1H); LCMS (METHOD 3) (ES): m/z 616.6, 618.6 [M+H]$^+$, RT=0.80 min.

Preparation 9

(2S)-2-(tert-butoxycarbonylamino)-2-(4,4-difluoro-cyclohexyl)acetic acid

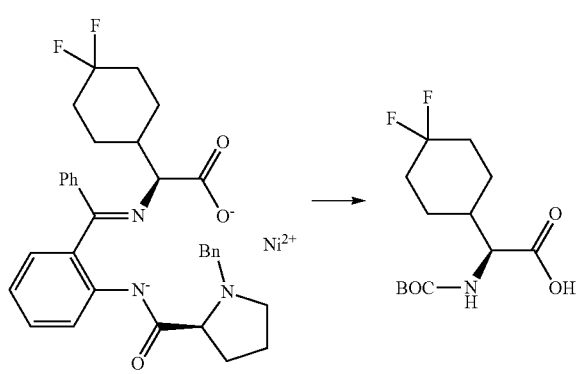

The compound of Preparation 8 (450 mg, 0.730 mmol) was taken up in MeOH (10 mL) and 4N HCl (2 mL). The reaction was stirred at 60° C. for 1 hour, during which time the dark red/orange solution became green. After cooling to room temperature, the solution was basified to pH 12 with 2N NaOH and extracted with TBME (×3) to remove the benzophenone by-product. To the basic solution of the amino acid was added Boc anhydride (474 mg, 2.17 mmol) dissolved in THF (5 mL). The reaction mixture was stirred at room temperature for 1 hour, carefully acidified with 2N HCl and extracted with DCM (×2). The combined organic phases were dried ($MgSO_4$) and concentrated in vacuo to give the title compound (161 mg, 76%). LCMS (METHOD 3) (ES−): m/z 292.4 [M−H]−, RT=0.65 min.

Preparation 10

Dimethyl 2-(benzhydrylideneamino)propanedioate

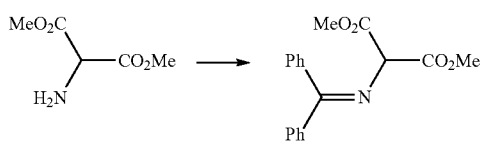 [SMILES: COC(=O)C(N)C(=O)OC ; COC(=O)C(N=C(c1ccccc1)c1ccccc1)C(=O)OC]

A mixture of benzophenone (25.0 g, 138 mmol) and dimethyl 2-aminopropanedioate hydrochloride (25.0 g, 136 mmol) in DCM (300 mL) was stirred at room temperature for 3 days. The solid material was filtered off and the filtrate was concentrated in vacuo. The residue was re-dissolved in TBME and washed with water, dried ($MgSO_4$) and concentrated in vacuo. The residue was purified by column chromatography (silica gel, eluting with 15-100% EtOAc in heptane) to give the title compound (27.0 g, 64%) as a colourless oil, which solidified on standing. 1H NMR (300 MHz, Chloroform-d) δ 7.78-7.63 (m, 2H), 7.51-7.28 (m, 6H), 7.24-7.11 (m, 2H), 4.90 (s, 1H), 3.78 (s, 6H); LCMS (METHOD 4) (ES): m/z 312.2 [M+H]+, RT=0.73 min.

Preparation 11

Dimethyl 2-(benzhydrylideneamino)-2-[(1R)-6-bromoindan-1-yl]propanedioate

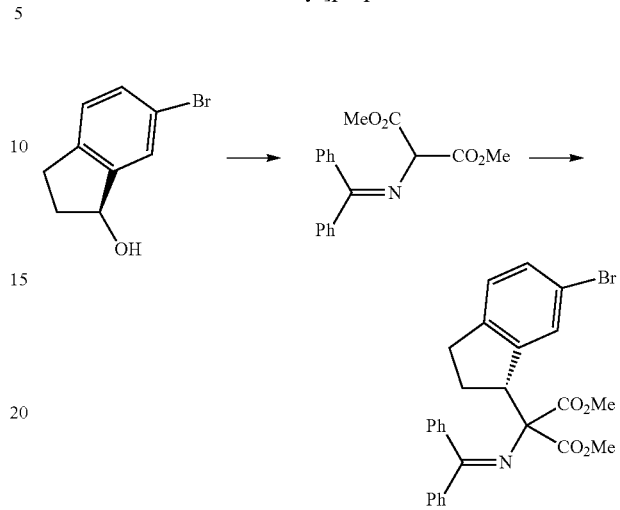

A solution of (1S)-6-bromoindan-1-ol (6.5 g, 31 mmol), the compound of Preparation 10 (14.0 g, 46 mmol) and trimethylphosphine (1M solution in THF, 46 mL, 46 mmol) in toluene (100 g) was cooled down to −75° C. Diethyl azodicarboxylate (40 wt % solution in toluene, 21 g, 48 mmol) was added dropwise over 30 minutes and the solution was stirred at −75° C. for 1.5 hours and at room temperature for 3 hours to give a dark brown solution. The solution was concentrated in vacuo and the residue was purified by column chromatography (silica gel, eluting with heptane/ethyl acetate 4:1) to give the title compound (9.6 g, 62%) as a yellow oil. 1H NMR (300 MHz, Chloroform-d) δ 7.84 (dd, J=1.9, 0.9 Hz, 1H), 7.64-7.49 (m, 2H), 7.47-7.22 (m, 7H), 7.22-7.14 (m, 2H), 7.05 (dd, J=8.0, 1.1 Hz, 1H), 4.26-4.03 (m, 1H), 3.44 (s, 3H), 3.25 (s, 3H), 2.94 (ddd, J=15.6, 9.2, 6.0 Hz, 1H), 2.76 (ddd, J=15.6, 9.1, 5.9 Hz, 1H), 2.55-2.17 (m, 2H); LCMS (METHOD 3) (ES): m/z 506.3, 508.3 [M+H]+, RT=1.03 min.

Preparation 12

2-Amino-2-[(1R)-6-bromoindan-1-yl]acetic acid hydrobromide

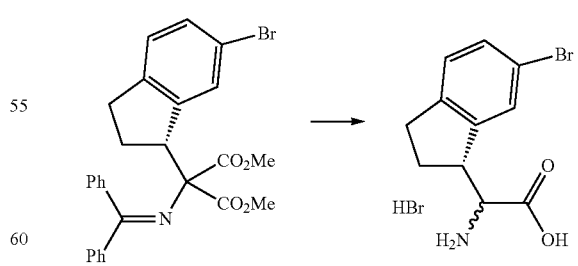

To a solution of the compound of Preparation 11 (9.6 g, 19 mmol) in THF (30 mL) at room temperature was added conc. HCl (10 mL) (exothermic). The solution was stirred at room temperature for 30 min and then diluted with TBME (70 mL) and water (30 mL). The phases were separated, the aqueous phase was extracted twice with TBME and then concentrated in vacuo, giving crude dimethyl 2-amino-2-[(1R)-6-bromoindan-1-yl]propanedioate hydrochloride as a colourless oil, which was used without further purification.

To a solution of dimethyl 2-amino-2-[(1R)-6-bromoindan-1-yl]propanedioate hydrochloride in water (20 mL) at room temperature was added conc. HBr (48% HBr, 20 mL). The solution was heated at reflux for 3 hours and the product precipitated. The suspension was cooled to room temperature and filtered. The filter cake was washed with TBME and dried in vacuo, giving the title compound (5.2 g, 78%) as a white solid as a mixture of diastereomers. 1H NMR (300 MHz, Deuterium Oxide+1 drop DCI) 67.38 (s, 0.33H), 7.34-7.21 (m, 1.67H), 7.15-6.96 (m, 1H), 4.41 (d, J=4.0 Hz, 0.33H), 4.32 (d, J=3.7 Hz, 0.67H), 3.91-3.81 (m, 0.33H), 3.75 (dt, J=9.3, 4.8 Hz, 0.67H), 3.07-2.54 (m, 2H), 2.50-2.01 (m, 1H), 1.99-1.64 (m, 1H); LCMS (METHOD 3) (ES): m/z 270.2, 272.2 [M+H]$^+$, RT=0.38 min.

Preparation 13

Nickelous (2S)-2-[(E)-[[2-[(2S)-1-benzylpyrrolidine-2-carbonyl]azanidylphenyl]-phenyl-methylene]amino]-2-[(1R)-6-bromoindan-1-yl]acetate

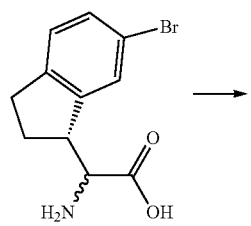

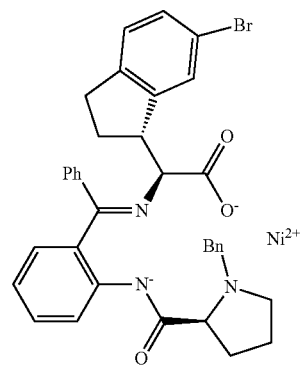

A mixture of (2S)—N-(2-benzoylphenyl)-1-benzyl-pyrrolidine-2-carboxamide (3.85 g, 10.0 mmol), the compound of Preparation 12 (3.2 g, 9.1 mmol), nickel (II) acetate hydrate (2.5 g, 8.6 mmol) and K$_2$CO$_3$ (7.0 g, 51 mmol) in MeOH (50 mL) was stirred at 80° C. for 18 h. The reaction was concentrated in vacuo and the residue was taken up in DCM and water. After separating the phases, the aqueous phase was extracted twice with DCM. The combined organic phases were dried (MgSO$_4$) and concentrated in vacuo. The crude product was purified by column chromatography (silica gel, eluting with EtOAc/DCM 1:3) to give a red foam. This was taken up in TBME (50 mL) and the mixture was shaken for 10 min. The solid material was filtered and washed with TBME (2×20 mL), giving the title compound (4.2 g, 66%) as a red solid.). 1H NMR (300 MHz, Chloroform-d) δ 8.56-8.34 (m, 1H), 8.12-7.93 (m, 2H), 7.60-7.45 (m, 3H), 7.41-7.23 (m, 5H), 7.19-7.07 (m, 3H), 6.71-6.57 (m, 3H), 4.36 (d, J=12.6 Hz, 1H), 4.26 (d, J=4.9 Hz, 1H), 3.49 (d, J=12.6 Hz, 1H), 3.45-3.34 (m, 2H), 3.29-3.18 (m, 1H), 3.12-2.94 (m, 2H), 2.91-2.75 (m, 1H), 2.75-2.36 (m, 3H), 2.30-2.09 (m, 1H), 2.07-1.93 (m, 1H), 1.81 (ddt, J=15.5, 8.0, 3.7 Hz, 1H); LCMS (METHOD 3) (ES): m/z 692.5, 694.5 [M+H]$^+$, RT=0.90 min.

Preparation 14

(2S)-2-[(1R)-6-bromoindan-1-yl]-2-(tert-butoxycarbonylamino)acetic acid

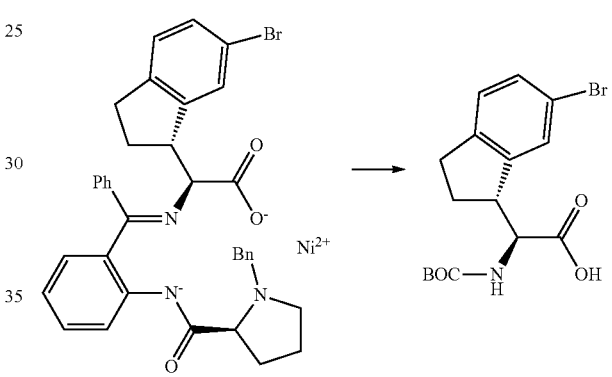

To a suspension of the compound of Preparation 13 (4.8 g, 6.9 mmol) in MeOH (40 mL) at room temperature was added 6M HCl (10 mL, 60 mmol). The suspension was heated at 60° C. for 30 minutes, by which time the dark red suspension became a blue solution. The solution was concentrated in vacuo, giving a solid residue. The residue was taken up in water (100 mL) and filtered, washing the solid with water (20 mL). The filtrate was carefully neutralised to pH 6 using sat. aq. NaHCO$_3$. The precipitate was collected by filtration and washed with water (2×20 mL) and DCM (2×25 mL), giving crude (2S)-2-amino-2-[(1R)-6-bromoindan-1-yl]acetic acid which was used without further purification. The crude (2S)-2-amino-2-[(1R)-6-bromoindan-1-yl]acetic acid (6.9 mmol) was taken up in water (50 mL) and the suspension was basified to pH 12. Dioxane (40 mL) was added followed by Boc anhydride (7.53 g, 34.5 mmol, 4 portions over 4 hours). On complete addition, the reaction mixture was stirred at room temperature for 4 hours. The reaction mixture was washed with DCM (2×50 mL), EtOAc (50 mL) was added and the mixture was acidified with 4N HCl to pH 2. The layers were separated and the aqueous phase was extracted with further EtOAc (30 mL). The combined organic phases were dried (MgSO$_4$) and concentrated in vacuo, giving the title compound (2.014 g, 79%) as a white solid. 1H NMR (300 MHz, DMSO-d6) δ 7.65-6.95 (m, 4H), 4.61 (br s, 1H), 3.67 (br s, 1H), 2.93-2.60 (m, 2H), 2.22-1.81 (m, 2H), 1.32 (s, 9H); LCMS (METHOD 3) (ES): m/z 370.4, 372.4 [M+H]$^+$, RT=0.76 min.

Preparation 15

2-Amino-2-[(1S)-6-bromoindan-1-yl]acetic acid

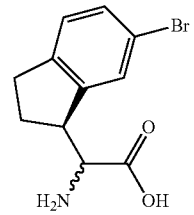 [SMILES: NC(C(=O)O)[C@H]1CCc2ccc(Br)cc21]

A solution of dimethyl 2-(benzhydrylideneamino)-2-[(1S)-6-bromoindan-1-yl]propanedioate (prepared according to the method of Preparation 11, starting from (1R)-6-bromoindan-1-ol) (2.6 g, 5.1 mmol) in conc. HBr (48% HBr, 7 mL) was heated at reflux for 3 hours. The reaction was cooled to room temperature and allowed to stand overnight. The precipitate was filtered off and washed with TBME, giving 2-amino-2-[(1S)-6-bromoindan-1-yl]acetic acid hydrobromide (0.91 g, 50%) as a white solid as a mixture of diastereomers. The filtrate was neutralized to pH6 with 5 N NaOH. The precipitate was filtered, washed with water (2×10 mL) and TBME (10 mL), giving 2-amino-2-[(1S)-6-bromoindan-1-yl]acetic acid (0.53 g, 38%) as a white solid as a mixture of diastereomers. 1H NMR (300 MHz, D2O+ NaOD) δ7.39-7.20 (m, 3H), 7.14-7.03 (m, 1H), 3.58 (d, J=4.3 Hz, 0.45H), 3.54-3.37 (m, 1H), 3.28 (d, J=4.9 Hz, 0.55H), 2.91-2.57 (m, 2H), 2.27-2.04 (m, 0.45H), 2.01-1.70 (m, 1.55H); LCMS (METHOD 3) (ES): m/z 270.2, 272.2 [M+H]$^+$, RT=0.38 min.

Preparation 16

Nickelous (2S)-2-[(E)-[[2-[(2S)-1-benzylpyrrolidine-2-carbonyl]azanidylphenyl]-phenyl-methylene]amino]-2-[(1S)-6-bromoindan-1-yl]acetate

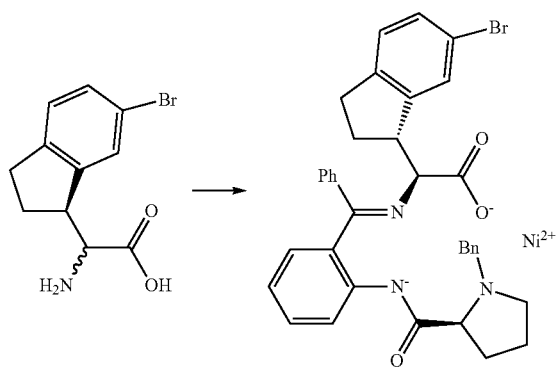

According to the method of Preparation 13 the HBr salt of the compound of Preparation 15 (345 mg, 0.983 mmol) was reacted to give the title compound (490 mg, 72%) as a red solid. 1H NMR (300 MHz, Chloroform-d) δ 8.44-8.31 (m, 1H), 8.16-7.99 (m, 2H), 7.57-7.41 (m, 2H), 7.39-7.29 (m, 2H), 7.28-7.11 (m, 5H), 6.96 (d, J=8.0 Hz, 1H), 6.75-6.58 (m, 3H), 5.98 (dt, J=7.7, 1.5 Hz, 1H), 4.46 (d, J=12.7 Hz, 1H), 4.02 (d, J=6.1 Hz, 1H), 3.92-3.80 (m, 1H), 3.69-3.45 (m, 4H), 3.00-2.80 (m, 2H), 2.78-2.48 (m, 4H), 2.28-2.05 (m, 2H); LCMS (METHOD 3) (ES): m/z 692.6, 694.6 [M+H]$^+$, RT=0.91 min.

Preparation 17

(2S)-2-[(1S)-6-bromoindan-1-yl]-2-(tert-butoxycarbonylamino)acetic Acid

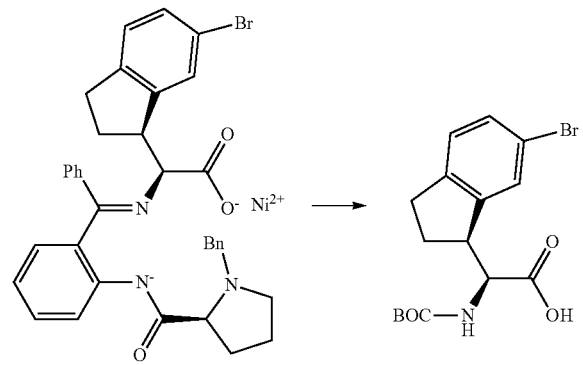

According to the method of Preparation 14 the compound of Preparation 16 (1.9 g, 2.7 mmol) was reacted to give the title compound (390 mg, 38%) as a brown foam. 1H NMR (300 MHz, DMSO-d6) δ 7.45 (s, 1H), 7.32 (dd, J=8.0, 1.8 Hz, 1H), 7.23 (d, J=8.9 Hz, 1H), 7.17 (d, J=8.0 Hz, 1H), 4.03 (t, J=8.6 Hz, 1H), 3.50-3.43 (partially obscured by H$_2$O peak, m, 1H), 2.92-2.64 (m, 2H), 2.23-2.04 (m, 1H), 2.01-1.83 (m, 1H), 1.37 (s, 9H); LCMS (METHOD 4) (ES): m/z 370.0, 372.0 [M+H]$^+$, RT=0.48 min.

Preparation 18

Dimethyl 2-(benzhydrylideneamino)-2-[(1R)-7-bromotetralin-1-yl]propanedioate

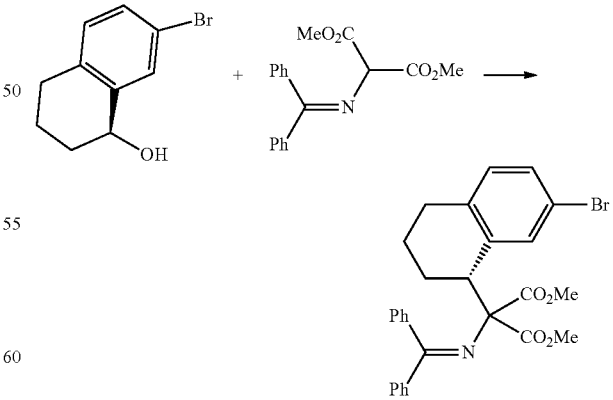

According to the method of Preparation 11 (1S)-7-bromotetralin-1-ol (4.80 g, 21.1 mmol) was reacted to give the title compound (7.90 g, 72%). LCMS (METHOD 4) (ES): m/z 520.3, 522.5 [M+H]$^+$, RT=1.05 min.

Preparation 19

2-Amino-2-[(1R)-7-bromotetralin-1-yl]acetic acid hydrobromide

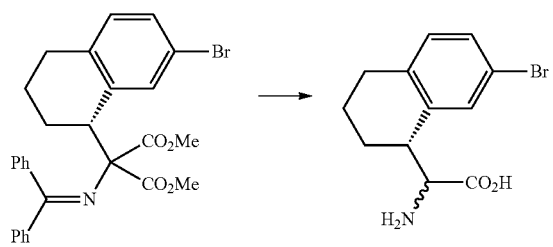 [SMILES: COC(=O)C(N=C(c1ccccc1)c1ccccc1)(C(=O)OC)[C@@H]1CCCc2ccc(Br)cc21 ; NC(C(=O)O)[C@@H]1CCCc2ccc(Br)cc21]

According to the method of Preparation 12 the compound of Preparation 18 (7.9 g, 15 mmol) was reacted to give the title compound (4.9 g, 87%) as a white solid. LCMS (METHOD 3) (ES): m/z 284.1, 286.1 [M+H]$^+$, RT=0.40 min.

Preparation 20

Nickelous (2S)-2-[(E)-[[2-[(2S)-1-benzylpyrrolidine-2-carbonyl]azanidylphenyl]-phenyl-methylene]amino]-2-[(1R)-7-bromotetralin-1-yl]acetate

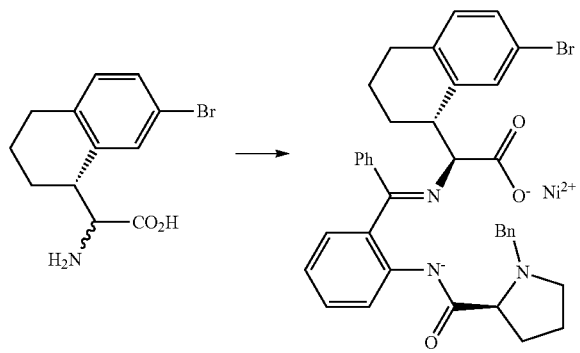

According to the method of Preparation 13 the compound of Preparation 19 (2.0 g, 5.5 mmol) was reacted to give the title compound (2.0 g, 52%) as a red solid. 1H NMR (300 MHz, Chloroform-d) δ 8.39 (dd, J=8.7, 1.1 Hz, 1H), 8.10-7.98 (m, 2H), 7.53-7.43 (m, 1H), 7.38 (tt, J=7.6, 1.3 Hz, 1H), 7.33-7.06 (m, 6H), 7.06-7.01 (m, 1H), 6.98-6.89 (m, 1H), 6.84 (d, J=8.2 Hz, 1H), 6.61 (ddd, J=8.1, 6.8, 1.2 Hz, 1H), 6.53 (dd, J=8.2, 1.8 Hz, 1H), 6.24 (d, J=7.6 Hz, 1H), 4.45 (d, J=2.6 Hz, 1H), 4.40 (d, J=12.6 Hz, 1H), 3.59-3.39 (m, 4H), 3.29-3.04 (m, 2H), 2.97-2.83 (m, 1H), 2.70-2.48 (m, 3H), 2.40-2.24 (m, 1H), 2.16-1.88 (m, 3H), 1.84-1.67 (m, 1H); LCMS (METHOD 3) (ES): m/z 706.3, 708.3 [M+H]$^+$, RT=0.93 min.

Preparation 21

(2S)-2-[(1S)-7-bromotetralin-1-yl]-2-(tert-butoxycarbonylamino)acetic acid

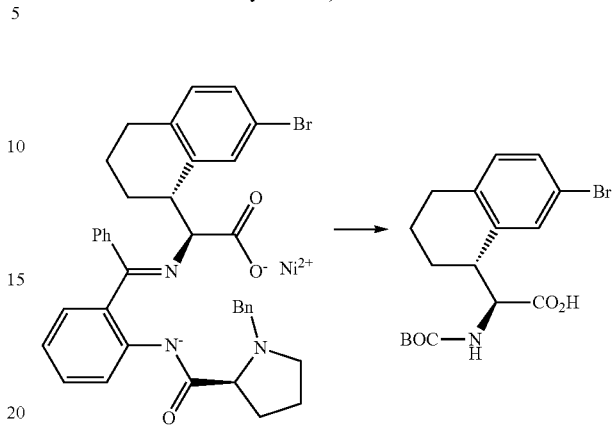

According to the method of Preparation 14 the compound of Preparation 20 (2.0 g, 2.83 mmol) was reacted to give the title compound (620 mg, 57%) as a white solid. 1H NMR (300 MHz, DMSO-d6) δ 12.7 (br s, 1H), 7.70-7.17 (m, 2H), 7.15-6.81 (m, 2H), 4.63 (br s, 1H), 3.29 (br s, 1H), 2.82-2.55 (m, 2H), 2.01-1.68 (m, 2H), 1.67-1.45 (m, 2H), 1.33 (s, 9H); LCMS (METHOD 3) (ES): m/z 384.4, 386.4 [M+H]$^+$, RT=0.78 min.

Preparation 22

2-[(1S)-7-bromotetralin-1-yl]-2-(tert-butoxycarbonylamino)acetic acid

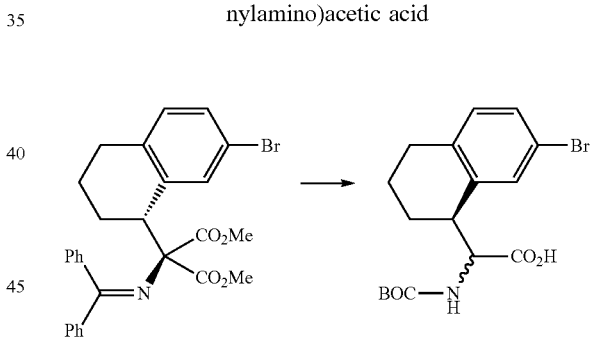

A mixture of dimethyl 2-(benzhydrylideneamino)-2-[(1S)-7-bromotetralin-1-yl]propanedioate (prepared from (1R)-7-bromotetralin-1-ol according to the method of Preparation 11) (2.3 g, 3.5 mmol) in conc. HBr (48% HBr, 15 mL) was heated at reflux for 3 hours. After cooling to room temperature the resulting suspension was basified to pH>12 with 4N NaOH. The mixture was washed twice with TBME to give a crude aqueous solution of 2-amino-2-[(1S)-7-bromotetralin-1-yl]acetic acid that was used directly without further purification. LCMS (METHOD 3) (ES): m/z 284.2, 286.2 [M+H]$^+$, RT=0.39 min.

Dioxane (20 mL) was added to the crude amino acid solution followed by Boc anhydride (2.0 g, 9.2 mmol) and the resulting mixture was stirred at room temperature for 2 hours. The reaction mixture was washed with DCM (2×50 mL), EtOAc (50 mL) was added and the mixture was acidified with 4N HCl to pH 2. The layers were separated and the aqueous phase was extracted with further EtOAc (30 mL). The combined organic phases were dried (MgSO$_4$) and concentrated in vacuo to give the title compound as a mixture of 2 diastereomers (1.22 g, 90%). LCMS (METHOD 3) (ES): m/z 382.4, 384.4 [M+H]$^+$, RT=0.79 (32%) and 0.81 (100%) min.

Preparation 23

Methyl (2S)-2-[(1S)-7-bromotetralin-1-yl]-2-(tert-butoxycarbonylamino)acetate

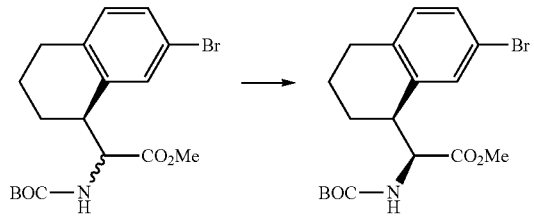 [SMILES: COC(=O)C(NC(=O)OC(C)(C)C)[C@H]1CCCc2ccc(Br)cc21 ; COC(=O)[C@@H](NC(=O)OC(C)(C)C)[C@H]1CCCc2ccc(Br)cc21]

To a solution of the compound from Preparation 22 (1.22 g, 3.17 mmol) in MeOH (3 mL) and DCM (12 mL) was added dropwise a solution of TMS diazomethane in heptane (2M, 3 mL, 6 mmol) over 20 min, until the yellow colour persisted. The solution was stirred for 1 hour then concentrated in vacuo, to give a white solid. The mixture of the two isomers was purified by column chromatography (silica gel, eluting with toluene/EtOAc 30:1; Rf=0.23 for S,S-isomer and 0.19 for S,R-isomer), giving the title compound (0.45 g, 1.1 mmol, 36%) as a white solid. 1H NMR (300 MHz, Chloroform-d) δ 7.34-7.17 (m, 2H), 6.95 (d, J=8.1 Hz, 1H), 5.02 (d, J=9.2 Hz, 1H), 4.61 (dd, J=9.2, 5.0 Hz, 1H), 3.70 (s, 3H), 3.42-3.26 (m, 1H), 2.77-2.60 (m, 2H), 2.08-1.57 (m, 4H), 1.41 (s, 9H); LCMS (METHOD 3) (ES): m/z 342.3, 344.3 [M+H−56]$^+$, RT=0.79 min.

Preparation 24

(2S)-2-[(1S)-7-bromotetralin-1-yl]-2-tert-butoxycarbonylamino) acetic acid

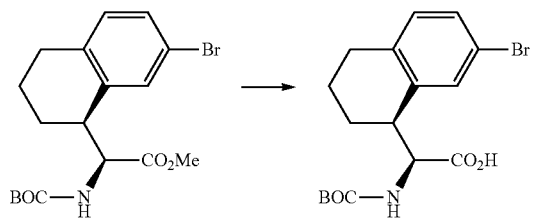 [SMILES: COC(=O)[C@@H](NC(=O)OC(C)(C)C)[C@H]1CCCc2ccc(Br)cc21 ; CC(C)(C)OC(=O)N[C@H](C(=O)O)[C@H]1CCCc2ccc(Br)cc21]

To a suspension of the compound of Preparation 23 (0.43 g, 1.1 mmol) in MeOH (15 mL) and water (4 mL) was added LiOH (1.0 g, 42 mmol). The suspension was warmed to 60° C. and then allowed to cool and stirred at room temperature for 1 hour. The precipitate was filtered (without washing) and the filter cake was taken up in water (20 mL) and EtOAc (20 mL). The mixture was acidified to pH2 with 6N HCl and the phases were separated. The aqueous phase was extracted with EtOAc and the combined organic phases were dried (MgSO$_4$) and concentrated in vacuo, to give the title compound (0.37 g, 89%) as a white solid. 1H NMR (300 MHz, DMSO-d6) δ 12.66 (s, 1H), 7.49 (d, J=2.5 Hz, 1H), 7.26 (dd, J=8.1, 2.1 Hz, 1H), 7.21 (d, J=9.3 Hz, 1H), 7.01 (d, J=8.2 Hz, 1H), 4.14 (t, J=8.9 Hz, 1H), 3.08-2.94 (m, 1H), 2.81-2.57 (m, 2H), 1.89-1.59 (m, 4H), 1.32 (s, 9H); LCMS (METHOD 3) (ES): m/z 384.4, 386.4 [M+H]$^+$, RT=0.81 min.

Preparation 25

(1-Cyclopropyl-2-methoxy-vinyl)cyclopropane

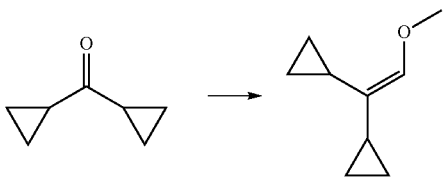

n-BuLi (2.5 M solution in heptanes, 26 mL, 65.6 mmol) was added slowly to a suspension of methoxymethyl(triphenyl)phosphonium chloride (22.5 g, 65.6 mmol) in dry THF (130 mL) at 5° C. under argon. The resulting deep red solution was stirred for 20 min, then dicyclopropylmethanone (5 mL, 4.82 g, 43.8 mmol) was added and the reaction mixture was stirred overnight at 60° C. under argon. The reaction mixture was allowed to cool to room temperature, concentrated in vacuo and the residue was purified by dry-flash chromatography (silica gel, eluting with hexane). Crude title compound (5.69 g, 94%) was isolated as a clear oil which was used without further purification. 1H NMR (300 MHz, Chloroform-d) δ 5.86 (dd, J=1.6, 0.7 Hz, 1H), 3.57 (s, 3H), 1.87-1.74 (m, 1H), 0.89-0.78 (m, 1H), 0.76-0.67 (m, 2H), 0.64-0.57 (m, 2H), 0.51-0.41 (m, 2H), 0.27-0.19 (m, 2H).

Preparation 26

2,2-Dicyclopropylacetaldehyde

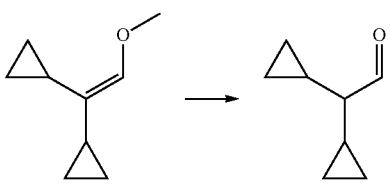

The compound of Preparation 25 (5.6 g, 41 mmol) was dissolved in THF (20 mL) and 6M HCl (20 mL) was added. The mixture was stirred vigorously for 1 week at room temperature. The reaction mixture was extracted with ether (2×50 mL), dried (Na$_2$SO$_4$) and carefully evaporated. Crude 2,2-dicyclopropylacetaldehyde (2.80 g, 56%) was isolated as a pale yellow oil which was used directly in the following step without any further purification.

Preparation 27

2-(tert-butoxycarbonylamino)-3,3-dicyclopropyl-propanoic acid

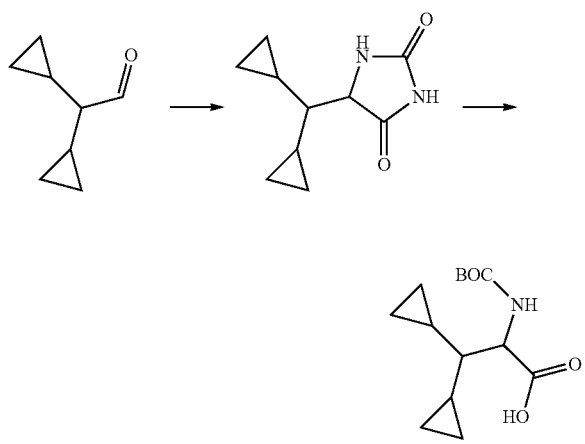

The compound of Preparation 26 (2.80 g, 22.5 mmol) was placed in a 20 mL microwave vial with KCN (2.20 g, 33.8 mmol) and ammonium carbonate (6.50 g, 67.6 mmol) in MeOH:water (8 mL:8 mL). The vial was capped and stirred at 60° C. (conventional heating) for 2 days to give a brown mixture with some precipitation. 4M HCl was added until the pH was less than 5. After cooling to room temperature the brown solid was filtered off, washed with water (3 mL) and dried to give crude hydantoin (4.38 g, 22.6 mmol) that was used without further purification.

The crude hydantoin (4.38 g, 22.6 mmol) was heated at reflux in 5M NaOH (30 mL) overnight, then cooled in an ice bath and 5M HCl (20 mL) was added slowly. THF (30 mL) was added followed by Boc anhydride (4.93 g, 22.6 mmol. The mixture was stirred at room temperature for 1 hour then 5M HCl was added carefully until the pH was between 3 and 4. The mixture was extracted with EtOAc (3×50 mL) and the combined organic extracts were dried ($Na_2SO_4$) and evaporated. Purification by column chromatography (silica gel, eluting with EtOAc:heptane) gave the title compound (1.32 g, 22%) as a pale yellow oil. 1H NMR (300 MHz, Chloroform-d) Mixture of rotamers 67.90 (br s, 1H), 5.78 (br, 0.15H), 5.26 (d, J=9.2 Hz, 0.85H), 4.55 (d, J=9.2 Hz, 0.85H), 4.37 (br, 0.15H), 1.46 (s, 9H), 1.33-1.21 (m, 1H), 0.85-0.64 (m, 2H), 0.61-0.36 (m, 4H), 0.32-0.13 (m, 4H); LCMS (METHOD 3) (ES): m/z 268.4 [M−H]−, RT=0.70 min.

Preparation 28

N-[(1 S)-2-[4-[3,5-dimethyl-1-(2-trimethylsilylethoxymethyl)pyrazol-4-yl]anilino]-2-oxo-1-[(1S)-tetralin-1-yl]ethyl]-2-methyl-pyrazole-3-carboxamide

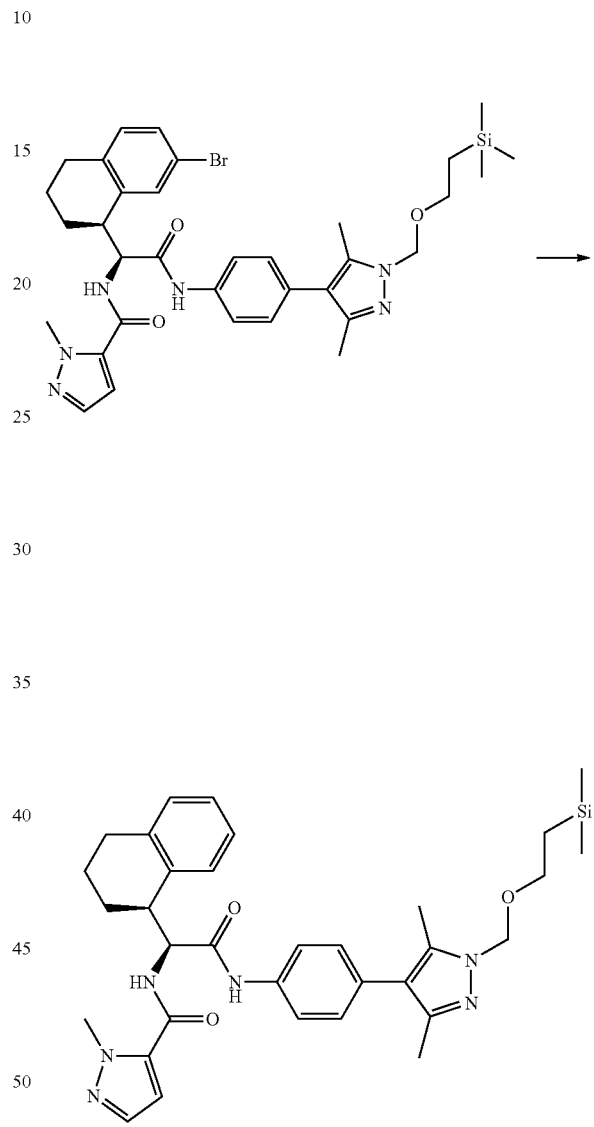

N-[(1S)-1-[(1S)-7-bromotetralin-1-yl]-2-[4-[3,5-dimethyl-1-(2-trimethylsilylethoxymethyl)pyrazol-4-yl]anilino]-2-oxo-ethyl]-2-methyl-pyrazole-3-carboxamide (synthesised from the compound of Preparation 24 according to the methods of Preparations 3 to 5) (35 mg, 0.0506 mmol) was dissolved in MeOH (5 mL) and 10% Pd/C (5 mg) was added under argon. The reaction mixture was stirred under a hydrogen atmosphere for 2 hours to give the title compound. LCMS (METHOD 3) (ES): m/z 613.8 [M+H]+, RT=0.97 min.

Preparations 29-30

Preparations 29 and 30 were synthesised according to the method of Preparation 28 from the compounds of Preparations 14 and 17 respectively.

| Prep. No. | Structure | Name | Mass ion | LCMS method and retention time (min) |
|---|---|---|---|---|
| 29 | 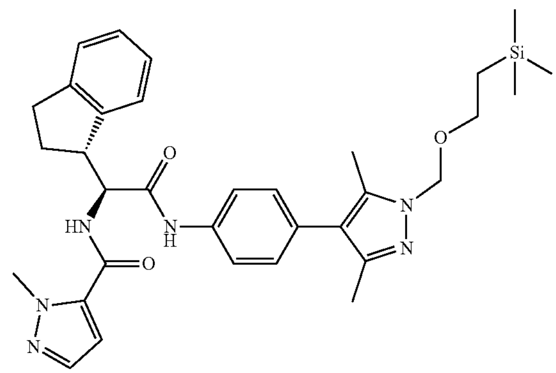 | N-[(1S)-2-[4-[3,5-dimethyl-1-(2-trimethylsilylethoxymethyl)pyrazol-4-yl]anilino]-1-[(1R)-indan-1-yl]-2-oxo-ethyl]-2-methyl-pyrazole-3-carboxamide | 599.7 | Method 3, 0.93 |
| 30 | 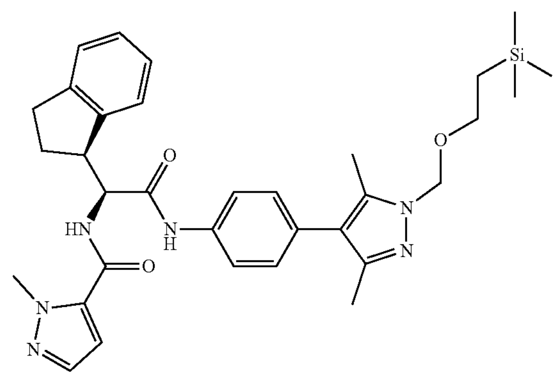 | N-[(1S)-2-[4-[3,5-dimethyl-1-(2-trimethylsilylethoxymethyl)pyrazol-4-yl]anilino]-1-[(1S)-indan-1-yl]-2-oxo-ethyl]-2-methyl-pyrazole-3-carboxamide | 597.3 [M − H]⁻ | Method 3, 0.93 |

Preparation 31

N-[(1S)-1-[(1S)-7-cyanotetralin-1-yl]-2-[4-[3,5-dimethyl-1-(2-trimethylsilylethoxymethyl)pyrazol-4-yl]anilino]-2-oxo-ethyl]-2-methyl-pyrazole-3-carboxamide

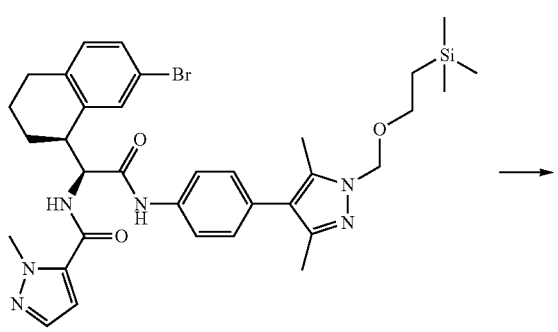

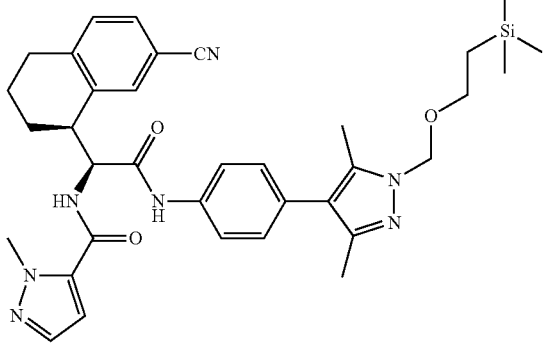

-continued

N-[(1S)-1-[(1S)-7-bromotetralin-1-yl]-2-[4-[3,5-dimethyl-1-(2-trimethylsilylethoxymethyl)pyrazol-4-yl]anilino]-2-oxo-ethyl]-2-methyl-pyrazole-3-carboxamide (synthesised from the compound of Preparation 24 according to the methods of Preparations 3 to 5) (35 mg, 0.0506 mmol) in a reaction vial was dissolved in DMF (2 mL) and degassed with argon for 8 minutes. Zinc cyanide (30 mg, 0.253 mmol) and tetrakis(triphenylphosphine)-palladium(0) (14.6 mg, 0.0127 mmol) were added and the vial was capped and shaken at 150° C. for 45 minutes. The reaction mixture was filtered and purified by acidic reverse phase chromatography to give the title compound. LCMS (METHOD 3) (ES): m/z 638.7 [M+H]⁺, RT=0.93 min.

Preparations 32-33

Preparations 32 and 33 were synthesised according to the method of Preparation 31 from the compounds of Preparations 14 and 17 respectively.

| Prep. No. | Structure | Name | Mass ion | LCMS method and retention time (min) |
|---|---|---|---|---|
| 32 | 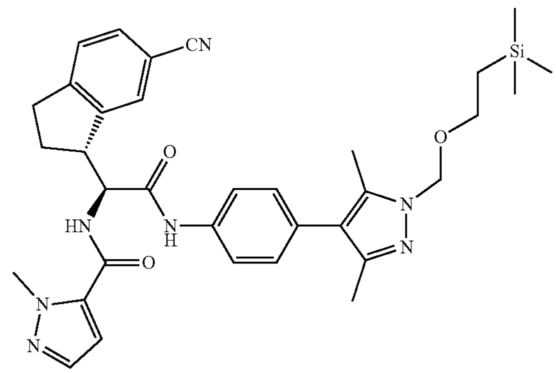 | N-[(1S)-1-[(1R)-6-cyanoindan-1-yl]-2-[4-[3,5-dimethyl-1-(2-trimethylsilylethoxymethyl)pyrazol-4-yl]anilino]-2-oxo-ethyl]-2-methyl-pyrazole-3-carboxamide | 624.8 | Method 3, 0.88 |
| 33 | 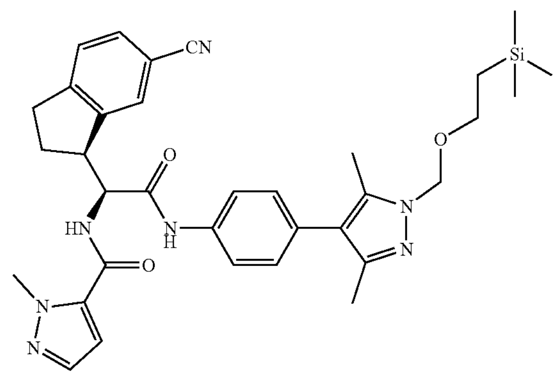 | N-[(1S)-1-[(1S)-6-cyanoindan-1-yl]-2-[4-[3,5-dimethyl-1-(2-trimethylsilylethoxymethyl)pyrazol-4-yl]anilino]-2-oxo-ethyl]-2-methyl-pyrazole-3-carboxamide | 624.8 | Method 3, 0.90 |

Preparation 34

N-[(1S)-1-[(1R)-6-chloroindan-1-yl]-2-[4-[3,5-dimethyl-1-(2-trimethylsilylethoxymethyl)pyrazol-4-yl]anilino]-2-oxo-ethyl]-2-methyl-pyrazole-3-carboxamide

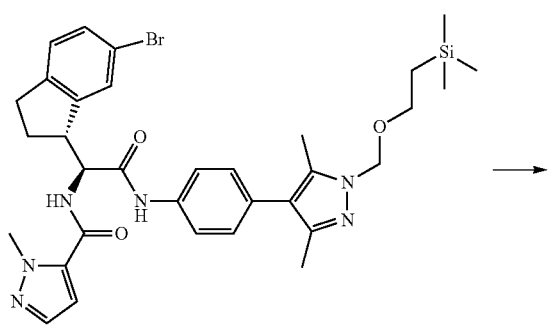

→

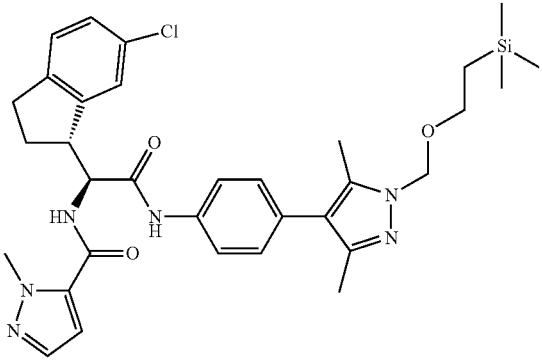

A solution of N-[(1S)-1-[(1R)-6-bromoindan-1-yl]-2-[4-[3,5-dimethyl-1-(2-trimethylsilylethoxymethyl)pyrazol-4-yl]anilino]-2-oxo-ethyl]-2-methyl-pyrazole-3-carboxamide (synthesised from the compound of Preparation 14 according to the methods of Preparations 3 to 5) (30 mg, 0.0443 mmol) in DMF (1 mL) in a reaction vial was flushed with argon for 5 min, zinc chloride (30 mg, 0.221 mmol) was added and the vial was sealed and stirred for 5 hours at 150° C. After cooling to room temperature the reaction mixture was filtered and purified by acidic reverse phase chromatography to give the title compound (8 mg, 29%). LCMS (METHOD 3) (ES): m/z 503.5 [M+H]⁺, RT=0.95 min.

Preparation 35

2-(tert-butoxycarbonylamino)-2-[(4S)-chroman-4-yl]acetic acid

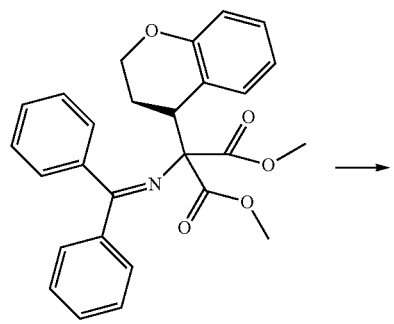

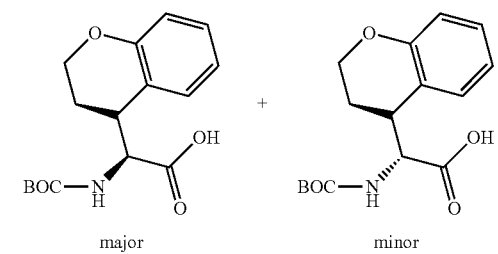

A mixture of dimethyl 2-(benzhydrylideneamino)-2-[(4S)-chroman-4-yl]propanedioate (synthesised from (4R)-chroman-4-ol according to the method of Preparation 11) (1.48 g, 3.33 mmol) in conc. HBr (48%, 10 mL) was heated at 100° C. for 3 hours. The reaction was cooled to room temperature, water (20 mL) was added and the mixture was washed with TBME (2×10 mL). The aqueous phase was then cooled on ice and 4N NaOH (approximately 20 mL) was added dropwise until pH 13. THF (20 mL) was added followed by Boc anhydride (2.18 g, 9.99 mmol) and the mixture was stirred for 20 hours. The aqueous phase was washed with TBME and the pH was adjusted to 1-2 with 1M HCl. EtOAc (50 mL) was added, the phases were separated and the aqueous phase was extracted with EtOAc (3×50 mL). The combined organic phases were washed with brine, dried (Na₂SO₄) and concentrated in vacuo to give the title compound as a mixture of diastereomers. LCMS (METHOD 3) (ES): m/z 306.4 [M−H]⁻, RT=0.64 min (minor) and 0.65 min (major).

Preparation 36

2-(tert-butoxycarbonylamino)-2-[(4R)-chroman-4-yl]acetic acid

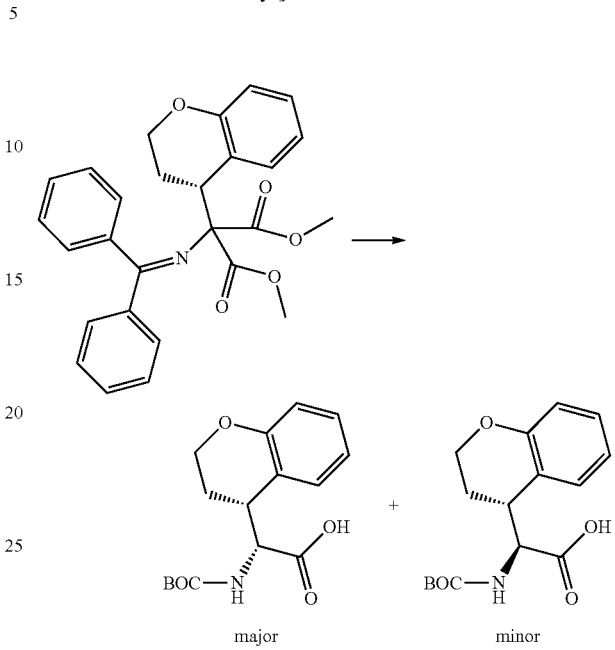

Dimethyl 2-(benzhydrylideneamino)-2-[(4R)-chroman-4-yl]propanedioate (synthesised from (4S)-chroman-4-ol according to the method of Preparation 11) was converted to the title compound following the method of Preparation 35. LCMS (METHOD 3) (ES): m/z 306.4 [M−H]⁻, RT=0.65 min (minor) and 0.66 min (major).

Preparation 37

Ethyl (2S)-2-(benzhydrylideneamino)-2-[(1S)-3-oxocycloheptyl]acetate

A solution of cyclohept-2-en-1-one (1.0 g, 9.1 mmol) in DCM (10 mL) was added dropwise over ca. 10 min to a mixture of ethyl 2-(benzhydrylideneamino)acetate (0.8 g, 3.0 mmol), cinchonidine alkaloid (0.2 g, 0.7 mmol), caesium hydroxide monohydrate (3.0 g, 17.9 mmol) in DCM at −78° C. After being stirred for 2 hours at the same temperature, the solution was allowed to warm to room temperature upon which the solution turned from yellow to dark brown. TBME (100 mL) and water (50 mL) were added. The organic phase was washed with water (50 mL), dried over MgSO$_4$, filtered and concentrated in vacuo. The crude product was purified by flash chromatography (silica gel, eluting with heptane/ethyl acetate 2:1) to give the title compound as an oil (1.02 g, 90%). LCMS (ES) (Method 3): m/z 378.5 [M+H]$^+$, RT=0.92 min.

Preparation 38

Ethyl (2S)-2-(tert-butoxycarbonylamino)-2-[(1S)-3-oxocycloheptyl]acetate

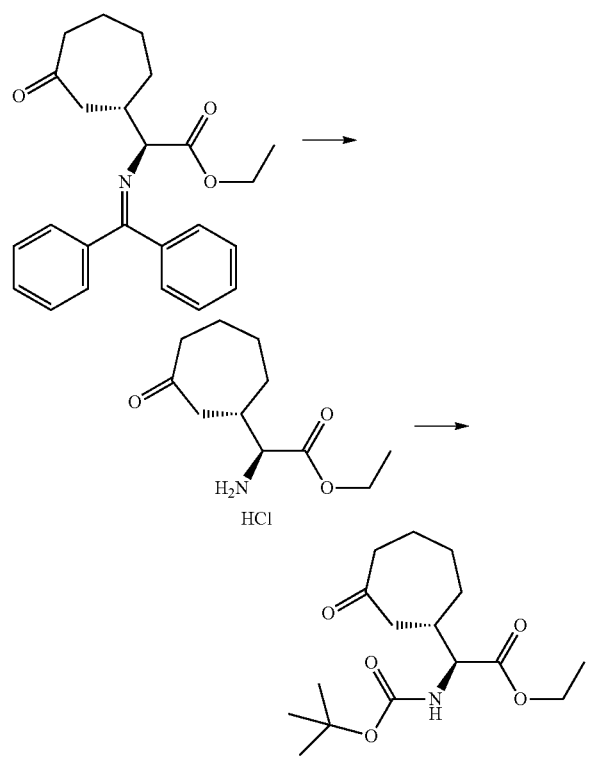

To a solution of the imine of Preparation 37 (1.0 g, 2.6 mmol) in THF (15 mL) was added 6M aq. HCl (5 mL, 30 mmol). The reaction mixture was stirred at room temperature for 1 hour (TLC control: heptane/ethyl acetate 2:1, staining: ninhydrin) and then diluted with water (20 mL). The mixture was washed with TBME and used directly in the next step without isolation.

The mixture was basified to pH 8 with solid K$_2$CO$_3$. To the mixture was added dioxane (5 mL), followed by BoC$_2$O (1.2 g, 5.5 mmol). The mixture was stirred at room temperature for 2 hours and extracted twice with TBME. The combined organic phases were dried over MgSO$_4$ and concentrated in vacuo. The residue was purified by flash chromatography (silica gel, eluting with heptane/EtOAc 2:1, R$_f$=0.32), to give the title compound (0.5 g, 60%) as a colourless oil. 1H NMR (300 MHz, CDCl$_3$) δ 5.09 (bd, J=6 Hz, 1H), 4.38-4.27 (m, 1H), 4.28-4.16 (m, 2H), 2.58-2.44 (m, 4H), 2.30-2.10 (m, 1H), 2.05-1.70 (m, 3H), 1.65-1.25 (m, 3H), 1.45 (s, 9H), 1.29 (t, J=6.0 Hz, 3H).

Preparation 39

Ethyl (2S)-2-(tert-butoxycarbonylamino)-2-[(1S)-3,3-difluorocycloheptyl]acetate

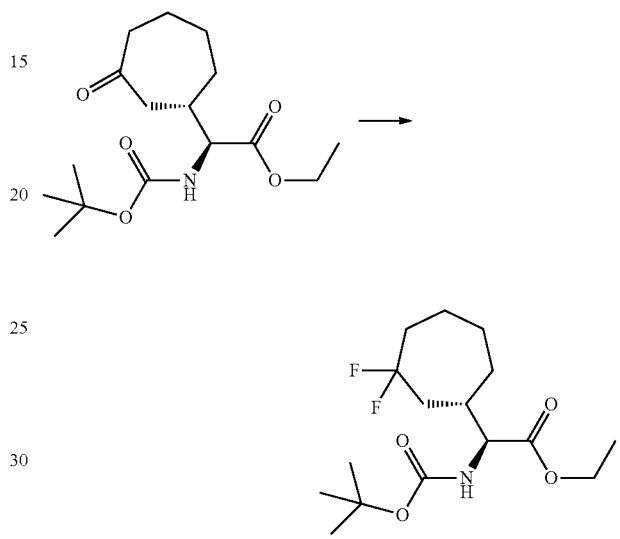

To a solution of the ester of Preparation 38 (0.50 g, 1.60 mmol) in DCM (5 mL) was added DAST (2.0 g, 112 mmol, 90%) at 5° C. The reaction was warmed to room temperature and stirred at this temperature for 18 hours. The reaction mixture was then added to 10% aq. NaHCO$_3$ solution (20 mL). The obtained mixture was extracted twice with TBME and the combined organic phases were dried over MgSO$_4$ and concentrated in vacuo. The residue was purified by flash chromatography (silica gel, heptane/EtOAc 5:1, Rf=0.3), to give the title compound as a brown oil (0.28 g, 42% yield and ca. 80% purity). 1H NMR (300 MHz, CDCl$_3$) δ 5.16-4.96 (m, 1H), 4.3-4.15 (m, 3H), 2.50-1.20 (m, 11H), 1.45 (s, 9H), 1.29 (t, J=6.0 Hz, 3H).

Preparation 40

(2S)-2-(tert-Butoxycarbonylamino)-2-[(1S)-3,3-difluorocycloheptyl]acetic acid

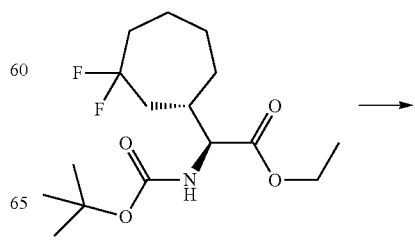

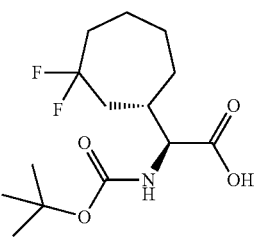

To a solution of the ester of Preparation 39 (0.27 g, 0.64 mmol, 80% purity) in water (3 mL) and methanol (12 mL) was added sodium hydroxide (0.5 g, 10 mmol). The solution was stirred at room temperature for 1 hour. The solution was concentrated in vacuo to remove methanol then diluted with water (10 mL) and washed twice with TBME. To the aqueous phase was added further TBME and the mixture was acidified to pH2. After phase separation, the aqueous phase was extracted with TBME and the combined organic phases were dried over MgSO₄ and concentrated in vacuo, giving the title compound as a yellow foam (0.2 g, 82% yield and ca. 80% purity). 1H NMR (600 MHz, CDCl₃) δ 5.17 (d, J=6.0 Hz, 0.17H), 5.09 (d, J=6.0 Hz, 0.83H), 4.43-4.35 (m, 1H), 2.70-1.15 (m, 11H), 1.45 (s, 9H).

Preparation 41

Methyl (2S)-2-(tert-butoxycarbonylamino)-2-[(1S)-3,3-difluorocyclohexyl]acetate

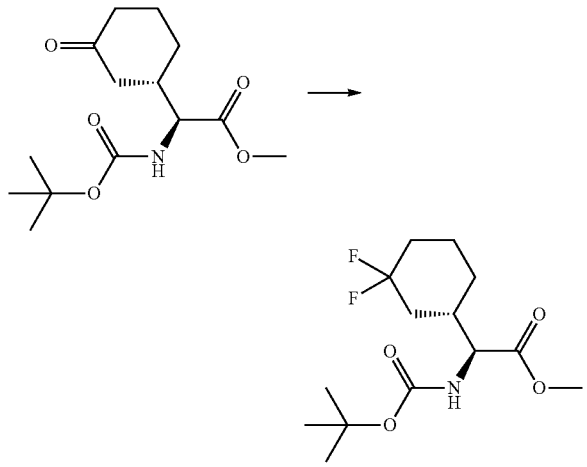

The starting material, methyl (2S)-2-(tert-butoxycarbonylamino)-2-(3-oxocyclohexyl)acetate, was obtained according to a literature procedure (Angew. Chem. 1988, 100, 1238-1239).

The title compound was prepared from methyl (2S)-2-(tert-butoxycarbonylamino)-2-(3-oxocyclohexyl)acetate (180 mg, 0.63 mmol) according to the method of Preparation 39. The title compound (112 mg, 42% yield) was obtained as a brown oil. 1H NMR (600 MHz, CDCl₃) δ 5.00 (d, J=6.0 Hz, 1H), 4.29-4.21 (m, 1H), 3.70 (s, 3H), 2.10-0.95 (m, 9H), 1.38 (s, 9H).

Preparation 42

(2S)-2-(tert-Butoxycarbonylamino)-2-[(1S)-3,3-difluorocyclohexyl]acetic acid

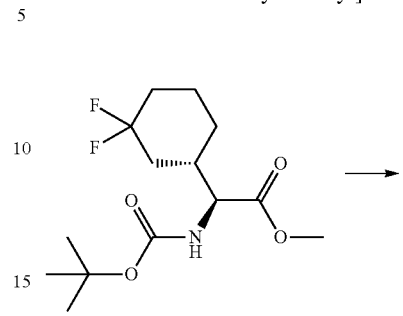

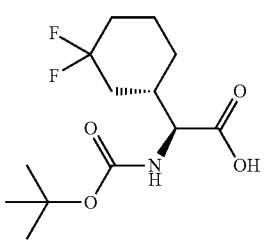

The title compound was prepared from the ester of Preparation 41 (110 mg, 0.36 mmol) according to the method of Preparation 40. The title compound (93 mg, 86% yield) was obtained as a brown oil. 1H NMR (600 MHz, CDCl₃) δ 10.40 (s, 1H), 5.20-4.85 (m, 1H), 4.40-4.00 (m, 1H), 2.35-0.95 (m, 9H), 1.38 (s, 9H).

Preparation 43

Methyl (2S)-2-(tert-butoxycarbonylamino)-2-[(1S)-3-methylenecyclohexyl]acetate

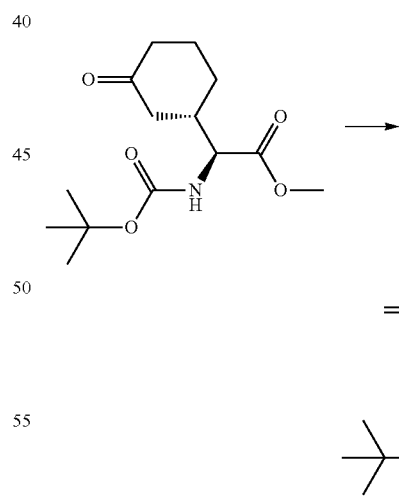

To a mixture of methyl (2S)-2-(tert-butoxycarbonylamino)-2-(3-oxocyclohexyl)acetate (prepared according to Angew. Chem. 1988, 100, 1238-1239) (0.50 g, 1.75 mmol) and methyl(triphenyl)phosphonium bromide (1.0 g, 2.8 mmol) in THF (20 mL) was added potassium tert-butoxide (300 mg, 2.67 mmol. The yellow mixture was stirred at room temperature for 4 hours and then diluted with TBME. The mixture was washed with water and the aqueous phase was extracted with TBME. The combined organic phases were dried over MgSO₄ and concentrated in vacuo. The residue was purified by column chromatography (silica gel, eluting with heptane/EtOAc, 9:1, R_f=0.30), to give the title compound (61 mg, 12%) as an oil. 1H NMR (300 MHz, CDCl₃) δ 5.0 (d, J=9.0 Hz, 1H), 4.69-4.61 (m, 2H), 4.40-4.00 (m, 1H), 2.35-2.10 (m, 2H), 2.00-1.60 (m, 5H), 1.45 (s, 9H), 1.40-1.10 (m, 2H).

Preparation 44

Methyl (2S)-2-(tert-butoxycarbonylamino)-2-[(7S)-spiro[2.5]octan-7-yl]acetate

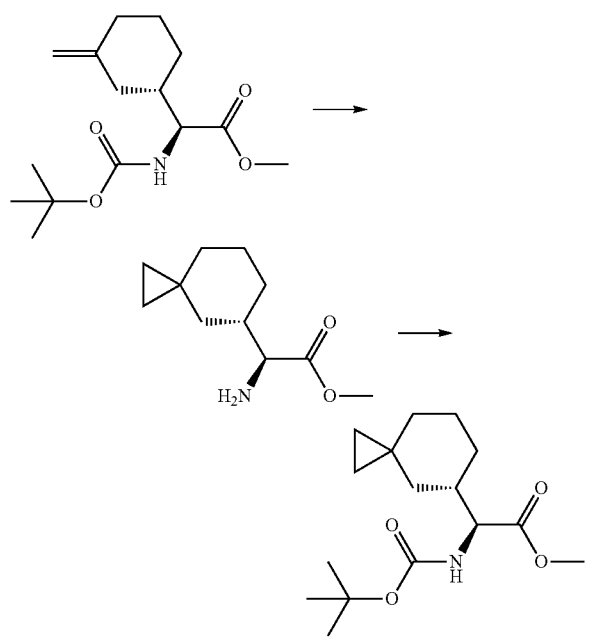

To a solution of the alkene of Preparation 43 (61 mg, 0.22 mmol) and diiodomethane (160 mg, 0.60 mmol) in heptane (3 mL) was added dropwise trimethylaluminium (2M in toluene, 0.3 mL, 0.6 mmol) at 5° C. The obtained solution was stirred at room temperature for 1 hour (TLC control, EtOAc, Rf=0.32, TLC was stained by KMnO₄. no immediate yellow colour was observed). The reaction was diluted with DCM (15 mL), cooled in an ice bath and quenched by the slow addition of KF (0.3 g, 5.16 mmol) in water (5 mL). The mixture was stirred at room temperature for 20 minutes and the phases were separated. The aqueous phase was extracted twice with DCM and the combined organic phases were dried over MgSO₄ and concentrated in vacuo, to give a crude amine, which was used without further purification.

To a solution of the crude methyl (2S)-2-amino-2-[(7S)-spiro[2.5]octan-7-yl]acetate, DMAP (48 mg, 0.39 mmol) and DIPEA (50 mg, 0.39 mmol) in DCM (3 mL) was added BoC₂O (70 mg, 0.32 mmol). The solution was stirred at room temperature over the weekend. The reaction solution was concentrated in vacuo and the residue was purified by column chromatography (silica gel, eluting with heptane/EtOAc 5:1, Rf=0.4), to give the title compound (11 mg, 17%) as a colourless oil. 1H NMR (600 MHz, CDCl₃) δ 5.02-4.92 (m, 1H), 4.22-4.16 (m, 1H), 3.70/3.69 (s, 3H), 1.98-1.85 (m, 1H), 1.75-1.30 (m, 5H), 1.42 (s, 9H), 1.15-1.00 (m, 1H), 0.77/0.68 (d, J=6.0, 2H), 0.30-0.085 (m, 4H).

Preparation 45

(2S)-2-(tert-Butoxycarbonylamino)-2-[(7S)-spiro[2.5]octan-7-yl]acetic acid

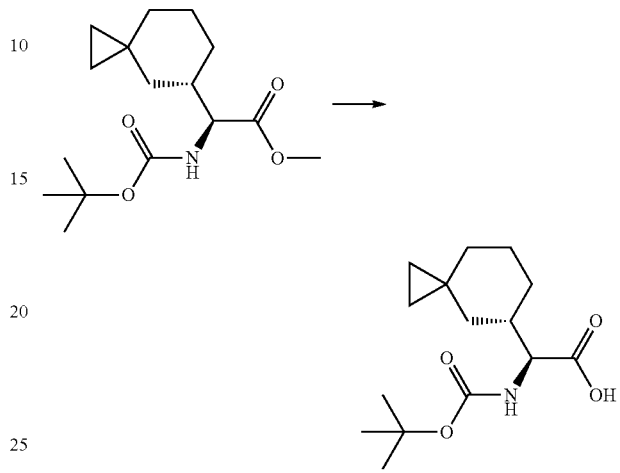

To a solution of the ester of Preparation 44 (11 mg, 0.037 mmol) in water (1 mL) and methanol (4 mL) was added sodium hydroxide (100 mg, 2.5 mmol). The reaction mixture was stirred at room temperature for 1 hour and then concentrated in vacuo. To the residue was added water and DCM and the mixture was acidified to pH 1-2 using 5N HCl. After phase separation, the aqueous phase was extracted twice with DCM. The combined organic phases were dried over MgSO₄ and concentrated in vacuo, to give the title compound (9 mg, 86%) as a colourless oil, which was used without purification or characterisation.

Preparation 45B (2S)-2-(tert-butoxycarbonylamino)-2-spiro[2.5]octan-7-yl-acetic acid

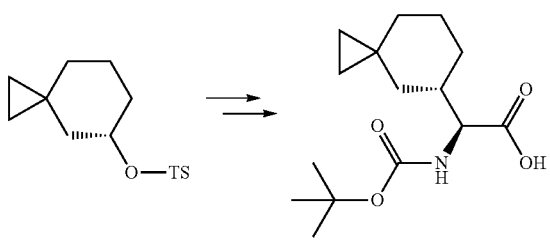

According to the methods of Preparations 7 to 9, spiro[2.5]octan-7-yl 4-methylbenzenesulfonate was converted to the title compound (220 mg) which was obtained as a colourless oil. 1H NMR (600 MHz, Chloroform-d) δ 5.93 (s, 0.25H), 5.00 (dd, J=20.1, 9.0 Hz, 0.75H), 4.33-4.18 (m, 0.75H), 4.12-3.92 (m, 0.25H), 2.13-1.87 (m, 1H), 1.83-1.37 (m, 14H), 1.23-1.05 (m, 1H), 0.95-0.70 (m, 2H), 0.37-0.25 (m, 2H), 0.24-0.14 (m, 2H).

Preparation 46

2-(2-Hydroxy-1-methyl-ethyl)pyrazole-3-carboxylic acid

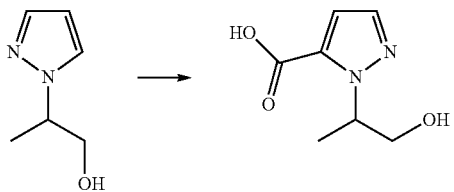

n-BuLi (2.5 M in hexanes, 15 mL 37.7 mmol) was added dropwise to a solution of 2-pyrazol-1-ylpropan-1-ol (1.90 g, 15.1 mmol) and TMEDA (4.52 mL, 3.50 g, 30.1 mmol) in dry THF (50 mL) at 0° C. under argon. The resulting suspension was stirred for 30 minutes at 0° C. and $CO_2$ gas was then passed through the solution for 10 minutes. The reaction mixture was concentrated in vacuo, 4M aq. HCl was slowly added until the pH was between 3 and 4 and the mixture was extracted with EtOAc (3×40 mL). The combined organic extracts were dried ($Na_2SO_4$) and concentrated in vacuo. The resulting pale solid was triturated with ether:hexane (1:1, 20 mL), filtered and dried in vacuo to give the title compound (1.60 g, 62%) as an off-white solid. 1H NMR (300 MHz, DMSO-d6) δ 13.16 (s, 1H), 7.54 (dd, J=1.9, 0.5 Hz, 1H), 6.78 (d, J=1.9 Hz, 1H), 5.71-5.18 (m, 1H), 3.69 (dd, J=10.6, 7.5 Hz, 1H), 3.59 (dd, J=10.6, 5.9 Hz, 1H), 1.34 (d, J=6.7 Hz, 3H).

Preparation 47

3-(4-Nitrophenyl)pentane-2,4-dione

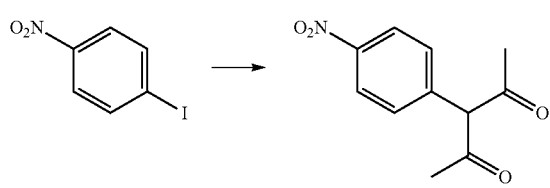 [SMILES: O=[N+]([O-])c1ccc(I)cc1 ; CC(=O)C(C(C)=O)c1ccc([N+](=O)[O-])cc1]

1-Iodo-4-nitro-benzene (5.0 g, 20.1 mmol), pentane-2,4-dione (4.01 g, 40.2 mmol) and $K_2CO_3$ (6.92 g, 50.2 mmol) were taken in dry DMSO (100 mL) and purged with Argon gas for 15 min. CuI (0.381 g, 2.00 mmol) was added, followed by (S)-Proline (0.461 g, 4.01 mmol). The resulting reaction mixture was stirred at 70° C. for 16 hours. The reaction mixture was diluted with water (100 mL) and extracted with EtOAc (2×100 mL). The combined organic layers were washed with water (100 mL) and brine (100 mL), dried ($Na_2SO_4$) and concentrated under reduced pressure. The residue was purified by column chromatography (silica, eluting with 5% EtOAc in petroleum ether) to give the title compound (1.8 g, 40%) as a yellow solid. 1H NMR ($CDCl_3$, 400 MHz): δ 16.76 (s, 1H), 8.27 (d, J=8.8 Hz, 2H), 7.39 (d, J=8.8 Hz, 2H), 1.90 (s, 6H); LCMS (ES): m/z=220 [M−H]⁻, RT=1.98 min.

Preparation 48

3,5-Dimethyl-4-(4-nitrophenyl)-1H-pyrazole

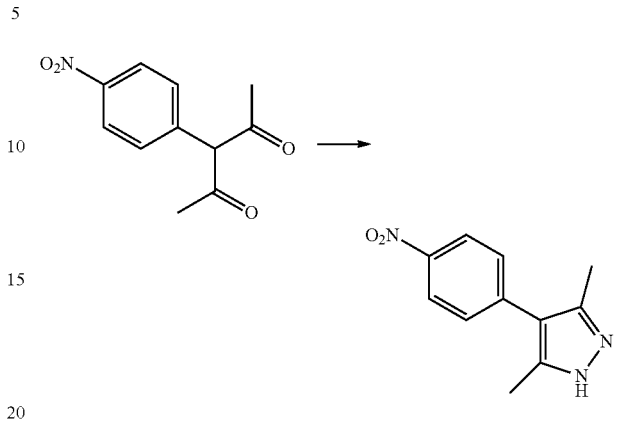

Hydrazine hydrate (56.5 mL, 1130 mmol) was added to a stirred solution of the compound of Preparation 47 (50 g, 226 mmol) in EtOH (1 L) at room temperature. The reaction mixture was then heated at 70° C. for 6 hours. The reaction mixture was concentrated under reduced pressure and the residue was diluted with water (1 L) and stirred at room temperature for 20 minutes. The precipitate was filtered, washed with cold water (300 mL) and hexane (300 mL). The solid was dried to give the title compound (35 g, 71%) as a yellow solid. 1H NMR (400 MHz, DMSO-d6) δ 12.55 (br s, 1H), 8.26-8.23 (d, J=8.8 Hz, 2H), 7.59-7.57 (d, J=9.2 Hz, 2H), 2.29 (s, 3H), 2.23 (s, 3H); LCMS (ES): m/z=218 [M+H]⁺, RT=5.62 min.

Preparation 49

Ditert-butyl [3,5-dimethyl-4-(4-nitrophenyl)pyrazol-1-yl]methyl phosphate

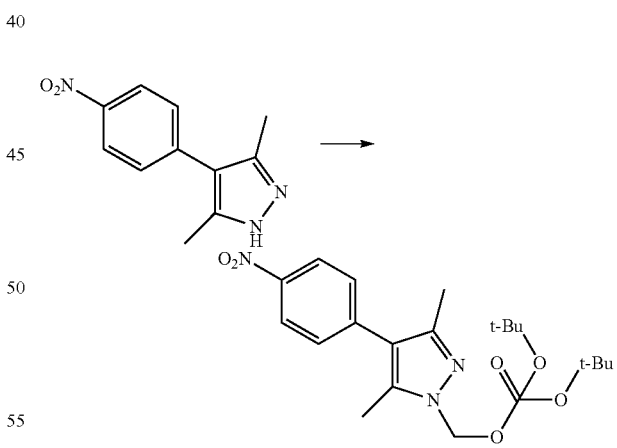

To a mixture of the pyrazole of Preparation 48 (5 g, 23.0 mmol) and caesium carbonate (10 g, 30.7 mmol) in DMF (100 mL) at room temperature was added ditert-butyl chloromethyl phosphate (6.5 mL). The mixture was stirred at room temperature for 18 h. The reaction mixture was diluted with TBME (150 mL) and washed with water (150 mL). The aqueous phase was extracted with TBME (2×50 mL). The combined organic phases were washed with water (2×100 mL), dried ($Na_2SO_4$) and concentrated in vacuo. The residue was purified by flash chromatography (silica, eluting with 0.25% Et₃N in EtOAc, Rf=0.42) to give the title compound (10.2 g, 100%) as a yellowish oil. 1H NMR (400 MHz, Chloroform-d) δ 8.38-8.16 (m, 2H), 7.51-7.33 (m, 2H), 5.84 (d, J=9.5 Hz, 2H), 2.42 (s, 3H), 2.28 (s, 3H), 1.47 (s, 18H); LCMS (METHOD 3) (ES): m/z 440.3 [M+H]⁺, RT=0.83 min.

Preparation 50

[4-(4-Aminophenyl)-3,5-dimethyl-pyrazol-1-yl]methyl ditert-butyl phosphate

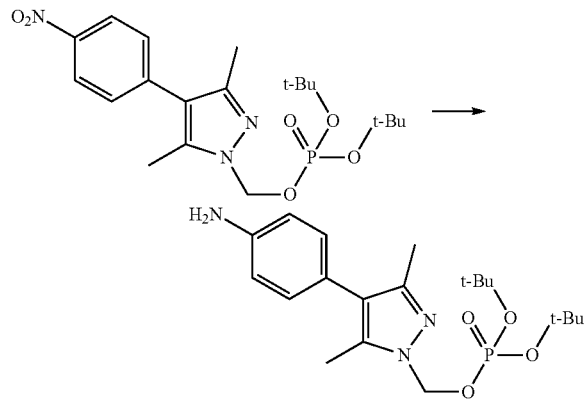

A mixture of the nitro compound of Preparation 49 (3.36 g, 7.65 mmol) and 10% Pd/C (340 mg, 0.32 mmol) in isopropanol (250 mL) was stirred at room temperature under 2 bars pressure of hydrogen for 3 hours. The reaction was then stirred under 4 bars pressure of hydrogen for 90 minutes. The reaction mixture was filtered through CPelite and the catalyst was washed with isopropanol. The filtrate was concentrated in vacuo to give the title compound (2.46 g, 79%) as a yellowish solid. 1H NMR (400 MHz, Chloroform-d) δ 7.11-6.95 (m, 2H), 6.81-6.66 (m, 2H), 5.82 (d, J=9.3 Hz, 2H), 2.33 (s, 3H), 2.22 (s, 3H); LCMS (METHOD 3) (ES): m/z 410.8 [M+H]⁺, RT=0.69 min.

Preparation 51

(4-Methoxyphenyl)methyl (2R)-2-(tert-butoxycarbonylamino)-3,3-dicyclopropyl-propanoate and (4-methoxyphenyl)methyl (2S)-2-(tert-butoxycarbonylamino)-3,3-dicyclopropyl-propanoate

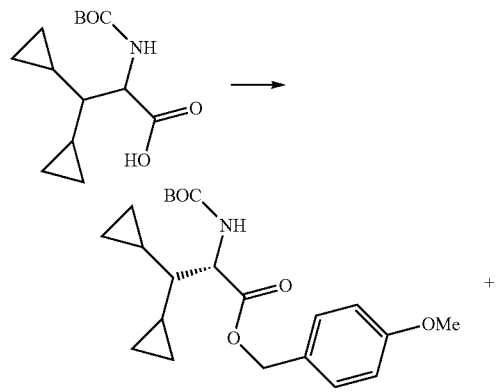

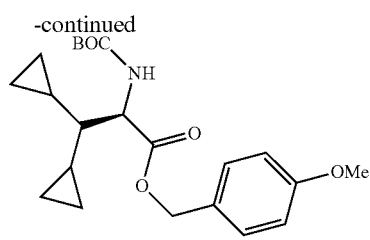

EDC (7.77 g, 40.5 mmol) was added to a mixture of the acid of Preparation 27 (7.28 g, 27.0 mmol), 4-methoxybenzylalcohol (4.48 g, 32.4 mmol) and DMAP (3.3 g, 27.0 mmol) in DCM (100 mL) and stirred overnight at room temperature. The reaction mixture was washed with 0.25M HCl (15 mL), dried (Na₂SO₄) and evaporated. Purification by column chromatography (silica, eluting with EtOAc:heptane) gave the racemic title compound (9.30 g, 88%) as a white solid. 1H NMR (300 MHz, Chloroform-d) δ 7.38-7.18 (m, 2H), 6.98-6.79 (m, 2H), 5.24 (d, J=9.3 Hz, 1H), 5.09 (s, 2H), 4.53 (d, J=9.3 Hz, 1H), 3.81 (s, 3H), 1.44 (s, 9H), 0.80-0.55 (m, 3H), 0.55-0.26 (m, 4H), 0.25-0.10 (m, 3H), 0.07--0.05 (m, 1H); LCMS (METHOD 3) (ES): m/z 390.3 [M+H]⁺, RT=0.95 min. The two enantiomers were separated by preparative chiral SFC giving (4-methoxyphenyl)methyl (2R)-2-(tert-butoxycarbonylamino)-3,3-dicyclopropyl-propanoate (Preparation 51a) (Column: Lux A2 (4.6 mm×250 mm, 5 μm), Eluent: 20:80 IPA:CO₂ (0.2% v/v NH₃), Temp: 40° C., Flow rate: 4 mL/min, BPR: 125 Bar, retention time: 1.4 min) and (4-methoxyphenyl)methyl (2S)-2-(tert-butoxycarbonylamino)-3,3-dicyclopropyl-propanoate (Preparation 51b) (Column: Lux A2 (4.6 mm×250 mm, 5 μm), Eluent: 20:80 IPA:CO₂ (0.2% v/v NH₃), Temp: 40° C., Flow rate: 4 mL/min, BPR: 125 Bar, retention time: 1.9 min).

Preparation 52

(2S)-2-(Tert-butoxycarbonylamino)-3,3-dicyclopropyl-propanoic acid

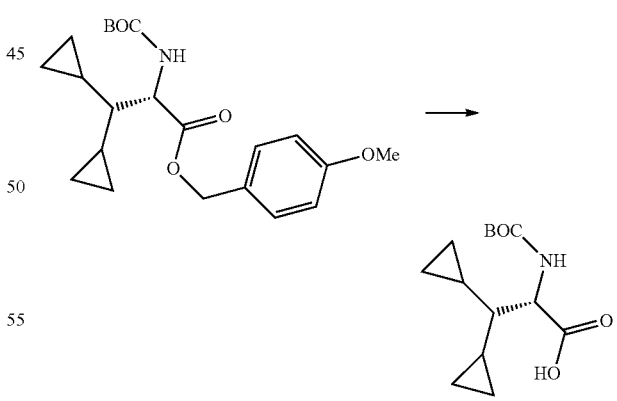

A solution of (4-methoxyphenyl)methyl (2S)-2-(tert-butoxycarbonylamino)-3,3-dicyclopropyl-propanoate (Preparation 51b) (5.30 g, 13.6 mmol) in MeOH (25 mL) was hydrogenated over 10% Pd/C (250 mg) using a hydrogen balloon. After 2½ hours the reaction mixture was filtered and evaporated. Purification by column chromatography (silica, eluting with EtOAc:heptane) gave the title compound (3.50 g, 96%) as a clear syrup. 1H NMR (400 MHz, DMSO-d6) Mixture of rotamers δ 12.41 (s, 1H), 6.81 (d, J=9.0 Hz, 0.82H), 6.48 (d, J=8.2 Hz, 0.18H), 4.12 (dd, J=9.0, 4.4 Hz, 0.82H), 4.05 (s, 0.18H), 1.39 (s, 7.4H), 1.25 (s, 1.6H), 1.02-0.88 (m, 1H), 0.83-0.72 (m, 1H), 0.56-0.42 (m, 2H), 0.41-0.20 (m, 4H), 0.19-0.01 (m, 3H); LCMS (METHOD 3) (ES): m/z 268.4 [M–H]⁻, RT=0.71 min.

Preparation 53

(2S)-2-Amino-3,3-dicyclopropyl-propanoic acid hydrochloride

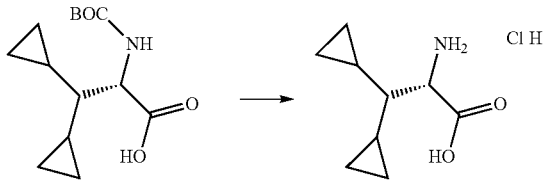 [SMILES: CC(C)(C)OC(=O)N[C@H](C(=O)O)C(C1CC1)C1CC1 ; N[C@H](C(=O)O)C(C1CC1)C1CC1 ; "Cl H"]

To a solution of the acid of Preparation 52 (4.52 g, 16.8 mmol) in MeOH (30 mL) was added conc. HCl (15 mL) dropwise. The reaction was stirred at room temperature for 30 minutes then concentrated to dryness, to give the title compound (3.24 g, 94%) as a white solid. 1H NMR (400 MHz, Deuterium Oxide) δ 4.19 (d, J=3.7 Hz, 1H), 1.06-0.79 (m, 3H), 0.76-0.35 (m, 6H), 0.35-0.24 (m, 2H).

Preparation 54

(2S)-3,3-dicyclopropyl-2-(9H-fluoren-9-ylmethoxycarbonylamino)propanoic acid

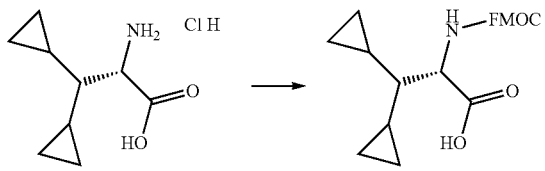

To a solution of the amino acid of Preparation 53 (3.24 g, 15.8 mmol) and sodium carbonate (6.68 g, 63.0 mmol in water (50 mL) and dioxane (50 mL) at room temperature was added FMOC chloride (4.89 g, 18.9 mmol). The mixture was stirred for 3 hours then water (50 mL) and TBME (50 mL) were added. The mixture was acidified to pH 1-2 with 5N HCl and the layers were separated. The aqueous phase was extracted with TBME (3×50 mL), the combined organic phases were dried over Na₂SO₄ and concentrated in vacuo. The residue was purified by flash chromatography (silica, eluting with heptane:ethyl acetate 3:1 containing 0.1% formic acid), to give the title compound (4.1 g, 66%) as a white solid. 1H NMR (400 MHz, DMSO-d6) δ 12.54 (s, 1H), 7.89 (d, J=7.5 Hz, 2H), 7.78 (dd, J=7.5, 2.7 Hz, 2H), 7.60 (d, J=9.1 Hz, 1H), 7.46-7.38 (m, 2H), 7.36-7.28 (m, 2H), 4.36-4.13 (m, 4H), 1.07-0.92 (m, 1H), 0.89-0.74 (m, 1H), 0.63-0.02 (m, 9H); LCMS (METHOD 3) (ES): m/z 390.7 [M–H]⁻, RT=0.83 min.

Preparation 55

9H-Fluoren-9-ylmethyl N-[(1S)-2,2-dicyclopropyl-1-[[4-[1-(ditert-butoxyphosphoryloxymethyl)-3,5-dimethyl-pyrazol-4-yl]phenyl]carbamoyl]ethyl]carbamate

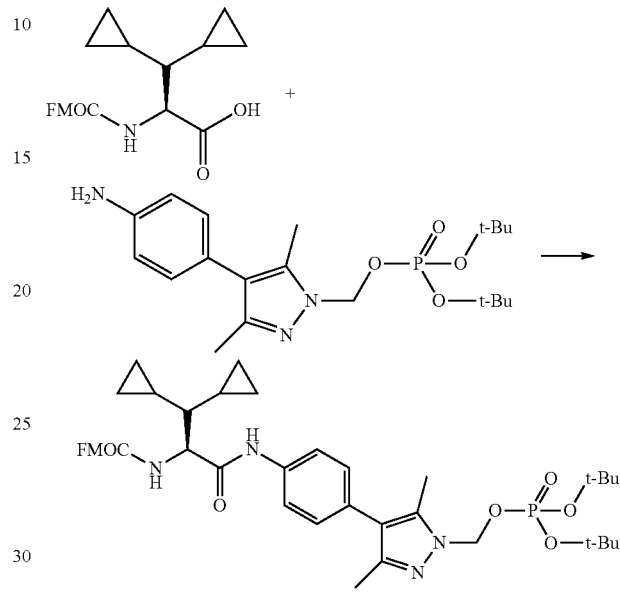

To a solution of the acid of Preparation 54 (2.17 g, 5.54 mmol), the aniline of Preparation 50 (2.2 g, 5.4 mmol) and DIPEA (2 mL) in MeCN (75 mL) at room temperature was added HATU (2.3 g, 6.0 mmol). The solution was stirred at room temperature for 5 hours then water (150 mL) was added. The precipitate was collected by filtration, washed with water (4×20 mL) and dried in vacuo to give the title compound (4.0 g, 92%) as a colourless solid, which was used without further purification. 1H NMR (400 MHz, Chloroform-d) δ 7.86 (s, 1H), 7.76 (d, J=7.7 Hz, 2H), 7.65-7.49 (m, 4H), 7.47-7.35 (m, 2H), 7.35-7.25 (m, 2H), 7.19 (d, J=8.0 Hz, 2H), 5.82 (d, J=9.2 Hz, 2H), 5.68 (s, 1H), 4.60-4.35 (m, 3H), 4.24 (t, J=6.8 Hz, 1H), 2.35 (t, J=1.4 Hz, 3H), 2.23 (t, J=1.4 Hz, 3H), 1.46 (t, J=1.3 Hz, 18H), 0.95-0.80 (m, 1H), 0.79-0.64 (m, 2H), 0.61-0.41 (m, 4H), 0.39-0.16 (m, 4H); LCMS (METHOD 3) (ES): m/z 784.2 [M+H]⁺, RT=0.99 min.

Preparation 56

[4-[4-[[(2S)-2-Amino-3,3-dicyclopropyl-propanoyl]amino]phenyl]-3,5-dimethyl-pyrazol-1-yl]methyl ditert-butyl phosphate

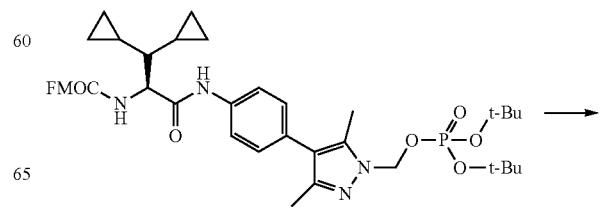

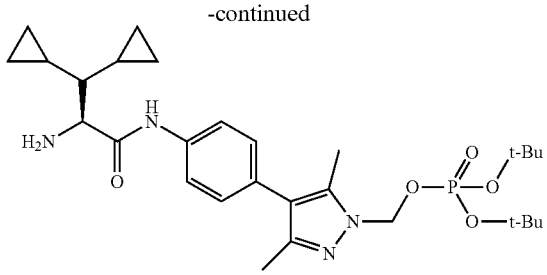

To a solution of the compound of Preparation 55 (4.0 g, 5.11 mmol) in DCM (30 mL) at room temperature was added diethylamine (4 mL). The solution was stirred at room temperature for 4 hours then placed at 4° C. overnight. The solution was concentrated in vacuo and the residue was purified by column chromatography (silica, eluting with 0.25% Et$_3$N in EtOAc/MeOH 1:0 to 9:1) to give the title compound (2.37 g, 83%) as a pink foam. 1H NMR (400 MHz, Chloroform-d) δ 9.69 (s, 1H), 7.64 (d, J=7.7 Hz, 2H), 7.20 (d, J=7.6 Hz, 2H), 5.83 (d, J=9.4 Hz, 2H), 3.64 (s, 1H), 2.36 (s, 3H), 2.24 (s, 3H), 1.53-1.39 (m, 18H), 1.09-0.99 (m, 1H), 0.85-0.68 (m, 2H), 0.68-0.58 (m, 1H), 0.53-0.14 (m, 7H); LCMS (METHOD 3) (ES): m/z 559.3 [M−H]⁻, RT=0.75 min.

Preparation 57

Ditert-butyl [4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl phosphate Method A

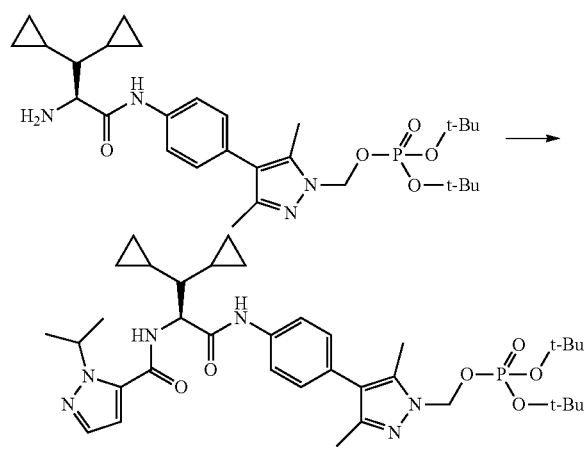

To a solution of 2-isopropylpyrazole-3-carboxylic acid (0.9 g, 6 mmol,) and the amine of Preparation 56 (2.3 g, 4.1 mmol) in MeCN (40 mL) was added EDC (1.1 g, 5.7 mmol) at room temperature. The solution was stirred at room temperature for 2 hours then concentrated in vacuo. The residue was taken up in water (75 mL) and DCM (75 mL) and the layers were separated. The aqueous phase was extracted with DCM (50 mL) and the combined organic phases were washed with water, dried (Na$_2$SO$_4$) and concentrated in vacuo. The residue was purified by column chromatography (silica, eluting with EtOAc+0.25% Et$_3$N), to give the title compound (2.07 g, 72%) as a white foam. 1H NMR (600 MHz, Chloroform-d) δ 8.40 (s, 1H), 7.59-7.54 (m, 2H), 7.52 (d, J=2.0 Hz, 1H), 7.22-7.17 (m, 2H), 7.15 (d, J=8.4 Hz, 1H), 6.59 (d, J=2.0 Hz, 1H), 5.82 (d, J=9.4 Hz, 2H), 5.46 (hept, J=6.6 Hz, 1H), 4.93 (dd, J=8.4, 4.8 Hz, 1H), 2.34 (s, 3H), 2.21 (s, 3H), 1.49 (d, J=6.6 Hz, 3H), 1.47-1.44 (m, 21H), 0.91-0.83 (m, 3H), 0.64-0.49 (m, 4H), 0.43-0.37 (m, 1H), 0.36-0.31 (m, 1H), 0.29-0.23 (m, 2H); LCMS (METHOD 4) (ES): m/z 698.2 [M+H]⁺, RT=0.88 min.

Preparation 57—Method B

Ditert-butyl [4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl phosphate

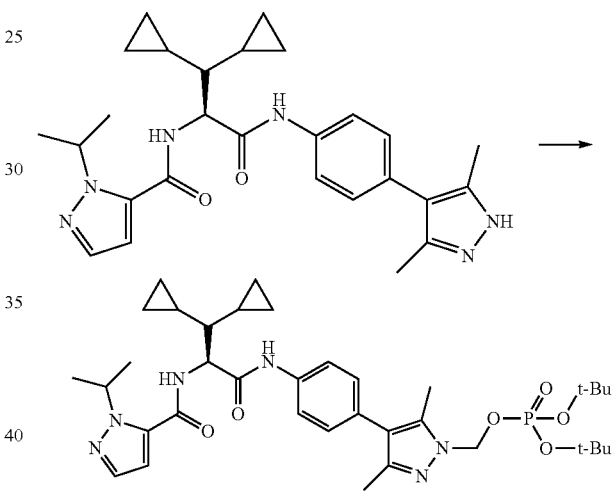

To a mixture of the compound of Example 32 (601 mg, 1.27 mmol), caesium carbonate (800 mg, 2.46 mmol) in DMSO (5 mL) was added ditert-butyl chloromethyl phosphate (0.7 mL) at room temperature. The mixture was stirred at room temperature for 20 hours and the reaction was then quenched by the addition of 10% brine (50 mL). The resulting mixture was extracted with DCM (8 times). The combined organic phases were dried (Na$_2$SO$_4$) and concentrated in vacuo. The residue was purified by column chromatography (silica, eluting with EtOAc+0.2% Et$_3$N) to give the title compound (577 mg, 65%) as a colourless oil, and recovered starting material (181 mg, 23%). 1H NMR (600 MHz, Chloroform-d) δ 8.40 (s, 1H), 7.59-7.54 (m, 2H), 7.52 (d, J=2.0 Hz, 1H), 7.22-7.17 (m, 2H), 7.15 (d, J=8.4 Hz, 1H), 6.59 (d, J=2.0 Hz, 1H), 5.82 (d, J=9.4 Hz, 2H), 5.46 (hept, J=6.6 Hz, 1H), 4.93 (dd, J=8.4, 4.8 Hz, 1H), 2.34 (s, 3H), 2.21 (s, 3H), 1.49 (d, J=6.6 Hz, 3H), 1.47-1.44 (m, 21H), 0.91-0.83 (m, 3H), 0.64-0.49 (m, 4H), 0.43-0.37 (m, 1H), 0.36-0.31 (m, 1H), 0.29-0.23 (m, 2H); LCMS (METHOD 3) (ES): m/z 695.3 [M−H]⁻, RT=0.82 min.

Preparation 58

Tert-butyl N-[(1S)-1-(dicyclopropylmethyl)-2-[4-[3,5-dimethyl-1-(2-trimethylsilylethoxymethyl)pyrazol-4-yl]anilino]-2-oxo-ethyl]carbamate

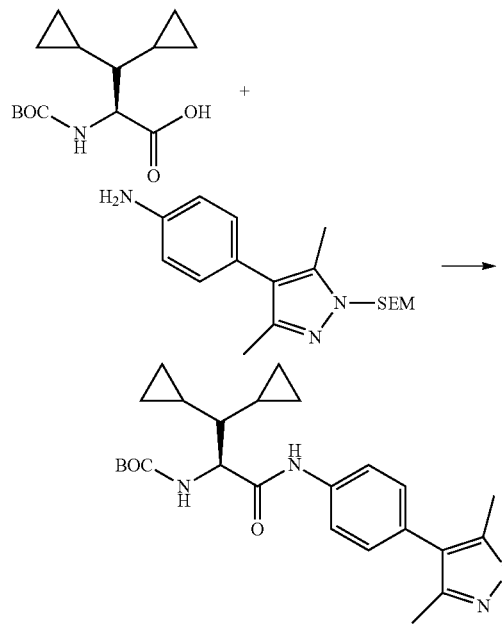

HATU (5.70 g, 15.0 mmol) was added to a solution of the acid of Preparation 52 (2.95 g, 11.0 mmol), the aniline of Preparation 2 (3.83 g, 12.0 mmol) and DIPEA (3.82 mL, 2.83 g, 21.9 mmol) in dry DMF (15 mL) and the mixture was stirred at room temperature for 18 hours. The reaction was poured into water (250 mL) and extracted with Et$_2$O (3×80 mL). The combined organic extracts were dried (Na$_2$SO$_4$), and concentrated in vacuo. The residue was purified by column chromatography (silica, eluting with 0-100% EtOAc in heptane) to give the title compound (5.97 g, 96%) as a pale yellow solid. LCMS (METHOD 3) (ES): m/z 567.5 [M−H]$^-$, RT=1.01 min.

Preparation 59

(2S)-2-Amino-3,3-dicyclopropyl-N-[4-[3,5-dimethyl-1-(2-trimethylsilylethoxymethyl)pyrazol-4-yl]phenyl]propanamide hydrochloride

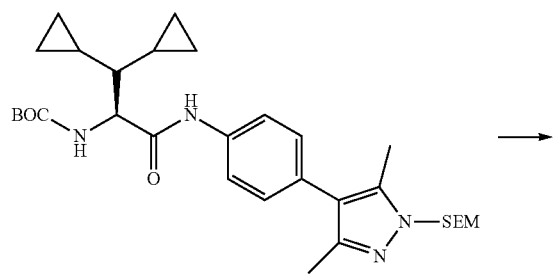

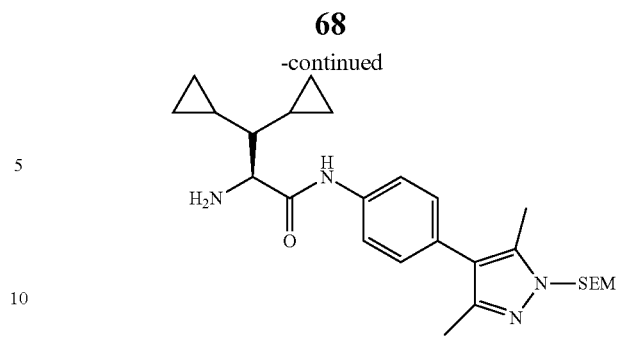

The compound of Preparation 58 (5.97 g, 10.5 mmol) was dissolved in 1M HCl in MeOH (50 mL) and the reaction was stirred at room temperature for 3 hours. The mixture was concentrated in vacuo to give the title compound (5.30 g, 100%) as an off-white solid. LCMS (METHOD 3) (ES): m/z 469.3 [M+H]$^+$, RT=0.71 min.

Preparation 60

N-[(1S)-1-(Dicyclopropylmethyl)-2-[4-[3,5-dimethyl-1-(2-trimethylsilylethoxymethyl)pyrazol-4-yl]anilino]-2-oxo-ethyl]-2-isopropyl-pyrazole-3-carboxamide

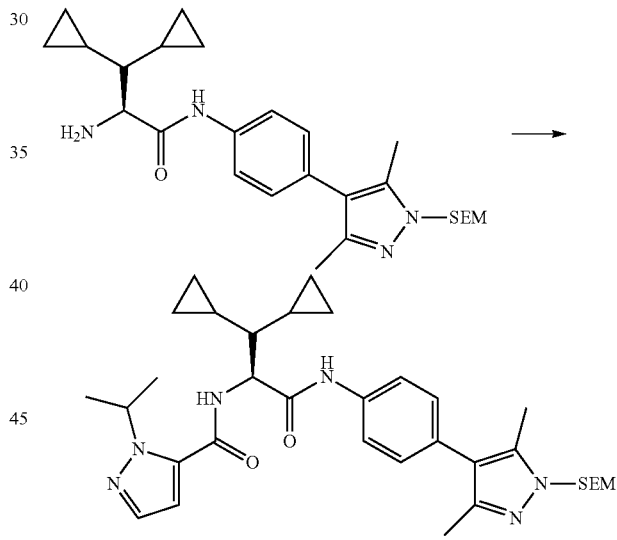

HATU (4.79 g, 12.6 mmol) was added to a solution of the amine of Preparation 59 (5.30 g, 10.5 mmol), 2-isopropylpyrazole-3-carboxylic acid (1.94 g, 12.6 mmol) and DIPEA (7.31 mL, 5.42 g, 42.0 mmol) in dry DMF (30 mL) and the mixture was stirred at room temperature for 18 hours. The reaction mixture was poured into water (120 mL) and extracted with ether (3×40 mL). The organic extracts were washed with 5% citric acid, dried (Na$_2$SO$_4$) and concentrated in vacuo. The residue was purified by column chromatography (silica, eluting with EtOAc/heptane) to give the title compound (5.20 g, 82%) as a white solid. 1H NMR (400 MHz, Chloroform-d) δ 8.03 (s, 1H), 7.60-7.55 (m, 2H), 7.53 (d, J=2.0 Hz, 1H), 7.26-7.21 (m, 2H), 7.11 (d, J=8.1 Hz, 1H), 6.59 (d, J=2.0 Hz, 1H), 5.49 (hept, J=6.7 Hz, 1H), 5.39 (s, 2H), 4.85 (dd, J=8.2, 4.8 Hz, 1H), 3.69-3.55 (m, 2H), 2.31

(s, 3H), 2.24 (s, 3H), 1.52 (d, J=6.6 Hz, 3H), 1.49 (d, J=6.6 Hz, 3H), 0.97-0.86 (m, 5H), 0.72-0.63 (m, 1H), 0.62-0.52 (m, 3H), 0.48-0.33 (m, 2H), 0.33-0.25 (m, 2H), 0.00 (s, 9H). LCMS (METHOD 3) (ES): m/z 605.5 [M+H]+, RT=0.99 min.

Preparation 61

Ditert-butyl [4-[4-[[(2S)-2-cyclohexyl-2-[(2-methylpyrazole-3-carbonyl)amino]acetyl]amino]phenyl]-3,5-dimethyl-pyrazol-1-yl]methyl phosphate

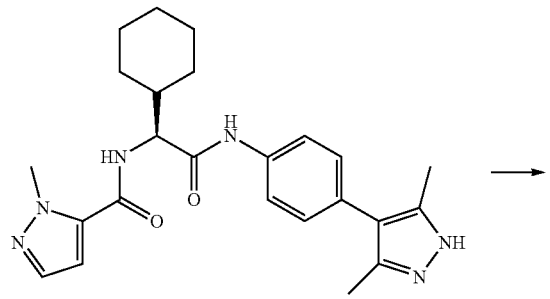

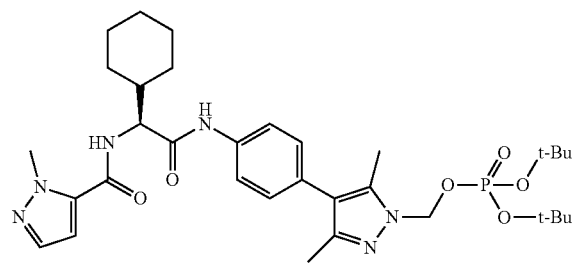

To a mixture of the compound of Example 1 (166 mg, 0.38 mmol) and caesium carbonate (200 mg, 0.61 mmol) in DMF (4 mL) was added ditert-butyl chloromethyl phosphate (150 mg, 0.58 mmol). The mixture was stirred at room temperature for 6 hours. Further caesium carbonate (150 mg, 0.46 mmol) and ditert-butyl chloromethyl phosphate (100 mg, 0.39 mmol) was added and the mixture was stirred at room temperature for 60 hours. The reaction mixture was filtered and the filter cake was washed with CH$_3$CN (10 mL). The combined filtrate was concentrated in vacuo (water bath temperature 35° C.) and the residue was taken up in DCM (20 mL). The mixture was washed with water (20 mL) and the aqueous phase was extracted with DCM. The combined organic phases were dried (Na$_2$SO$_4$) and concentrated in vacuo. The residue was purified by flash chromatography (eluting with EtOAc containing 0.2% Et$_3$N, Rf=0.15), to give the title compound (128 mg, 51%) as a white solid. 1H NMR (400 MHz, Chloroform-d) δ 8.06 (s, 1H), 7.64-7.54 (m, 2H), 7.45 (d, J=2.1 Hz, 1H), 7.23-7.15 (m, 2H), 6.77 (d, J=8.6 Hz, 1H), 6.62 (d, J=2.1 Hz, 1H), 5.82 (d, J=9.3 Hz, 2H), 4.50 (t, J=8.1 Hz, 1H), 4.16 (s, 3H), 2.34 (s, 3H), 2.21 (s, 3H), 2.02-1.64 (m, 6H), 1.46 (s, 18H), 1.36-1.06 (m, 5H); LCMS (METHOD 3) (ES): m/z 657.3 [M+H]+, RT=0.78 min.

Preparation 62

Ditert-butyl [3,5-dimethyl-4-[4-[[[(2S)-2-[(2-methylpyrazole-3-carbonyl)amino]-3,3-diphenyl-propanoyl]amino]phenyl]pyrazol-1-yl]methyl phosphate

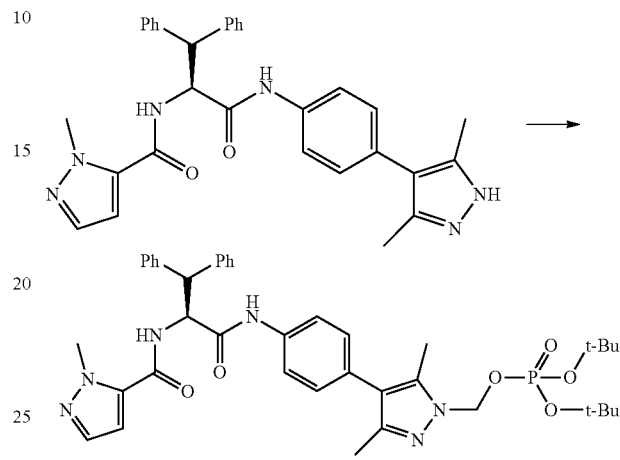

Ditert-butyl chloromethyl phosphate (62 mg, 0.24 mmol) was added to a stirred mixture of the compound of Example 2 (50 mg, 0.096 mmol) and caesium carbonate (79 mg, 0.24 mmol) in DMSO (1 mL). The mixture was stirred at room temperature for 4 hours then purified by reverse phase HPLC (acidic method) to give the title compound (33 mg, 46%). 1H NMR (300 MHz, DMSO-d6) δ 10.31 (s, 1H), 8.86 (d, J=8.8 Hz, 1H), 7.45 (dd, J=14.2, 7.6 Hz, 6H), 7.36 (d, J=2.1 Hz, 1H), 7.25 (q, J=7.2 Hz, 4H), 7.12 (dd, J=7.4, 1.2 Hz, 4H), 6.76 (d, J=2.1 Hz, 1H), 5.79-5.55 (m, 3H), 4.63 (d, J=11.7 Hz, 1H), 3.90 (s, 3H), 2.25 (s, 3H), 2.10 (s, 3H), 1.38 (s, 18H); LCMS (METHOD 3) (ES): m/z 741.6 [M+H]+, RT=0.84 min.

Preparation 63

(3-Nitrophenyl)methyl (2S)-2-(tert-butoxycarbonylamino)-3,3-di(cyclobutyl)propanoate and (3-nitrophenyl)methyl (2R)-2-(tert-butoxycarbonylamino)-3,3-di(cyclobutyl)propanoate

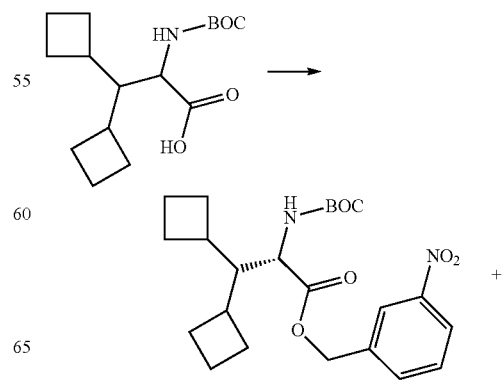

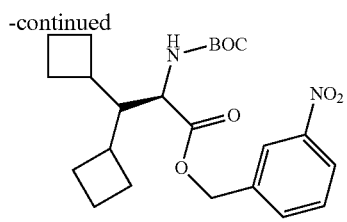

A solution of 2-(tert-butoxycarbonylamino)-3,3-di(cyclobutyl)propanoic acid (4.80 g, 16.1 mmol) in DMF (30 mL) was cooled in an ice bath. Caesium carbonate (5.26 g, 16.1 mmol) was added and the mixture was stirred at 0° C. for 1 hour before the addition of 1-(bromomethyl)-3-nitrobenzene (3.49 g, 16.1 mmol). The reaction mixture was stirred at 0° C. for 30 minutes and then at room temperature for 16 hours. The reaction mixture was poured into water (300 mL) and extracted with EtOAc (2×150 mL). The organic extracts were washed with brine (100 mL), combined, dried (Na$_2$SO$_4$) and concentrated in vacuo. The crude product was purified by column chromatography (silica, eluting with EtOAc/heptane) to give the title compound (7.07 g, 96%) as a yellow oil that crystallised on storage at 4° C. 1H NMR (600 MHz, Chloroform-d) δ 8.27 (t, J=1.9 Hz, 1H), 8.21 (ddd, J=8.3, 2.4, 1.1 Hz, 1H), 7.71 (dt, J=7.6, 1.2 Hz, 1H), 7.57 (t, J=7.9 Hz, 1H), 5.24 (d, J=13.0 Hz, 1H), 5.22 (d, J=13.0 Hz, 1H), 4.88 (d, J=9.5 Hz, 1H), 4.31 (dd, J=9.5, 2.6 Hz, 1H), 2.22-2.09 (m, 2H), 2.07-1.99 (m, 1H), 1.99-1.53 (m, 12H), 1.44 (s, 9H); LCMS (METHOD 3) (ES): m/z 455.4 [M+Na]$^+$, RT=1.04 min.

The two enantiomers were separated by preparative chiral SFC giving (3-nitrophenyl)methyl (2R)-2-(tert-butoxycarbonylamino)-3,3-di(cyclobutyl)propanoate (Preparation 63a) (Column: Lux A2 (4.6 mm×250 mm, 5 µm), Eluent: 25:75 MeOH:CO$_2$ (0.2% v/v NH$_3$), Temp: 40° C., Flow rate: 4 mL/min, BPR: 125 Bar, retention time: 1.3 min) and (3-nitrophenyl)methyl (2S)-2-(tert-butoxycarbonylamino)-3,3-di(cyclobutyl)propanoate (Preparation 63b) (Column: Lux A2 (4.6 mm×250 mm, 5 µm), Eluent: 20:80 IPA:CO$_2$ (0.2% v/v NH$_3$), Temp: 40° C., Flow rate: 4 mL/min, BPR: 125 Bar, retention time: 2.2 min).

Preparation 64

(2S)-2-(Tert-butoxycarbonylamino)-3,3-di(cyclobutyl)propanoic acid

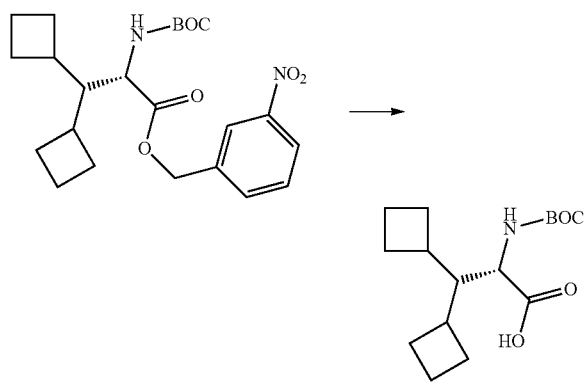

The ester of Preparation 63b (191 mg, 0.44 mmol) was dissolved in dioxane (880 µL) and 1 M aq. LiOH (0.88 mL, 0.88 mmol) was added to give an emulsion. This was stirred at room temperature for 16 hours to give a clear solution. The reaction mixture was concentrated in vacuo to give the crude title compound (assumed quantitative yield) which was used without further purification. LCMS (METHOD 3) (ES): m/z 296.2 [M−H]$^−$, RT=0.85 min.

Preparation 65

2-(3-hydroxypropyl)pyrazole-3-carboxylic acid

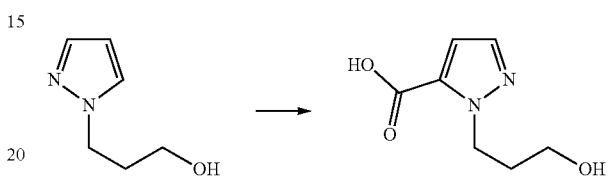

n-BuLi (6.2 mL of a 2.5M solution in hexanes, 15.5 mmol) was added dropwise to a solution of 3-pyrazol-1-ylpropan-1-ol (488 mg, 3.87 mmol) and TMEDA (1.16 mL, 899 mg, 7.74 mmol) in dry THF (12.8 mL) at 0° C. under argon. The resulting suspension was stirred for 30 min at 0° C. and CO$_2$ gas was passed through the solution for 30 min. 4M aq. HCl was slowly added until pH=2 and the mixture was extracted with EtOAc (3×40 mL), dried (Na$_2$SO$_4$) and concentrated in vacuo to give the desired product containing valeric acid. The crude mixture was taken up in water and EtOAc and the organic layer was extracted 10 times with water. The combined aqueous extracts were acidified with 4M aq. HCl and then extracted with EtOAc (4 times). The combined organic extracts were dried (Na$_2$SO$_4$) and concentrated in vacuo to give the title compound (285 mg, 43%). 1H NMR (400 MHz, Chloroform-d) δ 7.55 (d, J=2.2 Hz, 1H), 6.96 (d, J=2.3 Hz, 1H), 4.75 (d, J=6.2 Hz, 2H), 3.58 (d, J=6.1 Hz, 2H), 2.17-2.07 (m, 2H).

Preparation 66

Spiro[2.5]octan-6-yl 4-methylbenzenesulfonate

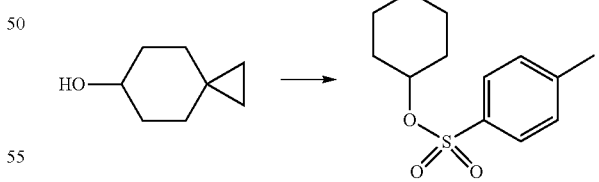

DABCO (891 mg, 7.94 mmol) was added to a solution of spiro[2.5]octan-6-ol (802 mg, 6.36 mmol) in DCM (8 mL) at 0° C. under argon followed by a solution of tosyl chloride (1.33 g, 6.99 mmol) in DCM (4 mL) over 6 minutes. The reaction was then stirred at room temperature for 30 minutes. The resulting suspension was poured into 0.5 M aq. HCl (40 mL) and extracted with TBME (2×60 mL). The organic layers were washed with brine (40 mL), combined, dried (Na$_2$SO$_4$) and concentrated in vacuo. The residue was purified by column chromatography (silica, eluting with EtOAc/heptane) to give the title compound (1.72 g, 92%) as a colourless crystalline solid. 1H NMR (600 MHz, Chloroform-d) δ 7.87-7.76 (m, 2H), 7.37-7.30 (m, 2H), 4.62 (tt, J=8.3, 3.8 Hz, 1H), 2.44 (s, 3H), 1.83-1.76 (m, 2H), 1.75-1.67 (m, 2H), 1.40-1.24 (m, 4H), 0.32-0.17 (m, 4H).

Preparation 67

Ethyl 2-(benzhydrylideneamino)-2-spiro[2.5]octan-6-yl-acetate

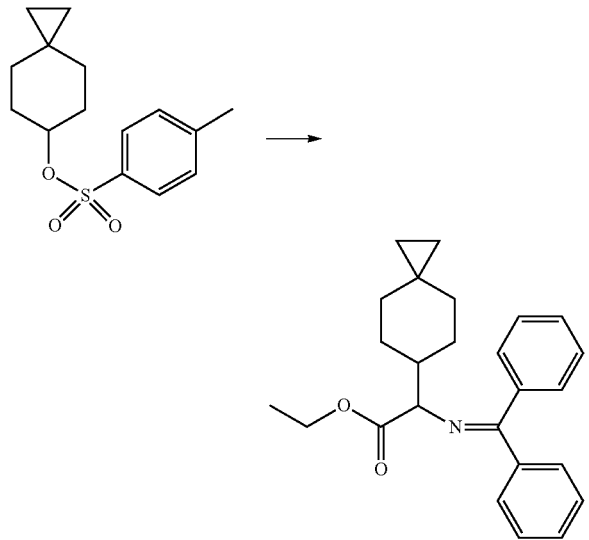

The title compound was prepared according to the method of Preparation 7 using ethyl 2-(benzhydrylideneamino)acetate (1.58 g, 5.92 mmol) and the tosylate of Preparation 66 (1.66 g, 5.92 mmol). This gave the title compound (1.60 g, 65%) as a yellow oil. 1H NMR (600 MHz, Chloroform-d) δ 7.71-7.62 (m, 2H), 7.49-7.42 (m, 3H), 7.40-7.36 (m, 1H), 7.37-7.29 (m, 2H), 7.19-7.11 (m, 2H), 4.18 (q, J=7.1 Hz, 2H), 3.87 (d, J=6.9 Hz, 1H), 2.19-2.04 (m, 1H), 1.86-1.67 (m, 4H), 1.55-1.45 (m, 1H), 1.33-1.23 (m, 4H), 1.18-1.13 (m, 1H), 0.89-0.79 (m, 2H), 0.32-0.20 (m, 2H), 0.19-0.08 (m, 2H); LCMS (METHOD 3) (ES): m/z 376.4 [M+H]$^+$, RT=1.08 min.

Preparation 68

Ethyl 2-(tert-butoxycarbonylamino)-2-spiro[2.5]octan-6-yl-acetate

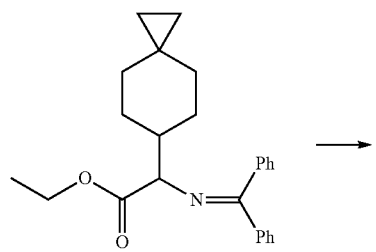

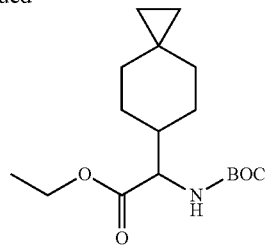

2M aq. HCl (7.2 mL) was added to a solution of the imine of Preparation 67 (1.60 g, 3.41 mmol) in THF (12 mL). The mixture was stirred for 1 hour at room temperature and the reaction was then concentrated in vacuo to remove THF. Water (10 mL) was added to the oily residue and the mixture was washed with EtOAc (2×30 mL). The organic washes were extracted with water (15 mL) and the combined aqueous layers were basified by the addition of sat. aq. NaHCO$_3$ (15 mL). The mixture was extracted with EtOAc (2×40 mL) and the organic layers were washed with brine (15 mL), combined, dried (Na$_2$SO$_4$) and concentrated in vacuo to give the crude free amino acid (719 mg) as a pale yellow oil. To this was added a solution of BOC anhydride (1.49 g, 6.81 mmol) in dioxane (30 mL) followed by DIPEA (2.32 mL, 1760 mg, 13.6 mmol). The reaction was stirred at room temperature for 67 hours then concentrated in vacuo. The residue was partitioned between sat. aq. NaHCO$_3$ (30 mL) and EtOAc (40 mL) and the aqueous layer was extracted with further EtOAc (40 mL). The organic extracts were washed with brine (30 mL), combined, dried (Na$_2$SO$_4$) and concentrated in vacuo. The residue was purified by column chromatography (silica, eluting with EtOAc/heptane) to give the title compound (1.08 g, 97%) as a colourless oil. 1H NMR (600 MHz, Chloroform-d) δ 5.20-4.91 (m, 1H), 4.35-4.09 (m, 3H), 1.83-1.67 (m, 3H), 1.67-1.61 (m, 1H), 1.61-1.52 (m, 1H), 1.45 (s, 9H), 1.34-1.22 (m, 5H), 0.93-0.83 (m, 2H), 0.31-0.23 (m, 2H), 0.22-0.13 (m, 2H).

Preparation 69

2-(Tert-butoxycarbonylamino)-2-spiro[2.5]octan-6-yl-acetic acid

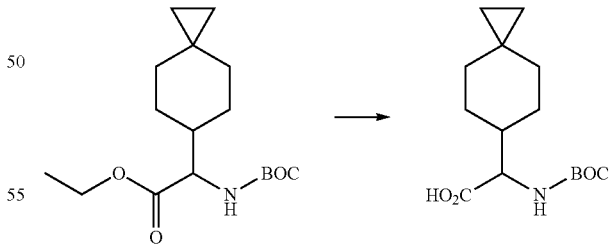

2M aq. NaOH (3.47 mL, 6.94 mmol) was added to a solution of the ester of Preparation 68 (1.08 g, 3.47 mmol) in EtOH (10 mL) and the reaction was stirred at room temperature for 1 hour. The solvent was removed in vacuo and brine (25 mL) and EtOAc (5 mL) were added to the residue. The mixture was cooled in an ice bath, carefully acidified with 2M aq. HCl (3.7 mL) and extracted with EtOAc (2×25 mL). The organic extracts were washed with brine (20 mL), combined, dried (Na$_2$SO$_4$) and concentrated in vacuo to give the title compound (897 mg, 87%) as a colourless solid. 1H NMR (600 MHz, Chloroform-d) δ 5.02 (d, J=9.0 Hz, 1H), 4.37-4.24 (m, 1H), 1.93-1.82 (m, 1H), 1.81-1.65 (m, 3H), 1.65-1.59 (m, 1H), 1.46 (s, 9H), 1.41-1.23 (m, 2H), 0.96-0.86 (m, 2H), 0.33-0.25 (m, 2H), 0.23-0.14 (m, 2H).

Preparation 69B 2-(Tert-butoxycarbonylamino)-3-cyclopropyl-butanoic acid

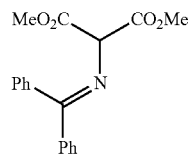

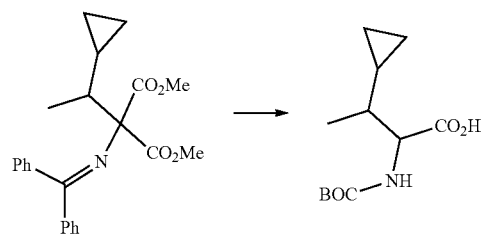

DIAD (17.4 mmol, 3520 mg, 3.43 mL) was added slowly over 5 min to a solution of 1-cyclopropylethanol (11.6 mmol, 1000 mg, 1.14 mL), dimethyl 2-(benzhydrylideneamino)propanedioate (15.1 mmol, 4700 mg) and 1M trimethylphosphine in toluene (17.4 mmol, 17.4 mL) in dry toluene (50 mL) at −60° C. under argon. After 1 h at −60° C. the cooling bath was removed and the reaction was allowed to warm to room temperature and stirred overnight. The resulting purple solution was evaporated and purified by column chromatography (silica, eluting with EtOAc:heptane) to give dimethyl 2-(benzhydrylideneamino)-2-(1-cyclopropylethyl)propanedioate (880 mg, 20%) as a pale yellow oil. This was dissolved in MeOH (20 mL), 4M NaOH (4 mL) was added and the mixture was heated at reflux for 18 hours. After cooling to room temperature most of the MeOH was evaporated and the pH was adjusted to 2 with 5M HCl (aq). The mixture was stirred at 60° C. for 18 h then cooled to room temperature. The pH was adjusted to 10-11 with 4M NaOH and a solution of BOC anhydride (2.3 mmol, 510 mg) in THF (10 mL) was added. The mixture was stirred vigorously for 2 h at room temperature then 5M HCl (aq) was added to pH=3. The mixture was extracted with EtOAc (3×25 mL), dried (Na$_2$SO$_4$) and evaporated. Purification by column chromatography (silica, eluting with EtOAc:heptane) gave the title compound (239 mg, 42% Yield) as a pale yellow oil. LCMS (METHOD 3) (ES): m/z 242.2 [M−H], RT=0.66 min.

Preparation 70

Methyl (2S)-2-amino-3-(3-hydroxyphenyl)propanoate hydrochloride

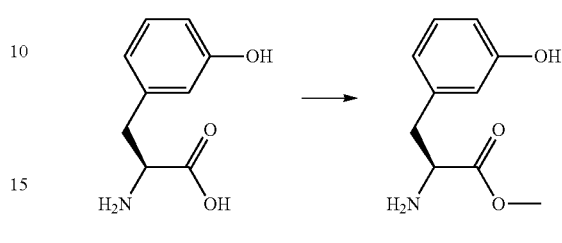

To a stirred solution of (S)-2-amino-3-(3-hydroxyphenyl) propanoic acid (25 g, 138.12 mmol) in MeOH (250 mL) was added SOCl$_2$ (29 mL, 414 mmol) at 0° C. dropwise and the reaction mixture was stirred at 70° C. for 6 h. The reaction mixture was concentrated under reduced pressure. The crude material was triturated with Et$_2$O (2×200 mL) to afford the title compound as an off-white solid (64 g, 100%). $^1$H NMR (400 MHz, DMSO-d$_6$) δ 9.51 (br s, 1H), 8.62 (br s, 3H), 7.13-7.09 (t, J=12 Hz, 1H), 6.70-6.67 (dd, J=7.6 Hz, 0.8 Hz, 1H), 6.63-6.62 (dd, J=7.6 Hz, 2 HZ, 2H), 4.19 (t, J=6.8 Hz, 1H), 3.68 (s, 3H), 3.11-2.90 (m, 2H). LCMS (METHOD 5) (ESI): m/z: 196 [M+H$^+$]; RT=2.09 min (ACQUITY BEH C18 column, 0.05% FA in water with MeCN); Chiral HPLC: 99%, RT: 4.09 min, Column: CHIRALPAC IG (4.6*250) mm, 5u, Co-Solvent: 0.5% of DEA in MeOH (25%), Column Temperature: 30° C., Flow: 3 mL/min.

Preparation 71

Methyl (2S)-2-((tert-butoxycarbonyl)amino)-3-(3-hydroxyphenyl)propanoate

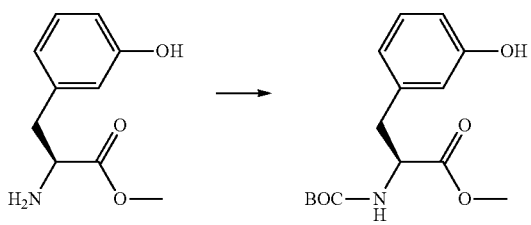 [SMILES: COC(=O)[C@@H](N)Cc1cccc(O)c1 ; COC(=O)[C@H](Cc1cccc(O)c1)NC(=O)OC(C)(C)C]

(BOC)$_2$O (29 mL, 138 mmol) was added to a stirred solution of the ester of Preparation 70 (32 g, 138 mmol) and NaHCO$_3$ (34.8 g, 415 mmol) in THF:H$_2$O (400:80 mL) at 0° C. The reaction mixture was stirred at room temperature for 16 h. On completion the reaction mixture was diluted with water (500 mL) and extracted with EtOAc (2×500 mL) and concentrated under reduced pressure. The crude material was triturated with Et$_2$O (2×200 mL) and dried under reduced pressure to afford the title compound as a viscous orange liquid (30 g, 75%). $^1$H NMR (400 MHz, DMSO-d$_6$) δ 7.14 (t, J=8.8 Hz, 1H), 6.72-6.71 (dd, 0.7=1.6 Hz, 7.6 Hz 1H), 6.7 (d, J=6.8 Hz, 1H), 6.38 (d, J=1.6 Hz, 1H), 5.71 (br s, 1H), 5.02 (d, J=7.6 Hz, 1H), 4.57 (d, J=3.9 Hz, 1H), 3.71 (s, 3H), 3.04-3.99 (m, 2H), 1.48 (S, 9H). LCMS (METHOD 5) (ESI): m/z: 296 [M+H$^+$]; 99%; RT=1.74 min (ACQUITY BEH C18 column, 0.05% FA in water with MeCN).

Preparation 72

Methyl (2S)-2-((tert-butoxycarbonyl)amino)-3-(2-chloro-5-hydroxyphenyl)propanoate

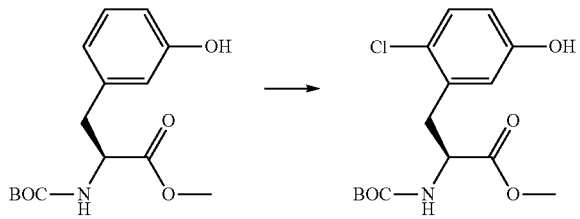 [SMILES: COC(=O)[C@H](Cc1cccc(O)c1)NC(=O)OC(C)(C)C ; COC(=O)[C@H](Cc1cc(O)ccc1Cl)NC(=O)OC(C)(C)C]

To a stirred solution of the phenol of Preparation 71 (44 g, 149.15 mmol) in THF (550 mL) was added N-chlorosuccinimide (19.9 g, 149 mmol) at 0° C. The resulting reaction mixture was stirred at room temperature for 10 h. On completion, the reaction mixture was diluted with water (1 L) and extracted with EtOAc (2×1 L). The combined organic layers were washed with water (1 L), brine (1 L), dried over anhydrous $Na_2SO_4$, filtered and concentrated under reduced pressure to afford crude compound. This was purified by silica gel (230-400 mesh) column chromatography (15% EtOAc in Hexane as an eluent) to afford the title compound as an off-white solid (40 g, 81%). $^1$H NMR (300 MHz, $CDCl_3$) δ 9.5 (S, 1H), 7.34 (d, J=11.2 Hz, 1H), 7.17 (d, J=11.2 Hz, 1H), 6.74 (d, J=4 Hz, 1H), 6.67-6.63 (dd, J=1H, 1H), 4.26-4.18 (m, 1H), 4.04 (q, J=8 Hz, 1H), 3.61 (s, 3H), 3.10-3.04 (m, 1H), 1.45 (S, 9H; LCMS (METHOD 5) (ESI): m/z: 330 [M+H$^+$]; RT=2.23 min (ACQUITY UPLC BEH C18 column, 0.1% FA in water with MeCN).

Preparation 73

Methyl-(2S)-2-((tert-butoxycarbonyl)amino)-3-(2-chloro-5-(((trifluoromethyl)sulfonyl)oxy)phenyl)propanoate

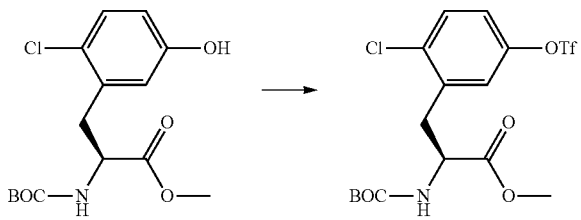 [SMILES: COC(=O)[C@H](Cc1cc(O)ccc1Cl)NC(=O)OC(C)(C)C ; COC(=O)[C@H](Cc1cc(OS(=O)(=O)C(F)(F)F)ccc1Cl)NC(=O)OC(C)(C)C]

PhN(Tf)$_2$ (3.5 g, 9.82 mmol) was added to a stirred solution of the phenol of Preparation 72 (3 g, 8.928 mmol) and TEA (3.8 mL, 26.78 mmol) in DCM (30 mL) at 0° C. The resulting reaction mixture was stirred at room temperature for 2 h. On completion, the reaction mixture was diluted with water (100 mL) and extracted with DCM (2×100 mL). The combined organic layers were washed with water (100 mL), brine (100 mL), dried over anhydrous $Na_2SO_4$, filtered and concentrated under reduced pressure to afford the title compound as an off-white solid (4 g, crude). $^1$H NMR (300 MHz, DMSO-$d_6$) δ 7.07 (m, 2H), 6.98-6.93 (d, J=7.5 Hz, 2H), 4.34-4.26 (m, 1H), 3.65 (s, 3H), 3.13-2.92 (m, 2H), 1.40 (s, 9H).

Preparation 74

Methyl (2S)-2-((tert-butoxycarbonyl)amino)-3-(2-chloro-5-cyanophenyl)propanoate

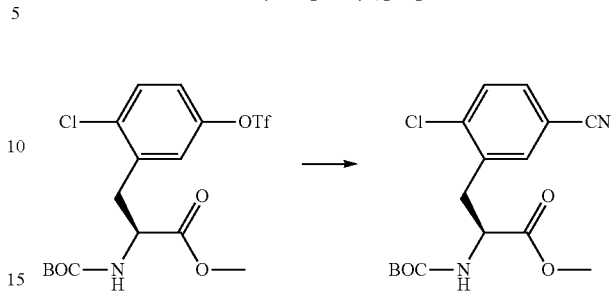

Pd$_2$(dba)$_3$ (1.091 g, 1.193 mmol) and dppf (1.32 g, 2.3 mmol) were added to a stirred solution of the ester of Preparation 73 (5.5 g, 11.93 mmol) and Zn(CN)$_2$ (1.39 g, 11.93 mmol) in DMF (550 mL) at room temperature. The resulting reaction mixture was stirred at 130° C. for 3 h. On completion the reaction mixture was cooled to room temperature, diluted with water (100 mL) and extracted with EtOAc (2×100 mL). The combined organic layers were washed with water (100 mL), brine (100 mL), dried over anhydrous $Na_2SO_4$, filtered and concentrated under reduced pressure to afford crude compound. This was purified by silica gel (100-200 mesh) column chromatography (12% EtOAc in Hexane as an eluent) to give the title compound as an off-white solid (1.2 g, 28%). $^1$H NMR (300 MHz, DMSO-$d_6$) δ 7.79-7.75 (m, 2H), 7.68-7.66 (m, 1H), 7.36 (d, J=9.3 Hz, 1H), 4.34-4.31 (m, 1H), 3.65 (s, 3H), 3.31-3.24 (dd, J=7.5 Hz, 16.8 Hz, 1H), 2.99-2.91 (dd, J=11 Hz, 14 Hz, 1H), 1.40 (S, 9H). LCMS (METHOD 5) (ESI): m/z: 339 [M+H$^+$]; RT=2.03 min (ACQUITY UPLC BEH C18 column, 0.1% FA in water with MeCN).

Preparation 75

(2S)-2-((tert-butoxycarbonyl)amino)-3-(2-chloro-5-cyanophenyl)propanoic acid

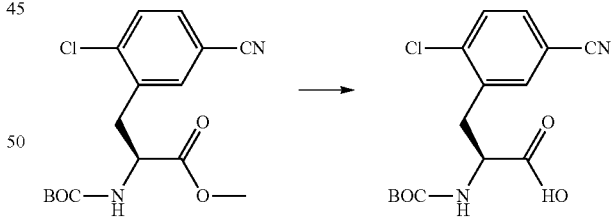

To a stirred solution of the ester of Preparation 74 (1.2 g, 3.55 mmol) in THF:H$_2$O (10 mL, 1:1) was added LiOH.H$_2$O (0.223 g, 5.32 mmol) at room temperature. The resulting reaction mixture was stirred for 3 h. On completion the reaction mixture was concentrated and diluted with water (50 mL). The aqueous layer was washed with EtOAc (50 mL) then acidified with sat. aq. citric acid to pH 4 and extracted with EtOAc (2×100 mL). The organic layers were combined, dried over anhydrous $Na_2SO_4$ filtered and concentrated under reduced pressure to afford the title compound as an off-white solid (0.82 g, 71%). $^1$H NMR (300 MHz, DMSO-$d_6$) δ 12.9 (br s, 1H), 7.82-7.65 (m, 3H), 7.68-7.66 (d, J=8.7 Hz, 1H), 4.28-4.20 (m, 1H), 3.27-3.26

(m, 1H), 2.94-2.86 (m, 1H), 1.40 (S, 9H); LCMS (METHOD 5) (ESI): m/z: 325 [M+H⁺]; RT=1.77 min (AC-QUITY UPLC BEH C18 column, 0.1% FA in water with MeCN).

Preparation 76

2,2,8,8-Tetrafluorodispiro[3.1.36.14]decane-5,10-dione

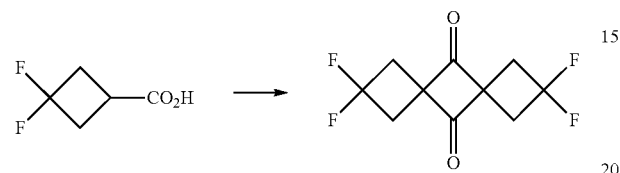

Oxalyl chloride (4.9 mL, 7.4 g, 58 mmol) was added slowly to a solution of 3,3-difluorocyclobutanecarboxylic acid (5.3 g, 39 mmol) and DMF (1 drop) in DCM (50 mL) and the mixture was stirred at room temperature for 4 hours. The mixture was concentrated in vacuo to give a semi solid that was dissolved in benzene (50 mL) and triethylamine (10.8 mL, 7.86 g, 77.6 mmol) was added slowly. The resulting orange suspension was stirred at 50° C. for 16 hours. After cooling to room temperature the solid was filtered off and the filtrate was washed with 1M HCl (40 mL), dried (Na₂SO₄) and evaporated to give the crude title compound as a brown oil which was used without any further purification.

Preparation 77

Bis(3,3-difluorocyclobutyl)methanone

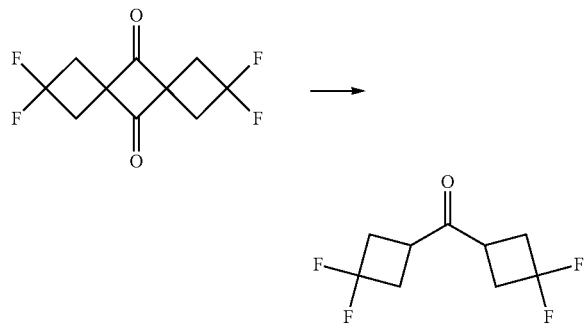

A mixture of the diketone of Preparation 76 (39 mmol) in 4M NaOH (20 mL) and THF (10 mL) was stirred and heated at reflux for 5 min and then stirred at room temperature for 16 hours. The mixture was diluted with water (20 mL), extracted with ether (2×50 mL) and the ether extracts were dried (Na₂SO₄) and evaporated. The crude product was purified by column chromatography (silica, eluting with EtOAc:hexane) to give the title compound (1.74 g, 43%) as a pale yellow oil. 1H NMR (300 MHz, Chloroform-d) δ 3.23-3.01 (m, 2H), 2.90-2.60 (m, 8H).

Preparation 78

3-[1-(3,3-Difluorocyclobutyl)-2-methoxy-vinyl]-1,1-difluoro-cyclobutane

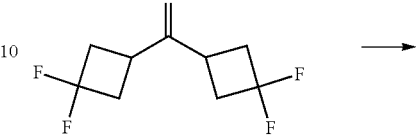

The ketone of Preparation 77 was reacted according to the method of Preparation 25 to give the title compound (1.99 g, 100%) as an impure pale yellow oil. 1H NMR (300 MHz, Chloroform-d) δ 5.83 (s, 1H), 3.59 (s, 3H), 2.81-2.56 (m, 8H), 2.48-2.24 (m, 2H).

Preparation 79

2,2-Bis(3,3-difluorocyclobutyl)acetaldehyde

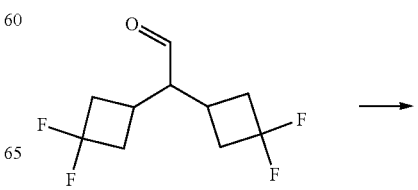

The vinyl ether of Preparation 78 was treated according to the method of Preparation 26 to give the title compound (1.70 g, 91%) as an impure clear oil. 1H NMR (300 MHz, Chloroform-d) δ 9.67 (d, J=2.2 Hz, 1H), 2.86-2.24 (m, 11H).

Preparation 80

5-[Bis(3,3-difluorocyclobutyl)methyl]imidazolidine-2,4-dione

-continued

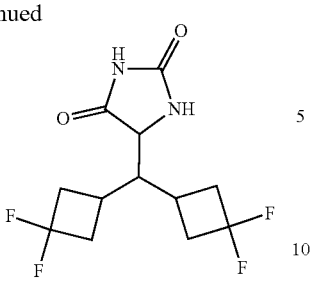

The aldehyde of Preparation 79 was treated with KCN and ammonium carbonate according to the method of Preparation 27 to give the title compound (1.60 g, 72%). 1H NMR (600 MHz, DMSO-d6) δ 10.72 (s, 1H), 7.95 (s, 1H), 4.02 (m, 1H), 2.60-2.47 (m, 5H), 2.43-2.18 (m, 3H), 2.13-1.98 (m, 3H); LCMS (METHOD 3) (ES): m/z 293.1 [M–H], RT=0.56 min.

Preparation 81

2-(Tert-butoxycarbonylamino)-3,3-bis(3,3-difluorocyclobutyl)propanoic acid

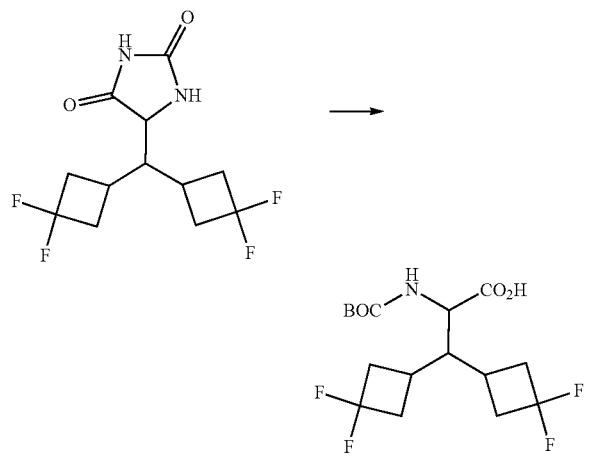

The hydantoin of Preparation 80 was hydrolysed and protected according to the method of Preparation 27 to give the title compound (209 mg, 49%) as a clear oil that solidified on standing. LCMS (METHOD 3) (ES): m/z 368.3 [M–H], RT=0.75 min.

Preparation 82

Ethyl 2-(benzhydrylideneamino)-2-(3,3-dimethylcyclopentyl)acetate

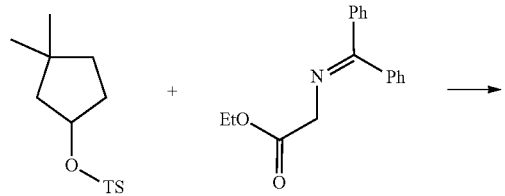

-continued

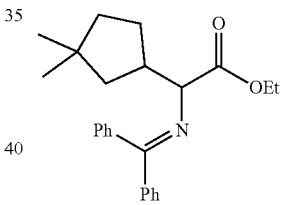

To a solution of (3,3-dimethylcyclopentyl) 4-methylbenzenesulfonate (400 mg, 1.49 mmol) and ethyl 2-(benzhydrylideneamino)acetate (400 mg, 1.50 mmol) in THF (5 mL) was added LiHMDS (1M solution in THF, 1.7 mL, 1.7 mmol). The solution was stirred at room temperature for 16 hours. The resulting suspension was diluted with diisopropyl ether (20 mL) and washed with a mixture of water (10 mL) and sat. aq. NH$_4$Cl (10 ml). The aqueous phase was extracted with diisopropyl ether and the combined organic phases were dried over MgSO$_4$ and concentrated in vacuo. The residue was purified by column chromatography (silica, heptane/EtOAc 4:1) to give the title compound (0.45 g, 74%) as a yellow oil. LCMS (METHOD 3) (ES): m/z 364.3 [M+H]$^+$, RT=1.07 min.

Preparation 83

Ethyl 2-(tert-butoxycarbonylamino)-2-(3,3-dimethylcyclopentyl)acetate

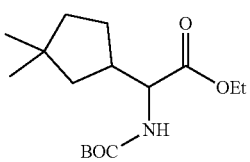

To a solution of the ester of Preparation 82 (0.45 g, 1.2 mmol) in THF (10 mL) was added 6M HCl (5 mL, 30 mmol) and the mixture was stirred at room temperature for 30 min. The reaction was diluted with water (20 mL) and washed twice with diisopropyl ether. The aqueous mixture was basified to pH 10 with solid Na$_2$CO$_3$ and THF (10 mL) was added followed by Boc$_2$O (540 mg, 2.47 mmol). The mixture was stirred at room temperature for 18 hours and the reaction mixture was extracted diisopropyl ether (2×20 mL). The combined organic phases were dried over MgSO$_4$ and concentrated in vacuo. The residue was purified by column chromatography (silica, eluting with EtOAc/heptane 1:8) to give the title compound (299 mg, 81%) as a colourless oil. 1H NMR (400 MHz, Chloroform-d) δ 5.00 (br s, 1H), 4.31-4.08 (m, 3H), 2.39 (m, 1H), 1.81-1.68 (m, 1H), 1.62-1.34 (m, 12H), 1.32-1.15 (m, 5H), 1.03 (2×s, 3H), 0.96 (s, 3H).

Preparation 84

2-(Tert-butoxycarbonylamino)-2-(3,3-dimethylcyclopentyl)acetic acid

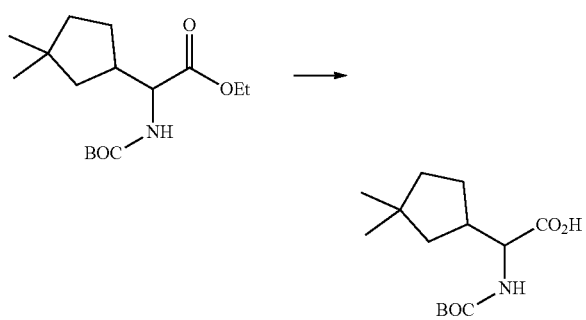

According to the method of Preparation 40 the ester of Preparation 83 was hydrolysed to give the title compound (254 mg, 99%) as a colourless solid.

Preparation 85

2-(Tert-butoxycarbonylamino)-2-(2-methylcyclopentyl)acetic acid

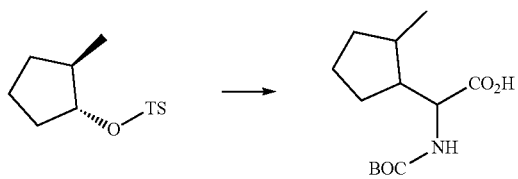

According to the methods of Preparation 82-84 [(trans-2-methylcyclopentyl] 4-methylbenzenesulfonate was converted to the title compound.

Preparation 86

Ethyl (2S)-2-(4-methoxyanilino)-2-[(7S)-6-oxospiro[2.5]octan-7-yl]acetate

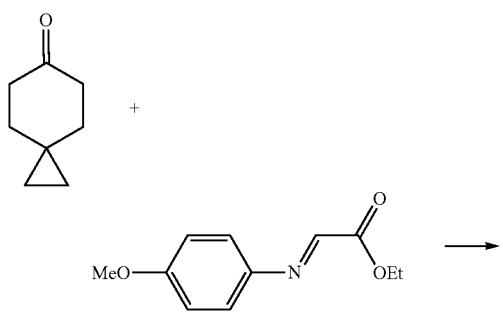

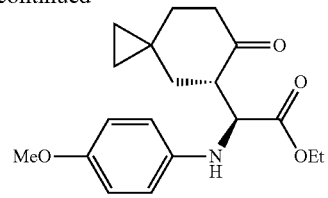

Ethyl (2E)-2-(4-methoxyphenyl)iminoacetate (1.5 g, 7.2 mmol) was dissolved in DMSO (4 mL) in a microwave vial and spiro[2.5]octan-6-one (1 g, 8.05 mmol) was added to the solution, followed by (S)-proline (90 mg, 0.8 mmol). The mixture was shaken at room temperature for 4 days. The mixture was poured into water (10 mL) and TBME (10 mL). The phases were separated and the aqueous phase was extracted twice with TBME. The combined organic phases were dried over $Na_2SO_4$ and concentrated in vacuo. The residue was purified by flash column chromatography (silica, eluting with heptane/EtOAc 3:1), to give the title compound (1.28 g, 53%) as an oil, which gradually solidified during storage. LCMS (METHOD 3) (ES): m/z 332.3 [M−H], RT=0.80 min.

Preparation 87

Ethyl (2S)-2-(tert-butoxycarbonylamino)-2-[(7S)-6-oxospiro[2.5]octan-7-yl]acetate (Diacetoxyiodo)benzene (4.47 g, 13.9 mmol) was dissolved in MeOH (30 mL) and a solution of the ester of Preparation 86 (1.15 g, 3.47 mmol) in MeOH (20 mL) was added over 30 min. The reaction mixture was stirred at room temperature for 40 min then 1M HCl (50 mL) was added. The obtained suspension was stirred at room temperature for 2 hours to give a solution. The mixture was concentrated in vacuo to remove most of the MeOH and washed with DCM (2×40 mL). To the aqueous phase was added DCM (20 mL) and then $BOC_2O$ (2 g, 9.16 mmol). The reaction mixture was basified to pH 9 with solid $K_2CO_3$ and the mixture was stirred at room temperature for 18 hours. The phases were separated and the aqueous phase was extracted with further DCM (2×30 mL). The combined organic phases were dried over $Na_2SO_4$ and concentrated in vacuo. The residue was purified by column chromatography (silica eluting with heptane/EtOAc 3:1) to give the title compound (0.46 g, 41%), containing 6-7% of a minor diastereomer, diastereomer, as a yellow oil. 1H NMR (400 MHz, Chloroform-d)

δ 5.36 (d, J=8.6 Hz, 1H), 4.32-4.06 (m, 3H), 3.07-2.85 (m, 1H), 2.66-2.31 (m, 3H), 2.14 (td, J=13.7, 5.4 Hz, 1H), 1.44 (s, 9H), 1.39-1.17 (m, 5H), 0.61-0.43 (m, 4H).

Preparation 88

Ethyl (2S)-2-(tert-butoxycarbonylamino)-2-[(7S)-6,6-difluorospiro[2.5]octan-7-yl]acetate

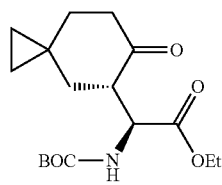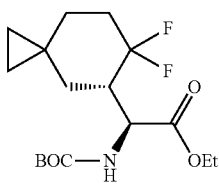

The ketone of Preparation 87 was treated with DAST according to the method of Preparation 39 to give the title compound (97 mg, 17%) as a brown oil. 1H NMR (400 MHz, Chloroform-d) δ 5.12 (d, J=9.2 Hz, 1H), 4.70-4.50 (m, 1H), 4.31-4.08 (m, 2H), 2.41 (dd, J=27.1, 12.8 Hz, 1H), 2.22-1.95 (m, 2H), 1.94-1.72 (m, 1H), 1.53-1.37 (m, 9H), 1.37-1.07 (m, 4H), 0.99-0.80 (m, 2H), 0.54-0.39 (m, 2H), 0.29 (dd, J=10.9, 4.7 Hz, 2H).

Preparation 89

(2S)-2-(Tert-butoxycarbonylamino)-2-[(7S)-6,6-difluorospiro[2.5]octan-7-yl]acetic acid

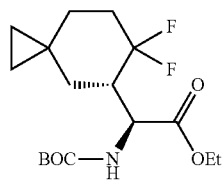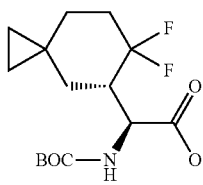

To a solution of the ester of Preparation 88 (97 mg, 0.279 mmol) in water (0.5 mL) and MeOH (2 mL) was added NaOH (150 mg, 3.75 mmol). The obtained mixture was stirred at room temperature for 2 hours then diluted with water (15 mL) and washed with DCM (15 mL). The aqueous phase was acidified with 5M HCl and extracted with DCM (2×15 mL). The combined organic phases were dried over Na$_2$SO$_4$ and concentrated in vacuo to give the title compound (82 mg, 78%) as a white foam.

Preparation 90

(2S)-2-(tert-butoxycarbonylamino)-2-[(1S)-2,2-difluoro-5,5-dimethyl-cyclohexyl]acetic acid

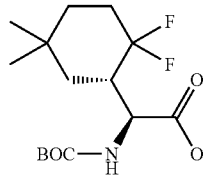

According to the methods of Preparations 86-89 4,4-dimethylcyclohexanone was converted to the title compound (190 mg). 1H NMR (400 MHz, Chloroform-d) δ 5.13 (d, J=8.7 Hz, 1H), 4.71 (d, J=8.6 Hz, 1H), 2.50 (dd, J=28.3, 13.2 Hz, 1H), 2.09-1.71 (m, 2H), 1.63-1.33 (m, 5H), 1.45 (s, 9H), 1.00 (s, 3H), 0.99 (s, 3H).

Preparation 91

6-Bromo-4-fluoro-2,3-dihydro-1H-inden-1-ol

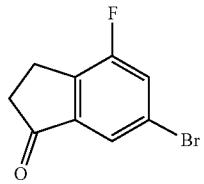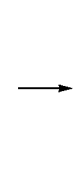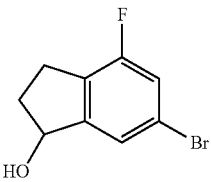

To a stirred solution of 6-bromo-4-fluoro-2,3-dihydro-1H-inden-1-one (9 g, 39.5 mmol) in EtOH (90 mL) at 0° C. was added sodium borohydride (1.49 g, 39.5 mmol). The reaction mixture was allowed to stir at room temperature for 2 hours then evaporated under vacuum. Water was added and the mixture was extracted with EtOAc (2×200 mL). The combined organic layers were washed with brine, dried over sodium sulfate, filtered and concentrated to afford the title compound as an oily liquid (8.2 g, 90%). 1H NMR (400 MHz, CHLOROFORM-d) δ 7.34 (d, J=0.76 Hz, 1H) 7.12 (dd, J=8.28, 1.42 Hz, 1H) 5.23 (q, J=6.10 Hz, 1H) 3.03 (ddd, J=16.40, 8.66, 4.36 Hz, 1H) 2.71-2.80 (m, 1H) 2.48-2.57 (m, 1H) 1.96-2.02 (m, 1H) 1.92-1.96 (m, 1H); LCMS (METHOD 5) (ESI): m/z 231 [M+H$^+$]; RT=3.34 min (ACQUITY UPLC BEH C18 column, 0.1% FA in water with MeCN).

Preparation 92

(S)-6-bromo-4-fluoro-2,3-dihydro-1H-inden-1-ol (Prep. 92A) and (R)-6-bromo-4-fluoro-2,3-dihydro-1H-inden-1-yl acetate (Prep. 92B)

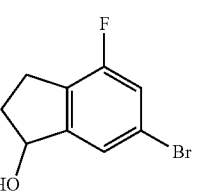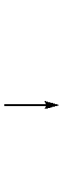

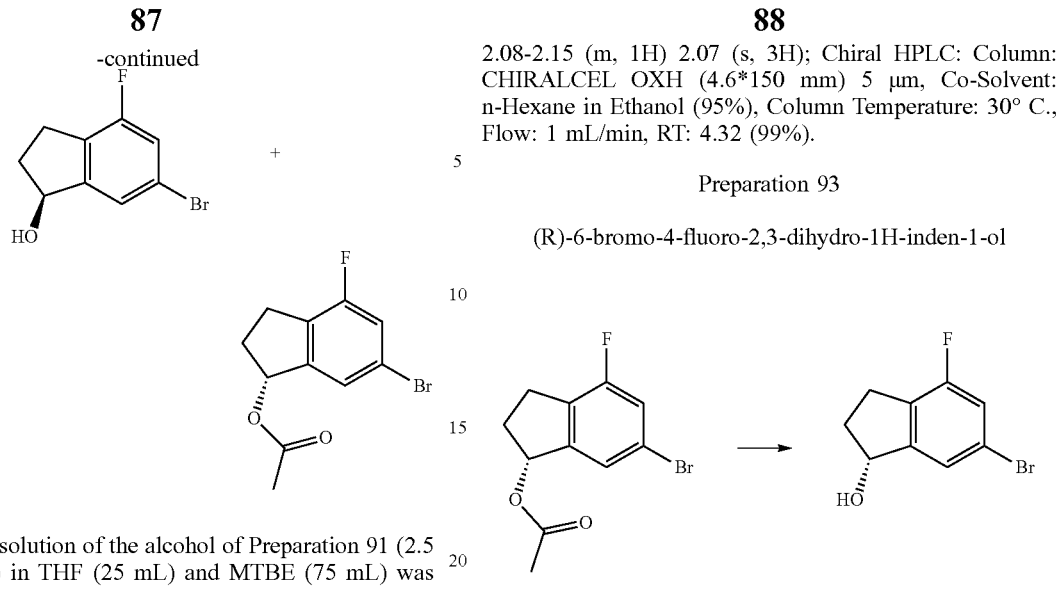

To a stirred solution of the alcohol of Preparation 91 (2.5 g, 10.9 mmol) in THF (25 mL) and MTBE (75 mL) was added vinyl acetate (5 mL) and CAL-B (enzyme, Lipase B *Candida Antarctica*, 410 mg, Sigma catalogue number 54326) at room temperature. The reaction mixture was stirred at room temperature for 60 hours, at which point analysis by chiral HPLC showed 99.9% conversion). The reaction mixture was filtered through Celite, washing with THF (50 mL). The filtrate was evaporated under vacuum and the crude product was purified by silica-gel column chromatography, using EtOAc: Hexane as an eluent, to afford (S)-6-bromo-4-fluoro-2,3-dihydro-1H-inden-1-ol (1.2 g, 48%) as a white solid and (R)-6-bromo-4-fluoro-2,3-dihydro-1H-inden-1-yl acetate (970 mg, 33%) as a viscous oil. Prep. 92A: (S)-6-bromo-4-fluoro-2,3-dihydro-1H-inden-1-ol: 1H NMR (400 MHz, CHLOROFORM-d) δ 7.33 (s, 1H) 7.11 (dd, J=8.31, 0.98 Hz, 1H) 5.22 (t, J=5.87 Hz, 1H) 3.02 (ddd, J=16.63, 8.80, 4.40 Hz, 1H) 2.70-2.80 (m, 1H) 2.47-2.57 (m, 1H) 1.91-2.02 (m, 1H) 1.81-1.89 (m, 1H); Chiral HPLC: Column: CHIRALCEL OD-3 (4.6*150 mm) 3 μm, Co-Solvent: 0.5% DEA in Methanol (10%), Column Temperature: 30° C., Flow: 3 g/min, RT: 1.62 (99.97%).

Prep. 92B: (R)-6-bromo-4-fluoro-2,3-dihydro-1H-inden-1-yl acetate: 1H NMR (400 MHz, CHLOROFORM-d) δ 7.35 (s, 1H) 7.11 (dd, J=8.31, 0.98 Hz, 1H) 6.13-6.16 (m, 1H) 3.01-3.09 (m, 1H) 2.82-2.88 (m, 1H) 2.48-2.56 (m, 1H) 2.08-2.15 (m, 1H) 2.07 (s, 3H); Chiral HPLC: Column: CHIRALCEL OXH (4.6*150 mm) 5 μm, Co-Solvent: n-Hexane in Ethanol (95%), Column Temperature: 30° C., Flow: 1 mL/min, RT: 4.32 (99%).

Preparation 93

(R)-6-bromo-4-fluoro-2,3-dihydro-1H-inden-1-ol

To a stirred solution of the ester of Preparation 92B (4.0 g, 14.6 mmol) in THF (120 mL), methanol (120 mL) and water (4 mL) at 0° C. was added LiOH hydrate (737 mg, 17.6 mmol) portion wise. The reaction mixture was stirred at room temperature for 2 hours then concentrated under reduced pressure. The residue was diluted with water (50 mL) and extracted with EtOAc (2×70 mL). The combined organic layers were dried over anhydrous $Na_2SO_4$ and concentrated under reduced pressure to afford the title compound (3.3 g, 86%). 1H NMR (400 MHz, CHLOROFORM-d) δ 7.35 (s, 1H) 7.13 (dd, J=8.28, 1.42 Hz, 1H) 5.24 (q, J=6.47 Hz, 1H) 3.04 (ddd, J=16.43, 8.69, 4.41 Hz, 1H) 2.71-2.82 (m, 1H) 2.54 (dddd, J=13.19, 8.45, 6.98, 4.41 Hz, 1H) 1.93-2.05 (m, 1H) 1.81 (d, J=6.87 Hz, 1H); Chiral HPLC: Column: CHIRALCEL OD-3 (4.6*150 mm) 3 μm, Co-Solvent: 0.5% DEA in Methanol (10%), Column Temperature: 30° C., Flow: 3 g/min, RT: 1.74 (99%).

Preparations 94-101

The alcohols of Preparations 94-101 were synthesised according to the methods of Preparations 91-93 from the appropriate ketones.

| Prep. No. | Structure | Name | 1H NMR and mass spec data |
|---|---|---|---|
| 94 | 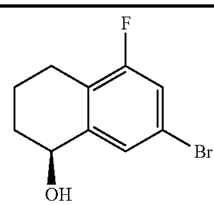 | (S)-7-bromo-5-fluoro-1,2,3,4-tetrahydronaphthalen-1-ol | 1H NMR (400 MHz, DMSO-d6) δ 7.43 (br s, 1H), 7.33-7.30 (dd, J = 2 Hz, 9.2 Hz, 1H), 5.42-5.41 (d, J = 5.6 Hz, 1H), 4.57-4.53 (m, 1H), 2.57-2.56 (m, 2H), 1.90-1.87 (m, 2H), 1.68-1.61 (m, 2H); LCMS (METHOD 5) (ESI): m/z: 245 [M − H]; RT = 3.54 min (ACQUITY UPLC BEH C18 column, 0.1% FA in water with MeCN). Chiral purity: 98% (RT: 3.99) Column: CHIRALPAK IG-3 (150 × 4.6 mm) 3 μm; Co-solvent: 0.5% DEA in MeOH, % of Co-solvent: 10, Total flow: 3 gm/min, ABPR: 1500 psi, Temperature: 30° C. |
| 95 | 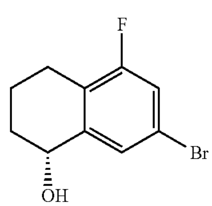 [SMILES: O[C@@H]1CCCc2c(F)cc(Br)cc21] | (R)-7-bromo-5-fluoro-1,2,3,4-tetrahydronaphthalen-1-ol | 1H NMR (400 MHz, CHLOROFORM-d) δ 7.43 (s, 1H), 7.10 (dd, J = 8.83, 1.96 Hz, 1H), 4.73 (br d, J = 4.14 Hz, 1H), 2.67-2.77 (m, 1H), 2.54-2.64 (m, 1H), 1.93-2.06 (m, 2H), 1.73-1.88 (m, 3H); Chiral Purity: 99% (RT: 5.19 min), Column: Chiralpak IG-3 (4.6 × 150 mm) 3 μm, Co-solvent: 0.5% DEA in MeOH, Flow: 3 gm/min, Temperature: 30° C. |

-continued

| Prep. No. | Structure | Name | 1H NMR and mass spec data |
|---|---|---|---|
| 96 | 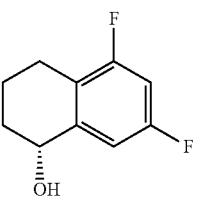 [SMILES: O[C@@H]1CCCc2c(F)cc(F)cc21] | (R)-5,7-difluoro-1,2,3,4-tetrahydronaphthalen-1-ol | 1H NMR (400 MHz, CHLOROFORM-d) δ 7.03-7.00 (dd, J = 2.8 Hz, 1H), 6.71-6.66 (m, 1H), 4.73-4.71 (m, 1H), 2.76-2.58 (m, 2H), 2.07-1.83 (m, 2H), 1.86-1.71 (m, 3H). |
| 97 | 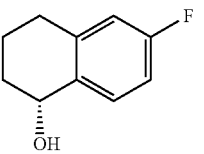 [SMILES: O[C@@H]1CCCc2cc(F)ccc21] | (R)-6-fluoro-1,2,3,4-tetrahydronaphthalen-1-ol | 1H NMR (300 MHz, DMSO-d6) δ 7.42-7.37 (dd, J = 8.4 Hz, 6.6 Hz, 1H), 6.98-6.84 (m, 2H), 5.13-5.10 (d, J = 5.4 Hz, 1H), 4.54-4.53 (m, 1H), 2.72-2.66 (m, 2H), 1.89-1.82 (m, 2H), 1.72-1.61 (m, 2H); LCMS (METHOD 5) ESI): m/z: 149 [M + H⁺ −18]; RT = 2.13 min (ACQUITY UPLC BEH C18 column, 0.1% FA in water with MeCN); chiral purity: 98% (RT: 5.57 min) Column: CHIRALPAK IG-3 (250 × 4.6 mm) 5 μm; Co-solvent: 0.5% DEA in MeOH, % of Co-solvent: 25, Total flow: 3 gm/min, ABPR: 1500 psi, Temperature: 30° C. |
| 98 | 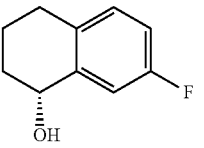 [SMILES: O[C@@H]1CCCc2ccc(F)cc21] | (R)-7-fluoro-1,2,3,4-tetrahydronaphthalen-1-ol | 1H NMR (400 MHz, CHLOROFORM-d) δ 7.16 (dd, J = 9.59, 2.72 Hz, 1H) 7.05 (dd, J = 8.45, 5.72 Hz, 1H) 6.89 (td, J = 8.45, 2.72 Hz, 1H) 4.74 (br d, J = 4.90 Hz, 1H) 2.60-2.89 (m, 2H) 1.90-2.09 (m, 2H) 1.70-1.89 (m, 3H): chiral HPLC: Column: Chiralpak AD-H(4.6 × 250 mm) 5 μm, Co-Solvent: 0.5% isopropylamine in IPA (20%), Column Temperature: 30° C., Flow: 3 mL/min, RT: 2.7 (99.8%). |
| 99 | 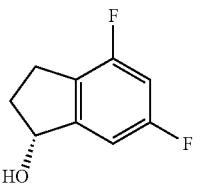 | (R)-4,6-difluoro-2,3-dihydro-1H-inden-1-ol | 1H NMR (400 MHz, CHLOROFORM-d) δ 6.93-6.91 (dd, J = 6, 2.0 Hz, 1H), 6.72-6.67 (td, J = 6.8 Hz, 2 Hz, 1H), 5.23-5.20 (m, 1H), 3.09 (m, 1H), 2.79- 2.75 (m, 1H), 2.55-2.52 (m, 1H), 2.04-1.94 (m, 2H). |
| 100 | 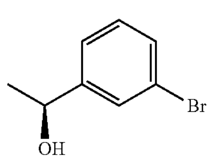 | (1S)-1-(3-bromophenyl)-ethanol | 1H NMR (400 MHz, CHLOROFORM-d) δ 7.58 (s, 1H), 7.40-7.38 (m, 1H), 7.30-7.19 (m, 2H), 4.89-4.84 (m, 1H), 1.85-1.84 (d, J = 4 Hz, 1H), 1.50 (d, J = 6.4 Hz, 3H) |
| 101 | 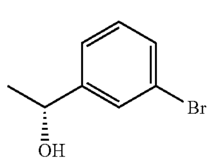 | (1R)-1-(3-bromophenyl)-ethanol | 1H NMR (400 MHz, CHLOROFORM-d) δ 7.55 (s, 1H), 7.45-7.35 ( m, 1H), 7.3-7.15 (m, 2H), 4.88-4.86 (m, 1H), 1.83 (d, J = 4.0 Hz, 1H), 1.45 (d, J = 6.4 Hz, 3H) |

Preparation 102

1-(3-bromophenyl) propan-1-ol

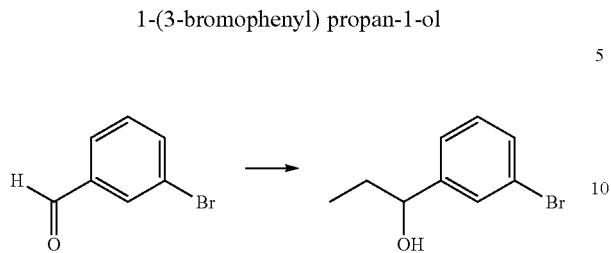

To a stirred solution of 3-bromobenzaldehyde (25 g, 134 mmol) in THF (200 mL) was added ethylmagnesium bromide (58.0 mL, 175 mmol, 3M in THF) dropwise at 0° C. The resulting reaction mixture was allowed to stir at room temperature for 1 h. The reaction was monitored by TLC and LCMS. On completion, saturated aqueous NH$_4$Cl solution (500 mL) was added dropwise at 0° C. The mixture was extracted with EtOAc (2×500 mL). The combined organic layers were washed with water (500 mL), brine (500 mL), dried over anhydrous Na$_2$SO$_4$, filtered and concentrated under reduced pressure to afford 1-(3-bromophenyl)propan-1-ol, as a light yellow oil (18 g, 61%). $^1$H NMR (CDCl$_3$, 400 MHz) δ 7.50 (t, J=4 Hz, 1H), 7.41-7.38 (m, 1H), 7.26-7.19 (m, 2H), 4.58 (t, J=6.4 Hz, 1H), 2.04-1.71 (m, 2H), 1.26 (t, J=4 Hz, 1H), 0.88-082 (m, 3H); LCMS (METHOD 5) (ESI): m/z: 216 [M+H$^+$]; RT=1.89 min (ACQUITY UPLC BEH C18 column, 0.1% FA in water with 0.1% FA in MeCN).

Preparation 103

[(1S)-1-(3-bromophenyl)propyl] (2S)-1-benzylpyrrolidine-2-carboxylate (Prep. 103A) and [(1R)-1-(3-bromophenyl)propyl] (2S)-1-benzylpyrrolidine-2-carboxylate (Prep. 103B)

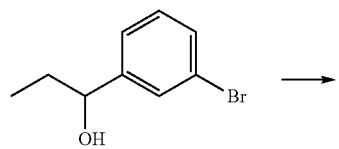

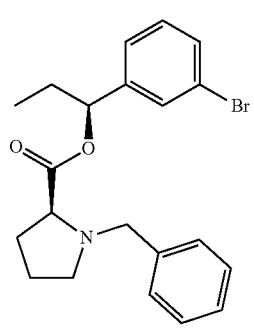

+

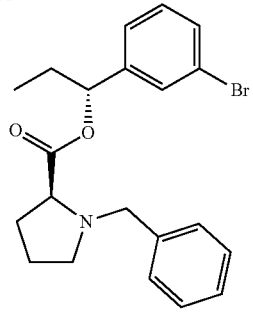

DIPEA (5.5 mL, 30.9 mmol) was added to a stirred solution of the alcohol of Preparation 102 (13.3 g, 61.9 mmol), benzyl-L-proline (19.2 g, 92.8 mmol), DMAP (1.5 g, 12.4 mmol), DIC (12.6 g, 68.0 mmol) in DCM (250 mL) at 0° C. The resulting reaction mixture was allowed to stir at room temperature for 16 h. The reaction mixture was diluted with DCM (500 mL) and washed with water (200 mL) and brine (200 mL). The organic layers were dried over anhydrous Na$_2$SO$_4$, filtered and concentrated under reduced pressure to afford crude residue. The obtained crude compound was purified by silica gel (100-200 mesh) column chromatography (5% EtOAc in hexane as eluent) to afford diastereomer 1 (10.5 g, 43%) and diastereomer 2 (10.2 g, 42%) as light yellow liquids.

(Prep. 103A): [(1S)-1-(3-bromophenyl)propyl] (2S)-1-benzylpyrrolidine-2-carboxylate. $^1$H NMR (CDCl$_3$, 400 MHz) δ 7.48 (s, 1H), 7.41-7.40 (m, 1H), 7.29-7.16 (m, 7H), 5.64 (d, 0.7=6.8 Hz, 1H), 3.93 (d, J=12.8 Hz, 1H), 3.30 (d, J=9.6 Hz, 1H), 2.40-2.38 (m, 1H), 2.38-2.11 (m, 1H), 1.91-1.90 (m, 1H), 1.90-1.80 (m, 5H), 1.79 (s, 1H), 0.87 (t, J=7.2 Hz, 3H); Chiral purity: 98% (RT: 3.18 min) Column: (R,R) WHELK-01 (250×4.6 mm) 5 μm; Co-solvent: Methanol, Total flow: 3 ml/min, % of co solvent: 20%, Temperature: 30° C.

(Prep. 103B): [(1R)-1-(3-bromophenyl)propyl] (2S)-1-benzylpyrrolidine-2-carboxylate. $^1$H NMR (CDCl$_3$, 400 MHz): δ (ppm) 7.48 (s, 1H), 7.43 (d, J=12 Hz, 1H), 7.26-7.18 (m, 7H), 5.68 (t, J=8 Hz, 1H), 3.92 (d, J=12 Hz, 1H), 3.46 (d, J=12 Hz, 1H), 3.02-2.99 (m, 1H), 2.42-2.40 (m, 1H), 2.15-2.11 (m, 1H), 1.98-1.78 (m, 6H), 0.88 (t, J=8 Hz, 3H); Chiral purity: 96% (RT: 3.58 min) Column: (R, R) WHELK-01 (250×4.6 mm) 5 μm; Co-solvent: Methanol, Total flow: 3 ml/min, % of co solvent: 20%, Temperature: 30° C.

Preparation 104

(R)-1-(3-bromophenyl) propan-1-ol

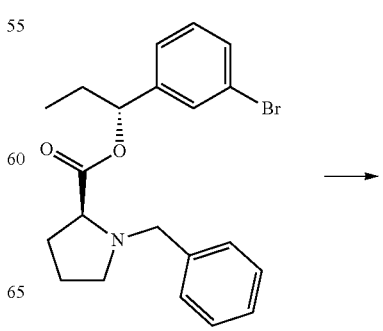

-continued

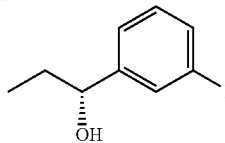

To a stirred solution of the ester of Preparation 103B (2.3 g, 5.23 mmol) in THF (34.5 mL) and $H_2O$ (10.5 mL) was added $LiOH \cdot H_2O$ (0.35 g, 8.60 mmol) at 0° C. The resulting reaction mixture was allowed to stir at room temperature for 48 h. On completion, the reaction mixture was diluted with $H_2O$ (100 mL) and extracted with EtOAc (2×100 mL). The combined organic layers were dried over anhydrous $Na_2SO_4$, filtered and concentrated under reduced pressure to afford crude residue. The obtained crude compound was purified by silica gel (100-200 mesh) column chromatography (5% EtOAc in hexane as eluent) to afford the title compound as a colourless oil (1.13 g, 91%). $^1H$ NMR ($CDCl_3$, 400 MHz) δ 7.51 (br s, 1H), 7.39 (d, J=12 Hz, 1H), 7.26-7.18 (m, 2H), 4.41 (br s, 1H), 1.89 (m, 3H), 0.9 (s, 3H); Chiral purity: 98% (RT: 1.84 min) 8<. 1% (RT: 2.47 min), Column: CHIRALPACK AD-3(150*4.6 mm) 3 μm; Co-solvent: 0.5% DEA in Methanol, Total flow: 3 g/min, % of co solvent: 10%, Temperature: 30° C.

Preparations 105-106

The Boc protected amino acids of Preparations 105-106 were synthesised according to the methods of Preparations 11-14 from the indicated alcohols.

| Prep. No. | SM | Structure | Name | 1H NMR and mass spec data |
|---|---|---|---|---|
| 105 | Prep. 92A | ![structure] | (2S)-2-[(1R)-6-bromo-4-fluoro-indan-1-yl]-2-(tert-butoxycarbonylamino)-acetic acid | 1H NMR (400 MHz, DMSO-d6) δ 12.4 (br s, 1H) 7.28 (d, J = 8.31 Hz, 1H) 7.24 (s, 1H) 7.09 (d, J = 9.29 Hz, 1H) 4.63 (d, J = 4.40 Hz, 1H) 3.76 (d, J = 2.93 Hz, 1H) 2.81-2.92 (m, 1H) 2.64-2.78 (m, 1H) 2.05 (d, J = 6.85 Hz, 2H) 1.31 (s, 9H) LCMS (METHOD 5) (ESI): m/z 387 [M − H]; RT = 2.14 min; (ACQUITY UPLC BEH C18 column, 0.1% FA in water with MeCN); Chiral HPLC: Column: CHIRALPAK IG (4.6 × 250 mm) 5 μm, Mobile Phase A: 0.2% TFA in MeOH, Mobile Phase B: EtOH; Isocratic of (A:B): 50:50, Column Temp.: 30° C., Flow: 1 mL/min, RT: 20.8 (96.4%). |
| 106 | Prep. 94 | ![structure] | (2S)-2-[(1R)-7-bromo-5-fluoro-tetralin-1-yl]-2-(tert-butoxycarbonylamino)-acetic acid | 1H NMR (300 MHz, DMSO-d6) δ 12.80 (br s, 1H), 7.30-7.27 (br d = 8.7 Hz, 1H), 7.20 (br s, 1H), 7.06-7.03 (br d, J = 9.3 Hz, 1H), 4.67-4.63 (m, 1H), 2.72-2.49 (m, 2H), 1.87-1.53 (m, 5H) 1.39.76 (s, 9H) LCMS (METHOD 5) (ESI): m/z: 402 [M + H⁺]; RT = 5.19 min (ACQUITY UPLC BEH C18 column, 0.1% FA in water with MeCN); Chiral purity: 97% (RT: 3.47 min) Column: CHIRALPAK IG (250 × 4.6 mm) 5 μm; Co-solvent: 0.5% DEA in Methanol, % of Co-solvent: 35, Total flow: 3 mL/min, Outlet pressure:100 bar Temp.: 30° C. |

Preparations 107-118

The Boc protected amino acids of Preparations 107-118 were synthesised according to the methods of Preparations 11 and 22 from the indicated alcohols.

| Prep. No. | SM | Structure | Name | 1H NMR and mass spec data |
|---|---|---|---|---|
| 107 | Prep. 93 | ![structure] | 2-[(1S)-6-bromo-4-fluoro-indan-1-yl]-2-(tert-butoxycarbonylamino)-acetic acid | 1H NMR (400 MHz, DMSO-d6) δ 12.4 (br s, 1H) 7.28 (d, J = 8.31 Hz, 1H) 7.24 (s, 1H) 7.09 (d, J = 9.29 Hz, 1H) 4.63 (d, J = 4.40 Hz, 1H) 3.76 (d, J = 2.93 Hz, 1H) 2.81-2.92 (m, 1H) 2.64-2.78 (m, 1H) 2.05 (d, J = 6.85 Hz, 2H) 1.31 (s, 9H); LCMS (METHOD 5) (ESI): m/z 387 [M + H⁺]; RT = 4.51 min and 4.57 min (3:7 ratio) (ACQUITY BEH C18 column, 0.1% FA in water with MeCN). |

| Prep. No. | SM | Structure | Name | 1H NMR and mass spec data |
|---|---|---|---|---|
| 108 | Prep.95 | 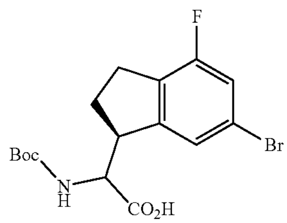 [SMILES: CC(C)(C)OC(=O)NC(C(=O)O)[C@H]1CCc2c(F)cc(Br)cc21] | 2-[(1S)-7-bromo-5-fluoro-tetralin-1-yl]-2-(tert-butoxycarbonylamino)-acetic acid | 1H NMR (300 MHz, DMSO-d6) δ 12.79 (br s, 1H) 7.38 (s, 1H) 7.30 (t, J = 9.35 Hz, 1H) 4.14 (t, J = 9.17 Hz, 1H) 2.99-3.10 (m, 1H) 2.54-2.76 (m, 2H) 1.51-1.94 (m, 4H) 1.31 (s, 9H); LCMS (METHOD 5) (ESI): m/z: 402 [M + H⁺]; RT = 2.65 and 2.69 min (1:4 ratio) (ACQUITY BEH C18 column, 0.1% FA in water with MeCN). |
| 109 | Prep.96 | 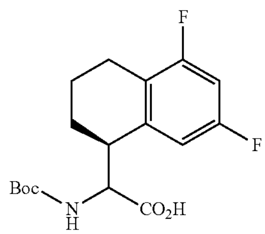 [SMILES: CC(C)(C)OC(=O)NC(C(=O)O)[C@H]1CCCc2c(F)cc(F)cc21] | 2-(tert-butoxycarbonylamino)-2-[(1S)-5,7-difluorotetralin-1-yl]acetic acid | 1H NMR (400 MHz, CHLOROFORM-d) δ 6.78 (d, J = 9.6 Hz, 1H), 6.92-6.64 (t, J = 9.2 Hz, 1H), 4.99 (m, 1H), 4.62-4.63 (m, 1H), 3.43 (m, 1H), 2.69-2.64 (m, 1H), 1.95-1.93 (m, 2H), 1.81-1.70 (m, 2H), 1.49 (s, 9H), 1.48-1.45 (m, 2H); LCMS (METHOD 5) (ESI): m/z: 340 [M − H]; RT =2.56 min (ACQUITY BEH C18 column (50 mm × 2.1 mm) 1.7 μm, 0.1% FA in water with MeCN). |
| 110 | Prep. 99 | 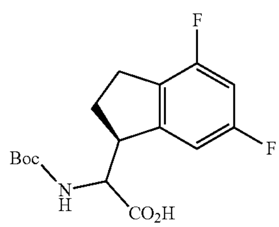 [SMILES: CC(C)(C)OC(=O)NC(C(=O)O)[C@H]1CCc2c(F)cc(F)cc21] | 2-(tert-butoxycarbonylamino)-2-[(1S)-4,6-difluoroindan-1-yl]acetic acid | 1H NMR (400 MHz, CHLOROFORM-d) δ 6.87-6.60 (m, 2H), 5.01-4.62 (m, 2H), 3.85-3.80 (m, 1H), 2.9-280 (m, 2H), 2.39-2.10 (m, 2H), 1.40 (s, 9H); LCMS (METHOD 5) (ESI): m/z: 328 [M + H⁺]; RT = 2.00 and 2.03 min (1:2 ratio), (ACQUITY BEH C18 column (50 mm + 2.1 mm) 1.7 μm, 0.1% FA in water with MeCN). |
| 111 | Prep.97 | 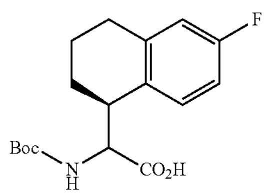 [SMILES: CC(C)(C)OC(=O)NC(C(=O)O)[C@H]1CCCc2cc(F)ccc21] | 2-(tert-butoxycarbonylamino)-2-[(1S)-6-fluorotetralin-1-yl]acetic acid | 1H NMR (400 MHz, DMSO-d6) δ 12.44 (br s, 1H), 7.31-7.28 (t, J = 7 Hz, 1H), 7.41-7.11 (d, J = 9.2 Hz 1H), 6.6-6.86 (m, 1H), 4.15-4.11 (t, J = 8.42 Hz, 1H), 3.03-3.01 (m, 1H), 2.78-2.62 (m, 1H), 1.82-1.71 (m, 4H), 1.38,1.31 (s, 9H); LCMS (METHOD 5) (ESI): m/z: 324 [M + H⁺]; RT = 4.62 min and 4.75 min (1:8 ratio) (ACQUITY UPLC BEH C18 column, 0.1% FA in water with MeCN). |
| 112 | Prep. 98 | 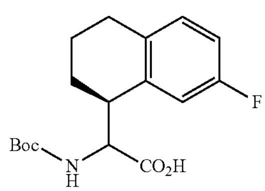 [SMILES: CC(C)(C)OC(=O)NC(C(=O)O)[C@H]1CCCc2ccc(F)cc21] | 2-(tert-butoxycarbonylamino)-2-[(1S)-7-fluorotetralin-1-yl]acetic acid | 1H NMR (400 MHz, DMSO-d6) δ 12.72 (br s, 1H), 7.21 (d, J = 9.30 Hz, 1H) 7.04-7.16 (m, 2H) 6.87-6.98 (m, 1H) 4.15 (t, J = 8.88 Hz, 1H) 2.93-3.08 (m, 1H) 2.62-2.74 (m, 2H) 1.74-1.88 (m, 2H) 1.64-1.71 (m, 2H) 1.30 (s, 9H); LCMS (METHOD 5) (ESI): m/z 322.22 [M − H]; RT = 2.14 min and 2.37 min (1:3 ratio); (Acquity BEH C18 column, 0.1% FA in water with MeCN). |
| 113 | | 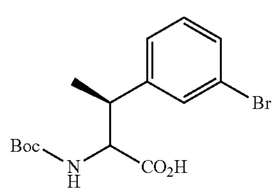 [SMILES: C[C@@H](c1cccc(Br)c1)C(NC(=O)OC(C)(C)C)C(=O)O] | Diastereomer 1 of (3S)-3-(3-bromophenyl)-2-(tert-butoxycarbonylamino) butanoic acid* | ¹H NMR (400 MHz, DMSO-d6) δ 12.58 (br s, 1H), 7.41-7.37 (m, 2H), 7.27-7.21 (m, 2H), 7.15 (d, J = 8.8 Hz, 0.8H), 6.70 (m, 0.2H), 4.16-4.12 (m, 1H), 3.25-3.18 (m, 1H), 1.36-1.15 (m, 12H); LCMS (METHOD 5) (ESI): m/z: 356.2 [M − H]; RT =4.73 min; (ACQUITY UPLC BEH C18 column, 0.05% FA in water with MeCN). Chiral HPLC: 99.9 %, RT: 2.6 min; Column: CHIRALPAK IG-3 (4.6 * 150 mm) 3 μm, Co-Solvent: 0.5% Isopropylamine in IPA, Column Temperature: 30° C., Flow: 3 mL/min. |

| Prep. No. | SM | Structure | Name | 1H NMR and mass spec data |
|---|---|---|---|---|
| 114 | (structure: (S)-1-(3-bromophenyl)ethanol) | (structure: Boc-NH-CH(CO2H)-CH(CH3)-(3-bromophenyl)) | Diastereomer 2 of (3S)-3-(3-bromophenyl)-2-(tert-butoxycarbonylamino) butanoic acid* | ¹H H NMR (400 MHz, DMSO-d6) δ 12.69 (br s, 1H), 7.44-7.376 (m, 2H), 7.28-7.22 (m, 2H), 6.92 (d, J = 8.8 Hz, 0.8H), 6.54 (d, J = 5.6 Hz,0.2H), 4.08-3.96 (m, 1H), 3.08-3.00 (m, 1H), 1.27(s, 9H), 1.18 (d, J = 7.2 Hz, 3H); LCMS (METHOD 5) (ESI): m/z: 356.2 [M − H]; RT = 4.75 min; (ACQUITY UPLC BEH C18 column, 0.05% FA in water with MeCN); Chiral HPLC: 99%, RT: 5.08 min; Column: CHIRALPAK IG-3 (4.6 * 150 mm) μm, Co-Solvent: 0.5% Isopropyl amine in IPA, Column Temperature: 30° C., Flow: 3 mL/min |
| 115 | (structure: (S)-1-(3-bromophenyl)ethanol) | (structure: Boc-NH-CH(CO2H)-CH(CH3)-(3-bromophenyl), wedge) | Diastereomer 1 of (3R)-3-(3-bromophenyl)-2-(tert-butoxy-carbonylamino) butanoic acid* | ¹H 1H NMR (400 MHz, DMSO-d6) δ 12.0 (br s, 1H), 7.41 (s, 1H), 7.37-7.34 (m, 1H), 7.27-7.20(m, 2H) 6.3 (br s, 1H), 4.14-4.10 (m, 1H), 3.12-3.07(m, 1H), 1.37 -1.23(m, 12H); LCMS (METHOD 5) (ESI): m/z: 356.2 [M − H]; RT = 2.84 min; (ACQUITY UPLC BEH C18 column, 0.05% FA in water with MeCN). Chiral HPLC: 99.9 %, RT: 6.08 min; Column: Chiralpak IG(250 × 4.6 mm): 5μ, Co-Solvent: 20% Isopropanol in n-Hexane, Column Temperature: 30° C., Flow: 1 ml/min. |
| 116 | (structure: (S)-1-(3-bromophenyl)ethanol) | (structure: Boc-NH-CH(CO2H)-CH(CH3)-(3-bromophenyl), wedge) | Diastereomer 2 of (3R)-3-(3-bromo-phenyl)-2-(tert-butoxy-carbonylamino) butanoic acid* | ¹H NMR (400 MHz, DMSO-d6) δ.54 (s, 1H), 7.42-7.37 (m, 2H), 7.27-7.17 (m, 2.8H), 6.78-6.71 (m, 0.2H), 4.17-4.09 (m, 1H), 3.32-3.20 (m, 1H), 1.33-1.18 (m, 12H); LCMS (METHOD 5) (ESI): m/z: 356 [M − H]; RT = 2.82 min; (ACQUITY UPLC BEH C18 column, 0.05% FA in water with MeCN); Chiral HPLC: 99.6%, RT: 15.4 min; Column: Chiralpak IG(250 × 4.6 mm): 5μ, Co-Solvent: 20 % Isopropanol in n-Hexane, Column Temperature: 30° C., Flow: 1 ml/min. |
| 117 | Prep. 104 | (structure: Boc-NH-CH(CO2H)-CH(Et)-(3-bromophenyl)) | Diastereomer 1 of (3S)-3-(3-bromo-phenyl)-2-(tert-butoxy-carbonylamino) pentanoic acid* | ¹H NMR (400 MHz, DMSO-d₆) δ 13.65 (br s, 1H), 7.395-7.391 (d, J = 1.6 Hz, 2H),7.27-7.21 (m, 2H), 6.73 (d, J= 8.4 Hz, 1H) 4.13 (t, J = 8.8 Hz 1H), 2.91-2.82 (m, 1H), 1.67-1.57 (m, 2H), 1.27 (s, 9H), 0.67 (t, J = 6.8 Hz, 3H). LCMS (METHOD 5) (ESI): m/z: 372 [M + H⁺]; RT: 5.05 min (ACQUITY UPLC BEH C18 column, 0.1% FA in water with MeCN). Chiral purity: 95% RT: 1.11 min, Column: CHIRALCEL OZ-3 (250 × 4.6 mm) 5 μm; Co-solvent: MeOH, Total flow: 3 mL/min, % of co solvent: 10%, Temperature: 30° C. |
| 118 | Prep. 104 | (structure: Boc-NH-CH(CO2H)-CH(Et)-(3-bromophenyl)) | Diastereomer 2 of (3S)-3-(3-bromo-phenyl)-2-(tert-butoxy-carbonylamino) pentanoic acid* | ¹H NMR (400 MHz, DMSO-d₆) δ 12.55 (br s, 1H), 7.40-7.37 (d, J = 1.2 Hz, 2H), 7.26-7.19 (m, 3H), 4.09 (t, J = 8 Hz, 1H), 2.94-2.86 (m, 1H), 1.71-1.64 (m, 2H), 1.35 (s, 9H), 0.63 (t, J = 6.8 Hz, 3H). LCMS (METHOD 5) (ESI): m/z: 372 [M + H⁺]; RT: 5.02 min (ACQUITY UPLC BEH C18 column, 0.1% FA in water with MeCN); Chiral purity: 97% RT: 1.30 min, Column: CHIRALCEL OZ-3 (250 × 4.6 mm) 5 μm; Co-solvent: MeOH, Total flow: 3 mL/min, % of co solvent: 10%, Temperature: 30° C. |

*The diastereomers were separated by chiral SFC.

Preparations 119 and 120

Preparations 119 and 120 were synthesised according to the method of Preparation 28 from the compounds of Preparations 93 and 95 respectively.

| Prep. No. | Structure | Name | Mass ion | LCMS method and retention time (min) |
|---|---|---|---|---|
| 119 | 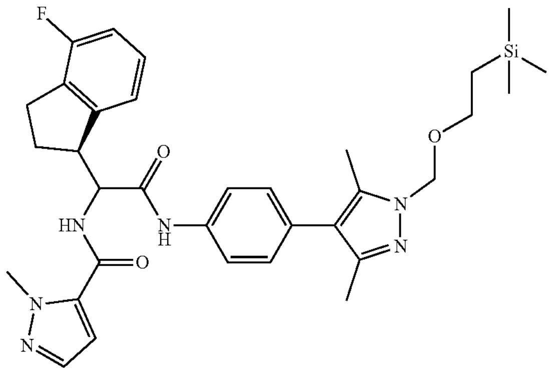 | N-[2-[4-[3,5-dimethyl-1-(2-trimethylsilyl-ethoxymethyl)pyrazol-4-yl]anilino]-1-[(1S)-4-fluoroindan-1-yl]-2-oxo-ethyl]-2-methyl-pyrazole-3-carboxamide | 617.8 | 5.43 and 5.50 1:8 ratio Method 5 (ACQUITY UPLC BEH C18 column, 0.1% FA in water with MeCN) |
| 120 | 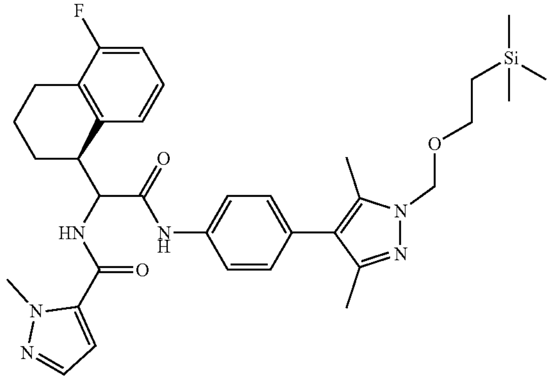 | N-[2-[4-[3,5-dimethyl-1-(2-trimethylsilyl-ethoxymethyl)pyrazol-4-yl]anilino]-1-[(1S)-5-fluorotetralin-1-yl]-2-oxo-ethyl]-2-methyl-pyrazole-3-carboxamide (single diastereomer) | 631 | 2.48 Method 5 (Acquity BEH C18 column, 0.1% FA in water with MeCN) |

Preparations 121-124

The Boc protected amino acids of Preparations 121-124 were synthesised as mixtures of diastereomers according to the methods of Preparations 11 and 35 from the indicated alcohols. The major component is the (S, S) diastereomer.

| Prep. No. | SM | Structure | Name | Mass spec data |
|---|---|---|---|---|
| 121 | | 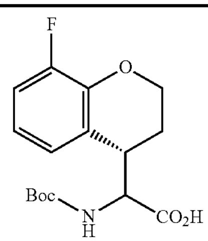 | 2-(tert-butoxycarbonylamino)-2-[(4S)-8-fluorochroman-4-yl]acetic acid | 324.2 [M − H] RT = 0.65 (minor) min and 0.66 (major) min (METHOD 3) |
| 122 | | 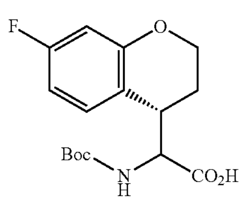 [SMILES: CC(C)(C)OC(=O)NC(C(=O)O)[C@H]1CCOc2cc(F)ccc21] | 2-(tert-butoxycarbonylamino)-2-[(4S)-7-fluorochroman-4-yl]acetic acid | 324.2 [M − H] RT = 0.68 (minor) min and 0.69 (major) min (METHOD 3) |

-continued

| Prep. No. | SM | Structure | Name | Mass spec data |
|---|---|---|---|---|
| 123 | (6-fluorochroman-4-ol) | (Boc-NH-CH(CO₂H)-(4S)-6-fluorochroman-4-yl) | 2-(tert-butoxycarbonylamino)-2-[(4S)-6-fluorochroman-4-yl]acetic acid | 324.2 [M − H] RT = 0.66 (minor) min and 0.68 (major) min (METHOD 3) |
| 124 | (6,8-difluorochroman-4-ol) | (Boc-NH-CH(CO₂H)-(4S)-6,8-difluorochroman-4-yl) | 2-(tert-butoxycarbonylamino)-2-[(4S)-6,8-difluorochroman-4-yl]acetic acid | 342.2 [M − H] RT = 0.67 (minor) min and 0.68 (major) min (METHOD 3) |

Preparation 125

(3-Bromophenyl)(cyclopropyl)methanol

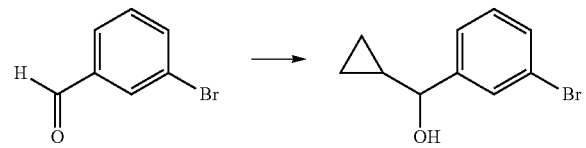 [SMILES: O=Cc1cccc(Br)c1 ; OC(c1cccc(Br)c1)C1CC1]

To a stirred solution of 3-bromobenzaldehyde (60 g, 324 mmol) in THF (300 mL) was added cyclopropyl magnesium bromide (843 ml, 421 mmol) at −5° C. The resulting reaction mixture was stirred at room temperature for 1 hour then quenched with saturated aq. ammonium chloride solution and extracted with EtOAc (2×200 mL). Th combined organic layers were washed with water (2×200 mL), brine (200 mL), dried over anhydrous Na₂SO₄ and concentrated under reduced pressure. The crude compound was purified by silica gel (100-200 mesh) column chromatography (5%-10% EtOAc in Hexane as eluent) to afford the title compound (38 g, 51%) as an oil. 1H NMR (400 MHz, CHLOROFORM-d) δ 7.60 (t, J=1.74 Hz, 1H) 7.40-7.44 (m, 1H), 7.35 (d, J=7.74 Hz, 1H), 7.19-7.25 (m, 1H), 3.98 (dd, J=8.34, 3.00 Hz, 1H), 1.96 (d, J=3.05 Hz, 1H), 1.10-1.24 (m, 1H), 0.53-0.72 (m, 2H), 0.44-0.51 (m, 1H), 0.35-0.43 (m, 1H); LCMS (METHOD 5) (ESI): m/z 228 [M+H⁺]; RT=1.9 min; (ACQUITY UPLC BEH C18 column, 0.1% FA in water with MeCN).

Preparation 126

(3-Bromophenyl)(cyclopropyl)methanone

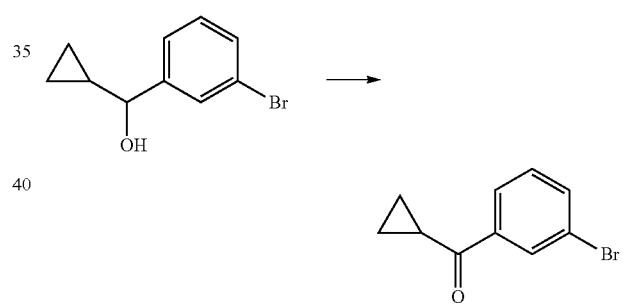

To a stirred solution of the alcohol of Preparation 125 (38 g, 168 mmol) in DCM (300 mL) was added Dess-Martin Periodinane (179 g, 422 mmol) at room temperature. The resulting reaction mixture was stirred at room temperature for 2 hours then diluted with saturated aq. sodium bicarbonate solution (250 mL) and 10% aq. sodium thiosulphate solution (250 mL). The aqueous layer was extracted with DCM (200 mL), the organic layer was washed with water (2×200 mL), brine (200 mL), dried over anhydrous Na₂SO₄ and concentrated under reduced pressure. The crude compound was purified by silica gel (100-200 mesh) column chromatography (2%-3% EtOAc in Hexane as an eluent) to afford the title compound (33 g, 87%) as an oil. 1H NMR (400 MHz, CHLOROFORM-d) δ 8.14 (t, J=1.74 Hz, 1H), 7.93 (dt, J=7.74, 1.31 Hz, 1H), 7.67-7.71 (m, 1H), 7.36 (t, J=7.85 Hz, 1H), 2.62 (tt, J=7.82, 4.50 Hz, 1H), 1.26 (quin, J=3.84 Hz, 2H), 1.08 (dq, J=7.44, 3.59 Hz, 2H); LCMS (METHOD 5) (ESI): m/z: 225 [M+H⁺]; RT=2.13 min; (ACQUITY UPLC BEH C18 column, 0.1% FA in water with MeCN).

Preparation 127

(Z)-1-Bromo-3-(1-cyclopropyl-2-methoxyvinyl)benzene

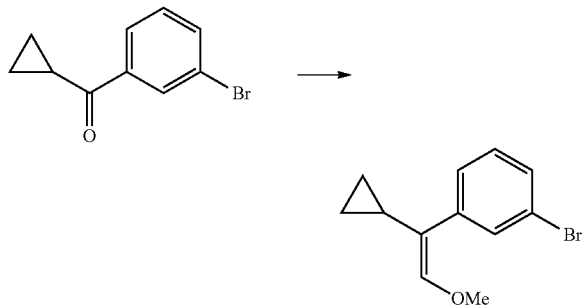

To a stirred solution of (methoxymethyl)triphenylphosphonium chloride (126.5 g, 370 mmol) in THF (300 mL) were added tBuOK (36.5 g, 325.5 mmol) and DMSO (25 g, 320.5 mmol) at 0° C. The reaction mixture was stirred at 0° C. for 30 min then the ketone of Preparation 126 was added. The reaction was stirred for 16 hours at room temperature then diluted with of water (300 mL), extracted with EtOAc (2×300 mL). The combined organic layers were washed with water (2×200 mL) and brine (200 mL), dried over anhydrous $Na_2SO_4$ and concentrated under reduced pressure. The crude product was purified by silica gel (100-200 mesh) column chromatography (1 %-2% EtOAc in Hexane as an eluent) to afford the title compound (30 g, 80%) as a viscous oil. 1H NMR (400 MHz, CHLOROFORM-d) δ 7.92, 7.44 (t, J=1.71 Hz, 1H), 7.70 (d, J=7.83 Hz, 1H), 7.28-7.36 (m, 1H), 7.09-7.25 (m, 1H), 6.27, 6.19 (d, J=0.98 Hz, J=1.47 Hz, 1H), 3.70, 3.71 (s, 3H), 1.59-1.68, 1.45-1.53 (m, 1H), 0.69-0.87 (m, 2H), 0.36-0.49 (m, 2H); LCMS (METHOD 5) (ESI): m/z 254 [M+H$^+$]; RT=2.46 min; (ACQUITY UPLC BEH C18 column, 0.1% FA in water with MeCN).

Preparation 128

2-(3-Bromophenyl)-2-cyclopropylacetaldehyde

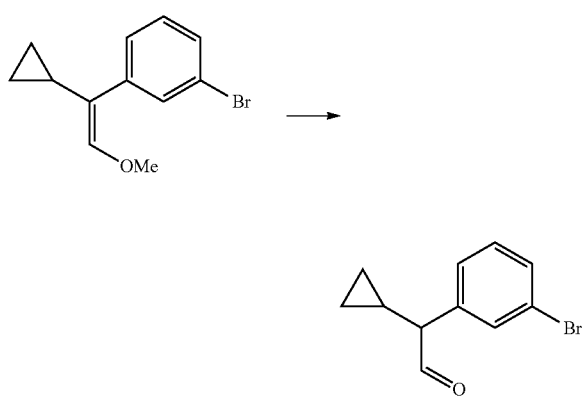 [SMILES: CO/C=C(\c1cccc(Br)c1)C1CC1 ; O=CC(c1cccc(Br)c1)C1CC1]

To a stirred solution of the compound of Preparation 127 (30 g, 118.5 mmol) in THF (150 mL) was added 5M HCl (90 ml) at room temperature. The resulting reaction mixture was stirred at room temperature for 48 hours then diluted with hexane (300 mL) The layers were separated and the aq. layer was extracted with hexane (300 mL). The combined organic layers were washed with water (2×200 mL) and brine (200 mL), dried over anhydrous $Na_2SO_4$ and concentrated under reduced pressure. The crude product was purified by silica gel (100-200 mesh) column chromatography (1% EtOAc in hexane as an eluent) to afford the title compound (25 g, yield 88%) as an oil. 1H NMR (400 MHz, CHLOROFORM-d) δ 9.74 (d, J=2.40 Hz, 1H), 7.42-7.47 (m, 2H), 7.23-7.28 (m, 1H), 7.16-7.20 (m, 1H), 2.76 (dd, J=9.81, 2.29 Hz, 1H), 1.23-1.32 (m, 1H), 0.74-0.81 (m, 1H), 0.65 (dddd, J=9.13, 8.12, 5.69, 4.85 Hz, 1H), 0.41 (dq, J=10.25, 4.80 Hz, 1H), 0.19-0.27 (m, 1H).

Preparation 129

5-((3-Bromophenyl)(cyclopropyl)methyl)imidazolidine-2,4-dione

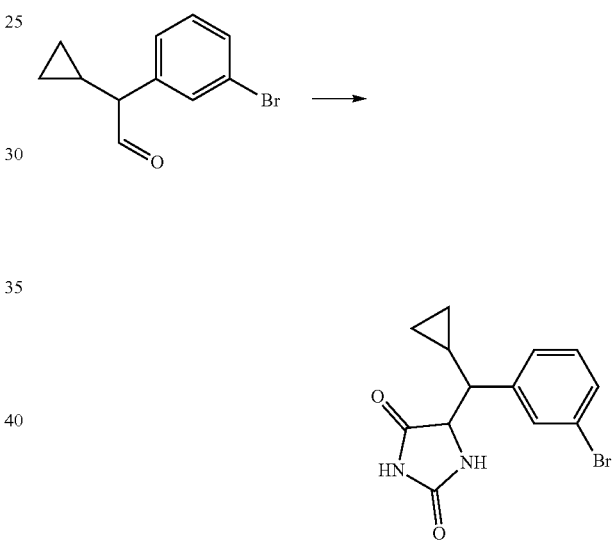

To a stirred solution of the aldehyde of Preparation 128 (25 g, 105 mmol) in MeOH (500 mL) and water (140 mL) was added KCN (10.3 g, 157.5 mmol) and $(NH_4)_2CO_3$ (30.3 g, 315 mmol) at room temperature. The resulting reaction mixture was stirred at 65° C. for 16 hours in an autoclave. After cooling to room temperature, the reaction was concentrated under reduced pressure, water (250 mL) was added and the mixture was extracted with EtOAc (2×250 mL). The combined organic layers were washed with water (2×200 mL) and brine (200 mL), dried over anhydrous $Na_2SO_4$ and concentrated under reduced pressure to afford the title compound (14 g, 43%) as a mixture of diastereomers as an off white solid. 1H NMR (400 MHz, DMSO-d6) δ 10.38 (s, 1H), 8.36 (s, 1H), 7.40-7.45 (m, 2H), 7.18-7.30 (m, 2H), 4.35 (d, J=2.45 Hz, 1H), 2.20-2.27 (m, 1H), 1.33-1.45 (m, 1H), 0.53-0.63 (m, 1H), 0.42-0.51 (m, 1H), 0.36 (dq, J=9.11, 4.63 Hz, 1H), 0.05-0.14 (m, 1H); LCMS (METHOD 5) (ESI): m/z: 310 [M+H$^+$]; RT=2.08+2.12 min (3;1 ratio); (ACQUITY UPLC BEH C18 column, 0.05% FA in water with MeCN).

Preparations 130A-D

Diastereomers 1 to 4 of 3-(3-bromophenyl)-2-((tert-butoxycarbonyl)amino)-3-cyclopropylpropanoic acid

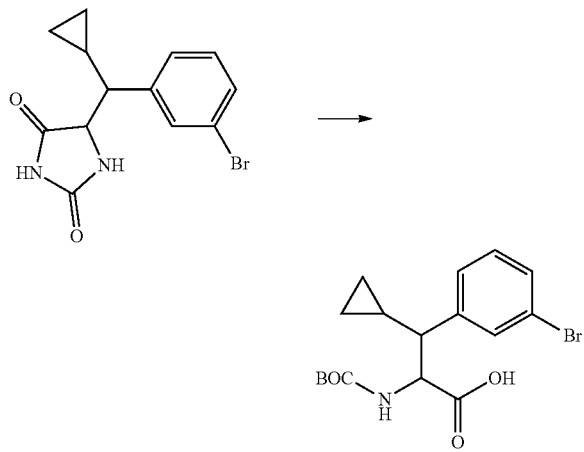

The dione of Preparation 129 (14 g, 45.3 mmol) was taken up in aq. NaOH (21 g in 140 mL of $H_2O$, 525 mmol). The resulting reaction mixture was stirred at 120° C. for 16 hours then cooled to 0° C., diluted with 1,4-dioxane (150 mL) and $(Boc)_2O$ (96.1 g, 419 mmol) was added. The resulting reaction mixture was stirred at room temperature for 6 hours, then cooled to 0° C. and acidified to pH 3 with 5M HCl. The reaction mixture was extracted with EtOAc (3×150 mL), the combined organic layers were washed with water (200 mL) and brine (200 mL), dried over anhydrous $Na_2SO_4$, filtered and concentrated under reduced pressure. The crude product was purified by silica gel (100-200 mesh) column chromatography (2% to 3% of EtOAc in hexane as an eluent) to give the title compound (13 g, 74%) as a mixture of diastereomers.

The isomers were separated by chiral SFC. First preparative SFC Conditions: Column/dimensions: Chiralpak IG (30×250 mm), 5u; % $CO_2$: 85%; % Co solvent: 15% (0.5 DEA in EtOH); Total flow: 90.0 g/min; Back pressure: 100 bar; UV: 214 nm. Second preparative SFC Condition: Column/dimensions: Chiralpak IG (30×250 mm), 5u; % $CO_2$: 75%; % Co solvent: 25.0% (0.5% isopropylamine in IPA); Total flow: 90.0 g/min; Back pressure: 120.0 bar; UV: 214 nm;

Diastereomer 1 (Prep. 130A): 1H NMR (400 MHz, DMSO-d6) δ 12.60 (s, 1H), 7.41-7.43 (m, 1H), 7.33-7.37 (m, 1H), 7.19-7.28 (m, 2H), 6.02-6.16 (m, 1H), 4.27 (t, J=8.40 Hz, 1H), 2.24 (dd, J=9.72, 8.40 Hz, 1H), 1.2-1.26 (m, 1H), 1.30 (s, 9H), 0.51-0.62 (m, 1H), 0.34-0.41 (m, 1H), 0.24-0.31 (m, 1H), −0.06--0.01 (m, 1H); LCMS (METHOD 5) (ESI): m/z: 383 [M−H]; RT=2.92 min; (ACQUITY UPLC BEH C18 column, 0.05% FA in water with MeCN). Chiral HPLC: Column: CHIRALPAK IG (4.6×250) mm, 5u, Co-Solvent: 0.5% DEA in EtOH (15%), Column Temp.: 30° C., Flow: 3 ml/min, RT: 3.46 (99%). Diastereomer 2 (Prep. 130B): 1H NMR (400 MHz, DMSO-d6) δ 12.60 (s, 1H), 7.42-7.45 (m, 1H), 7.32-7.36 (m, 1H), 7.17-7.27 (m, 2H), 6.28-6.46 (m, 1H), 4.24-4.30 (m, 1H), 2.38 (dd, J=10.37, 5.36 Hz, 1H), 1.33 (s, 9H), 0.50-0.57 (m, 1H), 0.31-0.41 (m, 2H), −0.16--0.08 (m, 1H); LCMS (METHOD 5) (ESI): m/z: 383 [M−H]; RT=2.91 min; (ACQUITY UPLC BEH C18 column, 0.05% FA in water with MeCN); Chiral HPLC: Column: CHIRALPAK IG (4.6×250) mm, 5u, Co-Solvent: 0.5% Isopropyl amine in IPA (20%), Column Temp.: 30° C., Flow: 3 ml/min, RT: 4.1 (99%).

Diastereomer 3 (Prep. 130C): 1H NMR (400 MHz, DMSO-d6) δ 12.60 (s, 1H), 7.41-7.43 (m, 1H), 7.33-7.37 (m, 1H), 7.19-7.28 (m, 2H), 6.02-6.16 (m, 1H), 4.27 (t, J=8.40 Hz, 1H), 2.24 (dd, J=9.72, 8.40 Hz, 1H), 1.2-1.26 (m, 1H), 1.30 (s, 9H), 0.51-0.62 (m, 1H), 0.34-0.41 (m, 1H), 0.24-0.31 (m, 1H), −0.06--0.01 (m, 1H); LCMS (METHOD 5) (ESI): m/z: 383 [M−H]; RT=2.89 min; (ACQUITY UPLC BEH C18 column, 0.05% FA in water with MeCN); Chiral HPLC: Column: CHIRALPAK IG (4.6×250) mm, 5u, Co-Solvent: 0.5% DEA in Ethanol (15%), Column Temp.: 30° C., Flow: 3 ml/min, RT: 5.07 (99%). Diastereomer 4 (Prep. 130D): 1H NMR (400 MHz, DMSO-d6) δ 12.60 (s, 1H), 7.42-7.45 (m, 1H), 7.32-7.36 (m, 1H), 7.17-7.27 (m, 2H), 6.28-6.46 (m, 1H), 4.24-4.30 (m, 1H), 2.38 (dd, J=10.37, 5.36 Hz, 1H), 1.33 (s, 9H), 0.50-0.57 (m, 1H), 0.31-0.41 (m, 2H), −0.16--0.08 (m, 1H); LCMS (METHOD 5) (ESI): m/z: 383 [M−H]; RT=2.95 min; (ACQUITY UPLC BEH C18 column, 0.05% FA in water with MeCN); Chiral HPLC: Column: CHIRALPAK IG (4.6×250) mm, 5u, Co-Solvent: 0.5% isopropylamine in IPA (20%), Column Temp.: 30° C., Flow: 3 ml/min, RT: 7.32 (99%).

Preparations 131-134

According to the methods of Preparation 3, 4, 5 and 28 the 4 diastereomers of Preparations 130A-D were converted to Preparations 131-134.

| Prep. No. | Structure | Name | Mass ion | LCMS method and retention time (min) |
|---|---|---|---|---|
| 131 | Diastereomer 1 | N-[1-[cyclopropyl-(phenyl)methyl]-2-[4-[3,5-dimethyl-1-(2-trimethylsilylethoxymethyl)pyrazol-4-yl]anilino]-2-oxo-ethyl]-2-methyl-pyrazole-3-carboxamide | 613 | 2.81 Method 5 (ACQUITY BEH C18 column, 0.05% FA in water with MeCN) |

| Prep. No. | Structure | Name | Mass ion | LCMS method and retention time (min) |
|---|---|---|---|---|
| 132 | Diastereomer 2 | N-[1-[cyclopropyl-(phenyl)methyl]-2-[4-[3,5-dimethyl-1-(2-trimethylsilylethoxymethyl)pyrazol-4-yl]anilino]-2-oxo-ethyl]-2-methyl-pyrazole-3-carboxamide | 613 | 2.80 min Method 5 (ACQUITY BEH C18 column, 0.05 % FA in water with MeCN) |
| 131 | Diastereomer 3 | N-[1-[cyclopropyl-(phenyl)methyl]-2-[4-[3,5-dimethyl-1-(2-trimethylsilylethoxymethyl)pyrazol-4-yl]anilino]-2-oxo-ethyl]-2-methyl-pyrazole-3-carboxamide | 613 | 2.80 Method 5 (ACQUITY BEH C18 column, 0.05 % FA in water with MeCN) |
| 131 | Diastereomer 4 | N-[1-[cyclopropyl-(phenyl)methyl]-2-[4-[3,5-dimethyl-1-(2-trimethylsilylethoxymethyl)pyrazol-4-yl]anilino]-2-oxo-ethyl]-2-methyl-pyrazole-3-carboxamide | 613 | 2.79 Method 5 (ACQUITY BEH C18 column, 0.05 % FA in water with MeCN) |

Preparation 135

Bis(3-chlorophenyl)methanol

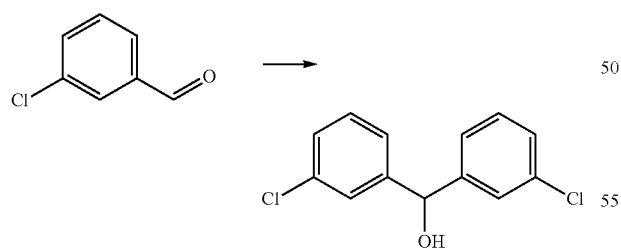

To a stirred solution of 3-chlorobenzaldehyde (15.0 g, 107 mmol) in THF (150 mL) at −78° C. was added (3-chlorophenyl)magnesium bromide (160 mL, 160 mmol, 1M in THF) slowly. The resulting reaction mixture was allowed warm to room temperature and stirred for 2 hours then cooled to 0° C. Saturated aqueous NH$_4$Cl solution (500 mL) was added drop-wise and the mixture was diluted with water (200 mL) and extracted with EtOAc (2×200 mL). The combined organic layers were washed with water (200 mL), brine (200 mL), dried over anhydrous Na$_2$SO$_4$, filtered and concentrated under reduced pressure. The crude product was purified by silica gel (100-200 mesh) column chromatography (10%-20% EtOAc in hexane as eluent) to give the title compound (20 g, 74%) as a brown oil. 1H NMR (300 MHz, DMSO-d6) δ 7.45 (s, 2H), 7.35-7.26 (m, 6H), 6.19-6.17 (d, J=3.19 Hz, 1H), 5.75-5.74 (d, J=3.9 Hz, 1H); GC-MS: m/z: 252 [M], RT=8.14 min.

Preparation 136

3,3'-(Bromomethylene)bis(chlorobenzene)

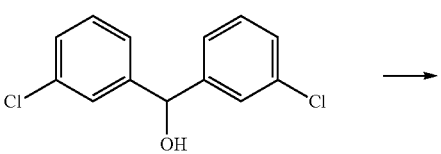

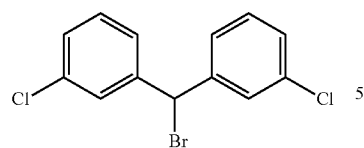

To a stirred solution of the alcohol of Preparation 135 (15 g, 59.3 mmol) in diethyl ether (500 mL) was added PBr₃ (15.39 g, 5.42 mL, 88.9 mmol) drop-wise at 0° C. The resulting reaction mixture was allowed to stir at room temperature for 6 hours, then cooled to 0° C. and ice cold water (500 mL) was added to it. This was extracted with EtOAc (2×250 mL). The combined organic layers were washed with water (250 mL), brine (250 mL), dried over anhydrous Na₂SO₄, filtered and concentrated under reduced pressure to give the title compound (15 g, 80%) as an oil. 1H NMR (400 MHz, Chloroform-d) δ 7.81-7.13 (m, 9H).

Preparation 137

Ethyl 3,3-bis(3-chlorophenyl)-2-((diphenylmethylene)amino)propanoate

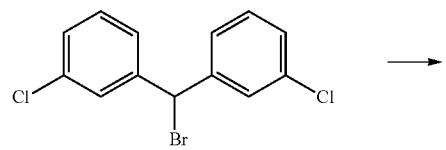

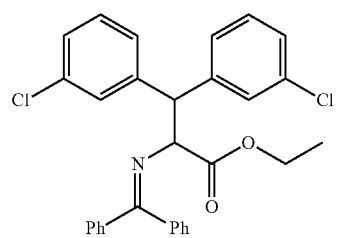

To a stirred solution of the bromide of Preparation 136 (20 g, 63.29 mmol) and ethyl 2-(benzhydrylideneamino)acetate (16.8 g, 63.3 mmol) in DCM (200 mL) was added tetrabutylammonium bromide (20.37 g, 63.3 mmol) followed by 50% aq. NaOH (200 mL) at 0° C. The reaction mixture was allowed to stir at room temperature for 16 hours then diluted with ice cold water (200 mL) and extracted with DCM (2×200 mL). The combined organic layers were washed with water (200 mL), brine (200 mL), dried over anhydrous Na₂SO₄, filtered and concentrated under reduced pressure to give the title compound (16 g, 48%) as a brown oil. 1H NMR (300 MHz, DMSO-d6) δ 7.04-7.81 (m, 18H), 4.89-4.86 (d, J=8.7 Hz, 1H), 4.67-4.64 (d, J=8.7 Hz, 1H), 3.98-3.91 (q, J=8.8 Hz, 2H), 0.94-0.90 (t, J=8.8 Hz, 3H); LCMS (METHOD 5) (ESI): m/z 502 [M]; RT=3.26 min; (ACQUITY UPLC BEH C18 column, 0.1% FA in water with MeCN).

Preparation 138

Ethyl 2-amino-3,3-bis(3-chlorophenyl)propanoate

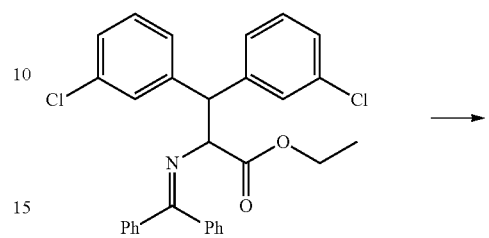

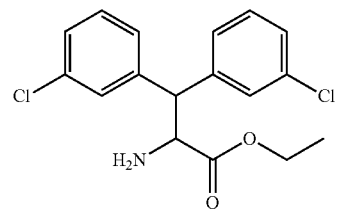

To a solution of the ester of Preparation 137 (11 g, 21.9 mmol) in DCM (200 mL) was added 6M HCl (55 mL) at 0° C. The reaction mixture was allowed to stir at room temperature for 16 hours then the layers were separated. The aqueous layer was basified with saturated aq. NaHCO₃ solution (~100 mL), extracted with EtOAc (2×200 mL) and the combined organic layers were washed with water (200 mL), brine (200 mL), dried over anhydrous Na₂SO₄, filtered and concentrated under reduced pressure to give the title compound (7 g, crude) as a brown oil. 1H NMR (400 MHz, Chloroform-d) δ 7.82-7.79 (m, 2H), 7.61-7.7.57 (m, 1H), 7.50-7.46 (m, 2H), 7.30-7.18 (m, 3H), 4.21-4.19 (d, J=8.0 Hz, 1H), 4.15-4.13 (d, J=8.0 Hz, 1H), 4.04-3.99 (q, J=1.6 Hz, 2H), 1.48 (br s, 2H), 1.07-1.03 (t, J=6.8 Hz, 3H); LCMS (METHOD 5) (ESI): m/z: 338 [M+H⁺]; RT=2.05 min; (ACQUITY UPLC BEH C18 column, 0.1% FA in water with MeCN).

Preparation 139

Ethyl 3,3-bis(3-chlorophenyl)-2-(1-methyl-1H-pyrazole-5-carboxamido)propanoate

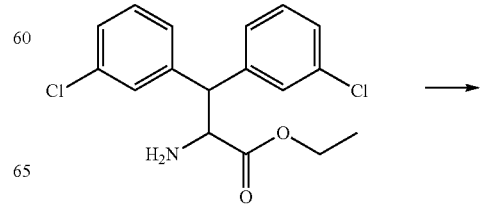

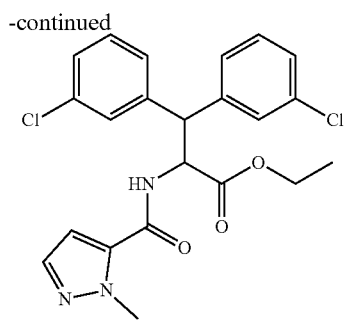

To a solution of the amine of Preparation 138 (7.5 g, 22.3 mmol) in DMF (100 mL) at 0° C. was added DIPEA (10 mL, 55.5 mmol) and HATU (12.6 g, 33.3 mmol), followed by 1-methyl-1H-pyrazole-5-carboxylic acid (2.8 g, 22.3 mmol). The resulting reaction mixture was stirred at room temperature for 16 hours then diluted with ice cold water (100 mL) and extracted with EtOAc (2×100 mL). The combined organic layers were washed with water (4×50 mL) a and brine (100 mL), dried over anhydrous Na$_2$SO$_4$ and concentrated under reduced. The obtained crude compound was purified by silica gel (100-200 mesh) column chromatography (20%-30% EtOAc in hexane as an eluent) to afford the title compound (5.5 g, 55%) as an off white solid; 1H NMR (300 MHz, Chloroform-d) δ 7.38-7.38 (d, J=2.0 Hz, 1H), 7.83-7.16 (m, 8H), 6.330-6.325 (d, J=2.0 Hz, 1H), 6.28-6.25 (d, J=9.2 Hz, 1H), 5.49-5.44 (t, J=9.2 Hz, 1H), 4.44-4.41 (d, J=9.2 Hz, 1H), 4.09 (s, 3H), 4.05-4.01 (q, J=1.6 Hz, 2H), 1.05-1.01 (t, J=6.8 Hz, 3H); LCMS (METHOD 5) (ESI): m/z: 445 [M]; RT=2.22 min; (ACQUITY UPLC BEH C18 column, 0.1% FA in water with MeCN).

Preparation 140

3,3-Bis(3-chlorophenyl)-2-(1-methyl-1H-pyrazole-5-carboxamido)propanoic acid

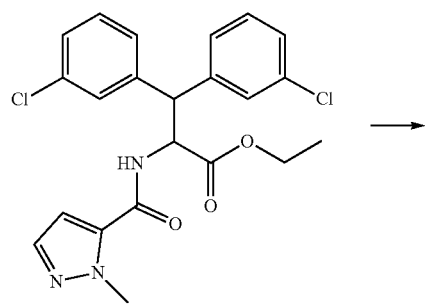

To a solution of the ester of Preparation 139 (5 g, 11.2 mmol) in THF (25 mL) and H$_2$O (25 mL) was added LiOH.H$_2$O (1.41 g, 33.7 mmol) at room temperature. The reaction mixture was stirred at room temperature for 16 hours and then the THF was removed under reduced pressure. The aqueous residue was acidified to ~pH 3 with 5M HCl then extracted with EtOAc (2×100 mL). The combined organic layers were washed with water (100 mL) and dried over anhydrous Na$_2$SO$_4$, filtered and concentrated under reduced pressure to give the title compound (3 g, 64%) as an off white solid. 1H NMR (300 MHz, DMSO-d6) δ 12.71 (br s, 1H), 8.89-8.86 (d, J=8.7 Hz, 1H), 7.51-7.48 (m, 2H), 7.43-7.19 (m, 7H), 6.68-6.67 (d, J=3.0 Hz, 1H), 5.39-5.33 (dd, J=12.0 Hz, 8.0 Hz, 1H), 4.57-4.53 (d, J=11.7 Hz, 1H), 3.91 (s, 3H); LCMS (METHOD 5) (ESI): m/z: 416 [M+H$^+$]; RT=1.94 min; (ACQUITY UPLC BEH C18 column, 0.1% FA in water with MeCN).

Preparation 141

3,3-Bis(3-Fluorophenyl)-2-(1-methyl-1H-pyrazole-5-carboxamido)propanoic acid

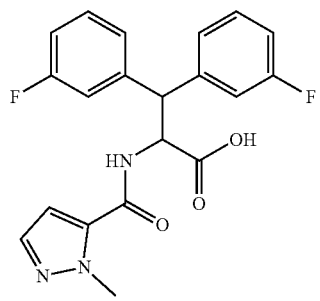 [SMILES: Cn1nccc1C(=O)NC(C(=O)O)C(c1cccc(F)c1)c1cccc(F)c1]

Preparation 141 was prepared according to the methods of Preparations 135-140 starting from 3-fluorobenzaldehyde and (3-fluorophenyl)magnesium bromide. The title compound (1.4 g, 50%) was obtained as an off white solid. 1H NMR (300 MHz, DMSO-d6) δ 12.41 (br s, 1H), 8.85-8.82 (d, J=8.7 Hz, 1H), 7.39-7.38 (d, J=2.1 Hz, 1H), 7.382-7.376 (d, J=1.8 Hz, 1H), 7.36-7.22 (m, 6H), 7.07-6.86 (m, 1H), 6.68-6.67 (d, J=2.1 Hz, 1H), 5.39-5.32 (dd, J=9.3 Hz, 12 Hz, 1H), 4.58-4.54 (d, J=11.7 Hz, 1H), 3.90 (s, 3H); LCMS (METHOD 5) (ESI): m/z: 386 [M+H$^+$]; RT=2.23 min; (ACQUITY UPLC BEH C18 column, 0.1% FA in water with MeCN).

Preparation 142

Cyclobutyl(phenyl)methanol

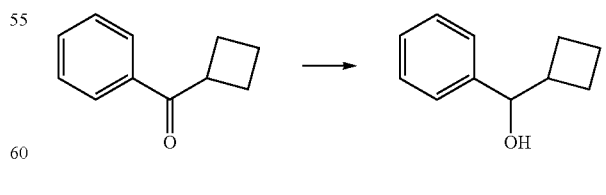

To a stirred solution of cyclobutyl(phenyl)methanone (10 g, 62.4 mmol) in THF (200 mL) was added lithium aluminium hydride (1M in THF, 156 mL, 156 mmol) at 0° C. The resulting reaction mixture was heated at 70° C. for 3 hours then cooled to 0° C. and cold water (5.9 mL) was added, followed by 15% aq. NaOH (5.9 mL) and a further portion of cold water (17.7 mL). The mixture was stirred at room temperature for 1 hour then filtered through a Celite pad and washed with EtOAc (200 mL). The filtrate was dried over anhydrous Na$_2$SO$_4$ and concentrated under reduced pressure to give the title compound (10 g, 100%) as a colourless viscous oil. 1H NMR (400 MHz, Chloroform-d) δ 7.33-7.24 (m, 5H), 4.58-4.56 (dd, J=8.0 Hz, 1H), 2.66-2.59 (m, 1H), 2.10-1.96 (m, 2H), 1.89-1.76 (m, 6H).

Preparation 143

(Bromo(cyclobutyl)methyl)benzene

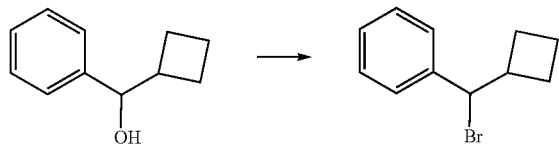 [SMILES: OC(c1ccccc1)C1CCC1 ; BrC(c1ccccc1)C1CCC1]

To a solution of the alcohol of Preparation 142 (6 g, 37.0 mmol) in benzene (30 mL) was added acetyl bromide (13.66 g, 111.1 mmol) at 0° C. The resulting reaction mixture was stirred at room temperature for 16 hours then diluted with water (100 mL) and extracted with EtOAc (2×100 mL). The combined organic layers were dried over anhydrous Na$_2$SO$_4$ and concentrated under reduced pressure to give the title compound (8 g, 95%) as a colourless viscous oil. 1H NMR (300 MHz, Chloroform-d) δ 7.40-7.22 (m, 5H), 4.93-4.83 (d, J=8.0 Hz, 1H), 3.19-3.04 (m, 1H), 2.34-2.22 (m, 1H), 2.10-1.70 (m, 5H).

Preparation 144

Ethyl 3-cyclobutyl-2-((diphenylmethylene)amino)-3-phenylpropanoate

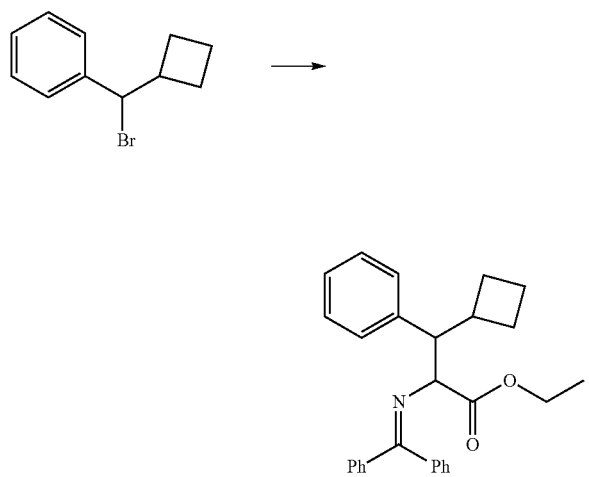

To a solution of the bromide of Preparation 143 (9 g, 40 mmol) in DMSO (40 mL) was added KOtBu (5.36 g, 48 mmol) and ethyl 2-(benzhydrylideneamino)acetate (5.34 g, 2.94 mmol) and the mixture was stirred at room temperature for 10 min (colour change from yellow to black). The reaction mixture was diluted with water (150 mL) and extracted with EtOAc (2×150 mL), the combined organic layers were dried over anhydrous Na$_2$SO$_4$ and concentrated under reduced pressure. The crude product was purified by silica gel (100-200 mesh) column chromatography (5-10% EtOAc in hexane as eluent) to afford the title compound (5.7 g, crude) as a brown viscous oil. LCMS (METHOD 5) (ESI): m/z: 412 [M+H$^+$]; RT=2.89 min; (ACQUITY UPLC BEH C18 column, 0.1% FA in water with MeCN).

Preparation 145

Ethyl 2-((tert-butoxycarbonyl)amino)-3-cyclobutyl-3-phenylpropanoate

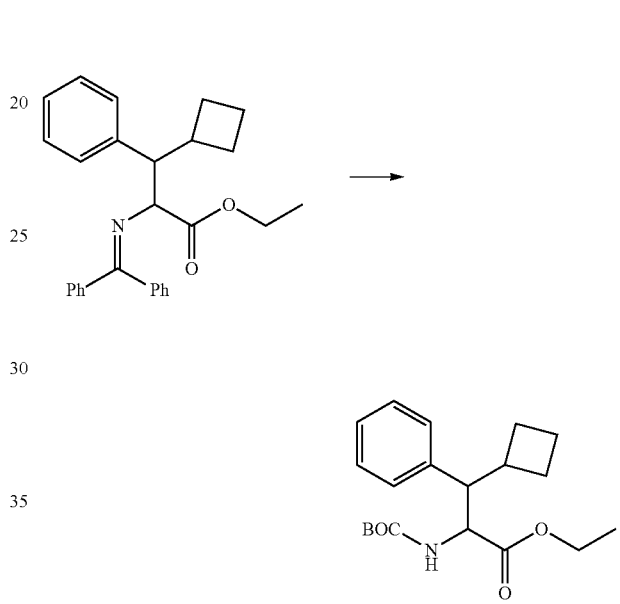

To a stirred solution of the imine of Preparation 144 (3.5 g, 8.51 mmol) in DCM (20 mL) was added 6M HCl (50 mL) at room temperature. The reaction mixture was stirred at room temperature for 16 hours then basified with aq. NaHCO$_3$ to pH~8-9 and extracted with EtOAc (2×150 mL). The combined organic layers were dried over anhydrous Na$_2$SO$_4$ and concentrated under reduced pressure. The residue was dissolved in THF (20 mL) and aq. NaHCO$_3$ (50 mL) and (Boc)$_2$O (2.8 mL, 12.8 mmol) were added. The reaction mixture was stirred at room temperature for 16 hours then diluted with water (100 mL) and extracted with EtOAc (2×100 mL). The combined organic layers were dried over anhydrous Na$_2$SO$_4$ and concentrated under reduced pressure. The crude product was purified by silica gel (100-200 mesh) column chromatography (0-10% EtOAc in hexane as eluent) to give the title compound as a mixture of diastereomers (2 g, 68%) as a yellow viscous oil. 1H NMR (300 MHz, Chloroform-d) δ 7.30-7.20 (m, 4H), 7.09-7.04 (m, 2H), 4.13-4.11 (m, 1H), 4.04-4.003 (m, 2H), 2.95-2.70 (m, 1H), 2.37-2.22 (m, 1H), 2.10-1.70 (m, 6H). 1.42 (s, 9H), 1.13-1.105 (m, 3H); LCMS (METHOD 5) (ESI): m/z: 348 [M+H$^+$]; 50%+45%; RT=2.62 min 8*. 2.64 min; (ACQUITY UPLC BEH C18 column, 0.1% FA in water with MeCN).

Preparation 146

2-((Tert-butoxycarbonyl)amino)-3-cyclobutyl-3-phenylpropanoic acid

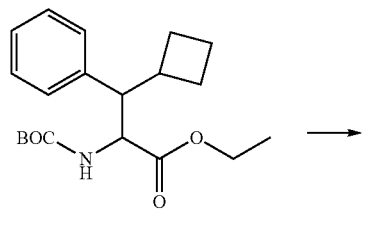

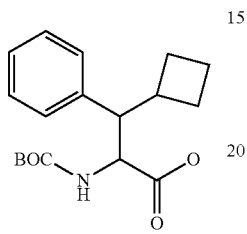

To a stirred solution of the ester of Preparation 145 (2 g, 5.76 mmol) in THF (15 mL) and water (15 mL) was added NaOH (2.3 g, 57.6 mmol) portion-wise at room temperature. The reaction mixture was stirred at 80° C. for 16 hours then the reaction mixture was concentrated under reduced pressure. The residue obtained was neutralized with aq. citric acid solution to pH~6-7 and extracted with EtOAc (2×100 mL). The combined organic layers were dried over anhydrous $Na_2SO_4$ and concentrated under reduced pressure. The crude product was washed with n-pentane to give the title compound (1.2 g, 66%). 1H NMR (500 MHz, DMSO-d6) δ 12.50 (br s, 1H), 7.26-7.23 (t, J=7.0 Hz, 1H), 7.18-7.13 (m, 4H), 6.86-6.84 (d, J=9.5 Hz, 1H), 4.17-4.14 (dd, J=6.5 Hz, 9.0 Hz, 1H), 3.06-3.03 (dd, J=6.5 Hz, 11.0 Hz, 1H), 2.05-1.95 (m, 1H), 1.88-183 (m, 1H), 1.76-1.67 (m, 2H), 1.60-1.39 (m, 3H), 1.40 (s, 9H); LCMS (METHOD 5) (ESI): m/z: 320 [M+H$^+$]; RT=2.32 min; (ACQUITY UPLC BEH C18 column, 0.1% FA in water with MeCN).

Preparation 147

(4,5,6,7-Tetrachloro-1,3-dioxo-isoindolin-2-yl) 2-isopropyl-3-methyl-butanoate

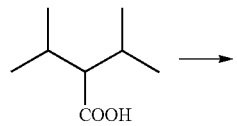

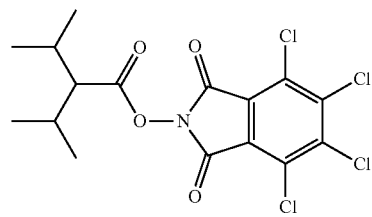

A dry round-bottomed flask was charged with 2-isopropyl-3-methyl-butanoic acid (3.5 g, 24.3 mmol), N-hydroxytetrachlorophthalimide (8.03 g, 1.1 eq.), and DMAP (0.593 g, 0.2 eq.). DCM was added (40 mL), and the mixture was stirred vigorously under a $N_2$ atmosphere. N,N'-Diisopropylcarbodiimide (4.08 mL, 3.29 g, 1.1 eq.) was then added dropwise via syringe, and the mixture was allowed to stir at room temperature until the acid was consumed (monitored by TLC). The mixture was filtered through a Celite pad, rinsed with additional DCM and concentrated under reduced pressure. The crude product was purified by silica gel (100-200 mesh) column chromatography (1% EtOAc in pet. ether as eluent) to afford the title compound (7.0 g, 67%) as a white solid. 1H NMR (400 MHz, Chloroform-d) δ 2.33-2.41 (m, 1H), 2.12 (dq, J=13.69, 6.85 Hz, 2H), 1.01-1.13 (m, 12H).

Preparation 148

Ethyl (2S)-3-isopropyl-4-methyl-2-[(2,4,6-trimethylphenyl)sulfinylamino]pentanoate

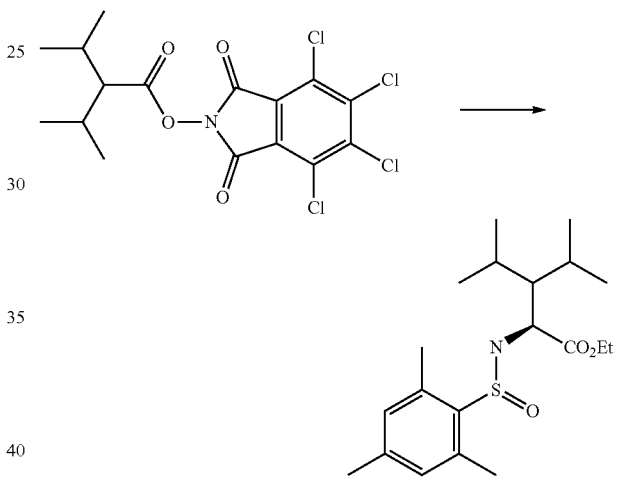

A culture tube was charged with the redox-active ester of Preparation 147 (2.0 g, 4.7 mmol), ethyl (E)-2-((2,4,6-trimethylphenyl)sulfinylamino)acetate (Synthesised according to *Angew. Chem. Int. Ed.* 2018, 57, 14560) (1.88 g, 1.5 eq.), Ni(OAc)$_2$.4H$_2$O (0.292 g, 0.25 eq.) and zinc-dust (0.923 g, 3 eq.). The tube was then evacuated and backfilled with argon (three times). Anhydrous NMP (20 mL) was added using a syringe. The mixture was stirred overnight at room temperature. Then, the reaction mixture was diluted with Et$_2$O and water and filtered through a Celite pad, and then extracted with Et$_2$O (2×30 mL) washed with water, brine and dried over Na$_2$SO$_4$. After filtration, the organic layer was concentrated under reduced pressure (water bath at 30° C.), and the residue was purified by silica gel (100-200 mesh) column chromatography (6-8% EtOAc in pet. ether as eluent) to afford the title compound (0.500 g, 29%) as a colourless gum. $^1$H NMR (400 MHz, Chloroform-d) 66.87 (s, 2H), 5.04 (br d, J=9.29 Hz, 1H), 4.23-4.25 (m, 2H), 4.15 (dd, J=9.54, 4.65 Hz, 1H), 2.60 (s, 6H), 2.29 (s, 3H), 1.77-1.98 (m, 2H), 1.50-1.57 (m, 1H), 1.31 (t, J=7.34 Hz, 3H), 0.99 (t, J=6.85 Hz, 6H), 0.89 (dd, J=6.85, 5.87 Hz, 6H); LCMS (METHOD 5) (ESI): m/z 368.45 [M+H$^+$]; RT=3.11 min; (ACQUITY UPLC BEH C18 column, 0.1% formic acid in water with MeCN).

Preparation 149

Ethyl (2S)-2-amino-3-isopropyl-4-methyl-pentanoate

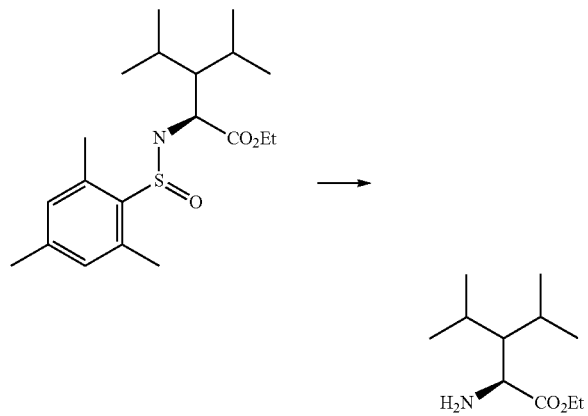

To a stirred solution of the compound of Preparation 148 (0.500 g, 1.36 mmol) in MeOH (10 mL) at 0° C. under $N_2$ was added 4M HCl in MeOH (2 mL). The reaction was stirred at room temperature for 4 hours. The reaction mixture was concentrated under reduced pressure and dried to afford the title compound (0.50 g, crude) as a light-yellow gum which was used in the next step without further purification.

Preparation 150

Ethyl (2S)-2-(tert-butoxycarbonylamino)-3-isopropyl-4-methyl-pentanoate

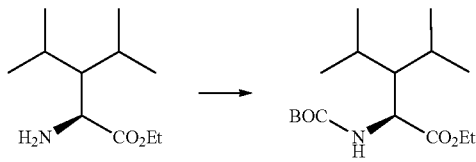 [SMILES: CCOC(=O)[C@@H](N)C(C(C)C)C(C)C ; CCOC(=O)[C@@H](NC(=O)OC(C)(C)C)C(C(C)C)C(C)C]

To a stirred solution of the amine of Preparation 149 (0.50 g, crude) in DCM (10 mL) was added triethylamine (0.38 mL, 2 eq.) and $Boc_2O$ (450 mg, 1.5 eq.) at 0° C. under $N_2$. The reaction was stirred at room temperature for 6 hours. The reaction was diluted with ice-cold water (10 mL) and extracted with DCM (2×30 mL). The combined organic layers were dried over $Na_2SO_4$ and concentrated under reduced pressure. The crude residue was purified by silica gel (100-200 mesh) column chromatography (1-2% EtOAc in pet. ether as eluent) to afford the title compound (0.50 g, impure) as a colourless gum which was used directly in the next step.

Preparation 151

(2S)-2-(Tert-butoxycarbonylamino)-3-isopropyl-4-methyl-pentanoic acid

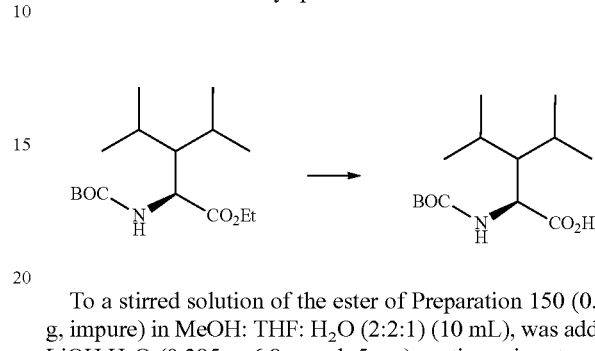

To a stirred solution of the ester of Preparation 150 (0.50 g, impure) in MeOH: THF: $H_2O$ (2:2:1) (10 mL), was added $LiOH·H_2O$ (0.285 g, 6.8 mmol, 5 eq.) portion-wise at room temperature. The reaction mixture was stirred at room temperature for 4 hours then concentrated in vacuo. The residue obtained was diluted in DCM (20 mL) and water (20 mL) and the organic layer was extracted with water (3×20 mL). The combined aqueous layers were acidified with 1M aq. HCl and extracted with EtOAc (2×30 mL). The combined EtOAc extracts were dried over $Na_2SO_4$ and concentrated under reduced pressure to afford the title compound (0.140 g, 54%) as white solid. $^1$H NMR (400 MHz, CHLOROFORM-d) δ 4.91 (br d, J=9.78 Hz, 1H), 4.59 (br d, J=9.29 Hz, 1H), 2.00 (tt, J=6.79, 3.24 Hz, 1H), 1.69-1.88 (m, 2H), 1.45 (s, 9H), 1.05 (br d, J=6.85 Hz, 3H), 0.98 (d, J=6.36 Hz, 3H), 0.94 (d, J=6.36 Hz, 3H), 0.86 (d, J=6.85 Hz, 3H); $^{13}$C NMR (100 MHz, CHLOROFORM-d) δ ppm: 179.1, 155.6, 80.1, 51.8, 51.7, 28.33, 27.8, 21.6; LCMS (METHOD 5) (ELSD) (ESI): m/z 272.34 [M–H]; RT=2.44 min (ACQUITY UPLC BEH C18 column, 0.1% formic acid in water with MeCN) and Chiral HPLC~99% SFC METHOD: Chiralcel OJHH (250×4.6) mm: 5µ, Co-solvent: n-hexane in Methanol, flow Rate: 1 mL/min, % Co-solvent: 10%, Temperature: 40° C., Outlet Pressure: 3.5 bar, RT: 3.5 min.

Preparations 152-177

The Boc protected amino acids of Preparations 152-177 were synthesised according to the methods of Preparations 147 to 151 starting from the appropriate carboxylic acid. The carboxylic acids are either commercially available or are known in the literature. LCMS spectra were recorded using LCMS Method 5.

| Prep. No. | Structure | Name | 1H NMR | Mass ion | LCMS RT (min) |
|---|---|---|---|---|---|
| 152 | ![structure] | (2S)-2-(tert-butoxycarbonyl amino)-2-(2,2-dimethylcyclohexyl)acetic acid | $^1$H NMR (400 MHz, DMSO-d$_6$) δ 12.47 (br s, 1H), 7.06, 6.67 (d, J = 8.34 Hz, J = 10.01 Hz, 1H), 4.41, 3.93 (dd, J = 10.01, dd, J = 8.23, 5.72 Hz, 1H), 1.38 (s, 9H), 1.34-1.36 (m, 3H), 1.06-1.33 (m, 6H), 0.97, 0.91 (s, 3H), 0.86, 0.8 (s, 3H) | 284.4 [M – H] isomer ratio 1:4 | 2.42 and 2.49 (ACQUITY UPLC BEH C18 column, 0.1% FA in water with MeCN) |

| Prep. No. | Structure | Name | 1H NMR | Mass ion | LCMS RT (min) |
|---|---|---|---|---|---|
| 153 | BocHN(S)—CO₂H (2,2-dimethylcyclopentyl) | (2S)-2-(tert-butoxycarbonyl amino)-2-(2,2-dimethylcyclopentyl)acetic acid | $^1$H NMR (400 MHz, DMSO-d$_6$) δ 12.4 (br s, 1H), 6.91-7.08 (m, 1H), 3.78-3.96 (m, 1H), 1.68-1.88 (m, 2H), 1.40-1.61 (m, 5H), 1.37 (s, 9H), 0.96 (s, 3H), 0.85 (s, 3H) | 270.4 [M − H] | 4.13 (ACQUITY UPLC BEH C18 column, 0.1% FA in water with MeCN) |
| 154 | BocHN(S)—CO₂H (2,2-dimethylcyclobutyl) | (2S)-2-(tert-butoxycarbonyl amino)-2-(2,2-dimethylcyclohexyl)acetic acid | $^1$H NMR (400 MHz, DMSO-d$_6$) δ 11.84-12.72 (m, 1H), 6.69-7.06 (m, 1H), 3.68-4.00 (m, 1H), 2.10-2.25 (m, 1H), 1.51-1.90 (m, 3H), 1.41-1.49 (m, 1H), 1.37 (s, 9H), 1.13 (s, 2H), 0.97-1.06 (m, 4H) | 256.4 [M − H] | 2.22 (ACQUITY UPLC BEH C18 column, 0.1% FA in water with MeCN) |
| 155 | BocHN(S)—CO₂H (bicyclo[3.1.0]hexanyl) | (2S)-2-(3-bicyclo[3.1.0]hexanyl)-2-(tert-butoxycarbonyl amino)acetic acid | $^1$H NMR (400 MHz, CHLOROFORM-d) δ 7.82 (br s, 1H), 4.88-5.10 (m, 1H), 3.96-4.28 (m, 1H), 1.92-2.17 (m, 2H), 1.51-1.89 (m, 2H), 1.44 (s, 9H), 1.22-1.33 (m, 3H), 0.32 (td, J = 7.82, 5.40 Hz, 1H), 0.12-0.20 (m, 1H) | 254.2 [M − H] | 4.9 (ACQUITY UPLC BEH C18 column, 0.1% FA in water with MeCN) |
| 156 | BocHN(S)—CO₂H (4,4-dimethylcyclohexyl) | (2S)-2-(tert-butoxycarbonyl amino)-2-(4,4-dimethylcyclohexyl)acetic acid | $^1$H NMR (400 MHz, DMSO-d$_6$) δ 12.38 (s, 1H), 6.98 (d, J = 8.4 Hz, 1H), 3.80-3.83 (m, 1H), 1 53-1.6 (m, 1H), 1.38 (s, 9H), 1.34-1.36 (m, 8H), 0.86 J =9.26 Hz, 6H) | 284.4 [M − H] | 2.49 (ACQUITY UPLC BEH C18 column, 0.1% FA in water with MeCN) |
| 157 | BocHN(S)—CO₂H (3,3-dimethylcyclohexyl) | (2S)-2-(tert-butoxycarbonyl amino)-2-(3,3-dimethylcyclohexyl)acetic acid | $^1$H NMR (400 MHz, DMSO-d$_6$) δ 12.39 (br s, 1H), 6.86-6.94 (m, 1H), 3.70-3.79 (m, 1H), 1.73-1.91 (m, 1H), 1.46-1.61 (m, 2H), 1.38 (s, 9H), 1.19-1.38 (m, 6H), 0.87 (s, 3H), 0.84 (d, J = 4.80 Hz, 3H) | 284.4 [M − H] | 2.49 (ACQUITY UPLC BEH C18 column, 0.1% FA in water with MeCN) |
| 158 | BocHN(S)—CO₂H (2,2,3,3-tetramethylcyclopropyl) | (2S)-2-(tert-butoxycarbonyl amino)-2-(2,2,3,3-tetramethylcyclopropyl)acetic acid | $^1$H NMR (400 MHz, CHLOROFORM-d) δ 10.1 (br s 1H), 4.87-4.98 (m, 1H), 3.76-3.95 (m, 1H), 1.44 (s, 9H), 1.20-1.29 (m, 1H), 1.13 (s, 3H), 1.10 (s, 3H), 1.07 (s, 3H), 1.03 (s, 3H) | 270.2 [M − H] | 6.45 (ACQUITY UPLC BEH C18 column, 0.05% TFA in water with MeCN) |
| 159 | BocHN(S)—CO₂H (norcaran-7-yl) | (2S)-2-(tert-butoxycarbonyl amino)-2-norcaran-7-yl-acetic acid | $^1$H NMR (400 MHz, CHLOROFORM-d) δ 8.10-8.72 (s, 1H), 4.9 -5.08 (m, 1H), 3.68-3.66 (m, 1H), 1.9-1.82 (m, 2H), 1.66-1.61 (m, 2H), 1.44 (s, 9H), 1.05-1.30 (m, 5H), 0.94-1.02 (m, 1H), 0.82-0.76 (m, 1H) | 268.2 [M − H] | 5.25 (ACQUITY UPLC BEH C18 column, 0.05% TFA in water with MeCN) |

| Prep. No. | Structure | Name | 1H NMR | Mass ion | LCMS RT (min) |
|---|---|---|---|---|---|
| 160 | BocHN*,,CO₂H Diastereomer 1* | Diastereomer 1 of (2S)-2-(tert-butoxycarbonyl amino)-3-cyclohexyl-pentanoic acid | ¹H NMR (400 MHz, DMSO-d₆) δ 12.46 (s, 1H), 6.81 (d, J = 9.37 Hz, 1H), 3.91-4.14 (m, 1H), 1.46-1.63 (m, 7H), 1.38-1.46 (m, 11H), 1.23-1.11 (m, 4H), 0.73-0.96 (m, 4H) | 244.1 [M + H-56] | 3.82 (ACQUITY UPLC BEH C18 column, 0.1% FA in water with MeCN). |
| 161 | BocHN*,,CO₂H Diastereomer 2* | Diastereomer 2 of (2S)-2-(tert-butoxycarbonyl amino)-3-cyclohexyl-pentanoic acid | ¹H NMR (400 MHz, DMSO-d₆) δ 12.24-12.59 (m, 1H), 6.74 (d, J =5.87 Hz, 1H), 4.14 (d, J = 4.77 Hz, 1H), 1.47-1.78 (m, 6H), 1.18-1.44 (m, 12H), 0.89-1.16 (m, 5H), 0.77-0.88 (m, 3H) | — | — |
| 162 | BocHN,,CO₂H (with 4,4-difluorocyclohexyl) | (2S)-2-(tert-butoxycarbonyl amino)-3-(4,4-difluorocyclo hexyl)propanoic acid | ¹H NMR (400 MHz, DMSO-d₆) δ 12.45 (br s, 1H), 7.08 (d, J = 8.23 Hz, 1H), 3.88-3.96 (m, 1H), 1.97 (br dd, J = 7.09, 3.99 Hz, 2H), 1.67-1.81 (m, 4H), 1.46-1.57 (m, 3H), 1.38 (s, 9H), 1.05-1.26 (m, 2H) | 306.3 [M − H] | 2.19 (ACQUITY UPLC BEH C18 column, 0.1% FA in water with MeCN) |
| 163 | BocHN,(S),CO₂H (bicyclo[2.2.2]octanyl) | (2S)-2-3-bicyclo[2.2.2] octanyl)-2-(tert-butoxycarbonyl amino)acetic acid | ¹H NMR (400 MHz, DMSO-d₆) δ 12.3 (br s, 1H), 6.98-.15 (m, 1H), 3.69-3.80 (m, 1H), 1.64-1.87 (m, 2H), 1.39-1.58 (m, 6H), 1.37-1.39 (m, 3H), 1.36 (s, 9H), 1.15-1.32 (m, 2H) | 282.3 [M − H] | 2.37 (ACQUITY UPLC BEH C18 column, 0.1% FA in water with MeCN) |
| 164 | BocHN,(S),CO₂H (bicyclo[3.1.0]hexanyl) | (2S)-2-(6-bicyclo[3.1.0] hexanyl)-2-(tert butoxycarbonyl amino)acetic acid | ¹H NMR (400 MHz, DMSO-d₆) δ 12.31 (br s, 1H), 7.22, 7.14 (d, J = 7.63 Hz, 1H), 3.52, 3.29 (dd, J = 11.27, 7.93 Hz, 2H), 1.79-1.90 (m, 2H), 1.44-1.72 (m, 3H), 1.37 (d, J = 2.74 Hz, 9H), 1.17-1.26 (m, 1H), 0.91-1.08 (m, 1H), 0.74-0.82 (m, 1H) | 256.4 [M + H] isomer ratio 1:3 | 2.10 and 2.14 (ACQUITY UPLC BEH C18 column, 0.1% FA in water with MeCN) |
| 165 | BocHN,,CO₂H (3,5-dimethylcyclohexyl) | (2S)-2-(tert-butoxycarbonyl amino)-2-[(3R,5S)-3-5-dimethylcyclohex yl]acetic acid | ¹H NMR (400 MHz, DMSO-d₆) δ 12.29 (s, 1H), 7.07, 6.88 (d, J = 8.46 Hz, 1H), 3.95, 3.77 (dd, J = 8.17, 6.62 Hz, 1H), 1.43-1.97 (m, 7H), 1.37 (s, 9H), 0.85 (s, 3H), 0.84 (s, 3H), 0.40-0.76 (m, 2H) | 284.5 [M− H] isomer ratio 1:8 | 2.53 and 2.56 (ACQUITY UPLC BEH C18 column, 0.1% FA in water with MeCN) |
| 166 | BocHN,(S),CO₂H (4-CF₃-cyclohexyl) | (2S)-2-(tert-butoxycarbonyl amino)-2-[4-(trifluoromethyl) cyclohexyl] acetic acid | ¹H NMR (400 MHz, DMSO-d₆) δ 12.5 (br s, 1H), 7.11, 6.97 (d, J = 8.46 Hz, 1H), 3.97, 3.8 (t, J = 9.36 Hz, 1H), 2.26-2.40 (m, 1H), 2.09-2.19 (m, 1H), 1.86 (d, J = 6.44 Hz, 2H), 1.46-1.75 (m, 4H), 1.38 (s, 9H), 1.09-1.27 (m, 2H) | 324.2 [M − H] isomer ratio 7:91 | 2.30 and 2.34 (ACQUITY UPLC BEH C18 column, 0.1% FA in water with MeCN) |

| Prep. No. | Structure | Name | 1H NMR | Mass ion | LCMS RT (min) |
|---|---|---|---|---|---|
| 167 | BocHN, CO₂H (with cyclopentyl and cyclohexyl groups) | (2S)-2-((tert-butoxycarbonyl)amino)-3-cyclohexyl-3-cyclopentylpropanoic acid | ¹H NMR (400 MHz,CDCl₃); 1.23 (d, J = 6.80 Hz, 3H) 1.40 (d, J = 6.58 Hz, 3H) 1.89-1.99 (m, 1H) 2.14 (s, 3H) 2.16-2.20 (m, 1H) 2.22 (s, 3H) 2.60-2.65 (m, 1H) 2.71-2.78 (m, 1H) 3.08-3.15 (m, 1H) 3.24-3.44 (m, 3H) 3.51-3.56 (m, 2H) 3.75-3.80 (m, 1H) 4.21-4.25 (m, 1H) 5.16-5.35 (m, 2H) 6.47 (s, 2H); | 374 [M + H] | 1.63 (ACQUITY UPLC BEH C18 column, 0.1% FA in water with MeCN) |
| 168 | BocHN, CO₂H (with tert-butyl group) | (2S)-2-(tert-butoxycarbonyl)amino)-3,4,4-trimethyl-pentanoic acid | ¹H NMR (400 MHz, DMSO-d₆) δ 12.47 (br s, 1H) 7.02-6.72 (br d, J = 8.11 Hz, J = 10.01 Hz, 1H) 4.40-3.96 (dd, J = 10.01 Hz, J = 7.93, 5.19 Hz, 1H) 1.81-1.53 (m, 1H) 1.34-1.41 (s, 9H) 0.88 (s, 9H) 0.80-0.85 (m, 3H) | 258.4 [M − H] isomer ratio 1:8 | 2.26 and 2.31 (ACQUITY UPLC BEH C18 column, 0.1% FA in water with MeCN) |
| 169 | BocHN, CO₂H (with cyclobutyl group) | (2S)-2-(tert-butoxycarbonyl)amino)-3-cyclobutyl-butanoic acid | ¹H NMR (400 MHz, DMSO-d₆) δ 12.37-12.54 (br s, 1H) 6.83-6.75 (m 1H) 3.99-3.83 (dd, J = 9.00 4.11 Hz, J = 8.34, 4.65 Hz, 1H 1.50-2.34 (m, 8H) 1.38 (s, 9H 0.72 (dd, J = 11.68, 6.91 Hz 3H) | 256.3 [M − H] | 2.27 (ACQUITY UPLC BEH C18 column, 0.1% FA in MeCN) |
| 170 | BocHN, CO₂H (with cyclopentyl group) | (2S)-2-(tert-butoxycarbonyl amino)-3-cyclopentyl-butanoic acid | ¹H NMR (400 MHz, DMSO-d₆) δ 12.33-12.55 (br s, 1H) 6.89 - 6.80 (br d, J = 8.23 Hz, J = 9.18 Hz, 1H) 4.14-3.96 (dd, J = 9.24, J = 8.11 Hz, 1H) 1.43-1.86 (m, 8H) 1.38 (s, 9H) 1.03-1.14 (m, 2H) 0.8 (t, J = 6.97 Hz, 3H) | 270.1 [M − H] isomer ratio 3:2 | 11.07 and 11.14 (XSelect CSH C18 column, 0.0% TFA in water with MeCN) |
| 171 | BocHN, CO₂H (with cyclohexyl group) | (2S)-2-(tert-butoxycarbonyl amino)-3-cyclohexyl-butanoic acid | ¹H NMR (400 MHz, DMSO-d₆) δ 12.26-12.57 (br s, 1H) 7.00-6.83 (br d, J = 8.58 Hz, J = 9.18 Hz, 1H) 4.14-3.85 (m, 1H) 1.69 (br d, J = 7.03 Hz, 4H) 1.49-1.63 (m, 2H) 1.38 (s, 9H) 1.22-1.26 (m, 2H) 1.01-1.20 (m, 5H) 0.83-1.01 (m, 2H) 0.79-0.75 (d, J = 7.03 Hz, 3H) | 284.3 [M − H] isomer ratio 7:13 | 4.53 and 4.55 (ACQUITY UPLC BEH C18 column, 0.1 % FA in water with MeCN) |
| 172 | BocHN, CO₂H (with isopropyl group) | (2S)-2-(tert-butoxycarbonyl amino)-3,4-dimethyl-pentanoic acid | ¹H NMR (400 MHz, DMSO-d₆) δ 12.43 (br s, 1H) 7.03-6.84 (m, 1H) 4.10-3.79 (m, 1H) 1.45-1.86 (m, 2H) 1.38 (s, 9H) 1.21-1.28 (m, 1H) 0.69-0.91 (m, 8H) | 244.32 [M − H] | 7.51 (X Bride C18 column, 10 mM in water with MeCN) |
| 173 | BocHN, CO₂H (with spiro[2.3]hexane group) | (2S)-2-(tert-butoxycarbonyl amino)-2-spiro[2.3]hexan-2-yl-acetic acid | ¹H NMR (400 MHz, DMSO-d₆) δ 12.09-12.30 (br s, 1H) 7.43-7.18 (m, 1H) 3.19-2.94 (m, 1H) 1.87-2.13 (m, 4H) 1.32-1.41 (m, 9H) 0.95-0.84 (m, 1H) 0.54-0.67 (m, 1H) 0.28-0.47 (m, 1H) 0.26-0.49 (m, 1H) | 254.3 [M − H] isomer ratio 11:9 | 3.66 and 3.71 (ACQUITY UPLC BEH C18 column, 0.1% FA in water with MeCN) |

| Prep. No. | Structure | Name | 1H NMR | Mass ion | LCMS RT (min) |
|---|---|---|---|---|---|
| 174 | | (2S)-2-(tert-butoxycarbonyl amino)-2-(2,2-dimethylcyclo propyl)acetic acid | $^1$H NMR (400 MHz, DMSO-d$_6$) δ 12.17-12.35 (br s, 1H) 7.33-7.19 (m, 1H) 3.46 (br dd, J = 10.49, 7.87 Hz, 1H) 1.42 (s, 9H) 1.12 (s, 6H) 0.73-0.87 (m, 1H) 0.48-0.42 (dd, J = 8.58, 4.53 Hz, J = 8.58, 4.29 Hz, 1H) 0.32-0.15 (t, J = 4.83 Hz, 1H) | 242.3 [M − H] isomer ratio 11:9 | 3.39 and 3.46 (ACQUITY UPLC BEH C18 column, 0.1% FA in water with MeCN) |
| 175 | BocHN—CO$_2$H (with isobutyl and neopentyl substituents) | (2S)-2-(tert-butoxycarbonyl amino)-3-5,5-trimethyl hexanoic acid | $^1$H NMR (400 MHz, DMSO-d$_6$) δ 12.49 (br s, 1H) 6.69-6.83 (m, 1H) 3.82-3.97 (m, 1H) 1.86-2.08 (m, 1H) 1.38 (d, J = 1.43 Hz, 9H) 1.21-1.27 (m, 1H) 0.82-1.06 (m, 13H) | 272.3 [M − H] | 8.29 (X Bride C18 column, 10 mM in water with MeCN) |
| 176 | BocHN—CO$_2$H (with adamantyl) | (2S)-2-(2-adamantyl)-2-(tert-butoxycarbonyl amino)acetic acid | $^1$H NMR (400 MHz, DMSO-d$_6$) δ 12.20-12.50 (br s, 1H) 7.03 (br d, J = 8.46 Hz, 1H) 4.17 (dd, J = 11.15, 8.64 Hz, 1H) 1.74-1.97 (m, 8H) 1.59 - 1.70 (m, 5H) 1.41-1.54 (m, 2H) 1.37 (s, 9H) | 308.3 [M − H] | 4.55 (ACQUITY UPLC BEH C18 column, 0.05% TFA in water with MeCN) |
| 177 | BocHN—CO$_2$H (with cyclopropylmethyl isopropyl) | (2S)-2-(tert-butoxycarbonyl amino)-4-cyclopropyl-3-methyl-butanoic acid | $^1$H NMR (400 MHz, DMSO-d$_6$) δ 12.43 (br s, 1H) 6.91-6.81 (m, 1H) 4.10-3.8 (m, 1H) 2.11-1.86 m, 1H) 1.4 (s, 9H) 1.35-1.28 (m, 2H) 0.8-0.91 (m, 3H) 0.6 (m, 1H) 0.4 (m, 2H) 0.1 (m, 2H) | 256.2 [M − H] | 3.84 (ACQUITY UPLC BEH C18 column, 0.1% FA in water |

The diastereomers were separated before removal of the (2,4,6-trimethylphenyl)sulfinyl group Preparation 178

Methyl 2-cyclooctylidene-2-formamidoacetate

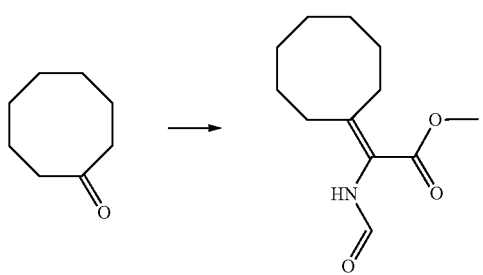 [SMILES: O=C1CCCCCCC1 ; COC(=O)C(NC=O)=C1CCCCCCC1]

A solution of methylisocyanoacetate (7.6 mL, 83.4 mmol, 1.05 eq.) in anhydrous THF (80 mL) was added dropwise to a solution of potassium-tert-butoxide in THF (1.0 M, 95 mL, 1.2 eq.) stirred at −70° C. under nitrogen atmosphere. After stirring for 5 minutes, a solution of cyclooctanone (10 g, 79.4 mmol, 1 eq.) in anhydrous THF (120 mL) was added slowly at −70° C. The reaction mixture was stirred at this temperature for 30 minutes, then allowed to warm to room temperature with stirring under nitrogen overnight. On completion of reaction the resultant deep red solution was quenched with water (200 mL) and stirred at room temperature for 1 h. The solution was extracted with EtOAc (3×200 mL). The combined organic extracts were washed with brine (100 mL) and dried over magnesium sulphate, filtered and concentrated in vacuo. The resulting crude viscous orange oil was purified by column chromatography using Grace automated system with a gradient of 35% of ethyl acetate in hexane to give the title compound as an orange viscous oil which solidified upon standing (6.80 g, 40% yield). $^1$H NMR (300 MHz, DMSO-d$_6$) δ 9.25 (br s, 1H), 8.00 (s, 1H), 3.59 (s, 3H), 2.34-2.25 (m, 2H), 1.70-1.61 (m, 5H), 1.52-1.40 (m, 7H); LCMS (ESI) m/z: 226 [M+H$^+$]; RT=2.14 min (ACQUITY BEH C18 column, 0.1% FA in water with MeCN).

Preparation 179

Methyl 2-cyclooctyl-2-formamidoacetate

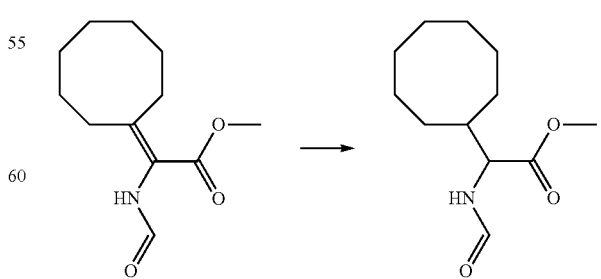

Pd(OH)$_2$ (1.6 g, 50% of moisture) was carefully added to a solution of the ester of Preparation 178 (6 g, 26.7 mmol)

in methanol (120 mL) under N$_2$. The reaction mixture was stirred under H$_2$ atmosphere for 16 h at 60 psi. On completion, the reaction mixture was filtered through a Celite pad and washed with methanol (100 mL). The filtrate was concentrated in vacuo to give the title compound as a colourless oil. (4.0 g, 81% yield); $^1$H NMR (300 MHz, DMSO-d$_6$) δ 8.48-8.44 (d, J=8.4 Hz, 1H), 4.31-4.27 (t, J=6 Hz, 1H), 3.64 (s, 3H), 1.61-1.18 (m, 16H). LCMS (ESI): m/z: 227 [M+H$^+$]; RT=2.25 min (ACQUITY BEH C18 column, 0.1% FA in water with MeCN).

Preparation 180

Methyl 2-amino-2-cyclooctyl-acetate hydrochloride

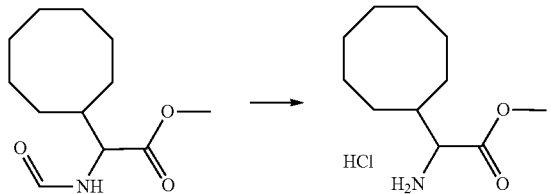 [SMILES: COC(=O)C(NC=O)C1CCCCCCC1 ; COC(=O)C(N)C1CCCCCCC1 ; Cl]

Conc. HCl (20 mL) was added to a solution of the ester of Preparation 179 (5 g, 22.0 mmol) in methanol (20 mL). The reaction mixture was stirred under N$_2$ at 90° C. for 5 h. On completion, the reaction mixture was concentrated in vacuo to give the title compound as an off-white solid yield. (4.0 g, 77% yield). $^1$H NMR (300 MHz, DMSO-d$_6$) δ ppm: 3.60 (s, 3H), 3.12-3.10 (d, J=5.7 Hz, 1H), 2.50-1.35 (m, 17H). LCMS (ESI): m/z: 200 [M+H$^+$]; 79%; RT=1.05 min (ACQUITY BEH C18 column, 0.1% FA in water with MeCN).

Preparation 181

Methyl 2-(tert-butoxycarbonylamino)-2-cyclooctyl-acetate

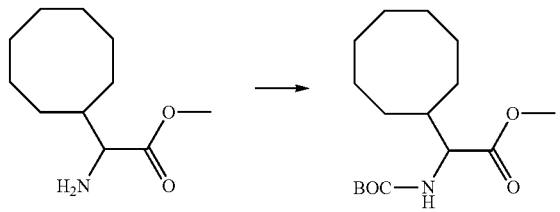 [SMILES: COC(=O)C(N)C1CCCCCCC1 ; COC(=O)C(NC(=O)OC(C)(C)C)C1CCCCCCC1]

Di-tert-butyl dicarbonate (7.1 mL, 32.5 mmol, 1.5 eq) was added slowly to a solution of the amine of Preparation 180 (4 g, 21.6 mmol) in 1,4-dioxane:H$_2$O (80 mL, 3:1) and saturated sodium bicarbonate (50 mL) at 0° C. The reaction mixture was stirred at room temperature for 6 h. On completion the reaction mixture was concentrated in vacuo and diluted with water (200 mL). The residue was extracted with EtOAc (2×200 mL) and the combined organic layers were dried over anhydrous sodium sulfate, concentrated in vacuo to afford the title compound as a colourless solid. (4.0 g, 65% yield). $^1$H NMR (300 MHz, DMSO-d$_6$) δ ppm: 3.88 (t, J=9 Hz, 1H), 3.61 (s, 3H), 2.00-1.95 (m, 1H), 1.62-1.25 (m, 23H). LCMS (ESI): m/z: 301 [M+H$^+$]; 90%; RT=2.04 min (ACQUITY BEH C18 column, 0.1% formic acid in water with MeCN).

Preparation 182

2-(tert-butoxycarbonylamino)-2-cyclooctyl-acetic acid

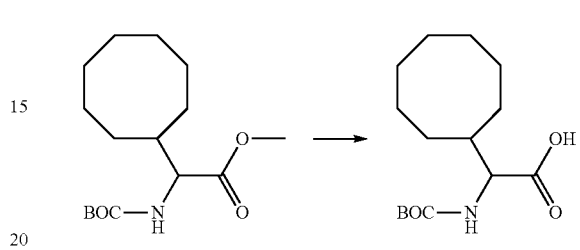

Lithium hydroxide monohydrate (1.6 g, 40.2 mmol) was added to the ester of Preparation 181 (4 g, 20.1 mmol) in THF:H$_2$O (45 mL, 10:3) at 0° C. The reaction mixture was stirred at room temperature for 2 h. On completion, the reaction mixture was concentrated and diluted with water (100 mL). The aqueous layer was washed with EtOAc (200 mL) then acidified with saturated citric acid to pH 4. This was then extracted with EtOAc (2×100 mL). The organic layers from the acidic wash were combined, dried over anhydrous sodium sulfate, filtered and concentrated in vacuo to afford crude product. The crude product was triturated with Et$_2$O (2×50 mL) to give the title compound as an off-white solid (3.1 g, 54% yield). $^1$HN MR (300 MHz, DMSO-d$_6$) δ 12.40 (br s, 1H), 6.90 (d, J=6 Hz, 1H), 3.82 (t, J=6 Hz, 1H), 1.94-1.90 (m, 1H), 1.61-1.37 (m, 23H). LCMS (ESI): m/z: 285 [M+H$^+$]; RT=1.81 min (ACQUITY BEH C18 column, 0.1% formic acid in water with MeCN).

Preparation 183

1s,3R,5S)-3,5-Dimethylcyclohexane-1-carboxylic acid

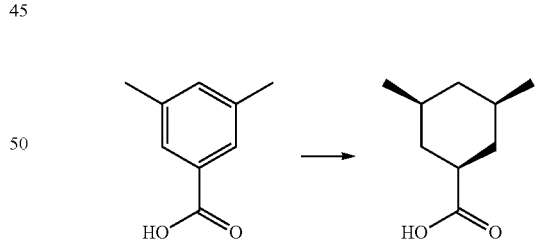

10% PtO$_2$ (2.5 g, 0.1 w/w) was added carefully under nitrogen to a solution of 3,5-dimethylbenzoic acid (25 g, 167 mmol) in ethanol (250 mL). The reaction mixture was shaken under a hydrogen atmosphere at 70 psi in Parr-shaker vessel at room temperature for 16 h. On completion, the reaction mixture was filtered through a Celite pad and washed with methanol (250 mL). The filtrate was concentrated in vacuo to afford the title compound as a light yellow oil (24 g, 92% yield). $^1$H NMR (300 MHz, DMSO-d$_6$) δ 11.99 (br s, 1H), 2.27-.2.18 (m, 1H), 1.82-1.78 (m, 2H), 1.61-1.57 (m, 1H), 1.47-1.36 (m, 2H), 0.96-0.89 (m, 8H), 0.56-0.44 (m, 1H).

Preparation 184

((1s, 3R,5S)-3,5-dimethyl cyclohexyl)methanol

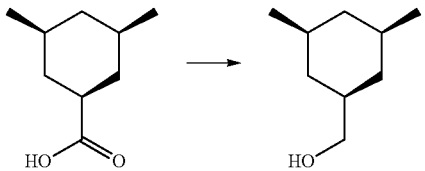

A solution of lithium aluminium hydride (166 mL, 167 mmol, 1 eq, 1M in THF) was added dropwise to a solution of the acid of Preparation 183 (26 g, 167 mmol) in THF (260 mL) over 30 min at 0° C. The reaction mixture was slowly warmed to room temperature and stirred for 16 h. On completion, the reaction mixture was re-cooled in an ice-salt bath and quenched by adding water (7 mL), 10% aq. NaOH solution (7 mL) and water (21 mL). The resulting viscous mixture was stirred for 10 minutes and filtered through a Celite pad. The filtrate was extracted with EtOAc (2×500 mL) and the combined organic layer was washed with water (500 mL), brine (500 mL), dried over sodium sulfate, filtered and concentrated in vacuo to give the title compound as a light yellow oil. (22 g, 93% yield). $^1$HN MR (400 MHz, CDCl$_3$) δ 3.44 (d, J=6.4 Hz, 2H), 1.73-1.63 (m, 3H), 1.59-1.50 (m, 1H), 1.49-1.40 (m, 3H), 0.89 (d, 0.7=6.4 Hz, 6H), 0.57-0.47 (dd, J=24.0 Hz, 13.2 Hz, 3H).

Preparation 185

(1s,3R,5S)-3,5-Dimethylcyclohexan-1-carbaldehyde

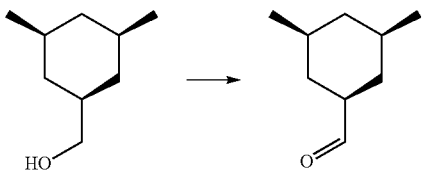

DMSO (9 mL, 127 mmol) was added to a solution of oxalyl chloride (8 mL, 95.1 mmol) in DCM (200 mL) at −78° C. and stirred at this temperature for 10 min. A solution of the alcohol of Preparation 184 (30 g, 63.38 mmol) in DCM (250 mL) was added dropwise at −78° C. and stirred for 30 min, followed by addition of Et$_3$N. (30 mL, 209 mmol) The reaction mixture was stirred for a further 30 min at −78° C. The cooling bath was removed and the reaction mixture was allowed to warm to room temperature over 1 h. On completion, the pale yellow reaction mixture was quenched with water (200 mL) and the aqueous phase was extracted with DCM (2×200 mL). The combined organic layer was washed with brine (200 mL), dried over sodium sulfate, filtered and concentrated in vacuo to afford crude compound. The crude product was purified by column chromatography (SiO$_2$, 1% EtOAc in Hexane as gradient) to afford the title compound as a yellow oil. (7.0 g, 79% yield). $^1$H NMR (300 MHz, CDCl$_3$) δ 9.60 (d, J=1.5 Hz, 1H), 2.44-2.26 (m, 1H), 1.93-1.87 (m, 2H), 1.72-1.65 (m, 1H), 1.72-1.41 (m, 2H), 1.01-0.80 (m, 8H), 0.62-0.50 (m, 1H).

Preparation 186

(S)—N—((Z)-((1s,3R,5S)-3,5-Dimethylcyclohexyl)methylene)-4-methylbenzenesulfinamide

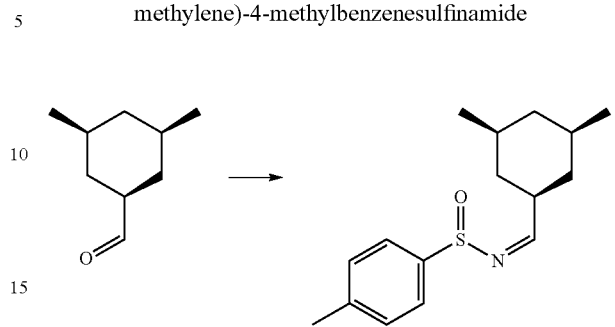

(S)-4-methylbenzene-5-sulphonamide (15.5 g, 100 mmol) was added to a solution of the aldehyde of Preparation 185 (14 g, 100 mmol) in DCM (600 mL). Titanium (IV) ethoxide (85-90% purity, 64 mL, 300 mmol) was added at room temperature. The resulting solution was heated at 50° C. for 2 h. On completion, the reaction mixture was cooled to ambient temperature then water (200 mL) was added slowly. The resulting thick paste was filtered through a Celite pad and rinsed with DCM (200 mL). The filtrate was washed with water (300 mL), brine (300 mL), dried over anhydrous sodium sulfate, filtered and concentrated in vacuo to obtain a crude residue, which was purified by column chromatography (SiO$_2$, 5% EtOAc in hexane as gradient) to afford the title compound as an off-white solid (22 g, 91% yield). $^1$H NMR (400 MHz, DMSO-d$_6$) δ 8.58 (d, J=4.4 Hz, 1H), 7.52-7.50 (dd, J=6.4 Hz, 1.6 Hz, 2H), 7.39-7.37 (m, 2H), 2.36 (s, 3H), 1.76 (d, J=12.8 Hz, 2H), 1.63-1.59 (m, 1H), 1.49-1.43 (m, 2H), 0.99-0.71 (m, 9H), 0.56-0.47 (dd, J=24.0 Hz, 12 Hz, 1H). LCMS (ESI): m/z: 278 [M+H$^+$]; RT=5.34 min, (ACQUITY BEH C18 column, 0.05% formic acid in water with MeCN).

Preparation 187

(S)—N-(Cyano((1s,3R,5S)-3,5-dimethylcyclohexyl)methyl)-4-methylbenzenesulfinamide

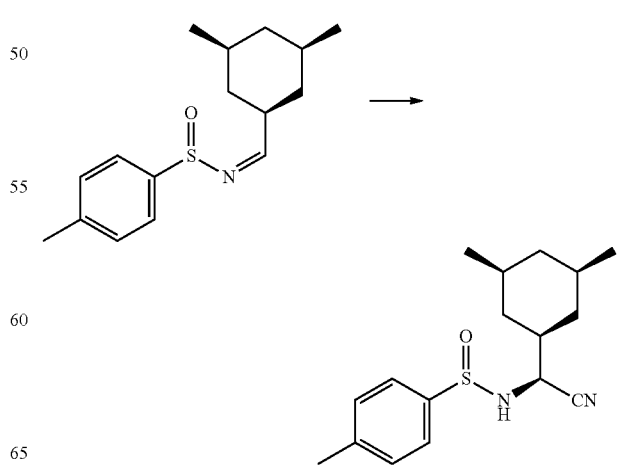

IPA (5 mL, 79.4 mmol) was added dropwise to a solution of diethyl aluminium cyanide (120 mL, 119 mmol, 1.0 M in THF) in dry THF (400 mL) at −78° C. The reaction mixture was stirred at −78° C. for 45 minutes and then added via a canula into a solution of the compound of Preparation 186 (22 g, 79.42 mmol) in THF (1 L) at −78° C. over 45 minutes. The reaction mixture was allowed to warm to room temperature and stirred for 16 h. On completion, the reaction mixture was cooled to −30° C., and quenched by the careful addition of saturated aq. NH₄Cl solution (300 mL). After 1 h the reaction mixture was filtered through a Celite pad and washed with water (300 mL). The filtrate was extracted with EtOAc (2×400 mL). The combined organic layer was washed with water (300 mL), brine (300 mL), dried over sodium sulfate, filtered and concentrated in vacuo to afford the crude residue. The crude residue was purified by column chromatography using Combi-Flash automated system (1% Et₂O in DCM as gradient) to afford the title compound as an off-white solid (10 g, 41% yield). ¹H NMR (400 MHz, CDCl₃) δ 7.62-7.60 (dd, J=6.4 Hz, 1.6 Hz, 2H), 7.36 (d, J=8.4 Hz, 2H), 4.50 (d, J=8.0 Hz, 1H), 3.98-3.95 (dd, J=7.6, 5.2 Hz, 1H), 2.43 (s, 3H), 1.83-1.67 (m, 4H), 1.49-1.44 (m, 2H), 0.94 (d, J=6.4 Hz, 3H), 0.91 (d, 0.7=6.8 Hz, 3H), 0.81-0.70 (m, 2H), 0.60-0.55 (m, 1H); LCMS (ESI): m/z: 305 [M+H⁺];RT: 2.66 min, (ACQUITY BEH C18 column, 0.05% formic acid in water with MeCN).

Preparation 188

(2S)-2-Amino-2-((1s,3R,5S)-3,5-dimethylcyclohexyl)acetonitrile hydrochloride

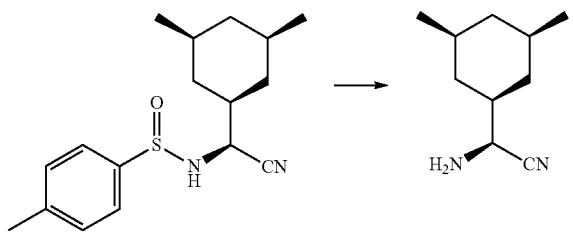

HCl (4M in 1,4-dioxane, 28 mL) was added dropwise over 10 minutes to a solution of the nitrile of Preparation 187 (7.0 g, 23.0 mmol) in dry methanol (30 mL). The reaction mixture was stirred at ambient temperature for 2 h. On completion, the reaction mixture was concentrated in vacuo and triturated with Et₂O (100 mL). The solid was filtered, then dried under a stream of nitrogen gas to give the title compound as an off-white solid (4.4 g, 95% yield). ¹H NMR (300 MHz, DMSO-d₆) δ 9.23 (br s, 3H), 4.52 (d, J=7.4 Hz, 1H), 2.08-1.99 (m, 1H), 1.93-1.75 (m, 2H), 1.65-1.61 (m, 1H), 1.44-1.42 (m, 2H), 1.18-1.01 (m, 2H), 0.92-0.88 (m, 6H), 0.75-0.47 (m, 3H).

Preparation 189

(2S)-2-Amino-2-((1s,3R,5S)-3,5-dimethylcyclohexyl)acetic acid hydrochloride

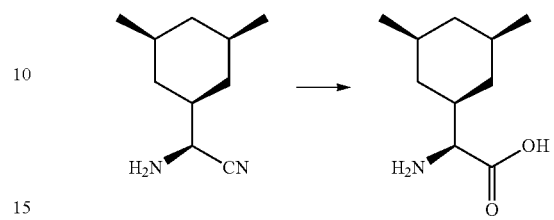

Conc. HCl (48 mL) was added to the nitrile of Preparation 188 (4.4 g, 23.8 mmol) at room temperature. The resultant reaction mixture was heated at 80° C. for 16 h. On completion, the reaction mixture was concentrated in vacuo to get the crude residue which was triturated with Et₂O (100 mL). The solid obtained was filtered and dried to afford the title compound as an off-white solid (4 g, 82% yield). ¹H NMR (300 MHz, DMSO-d₆) δ 13.87 (br s, 1H), 8.22 (br s, 3H), 3.71 (m, 1H), 1.93-1.75 (m, 1H), 1.72-1.53 (m, 3H), 1.50-1.30 (m, 2H), 0.93-0.78 (m, 6H), 0.71-0.60 (m, 1H), 0.53-0.41 (m, 1H); LCMS (ESI): m/z: 186 [M+H⁺]; RT=1.08 min, (ACQUITY BEH C18 column, 0.05% formic acid in water with MeCN).

Preparation 190

(2S)-2-(tert-Butoxycarbonylamino)-2-((1s,3R,5S)-3,5-dimethylcyclohexyl)acetic acid

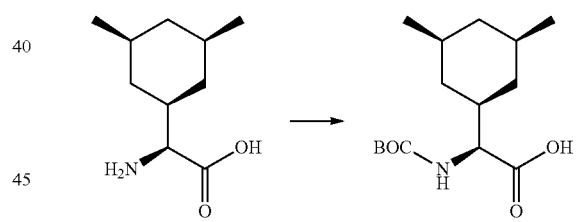

Di-tert-butyl dicarbonate (10 mL, 43.2 mmol) was added slowly to a solution of the amine of Preparation 189 (4 g, 21.6 mmol)) and sodium bicarbonate (10 g, 125 mmol) in acetone:H₂O (200 mL, 1:1) at 0° C. The reaction mixture was stirred at room temperature for 16 h. On completion, the reaction mixture was concentrated in vacuo and the crude compound was diluted with ice cold water and washed with EtOAc. (100 mL) The aqueous layer was cooled to 0° C., acidified with 1M HCl to pH 1 and stirred for 30 min. The mixture was extracted with EtOAc (2×200 mL). The combined organic layer was dried over sodium sulfate and concentrated in vacuo to afford the title compound as an off-white solid (2.1 g, 41% yield). ¹H NMR (400 MHz, DMSO-d₆) δ 12.41 (br s, 1H), 6.89 (d, J=8.4 Hz, 1H), 3.78 (q, J=6.4 Hz, 1H), 1.73-1.69 (m, 1H), 1.58-1.50 (m, 3H), 1.48-1.40 (m, 11H), 0.85 (d, J=6.4 Hz, 6H), 0.71-0.0.64 (m, 2H), 0.50-0.45 (m, 1H).LCMS (ELSD): m/z: 286 [M+H⁺]; RT=2.52 min, (ACQUITY BEH C18 column, 0.05% formic acid in water with MeCN)

Preparation 191

2-(3-Hydroxy-1-methyl-propyl)pyrazole-3-carboxylic acid

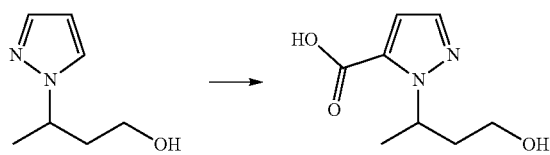

The title compound was prepared according to the method of Preparation 65 from 3-pyrazol-1-ylbutan-1-ol. The crude product was used without further purification.

Preparation 192

Ethyl 2-[(1S)-2-benzyloxy-1-methyl-ethyl]pyrazole-3-carboxylate

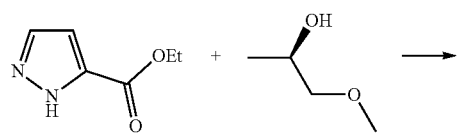

Diethyl azodicarboxylate (52.3 mL, 53.7 g, 265 mmol) was added slowly to a mixture of ethyl 1H-pyrazole-5-carboxylate (31.0 g, 221 mmol), (2R)-1-benzyloxypropan-2-ol (44.0 g, 265 mmol), triphenylphosphine (69.6 g, 265 mmol) and molecular sieves (4A, 25 g, pre-activated by heating under vacuum for 2 hours) in dry THF (500 mL) at −5° C. under argon. The reaction was stirred at 0° C. for 1 hour, then warmed to room temperature and stirred for 1 hour. Most of the THF (ca. 400 mL) was evaporated, heptane (400 mL) was added to the orange solution under mechanical stirring and the mixture was stirred for 16 hours. The mixture was filtered (to remove the mixture of triphenylphospine oxide and reduced diethyl azodicarboxylate) and the filtrate was concentrated in vacuo. The residue was purified by column chromatography (silica gel, eluting with heptane/EtOAc) to give the title compound (45.7 g, 72%) as a pale pink oil. 1H NMR (600 MHz, Chloroform-d) δ 7.53 (d, J=1.9 Hz, 1H), 7.34-7.16 (m, 5H), 6.83 (d, J=2.0 Hz, 1H), 5.80-5.63 (m, 1H), 4.46 (d, J=12.2 Hz, 1H), 4.42 (d, J=12.2 Hz, 1H), 4.31 (qd, J=7.1, 1.3 Hz, 2H), 3.85 (dd, J=9.9, 8.0 Hz, 1H), 3.69 (dd, J=9.9, 5.3 Hz, 1H), 1.51 (d, J=6.8 Hz, 3H), 1.35 (t, J=7.1 Hz, 3H); LCMS (METHOD 3) (ES): m/z 289.3 [M+H]+, RT=0.84 min.

Preparation 193

2-[(1S)-2-Benzyloxy-1-methyl-ethyl]pyrazole-3-carboxylic acid

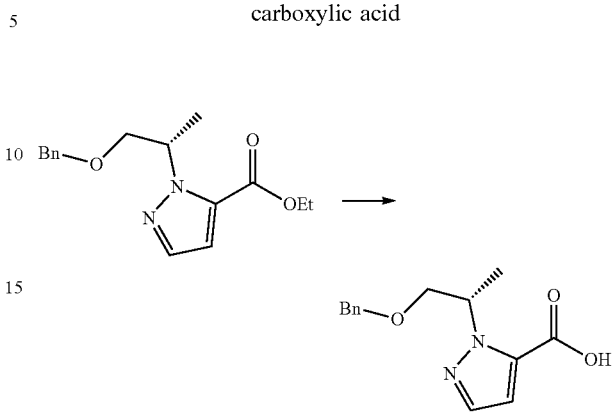

The ester of Preparation 192 (45.74 g, 159 mmol) was dissolved in MeOH (100 mL) and 5M NaOH (40 mL) was added. The mixture was stirred overnight at room temperature. Most of the MeOH was evaporated, the pH was adjusted to 2-3 with 6M aq. HCl and the mixture was extracted with TBME (3×100 mL). The combined organic extracts were dried (Na₂SO₄) and evaporated to give the title compound which was used directly without further purification. LCMS (METHOD 3) (ES): m/z 261.2 [M+H]+, RT=0.61 min.

Preparation 194

2-[(1S)-2-Hydroxy-1-methyl-ethyl]pyrazole-3-carboxylic acid

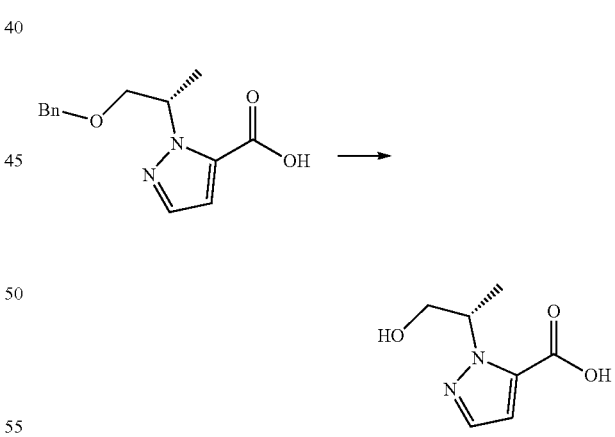

The acid of Preparation 193 (41.3 g, 159 mmol) was dissolved in MeOH (250 mL) and hydrogenated over 10% Pd/C (2 g) at 1.5 bar on a Parr shaker. Filtration through Celite and evaporation of the filtrate gave the title compound (26.8 g, 99%) as a white solid. 1H NMR (600 MHz, DMSO-d6) δ 13.22 (s, 1H), 7.54 (d, J=1.9 Hz, 1H), 6.78 (d, J=1.9 Hz, 1H), 5.58-5.20 (m, 1H), 4.80 (s, 1H), 3.69 (dd, J=10.7, 7.6 Hz, 1H), 3.59 (dd, J=10.7, 5.8 Hz, 1H), 1.35 (d, J=6.7 Hz, 3H); LCMS (METHOD 3) (ES): m/z 171.2 [M+H]+, RT=0.27 min.

Preparation 195

2-[(1R)-2-Hydroxy-1-methyl-ethyl]pyrazole-3-carboxylic acid

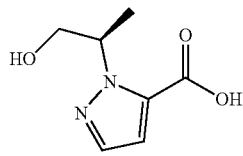

The title compound was prepared according to the methods of Preparations 192-194 starting from (2S)-1-benzyloxypropan-2-ol.

Preparation 196

2-[(1S)-2-Acetoxy-1-methyl-ethyl]pyrazole-3-carboxylic acid

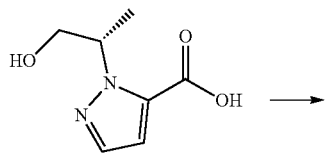 →

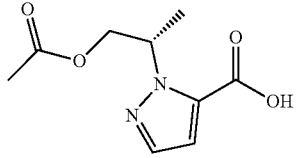

The alcohol of Preparation 194 (3.02 g, 17.7 mmol) was heated at reflux in a mixture of acetyl chloride (20 mL, 22.0 g, 280 mmol) and MeCN (20 mL) until a clear solution was obtained (ca. 30 min reflux. The reaction mixture was cooled to room temperature and concentrated under reduced pressure. The residue was taken up in MeCN (5 mL) and water (5 mL) was added. The mixture was stirred overnight at room temperature then diluted with water (25 mL) and extracted with EtOAc (3×50 mL) The combined organic layers were dried ($Na_2SO_4$) and evaporated. Recrystallisation from heptane gave the title compound (3.36 g, 89%) as a white solid. 1H NMR (600 MHz, DMSO-d6) δ 13.38 (s, 1H), 7.59 (d, J=2.0 Hz, 1H), 6.81 (d, J=1.9 Hz, 1H), 5.62 (dqd, J=8.8, 6.8, 4.4 Hz, 1H), 4.36 (dd, J=11.1, 4.5 Hz, 1H), 4.20 (dd, J=11.1, 8.8 Hz, 1H), 1.89 (s, 3H), 1.42 (d, J=6.8 Hz, 3H); LCMS (METHOD 3) (ES): m/z 213.2 [M+H]$^+$, RT=0.38 min.

Preparations 197-202

The acids of Preparations 197-202 were synthesised according to the methods of Preparations 192 and 193 from the appropriate alcohols and ethyl 1H-pyrazole-5-carboxylate.

| Prep. No. | Structure | Name | 1H NMR and mass spec data |
|---|---|---|---|
| 197 | 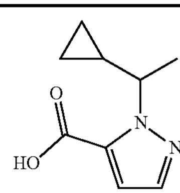 | 2-(1-cyclopropylethyl)pyrazole-3-carboxylic acid | 1H NMR (400 MHz, Chloroform-d) δ 7.60 (d, J =2.0 Hz, 1H), 6.94 (d, J = 2.2 Hz, 1H), 4.67 (p, J = 7.2 Hz, 1H), 1.60 (d, J = 6.7, Hz, 3H), 1.46 (dq, J = 13.7, 8.6, 7.0 Hz, 1H), 0.72-0.61 (m, 1H), 0.49-0.39 (m, 1H), 0.39-0.27 (m, 2H); LCMS (METHOD 3) (ES): m/z 179.4 [M − H], RT = 0.49 min |
| 198 | 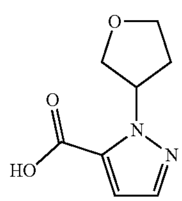 [SMILES: O=C(O)c1ccnn1C1CCOC1] | 2-tetrahydrofuran-3-ylpyrazole-3-carboxylic acid | 1H NMR (400 MHz, Chloroform-d) δ 7.56 (d, J = 2.3 Hz, 1H), 6.97 (d, J = 1.8 Hz, 1H) 6.04-5.77 (m, 1H), 4.26-4.10 (m, 2H), 4.09-3.94 (m, 2H), 2.61-2.48 (m, 2H), 2.48-2.30 (m, 1H); LCMS (METHOD 3) (ES): m/z 183.2 [M + H]$^+$, RT = 0.33 min |
| 199 | 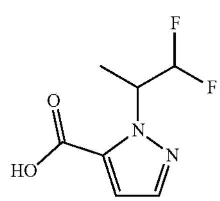 | 2-(2,2-difluoro-1-methyl-ethyl)pyrazole-3-carboxylic acid | 1H NMR (400 MHz, Chloroform-d) δ 7.63 (s, 1H), 7.00 (s, 1H), 6.22-5.87 (m, 1H), 5.73 (m, 1H), 1.66 (d, J = 7.0 Hz, 3H); LCMS (METHOD 3) (ES): m/z 191.2 [M + H]$^+$, RT = 0.41 min |
| 199B | 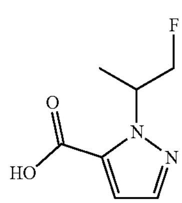 | 2-(2-fluoro-1-methyl-ethyl)pyrazole-3-carboxylic acid | 1H NMR (400 MHz, Chloroform-d) δ 7.61 (d, 1H), 6.98 (s, 1H), 5.77 (m, 1H), 4.80 (dt, J = 46.8, 8.6 Hz, 1H), 4.60 (ddd, J = 46.6, 9.7, 5.0 Hz, 1H), 1.53 (d, J = 6.6 Hz, 3H); LCMS (METHOD 3) (ES): m/z 173.1 [M + H]$^+$, RT = 0.38 min |

| Prep. No. | Structure | Name | 1H NMR and mass spec data |
|---|---|---|---|
| 200 | (structure) | 2-[2-fluoro-1-(fluoromethyl)-ethyl]pyrazole-3-carboxylic acid | 1H NMR (400 MHz, Chloroform-d) δ 7.63 (s, 1H), 6.99 (s, 1H), 6.00-5.88 (m, 1H), 5.17-4.67 (m, 4H); LCMS (METHOD 3) (ES): m/z 191.1 [M+H]$^+$, RT = 0.36 min |
| 201 | (structure) | 2-(2-benzyloxypropyl)pyrazole-3-carboxylic acid | LCMS (METHOD 3) (ES): m/z 261.2 [M + H]$^+$, RT = 0.59 min |
| 202 | (structure) | 2-(3-hydroxybutyl)pyrazole-3-carboxylic acid | 1H NMR (600 MHz, DMSO-d6) δ 13.28 (br s, 1H), 7.51 (d, J = 2.0 Hz, 1H), 6.80 (d, J = 2.0 Hz, 1H), 5.13-4.16 (m, 2H), 3.59 (h, J = 6.2 Hz, 1H), 1.91-1.69 (m, 2H), 1.07 (d, J = 6.2 Hz, 3H); LCMS (METHOD 3) (ES): m/z 185.2 [M + H]$^+$, RT = 0.31 min |

Preparation 202B 2-(3-hydroxy-1-methyl-propyl)pyrazole-3-carboxylic acid

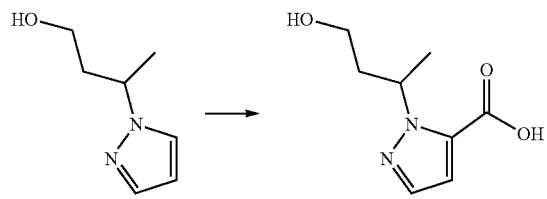

According to the method of Preparation 46, 3-pyrazol-1-ylbutan-1-ol was lithiated and reacted with carbon dioxide to give crude title compound (620 mg, 26%) which was used without purification.

Preparation 203

Ethyl 2-(2-methylsulfonylethyl)pyrazole-3-carboxylate

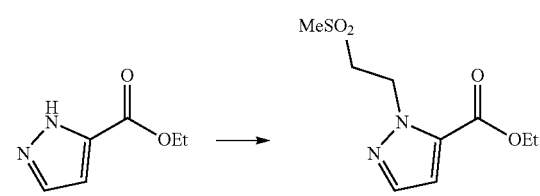

Ethyl 1H-pyrazole-5-carboxylate (150 mg, 1.07 mmol) was dissolved in MeCN (4 mL) and K$_2$CO$_3$ (370 mg, 2.68 mmol) and 1-chloro-2-methylsulfonyl-ethane (229 mg, 1.61 mmol) were added and the mixture was heated at 80° C. for 6 hours. The reaction was cooled then filtered and evaporated to dryness. The residue, containing the undesired 1-substituted isomer, was purified by prep. acidic HPLC to give the title compound (28 mg, 11%) as a colourless solid. 1H NMR (400 MHz, Chloroform-d) δ 7.54 (d, J=2.0 Hz, 1H), 6.88 (d, J=2.0 Hz, 1H), 5.18-4.95 (m, 2H), 4.37 (q, J=7.1 Hz, 2H), 3.71-3.49 (m, 2H), 2.88 (t, J=0.8 Hz, 3H), 1.39 (t, J=7.1 Hz, 3H); LCMS (METHOD 3) (ES): m/z 247.2 [M+H]$^+$, RT=0.49 min.

Preparation 204

2-(2-Methylsulfonylethyl)pyrazole-3-carboxylic acid

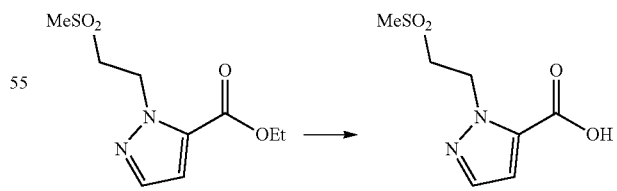

To a solution of the ester of Preparation 203 (28 mg, 0.112 mmol) in MeOH (0.56 mL) was added a solution of LiOH (8.08 mg, 0.337 mmol) in water (0.84 mL) and the mixture was stirred at room temperature for 2 hours. The pH was adjusted with aq. citric acid (5%) until pH~ 3. The mixture was extracted with EtOAc (×3) and the combined organic extracts were dried with Na$_2$SO$_4$ and evaporated. The residue was purified by acidic prep. HPLC to give the title compound (18.5 mg, 75%) as a colourless solid. LCMS (METHOD 3) (ES): m/z 219.1 [M+H]$^+$, RT=0.23 min.

Preparation 205

Ethyl 2-[(1R,2R)-2-hydroxy-1-methyl-propyl]pyrazole-3-carboxylate and ethyl 2-[(1S,2S)-2-hydroxy-1-methyl-propyl]pyrazole-3-carboxylate

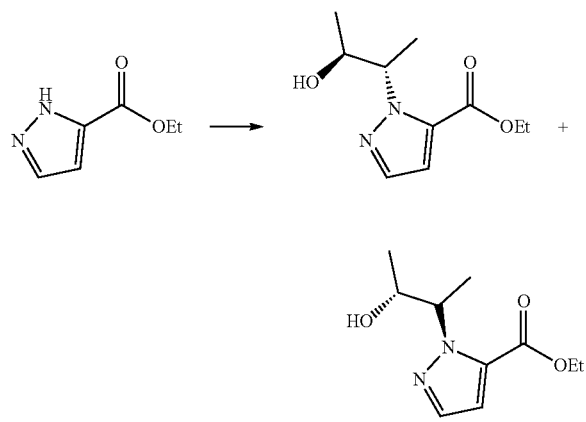

Caesium carbonate (465 mg, 1.43 mmol) and cis-2,3-epoxybutane (62 µL, 51 mg, 0.714 mmol) were added to a solution of ethyl 1H-pyrazole-5-carboxylate (100 mg, 0.714 mmol) in DMF (4 mL) and the mixture was shaken and heated at 120° for 75 min. After cooling to room temperature, the solvent was decanted off and the reaction mixture was purified by prep acidic HPLC to give the title compound (27 mg, 18%) as a clear oil. 1H NMR (600 MHz, Chloroform-d) δ 7.51 (d, J=2.3 Hz, 1H), 6.81 (d, J=2.3 Hz, 1H), 4.39 (qd, J=7.1, 1.6 Hz, 2H), 4.27 (qd, J=7.0, 5.7 Hz, 1H), 4.09 (p, J=6.3 Hz, 1H), 1.56 (d, J=7.0 Hz, 3H), 1.39 (t, J=7.1 Hz, 3H), 1.15 (d, J=6.4 Hz, 3H); LCMS (METHOD 3) (ES): m/z 213.2 [M+H]$^+$, RT=0.48 min.

Preparation 206

2-[(1R,2R)-2-Hydroxy-1-methyl-propyl]pyrazole-3-carboxylic acid and 2-[(1S,2S)-2-hydroxy-1-methyl-propyl]pyrazole-3-carboxylic acid

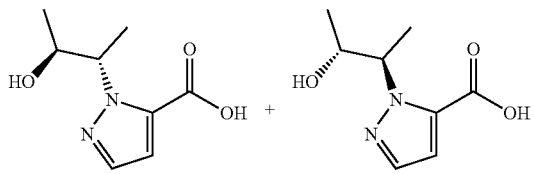

The title compound was prepared from the ester of Preparation 205 according to the method of Preparation 204. LCMS (METHOD 3) (ES): m/z 185.2 [M+H]$^+$, RT=0.31 min.

Preparation 207

Ethyl 2-(2-methylallyl)pyrazole-3-carboxylate

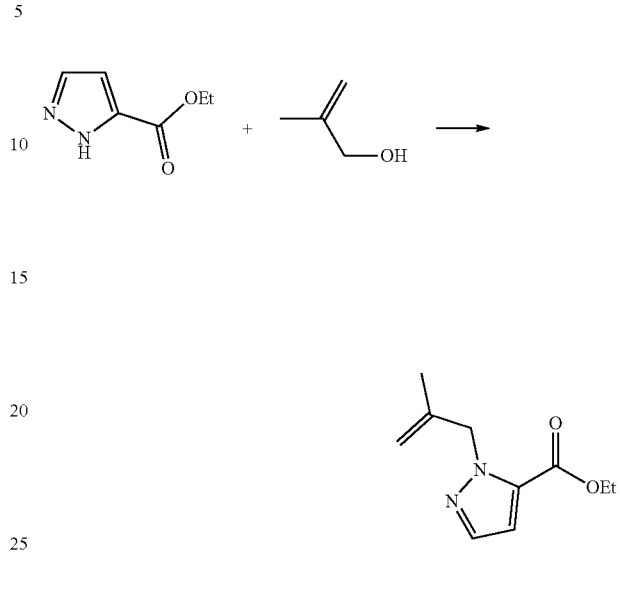

The title compound (453 mg, 46%) was prepared as a colourless oil from ethyl 1H-pyrazole-5-carboxylate and 2-methylprop-2-en-1-ol according to the method of Preparation 192. 1H NMR (400 MHz, Chloroform-d) δ 7.53 (s, 1H), 6.87 (s, 1H), 5.13 (s, 2H), 4.95-4.77 (m, 1H), 4.49 (s, 1H), 4.33 (q, J=7.1 Hz, 2H), 1.71 (s, 3H), 1.37 (t, J=7.2 Hz, 3H); LCMS (METHOD 3) (ES): m/z 195.2 [M+H]$^+$, RT=0.72 min.

Preparation 208

Ethyl 2-acetonylpyrazole-3-carboxylate

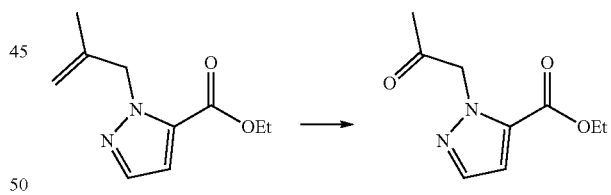

OsO$_4$ (736 mg, 0.116 mmol) was added to a solution of the alkene of Preparation 207 (450 mg, 2.32 mmol), pyridine (0.56 mL, 6.95 mmol) and N-methylmorpholine-N-oxide (407 mg, 3.48 mmol) in dioxane (5 mL) and water (1 mL) and the mixture was stirred at room temperature for 20 hours. Sodium periodate (743 mg, 3.48 mmol) was added and the mixture was stirred for 2 days. The reaction mixture was partitioned between EtOAc and brine and the organic layer was dried and concentrated in vacuo onto Celite. Purification by column chromatography (silica, eluting with heptane/EtOAc) gave the title compound (272 mg, 60%) as a colourless oil. 1H NMR (400 MHz, Chloroform-d) δ 7.56 (s, 1H), 6.91 (s, 1H), 5.35 (s, 2H), 4.31 (q, J=7.1 Hz, 2H), 2.19 (s, 3H), 1.35 (d, J=7.1 Hz, 3H). LCMS (METHOD 3) (ES): m/z 195.2 [M+H]$^+$, RT=0.52 min.

Preparation 209

Ethyl 2-(2,2-difluoropropyl)pyrazole-3-carboxylate

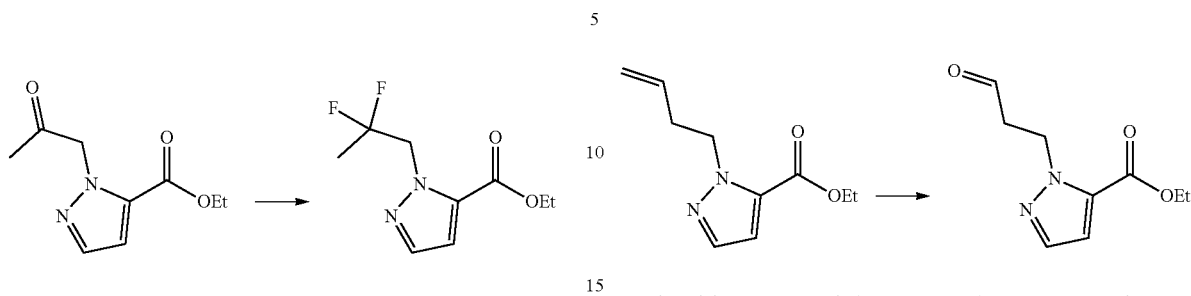

A solution of the ester of Preparation 208 (272 mg, 1.39 mmol) in DCM (2.5 mL) was cooled in an ice batch and DAST (0.40 mL, 492 mg, 3.05 mmol) was added dropwise over 3 min. The reaction was allowed to warm to room temperature and stirred for 6 hours. A further portion of DAST (0.40 mL, 492 mg, 3.05 mmol) was added and the reaction was stirred at room temperature for 64 hours. The reaction mixture was added to ice cold sat. aq. sodium bicarbonate solution (20 mL) and the mixture was extracted with DCM (2×25 mL). The combined organic layers were washed with brine (20 mL), dried with sodium sulfate, filtered and concentrated in vacuo. The crude product was purified by column chromatography to give the title compound (64 mg, 21%) as a yellow liquid. 1H NMR (300 MHz, Chloroform-d) δ 7.57 (d, J=2.0 Hz, 1H), 6.89 (d, J=2.0 Hz, 1H), 5.30-4.76 (m, 2H), 4.36 (q, J=7.1 Hz, 2H), 1.58 (t, J=18.7 Hz, 3H), 1.38 (t, J=7.1 Hz, 3H); LCMS (METHOD 3) (ES): m/z 219.2 [M+H]$^+$, RT=0.67 min.

Preparation 210

Ethyl 2-but-3-enylpyrazole-3-carboxylate

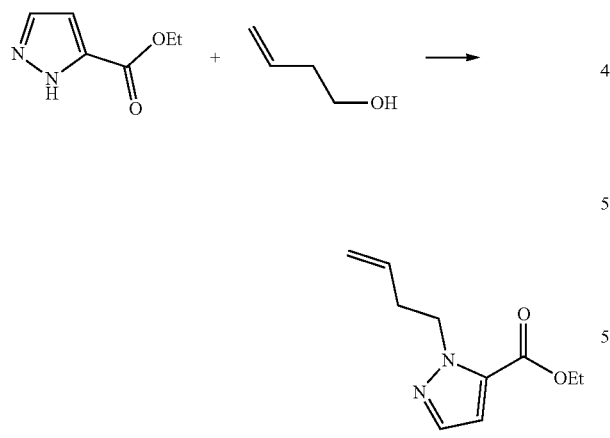

The title compound (7.1 g, 85%) was prepared as a colourless oil from ethyl 1H-pyrazole-5-carboxylate and but-3-en-1-ol according to the method of Preparation 192. 1H NMR (600 MHz, Chloroform-d) δ 7.47 (d, J=2.0 Hz, 1H), 6.82 (d, J=2.0 Hz, 1H), 5.79 (ddt, J=17.2, 10.2, 6.9 Hz, 1H), 5.14-4.92 (m, 2H), 4.73-4.53 (m, 2H), 4.35 (q, J=7.1 Hz, 2H), 2.74-2.47 (m, 2H), 1.38 (t, J=7.1 Hz, 3H).

Preparation 211

Ethyl 2-(3-oxopropyl)pyrazole-3-carboxylate

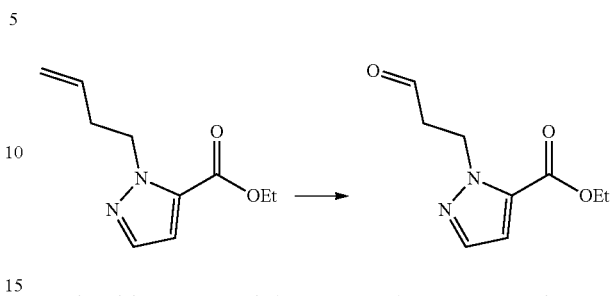

The title compound (667 g, 67%) was prepared as an orange oil from the alkene of Preparation 210 according to the method of Preparation 208. 1H NMR (300 MHz, Chloroform-d) 69.84 (t, J=1.3 Hz, 1H), 7.48 (d, J=2.0 Hz, 1H), 6.83 (d, J=2.0 Hz, 1H), 4.92 (t, J=6.8 Hz, 2H), 4.35 (q, J=7.1 Hz, 2H), 3.03 (td, J=6.8, 1.3 Hz, 2H), 1.38 (t, J=7.1 Hz, 3H).

Preparation 212

Ethyl 2-(3,3-difluoropropyl)pyrazole-3-carboxylate

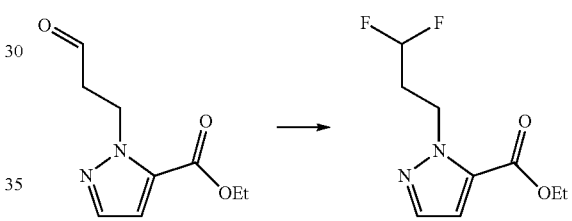

DAST (1.1 g, 6.80 mmol) was added slowly to a solution of the aldehyde of Preparation 211 (667 mg, 3.40 mmol) in DCM (10 mL) at 5° C. under argon. The resulting pale orange solution was stirred at room temperature for 18 hours then diluted with DCM (25 mL), washed with sat NaHCO$_3$ (20 mL), dried (Na$_2$SO$_4$) and evaporated. The crude product was purified on by column chromatography (silica, eluting with EtOAc:heptane) to give the title compound (230 mg, 31%) as a yellow oil. 1H NMR (400 MHz, Chloroform-d) δ 7.50 (s, 1H), 6.85 (s, 1H), 5.91 (tt, J=56.2, 5.0 Hz, 1H), 4.76 (t, J=7.0 Hz, 2H), 4.36 (d, J=7.2 Hz, 2H), 2.58-2.24 (m, 2H), 1.39 (t, J=7.2 Hz, 3H); LCMS (METHOD 3) (ES): m/z 219.2 [M+H]$^+$, RT=0.67 min.

Preparation 213

2-(3,3-Difluoropropyl)pyrazole-3-carboxylic acid

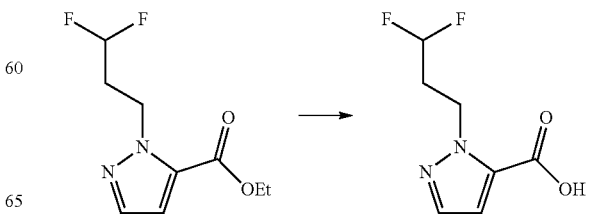

The title compound (169 mg, 84%) was prepared as an off-white solid according to the method of Preparation 193 from the ester of Preparation 212. 1H NMR (400 MHz, DMSO-d6) δ 13.42 (s, 1H), 7.56 (d, J=2.0 Hz, 1H), 6.84 (d, J=2.0 Hz, 1H), 6.12 (tt, J=56.2, 4.4 Hz, 1H), 4.67 (t, J=7.0 Hz, 2H), 2.36 (ttd, J=18.0, 7.0, 4.4 Hz, 2H); LCMS (METHOD 3) (ES): m/z 191.2 [M+H]+, RT=0.49 min.

Preparation 214

Ethyl 2-(4,4,4-trifluoro-3-trimethylsilyloxy-butyl)pyrazole-3-carboxylate

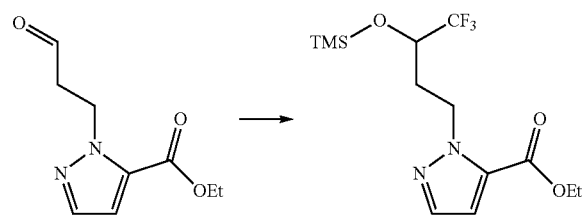 [SMILES: CCOC(=O)c1ccnn1CCC=O ; CCOC(=O)c1ccnn1CCC(O[Si](C)(C)C)C(F)(F)F]

The aldehyde of Preparation 211 (250 mg, 1.27 mmol) was dissolved in THF (0.1 mL) in a microwave vial. Caesium fluoride (1.9 mg, 0.013 mmol) was added and the vial was placed under argon. Trimethyl(trifluoromethyl)silane (207 μL, 199 mg, 1.40 mmol) was added dropwise over 5 minutes and the reaction mixture was stirred at room temperature for 16 hours. The reaction mixture was diluted with water and extracted with EtOAc (×2). The combined organic phases were washed with brine, dried with Na2SO4, filtered and evaporated in vacuo. The crude product was purified by flash chromatography (silica, eluting with heptane:EtOAc) to give the title compound (193 mg, 44%). 1H NMR (600 MHz, Chloroform-d) δ 7.30 (d, J=2.0 Hz, 1H), 6.67 (d, J=2.0 Hz, 1H), 4.58 (ddd, J=13.2, 7.8, 5.3 Hz, 1H), 4.41 (dt, J=13.5, 7.6 Hz, 1H), 4.17 (q, J=7.1 Hz, 2H), 3.86 (dqd, J=9.7, 6.5, 3.3 Hz, 1H), 2.05 (dtd, J=14.1, 7.7, 3.3 Hz, 1H), 1.98-1.85 (m, 1H), 1.20 (t, J=7.1 Hz, 3H), 0.00 (s, 9H); LCMS (METHOD 3) (ES): m/z 339.3 [M+H]+, RT=0.97 min.

Preparation 215

2-(4,4,4-trifluoro-3-hydroxy-butyl)pyrazole-3-carboxylic acid

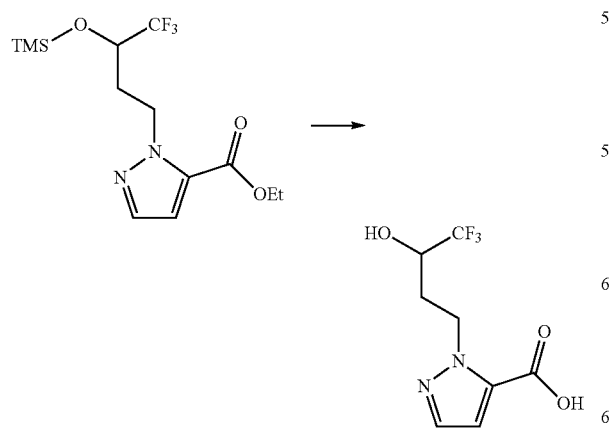

The title compound (120 mg, 95%) was prepared as an off-white solid according to the method of Preparation 193 from the ester of Preparation 214. 1H NMR (400 MHz, DMSO-d6) δ 13.42 (br s, 1H), 7.55 (d, J=1.9 Hz, 1H), 6.82 (d, J=1.9 Hz, 1H), 6.41 (s, 1H), 4.80-4.52 (m, 2H), 3.91 (ddt, J=14.6, 10.1, 5.1 Hz, 1H), 2.11 (dtd, J=13.7, 7.9, 2.9 Hz, 1H), 2.04-1.81 (m, 1H); LCMS (METHOD 3) (ES): m/z 239.2 [M+H]+, RT=0.39 min.

Preparation 216

Ethyl 2-(1-cyanoethyl)pyrazole-3-carboxylate (Prep. 216A) and ethyl 1-(1-cyanoethyl)pyrazole-3-carboxylate (Prep. 216B)

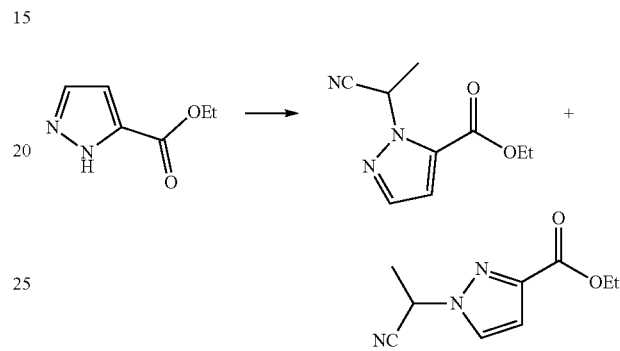

To a solution of ethyl 1H-pyrazole-5-carboxylate (600 mg, 4.28 mmol) in DMF (10 mL) was added Cs2CO3 (2.32 g, 7.12 mmol) and 2-bromopropanenitrile (617 μL, 956 mg, 7.14 mmol). The reaction mixture was stirred at 60° C. for 16 hours, cooled to room temperature and then diluted with water. The mixture was extracted with EtOAc (×2) and the combined organic phases were washed with brine, dried with Na2SO4, filtered and concentrated in vacuo. Purification by flash chromatography (silica, eluting with heptane to 50% EtOAc in heptane) gave ethyl 2-(1-cyanoethyl)pyrazole-3-carboxylate (Prep. 216A) (TLC: rf=0.7 in 1:1 EtOAc:heptane) (367 mg, 44%) as a crystalline solid and ethyl 1-(1-cyanoethyl)pyrazole-3-carboxylate (Prep. 216B) (TLC: rf=0.5 in 1:1 EtOAc:heptane) (387 mg, 47%).

Prep. 216A: 1H NMR (400 MHz, Chloroform-d) δ 7.63 (s, 1H), 6.90 (s, 1H), 6.46 (q, J=7.0 Hz, 1H), 4.38 (d, J=7.0 Hz, 1H), 1.91 (d, J=7.0 Hz, 3H), 1.40 (t, J=7.2 Hz, 2H); LCMS (METHOD 3) (ES): m/z 194.2 [M+H]+, RT=0.63 min.

Prep. 216B: 1H NMR (400 MHz, Chloroform-d) δ 7.68 (s, 1H), 6.91 (s, 1H), 5.44 (q, J=7.0 Hz, 1H), 4.42 (d, J=7.2 Hz, 2H), 1.95 (d, J=7.3 Hz, 3H), 1.41 (t, J=7.1 Hz, 2H); LCMS (METHOD 3) (ES): m/z 194.2 [M+H]+, RT=0.52 min.

Preparation 217

2-(1-Cyanoethyl)pyrazole-3-carboxylic acid

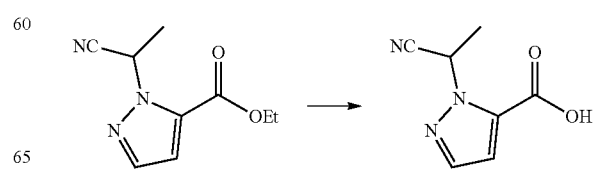

The title compound was prepared according to the method of Preparation 193 from the ester of Preparation 216A. 1H NMR (400 MHz, DMSO-d6) δ 7.72 (d, J=1.9 Hz, 1H), 6.92 (d, J=1.9 Hz, 1H), 6.51 (q, J=7.0 Hz, 1H), 1.78 (d, J=7.0 Hz, 3H); LCMS (METHOD 3) (ES): m/z 164.1 [M–H], RT=0.29 min.

Preparation 218

1-(1-Cyanoethyl)pyrazole-3-carboxylic acid

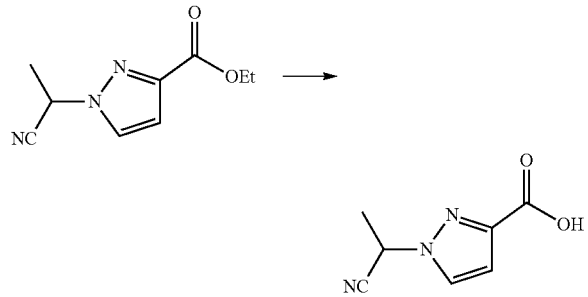

The title compound was prepared according to the method of Preparation 193 from the ester of Preparation 216B. 1H NMR (400 MHz, DMSO-d6) δ 7.73 (d, J=1.9 Hz, 1H), 6.93 (d, J=1.9 Hz, 1H), 6.49 (q, J=7.0 Hz, 1H), 1.78 (d, J=7.0 Hz, 3H); LCMS (METHOD 3) (ES): m/z 166.1 [M+H]$^+$, RT=0.30 min.

Preparation 219

Phenyl 4,5-dichloro-6-oxopyridazine-1(6H)-carboxylate

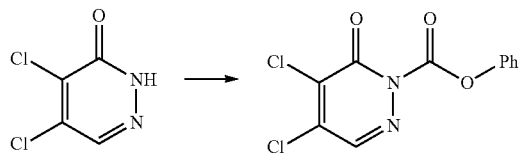 [SMILES: O=c1[nH]ncc(Cl)c1Cl ; O=C(Oc1ccccc1)n1ncc(Cl)c(Cl)c1=O]

To a stirred solution of 4,5-dichloropyridazin-3(2H)-one (2.0 g, 12.1 mmol) in DCM (20 mL) at 0° C. was added triethylamine (2 mL, 14.5 mmol) followed by phenyl chloroformate (1.98 mL, 15.8 mmol). The reaction mixture was stirred at the same temperature for 30 min. The reaction mixture was diluted with DCM (200 mL). The organic layer was washed with water (100 mL), brine (100 mL), dried over Na$_2$SO$_4$ and concentrated under reduced pressure to afford the title compound as an off white solid (3.1 g, 91%). This compound was used as such for the next step without further purification. $^1$H NMR (400 MHz, CDCl$_3$) δ 7.90 (br s, 1H), 7.47-7.43 (m, 2H), 7.37-7.23 (m, 3H); LCMS (METHOD 5) (ESI): m/z 285 [M+H$^+$]; RT=1.92 min (ACQUITY BEH C18 column, 0.1% FA in water with MeCN).

Preparation 220

Phenyl (S)-(1-cyclohexyl-2-((4-(3,5-dimethyl-1-((2-(trimethylsilyl)ethoxy)methyl)-1H-pyrazol-4-yl)phenyl)amino)-2-oxoethyl)carbamate

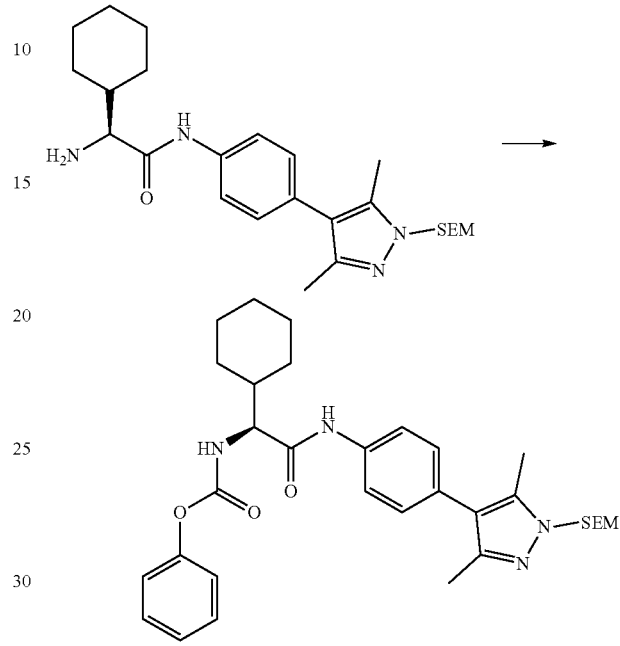

To a stirred solution of the amine of Preparation 4 (200 mg, 0.406 mmol) in DCM (5 mL) at 0° C. was added triethylamine (0.2 mL, 1.63 mmol) followed by the compound of Preparation 219 (127 mg, 0.447 mmol). The reaction mixture was stirred at the same temperature for 30 min. The reaction mixture was diluted with DCM (100 mL). The organic layer was washed with water (50 mL), brine (50 mL), dried over Na$_2$SO$_4$ and concentrated under reduced pressure to get crude. The crude was triturated with n-pentane (2×30 mL) to give the title compound as an off white solid (0.2 g, crude). This compound was used as such for the next step without further purification. LCMS (METHOD 5) (ESI): m/z: 577 [M+H$^+$]; RT=3.93 min; (ACQUITY BEH C18 column, 0.05% TFA in water with CAN).

Preparation 221

(2S)-2-cyclohexyl-N-[4-[3,5-dimethyl-1-(2-trimethylsilylethoxymethyl)pyrazol-4-yl]phenyl]-2-[[3-hydroxypropyl(methyl)carbamoyl]amino]acetamide

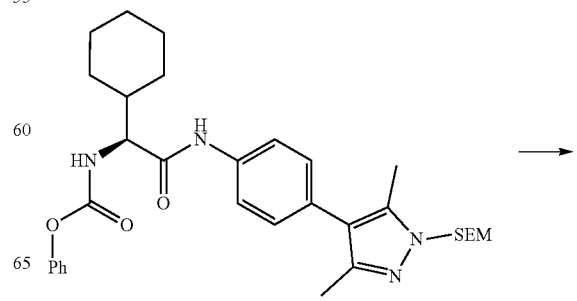

147

-continued

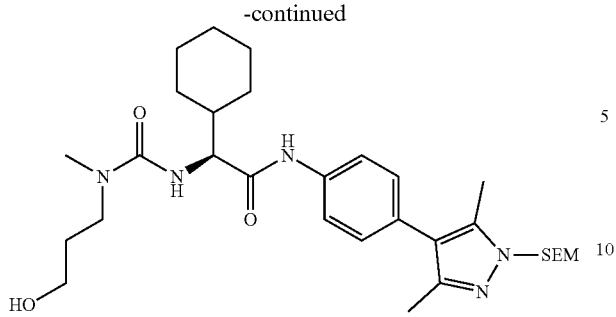

To a stirred solution of the compound of Preparation 220 (200 mg, 0.347 mmol) in DCM (10 mL) at room temperature was added 3-(methylamino)propan-1-ol (92 mg, 1.04 mmol), DIPEA (0.3 mL, 1.73 mmol) and DMAP (5 mg). The reaction mixture was heated to 60° C. for 16 h. The reaction mixture was diluted with DCM (100 mL). The organic layer was washed with water (20 mL), brine (20 mL), dried over Na$_2$SO$_4$ and concentrated under reduced pressure to afford the title compound as an off white solid (130 mg, crude) which was used without further purification. LCMS (METHOD 5) (ESI): m/z: 573 [M+H$^+$]; RT=2.27 min; (ACQUITY BEH C18 column, 0.1% FA in water with MeCN).

Preparation 222

2-[(5-Bromo-4-iodo-3-methyl-pyrazol-1-yl) methoxy]ethyl-trimethyl-silane

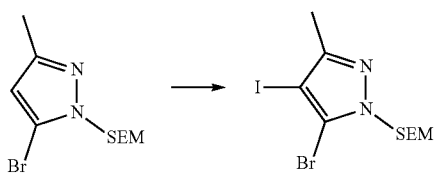 [SMILES: Cc1cc(Br)n(COCC[Si](C)(C)C)n1 ; Cc1nn(COCC[Si](C)(C)C)c(Br)c1I]

A solution of 2-[(5-Bromo-3-methyl-pyrazol-1-yl) methoxy]ethyl-trimethyl-silane (2.1 g, 7.2 mmol) and N-iodosuccinimide (2.5 g, 11 mmol) in DMF (20 mL) was stirred at room temperature for 4 days. The reaction was diluted with TBME (75 mL) and washed with water (75 mL) and aq. sodium thiosulphate (10%, 20 mL). The organic phase was dried over MgSO$_4$ and concentrated in vacuo, to give the title compound (2.6 g, 86%) as a mixture of 2 regioisomers, as a colourless oil. 1H NMR (300 MHz, Chloroform-d) δ 5.47 and 5.41 (2×s, 2H), 3.70-3.51 (m, 2H), 2.41 and 2.31 (2×s, 3H), 0.97-0.85 (m, 2H), 0.00 (s, 9H); LCMS (METHOD 3) (ES): m/z 359.0, 361.0 [M+H]$^+$, RT=0.98 and 0.99 min.

148

Preparation 223

Tert-butyl N-[4-[5-bromo-3-methyl-1-(2-trimethylsilylethoxymethyl)pyrazol-4-yl]phenyl]carbamate

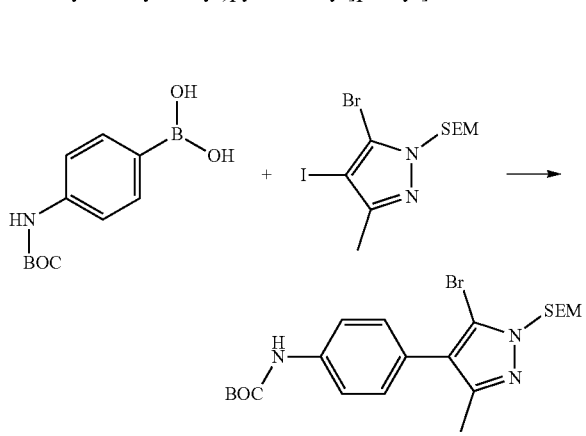

A mixture of [4-(tert-butoxycarbonylamino)phenyl]boronic acid (680 mg, 2.9 mmol), the iodide of Preparation 222 (1.0 g, 2.4 mmol), Pd(dppf)Cl$_2$ (100 mg, 0.123 mmol) and K$_2$CO$_3$ (500 mg, 3.62 mmol) in water (1 mL) and DMF (10 mL) was degassed with argon then heated at 90° C. for 5 hours. The mixture was poured into water (50 mL) and TBME (50 mL). The organic phase was washed with water (50 mL) and concentrated in vacuo. The residue was purified by column chromatography (silica, eluting with heptane/EtOAc 5:1) to give the title compound (800 mg, 69%) as a mixture of regioisomers. 1H NMR (300 MHz, Chloroform-d) δ 7.52-7.37 (m, 2H), 7.36-7.23 (m, 2H), 6.61 (s, 1H), 5.48 and 5.40 (2×s, 2H), 3.84-3.52 (m, 2H), 2.34 and 2.28 (2×s, 3H), 1.10-0.77 (m, 2H), 0.00 (s, 9H); LCMS (METHOD 3) (ES): m/z 482.4, 484.4 [M+H]$^+$, RT=1.02 min.

Preparation 224

Tert-butyl N-[4-[3-methyl-1-(2-trimethylsilylethoxymethyl)-5-vinyl-pyrazol-4-yl]phenyl]carbamate

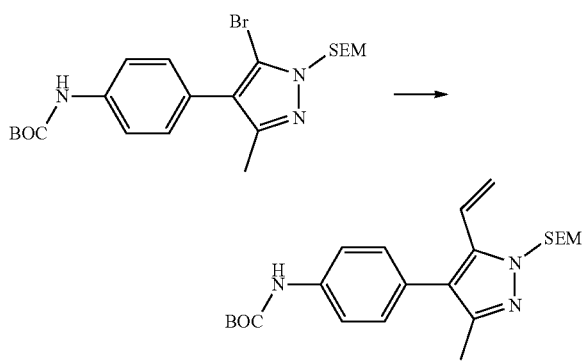

A mixture of the bromide of Preparation 223 (300 mg, 0.622 mmol), 4,4,5,5-tetramethyl-2-vinyl-1,3,2-dioxaborolane (200 mg, 1.30 mmol), Pd(dppf)Cl$_2$ (50 mg, 0.061 mmol), and K$_2$CO$_3$ (100 mg, 0.724 mmol) in water (1 mL) and dioxane (5 mL) was degassed and placed under argon. The reaction was heated in a microwave at 150° C. for 20 min. After cooling to room temperature, the reaction mixture was poured into water (10 mL) and extracted with TBME (3×5 mL). The combined organic phases were concentrated in vacuo and the residue was purified by column chromatography (silica, EtOAc/heptane 1:5), to give the title compound (185 mg, 69%) as a mixture of regioisomers as a brown oil. 1H NMR (300 MHz, Chloroform-d) δ 7.46-7.37 (m, 2H), 7.25-7.14 (m, 2H), 6.70 (s, 1H), 6.64-6.49 (m, 1H), 5.74 (dd, J=17.8, 1.8 Hz) and 5.64 (dd, J=17.9, 1.3 Hz) (1H), 5.45 and 5.44 (2×s, 2H), 5.35 (dd, J=11.9, 1.3 Hz) and 5.17 (dd, J=11.3, 1.8 Hz) (1H), 3.82-3.58 (m, 2H), 2.27 and 2.20 (2×s, 3H), 1.54 (s, 9H), 1.06-0.82 (m, 2H), 0.00 and 0.00 (2×s, 9H); LCMS (METHOD 3) (ES): m/z 430.5 [M+H]+, RT=1.01 and 1.03 min.

Preparation 225

4-[3-Methyl-1-(2-trimethylsilylethoxymethyl)-5-vinyl-pyrazol-4-yl]aniline hydrochloride

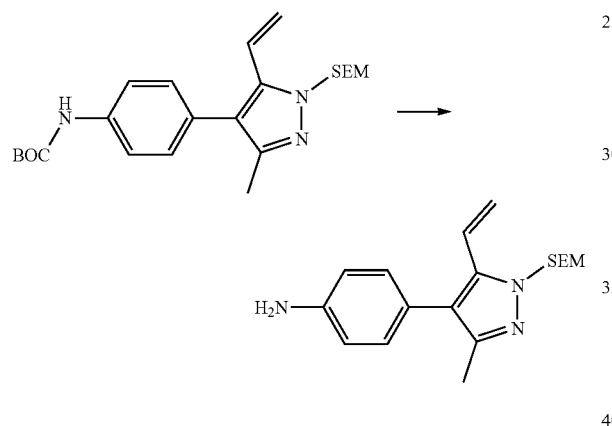

To a solution of the compound of Preparation 224 (185 mg, 0.431 mmol) in MeOH (3 mL) was added 4M HCl (2 mL, 8 mmol) in dioxane at room temperature. The resulting solution was stirred at room temperature for 5 hours then concentrated to dryness to give the title compound (162 mg, quantitative yield) as a mixture of regioisomers as a brown foam. LCMS (METHOD 3) (ES): m/z 330.4 [M+H]+, RT=0.86 and 0.88 min.

Preparation 226

Tert-butyl N-[(1S)-1-(dicyclopropylmethyl)-2-[4-[3-methyl-1-(2-trimethylsilylethoxymethyl)-5-vinyl-pyrazol-4-yl]anilino]-2-oxo-ethyl]carbamate

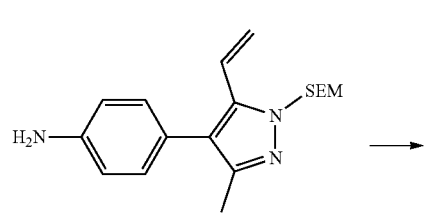

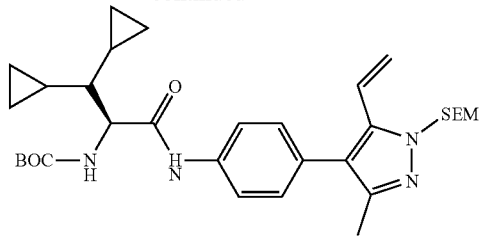

According to the method of Preparation 3 the aniline of Preparation 225 was reacted with the acid of Preparation 52 to give the title compound (106 mg, 100%). LCMS (METHOD 3) (ES): m/z 582.0 [M+H]+, RT=1.04 min.

Preparation 227

(2S)-2-Amino-3,3-dicyclopropyl-N-[4-[3-methyl-1-(2-trimethylsilylethoxymethyl)-5-vinyl-pyrazol-4-yl]phenyl]propenamide hydrochloride

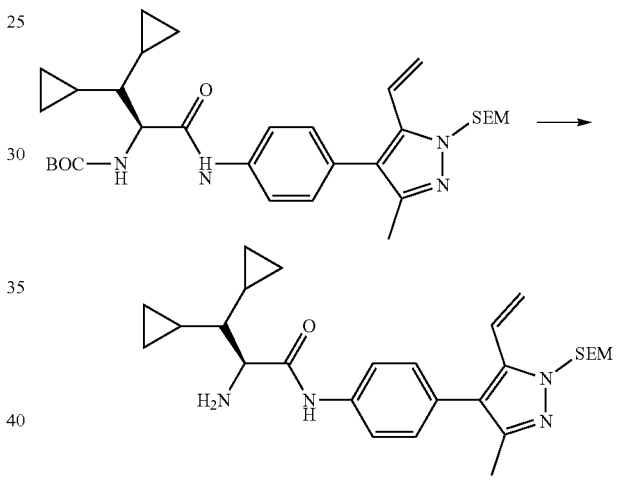

According to the method of Preparation 4 the compound of Preparation 226 was deprotected to give the title compound (94 mg, 100%). LCMS (METHOD 3) (ES): m/z 481.3 [M+H]+, RT=0.76 min.

Preparation 228

N-[(1S)-1-(Dicyclopropylmethyl)-2-[4-[3-methyl-1-(2-trimethylsilylethoxymethyl)-5-vinyl-pyrazol-4-yl]anilino]-2-oxo-ethyl]-2-isopropyl-pyrazole-3-carboxamide

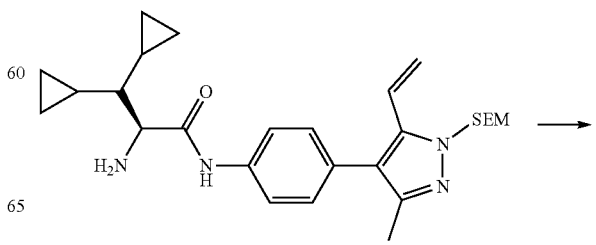

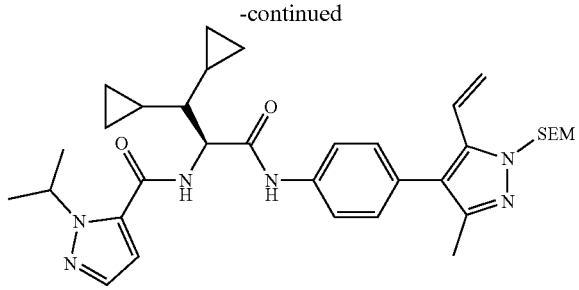

According to the method of Preparation 5 the amine of Preparation 227 was reacted with 2-isopropylpyrazole-3-carboxylic acid to give the title compound (54 mg, 48%). 1H NMR (400 MHz, DMSO-d6) δ 10.24 (s, 1H), 8.44 (d, J=8.8 Hz, 1H), 7.72-7.62 (m, 2H), 7.50 (d, J=2.0 Hz, 1H), 7.27-7.17 (m, 2H), 6.93 (d, J=2.0 Hz, 1H), 6.62 (dd, J=17.9, 11.9 Hz, 1H), 5.51 (dd, J=17.9, 1.6 Hz, 1H), 5.45-5.34 (m, 4H), 4.87-4.76 (m, 1H), 3.67-3.58 (m, 2H), 2.10 (s, 3H), 1.39 (d, J=6.5 Hz, 3H), 1.35 (d, J=6.6 Hz, 3H), 0.95-0.71 (m, 5H), 0.55-0.08 (m, 8H), −0.03 (s, 9H); LCMS (METHOD 3) (ES): m/z 618.1 [M+H]$^+$, RT=1.01 min.

Preparation 229

N-[(1S)-1-(Dicyclopropylmethyl)-2-[4-[5-formyl-3-methyl-1-(2-trimethylsilyl-ethoxymethyl)pyrazol-4-yl]anilino]-2-oxo-ethyl]-2-isopropyl-pyrazole-3-carboxamide

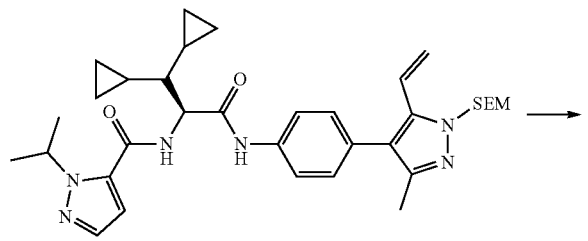

The alkene of Preparation 228 was reacted according to the method of Preparation 208 to give the title compound (51 mg, 99%). LCMS (METHOD 3) (ES): m/z 620.1 [M+H]$^+$, RT=0.99 min.

Preparation 230

N-[(1S)-1-(dicyclopropylmethyl)-2-[4-[5-(hydroxymethyl)-3-methyl-1-(2-trimethylsilyl-ethoxymethyl)pyrazol-4-yl]anilino]-2-oxo-ethyl]-2-isopropyl-pyrazole-3-carboxamide

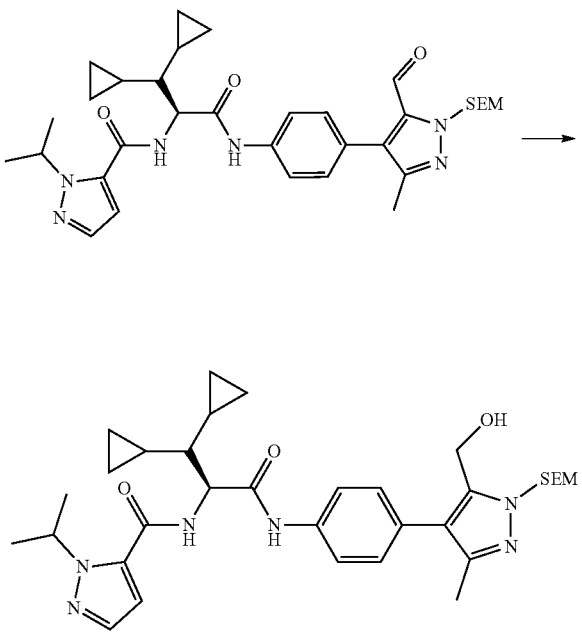

The aldehyde of Preparation 229 (51 mg, 0.8 mmol) was reduced with sodium borohydride (4.7 mg, 0.12 mmol) to give the title compound (46 mg, 89%). LCMS (METHOD 3) (ES): m/z 622.1 [M+H]$^+$, RT=0.90 min.

Preparation 231

(2-Benzyl-4-bromo-5-methyl-pyrazol-3-yl)methanol

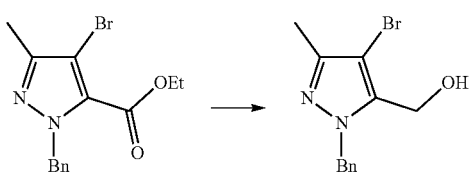 [SMILES: CCOC(=O)c1c(Br)c(C)nn1Cc1ccccc1 ; Cc1nn(Cc2ccccc2)c(CO)c1Br]

Ethyl 2-benzyl-4-bromo-5-methyl-pyrazole-3-carboxylate (3.02 g, 9.34 mmol) was dissolved in THF (75 mL) and cooled to 0° C. Lithium aluminium hydride (1M in THF, 9.81 mL, 9.81 mmol) was added and the mixture was stirred for 1.5 hours. The reaction was quenched by adding dropwise water (2 mL), followed by 4M NaOH (1 mL), and followed by water (2 mL). The mixture was dried (MgSO$_4$) and concentrated in vacuo, then purified by column chromatography (silica, eluting with EtOAc/Heptane) to give the title compound (2.37 g, 90%). LCMS (METHOD 3) (ES): m/z 281.2, 283.2 [M+H]$^+$, RT=0.64 min.

Preparation 232

2-Benzyl-4-bromo-5-methyl-pyrazole-3-carbaldehyde

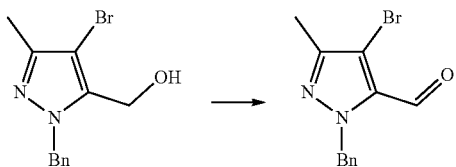 [SMILES: Cc1nn(Cc2ccccc2)c(CO)c1Br ; Cc1nn(Cc2ccccc2)c(C=O)c1Br]

Oxalyl chloride (0.86 mL, 1.29 g, 10.2 mmol) was dissolved in DCM (53 mL) and cooled to −78° C. DMSO (1.45 mL, 1.59 g, 20.4 mmol) in DCM (0.9 mL) was added and the mixture was stirred for 20 min. A solution of the alcohol of Preparation 231 (1.91 g, 6.79 mmol) in DCM (9 mL) was added and the reaction was stirred for 1 hour at −78° C. Triethylamine (5.68 mL, 4.12 g, 40.8 mmol) was added dropwise and the mixture was allowed to warm to 0° C. over 1 hour. The mixture was poured onto ice water and the phases were separated. The aqueous phase was extracted with DCM and the combined organic phases were washed with brine, dried with MgSO$_4$, filtered and concentrated in vacuo. The residue was purified by column chromatography (silica, eluting with EtOAc/Heptane) to give the title compound (1.73 g, 91%) as a white solid. LCMS (METHOD 3) (ES): m/z 279.2, 281.2 [M+H]$^+$, RT=0.75 min.

Preparation 233

1-(2-Benzyl-4-bromo-5-methyl-pyrazol-3-yl)ethanol

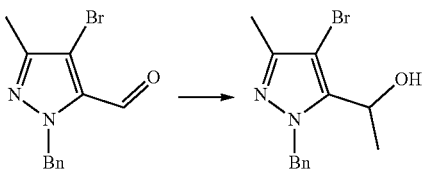 [SMILES: Cc1nn(Cc2ccccc2)c(C=O)c1Br ; Cc1nn(Cc2ccccc2)c(C(C)O)c1Br]

The aldehyde of Preparation 232 (500 mg, 1.791 mmol) was dissolved in THF (10.7 mL) and cooled to −78° C. Methylmagnesium bromide (3M solution in diethyl ether, 0.72 mL, 2.15 mmol) was added. The reaction was allowed to warm to room temperature and stirred for 2 hours. The reaction was re-cooled to −78° C. and further methylmagnesium bromide (0.20 mL, 0.60 mmol) was added. The mixture was allowed to warm to room temperature and stirred. The reaction was cooled to 0° C., quenched with water and diluted with EtOAc. The mixture was washed with water, the aqueous layer was extracted with EtOAc and the combined organic layers were washed with brine, dried with MgSO$_4$, filtered and concentrated in vacuo. The residue was purified by column chromatography (silica, eluting with EtOAc/Heptane) to give the title compound (331 mg, 63%) as a white solid. LCMS (METHOD 3) (ES): m/z 295.2, 297.2 [M+H]$^+$, RT=0.69 min.

Preparation 234

2-(2-Benzyl-4-bromo-5-methyl-pyrazol-3-yl)propan-2-ol

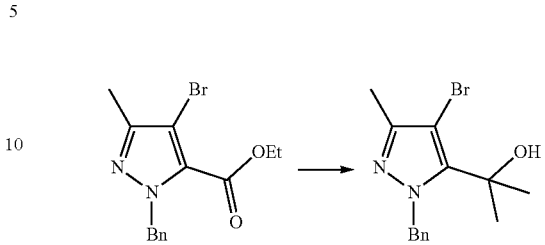

Ethyl 2-benzyl-4-bromo-5-methyl-pyrazole-3-carboxylate (1.51 g, 4.67 mmol) was dissolved in THF (28 mL) and cooled to −78° C. Methylmagnesium bromide (3M solution in diethyl ether, 4.67 mL, 14.0 mmol) was added and the reaction was allowed to warm to room temperature and stirred for 2 hours. The reaction was cooled to 0° C., quenched with water and the mixture was extracted with EtOAc (×2). The combined organic layers were washed with brine, dried with Na$_2$SO$_4$, filtered and concentrated in vacuo. The residue was purified by column chromatography (silica, eluting with EtOAc/Heptane) to give the title compound (1.24 g, 86%). LCMS (METHOD 3) (ES): m/z 309.3, 311.3 [M+H]$^+$, RT=0.76 min.

Preparation 235

1-[2-Benzyl-5-methyl-4-(4-nitrophenyl)pyrazol-3-yl]ethanol

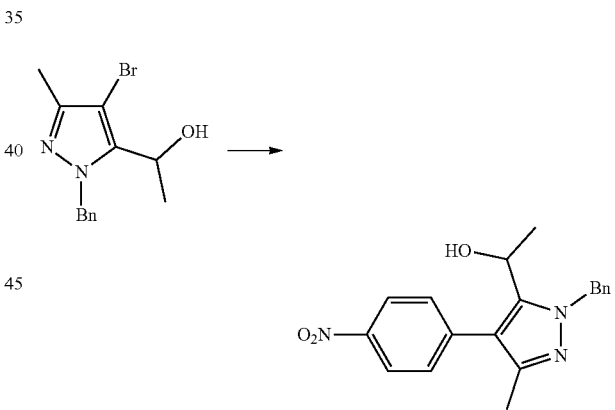

The alcohol of Preparation 233 (331 mg, 1.12 mmol), 4,4,5,5-tetramethyl-2-(4-nitrophenyl)-1,3,2-dioxaborolane (307 mg, 1.23 mmol), K$_2$CO$_3$ (310 mg, 2.24 mmol) and Pd(dppf)Cl$_2$ (46 mg, 0.056 mmol) were combined with MeOH (0.37 mL), THF (2.2 mL) and water (1.1 mL) in a 20 mL vial. The mixture was degassed and placed under argon then placed in a preheated heat block at 90° C. and stirred for 18 hours. After cooling to room temperature, the reaction was filtered through a pad of Celite, the filter pad was washed with EtOAc and the filtrate was washed with water. The aqueous layer was extracted with EtOAc and the combined organic layers were washed with brine, dried with MgSO$_4$, filtered and concentrated in vacuo. The residue was purified by column chromatography (silica, eluting with EtOAc/Heptane) to give the title compound (145 mg, 38%). 1H NMR (600 MHz, Chloroform-d) δ 8.28-8.22 (m, 2H), 7.54-7.47 (m, 2H), 7.37-7.31 (m, 2H), 7.31-7.27 (m, 1H), 7.18-7.13 (m, 2H), 5.33 (s, 2H), 4.95 (q, J=6.6 Hz, 1H), 2.66 (br s, 1H), 2.18 (s, 3H), 1.48 (d, J=6.6 Hz, 3H); LCMS (METHOD 3) (ES): m/z 338.3 [M+H]$^+$, RT=0.76 min.

Preparation 236

1-[4-(4-Aminophenyl)-2-benzyl-5-methyl-pyrazol-3-yl]ethanol

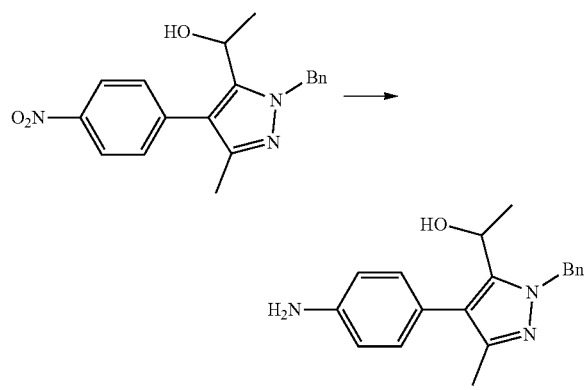

According to the method of Preparation 2 the nitro compound of Preparation 235 was reduced to give the title compound (122 mg, 93%). LCMS (METHOD 3) (ES): m/z 308.4 [M+H]$^+$, RT=0.59 min.

Preparation 237

Tert-butyl N-[(1S)-2-[4-[1-benzyl-5-(1-hydroxyethyl)-3-methyl-pyrazol-4-yl]anilino]-1-cyclohexyl-2-oxo-ethyl]carbamate

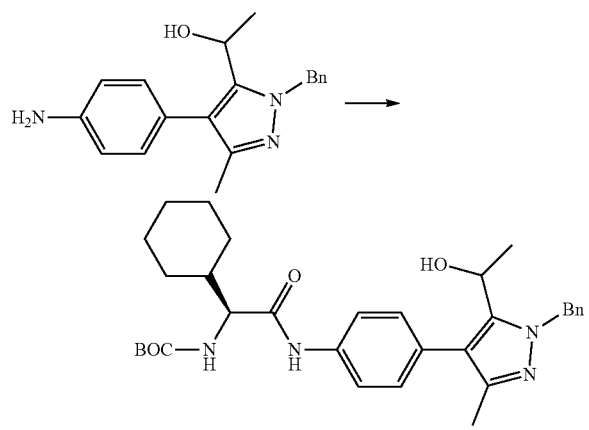

According to the method of Preparation 3 the aniline of Preparation 236 was reacted with (2S)-2-(tert-butoxycarbonylamino)-2-cyclohexyl-acetic acid to give the title compound (76 mg, 70%). LCMS (METHOD 3) (ES): m/z 547.7 [M+H]$^+$, RT=0.88 min.

Preparation 238

(2S)-2-Amino-N-[4-[1-benzyl-5-(1-hydroxyethyl)-3-methyl-pyrazol-4-yl]phenyl]-2-cyclohexyl-acetamide hydrochloride

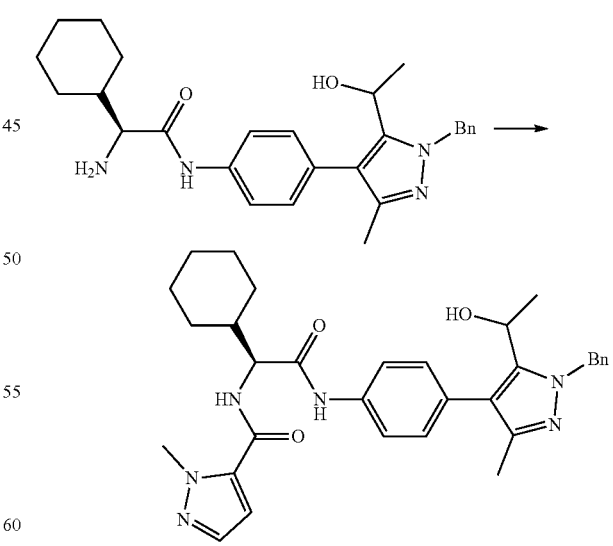

According to the method of Preparation 4 the compound of Preparation 237 was deprotected to give the title compound (assumed quantitative yield). LCMS (METHOD 3) (ES): m/z 447.5 [M+H]$^+$, RT=0.60 min.

Preparation 239

N-[(1S)-2-[4-[1-Benzyl-5-(1-hydroxyethyl)-3-methyl-pyrazol-4-yl]anilino]-1-cyclohexyl-2-oxo-ethyl]-2-methyl-pyrazole-3-carboxamide According to the method of Preparation 5 the amine of Preparation 238 was reacted with 2-methylpyrazole-3-carboxylic acid to give the title compound (22 mg, 73%). LCMS (METHOD 3) (ES): m/z 555.6 [M+H]$^+$, RT=0.78 min.

Preparation 240

5-Methyl-4-(4-nitrophenyl)-1-(2-trimethylsilylethoxymethyl)pyrazol-3-amine

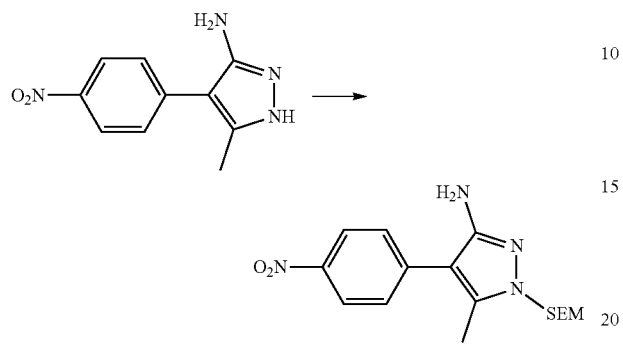

5-Methyl-4-(4-nitrophenyl)-1H-pyrazol-3-amine (200 mg, 0.917 mmol) was dissolved in NMP (5 mL) and $K_2CO_3$ (1.8331 mmol, 253.34 mg) and SEM chloride (0.195 mL, 183 mg, 1.10 mmol) were added. The reaction mixture was stirred at room temperature for 16 hours then filtered and purified by basic prep. HPLC to give the title compound (170 mg, 53%). 1H NMR (300 MHz, DMSO-d6) δ 8.35-8.11 (m, 2H), 7.73-7.47 (m, 2H), 5.74 (s, 2H), 5.28 (s, 2H), 3.70-3.49 (m, 2H), 2.18 (s, 3H), 0.98-0.74 (m, 2H), 0.00 (s, 9H); LCMS (METHOD 3) (ES): m/z 349.4 [M+H]$^+$, RT=0.85 min.

Preparation 241

4-(4-Aminophenyl)-5-methyl-1-(2-trimethylsilylethoxymethyl)pyrazol-3-amine

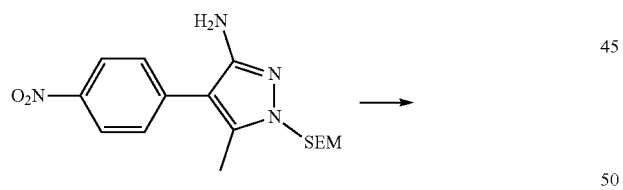

According to the method of Preparation 2 the nitro compound of Preparation 240 was reduced to give the title compound (80 mg, 53%). 1H NMR (300 MHz, DMSO-d6) δ 7.03-6.88 (m, 2H), 6.69-6.55 (m, 2H), 5.21 (s, 2H), 4.95 (s, 2H), 4.86 (s, 2H), 3.70-3.50 (m, 2H), 2.03 (s, 3H), 0.99-0.75 (m, 2H), 0.00 (s, 9H); LCMS (METHOD 3) (ES): m/z 319.4 [M+H]$^+$, RT=0.68 min.

Preparation 242A and B

N,5-Dimethyl-4-(4-nitrophenyl)-1-(2-trimethylsilylethoxymethyl)pyrazol-3-amine (Prep. 242A) and N,N,5-trimethyl-4-(4-nitrophenyl)-1-(2-trimethylsilylethoxymethyl)pyrazol-3-amine (Prep. 242B)

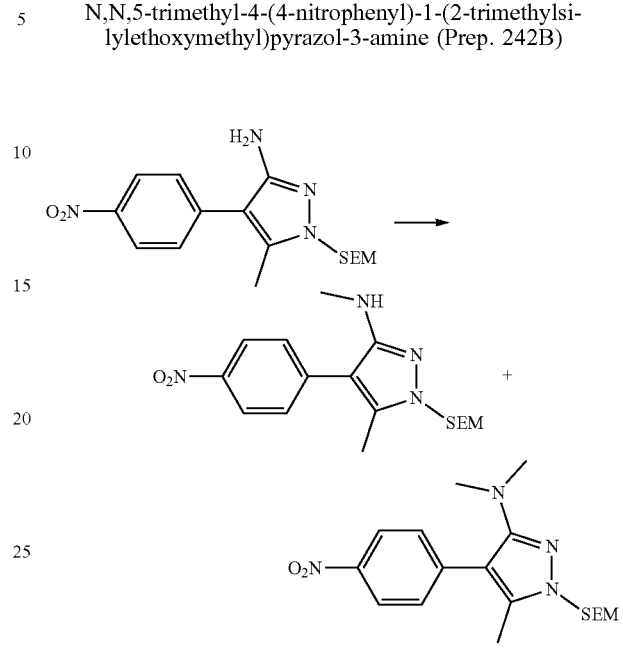

The pyrazole of Preparation 240 (100 mg, 0.287 mmol) was dissolved in acetone (5 mL) under argon, $K_2CO_3$ (198 mg, 1.43 mmol) was added, the mixture was cooled to 0° C. and methyl iodide (0.090 mL, 1.43 mmol) was added. The reaction was allowed to warm to room temperature and stirred for 65 hours. Further methyl iodide (0.54 mL, 8.61 mmol) was added and the mixture was heated at reflux for 6 hours. After cooling to room temperature, the reaction mixture was filtered and concentrated in vacuo. The residue was purified by acidic prep. HPLC to give Preparation 242A (6 mg, 6%) and Preparation 242B (10 mg, 9%) as yellow oils.

Prep. 242A: LCMS (METHOD 3) (ES): m/z 363.5 [M+H]$^+$, RT=0.92 min. Prep. 242B: LCMS (METHOD 3) (ES): m/z 377.5 [M+H]$^+$, RT=1.01 min.

Preparation 243

4-(4-Aminophenyl)-N,5-dimethyl-1-(2-trimethylsilylethoxymethyl)pyrazol-3-amine

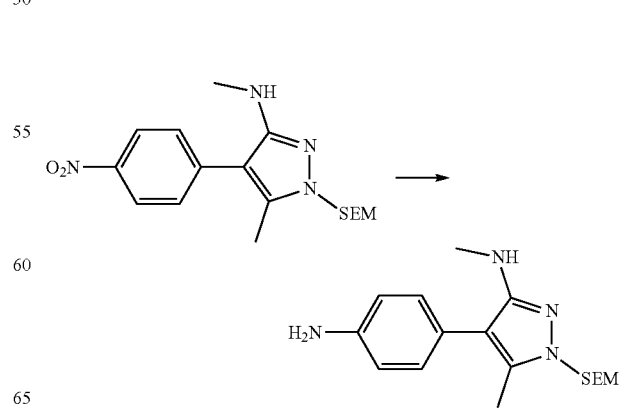

According to the method of Preparation 2 the nitro compound of Preparation 242A was reduced to give the title compound. LCMS (METHOD 3) (ES): m/z 333.4 [M+H]+, RT=0.77 min.

Preparation 244

4-(4-Aminophenyl)-N,N,5-trimethyl-1-(2-trimethylsilylethoxymethyl)pyrazol-3-amine

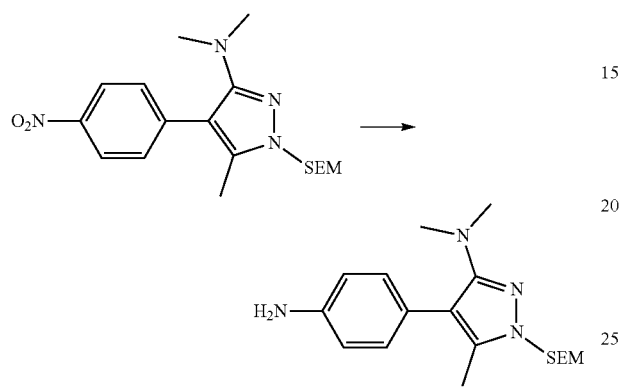

According to the method of Preparation 2 the nitro compound of Preparation 242B was reduced to give the title compound. LCMS (METHOD 3) (ES): m/z 347.5 [M+H]+, RT=0.86 min.

Preparation 245

Tert-butyl N-[(1S)-1-[(2-chlorophenyl)methyl]-2-(4-iodoanilino)-2-oxo-ethyl]carbamate

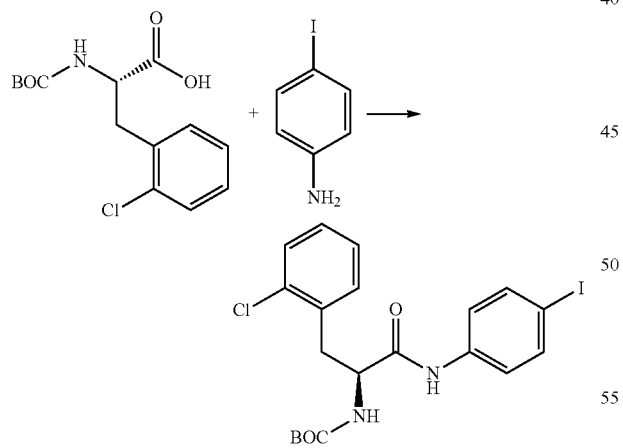

According to the method of Preparation 3 (2S)-2-(tert-butoxycarbonylamino)-3-(2-chlorophenyl)propanoic acid was reacted with 4-iodoaniline to give the title compound (2.3 g, 69%) as a colourless crystalline solid. 1H NMR (300 MHz, DMSO-d6) δ 9.98 (s, 1H), 7.69-7.58 (m, 2H), 7.45-7.36 (m, 3H), 7.36-7.29 (m, 1H), 7.27-7.19 (m, 2H), 7.12 (d, J 5=8.2 Hz, 1H), 4.60-4.28 (m, 1H), 3.13 (dd, J=14.1, 6.0 Hz, 1H), 2.99 (dd, J=14.1, 8.8 Hz, 1H), 1.32 (s, 9H); LCMS (METHOD 3) (ES): m/z 501.1 [M+H]+, RT=0.91 min.

Preparation 246

Tert-butyl N-[(1S)-2-(4-azidoanilino)-1-[(2-chlorophenyl)methyl]-2-oxo-ethyl]carbamate

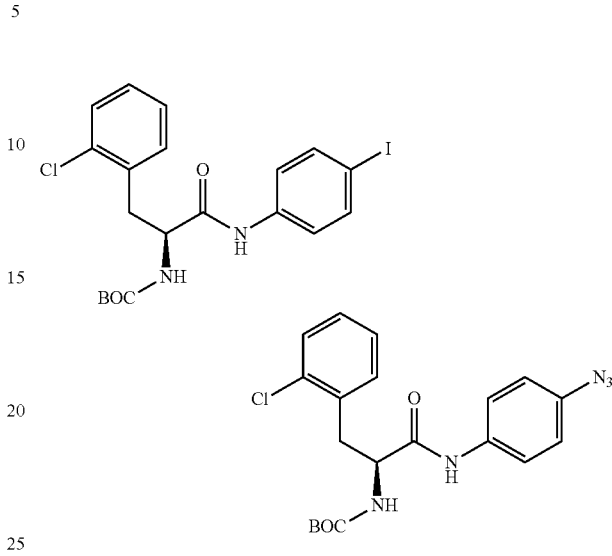

The iodide of Preparation 245 (560 mg, 1.1 mmol), NaN3 (150 mg, 2.2 mmol), ascorbic acid (10 mg, 0.056 mmol), CuI (21 mg, 0.11 mmol) and (1S,2S)—N1,N2-dimethylcyclohexane-1,2-diamine (24 mg, 0.17 mmol) were combined in DMSO (20 mL) and water (4 mL). The mixture was degassed and placed under argon then stirred at 80° C. for 1 h. After cooling to room temperature, the reaction mixture was partitioned between brine and diethyl ether. The aqueous phase was extracted with further diethyl ether (×3) and the combined organic phases were washed with brine and concentrated in vacuo to give the product (0.46 g, 99%) as a yellowish solid. 1H NMR (300 MHz, DMSO-d6) δ 9.98 (s, 1H), 7.77-7.53 (m, 2H), 7.46-7.38 (m, 1H), 7.38-7.31 (m, 1H), 7.29-7.21 (m, 2H), 7.18-7.04 (m, 3H), 4.57-4.25 (m, 1H), 3.15 (dd, J=14.0, 5.9 Hz, 1H), 3.01 (dd, J=14.1, 8.9 Hz, 1H), 1.33 (s, 9H); LCMS (METHOD 3) (ES): m/z 416.1 [M+H]+, RT=0.87 min.

Preparation 247

5-(2-Methoxy-4-nitro-phenyl)-1-methylimidazole

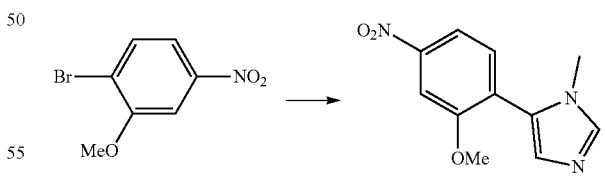

1-Bromo-2-methoxy-4-nitro-benzene (3.00 g, 12.9 mmol), N-methylimidazole (3.18 g, 38.8 mmol), potassium carbonate (2.68 g, 19.4 mmol), tricyclohexylphosphane (20 wt % in toluene, 836 μL, 725 mg, 0.52 mmol), pivalic acid (396 mg, 3.88 mmol) and palladium II acetate (145 mg, 0.65 mmol) were combined in DMF (12.9 mL) and the mixture was split between two 20 mL microwave vials. The vials were flushed with argon for 2 min then capped and stirred at 180° C. with microwave heating for 10 min. After cooling to room temperature, the reaction mixtures were combined and diluted with EtOAc (100 mL), washed with water (2×20 mL) and brine (20 mL), dried (MgSO$_4$), filtered and concentrated in vacuo to give a dark oil. Purification by column chromatography (silica, eluting with EtOAc/heptane) gave the title compound (1.243 g, 41%). 1H NMR (600 MHz, Chloroform-d) δ 7.91 (dd, J=8.3, 2.2 Hz, 1H), 7.84 (d, J=2.2 Hz, 1H), 7.58 (d, J=1.0 Hz, 1H), 7.43 (d, J=8.3 Hz, 1H), 7.13 (d, J=1.1 Hz, 1H), 3.95 (s, 3H) 3.56 (s, 3H); LCMS (METHOD 3) (ES): m/z 216.2, 234.5 [M+H]$^+$, RT=0.37 min.

Preparation 248

3-Methoxy-4-(3-methylimidazol-4-yl)aniline

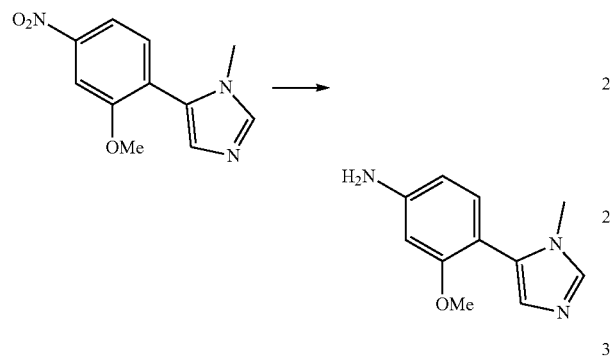

The nitro compound of Preparation 247 was reduced according to the method of Preparation 2 to give the title compound (1.06 g, 99%) as a colourless oil. 1H NMR (600 MHz, DMSO-d6) δ 7.56 (d, J=1.0 Hz, 1H), 6.82 (d, J=8.1 Hz, 1H), 6.68 (d, J=1.2 Hz, 1H), 6.30 (d, J=2.0 Hz, 1H), 6.19 (dd, J=8.1, 2.1 Hz, 1H), 5.33 (s, 2H), 3.67 (s, 3H), 3.38 (s, 3H); LCMS (METHOD 3) (ES): m/z 204.5 [M+H]$^+$, RT=0.26 min.

Preparation 249

Tert-butyl N-[(1S)-1-cyclohexyl-2-[3-methoxy-4-(3-methylimidazol-4-yl)anilino]-2-oxo-ethyl]carbamate

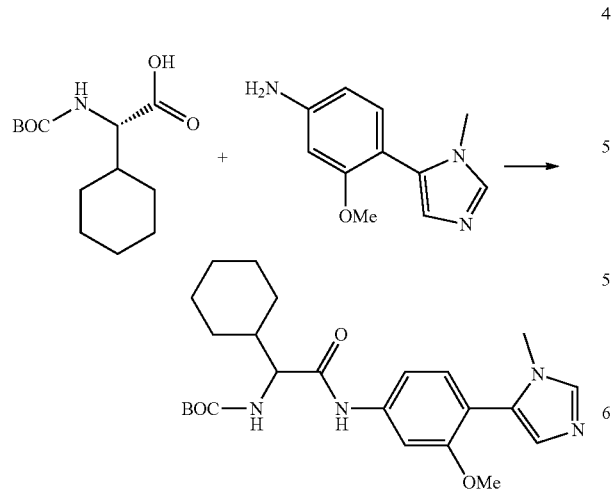

According to the method of Preparation 3 the aniline of Preparation 248 was reacted with (2S)-2-(tert-butoxycarbonylamino)-2-cyclohexyl-acetic acid to give the title compound (183 mg, 100%). 1H NMR (300 MHz, DMSO-d6) δ 10.38 (s, 1H), 8.59 (s, 1H), 7.60 (d, J=1.9 Hz, 1H), 7.43-7.29 (m, 2H), 7.22 (d, J=8.3 Hz, 1H), 6.94 (d, J=8.5 Hz, 1H), 3.97 (t, J=8.2 Hz, 1H), 3.77 (s, 3H), 3.56 (s, 3H), 1.87-1.46 (m, 6H), 1.38 (s, 9H), 1.29-0.91 (m, 5H); LCMS (METHOD 3) (ES): m/z 443.5 [M+H]$^+$, RT=0.68 min.

Preparation 250

(2S)-2-Amino-2-cyclohexyl-N-[3-methoxy-4-(3-methylimidazol-4-yl)phenyl]acetamide

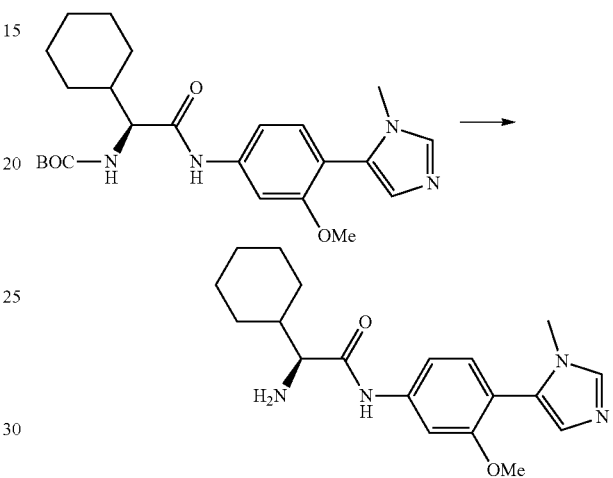

The protected compound of Preparation 249 was reacted according the method of Preparation 4 to give the title compound (144 mg, 98%) as a colourless solid. LCMS (METHOD 3) (ES): m/z 343.4 [M+H]$^+$, RT=0.36 min.

Preparation 251

(2S)-2-Amino-2-cyclohexyl-N-[3-hydroxy-4-(3-methylimidazol-4-yl)phenyl]acetamide

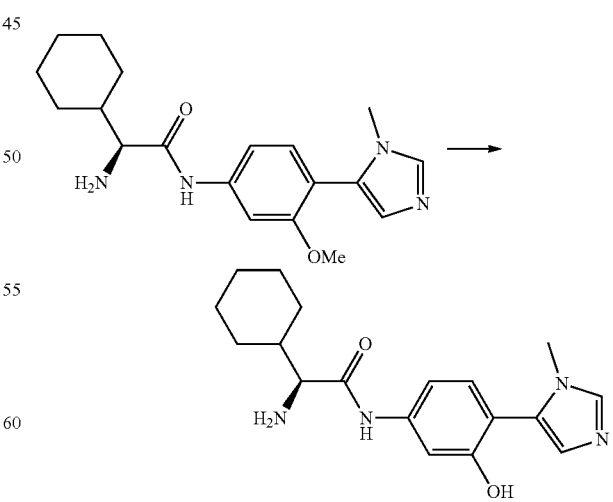

To an ice cold mixture of the amine of Preparation 250 (75 mg, 0.198 mmol) in DCM (1 mL) was added BBr$_3$ (1M soln. in DCM, 1.979 mL, 1.979 mmol). The mixture was stirred at room temperature for 16 hours, added to ice cold MeOH (25 mL), then concentrated in vacuo. The residue was re-dissolved in MeOH (2 mL) and aq. ammonia (0.5 mL) and purified by prep. basic HPLC to give recovered starting material (17 mg) and the title compound (11 mg, 17%). LCMS (METHOD 4) (ES): m/z 329.4 [M+H]+, RT=0.49 min.

Preparation 252

N-[(1S)-1-cyclohexyl-2-[3-methoxy-4-(3-methylimidazol-4-yl)anilino]-2-oxo-ethyl]-2-methyl-pyrazole-3-carboxamide

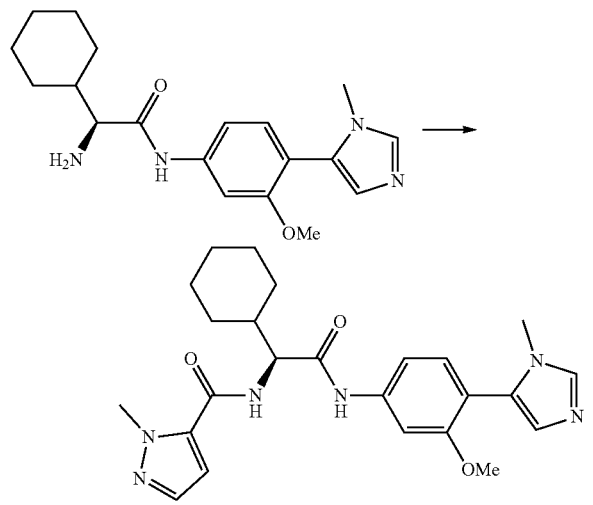

The amine of Preparation 251 was reacted with 2-methylpyrazole-3-carboxylic acid according to the method of Preparation 5 to give the title compound (61 mg, 71%). LCMS (METHOD 3) (ES): m/z 451.5 [M+H]+, RT=0.56 min.

Preparation 253

5-(2-Methoxy-4-nitro-phenyl)-1,4-dimethyl-imidazole

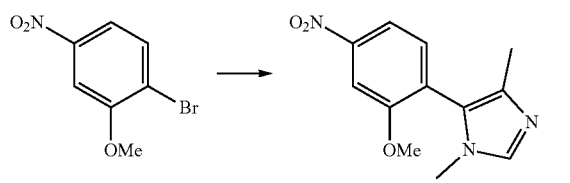 [SMILES: COc1cc([N+](=O)[O-])ccc1Br ; COc1cc([N+](=O)[O-])ccc1-c1c(C)ncn1C]

1-Bromo-2-methoxy-4-nitro-benzene (600 mg, 2.59 mmol), bis(pinacolato)diboron (788 mg, 3.10 mmol), potassium acetate (279 mg, 2.84 mmol) and Pd(dppf)Cl₂ (211 mg, 0.26 mmol) were combined in dioxane (10 mL) in a 20 mL microwave vial. The vial was flushed with argon for 5 min, capped and stirred for 5 hours at 80° C., then allowed to cool to room temperature and left for 16 hours. The reaction mixture was diluted with EtOAc (50 mL), washed with 1M HCl (10 mL), water (10 mL) and brine (10 mL), dried (MgSO₄), filtered and concentrated in vacuo to give an intermediate boronic ester that was used without further purification.

The crude boronic ester (2.59 mmol), 5-bromo-1,4-dimethyl-imidazole (453 mg, 2.59 mmol), potassium carbonate (715 mg, 5.17 mmol), water (2.6 mL) and Pd(dppf)Cl₂ (211 mg, 0.26 mmol) were combined in THF (10 mL) and MeOH (0.85 mL) in a 20 mL microwave vial. The vial was flushed with argon for 5 min, capped and stirred for 20 min at 90° C., then allowed to cool to room temperature and diluted with EtOAc (50 mL), washed with water (2×10 mL) and brine (10 mL), dried (MgSO₄), filtered and concentrated in vacuo. The residue was purified by column chromatography (silica, eluting with EtOAc/MeOH) to give the title compound (235 mg, 37%). 1H NMR (600 MHz, DMSO-d6) δ 7.91 (dd, J=8.2, 2.2 Hz, 1H), 7.88 (d, J=2.2 Hz, 1H), 7.63 (s, 1H), 7.51 (d, J=8.3 Hz, 1H), 3.92 (s, 3H), 3.41 (s, 3H), 2.00 (s, 3H); LCMS (METHOD 3) (ES): m/z 248.5 [M+H]+, RT=0.42 min.

Preparation 254

2-(3,5-Dimethylimidazol-4-yl)-5-nitro-phenol

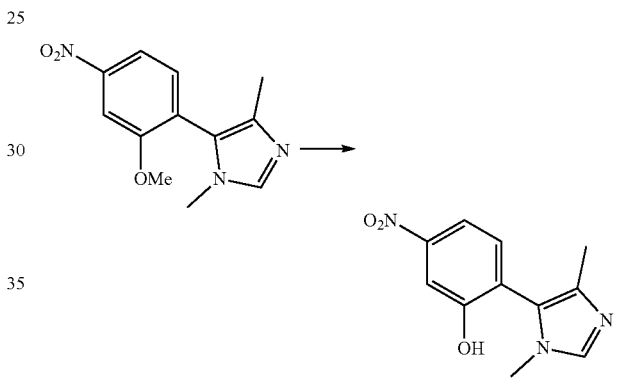

BBr₃ (1M soln. in DCM, 3.66 mL, 3.66 mmol) was added to an ice cold solution of the imidazole of Preparation 253 (181 mg, 0.732 mmol) in DCM (2 mL) under argon causing precipitation. The mixture was stirred 15 min at 0° C., then for 4 hours at room temperature. The reaction was concentrated in vacuo, then stored in a freezer for 3 days before being re-dissolved in MeOH (5 mL). the mixture was concentrated in vacuo then purified by prep. acidic HPLC to give the title compound (96 mg, 56%). 1H NMR (600 MHz, DMSO-d6) δ 10.81 (s, 1H), 7.77 (d, J=2.4 Hz, 1H), 7.74 (dd, J=8.3, 2.4 Hz, 1H), 7.65 (s, 1H), 7.42 (d, J=8.3 Hz, 1H), 3.45 (s, 3H), 2.01 (s, 3H); LCMS (METHOD 3) (ES): m/z 234.2 [M+H]+, RT=0.37 min.

Preparation 255

5-Amino-2-(3,5-dimethylimidazol-4-yl)phenol

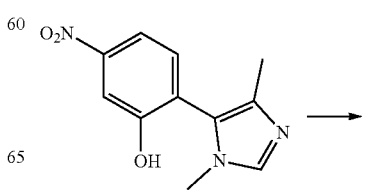

-continued

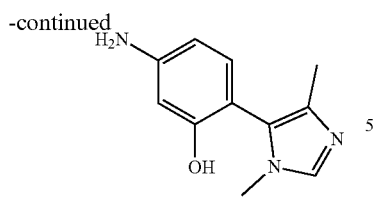

The nitro compound of Preparation 254 was reduced according to the method of Preparation 2 to give the title compound (2.11 g, 84%). 1H NMR (600 MHz, Methanol-d4) δ 8.88 (d, J=0.8 Hz, 1H), 7.41 (d, J=8.1 Hz, 1H), 7.04 (d, J=2.1 Hz, 1H), 6.99 (dd, J=8.1, 2.2 Hz, 1H), 3.71 (d, J=0.7 Hz, 3H), 2.23 (s, 3H); LCMS (METHOD 3) (ES): m/z 204.2 [M+H]$^+$, RT=0.25 min.

Preparation 256

2-[(2-Bromo-5-nitro-phenoxy)methoxy]ethyl-trimethyl-silane

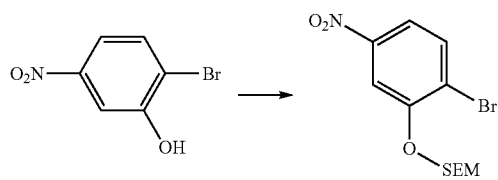 [SMILES: O=[N+]([O-])c1ccc(Br)c(O)c1 ; C[Si](C)(C)CCOCOc1cc([N+](=O)[O-])ccc1Br]

To a mixture of 2-bromo-5-nitro-phenol (8,2 g, 38 mmol) and triethylamine (7.6 g, 10 mL, 75 mmol) in DCM (50 mL) at 0° C. under argon was added SEM chloride (11 g, 12 mL, 68 mmol). The mixture was stirred at room temperature for 2 hours then washed with water (50 mL). The aqueous phase was extracted with DCM (2×50 mL) and the combined organic phases were washed with brine and concentrated in vacuo. Purification by column chromatography (silica, eluting with 0-10% EtOAc in heptane) gave the title compound (11.58 g, 88%) as a yellow oil. 1H NMR (300 MHz, DMSO-d6) δ 8.05 (d, J=2.6 Hz, 1H), 7.97 (d, J=8.7 Hz, 1H), 7.85 (dd, J=8.7, 2.6 Hz, 1H), 5.55 (s, 2H), 3.91-3.70 (m, 2H), 1.09-0.87 (m, 2H), −0.00 (s, 9H); LCMS (METHOD 3) (ES): m/z 216.2, 218.1 [M+H-SEM]$^+$, RT=1.01 min.

Preparation 257

2-[[3,5-Dimethyl-4-[4-nitro-2-(2-trimethylsilylethoxymethoxy)phenyl]pyrazol-1-yl]methoxy]ethyl-trimethyl-silane

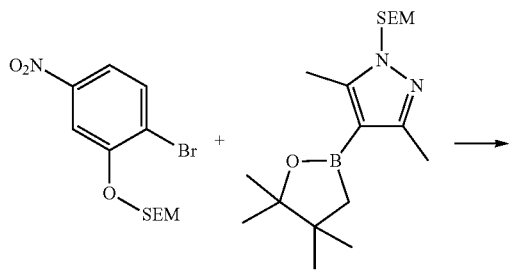

-continued

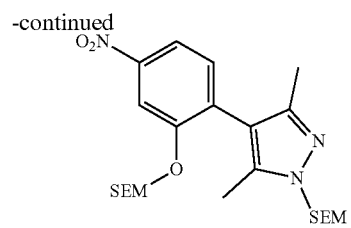

The bromo compound of Preparation 256 was reacted according to the method of Preparation 1 to give the title compound (2.69 g, 82%) as an orange oil. 1H NMR (300 MHz, DMSO-d6) δ 8.06 (d, J=2.3 Hz, 1H), 7.95 (dd, J=8.4, 2.3 Hz, 1H), 7.45 (d, J=8.4 Hz, 1H), 5.39 (s, 2H), 5.36 (s, 2H), 3.80-3.56 (m, 4H), 2.19 (s, 3H), 2.07 (s, 3H), 1.07-0.78 (m, 4H), −0.00 (s, 9H), −0.03 (s, 9H); LCMS (METHOD 3) (ES): m/z 494.5 [M+H]$^+$, RT=1.10 min.

Preparation 258

4-[3,5-Dimethyl-1-(2-trimethylsilylethoxymethyl)pyrazol-4-yl]-3-(2-trimethylsilylethoxymethoxy)aniline

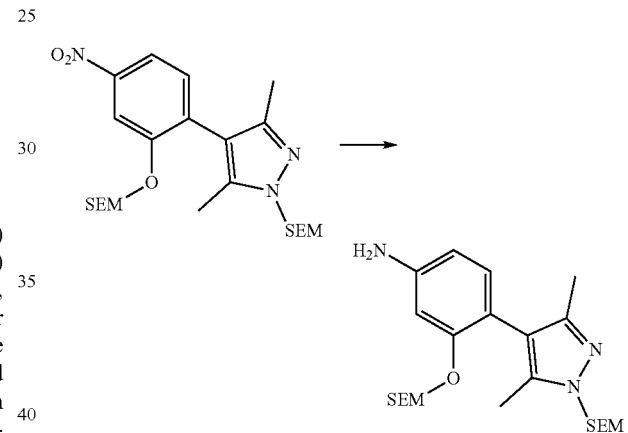

The nitro compound of Preparation 257 was reduced according to the method of Preparation 2 to give the title compound (2.11 g, 84%) as a colourless oil. 1H NMR (300 MHz, DMSO-d6) δ 6.73 (d, J=8.1 Hz, 1H), 6.46 (d, J=2.1 Hz, 1H), 6.28 (dd, J=8.1, 2.1 Hz, 1H), 5.32 (s, 2H), 5.13 (s, 2H), 5.05 (s, 2H), 3.77-3.51 (m, 4H), 2.12 (s, 3H), 2.00 (s, 3H), 1.05-0.79 (m, 4H), 0.01 (s, 9H), 0.00 (s, 9H); LCMS (METHOD 3) (ES): m/z 464.6 [M+H]$^+$, RT=0.99 min.

Preparation 259

Tert-butyl N-[(1S)-1-(dicyclopropylmethyl)-2-[4-[3,5-dimethyl-1-(2-trimethylsilylethoxymethyl)pyrazol-4-yl]-3-(2-trimethylsilylethoxymethoxy)anilino]-2-oxo-ethyl]carbamate

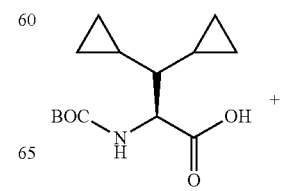

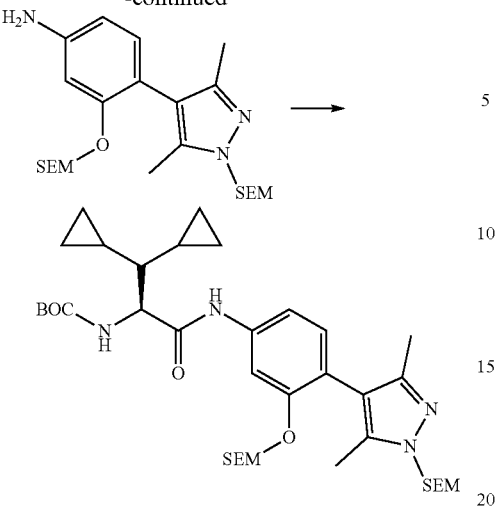

According to the method of Preparation 3 the aniline of Preparation 258 was reacted with the acid of Preparation 52 to give the title compound (1.63 g, 89%) as a yellow oil. 1H NMR (400 MHz, Chloroform-d) δ 7.93 (s, 1H), 7.38 (s, 1H), 7.29 (d, J=8.5 Hz, 1H), 7.07 (d, J=8.1 Hz, 1H), 5.37 (br s, 1H), 5.37 (s, 2H), 5.13 (s, 2H), 4.44-4.31 (m, 1H), 3.89-3.48 (m, 4H), 2.19 (s, 3H), 2.13 (s, 3H), 1.48 (s, 9H), 1.02-0.86 (m, 5H), 0.83-0.70 (m, 2H), 0.62-0.40 (m, 4H), 0.40-0.20 (m, 4H), −0.02 (s, 9H), −0.02 (d, J=0.9 Hz, 9H); LCMS (METHOD 3) (ES): m/z 716.7 [M+H]$^+$, RT=1.12 min.

Preparation 260

(2S)-2-Amino-3,3-dicyclopropyl-N-[4-[3,5-dimethyl-1-(2-trimethylsilylethoxymethyl)pyrazol-4-yl]-3-hydroxy-phenyl]propanamide

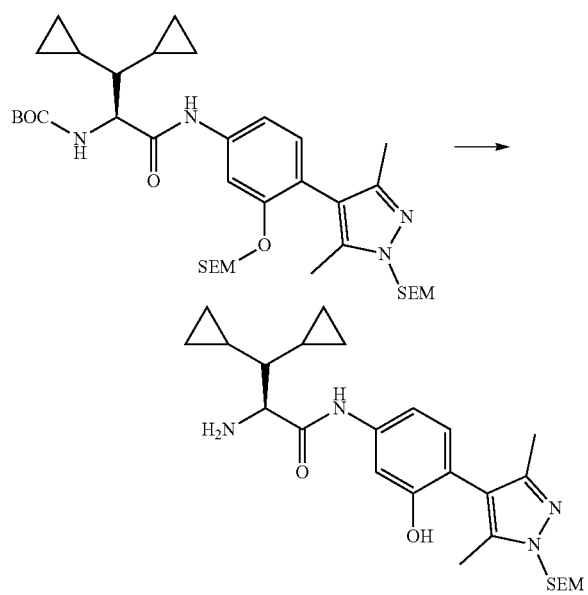

The protected compound of Preparation 259 was reacted according the method of Preparation 4 to give the title compound (1.19 g) as a colourless solid. LCMS (METHOD 3) (ES): m/z 485.5 [M+H]$^+$, RT=0.69 min.

Preparation 261

N-[(1S)-1-(Dicyclopropylmethyl)-2-[4-[3,5-dimethyl-1-(2-trimethylsilylethoxymethyl)pyrazol-4-yl]-3-hydroxy-anilino]-2-oxo-ethyl]-2-isopropyl-pyrazole-3-carboxamide

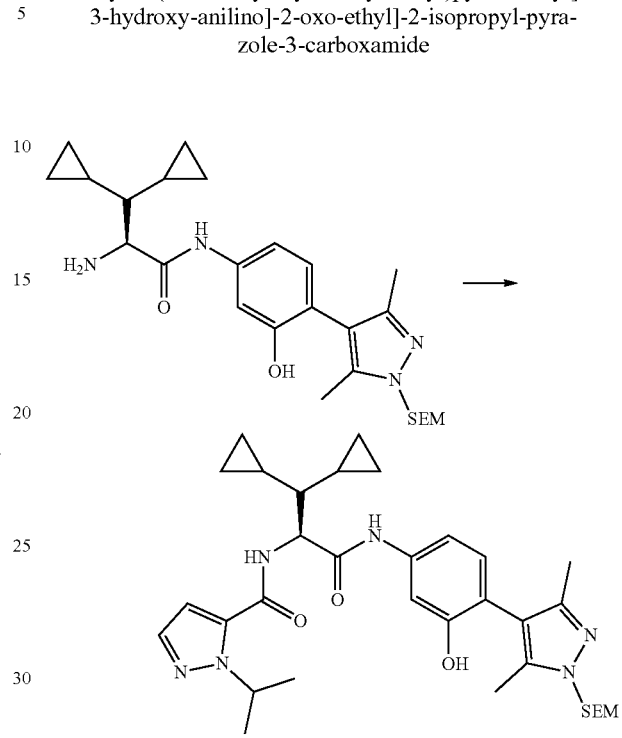

The amine of Preparation 260 was reacted with 2-isopropylpyrazole-3-carboxylic acid according to the method of Preparation 5 to give the title compound (1.098 g, 78%). LCMS (METHOD 3) (ES): m/z 621.5 [M+H]$^+$, RT=0.91 min.

Preparation 262

2-(2-methoxy-4-nitrophenyl)-4,4,5,5-tetramethyl-1,3,2-dioxaborolane

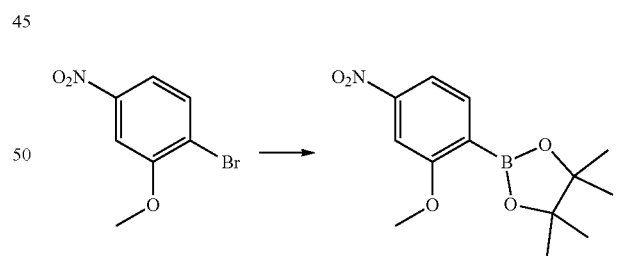

To a stirred solution of 1-bromo-2-methoxy-4-nitrobenzene (10 g, 43.10 mmol) in 1,4-dioxane (100 mL) in a sealed tube was added bis(pinacolato)diboron (13.1 g, 51.7 mmol) and KOAc (10.5 g, 108 mmol) under an inert atmosphere. The resulting reaction mixture was purged with argon gas for 20 min, followed by added Pd(dppf)Cl$_2$.DCM (3.5 g, 4.31 mmol) and heated at 110° C. for 16 h. The reaction mass was cooled to room temperature and diluted with ice cold water (300 mL). The compound was extracted with EtOAc (2×200 mL). The combined organics were washed with water (200 mL) and brine (200 mL), dried over anhydrous Na$_2$SO$_4$, filtered and concentrated under reduced pressure. The obtained crude compound was purified by silica gel (100-200 mesh) column chromatography (10%-20% EtOAc in pet ether as eluent) to afford the title compound as a light yellow solid (4.3 g, 35%). 1H NMR (400 MHz, CDCl₃): δ (ppm) 7.78 (s, J=1.2 Hz, 2H), 7.66 (s, 1H), 3.92 (s, 3H), 1.37 (s, 12H); LCMS (METHOD 5) (ESI): m/z: 279 [M+H]⁺; RT=4.00 min (ACQUITY UPLC BEH C18 column, 0.1% FA in water with MeCN).

Preparation 263

2-[[2-(2,4-Dimethylpyrazol-3-yl)-5-nitro-phenoxy]methoxy]ethyl-trimethyl-silane

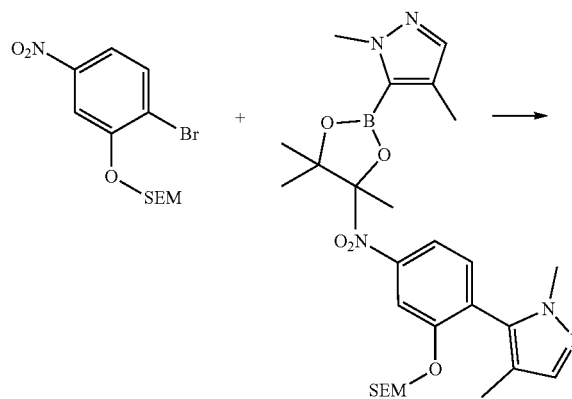

To a mixture of 1,4-dimethyl-5-(4,4,5,5-tetramethyl-1,3,2-dioxaborolan-2-yl)-1H-pyrazole (416 mg, 1.873 mmol) and the bromide of Preparation 256 (652 mg, 1.873 mmol) in THF (3.75 mL) and MeOH (0.65 mL) in a 5 mL microwave vial was added a solution of K₂CO₃ (518 mg, 3.75 mmol) in water (1.87 mL) and Pd(dppf)Cl₂ (76.5 mg, 0.0937 mmol). The vial was degassed with argon for 10 min, capped and stirred for 1 hour at 90° C. After cooling to room temperature, the reaction mixture was diluted with EtOAc (50 mL), washed with water (2×20 mL) and brine (20 mL), dried (MgSO₄), filtered and concentrated in vacuo. The residue was purified by column chromatography (silica, eluting with 0-60% EtOAc in heptane) to give the title compound (407 mg, 60%). 1H NMR (400 MHz, DMSO-d6) δ 8.15 (d, J=2.2 Hz, 1H), 8.04 (dd, J=8.4, 2.2 Hz, 1H), 7.62 (d, J=8.3 Hz, 1H), 7.41 (s, 1H), 5.46 (br d, J=13.6 Hz, 2H), 3.69 (t, J=8.1 Hz, 2H), 3.66 (s, 3H), 1.94 (s, 3H), 0.91 (t, J=8.0 Hz, 2H), 0.00 (s, 9H); LCMS (METHOD 3) (ES): m/z 364.3 [M+H]⁺, RT=0.95 min.

Preparation 264

4-(2,4-dimethylpyrazol-3-yl)-3-(2-trimethylsilylethoxymethoxy)aniline

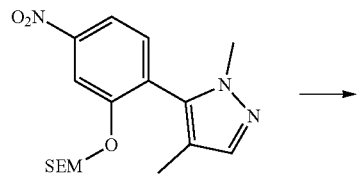

-continued

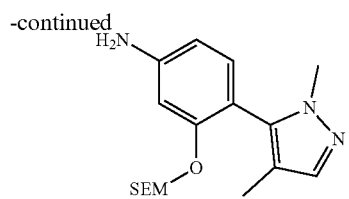

The nitro compound of Preparation 263 was reduced according to the method of Preparation 2 to give the title compound (351 mg, 90%). 1H NMR (400 MHz, DMSO-d6) δ 7.24 (s, 1H), 6.83 (d, J=8.1 Hz, 1H), 6.50 (d, J=2.0 Hz, 1H), 6.33 (dd, J=8.1, 2.0 Hz, 1H), 5.43 (s, 2H), 5.11 (s, 2H), 3.66-3.51 (m, 5H), 1.86 (s, 3H), 0.88 (dd, J=9.2, 7.5 Hz, 2H), 0.00 (s, 9H); LCMS (METHOD 3) (ES): m/z 334.3 [M+H]⁺, RT=0.81 min.

Preparation 265

Tert-butyl N-[(1S)-1-(dicyclopropylmethyl)-2-[4-(2,4-dimethylpyrazol-3-yl)-3-(2-trimethylsilylethoxymethoxy)anilino]-2-oxo-ethyl]carbamate

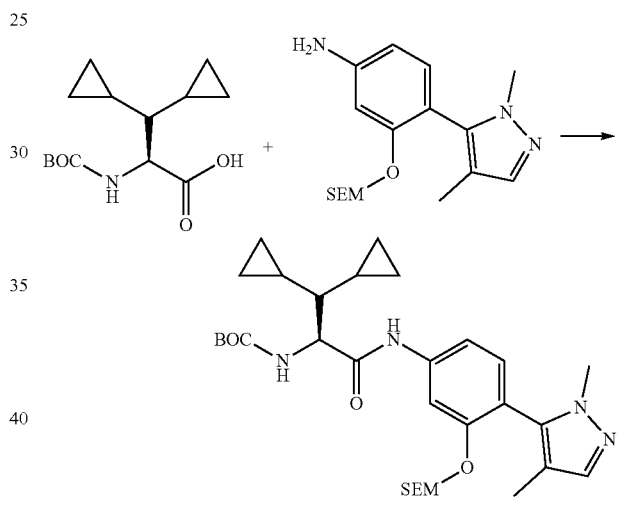

According to the method of Preparation 3 the aniline of Preparation 264 was reacted with the acid of Preparation 52 to give the title compound (30 mg, 69%). LCMS (METHOD 3) (ES): m/z 585.2 [M+H]⁺, RT=1.00 min.

Preparation 266

(2S)-2-Amino-3,3-dicyclopropyl-N-[4-(2,4-dimethylpyrazol-3-yl)-3-hydroxy-phenyl]propanamide

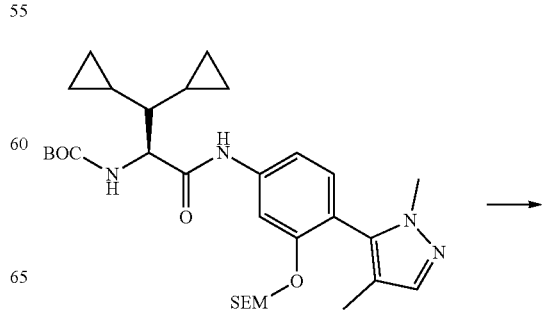

-continued

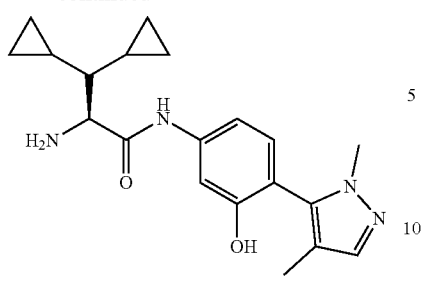

The protected compound of Preparation 265 was reacted according the method of Preparation 4 to give the title compound (18 mg). LCMS (METHOD 3) (ES): m/z 355.4 [M+H]+, RT=0.47 min.

Preparation 267

2-[[4-(2-Methoxy-4-nitro-phenyl)-3-methyl-pyrazol-1-yl]methoxy]ethyl-trimethyl-silane

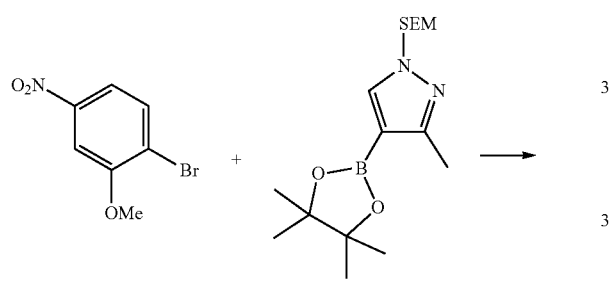

1-Bromo-2-methoxy-4-nitrobenzene was reacted with trimethyl-[2-[[3-methyl-4-(4,4,5,5-tetramethyl-1,3,2-dioxaborolan-2-yl)pyrazol-1-yl]methoxy]ethyl]silane according to the method of Preparation 263 to give the title compound (1.25 g, 78%) as a 2:1 mixture of SEM regioisomers. 1H NMR (600 MHz, DMSO-d6) δ 8.13 (s, 0.67H), 7.93-7.85 (m, 1H), 7.86-7.80 (m, 1H), 7.64 (s, 0.33H), 7.58 (d, J=8.5 Hz, 0.67H), 7.49 (d, J=8.3 Hz, 0.33H), 5.46 (s, 0.67H), 5.37 (s, 1.33H), 3.94 (s, 2H), 3.92 (s, 1H), 3.64-3.50 (m, 2H), 2.30 (s, 1H), 2.24 (s, 2H), 0.90-0.79 (m, 2H), −0.03 (s, 6H), −0.04 (s, 3H); LCMS (METHOD 3) (ES): m/z 364.3 [M+H]+, RT=0.94 and 0.95 min.

Preparation 268

3-Methoxy-4-[3-methyl-1-(2-trimethylsilylethoxymethyl)pyrazol-4-yl]aniline

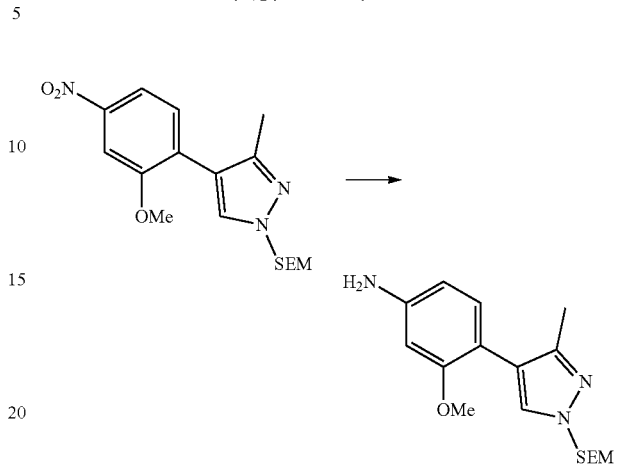

The nitro compound of Preparation 268 was reduced according to the method of Preparation 2 to give the title compound (1.113 g, 99%) as a 2:1 mixture of SEM regioisomers. LCMS (METHOD 3) (ES): m/z 334.4 [M+H]+, RT=0.78 and 0.79 min.

Preparation 269

Tert-butyl N-[(1S)-1-benzhydryl-2-[3-methoxy-4-[3-methyl-1-(2-trimethylsilylethoxymethyl)pyrazol-4-yl]anilino]-2-oxo-ethyl]carbamate

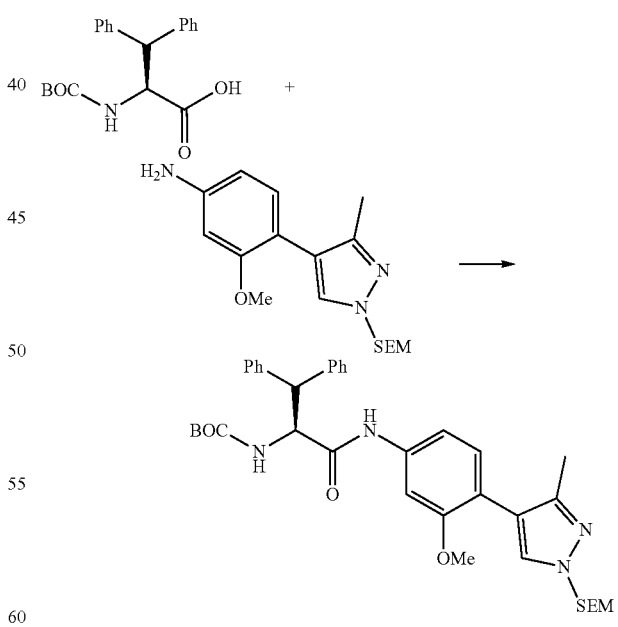

According to the method of Preparation 3 the aniline of Preparation 268 was reacted with (2S)-2-(tert-butoxycarbonylamino)-3,3-diphenyl-propanoic acid to give the title compound (74 mg, 77%) as a mixture of SEM regioisomers. LCMS (METHOD 3) (ES): m/z 657.6 [M+H]+, RT=0.99 and 1.00 min.

Preparation 270

(2S)-2-Amino-N-[3-methoxy-4-[3-methyl-1-(2-trimethylsilylethoxymethyl)pyrazol-4-yl]phenyl]-3,3-diphenyl-propanamide

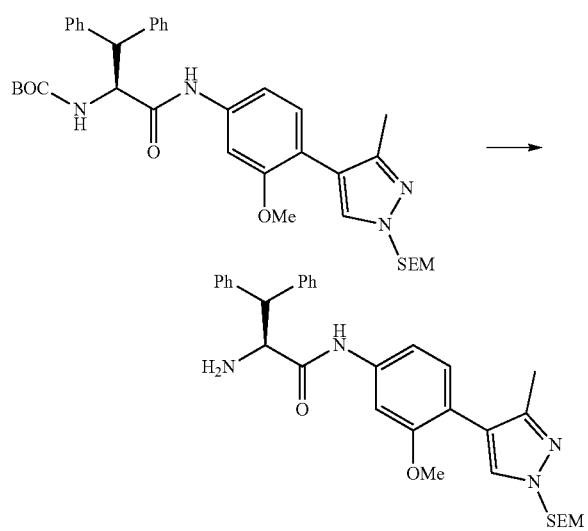

The protected compound of Preparation 269 was reacted according to the method of Preparation 4 to give the title compound (64 mg) as a mixture of SEM regioisomers. LCMS (METHOD 3) (ES): m/z 557.5 [M+H]⁺, RT=0.78 and 0.79 min.

Preparation 271

N-[(1S)-1-Benzhydryl-2-[3-methoxy-4-[3-methyl-1-(2-trimethylsilylethoxymethyl)pyrazol-4-yl]anilino]-2-oxo-ethyl]-2-methyl-pyrazole-3-carboxamide

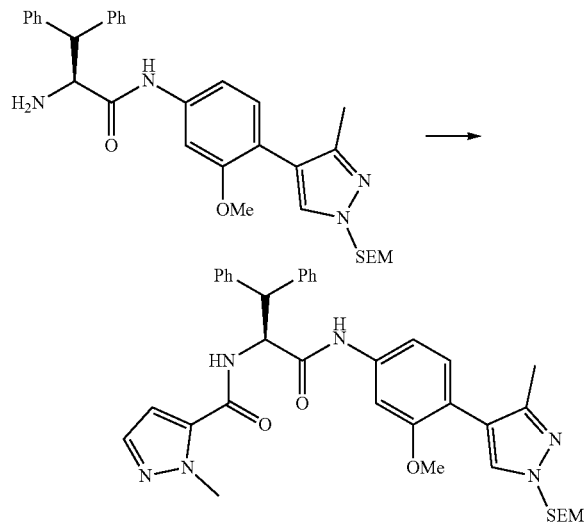

The amine of Preparation 270 was reacted with 2-methylpyrazole-3-carboxylic acid according to the method of Preparation 5 to give the title compound (53 mg, 74%) as a mixture of SEM regioisomers. 1H NMR (300 MHz, DMSO-d6) δ 10.26 (s, 1H), 8.84 (d, J=8.8 Hz, 1H), 7.78 (s, 0.67H), 7.52-7.38 (m, 4.33H), 7.37 (d, J=2.0 Hz, 1H), 7.31-7.20 (m, 4H), 7.19-6.99 (m, 5H), 6.76 (d, J=2.1 Hz, 1H), 5.62 (dd, J=11.7, 8.8 Hz, 1H), 5.38 (s, 0.67H), 5.29 (s, 1.33H), 4.63 (d, J=11.7 Hz, 1H), 3.90 (s, 3H), 3.69 (s, 2H), 3.67 (s, 1H), 3.61-3.48 (m, 2H), 2.18 (s, 1H), 2.10 (s, 2H), 0.93-0.76 (m, 2H), −0.04 (s, 6H), −0.05 (s, 3H); LCMS (METHOD 3) (ES): m/z 665.6 [M+H]⁺, RT=0.91 and 0.92 min.

Preparation 272

4-[3-Methyl-1-(2-trimethylsilylethoxymethyl)pyrazol-4-yl]aniline

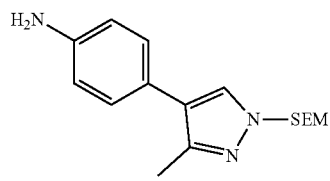 [SMILES: Cc1nn(COCC[Si](C)(C)C)cc1-c1ccc(N)cc1]

The title compound (1.07 g) was prepared, as a 2:1 mixture of SEM regioisomers, according to the methods of Preparations 267-268 from 1-bromo-4-nitro-benzene. 1H NMR (600 MHz, DMSO-d6) δ 7.82 (s, 0.67H), 7.49 (s, 0.33H), 7.13-7.01 (m, 2H), 6.65-6.53 (m, 2H), 5.39 (s, 0.67H), 5.28 (s, 1.33H), 5.04 (s, 0.67H), 5.03 (s, 1.33H), 3.53 (m, 2H), 2.34 (s, 1H), 2.24 (s, 2H), 0.92-0.75 (m, 2H), −0.04 (s, 6H), −0.05 (s, 3H).LCMS (METHOD 3) (ES): m/z 304.3 [M+H]⁺, RT=0.78 and 0.80 min.

Preparation 273

(2S)-2-Amino-3,3-dicyclopropyl-N-[4-(3,5-dimethyl-1H-pyrazol-4-yl)phenyl]propenamide dihydrochloride

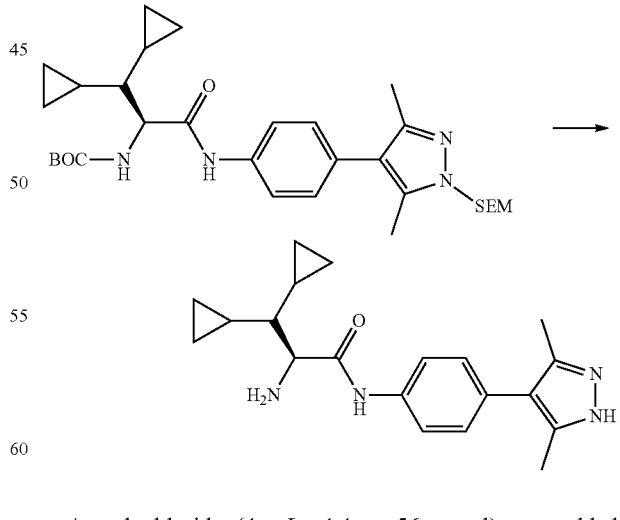

Acetyl chloride (4 mL, 4.4 g, 56 mmol) was added dropwise to MeOH (50 mL) cooled in an ice-bath. The mixture was stirred for 5 minutes and then added to the compound of Preparation 4 (7.95 g, 14.0 mmol). The mixture was stirred at 40° C. for 24 hours then concentrated in vacuo to give the title compound (assumed quantitative yield) as an off-white solid. LCMS (METHOD 3) (ES): m/z 339.4 [M+H]⁺, RT=0.55 min.

Preparation 274

2-[[4-(2-Fluoro-4-nitro-phenyl)-3,5-dimethyl-pyrazol-1-yl]methoxy]ethyl-trimethyl-silane

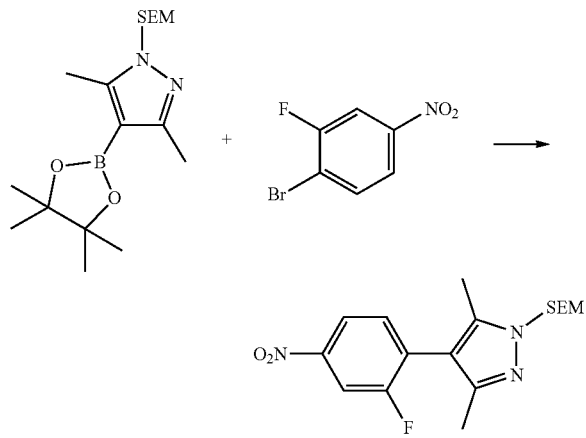

A solution of K₂CO₃ (1.256 g, 9.09 mmol) in water (4.5 mL) and Pd(dppf)Cl₂ (186 mg, 0.227 mmol) were added to a mixture of 4-bromo-3-fluoronitrobenzene (1.0 g, 4.55 mmol) and 2-[[3,5-dimethyl-4-(4,4,5,5-tetramethyl-1,3,2-dioxaborolan-2-yl)pyrazol-1-yl]methoxy]ethyl-trimethyl-silane (WO 2008001076, R. P. Alexander et al.) (2.08 g, 5.90 mmol) in THF (9 mL) and MeOH (1.6 mL) in a 20 mL microwave vial. The mixture was degassed by bubbling argon through it for 10 min, then the vial was capped and stirred for 1 hour at 90° C. After cooling to room temperature, the reaction mixture was poured into EtOAc (50 mL), washed with water (2×50 mL) and brine (20 mL), dried (MgSO₄), filtered and concentrated in vacuo. Purification by column chromatography (silica, eluting with 0-50% EtOAc in heptane) gave the title compound (1.58 g, 95%). 1H NMR (400 MHz, DMSO-d6) δ 8.25 (dd, J=9.8, 2.3 Hz, 1H), 8.18 (dd, J=8.9, 2.5 Hz, 1H), 7.67 (dd, J=8.5, 7.5 Hz, 1H), 5.43 (s, 2H), 3.62 (dd, J=8.4, 7.4 Hz, 2H), 2.26 (d, J=1.3 Hz, 3H), 2.14 (d, J=1.1 Hz, 3H), 0.88 (dd, J=8.4, 7.4 Hz, 2H), -0.00 (s, 9H); LCMS (METHOD 3) (ES): m/z 366.3 [M+H]⁺, RT=0.95 min.

Preparation 275

4-[3,5-Dimethyl-1-(2-trimethylsilylethoxymethyl)pyrazol-4-yl]-3-fluoro-aniline

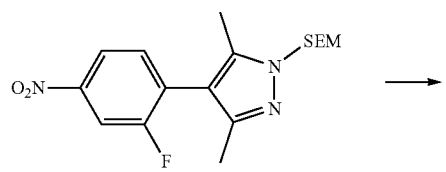

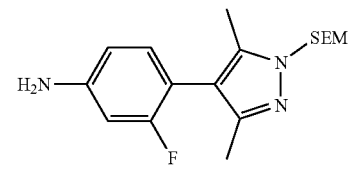

The nitro compound of Preparation 274 (1.58 g, 4.32 mmol) was dissolved in MeOH (20 mL) and the flask was flushed with argon. 10% Pd/C (50 mg) was added, the flask was flushed with argon and evacuated. The flask was equipped with a H₂ balloon and the reaction was stirred for 1 hour at room temperature. The reaction mixture was filtered through a plug of silica and the filtrate was evaporated to dryness to give the title compound (1.32 g, 91%). 1H NMR (400 MHz, DMSO-d6) δ 6.90 (t, J=8.5 Hz, 1H), 6.62-6.33 (m, 2H), 5.44 (s, 2H), 5.35 (s, 2H), 3.59 (t, J=7.8 Hz, 2H), 2.17 (s, 3H), 2.05 (s, 3H), 0.87 (t, J=7.9 Hz, 2H), -0.00 (s, 9H); 1H NMR (400 MHz, DMSO-d6) δ 6.90 (t, J=8.5 Hz, 1H), 6.62-6.33 (m, 2H), 5.44 (s, 2H), 5.35 (s, 2H), 3.59 (t, J=7.8 Hz, 2H), 2.17 (s, 3H), 2.05 (s, 3H), 0.87 (t, J=7.9 Hz, 2H), -0.00 (s, 9H); LCMS (METHOD 3) (ES): m/z 336.4 [M+H]⁺, RT=0.83 min.

Preparation 276

Tert-butyl N-[(1S)-1-(dicyclopropylmethyl)-2-[4-[3,5-dimethyl-1-(2-trimethylsilylethoxymethyl)pyrazol-4-yl]-3-fluoro-anilino]-2-oxo-ethyl]carbamate

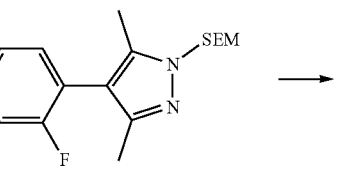

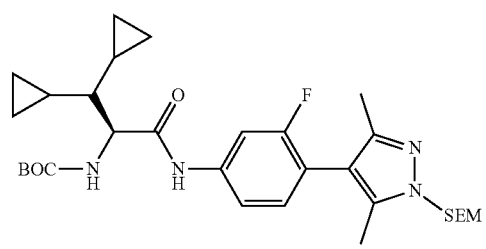

According to the method of Preparation 3 the aniline of Preparation 275 was reacted with the acid of Preparation 52 to give the title compound (88 mg, 40%). LCMS (METHOD 3) (ES): m/z 587.6 [M+H]⁺, RT=1.02 min.

Preparation 277

(2S)-2-Amino-3,3-dicyclopropyl-N-[4-(3,5-dimethyl-1H-pyrazol-4-yl)-3-fluorophenyl]propenamide dihydrochloride

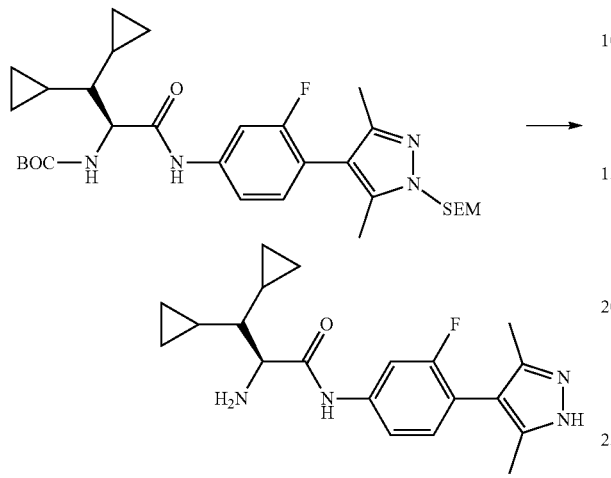

The Boc protected compound of Preparation 276 was treated according to the method of Preparation 273 to give the title compound. LCMS (METHOD 3) (ES): m/z 357.3 [M+H]$^+$, RT=0.50 min.

Preparation 278

Tert-butyl (S)-(1,1-dicyclopropyl-3-((4-iodophenyl)amino)-3-oxopropan-2-yl)carbamate

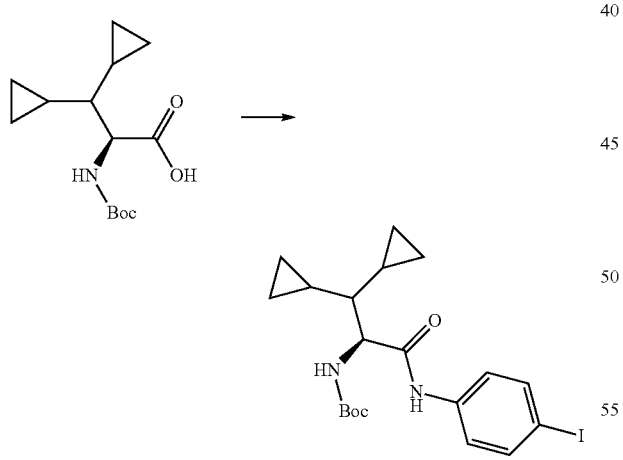

To a stirred solution of the acid of Preparation 52 (500 mg, 1.85 mmol) in DMF (10 mL) was added HATU (1.05 g, 2.78 mmol), 4-iodoaniline (405 mg, 1.85 mmol) and DIPEA (1.0 mL, 5.57 mmol) at 0° C. The Resulting reaction mixture was stirred at room temperature for 4 hours. The reaction mixture was diluted with water (20 mL) and stirred for 20 min. The precipitated solid was filtered, washed with water (20 mL) and dried under reduced pressure to afford the title compound (500 mg, 85%) as an off white solid. 1H NMR (400 MHz, Chloroform-d) δ 8.02 (br s, 1H), 7.62-7.60 (d, J=8 Hz, 2H), 7.31-7.29 (d, J=8 Hz, 2H), 5.37 (br s, 1H), 4.38-4.34 (m, 1H), 1.46 (s, 9H) 0.94-0.88 (m, 1H), 0.79-0.71 (m, 2H), 0.57-0.39 (m, 4H), 0.32-0.14 (m, 4H); LCMS (METHOD 5) (ESI): m/z: 471 [M+H$^+$]; RT=2.86 min (ACQUITY UPLC BEH C18 column, 0.1% FA in water with MeCN).

Preparation 279

(S)-2-Amino-3,3-dicyclopropyl-N-(4-iodophenyl)propanamide hydrochloride

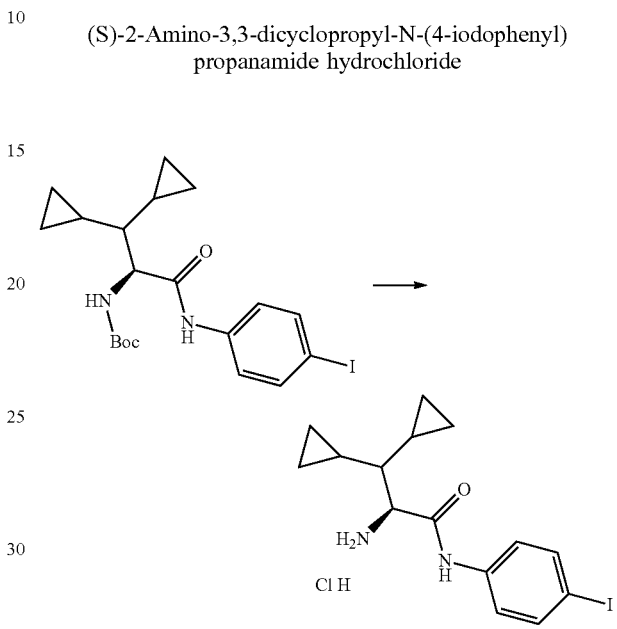

To a stirred solution of the amide of Preparation 278 (500 mg, 1.063 mmol) in methanol (20 mL) was added 4M HCl in 1,4-dioxane (20 mL) at 0° C. The Resulting reaction mixture was stirred at room temperature for 3 hours, then concentrated under reduced pressure and dried to afford the title compound (500 mg, crude) as an off white solid. This compound was used as such for the next step without further purification. 1H NMR (400 MHz, Chloroform-d) δ 10.17 (br s, 1H), 8.28 (br s, 3H), 7.51-7.50 (d, J=8 Hz, 2H), 7.33-7.31 (d, J=8 Hz, 2H), 4.68-4.64 (m, 1H), 0.76 (br s, 3H), 0.46-0.177 (m, 8H); LCMS (METHOD 5) (ESI): m/z: 371 [M+H$^+$]; RT=3.32 min; (ACQUITY UPLC BEH C18 column, 0.1% FA in water with MeCN).

Preparation 280

(S)—N-(1,1-dicyclopropyl-3-((4-iodophenyl)amino)-3-oxopropan-2-yl)-1-isopropyl-1H-pyrazole-5-carboxamide

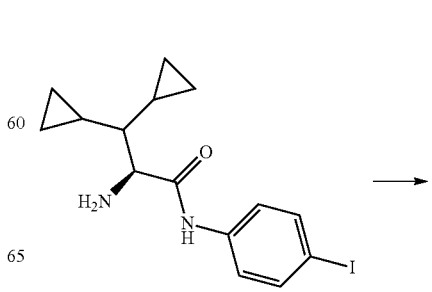

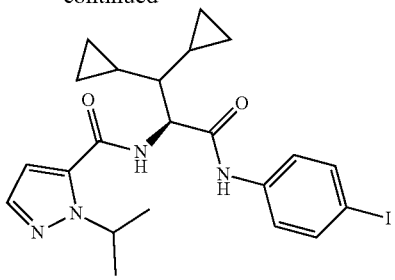

To a stirred solution of the amine of Preparation 279 (500 mg, 1.23 mmol) in DMF (10 mL) was added HATU (701 mg, 1.84 mmol), 1-isopropyl-1H-pyrazole-5-carboxylic acid (189 mg, 1.23 mmol) and DIPEA (0.858 mL, 4.92 mmol) at 0° C. The resulting reaction mixture was stirred at room temperature for 16 hours then diluted with water (20 mL) and stirred for 20 min. The precipitated solid was filtered and washed with water (10 mL) then dried under reduced pressure to give the title compound (400 mg, 64%) as an off white solid. 1H NMR (400 MHz, Chloroform-d) δ 7.89 (br s, 1H), 7.64-7.62 (d, J=8 Hz, 2H), 7.31-7.29 (d, J=8 Hz, 2H), 7.522-7.627 (d, J=2.0 Hz, 1H), 7.04-7.02 (d, 7.6 Hz, 1H), 6.554-6.549 (d, 3=2 Hz, 1H), 5.49-5.43 (m, 1H), 4.77-4.74 (m, 1H), 1.51-1.48 (m, 6H), 0.92-0.79 (m, 3H), 0.66-0.61 (m, 1H), 0.56-0.48 (m, 3H), 0.38-0.34 (m, 2H), 0.28-0.22 (m, 2H); LCMS (METHOD 5) (ESI): m/z: 507 [M+H⁺]; RT=2.73 min (ACQUITY UPLC BEH C18 column, 0.1% FA in water with MeCN).

Preparation 281

(S)—N-(1,1-dicyclopropyl-3-oxo-3-((4-(4,4,5,5-tetramethyl-1,3,2-dioxaborolan-2-yl)phenyl)amino)propan-2-yl)-1-isopropyl-1H-pyrazole-5-carboxamide

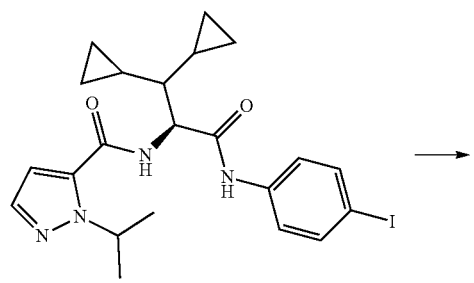

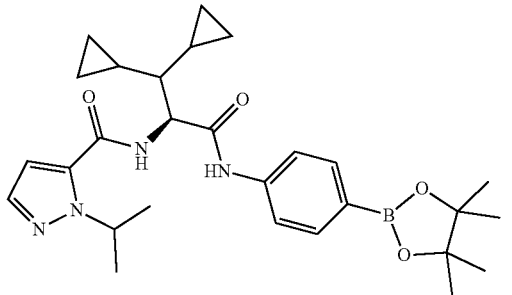

To a stirred solution of the iodide of Preparation 280 (1.8 g, 3.55 mmol), in 1,4-dioxane (36 mL) in a sealed tube was added bis(pinacolato)diboron (2.7 g, 10.7 mmol) and KOAc (1.57 g, 16.0 mmol) under an inert atmosphere. The resulting reaction mixture was purged with Argon gas for 20 min, then Pd(dppf)Cl₂.DCM (464 mg, 0.569 mmol) was added and the mixture was heated at 110° C. for 16 hours. The reaction was cooled to room temperature and diluted with ice cold water (100 mL). The compound was extracted with EtOAc (3×70 mL). The combined organics were washed with water (100 mL), brine (100 mL), dried over anhydrous Na₂SO₄, filtered and concentrated under reduced pressure to afford the title compound (1.8 g, crude) as a brown oil. 1H NMR (400 MHz, Chloroform-d) δ 7.95 (br s, 1H), 7.81-7.77 (m, 2H), 7.54-7.48 (m, 3H), 7.10-7.08 (d, J=8 Hz 1H), 6.568-6.563 (d, J=2.0 Hz, 1H), 5.48-5.45 (m, 1H), 4.85-4.75 (m, 1H), 1.348-1.337 (d, J=4.4 Hz, 6H), 1.28 (s, 12H), 0.90-0.83 (m, 3H), 0.54-0.51 (m, 4H), 0.42-0.23 (m, 4H); LCMS (METHOD 5) (ESI): m/z: 505 [M−H]; RT=4.00 min (ACQUITY UPLC BEH C18 column, 0.1% FA in water with MeCN).

Preparation 282

5-Bromo-4-isopropyl-1H-imidazole

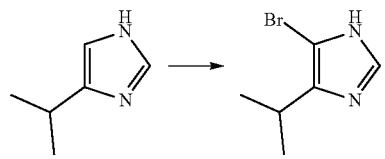

To a stirred solution of 4-isopropyl-1H-imidazole (700 mg, 6.36 mmol) in DMF, was added NBS (1.13 g, 6.36 mmol) at 0° C. The resulting reaction mixture was stirred at 0° C. for 15 min. The reaction mixture was diluted with water (100 mL) and extracted with EtOAc (2×50 mL). The combined organic layers were washed with water (3×50 mL), brine (50 mL), dried over anhydrous Na₂SO₄, filtered and concentrated under reduced pressure. The obtained crude compound was purified by silica gel (100-200 mesh) column chromatography (30% EtOAc in hexane as eluent) to afford the title compound (300 mg, 24%) as pale brown solid. 1H NMR (400 MHz, Chloroform-d) δ 7.501 (s, 1H), 3.15-3.08 (m, 1H), 1.29-1.27 (d, J=8 Hz 6H); LCMS (METHOD 5) (ESI): m/z: 188 [M]; RT=2.92 min (ACQUITY UPLC BEH C18 column, 0.1% FA in water with MeCN).

Preparation 283A and B

5-Bromo-4-isopropyl-1-methyl-1H-imidazole (Prep. 283A) and 4-bromo-5-isopropyl-1-methyl-1H-imidazole (Prep. 283B)

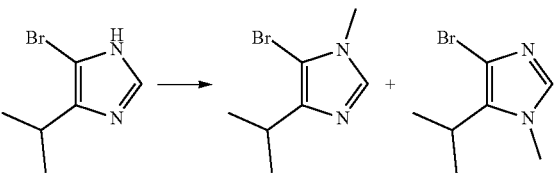

To a stirred solution of the compound of Preparation 282 (100 mg, 0.52 mmol) in DMF, was added K₂CO₃ (109 mg, 0.79 mmol), followed by MeI (0.042 mL, 0.68 mmol) at 0° C. The resulting reaction mixture was stirred at room temperature for 16 hours then diluted with water (100 mL) and extracted with EtOAc (2×50 mL). The combined organic layers were washed with water (3×50 mL), brine (50 mL), dried over anhydrous $Na_2SO_4$, filtered and concentrated under reduced pressure. The crude product was purified by silica gel column chromatography to afford 5-bromo-4-isopropyl-1-methyl-1H-imidazole, (25 mg, 23%) and 4-bromo-5-isopropyl-1-methyl-1H-imidazole (15 mg, 14%) as pale yellow liquids. Prep. 283A: 1H NMR (400 MHz, Chloroform-d) δ 7.61 (s, 1H), 3.52 (s, 3H), 2.85-2.78 (m, 1H), 1.14-1.12 (d, J=8 Hz, 6H); LCMS (METHOD 5) (ESI): m/z: 202 [M]; RT=1.15 min (ACQUITY UPLC BEH C18 column, 0.1% FA in water with MeCN).

Prep. 283B: 1H NMR (400 MHz, Chloroform-d) δ 7.47 (s, 1H), 3.59 (s, 3H), 2.85-2.78 (m, 1H), 1.14-1.12 (d, J=8 Hz, 6H); LCMS (METHOD 5) (ESI): m/z: 202 [M]; RT=1.32 min (ACQUITY UPLC BEH C18 column, 0.1% FA in water with MeCN).

Preparation 284

5-Bromo-4-cyclopropyl-1H-imidazole

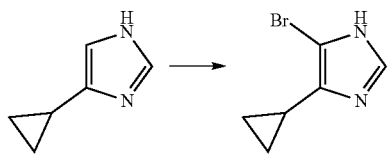 [SMILES: c1nc(C2CC2)c[nH]1 ; Brc1[nH]cnc1C1CC1]

The title compound was prepared according to the method of Preparation 282 from 4-cyclopropyl-1H-imidazole and was isolated as a pale yellow solid (1.2 g, 87%). 1H NMR (400 MHz, DMSO-d6) δ 12.01 (br s, 1H), 7.43 (s, 1H), 1.84-1.74 (m, 1H), 0.97-0.95 (m, 2H), 0.78-0.74 (m, 2H); LCMS (METHOD 5) (ESI): m/z: 188 [M+H⁺]; RT=1.09 min (ACQUITY UPLC BEH C18 column, 0.1% FA in water with MeCN).

Preparation 285A and B

5-Bromo-4-cyclopropyl-1-methyl-1H-imidazole (Prep. 285A) and 4-bromo-5-cyclopropyl-1-methyl-1H-imidazole (Prep. 285B)

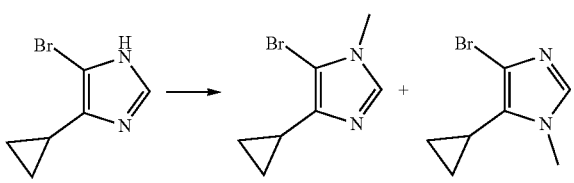

The title compound was prepared from the imidazole of Preparation 284 according to the method of Preparation 283 to give 5-bromo-4-cyclopropyl-1-methyl-1H-imidazole (40 mg, 3%) and 4-bromo-5-cyclopropyl-1-methyl-1H-imidazole (40 mg, 3%) as off white solids. Prep. 285A: 1H NMR (400 MHz, DMSO-d6) δ 7.63 (s, 1H), 3.51 (s, 3H), 1.73-1.68 (m, 1H), 0.80-0.76 (m, 2H), 0.70-0.67 (m, 2H); LCMS (METHOD 5) (ESI): m/z: 201 [M+H⁺]; RT=1.08 min (ACQUITY UPLC BEH C18 column, 0.1% FA in water with MeCN).

Prep. 285B: 1H NMR (400 MHz, DMSO-d6) δ 7.53 (s, 1H), 3.62 (s, 3H), 1.64-1.57 (m, 1H), 0.94-0.89 (m, 2H), 0.72-0.68 (m, 2H); LCMS (METHOD 5) (ESI): m/z: 201 [M+H⁺]; RT=1.33 min (ACQUITY UPLC BEH C18 column, 0.1% FA in water with MeCN).

Preparation 286

5-Bromo-4-cyclopropyl-1-((2-(trimethylsilyl)ethoxy)methyl)-1H-imidazole and 4-bromo-5-cyclopropyl-1-((2-(trimethylsilyl)ethoxy)methyl)-1H-imidazole

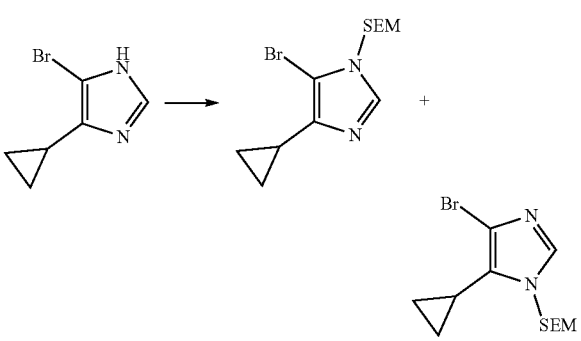

To a stirred solution of the imidazole of Preparation 285A (100 mg, 0.52 mmol) in DMF (1 mL) was added 60% NaH (15 mg, 0.63 mmol) followed by SEM-Cl (0.1 mL, 0.58 mmol) at 0° C. The resulting reaction mixture was stirred at 0° C. for 2 hours, then poured into ice cold water (100 mL) and extracted with EtOAc (2×50 mL). The combined organic layers were washed with water (2×30 mL), brine (30 mL), dried over anhydrous $Na_2SO_4$ and concentrated under reduced pressure. The obtained crude compound was purified by silica gel (100-200 mesh) column chromatography (10%-20% EtOAc in pet ether as eluent) to afford a mixture of the title compounds (120 mg, 75%) as a yellow liquid. 1H NMR (400 MHz, Chloroform-d) δ 7.54 (s, 0.65H), 7.41 (s, 0.35H), 5.30 (s, 0.5H).5.22 (s, 1.5H), 3.63-3.59 (m, 1H), 3.54-3.48 (m, 2H), 0.96-0.84 (m, 4H), −0.003 (s, 9H); LCMS (METHOD 5) (ESI): m/z: 317 [M+H⁺]; RT=2.56 min and 2.69 min; (ACQUITY BEH C18 column, 0.05% FA in water with MeCN).

Preparation 287

5-Bromo-4-isopropyl-1-((2-(trimethylsilyl)ethoxy)methyl)-1H-imidazole and 4-bromo-5-isopropyl-1-((2-(trimethylsilyl)ethoxy)methyl)-1H-imidazole

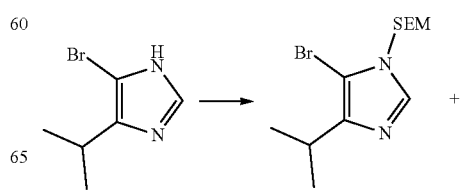

-continued

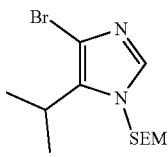

The title compounds were prepared, as a brown liquid (90 mg) according to the method of Preparation 286 from the imidazole of Preparation 282. 1H NMR (400 MHz, Chloroform-d) δ 7.64 (s, 0.55H), 7.35 (s, 0.45H), 5.25 (s, 1.25H), 5.22 (s, 0.75H), 3.56-3.52 (m, 1H), 3.49-3.45 (m, 1H), 3.23-3.12 (m, 0.42H), 3.05-2.90 (m, 0.58H), 1.281-1.277 (d, J=1.6 Hz, 3H), 1.277-1.273 (d, J=1.6 Hz, 3H), 0.94-0.89 (m, 2H), 0.013 (s, 9H); LCMS (METHOD 5) (ESI): m/z: 319 [M+H$^+$]; RT=2.79 min and 2.56 min; (ACQUITY BEH C18 column, 0.05% FA in water with MeCN).

Preparation 288

5-Bromo-4-methyl-1-((2-(trimethylsilyl)ethoxy)methyl)-1H-imidazole and 4-bromo-5-methyl-1-((2-(trimethylsilyl)ethoxy)methyl)-1H-imidazole

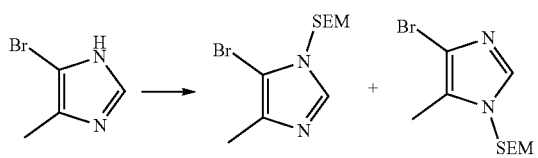

The title compounds were prepared, as a pale yellow liquid (1.0 g, 56%) according to the method of Preparation 286 from 5-bromo-4-methyl-1H-imidazole. 1H NMR (400 MHz, Chloroform-d) δ 7.60, 7.41 (s, 1H), 5.22, 5.18 (s, 1H), 5.10 (s, 1H), 3.53-3.44 (m, 2H), 2.23, 2.20 (s, 3H), 0.92-0.87 (m, 2H), 0.019, 0.008 (s, 9H); LCMS (METHOD 5) (ESI): m/z: 291 [M+H$^+$]; RT=3.83 min (ACQUITY BEH C18 column, 0.05% FA in water with MeCN).

Preparation 289

4-Bromo-3-cyclopropyl-5-methyl-1-((2-(trimethylsilyl)ethoxy)methyl)-1H-pyrazole and 4-bromo-5-cyclopropyl-3-methyl-1-((2-(trimethylsilyl)ethoxy)methyl)-1H-pyrazole

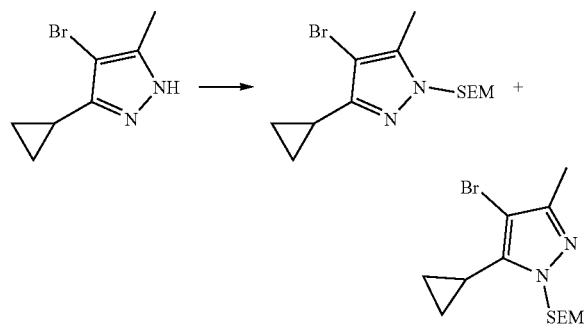

The title compounds were prepared, as a pale yellow liquid (140 mg, 54%) according to the method of Preparation 286 from 4-bromo-3-cyclopropyl-5-methyl-1H-pyrazole. 1H NMR (400 MHz, Chloroform-d) δ 5.43 and 5.29 (2×s, 2H), 3.69-3.56 and 3.52-3.48 (2×m, 2H), 2.29 and 2.19 (2×s, 3H), 1.84-1.71 (m, 2H), 0.97-0.84 (m, 6H), −0.018 (s, 9H); LCMS (METHOD 5) (ESI): m/z: 331 [M+H$^+$]; RT=3.06 min and 3.09 min; (ACQUITY BEH C18 column, 0.05% FA in water with MeCN).

Preparation 290

4-Bromo-3-isopropyl-5-methyl-1-((2-(trimethylsilyl)ethoxy)methyl)-1H-pyrazole and 4-bromo-5-isopropyl-3-methyl-1-((2-(trimethylsilyl)ethoxy)methyl)-1H-pyrazole

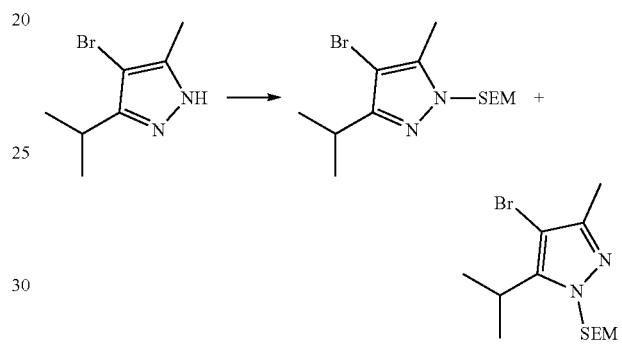

The title compounds were prepared, as a pale yellow liquid (130 mg, 54%) according to the method of Preparation 286 from 4-bromo-3-isopropyl-5-methyl-1H-pyrazole. 1H NMR (400 MHz, Chloroform-d) δ 5.35 (s, 0.7H), 5.34 (s, 1.3H), 3.54-3.49 (m, 2H), 3.33-3.22 (m, 0.3H), 3.15-2.95 (m, 0.7H), 2.29 (s, 2H), 2.19 (s, 1H), 1.37-1.36 (d, J=4 Hz, 3H), 1.267-1.256 (d, 3=4 Hz, 3H), 0.90-0.84 (m, 2H), −0.042 (s, 9H).

Preparation 291

5-Bromo-4-methyl-1-((2-(trimethylsilyl)ethoxy)methyl)-1H-pyrazole and 3-bromo-4-methyl-1-((2-(trimethylsilyl)ethoxy)methyl)-1H-pyrazole

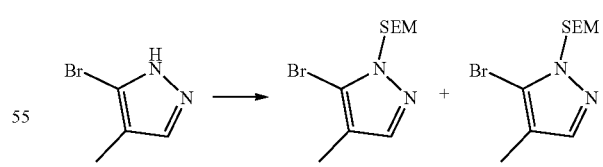

The title compounds were prepared as a pale yellow liquid (500 mg, 54%) according to the method of Preparation 286 from 5-bromo-4-methyl-1H-pyrazole. 1H NMR (400 MHz, Chloroform-d) δ 7.40 (s, 0.3H), 7.28 (s, 0.7H), 5.44 (s, 0.7H), 5.30 (s, 1.3H), 3.60-3.53 (m, 2H), 2.02 (s, 3H), 0.92-0.87 (m, 2H), −0.028 (s, 9H); LCMS (METHOD 5) (ESI): m/z: 291 [M+H$^+$]; RT=5.25 min and 5.32 min; (ACQUITY BEH C18 column, 0.05% FA in water with MeCN).

Preparation 292

(S)—N-(1,1-dicyclopropyl-3-((4-(4-isopropyl-1-((2-(trimethylsilyl)ethoxy)methyl)-1H-imidazol-5-yl)phenyl)amino)-3-oxopropan-2-yl)-1-isopropyl-1H-pyrazole-5-carboxamide and (S)—N-(1,1-dicyclopropyl-3-((4-(5-isopropyl-1-((2-(trimethylsilyl)ethoxy)methyl)-1H-imidazol-4-yl)phenyl)amino)-3-oxopropan-2-yl)-1-isopropyl-1H-pyrazole-5-carboxamide

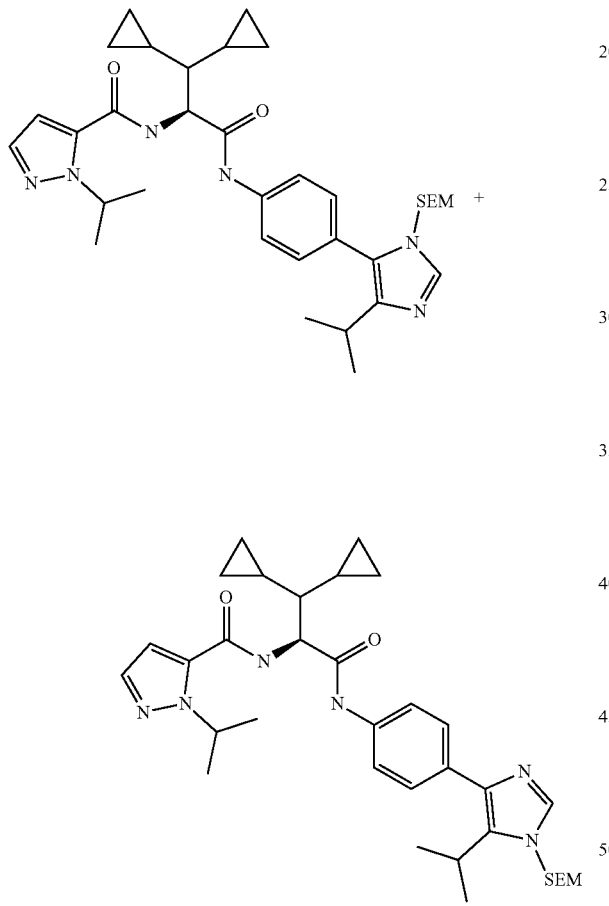

To a stirred solution of the boronic ester of Preparation 281 (119 mg, 0.235 mmol) and the bromides of Preparation 287 (50 mg, 0.157 mmol, mixture of isomers) in 1,4-dioxane (5 mL) and H₂O (1 mL), was added Na₂CO₃ (50 mg, 0.471 mmol) at room temperature. The resulting reaction mixture was purged with argon for 15 min, Pd(dppf)Cl₂·CH₂Cl₂ was added and the mixture was heated at 120° C. for 16 hours. The reaction mixture was filtered through a Celite pad and washed with EtOAc (50 mL). The organic layer was separated, dried over dry Na₂SO₄, filtered and concentrated under reduced pressure to give a mixture of the title compounds (50 mg, crude) as a black oil. LCMS (METHOD 5) (ESI): m/z: 619 [M+H⁺]; RT=4.78 min (ACQUITY BEH C18 column, 0.01% FA in water with MeCN).

Preparation 293

(S)—N-(1,1-dicyclopropyl-3-((4-(4-cyclopropyl-1-((2-(trimethylsilyl)ethoxy)methyl)-1H-imidazol-5-yl)phenyl)amino)-3-oxopropan-2-yl)-1-isopropyl-1H-pyrazole-5-carboxamide and (S)—N-(1,1-dicyclopropyl-3-((4-(5-cyclopropyl-1-((2-(trimethylsilyl)ethoxy)methyl)-1H-imidazol-4-yl)phenyl)amino)-3-oxopropan-2-yl)-1-isopropyl-1H-pyrazole-5-carboxamide

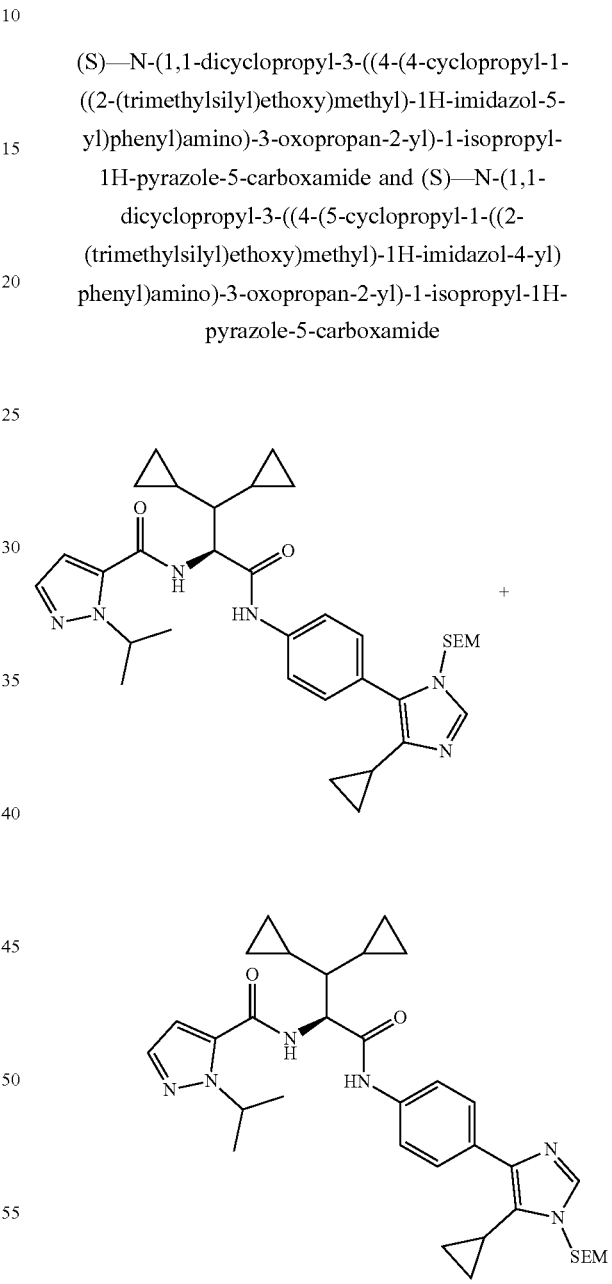

The title compounds were prepared according to the method of Preparation 292 using the boronic ester of Preparation 281 and the bromides of Preparation 286. LCMS (METHOD 5) (ESI): m/z: 617 [M+H⁺]; RT=1.96 min (ACQUITY UPLC BEH C18 column, 0.05% FA in water with MeCN).

Preparation 294

(S)—N-(1,1-dicyclopropyl-3-((4-(4-methyl-1-((2-(trimethylsilyl)ethoxy)methyl)-1H-pyrazol-5-yl)phenyl)amino)-3-oxopropan-2-yl)-1-isopropyl-1H-pyrazole-5-carboxamide and (S)—N-(1,1-dicyclopropyl-3-((4-(4-methyl-1-((2-(trimethylsilyl)ethoxy)methyl)-1H-pyrazol-3-yl)phenyl)amino)-3-oxopropan-2-yl)-1-isopropyl-1H-pyrazole-5-carboxamide

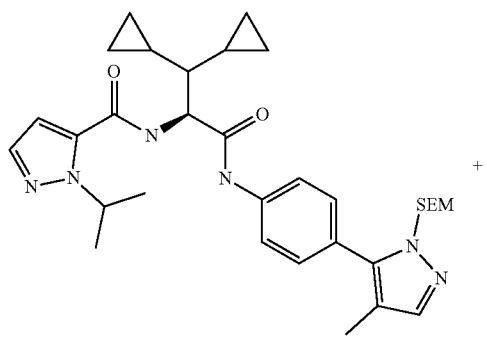

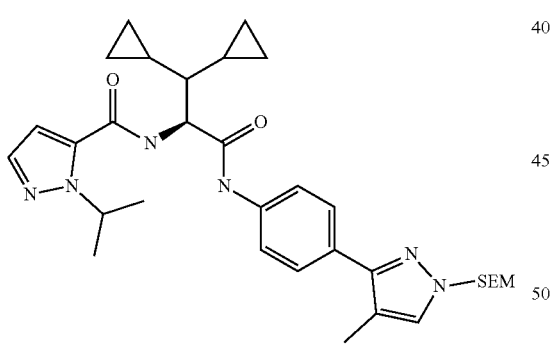

The title compounds were prepared according to the method of Preparation 292 using the boronic ester of Preparation 281 and the bromides of Preparation 291. 1H NMR (400 MHz, DMSO-d6) δ 10.19, 10.11 (s, 1H), 8.50-8.44 (m, 1H), 7.76-7.66 (m, 2H), 7.62-7.60 (d, J=8.0 Hz, 1H), 7.506-7.501 (d, J=2.0 Hz, 1H), 7.43-7.40 (m, 2H), 6.933-6.928 (d, J=2.0 Hz, 1H), 5.44-5.37 (m, 1H), 5.34, 5.25 (s, 2H), 4.83-4.79 (t, J=8.2 Hz, 1H), 3.57-3.47 (m, 2H), 2.18 (s, 1H), 1.98 (s, 2H), 1.39-1.37 (d, J=6.4 Hz, 3H), 1.35-1.33 (d J=6.4 Hz, 3H), 0.90-0.73 (m, 5H), 0.47-0.12 (m, 8H), −0.043, −0.07 (s, 9H), LCMS (METHOD 5) (ESI): m/z: 591 [M+H⁺]; RT=2.51 min (ACQUITY UPLC BEH C18 column, 0.05% FA in water with MeCN).

Preparation 295

S)—N-(1,1-dicyclopropyl-3-((4-(3-cyclopropyl-5-methyl-1-((2-(trimethylsilyl)ethoxy)methyl)-1H-pyrazol-4-yl)phenyl)amino)-3-oxopropan-2-yl)-1-isopropyl-1H-pyrazole-5-carboxamide and S)—N-(1,1-dicyclopropyl-3-((4-(5-cyclopropyl-3-methyl-1-((2-(trimethylsilyl)ethoxy) methyl)-1H-pyrazol-4-yl)phenyl)amino)-3-oxopropan-2-yl)-1-isopropyl-1H-pyrazole-5-carboxamide

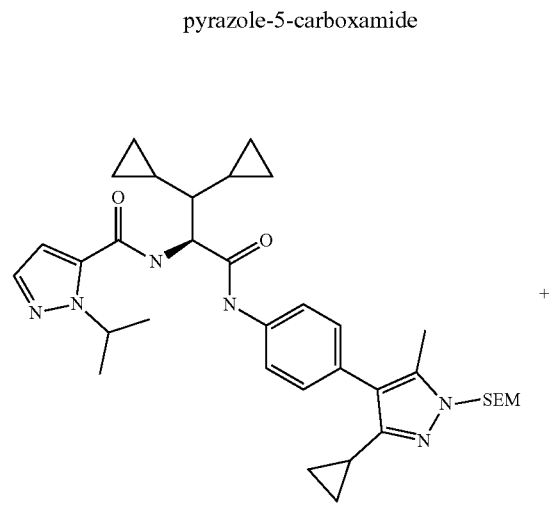

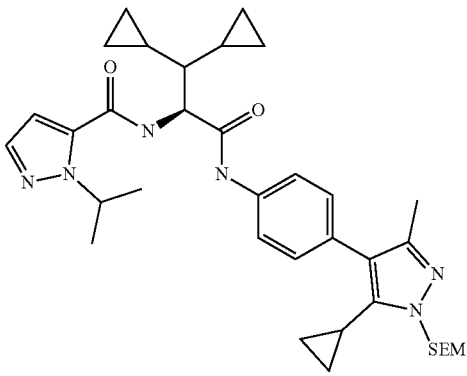

The title compounds were prepared according to the method of Preparation 292 using the boronic ester of Preparation 281 and the bromides of Preparation 289. LCMS (METHOD 5) (ESI): m/z: 631 [M+H⁺]; RT=2.60 min and 2.64 (ACQUITY UPLC BEH C18 column, 0.05% FA in water with MeCN).

Preparation 296

(S)—N-(1,1-dicyclopropyl-3-((4-(3-isopropyl-5-methyl-1-((2-(trimethylsilyl)ethoxy)methyl)-1H-pyrazol-4-yl)phenyl)amino)-3-oxopropan-2-yl)-1-isopropyl-1H-pyrazole-5-carboxamide and (S)—N-(1,1-dicyclopropyl-3-((4-(5-isopropyl-3-methyl-1-((2-(trimethylsilyl)ethoxy)methyl)-1H-pyrazol-4-yl)phenyl)amino)-3-oxopropan-2-yl)-1-isopropyl-1H-pyrazole-5-carboxamide

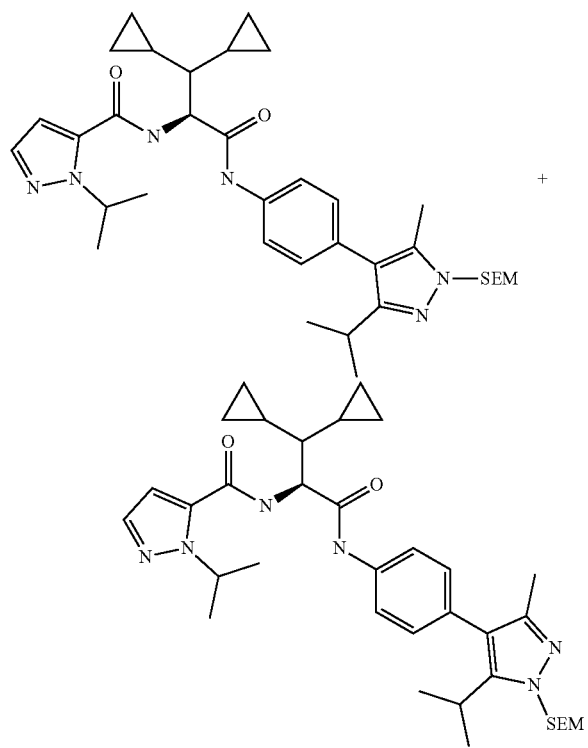

The title compounds were prepared according to the method of Preparation 292 using the boronic ester of Preparation 281 and the bromides of Preparation 290. LCMS (METHOD 5) (ESI): m/z: 633 [M+H$^+$]; RT=2.63 min and 2.65 min (ACQUITY UPLC BEH C18 column, 0.05% FA in water with MeCN).

Preparation 297

Tert-butyl (4-(4-methyl-1-((2-(trimethylsilyl)ethoxy)methyl)-1H-imidazol-5-yl)phenyl)carbamate and tert-butyl (4-(5-methyl-1-((2-(trimethylsilyl)ethoxy)methyl)-1H-imidazol-4-yl)phenyl)carbamate

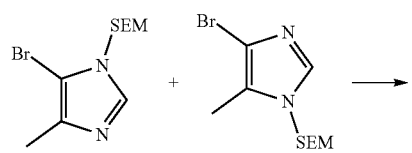

-continued

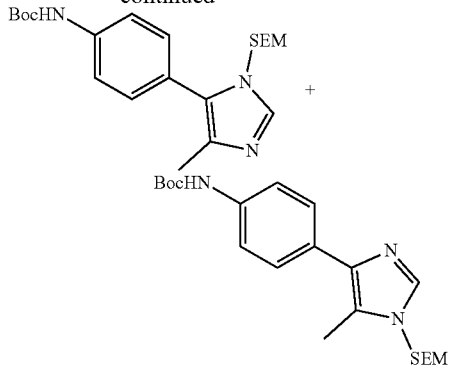

To a stirred solution of (4-((tert-butoxycarbonyl)amino)phenyl)boronic acid (100 mg, 0.344 mmol) and the bromides of Preparation 288 (98 mg, 0.41 mmol) in DMF (5 mL) and water (0.5 ml) was added K$_2$CO$_3$ (71 mg, 0.51 mmol) at room temperature. The resulting reaction mixture was purged with argon for 15 min and then Pd(dppf)Cl$_2$.CH$_2$Cl$_2$ (14 mg, 0.017 mmol) was added. The reaction mixture was heated at 110° C. for 16 hours then cooled to room temperature, diluted with water (20 mL) and extracted with EtOAc (2×30 mL). The combined organic layers were washed with water (20 mL) and brine (20 mL), dried over anhydrous Na$_2$SO$_4$, filtered and concentrated under reduced pressure to afford the title compounds (150 mg, crude) as a brown liquid. 1H NMR (400 MHz, Chloroform-d) δ 7.60-7.57 (d, J=8.0 Hz, 2H), 7.55 (s, 1H), 7.45-7.43 (d, J=8.0 Hz, 2H), 6.55, 6.48 (br s, 1H), 5.24, 5.19 (s, 2H), 3.53-3.44 (m, 2H), 2.43, 2.21 (s, 3H), 1.52 (s, 9H), 0.93-0.85 (m, 2H), −0.013 (s, 9H); LCMS (METHOD 5) (ESI): m/z: 404 [M+H$^+$]; RT=2.35 min (ACQUITY BEH C18 column, 0.05% FA in water with MeCN).

Preparation 298

4-(4-Methyl-1-((2-(trimethylsilyl)ethoxy)methyl)-1H-imidazol-5-yl)aniline hydrochloride and 4-(5-methyl-1-((2-(trimethylsilyl)ethoxy)methyl)-1H-imidazol-4-yl)aniline hydrochloride

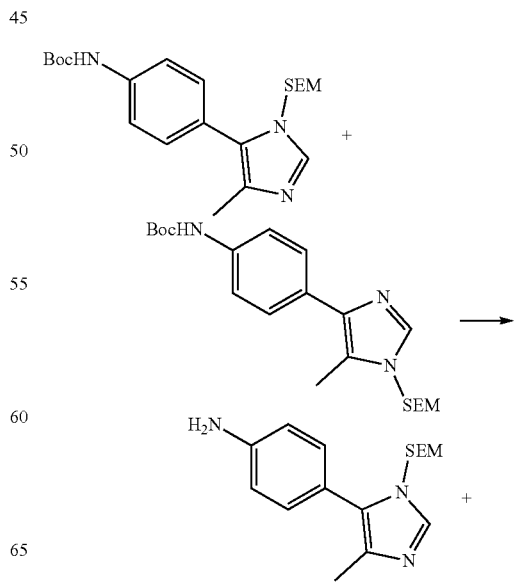

-continued

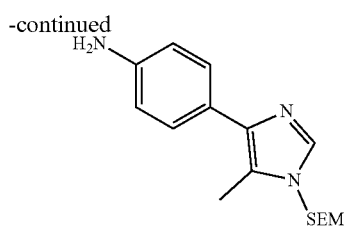

To a stirred solution of the compounds of Preparation 297 (50 mg, 0.10 mmol) in MeOH (1 mL) was added 4M HCl in 1,4-dioxane (1 mL) at 0° C. The resulting reaction mixture was stirred at room temperature for 30 min then concentrated under reduced pressure and dried give the title compounds (80 mg, crude) as a brown liquid. This was used as such for the next step without further purification. 1H NMR (300 MHz, Chloroform-d) δ 9.36-9.34 (d, J=8.8 Hz, 1H), 7.55-7.48 (m, 2H), 7.36-7.33 (d, J=8.1 Hz, 1H) 7.12-7.09, 7.03-7.00 (d, J=8.4 Hz, 2H), 5.59, 5.39 (s, 1H), 3.63-3.46 (m, 2H), 2.43, 2.24 (s, 3H), 0.93-0.78 (m, 2H), −0.01, −0.04 (s, 9H); LCMS (METHOD 5) (ESI): m/z: 304 [M+H$^+$]; RT=1.60 min & 1.66 min; (ACQUITY BEH C18 column, 0.1% FA in water with MeCN).

Preparation 299

Tert-butyl (4-(3-cyclopropyl-5-methyl-1-((2-(trimethylsilyl)ethoxy)methyl)-1H-pyrazol-4-yl)phenyl)carbamate

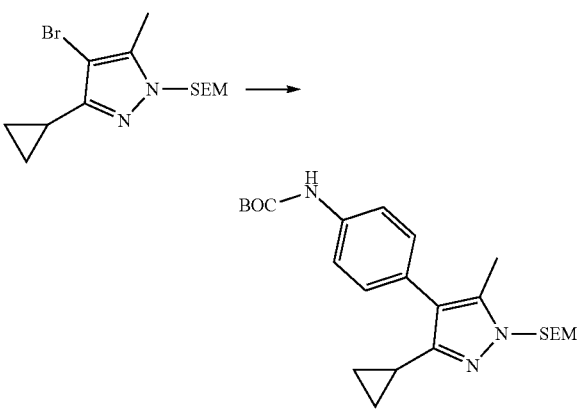

Na$_2$CO$_3$ (626 mg, 5.90 mmol) was added to a stirred solution of the bromides of Preparation 289 (650 mg, 1.96 mmol) and (4-((tert-butoxycarbonyl)amino)phenyl)-boronic acid (513 mg, 2.16 mmol) in 1,4-dioxane and H$_2$O (9:1), at room temperature. The resulting reaction mixture was purged with argon for 15 min, followed by addition of Pd(dppf)Cl$_2$.CH$_2$Cl$_2$. The reaction mixture was heated to 100° C. for 16 h. The reaction mixture was filtered through a Celite pad and washed with EtOAc (50 mL). The organic layer was separated, dried over dry Na$_2$SO$_4$, filtered and concentrated under reduced pressure to afford of crude residue. The crude residue was purified by silica gel (100-200 mesh) column chromatography (5%-10% EtOAc in hexanes) to afford the title compound as a mixture of regio-isomers (320 mg, 36%) as a light brown solid. $^1$H NMR (300 MHz, DMSO-d$_6$) δ 9.37 (br s, 1H), 7.50 (br d, J=4.77 Hz, 2H), 7.20 (br dd, J=14.12, 8.62 Hz, 2H), 5.24- 5.45 (m, 2H), 3.47-3.67 (m, 2H), 2.56 (br d, J=2.57 Hz, 3H), 2.21 (s, 1H), 1.48 (s, 9H), 0.69-0.90 (m, 6H), −0.08-0.05 (m, 9H); LCMS (METHOD 5) (ESI): m/z: 444 [M+H$^+$]; 43% and 47%; RT=6.0 min and 6.13 min (ACQUITY BEH C18 column, 0.1% FA in water with MeCN).

Preparation 300

4-(3-Cyclopropyl-5-methyl-1-((2-(trimethylsilyl)ethoxy)methyl)-1H-pyrazol-4-yl)aniline hydrochloride

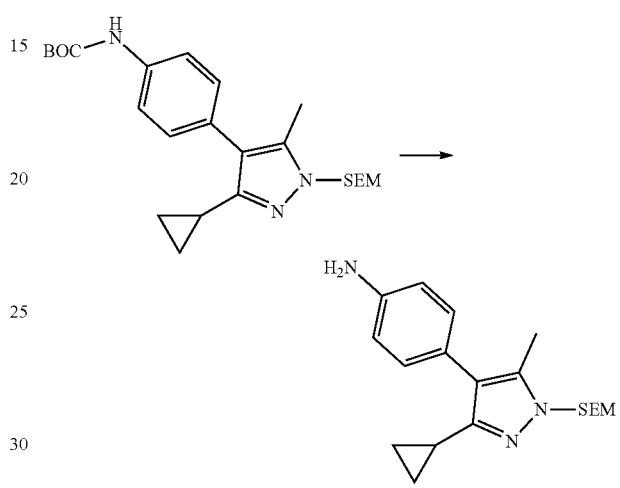

To a stirred solution of the compound of Preparation 299 (320 mg, 0.72 mmol) in MeOH (9.6 mL) at 0° C. was added 4N HCl in 1,4-dioxane (9.6 mL). The reaction mixture was stirred at room temperature for 30 min. The reaction mixture was concentrated under reduced pressure to afford the title compound as a brown solid, mixture of regio-isomers (260 mg, crude). This compound was used as such for the next step without further purification. $^1$H NMR (300 MHz, DMSO-d$_6$) δ 6.95 (dd, J=15.77, 8.44 Hz, 2H), 6.60 (dd, 7=12.47, 8.44 Hz, 2H), 5.39 (s, 1H) 5.26 (s, 1H) 5.04 (br d, J=6.97 Hz, 2H), 3.60 (t, 7=8.07 Hz, 1H), 3.51 (t, 7=7.89 Hz, 1H), 2.04-2.20 (m, 3H), 1.66-1.85 (m, 1H), 0.69-0.89 (m, 5H), 0.30 (dd, J=5.14, 1.83 Hz, 1H), −0.07-0.01 (m, 9H); LCMS (ESI): m/z 344 [M+H$^+$]; 49% and 48%; RT=2.03 and 2.09 min; (ACQUITY UPLC BEH C18 column, 0.05% FA in water with MeCN).

Preparation 301

Ethyl 2-(4-nitrophenyl)-3-oxobutanoate

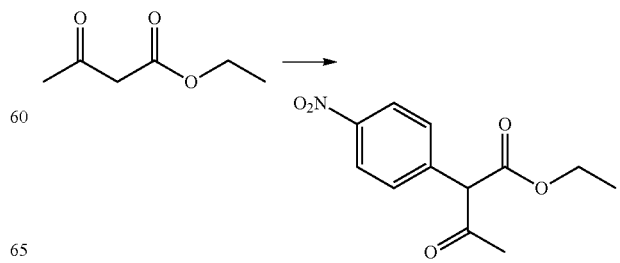

To a stirred solution of 1-chloro-4-nitrobenzene in toluene was added ethyl 3-oxobutanoate and $K_3PO_4$ at room temperature. The resulting reaction mixture was purged with argon gas for 15 min and then $Pd(OAc)_2$ and X-phos were added. The reaction mixture was stirred at 90° C. for 16 hours then filtered through a Celite pad and washed with EtOAc (100 mL). The filtrate was concentrated under reduced pressure and the crude product was purified by silica gel (100-200 mesh) column chromatography (10% EtOAc in hexane as eluent) to afford the title compound (3.5 g, 43%) as a brown oil. 1H NMR (400 MHz, DMSO-d6) δ 8.26-8.18 (m, 2H), 7.62-7.51 (m, 2H), 4.20-4.02 (m, 3H), 2.22 (s, 3H), 1.26-1.18 (m, 3H); LCMS (METHOD 5) (ESI): m/z: 250 [M−H]; RT=3.95 min; (ACQUITY BEH C18 column, 0.1% FA in water with MeCN).

Preparation 302A and B

3-Methyl-4-(4-nitrophenyl)-1H-pyrazol-5-ol (Prep. 302A) and 5-ethoxy-3-methyl-4-(4-nitrophenyl)-1H-pyrazole (Prep. 302B

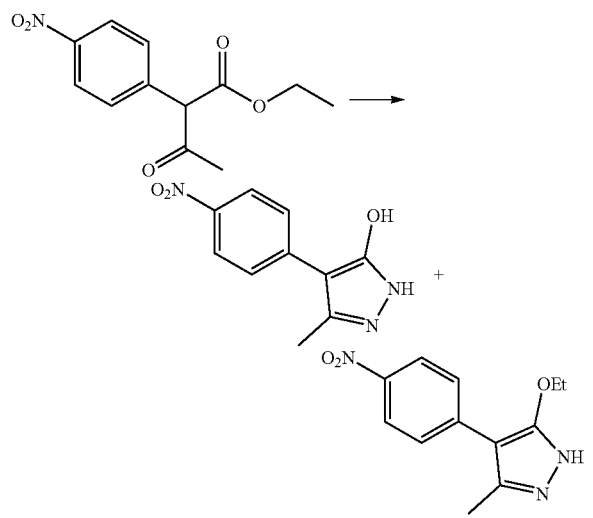

To a stirred solution of the keto ester of Preparation 301 (5 g, 19.9 mmol) in MeOH (150 mL) was added hydrazine hydrochloride (2.88 g, 49.8 mmol) and the mixture was stirred at 70° C. for 48 hours. The reaction mixture was concentrated under reduced pressure then diluted with water (100 mL) and extracted with EtOAc (2×100 mL). The combined organic layers were washed with water (100 mL) and brine (100 mL), dried over $Na_2SO_4$, filtered and concentrated under reduced pressure. The crude product was purified by column chromatography using silica (100-200 mesh) and eluted with 1%-10% MeOH in DCM to give 3-methyl-4-(4-nitrophenyl)-1H-pyrazol-5-ol (1.0 g, 22%) and 5-ethoxy-3-methyl-4-(4-nitrophenyl)-1H-pyrazole (1.2 g, 24%) as yellow solids.

Prep. 302A: 1H NMR (400 MHz, DMSO-d6) δ 11.81 (br s, 1H), 10.45 (br s, 1H), 8.21-8.19 (d, J=8.8 Hz, 2H), 7.79-7.77 (d, J=8.8 Hz, 2H), 2.37 (s, 3H); LCMS (METHOD 5) (ESI): m/z: 220 [M+H⁺]; RT=1.44 min; (ACQUITY BEH C18 column (50×2.1 mm) 1.7 μm, 0.1% FA in water with MeCN).

Prep. 302B: 1H NMR (400 MHz, DMSO-d6) δ 12.10 (br s, 1H), 8.23-8.21 (d, J=8.8 Hz, 2H), 7.75-7.73 (d, J=8.8 Hz, 2H), 2.37 (s, 3H), 4.28-4.23 (q, J=8.0 Hz, 2H), 1.36-1.32 (t, J=9.2 Hz, 3H); LCMS (METHOD 5) (ESI): m/z: 248 [M+H⁺]; RT=1.86 min; (ACQUITY BEH C18 column (50× 2.1 mm) 1.7 μm, 0.1% FA in water with MeCN).

Preparation 303

5-Methoxy-3-methyl-4-(4-nitrophenyl)-1H-pyrazole

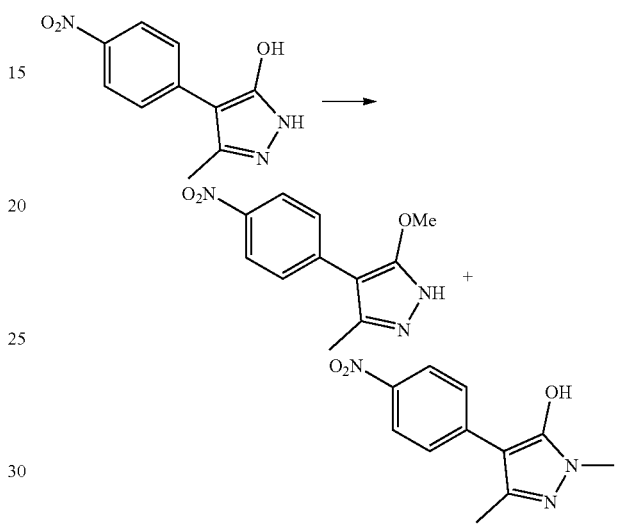

To a stirred solution of the pyrazole of Preparation 302A (1.0 g, 4.56 mmol) in MeCN was added $K_2CO_3$ (109 mg, 9.13 mmol), followed by MeI (0.22 mL, 3.65 mmol) at 0° C. The resulting reaction mixture was stirred at room temperature for 6 hours then diluted with water (100 mL) and extracted with EtOAc (2×50 mL). The combined organic layers were washed with water (50 mL) and brine (50 mL), dried over anhydrous $Na_2SO_4$, filtered and concentrated under reduced pressure. The crude product, containing the unwanted N-methylpyrazole, was purified by Prep. HPLC to give 5-methoxy-3-methyl-4-(4-nitrophenyl)-1H-pyrazole (200 mg, 18%) as a yellow solid. 1H NMR (400 MHz, DMSO-d6) δ 12.20 (br s, 1H), 8.26-8.24 (d, J=8.8 Hz, 2H), 7.78-7.75 (d, J=8.8 Hz, 2H), 3.92 (s, 3H), 2.42 (s, 3H); LCMS (METHOD 5) (ESI): m/z: 234 [M+H⁺]; RT=1.74 min; (ACQUITY BEH C18 column (50×2.1 mm) 1.7 μm, 0.1% FA in water with MeCN).

Preparation 304

5-Methoxy-3-methyl-4-(4-nitrophenyl)-1-((2-(trimethylsilyl)ethoxy) methyl)-1H-pyrazole

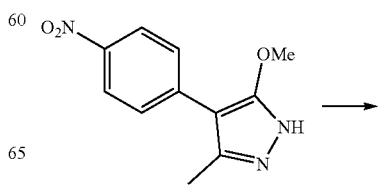

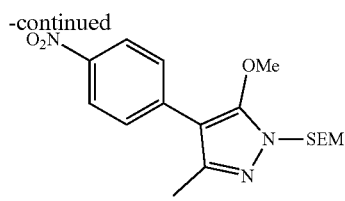

To a stirred solution of the pyrazole of Preparation 303 (380 mg, 1.63 mmol) in DMF (5 mL) was added 60% NaH (130 mg, 3.26 mmol) followed by SEM-Cl (0.43 mL, 2.44 mmol) at 0° C. The Resulting reaction mixture was stirred at 0° C. for 4 hours then poured into ice cold water (50 mL) and extracted with EtOAc (2×50 mL). The combined organic layers were washed with water (3×30 mL) and brine (50 mL), dried over anhydrous Na$_2$SO$_4$ and concentrated under reduced pressure. The crude product was purified by silica gel (100-200 mesh) column chromatography (5% EtOAc in hexane as eluent) to give the title compound as a 5:1 mixture of isomers (350 mg, 59%) as a yellow solid. 1H NMR (400 MHz, DMSO-d6) δ 8.26-8.23 (dd, J=6.8 Hz, 2 Hz, 2H), 7.69-7.67 (dd, J=6.8 Hz, 2 Hz, 2H), 5.34 (s, 2H), 3.88 (s, 3H), 3.62-3.58 (t, J=8.0 Hz, 2H), 2.41 (s, 3H), 0.87-0.84 (t, J=8.0 Hz, 2H), −0.029 (s, 9H); LCMS (METHOD 5) (ESI): m/z: 364 [M+H$^+$]; RT=2.46 min and 2.55 min; (ACQUITY BEH C18 column (50×2.1 mm) 1.7 μm, 0.1% FA in water with MeCN).

Preparation 305

4-(5-Methoxy-3-methyl-1-((2-(trimethylsilyl)ethoxy)methyl)-1H-pyrazol-4-yl)aniline

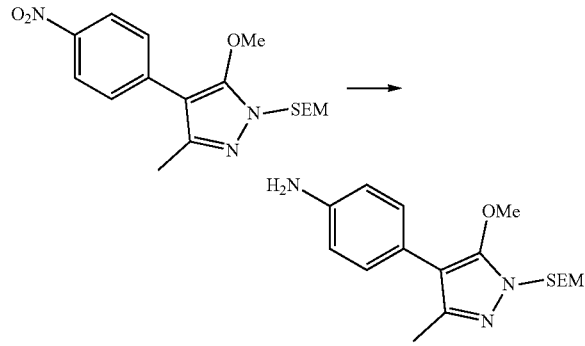

To a stirred solution of the nitro compound of Preparation 304 (350 mg, 0.964 mmol) in MeOH (10 mL) was added 10% Pd/C (35 mg) and the mixture was stirred under a hydrogen balloon at room temperature for 16 hours. The reaction mixture was filtered through a Celite pad and washed with MeOH (50 mL). The filtrate was concentrated under reduced pressure and the crude product was purified by silica gel (100-200 mesh) column chromatography (12% EtOAc in hexane as eluent) to give the title compound as a 5:1 mixture of isomers (290 mg, 90%) as a brown liquid. 1H NMR (400 MHz, DMSO-d6) δ 6.99-6.97 (d, J=8.8 Hz, 2H), 6.58-6.56 (d, J=8.4 Hz, 2H), 5.24 (s, 2H), 5.01 (s, 2H), 3.78 (s, 3H), 3.57-3.53 (t, J=7.6 Hz, 2H), 2.24 (s, 3H), 0.85-0.81 (t, J=8.0 Hz, 2H), −0.03 (s, 9H); LCMS (METHOD 5) (ESI): m/z: 334 [M+H$^+$]; RT=4.70 min and 4.84 min; (ACQUITY BEH C18 column (100×2.1 mm) 1.7 μm, 0.05% TFA in water with MeCN).

Preparation 306

5-Ethoxy-3-methyl-4-(4-nitrophenyl)-1-((2-(trimethylsilyl)ethoxy)methyl)-1H-pyrazole

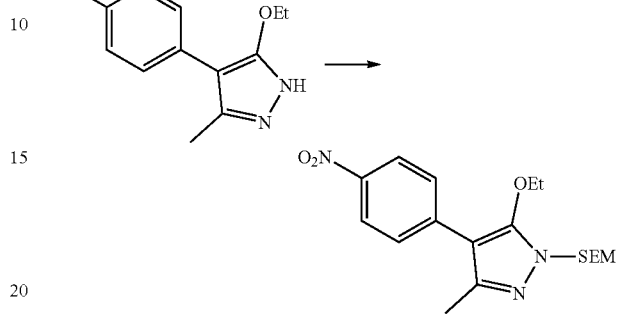

The pyrazole of Preparation 302B was treated according to the method of Preparation 304 to give the title compound (800 mg, 61%) as an off white solid (800 mg, 61%). 1H NMR (400 MHz, DMSO-d6) δ 8.29-8.27 (dd, J=7.2 Hz, 2.0 Hz, 2H), 7.74-7.71 (d, J=7.2 Hz, 2.0 Hz, 2H), 5.57 (s, 2H), 4.31-4.26 (q, J=7.2 Hz, 2H), 3.65-3.61 (t, J=8.0 Hz, 2H), 2.44 (s, 3H), 1.38-1.34 (t, J=7.2 Hz, 2H), 0.91-0.87 (t, J=8.0 Hz, 2H), −0.01 (s, 9H); LCMS (METHOD 5) (ESI): m/z: 378 [M+H$^+$]; RT=2.63 min; (ACQUITY BEH C18 column (100×2.1 mm) 1.7 μm, 0.05% TFA in water with MeCN).

Preparation 307

4-(5-Ethoxy-3-methyl-1-((2-(trimethylsilyl)ethoxy)methyl)-1H-pyrazol-4-yl)aniline

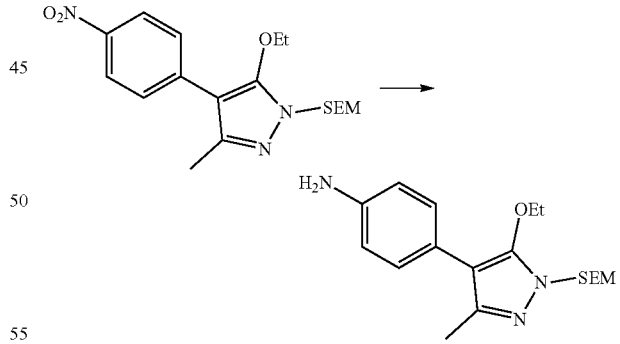

The nitro compound of Preparation 306 was treated according to the method of Preparation 305 to give the title compound (400 mg, 43%) as a brown liquid. 1H NMR (400 MHz, DMSO-d6) δ 7.01-6.99 (d, J=8.8 Hz, 2H), 6.58-6.56 (d, J=8.4 Hz, 2H), 5.23 (s, 2H), 5.00 (s, 2H), 4.16-4.12 (q, J=7.6 Hz, 2H), 3.57-3.53 (t, J=7.6 Hz, 2H), 2.23 (s, 3H), 1.28-1.25 (t, J=7.2 Hz, 2H), 0.85-0.81 (t, J=8.0 Hz, 2H), −0.04 (s, 9H); LCMS (METHOD 5) (ESI): m/z: 348 [M+H$^+$]; RT=2.41 min; (ACQUITY BEH C18 column (100×2.1 mm) 1.7 μm, 0.05% TFA in water with MeCN).

Preparation 308

3,5-Diethyl-1H-pyrazole

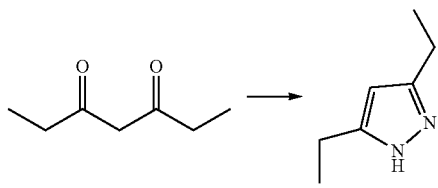

To a stirred solution of heptane-3,5-dione (30 g, 234.37 mmol) in ethanol (100 mL), hydrazine hydrate (19.5 g, 390 mmol) was added. The reaction mixture was allowed to stir at 80° C. for 5 h. The reaction mixture was reduced to dryness, diluted with water (500 mL) and extracted with EtOAc (2×500 mL). The organic layer was dried over anhydrous sodium sulfate, filtered and reduced under vacuum to give the title compound as an oil (28 g, 96%). $^1$H NMR (400 MHz, Chloroform-d) δ 5.89 (s, 1H) 2.65 (q, J=7.59 Hz, 4H) 1.25 (t, J=7.63 Hz, 6H); LCMS (METHOD 5) (ESI): m/z: 125 [M+H$^+$]; RT=1.61 min (ACQUITY BEH C18 column, 0.05% FA in water with MeCN).

Preparation 309

4-bromo-3,5-diethyl-1H-pyrazole

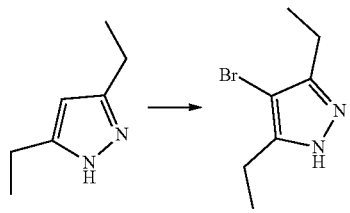

To the stirred solution of the pyrazole of Preparation 308 (28 g, 225.8 mmol) in DCM (350 mL), at 0° C., NBS (40.1 g, 225.8 mmol) was added. The reaction mixture was stirred at 0° C. for 30 min. The reaction mixture was diluted with water (500 mL), extracted with DCM (2×500 mL). Organic layer was dried over anhydrous sodium sulfate, reduced to dryness under vacuum to afford crude residue. The crude residue was purified by silica gel (100-200 mesh) column chromatography (5% EtOAc in hexanes) to afford the title compound (40 g, 87%) as a yellow solid. $^1$H NMR (400 MHz, Chloroform-d) δ 2.64 (q, J=7.63 Hz, 4H) 1.26 (t, J=7.57 Hz, 6H); LCMS (METHOD 5) (ESI): m/z: 203 [M+H$^+$]; RT=2.26 min (ACQUITY BEH C18 column, 0.05% FA in water with MeCN).

Preparation 310

4-bromo-3,5-diethyl-1-((2-(trimethylsilyl)ethoxy)methyl)-1H-pyrazole

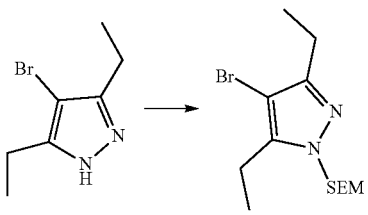

To a stirred solution of the compound of Preparation 309 (40 g, 197 mmol) in DMF (100 mL) at 0° C., NaH (63%, 10.2 g, 256 mmol) was added followed by SEM-Cl (38 mL, 217 mmol). The reaction mixture was allowed to stir at room temperature for 3 h. The reaction mixture was diluted with water (500 mL), extracted with EtOAc (2×500 mL). The organic layer was dried over anhydrous sodium sulfate, reduced to dryness under vacuum to afford crude residue. The crude was purified by silica gel (100-200 mesh) column chromatography (1% EtOAc in hexanes) to afford the title compound (40 g, 60%) as a pale brown oil. $^1$H NMR (400 MHz, Chloroform-d) δ 5.35 (s, 2H), 3.46-3.60 (m, 2H), 2.71 (q, J=7.63 Hz, 2H), 2.60 (q, 7=7.52 Hz, 2H), 1.21 (dt, J=10.93, 7.62 Hz, 6H), 0.83-0.92 (m, 2H), −0.03 (s, 9H); LCMS (METHOD 5) (ESI): m/z: 333 [M+H$^+$]; RT=6.8 min (ACQUITY BEH C18 column, 0.05% FA in water with MeCN).

Preparation 311

Tert-butyl (4-(3,5-diethyl-1-((2-(trimethylsilyl)ethoxy)methyl)-1H-pyrazol-4-yl)phenyl)carbamate

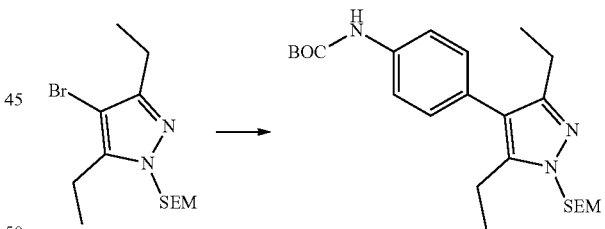

To a stirred solution of the bromide of Preparation 310 (1.0 g, 3.01 mmol), (4-((tert-butoxycarbonyl)amino)phenyl) boronic acid (785 mg, 3.31 mmol) in 1,4-dioxane (10 mL) and water (2 mL) potassium carbonate (1.2 g, 9.03 mmol) were added. The reaction mixture was de-oxygenated with argon for 10 min. To the reaction mixture was added Pd(dppf)Cl$_2$.DCM (491 mg, 0.60 mmol). The reaction mixture was allowed to stir at 100° C. for 16 h. The reaction mixture was evaporated, EtOAc was added (100 mL), and the mixture was filtered through Celite. The filtrate was concentrated under vacuum to afford the title compound (1.5 g, crude) as a brown solid. $^1$H NMR (400 MHz, CDCl$_3$) δ 7.39 (d, J=8.39 Hz, 2H), 7.17 (d, J=8.50 Hz, 2H), 6.51 (s, 1H), 5.40 (s, 2H), 3.49-3.75 (m, 2H), 2.65 (q, J=7.52 Hz, 2H), 2.57 (q, J=7.59 Hz, 2H), 1.53 (s, 9H), 1.12 (td, J=7.52, 5.01 Hz, 6H), 0.91 (dd, J=8.83, 7.74 Hz, 2H), −0.01 (s, 9H);

LCMS (METHOD 5) (ESI): m/z: 446 [M+H⁺]; RT=3.18 min (ACQUITY BEH C18 column, 0.05% FA in water with MeCN).

Preparation 312

4-(3,5-diethyl-1-((2-(trimethylsilyl)ethoxy) methyl)-1H-pyrazol-4-yl)aniline

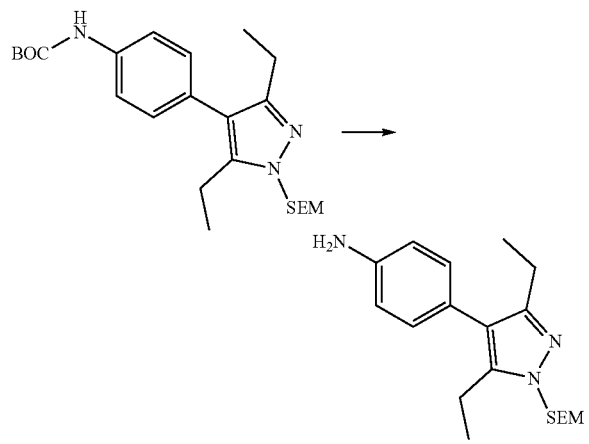

Treatment of the compound of Preparation 311 according to the method of Preparation 2 gave the title compound as a pale yellow solid (1.7 g, crude). LCMS (METHOD 5) (ESI): m/z: 346 [M+H⁺]; RT=2.66 min (ACQUITY BEH C18 column, 0.05% FA in water with MeCN).

Preparation 313

3,5-diethyl-4-(2-methoxy-4-nitrophenyl)-1-((2-(trimethylsilyl)ethoxy) methyl)-1H-pyrazole

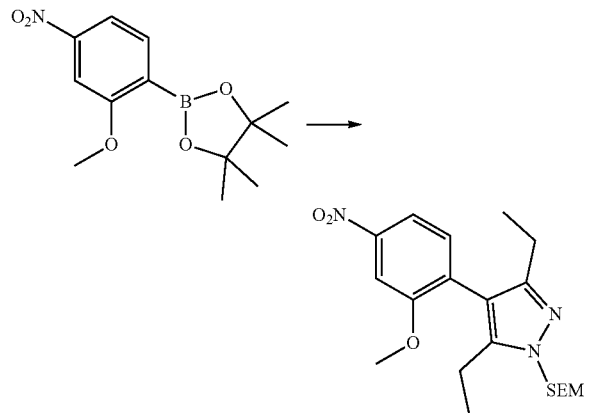

The compound of Preparation 262 was reacted with the bromide of Preparation 310 according to the method of Preparation 292 to give the title compound as a yellow solid (2.2 g, 91%). LCMS (METHOD 5) (ESI): m/z: 406[M+H⁺]; RT=2.62 min (ACQUITY BEH C18 column, 0.05% FA in water with MeCN).

Preparation 314

Synthesis of 3,5-diethyl-4-(2-methoxy-4-nitrophenyl)-1H-pyrazole

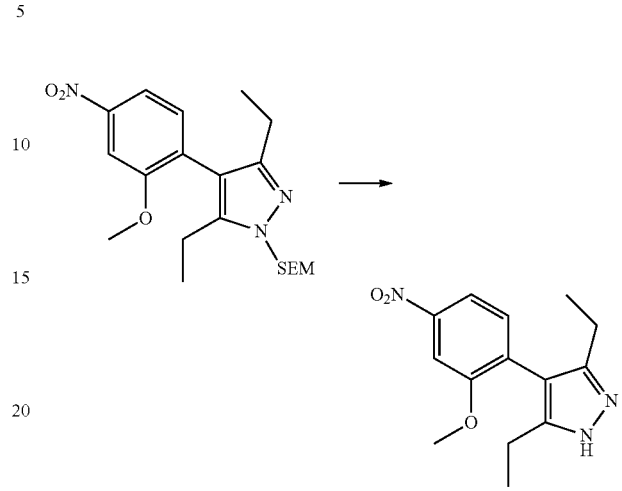

The compound of Preparation 313 was treated according to the method of Example 1 to give the title compound as a brown solid (1.5 g, 95%). ¹H NMR (400 MHz, CDCl₃): δ (ppm) 7.95 (br s, 1H), 7.95-7.91 (ms, 1H), 7.85-7.84 (m, 1H), 7.32-7.26 (m, 1H), 3.91 (s, 3H), 2.74-2.66 (m, 4H), 1.372-1.10 (m, 6H); LCMS (METHOD 5) (ESI): m/z: 276 [M+H⁺]; RT=2.33 min (ACQUITY UPLC BEH C18 column, 0.05% FA in water with MeCN).

Preparation 315

2-(3,5-diethyl-1H-pyrazol-4-yl)-5-nitrophenol

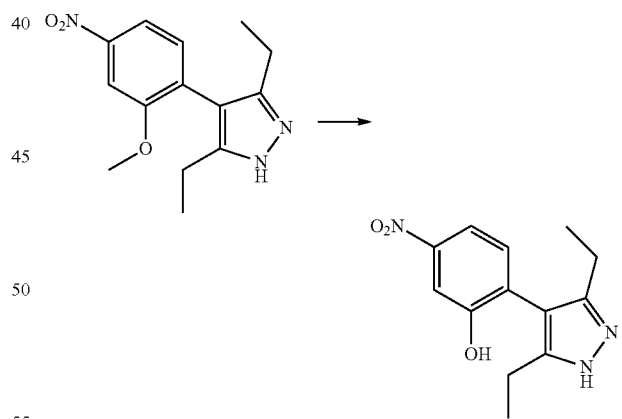

To a stirred solution of the pyrazole of Preparation 314 (1.0 g, 3.63 mmol) in DCM (30 mL) was added 1 M BBr₃ (18 mL, 18.18 mmol) in DCM at 0° C. The resulting reaction mixture was stirred at room temperature for 24 h. After completion, the reaction mixture was poured into ice cold water (100 mL) and basified with aq. Na₂CO₃ (pH~8) and extracted with EtOAc (2×100 mL). The combined organic layers were washed with brine (100 mL), dried over anhydrous Na₂SO₄, filtered and concentrated under reduced pressure to afford crude compound. This was purified by silica gel (100-200 mesh) column chromatography (5%

MeOH in DCM as an eluent) to afford the title compound as a brown solid (450 mg, 47%). LCMS (METHOD 5) (ESI): m/z: 262 [M+H⁺]; RT=2.92 min (ACQUITY UPLC BEH C18 column, 0.05% FA in water with MeCN).

Preparation 316

3,5-diethyl-4-(4-nitro-2-((2-(trimethylsilyl)ethoxy) methoxy)phenyl)-1-((2-(trimethylsilyl)ethoxy) methyl)-1H-pyrazole

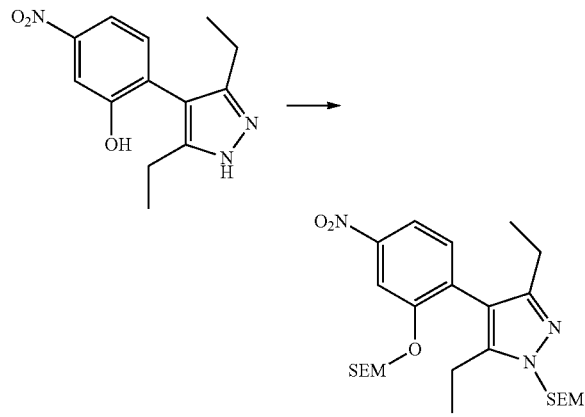

The phenol of Preparation 315 was protected according to the method of Preparation 286 to give the title compound as a yellow solid (450 mg, 50%). LCMS (METHOD 5) (ESI): m/z: 522 [M+H⁺]; RT=3.57 min (ACQUITY UPLC BEH C18 column, 0.05% FA in water with MeCN).

Preparation 317

4-(3,5-diethyl-1-((2-(trimethylsilyl)ethoxy)methyl)-1H-pyrazol-4-yl)-3-((2-(trimethylsilyl)ethoxy) methoxy)aniline

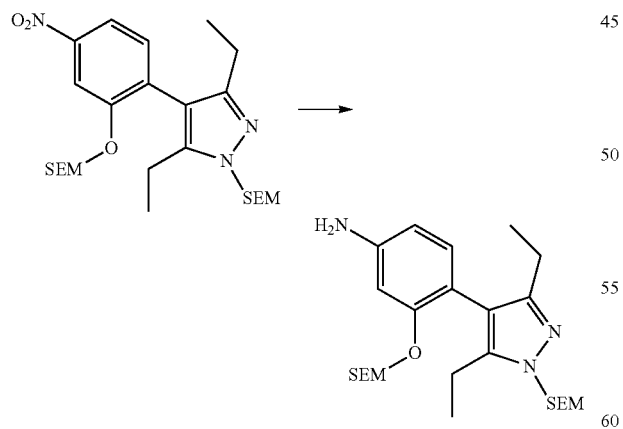

A suspension of the nitro compound of Preparation 316 (450 mg, 0.86 mmol) and 10% Pd/C (100 mg, 50% of moisture) in methanol (10 mL) was stirred under H₂ gas (balloon pressure) at room temperature for 16 h. On completion, the reaction mixture was filtered through a Celite pad and washed with methanol (20 mL). The filtrate was concentrated under reduced pressure to afford crude compound which was purified by silica gel (100-200 mesh) column chromatography (5% MeOH in DCM as an eluent) to afford the title compound as an off white solid (450 mg, 33%). ¹H NMR (400 MHz, CDCl₃) δ 6.90 (d, J=8.0, 1H), 6.64 (d, J=2.0, 1H), 6.38 (dd, J₁=8.0 Hz, J₂=8.4 Hz, 1H), 5.41 (s, 2H), 5.09 (s, 2H), 3.72-3.61 (m, 6H), 2.62-2.46 (m, 4H), 1.27-1.06 (m, 6H), 1.10-1.06 (m, 4H), 0.02 (s, 18H); LCMS (METHOD 5) (ESI): m/z: 492 [M+H⁺]; RT=5.52 min (ACQUITY UPLC BEH C18 column, 0.05% FA in water with MeCN).

Preparation 318

Ethyl 5-(4-((tert-butoxycarbonyl)amino)phenyl)-1-methyl-1H-pyrazole-4-carboxylate

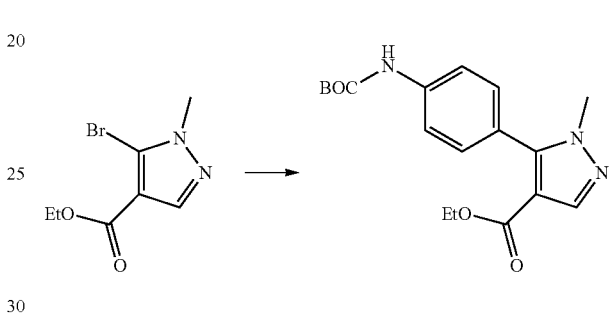

The title compound was prepared in the same manner as the compound of Preparation 311 from (4-((tert-butoxycarbonyl)amino)phenyl)boronic acid and ethyl 5-bromo-1-methyl-pyrazole-4-carboxylate and was obtained as an off white solid (2.0 g, 90%). ¹H NMR (400 MHz, CDCl₃) δ 7.97 (s, 1H), 7.49-7.47 (m, 2H), 7.31-7.26 (m, 2H), 6.58 (br s, 1H), 4.16 (q, J=6.8 Hz, 2H), 3.73 (s, 3H), 1.54 (s, 9H), 1.19 (t, J=8.0 Hz, 3H); LCMS (METHOD 5) (ESI): m/z: 345 [M]; RT=3.23 min (ACQUITY UPLC BEH C18 column, 0.05% TFA in water with MeCN).

Preparation 319

Tert-butyl (4-(4-(1-hydroxycyclopropyl)-1-methyl-1H-pyrazol-5-yl)phenyl)carbamate

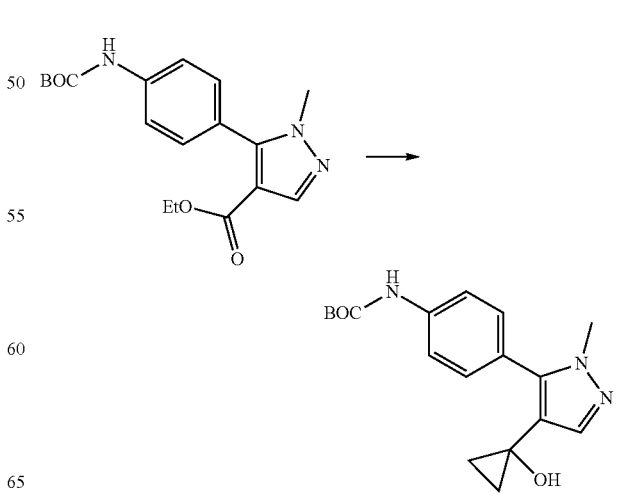

To a stirred solution of the ester of Preparation 318 (1.3 g, 3.76 mmol) in dry THF (30 mL) was added ethylmagnesium bromide (15 mL, 15.1 mmol) followed by titanuim (IV)isopropoxide (4.6 mL, 15.1 mmol) at 0° C. The reaction was stirred at room temperature for 1 h. The reaction mixture was cooled to 0° C. and diluted with 4N HCl (5 mL) and extracted with EtOAc (2×100 mL). The combined organic layers were washed with water (100 mL), brine (100 mL), dried over anhydrous $Na_2SO_4$, filtered and concentrated under reduced pressure to afford crude compound. This was purified by silica gel (100-200 mesh) column chromatography (30% EtOAc in Hexane as eluent) to give the title compound as a brown solid (600 mg, 89%). LCMS (METHOD 5) (ESI): m/z: 330 [M]; RT=2.24 min (ACQUITY UPLC BEH C18 column, 0.05% FA in water with MeCN).

Preparation 320

1-(5-(4-aminophenyl)-1-methyl-1H-pyrazol-4-yl)cyclopropan-1-ol

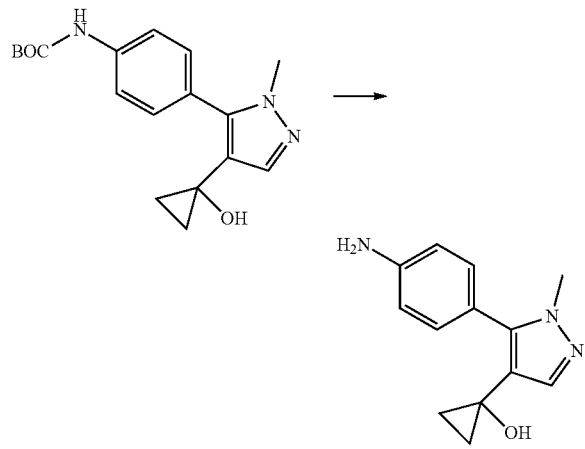

To a stirred solution of the compound of Preparation 319 (700 mg, 2.12 mmol) in 1,4-dioxane (20 mL) was added 4N HCl in 1,4-dioxane (15 mL) at 0° C. The reaction mass was stirred at room temperature for 16 h. The reaction mass was concentrated under reduced pressure to afford crude compound. The crude compound was purified by prep. HPLC to give the title compound as a brown solid (110 mg, 29%). $^1$H NMR (400 MHz, DMSO-$d_6$) δ 7.42 (s, 1H), 7.20-7.18 (m, 2H), 6.67-6.65 (m, 2H), 5.41 (s, 1H), 5.32 (s, 2H), 3.63 (s, 3H), 0.72-0.69 (m, 2H), 0.41-0.38 (m, 2H); LCMS (METHOD 5) (ESI): m/z: 230.14 [M]; RT=1.57 min (ACQUITY UPLC BEH C18 column, 0.05% FA in water with MeCN).

Preparation 321

4-Bromo-3,5-dicyclopropyl-1H-pyrazole

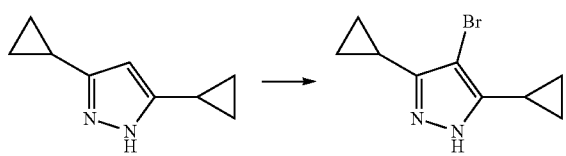 [SMILES: c1c(C2CC2)n[nH]c1C1CC1 ; Brc1c(C2CC2)n[nH]c1C1CC1]

To a stirred solution of 3,5-dicyclopropyl-1H-pyrazole (7.0 g, 47.3 mmol), in AcOH (70 mL), was added NBS (1.13 g, 6.36 mmol) at 0° C. The resulting reaction mixture was stirred at room temperature for 2 h. On completion, the reaction mixture was concentrated under reduced pressure, diluted with water (300 mL) and extracted with EtOAc (2×250 mL). The combined organic layers were washed with water (150 mL), brine (150 mL), dried over anhydrous $Na_2SO_4$, filtered and concentrated under reduced pressure to give the title compound (10 g, crude) as a pale yellow oil. $^1$H NMR (400 MHz, DMSO-$d_6$) δ ppm 10.66 (br s, 2H), 1.90 (S, 2H), 1.88-1.83 (m, 1H), 0.98-0.91 (m, 2H), 0.90-0.86 (m, 4H); LCMS (METHOD 5) (ESI): m/z: 227 [M]; RT=1.84 min (ACQUITY UPLC BEH C18 column, 0.1% FA in water with MeCN).

Preparation 322

2-[(4-Bromo-3,5-dicyclopropyl-pyrazol-1-yl)methoxy]ethyl-trimethyl-silane

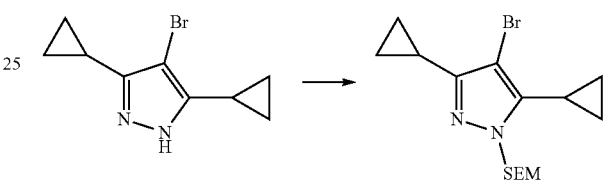

To a stirred solution of the pyrazole of Preparation 321 (10 g, 44.0 mmol) in THF (100 mL) was added 60% NaH (1.5 g, 66.1 mmol) followed by SEM-Cl (11.7 mL, 66.1 mmol) at 0° C. The resulting reaction mixture was stirred at room temperature for 16 h. After completion of the reaction the reaction mixtures was poured into ice cold water (1 L) and extracted with EtOAc (2×500 mL). Combined organic layer washed with water (2×500 mL), brine (500 mL). Combined organic layer was dried over anhydrous $Na_2SO_4$ and concentrated under reduced pressure. The resulting residue was purified by silica gel (100-200 mesh) column chromatography (10% EtOAc in pet ether as eluent) to afford the title compound (5.1 g, 32%) as a colourless oil. $^1$H NMR (400 MHz, DMSO-$d_6$) δ ppm 10.66 (br s, 2H), 9.14 (S, 1H), 5.39-5.37 (m, 2H), 3.55 (t, J=8.8 Hz, 2H), 1.90 (S, 2H), 1.88-1.83 (m, 1H), 0.98-0.91 (m, 2H), 0.90-0.86 (m, 4H), 0.04-0.03 (m, 9H); LCMS (METHOD 5) (ESI): m/z: 357 [M+H$^+$]; RT=6.39 min (ACQUITY UPLC BEH C18 column, 0.1% FA in water with MeCN).

Preparation 323

N-(1,1-dicyclopropyl-3-((4-(3,5-dicyclopropyl-1-((2-(trimethylsilyl)ethoxy)methyl)-1H-pyrazol-4-yl)phenyl)amino)-3-oxopropan-2-yl)-1-isopropyl-1H-pyrazole-5-carboxamide

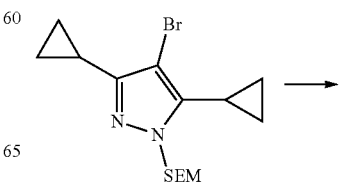

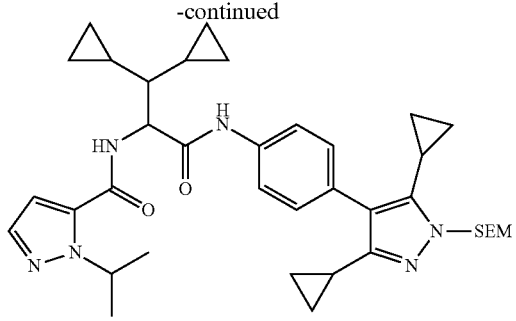

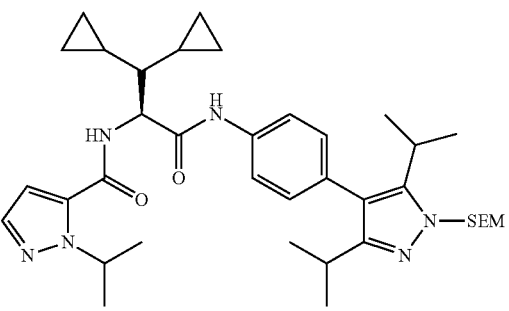

The title compound was prepared according to the method of Preparation 292 using the boronic ester of Preparation 281 and the bromide of Preparation 322 and was obtained as an off white solid (100 mg, 54%). LCMS (METHOD 5) (ESI): m/z: 656 [M+H⁺]; RT=2.68 min (ACQUITY UPLC BEH C18 column, 0.1% FA in water with MeCN).

Preparation 324

2-[(4-Bromo-3,5-diisopropyl-pyrazol-1-yl)methoxy]ethyl-trimethyl-silane

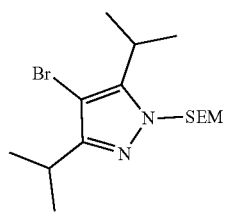 [SMILES: CC(C)c1nn(COCC[Si](C)(C)C)c(C(C)C)c1Br]

The title compound was prepared according to the methods of Preparation 309 and 310 from 3,5-diisopropyl-1H-pyrazole.

Preparation 325

N-[(1S)-1-(dicyclopropylmethyl)-2-[4-[3,5-diisopropyl-1-(2-trimethylsilylethoxymethyl)pyrazol-4-yl]anilino]-2-oxo-ethyl]-2-isopropyl-pyrazole-3-carboxamide

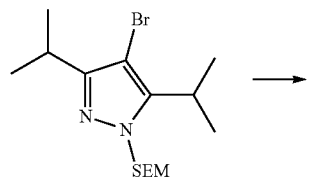

The title compound was prepared according to the method of Preparation 292 using the boronic ester of Preparation 281 and the bromide of Preparation 324 and was obtained as an off white solid (80 mg). LCMS (METHOD 5) (ESI): m/z: 661 [M−H]; RT=3.23 min (ACQUITY UPLC BEH C18 column, 0.1% FA in water with MeCN).

Preparation 326

(S)—N-(1,1-dicyclopropyl-3-((4-(4-methyl-1-((2-(trimethylsilyl)ethoxy)methyl)-1H-imidazol-5-yl)phenyl)amino)-3-oxopropan-2-yl)-1-isopropyl-1H-pyrazole-5-carboxamide and (S)—N-(1,1-dicyclopropyl-3-((4-(5-methyl-1-((2-(trimethylsilyl)ethoxy)methyl)-1H-imidazol-4-yl)phenyl)amino)-3-oxopropan-2-yl)-1-isopropyl-1H-pyrazole-5-carboxamide

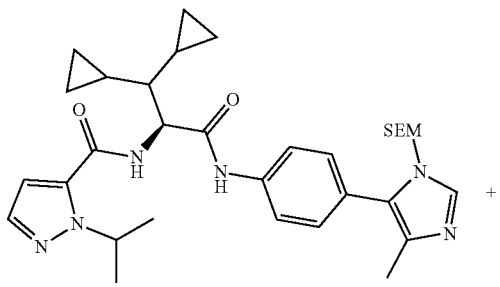

+

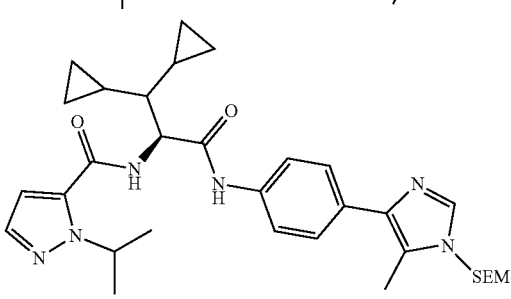

The title compounds were prepared according to the methods of Preparations 3 to 5 from the anilines of Preparation 298, the Boc protected amino acid of Preparation 52 and 1-isopropyl-1H-pyrazole-5-carboxylic acid. LCMS (METHOD 5) (ESI): m/z: 591 [M+H⁺]; RT=1.92 min 8*. 1.96 min (ACQUITY BEH C18 column, 0.1% FA in water with MeCN).

Preparation 327

Methyl 5-bromo-1-methyl-1H-imidazole-4-carboxylate

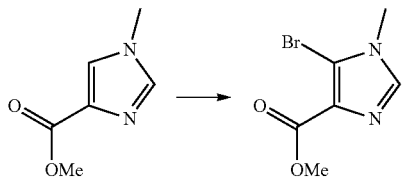

To a stirred solution of methyl 1-methyl-1H-imidazole-4-carboxylate (4.0 g, 28.6 mmol) in acetic acid (20 mL), NBS (5 g, 28.57 mmol) was added at room temperature. The reaction mixture was stirred at 70° C. for 5 h. The reaction mixture was evaporated under reduced pressure. The residue was diluted with water (50 mL) and extracted with EtOAc (2×100 mL). The combined organic layers were dried over anhydrous $Na_2SO_4$ filtered and concentrated under reduced pressure. The obtained crude compound was purified by silica gel (100-200 mesh) column chromatography (50% EtOAc in hexanes) to afford the title compound as a pale yellow solid (1.6 g, 27%). $^1$H NMR (400 MHz, $CDCl_3$) δ 7.60 (s, 1H), 3.92 (s, 3H), 3.62-3.71 (m, 3H); LCMS (METHOD 5) (ESI): m/z: 220 [M+H$^+$]; RT=1.24 min; (ACQUITY BEH C18 column, 0.1% FA in water with MeCN).

Preparation 328

(5-bromo-1-methyl-1H-imidazol-4-yl)methanol

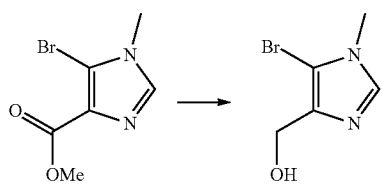

To a stirred solution of the ester of Preparation 327 (1.0 g, 4.56 mmol) in THF (10 mL), DIBAL (13 mL, 13 mmol, 1M in THF) was added at −78° C. The reaction mixture was stirred at room temperature for 2 h. The reaction mixture was quenched with sat. aq. $NH_4Cl$ solution (30 mL). The aqueous layer was extracted with 10% MeOH in DCM (2×20 mL). The combined organic layer was dried over anhydrous $Na_2SO_4$ and concentrated under reduced pressure to afford the title compound as a yellow solid (270 mg, crude). This compound was used as such for the next step without further purification. $^1$H NMR (400 MHz, $CDCl_3$) δ 7.56 (s, 1H), 4.57 (s, 2H), 3.61 (s, 3H); LCMS (METHOD 5) (ESI): m/z: 192 [M+H$^+$]; RT=0.65 min (ACQUITY BEH C18 column, 0.05% FA in water with MeCN).

Preparation 329

Methyl 5-(4-aminophenyl)-1-methyl-1H-imidazole-4-carboxylate

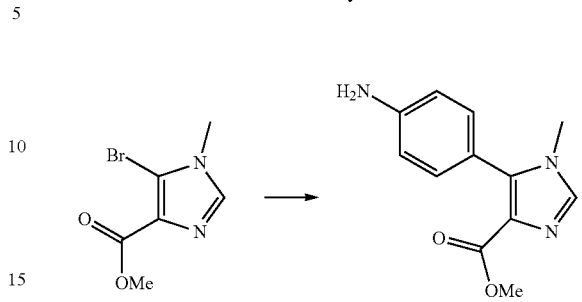

$Na_2CO_3$ (146 mg, 1.37 mmol) was added to a stirred solution of the bromide of Preparation 327 (100 mg, 0.45 mmol) and (4-aminophenyl)boronic acid (100 mg, 0.45 mmol) in 1,4-dioxane:$H_2O$ (9:1) at room temperature. The resulting reaction mixture was purged with argon for 15 min, followed by the addition of Pd(dppf)$Cl_2$.$CH_2Cl_2$ and then heated to 110° C. for 1 h in microwave. The reaction mixture was filtered through a Celite pad and washed with EtOAc (50 mL). The organic layer was separated, dried over $Na_2SO_4$, filtered and concentrated under reduced pressure to afford a crude residue. The obtained crude compound was purified by silica gel (100-200 mesh) column chromatography (5% MeOH in DCM) to afford the title compound (80 mg, 80%) as a light brown solid. $^1$H NMR (400 MHz, $CDCl_3$) δ 7.50 (s, 1H), 7.17 (d, J=8.80 Hz, 2H), 6.76 (d, J=8.31 Hz, 2H), 3.80 (s, 3H), 3.51 (s, 3H); LCMS (METHOD 5) (ESI): m/z: 232 [M+H+]; RT=1.67 min (ACQUITY BEH C18 column, 0.05% TFA in water with MeCN).

Preparation 330

Methyl (S)-5-(4-(2-((tert-butoxycarbonyl)amino)-3,3-dicyclopropylpropanamido)phenyl)-1-methyl-1H-imidazole-4-carboxylate

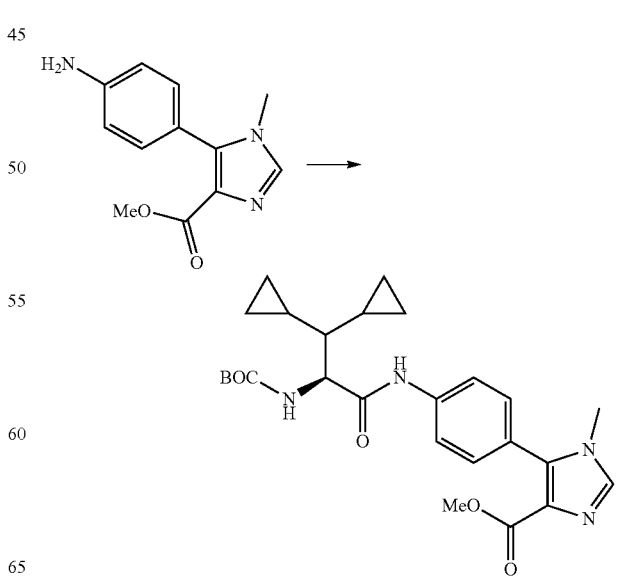

The title compound was prepared according to the method of Preparation 3 from the aniline of Preparation 329 and the acid of Preparation 52 and was obtained as an oil (100 mg, crude). LCMS (METHOD 5) (ESI): m/z: 483 [M+H⁺]; RT=1.89 min (ACQUITY BEH C18 column, 0.1% FA in water with MeCN).

Preparation 331

Methyl (S)-5-(4-(2-amino-3,3-dicyclopropylpropanamido)phenyl)-1-methyl-1H-imidazole-4-carboxylate

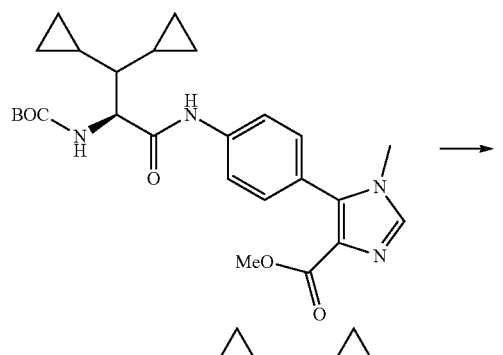

The compound of Preparation 330 was treated according to the method of Preparation 4 to give the title compound as a brown solid (130 mg, crude). LCMS (METHOD 5) (ESI): m/z: 383 [M+H⁺]; RT=1.25 min (ACQUITY BEH C18 column, 0.1% FA in water with MeCN).

Preparation 332

Methyl (S)-5-(4-(3,3-dicyclopropyl-2-(1-isopropyl-1H-pyrazole-5-carboxamido)propanamido)phenyl)-1-methyl-1H-imidazole-4-carboxylate

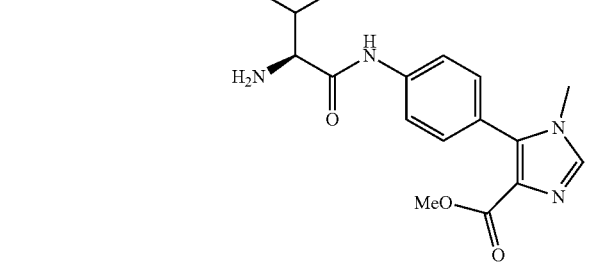

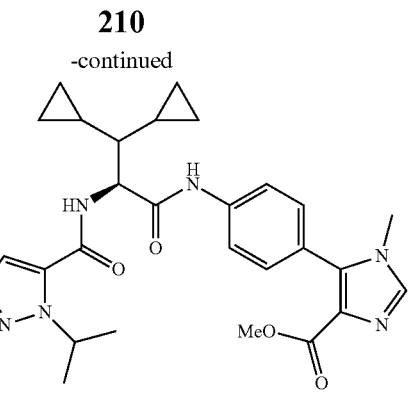

The title compound was prepared according to the method of Preparation 5 from the amine of Preparation 331 and 2-isopropylpyrazole-3-carboxylic acid and was obtained as a pale brown solid (100 mg, crude). ¹H NMR (400 MHz, CDCl₃) δ 8.02 (br s, 1H), 7.66 (d, J=8.61 Hz, 2H), 7.52-7.56 (m, 2H), 7.37 (d, J=8.50 Hz, 2H), 7.07 (br d, J=8.28 Hz, 1H), 6.57 (d, 0.7=1.96 Hz, 1H), 5.44-5.55 (m, 1H), 4.80 (dd, J=8.01, 4.96 Hz, 1H), 3.79 (s, 3H), 3.52 (s, 3H), 1.49-1.51 (m, 6H), 0.84-0.93 (m, 8H), 0.53-0.60 (m, 1H), 0.40 (m, 1H), 0.27 (m, 1H); LCMS (METHOD 5) (ESI): m/z: 519 [M+H⁺]; RT=1.79 min (ACQUITY BEH C18 column, 0.1% FA in water with MeCN).

Preparation 333

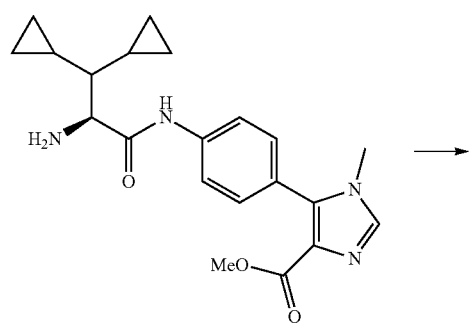

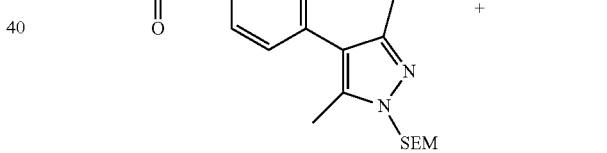

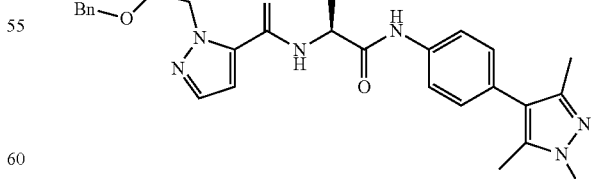

According to the method of Preparation 60 the amine of Preparation 59 and the acid of Preparation 201 were reacted to give the title compound. LCMS (METHOD 3) (ES): m/z 711.7 [M+H]⁺, RT=1.02 min.

Preparation 334

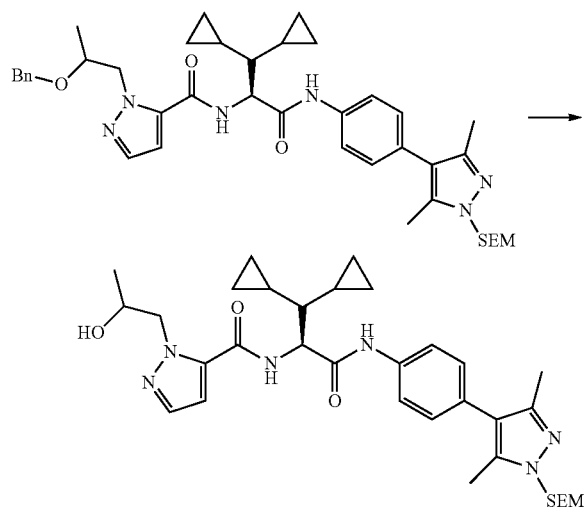

According to the method of Preparation 194 the ether of Preparation 333 was reacted to give the title compound. LCMS (METHOD 3) (ES): m/z 621.7 [M+H]$^+$, RT=0.89 min.

Preparation 335

(S)-2-Amino-2-cyclohexyl-N-(4-(5-methoxy-3-methyl-1H-pyrazol-4-yl)phenyl)acetamide

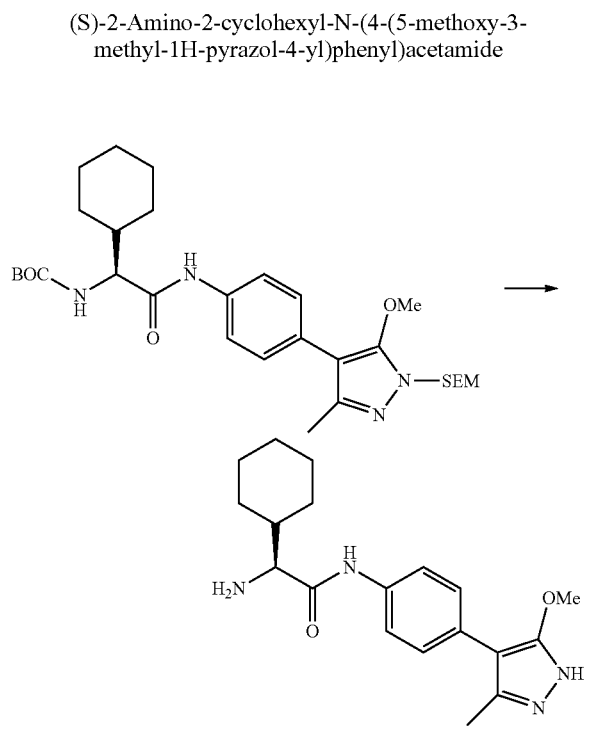

To a stirred solution of tert-butyl (S)-(1-cyclohexyl-2-((4-(5-methoxy-3-methyl-1-((2-(trimethylsilyl) ethoxy)methyl)-1H-pyrazol-4-yl)phenyl)amino)-2-oxoethyl)carbamate (Prepared from (2S)-2-(tert-butoxycarbonylamino)-2-cyclohexyl-acetic acid and the aniline of Preparation 305 according to the method of Preparation 3) (100 mg, 0.122 mmol) in 1,4-dioxane (2.5 mL) was added 4M HCl in 1,4-dioxane (2.5 mL) at 0° C. The reaction was stirred at room temperature for 1 hour then concentrated under reduced pressure to give the title compound (90 mg) as an off-white solid. The crude product was used as such for the next step without further purification. 1H NMR (300 MHz, DMSO-d6) δ 10.42 (s, 1H), 8.24 (br s, 3H), 7.62-7.59 (d, J=7.6 Hz, 2H), 7.42-7.39 (d, J=7.6 Hz, 2H), 4.45-4.48 (m, 1H), 3.82 (s, 3H), 2.28 (s, 3H), 1.82-1.61 (m, 6H), 1.29-1.00 (m, 5H); LCMS (METHOD 5) (ESI): m/z: 343 [M+H$^+$]; RT=1.40 min; (ACQUITY UPLC BEH C18 column, 0.1% FA in water with MeCN).

Preparation 336

(S)-2-Amino-2-cyclohexyl-N-(4-(5-methoxy-3-methyl-1H-pyrazol-4-yl)phenyl)acetamide dihydrochloride

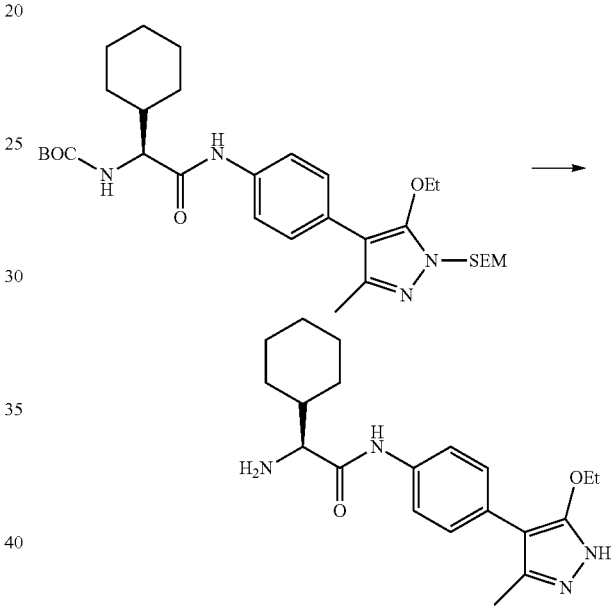

The title compound was prepared according to the method of Preparations 3 and 335 from (2S)-2-(tert-butoxycarbonylamino)-2-cyclohexyl-acetic acid and the aniline of Preparation 306 to give an oil (50 mg, crude). This compound was used as such for the next step without further purification. LCMS (METHOD 5) (ESI): m/z: 357 [M+H$^+$]; RT: 3.46 min; (ACQUITY UPLC, Column: BEH C18 (50 mm×4.6 mm, 2.5 um), Mobile Phase: A: 5 mM Ammonium Bicarbonate; B: MeCN).

Preparation 337

4-[3-Methyl-5-(trifluoromethyl)imidazol-4-yl]aniline

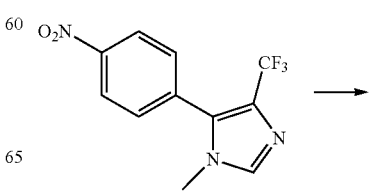

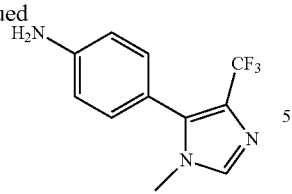

The title compound (217 mg) was prepared according to the method of Preparation 2 from 1-methyl-5-(4-nitrophenyl)-4-(trifluoromethyl)imidazole (prepared according to Heterocycles, 2007, 74, 351-356). 1H NMR (400 MHz, Chloroform-d) δ 7.50 (s, 1H), 7.18-6.99 (m, 2H), 6.82-6.67 (m, 2H), 3.87 (br s, 2H), 3.48 (s, 3H).

Preparation 338

4-[1-Methyl-5-(trifluoromethyl)imidazol-4-yl]aniline

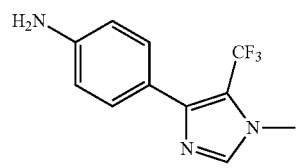

The title compound (80 mg) was prepared according to the method of Preparation 2 from 1-methyl-4-(4-nitrophenyl)-5-(trifluoromethyl)imidazole (prepared according to Heterocycles, 2007, 74, 351-356). 1H NMR (400 MHz, Chloroform-d) δ 7.51 (s, 1H), 7.45-7.32 (m, 2H), 6.80-6.64 (m, 2H), 3.77 (s, 3H).

Preparation 339

(2S)-2-Amino-2-cyclohexyl-N-[4-(3,5-dimethylimidazol-4-yl)phenyl]acetamide hydrochloride

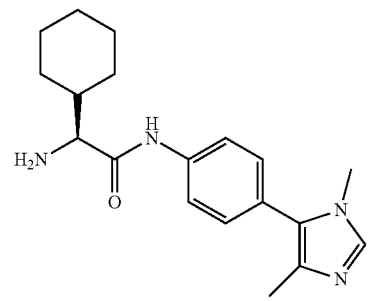

The Boc protected amine of Example 83 (12 mg, 0.028 mmol) was dissolved in MeOH (1 mL) and 4M HCl in dioxane (0.5 mL) was added. The mixture was stirred at room temperature for 1 hour, diluted with MeOH (5 mL) and concentrated in vacuo to give the title compound as a colourless solid (10.2 mg, 100%) that was used without further purification. LCMS (ES) (METHOD 4): m/z 327.2 [M+H]$^+$; RT=0.55 min.

Preparations 340-370

Preparations 340 to 370 were synthesised according to the method of Preparation 339 from the indicated Examples.

| Prep. No. | SM | Structure | Name | Mass ion | LCMS method and RT (min) |
|---|---|---|---|---|---|
| 340 | Ex. 305B | 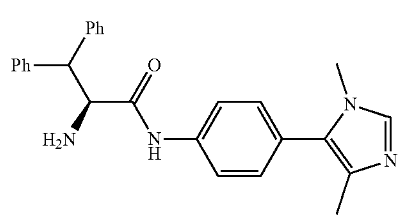 [SMILES: Cc1ncn(C)c1-c1ccc(NC(=O)[C@@H](N)C(c2ccccc2)c2ccccc2)cc1] | (2S)-2-amino-N-[4-(3,5-dimethylimidazol-4-yl)phenyl]-3,3-diphenyl-propanamide | 599.7 | 0.93 (Method 3) |

-continued

| Prep. No. | SM | Structure | Name | Mass ion | LCMS method and RT (min) |
|---|---|---|---|---|---|
| 341 | Ex. 85 | 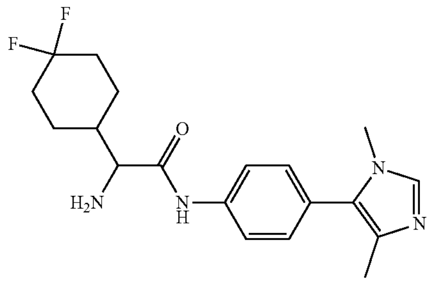 [SMILES: Cc1ncn(C)c1-c1ccc(NC(=O)C(N)C2CCC(F)(F)CC2)cc1] | Enantiomer 1 of 2-amino-2-(4,4-difluorocyclohexyl)-N-[4-(3,5-dimethyl-imidazol-4-yl)-phenyl]acetamide | 363.5 | 0.32 (Method 3) |
| 342 | Ex. 86 | 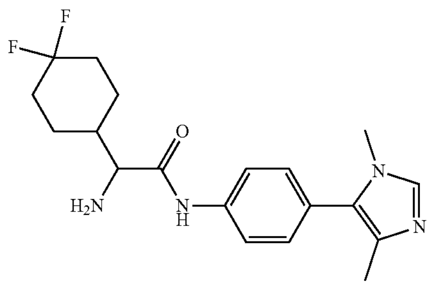 [SMILES: Cc1ncn(C)c1-c1ccc(NC(=O)C(N)C2CCC(F)(F)CC2)cc1] | Enantiomer 2 of 2-amino-2-(4,4-difluorocyclohexyl)-N-[4-(3,5-dimethyl-imidazol-4-yl)-phenyl]acetamide | 363.5 | 0.32 (Method 3) |
| 343 | Ex. 84 | 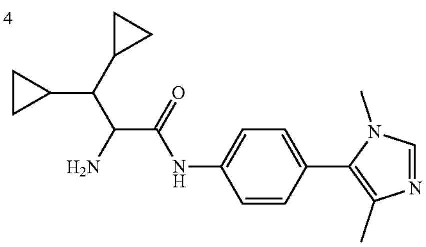 | 2-amino-3,3-dicyclopropyl-N-[4-(3,5-dimethyl-imidazol-4-yl)phenyl]propan-amide | 339.5 | 0.33 (Method 3) |
| 344 | Ex. 305 | 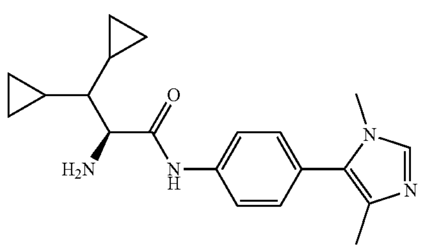 [SMILES: Cc1ncn(C)c1-c1ccc(NC(=O)[C@@H](N)C(C2CC2)C2CC2)cc1] | (2S)-2-amino-3,3-dicyclopropyl-N-[4-(3,5-dimethylimidazol-4-yl)phenyl]propan-amide | 339.5 | 0.33 (Method 3) |
| 345 | Ex. 87 | 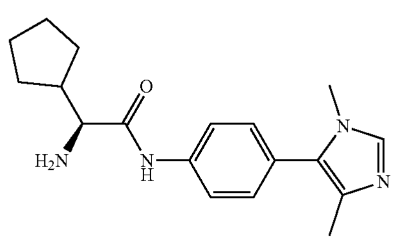 [SMILES: Cc1ncn(C)c1-c1ccc(NC(=O)[C@@H](N)C2CCCC2)cc1] | (2S)-2-amino-2-cyclopentyl-N-[4-(3,5-dimethyl-imidazol-4-yl)-phenyl]acetamide | 313.4 | 0.32 (Method 3) |
| 346 | Ex. 88 | 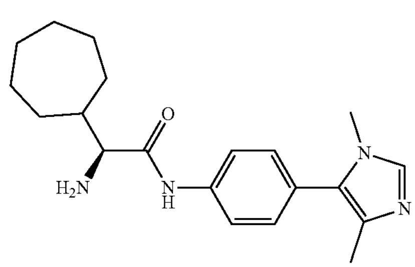 [SMILES: Cc1ncn(C)c1-c1ccc(NC(=O)[C@@H](N)C2CCCCCC2)cc1] | (2S)-2-amino-2-cycloheptyl-N-[4-(3,5-dimethyli-midazol-4-yl)-phenyl]acetamide | 341.4 | 0.40 (Method 3) |

-continued

| Prep. No. | SM | Structure | Name | Mass ion | LCMS method and RT (min) |
|---|---|---|---|---|---|
| 347 | Ex. 307 | 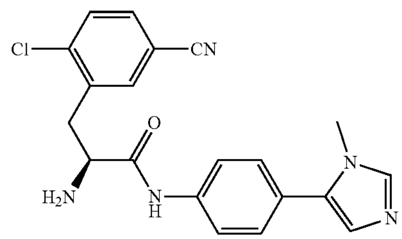 [SMILES: Cn1cncc1-c1ccc(NC(=O)[C@@H](N)Cc2cc(C#N)ccc2Cl)cc1] | (2S)-2-amino-3-(2-chloro-5-cyano-phenyl)-N-[4-(3-methylimidazol-4-yl)phenyl]propanamide | — | — |
| 348 | Ex. 101 | 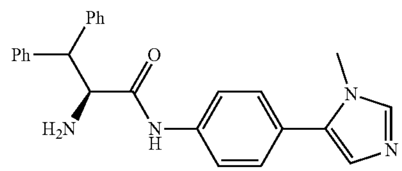 [SMILES: Cn1cncc1-c1ccc(NC(=O)[C@@H](N)C(c2ccccc2)c2ccccc2)cc1] | (2S)-2-amino-N-[4-(3-methylimidazol-4-yl)phenyl]-3,3-diphenyl-propanamide | 397.3 | 0.41 (Method 3) |
| 349 | Ex. 100 | 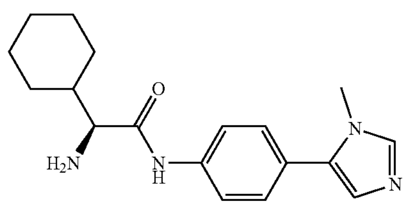 [SMILES: Cn1cncc1-c1ccc(NC(=O)[C@@H](N)C2CCCCC2)cc1] | (2S)-2-amino-2-cyclohexyl-N-[4-(3-methylimidazol-4-yl)phenyl]-acetamide | 313.3 | 0.53 (Method 3) |
| 350 | Ex. 306 | 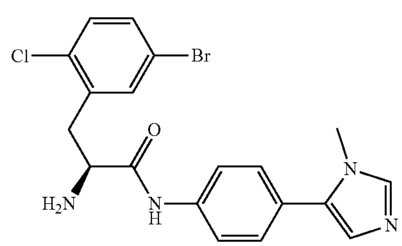 | (2S)-2-amino-3-(5-bromo-2-chloro-phenyl)-N-[4-(3-methylimidazol-4-yl)phenyl]propan-amide | 433.3 435.3 | 0.39 (Method 3) |
| 351 | Ex. 90 | 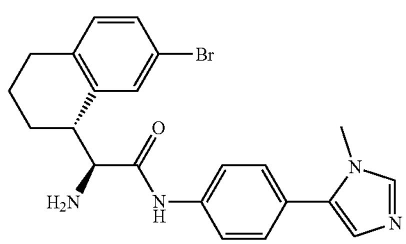 | (2S)-2-amino-2-[(1R)-7-bromotetralin-1-yl]-N-[4-(3-methyl-imidazol-4-yl)-phenyl]acetamide | 439.3 441.3 | 0.44 (Method 3) |
| 352 | Ex. 308 | 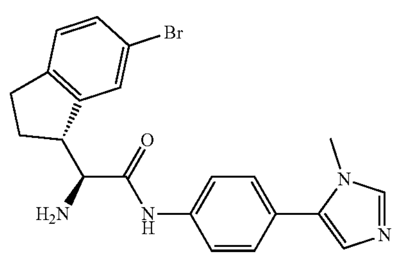 | (2S)-2-amino-2-[(1R)-6-bromoindan-1-yl]-N-[4-(3-methylimidazol-4-yl)phenyl]-acetamide | 425.4 427.4 | 0.38 (Method 3) |

-continued

| Prep. No. | SM | Structure | Name | Mass ion | LCMS method and RT (min) |
|---|---|---|---|---|---|
| 353 | Ex. 309 | 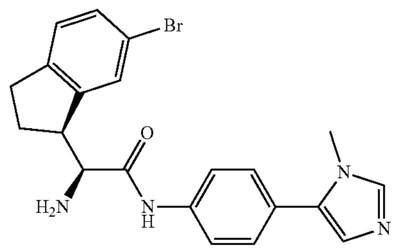 | (2S)-2-amino-2-[(1S)-6-bromoindan-1-yl]-N-[4-(3-methylimidazol-4-yl)phenyl]-acetamide | 425.3 427.3 | 0.41 (Method 3) |
| 354 | Ex. 314 | 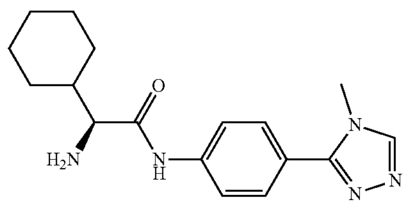 | (2S)-2-amino-2-cyclohexyl-N-[4-(4-methyl-1,2,4-triazol-3-yl)-phenyl]acetamide | 313.45 | 0.37 (Method 3) |
| 355 | Ex. 315 | 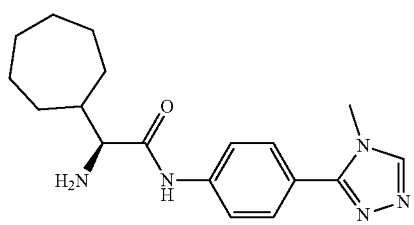 | (2S)-2-amino-2-cycloheptyl-N-[4-(4-methyl-1,2,4-triazol-3-yl)-phenyl]acetamide | 328.4 | 0.41 (Method 3) |
| 356 | Ex. 316 | 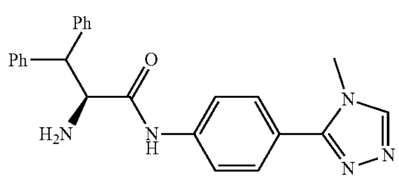 | (2S)-2-amino-N-[4-(4-methyl-1,2,4-triazol-3-yl)phenyl]-3,3-diphenyl-propanamide | 398.3 | 0.45 (Method 3) |
| 357 | Ex. 317 | 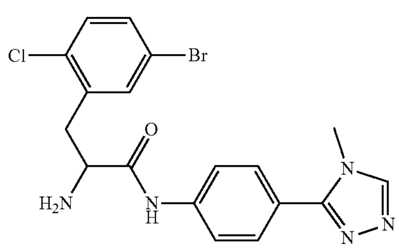 | 2-amino-3-(5-bromo-2-chloro-phenyl)-N-[4-(4-methyl-1,2,4-triazol-3-yl)phenyl]propan-amide | 434.1 436.1 | 0.48 (Method 3) |
| 358 | Ex. 318 | 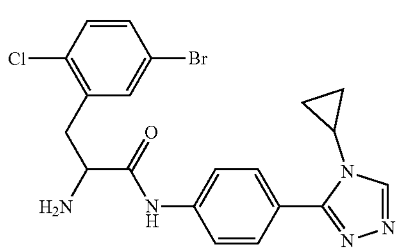 | 2-amino-3-(5-bromo-2-chloro-phenyl)-N-[4-(4-cyclopropyl-1,2,4-tiazol-3-yl)phenyl]propan-amide | 460.1 462.1 | 0.52 (Method 3) |

-continued

| Prep. No. | SM | Structure | Name | Mass ion | LCMS method and RT (min) |
|---|---|---|---|---|---|
| 359 | Ex. 322 | 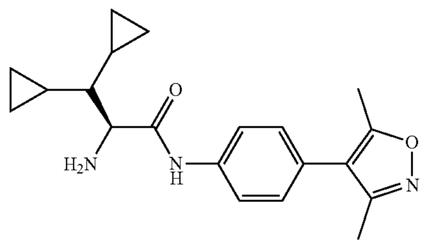 | (2S)-2-amino-3,3-dicyclopropyl-N-[4-3,5-dimethylisoxazol-4-yl)phenyl]propan-amide | 340 | 1.89 (Method 5, ACQUITY UPLC BEH C18 column, 0.1% FA in water with MeCN) |
| 360 | Ex. 323 | 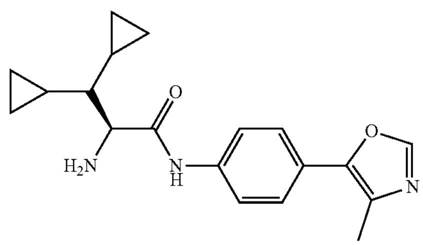 | (2S)-2-amino-3,3-dicyclopropyl-N-[4-(4-methyloxazol-5-yl)phenyl]propan-amide | 326 | 1.39 (Method 5, ACQUITY UPLC BEH C18 column, 0.1% FA in water with MeCN) |
| 361 | Ex. 324 | 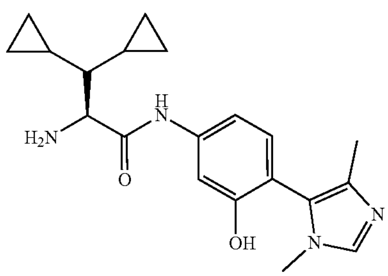 [SMILES: Cc1ncn(C)c1-c1ccc(NC(=O)[C@@H](N)C(C2CC2)C2CC2)cc1O] | (2S)-2-amino-3,3-dicyclopropyl-N-[4-(3,5-dimethylimidazol-4-yl)-3-hydroxy-phenyl]propan-amide | 355.4 | 0.35 (Method 3) |
| 362 | Ex. 312 | 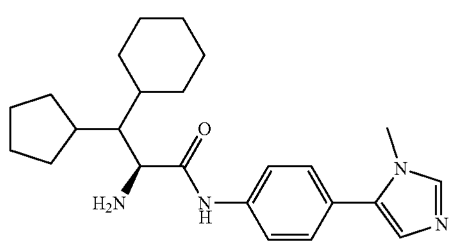 | Diastereomer 1 of (2S)-2-amino-3-cyclohexyl-3-cyclopentyl-N-[4-(3-methylimidazol-4-yl)phenyl]-propanamide | 395.6 | 0.52 (Method 3) |
| 363 | Ex. 313 | 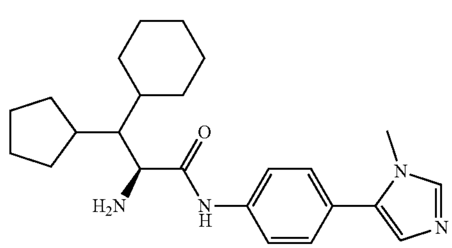 | Diastereomer 2 of (2S)-2-amino-3-cyclohexyl-3-cyclopentyl-N-[4-(3-methylimidazol-4-yl)phenyl]-propanamide | 395.6 | 0.55 (Method 3) |

-continued

| Prep. No. | SM | Structure | Name | Mass ion | LCMS method and RT (min) |
|---|---|---|---|---|---|
| 364 | Ex. 325 | 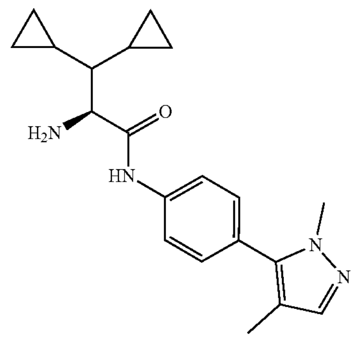 [SMILES: Cc1cnn(C)c1-c1ccc(NC(=O)[C@@H](N)C(C2CC2)C2CC2)cc1] | (2S)-2-amino-3,3-dicyclopropyl-N-[4-(2,4-dimethylpyrazol-3-yl)phenyl]-propanamide | 339 | 1.42 min (Method 5) (ACQUITY UPLC BEH C18 column, 0.1% FA in water with MeCN). |
| 365 | Ex. 326 | 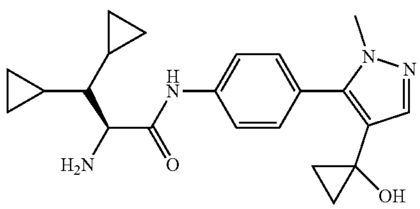 | (2S)-2-amino-3,3-dicyclopropyl-N-[4-[4-(1-hydroxycyclopropyl)-2-methyl-pyrazol-3-yl]phenyl]-propanamide | 381 | 1.75 min (Method 5) (ACQUITY BEH C18 column, 0.05% FA in water with MeCN). |
| 366 | Ex. 327 | 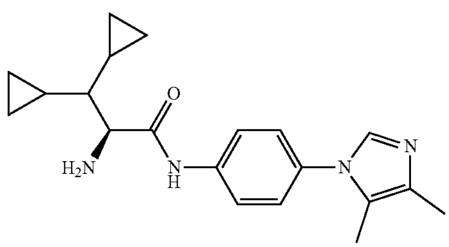 | (2S)-2-amino-3,3-dicyclopropyl-N-[4-(4,5-dimethyl-imidazol-1-yl)phenyl]propan-amide | 339 | 1.87 min (Method 5) (ACQUITY BEH C18 column, 0.5% TFA in water with MeCN) |
| 367 | Ex. 328 | 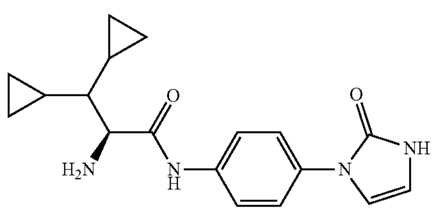 | (2S)-2-amino-3,3-dicyclopropyl-N-[4-(2-oxo-1H-imidazol-3-yl)phenyl]-propanamide | 326 | 1.86 min (Method 5) (ACQUITY BEH C18 column, 0.5% FA in water with MeCN) |
| 368 | Ex. 329 | 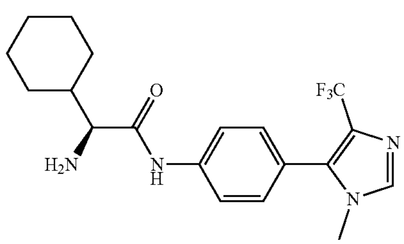 | (2S)-2-amino-2-cyclohexyl-N-[4-[3-methyl-5-(trifluoromethyl)imidazol-4-yl]-phenyl]acetamide | — | — |
| 369 | Ex. 330 | 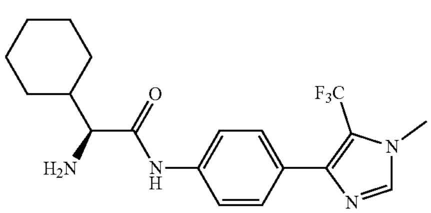 | (2S)-2-amino-2-cyclohexyl-N-[4-[1-methyl-5-(trifluoromethyl)imidazol-4-yl]-phenyl]acetamide | — | — |

| Prep. No. | SM | Structure | Name | Mass ion | LCMS method and RT (min) |
|---|---|---|---|---|---|
| 370 | Ex. 331 | 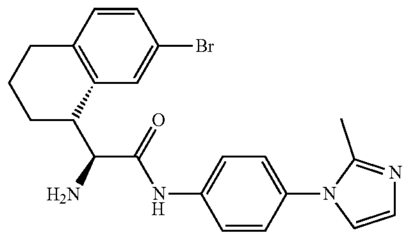 | (2S)-2-amino-2-[(1R)-7-bromotetralin-1-yl]-N-[4-(2-methyl-imidazol-1-yl)-phenyl]acetamide | 439.1 441.1 | 0.66 (Method 3) |

Preparations 371-373

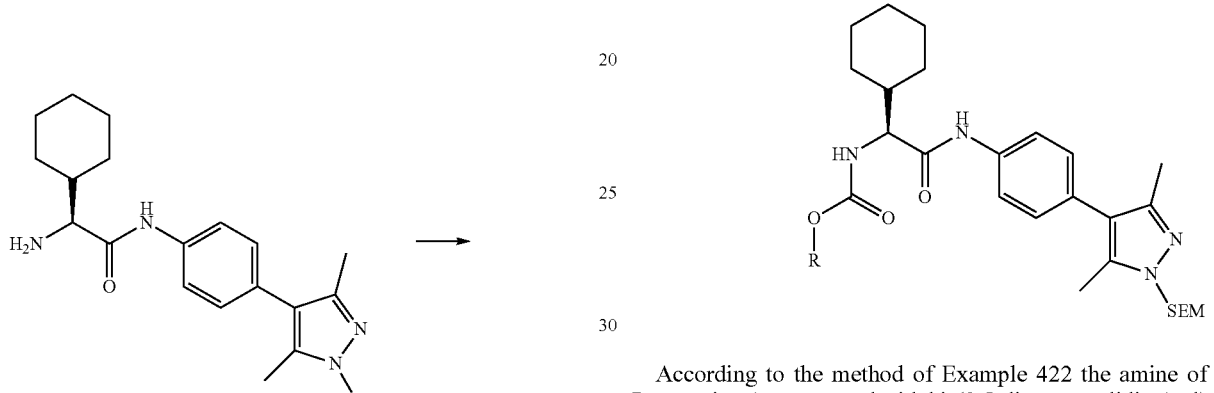

According to the method of Example 422 the amine of Preparation 4 was reacted with bis(2,5-dioxopyrrolidin-1-yl) carbonate and the appropriate alcohol to give Preparations 371-373.

| Prep. No. | Structure | Name | Mass ion | LCMS method and retention time (min) |
|---|---|---|---|---|
| 371 | 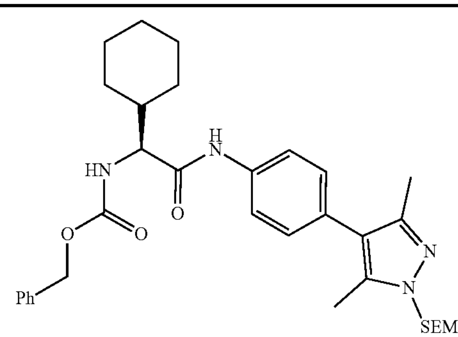 | Benzyl N-[(1S)-1-cyclohexyl-2-[4-[3,5-dimethyl-1-(2-trimethylsilylethoxymethyl)pyrazol-4-yl]anilino]-2-oxo-ethyl]carbamate | 591.7 | 1.01 (Method 3) |
| 372 | 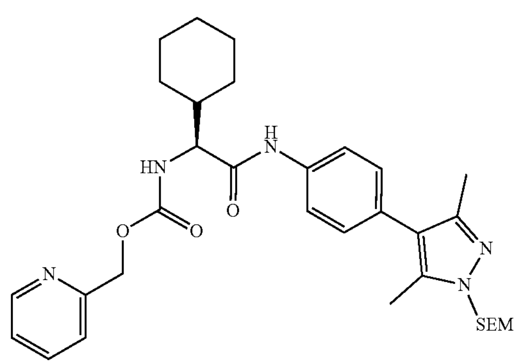 [SMILES: Cc1nn(COCC[Si](C)(C)C)c(C)c1-c1ccc(NC(=O)[C@@H](NC(=O)OCc2ccccn2)C2CCCCC2)cc1] | 3-Pyridylmethyl N-[(1S)-1-cyclohexyl-2-[4-[3,5-dimethyl-1-(2-trimethylsilylethoxymethyl)pyrazol-4-yl]anilino]-2-oxo-ethyl]carbamate | 592.7 | 0.92 (Method 3) |

| Prep. No. | Structure | Name | Mass ion | LCMS method and retention time (min) |
|---|---|---|---|---|
| 373 | 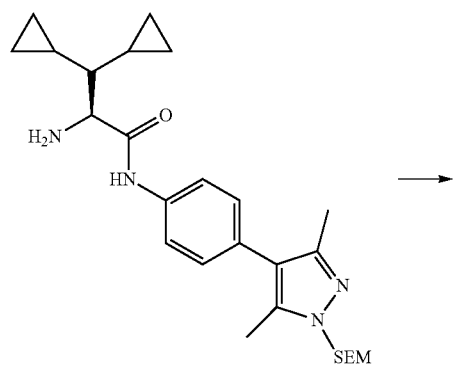 | 2-Pyridylmethyl N-[(1S)-1-cyclohexyl-2-[4-[3,5-dimethyl-1-(2-trimethylsilylethoxymethyl)pyrazol-4-yl]anilino]-2-oxo-ethyl]carbamate | 592.8 | 0.94 (Method 3) |

Preparation 374

Cyclobutyl N-[(1S)-1-(dicyclopropylmethyl)-2-[4-[3,5-dimethyl-1-(2-trimethylsilylethoxymethyl)pyrazol-4-yl]anilino]-2-oxo-ethyl]carbamate

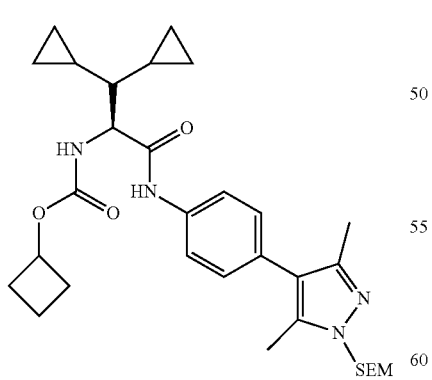

According to the method of Example 422 the amine of Preparation 59 was reacted with bis(2,5-dioxopyrrolidin-1-yl) carbonate and cyclobutanol to give the title compound. LCMS (METHOD 3) (ES): m/z 567.3 [M+H]⁺, RT=0.99 min.

Preparation 375

4-[Tert-butyl(dimethyl)silyl]oxybutan-1-ol

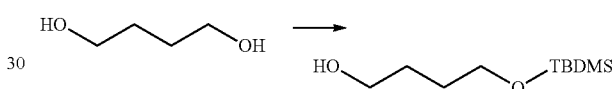

Butane-1,4-diol (500 mg, 5.55 mmol) was dissolved in DMF (5 mL). Imidazole (755 mg, 11.1 mmol) was added followed by tert-butylchlorodimethylsilane (836 mg, 5.55 mmol) at 0° C. The reaction mixture was stirred at room temperature for 16 h then the reaction mixture was partitioned between water (25 mL) and EtOAc (25 mL). The organic layer was separated, dried over anhydrous sodium sulfate and filtered. The filtrate was concentrated in vacuo to afford the title compound (350 mg, 30%) as a colourless liquid. 1H NMR (400 MHz, CDCl$_3$) δ 4.36-4.33 (t, J=5.2 Hz, 1H), 3.59-3.55 (t, J=6.4 Hz, 2H), 3.4-3.36 (q, J=6.4 Hz, 2H), 1.47-1.41 (m, 4H), 0.86 (s, 9H), 0.02 (s, 6H).

Preparation 376

4-[Tert-butyl(dimethyl)silyl]oxybutyl (4-nitrophenyl) carbonate

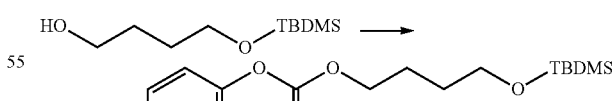

The alcohol of Preparation 375 (100 mg, 0.48 mmol) was dissolved in DCM (5 mL). 4-nitrophenyl carbonochloridate (211 mg, 0.55 mmol) and triethylamine (123.7 mg, 0.48 mmol) were added sequentially at 0° C. The resulting reaction mixture was stirred at room temperature for 2 h. On completion, the reaction mixture was diluted with DCM (20 mL) and washed with cold water (15 mL), dried over sodium sulfate, filtered and concentrated in vacuo to afford crude residue. The crude compound was purified by column chromatography on silica gel (100-200 mesh) by elution with 10% EtOAc in hexane to give the title compound (100 mg, 57%) as a colourless liquid. 1H NMR (400 MHz, CDCl₃) δ 8.28 (d, J=9.6 Hz, 2H), 7.39 (d, J=9.2 Hz, 2H), 4.34-4.31 (t, J=6.4 Hz 2H), 3.69-3.65 (t, J=6.0 Hz, 2H), 1.86-1.82 (m, 2H), 1.66-1.63 (m, 2H), 0.90 (s, 9H), 0.06 (s, 6H).

Preparation 377

4-[Tert-butyl(dimethyl)silyl]oxybutyl N-[(1S)-1-(dicyclopropylmethyl)-2-[4-[3,5-dimethyl-1-(2-trimethylsilylethoxymethyl)pyrazol-4-yl]anilino]-2-oxo-ethyl]carbamate

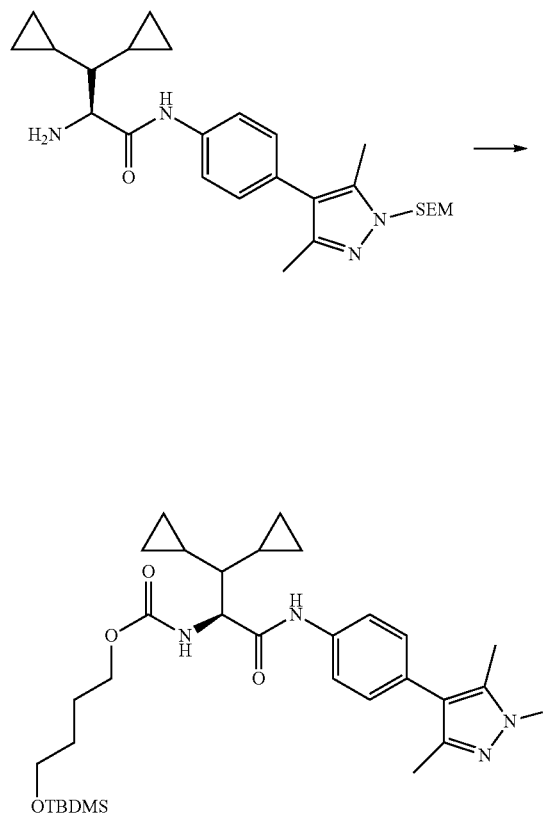

The carbonate of Preparation 376 (50 mg, 0.245 mmol) was dissolved in THF (1.0 mL). DIPEA (0.13 mL, 0.735 mmol) and the amine of Preparation 59 (115 mg, 0.245 mmol) were added sequentially at 0° C. The reaction mixture was stirred at room temperature for 16 h. The reaction mixture was concentrated in vacuo to get the residue. This was partitioned between water and EtOAc (20 mL). The organic layer was separated, dried over anhydrous sodium sulfate, filtered and concentrated in vacuo to afford the title compound (50 mg) as a light brown oil. This compound was used as such in the next step without further purification. LCMS (ESI): m/z: 699 [M+H⁺]; RT=3.49 min and 4 min (ACQUITY BEH C18 column, 0.05% formic acid in water with MeCN).

Preparation 378

Ditert-butyl [4-[4-[[(2S)-3,3-dicyclopropyl-2-[(2-ethylpyrazole-3-carbonyl)amino]propanoyl]amino]phenyl]-3,5-dimethyl-pyrazol-1-yl]methyl phosphate

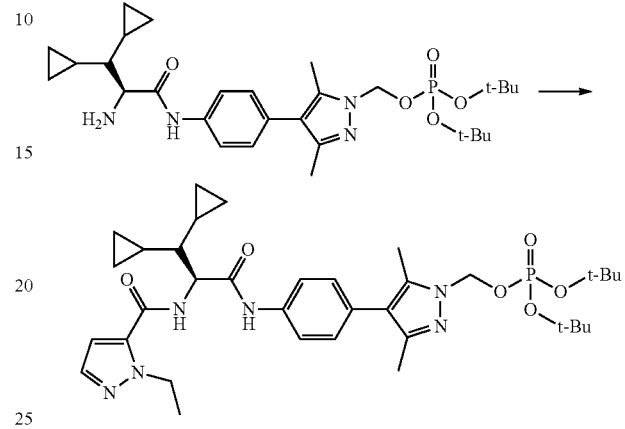

To a solution of 2-ethylpyrazole-3-carboxylic acid (2.884 g, 20.58 mmol) and the amine of Preparation 56 (10.49 g, 18.71 mmol) in MeCN (50 mL,) was added EDC (4.304 g, 22.45 mmol) at room temperature. The solution was stirred at room temperature for 1 hour then the mixture was concentrated in vacuo to half of the volume. To the residue was added water (200 mL) and the mixture was stirred for 15 min. The solid material was filtered and washed with water then dissolved in EtOAc (200 mL). The solution was washed with brine, dried over MgSO₄ and concentrated in vacuo. The crude product was purified by column chromatography (silica, eluting with EtOAc containing 0.2% Et₃N) to give the title compound (9.6 g, 75%) as a white foam. 1H NMR (600 MHz, Chloroform-d) δ 8.04 (s, 1H), 7.59-7.54 (m, 2H), 7.49 (d, J=2.1 Hz, 1H), 7.22-7.18 (m, 2H), 7.10 (d, J=8.2 Hz, 1H), 6.60 (d, J=2.0 Hz, 1H), 5.82 (d, J=9.4 Hz, 2H), 4.83 (dd, J=8.2, 5.3 Hz, 1H), 4.60 (q, J=7.3 Hz, 2H), 2.34 (s, 3H), 2.22 (s, 3H), 1.46 (s, 18H), 1.44 (t, J=7.2 Hz, 3H), 0.99-0.81 (m, 3H), 0.70-0.62 (m, 1H), 0.61-0.50 (m, 3H), 0.47-0.33 (m, 2H), 0.31-0.20 (m, 2H); LCMS (METHOD 3) (ES): m/z 683.5 [M+H]⁺, RT=0.85 min.

Preparation 379

[(2S)-2-[5-[[(1S)-2,2-Dicyclopropyl-1-[[4-[1-(ditert-butoxyphosphoryloxymethyl)-3,5-dimethyl-pyrazol-4-yl]phenyl]carbamoyl]ethyl]carbamoyl]pyrazol-1-yl]propyl] acetate

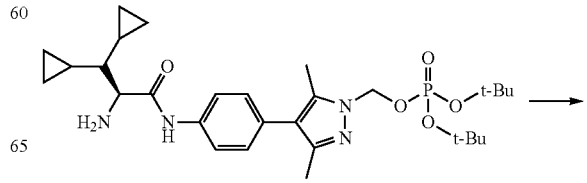

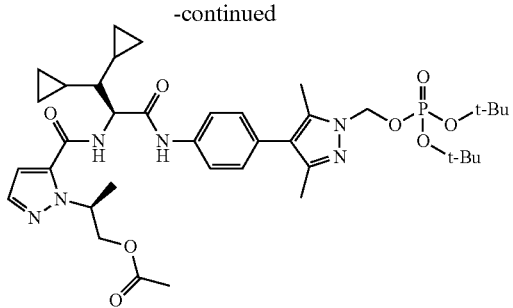

Oxalyl chloride (0.338 mL, 508 mg, 4.00 mmol) was added slowly to a solution of the acid of Preparation 196 (424 mg, 2.00 mmol) and DMF (1 drop) in DCM (9 mL) at room temperature. The mixture was stirred for 30 min at room temperature then evaporated under reduced pressure. Toluene (10 mL) was added and removed in vacuo. The residue was dissolved in DCM (5 mL) and added slowly to a stirred solution of the amine of Preparation 56 (1.00 g, 1.78 mmol) and DIPEA (2 mL, 1.50 g, 11 mmol) in DCM (15 mL) at 5° C. After 10 min the reaction mixture was washed with sat. aq. NaHCO₃ (10 mL), dried (Na₂SO₄) and evaporated. The residue was purified by column chromatography (silica, eluting with EtOAc:heptane) to give the title compound (850 mg, 63%) as a pale yellow solid. 1H NMR (600 MHz, Chloroform-d) δ 8.05 (s, 1H), 7.59-7.55 (m, 2H), 7.55 (d, J=2.0 Hz, 1H), 7.22-7.16 (m, 2H), 7.12 (d, J=8.3 Hz, 1H), 6.60 (d, J=2.0 Hz, 1H), 5.82 (d, J=9.4 Hz, 2H), 5.65 (q, J=6.9 Hz, 1H), 4.83 (dd, J=8.2, 5.2 Hz, 1H), 4.52-4.30 (m, 2H), 2.34 (s, 3H), 2.22 (s, 3H), 1.96 (s, 3H), 1.51 (d, J=6.9 Hz, 3H), 1.46 (s, 18H), 0.99-0.80 (m, 3H), 0.71-0.61 (m, 1H), 0.61-0.49 (m, 3H), 0.47-0.34 (m, 2H), 0.32-0.23 (m, 2H); LCMS (METHOD 3) (ES): m/z 755.6 [M+H]⁺, RT=0.85 min.

Preparation 380

[4-[4-[[(2S)-3,3-Dicyclopropyl-2-[(2-isopropylpyrazole-3-carbonyl)amino]propanoyl]-amino]phenyl]-3,5-dimethyl-pyrazol-1-yl]methyl (2S)-2-(tert-butoxycarbonylamino)-3-methyl-butanoate

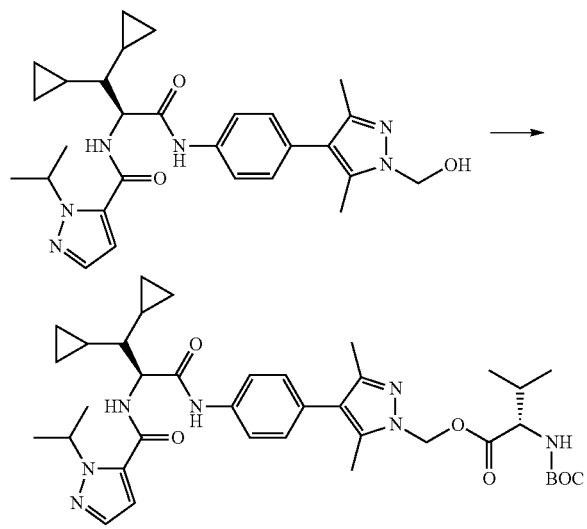

To a solution of the compound of Example 484 (59 mg, 0.117 mmol) in DCM (1 mL) and NMP (0.20 mL) was added (2S)-2-(tert-butoxycarbonylamino)-3-methyl-butanoic acid (30.5 mg, 0.140 mmol), DMAP (3 mg, 0.025 mmol) and diisopropyl carbodiimide (29.5 mg, 0.036 mL, 0.234 mmol). The mixture was stirred at room temperature for 1.5 hours then concentrated in vacuo. The resulting residue was purified by acidic prep. HPLC to give the title compound (57 mg, 69%). 1H NMR (400 MHz, DMSO) δ 10.23 (s, 1H), 8.44 (d, J=8.8 Hz, 1H), 7.75-7.60 (m, 2H), 7.50 (d, J=1.9 Hz, 1H), 7.23 (dd, J=13.4, 8.2 Hz, 3H), 6.93 (d, J=2.0 Hz, 1H), 6.08 (d, J=11.2 Hz, 1H), 5.99 (d, J=11.1 Hz, 1H), 5.48-5.34 (m, 1H), 4.81 (t, J=8.2 Hz, 1H), 3.82 (t, J=7.2 Hz, 1H), 2.25 (s, 3H), 2.13 (s, 3H), 2.04-1.89 (m, 1H), 1.48-1.21 (m, 15H), 0.96-0.71 (m, 9H), 0.55-0.09 (m, 8H); LCMS (METHOD 3) (ES): m/z 704.6 [M+H]⁺, RT=0.90 min.

EXAMPLES

Example 1

N-[(1S)-1-cyclohexyl-2-[4-(3,5-dimethyl-1H-pyrazol-4-yl)anilino]-2-oxo-ethyl]-2-methyl-pyrazole-3-carboxamide

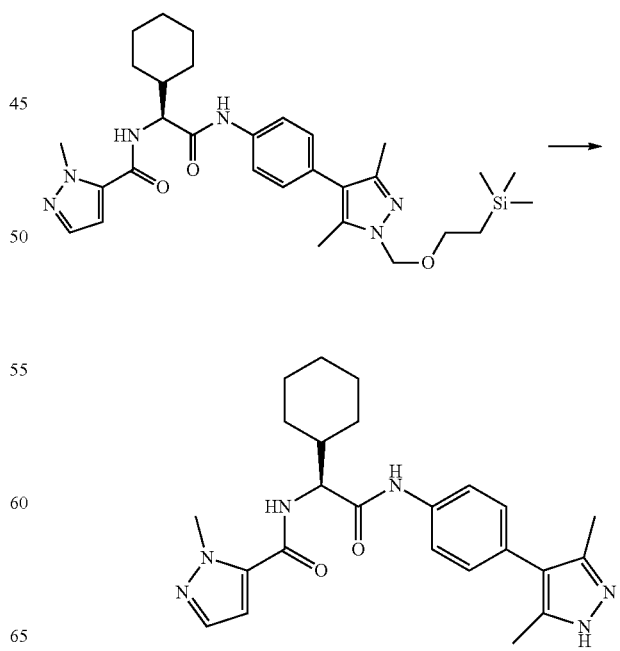

TFA (2 mL) was added to a stirred solution of the compound of Preparation 5 (134 mg, 0.237 mmol) in DCM (2 mL) and the reaction was stirred at 40° C. for 30 min. The reaction was concentrated in vacuo to afford the crude compound which was diluted with DMF (1 mL) and purified by acidic HPLC (10-100% MeCN in 0,1% HCOOH/H2O over 9 min) to afford the title compound as a colourless solid (103 mg, 100%).1H NMR (600 MHz, DMSO-d6) δ 12.23 (s, 1H), 10.21 (s, 1H), 8.48 (d, J=8.3 Hz, 1H), 7.75-7.58 (m, 2H), 7.46 (d, J=2.1 Hz, 1H), 7.29-7.13 (m, 2H), 7.07 (d, J=2.1 Hz, 1H), 4.41 (t, J=8.6 Hz, 1H), 4.03 (s, 3H), 2.20 (s, 3H), 2.14 (s, 3H), 1.88-1.83 (m, 2H), 1.75-1.70 (m, 2H), 1.65-1.60 (m, 2H), 1.25-1.15 (m, 4H), 1.05-1.00 (m, 1H); LCMS (ES): m/z 435.251 [M+H]+; RT=2.14 min.

Examples 2-75, 102-133 and 141-300

Examples 2-75, 102-133 and 141-300 were synthesised according to the methods of Preparations 3 to 5 and Example 1 from the appropriate Boc protected amino acid, the compound of Preparation 2 and the required carboxylic acid. The Boc protected amino acids are either commercially available, known in the literature or can be synthesised as outlined in the indicated Preparation.

An arrow denotes the point of attachment of the substituent $R_x$ or $R_y$ to the parent molecule.

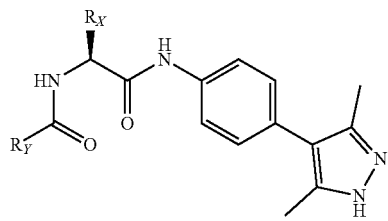

| Ex. No. | $R_X$ | $R_Y$ | Name | Mass ion | LCMS retention time (min) |
|---|---|---|---|---|---|
| 2 | Ph, Ph | | N-[(1S)-1-benzhydryl-2-[4-(3,5-dimethyl-1H-pyrazol-4-yl)anilino]-2-oxo-ethyl]-2-methyl-pyrazole-3-carboxamide | 519.251 | 2.19 |
| 3 | cycloheptyl | | N-[(1S)-1-cycloheptyl-2-[4-(3,5-dimethyl-1H-pyrazol-4-yl)anilino]-2-oxo-ethyl]-2-methyl-pyrazole-3-carboxamide | 449.266 | 2.22 |
| 4 | (1R)-6-bromoindanyl (Preparation 14) | | N-[(1S)-1-[(1R)-6-bromoindan-1-yl]-2[4-(3,5-dimethyl-1H-pyrazol-4-yl)anilino]-2-oxo-ethyl]-2-methyl-pyrazole-3-carboxamide | 547.146 | 2.24 |
| 5 | (1S)-6-bromoindanyl (Preparation 17) | | N-[(1S)-1-[(1S)-6-bromoindan-1-yl]-2[4-(3,5-dimethyl-1H-pyrazol-4-yl)anilino]-2-oxo-ethyl]-2-methyl-pyrazole-3-carboxamide | 547.146 | 2.27 |
| 6 | (1S)-7-bromotetralinyl (Preparation 24) | | N-[(1S)-1-[(1S)-7-bromotetralin-1-yl]-2-[4(3,5-dimethyl-1H-pyrazol-4-yl)anilino]-2-oxo-ethyl]-2-methyl-pyrazole-3-carboxamide | 561.161 | 2.32 |
| 7 | 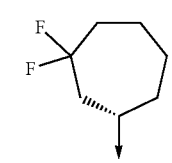 Preparation 40 | | N-[(1S)-1-[(1S)-3,3-difluorocycloheptyl]-2-[4-(3,5-dimethyl-1H-pyrazol-4-yl)anilino]-2-oxo-ethyl]-2-methyl-pyrazole-3-carboxamide | 485.247 | 2.20 |

-continued

| Ex. No. | R_X | R_Y | Name | Mass ion | LCMS retention time (min) |
|---|---|---|---|---|---|
| 8 | 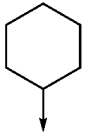 | 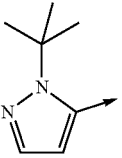 | 2-tert-butyl-N-[(1S)-1-cyclohexyl-2-[4-(3,5-dimethyl-1H-pyrazol-4-yl)anilino]-2-oxo-ethyl]pyrazole-3-carboxamide | 477.298 | 2.35 |
| 9 | 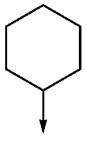 | 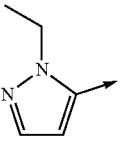 | N-[(1S)-1-cyclohexyl-2-[4-(3,5-dimethyl-1H-pyrazol-4-yl)anilino]-2-oxo-ethyl]-2-ethyl-pyrazole-3-carboxamide | 449.267 | 2.20 |
| 10 | 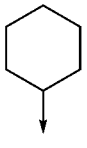 | 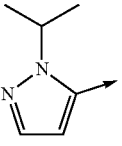 | N-[(1S)-1-cyclohexyl-2-[4-(3,5-dimethyl-1H-pyrazol-4-yl)anilino]-2-oxo-ethyl]-2-isopropyl-pyrazole-3-carboxamide | 463.283 | 2.27 |
| 11 | 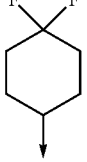<br>Preparation 9 | 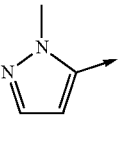 | N-[(1S)-1-(4,4-difluorocyclohexyl)-2-[4-(3,5-dimethyl-1H-pyrazol-4-yl)anilino]-2-oxo-ethyl]-2-methyl-pyrazole-3-carboxamide | 471.232 | 2.13 |
| 12 | <br>Preparation 9 | 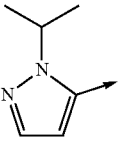 | N-[(1S)-1-(4,4-difluorocyclohexyl)-2-[4-(3,5-dimethyl-1H-pyrazol-4-yl)anilino]-2-oxo-ethyl]-2-isopropyl-pyrazole-3-carboxamide | 499.264 | 2.20 |
| 13 | 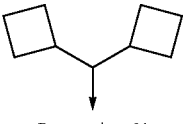<br>Preparation 64 | 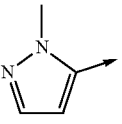 | N-[(1S)-1-[di(cyclobutyl)methyl]-2-[4-(3,5-dimethyl-1H-pyrazol-4-yl)anilino]-2-oxo-ethyl]-2-methyl-pyrazole-3-carboxamide | 475.283 | 2.35 |
| 14 | 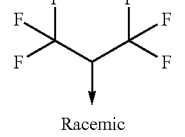<br>Racemic | 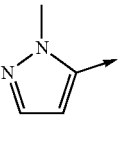 | N-[1-[4-(3,5-dimethyl-1H-pyrazol-4-yl)phenyl]carbamoyl]-3,3,3-trifluoro-2-(trifluoromethyl)propyl]-2-methyl-pyrazole-3-carboxamide | 503.164 | 2.18 |
| 15 | 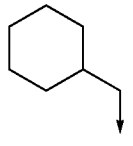 | 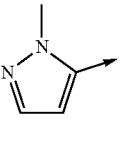 | N-[(1S)-1-(cyclohexylmethyl)-2-[4-(3,5-dimethyl-1H-pyrazol-4-yl)anilino]-2-oxo-ethyl] 2-methyl-pyrazole-3-carboxamide | 449.267 | 2.23 |
| 16 | 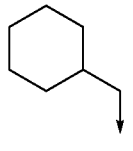 | 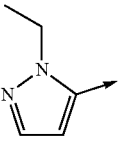 | N-[(1S)-1-(cyclohexylmethyl)-2-[4-(3,5-dimethyl-1H-pyrazol-4-yl)anilino]-2-oxo-ethyl]-2-ethyl-pyrazole-3-carboxamide | 463.282 | 2.20 |

| Ex. No. | R_X | R_Y | Name | Mass ion | LCMS retention time (min) |
|---|---|---|---|---|---|
| 17 | 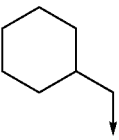 | 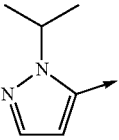 | N-[(1S)-1-(cyclohexylmethyl)-2-[4-(3,5-dimethyl-1H-pyrazol-4-yl)anilino]-2-oxo-ethyl]-2-isopropyl-pyrazole-3-carboxamide | 477.298 | 2.37 |
| 18 | 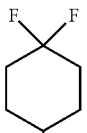<br>Preparation 14 | 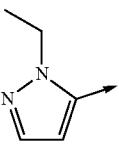 | N-[(1S)-1-(4,4-difluorocyclohexyl)-2-[4-(3,5-dimethyl-1H-pyrazol-4-yl)anilino]-2-oxo-ethyl]-2-ethyl-pyrazole-3-carboxamide | 485.248 | 2.13 |
| 19 | 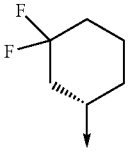<br>Preparation 42 | 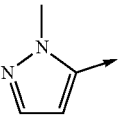 | N-[(1S)-1-[(1S)-3,3-difluorocyclohexyl]-2-[4-(3,5-dimethyl-1H-pyrazol-4-yl)anilino]-2-oxo-ethyl]-2-methyl-pyrazole-3-carboxamide | 471.233 | 2.09 |
| 20 | 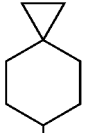<br>Racemic<br>Preparation 69 | 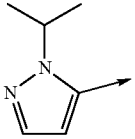 | N-[2-[4-(3,5-dimethyl-1H-pyrazol-4-yl)anilino]-2-oxo-1-spiro[2.5]octan-6-yl-ethyl]-2-isopropyl-pyrazole-3-carboxamide | 489.299 | 2.36 |
| 21 | 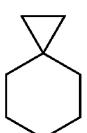<br>Racemic<br>Preparation 69 | 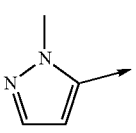 | N-[2-[4-(3,5-dimethyl-1H-pyrazol-4-yl)anilino]-2-oxo-1-spiro[2.5]octan-6-yl-ethyl]-2-methyl-pyrazole-3-carboxamide | 461.267 | 2.22 |
| 22 | 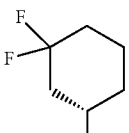<br>Preparation 42 | 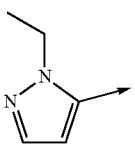 | N-[(1S)-1-[(1S)-3,3-difluorocyclohexyl]-2-[4-(3,5-dimethyl-1H-pyrazol-4-yl)anilino]-2-oxo-ethyl]-2-ethyl-pyrazole-3-carboxamide | 485.248 | 2.15 |
| 23 | 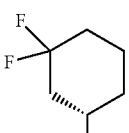<br>Preparation 42 | 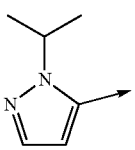 | N-[(1S)-1-[(1S)-3,3-difluorocyclohexyl]-2-[4-(3,5-dimethyl-1H-pyrazol-4-yl)anilino]-2-oxo-ethyl]-2-isopropyl-pyrazole-3-carboxamide | 499.264 | 2.21 |

-continued

| Ex. No. | R$_X$ | R$_Y$ | Name | Mass ion | LCMS retention time (min) |
|---|---|---|---|---|---|
| 24 | 2-chlorobenzyl | 1-isopropyl-pyrazol-5-yl | N-[(1S)-1-[2-chlorophenyl)methyl]-2-[4-(3,5-dimethyl-1H-pyrazol-4-yl)anilino]-2-oxo-ethyl]-2-isopropyl-pyrazole-3-carboxamide | 505.212 | 2.27 |
| 25 | 2-chlorobenzyl | 1-methyl-pyrazol-5-yl | N-[(1S)-1-[2-chlorophenyl)methyl]-2-[4-(3,5-dimethyl-1H-pyrazol-4-yl)anilino]-2-oxo-ethyl]-2-methyl-pyrazole-3-carboxamide | 477.181 | 2.14 |
| 26 | (4R)-chroman-4-yl (1:3 mixture of diastereomers, Preparation 36) | 1-methyl-pyrazol-5-yl | 1:3 mixture of N-[(1S)-1-[(4R)-chroman-4-yl]-2-[4-(3,5-dimethyl-1H-pyrazo 4-yl)anilino]-2-oxo-ethyl]-2-methyl-pyrazole-3-carboxamide and N-[(1R)-1-[(4R)-chroman-4-yl]-2-[4-(3,5-dimethyl-1H-pyrazol-4-yl)anilino]-2-oxo-ethyl]-2-methyl-pyrazole-3-carboxamide | 485.231 | 2.11 |
| 27 | cyclohexyl | 1-cyclopropyl-pyrazol-5-yl | N-[(1S)-1-cyclohexyl-2-[4-(3,5-dimethyl-1H-pyrazol-4-yl)anilino]-2-oxo-ethyl]-2-cyclopropyl-pyrazole-3-carboxamide | 461.267 | 2.22 |
| 28 | cyclohexyl | 1-(difluoromethyl)-pyrazol-5-yl | N-[(1S)-1-cyclohexyl-2-[4-(3,5-dimethyl-1H-pyrazol-4-yl)anilino]-2-oxo-ethyl]-2-(difluoromethyl)pyrazole-3-carboxamide | 471.233 | 2.25 |
| 29 | cyclohexyl | 1-(2,2,2-trifluoroethyl)-pyrazol-5-yl | N-[(1S)-1-cyclohexyl-2-[4-(3,5-dimethyl-1H-pyrazol-4-yl)anilino]-2-oxo-ethyl]-2-(2,2,2-(trifluoroethyl)pyrazole-3-carboxamide | 503.239 | 2.30 |
| 30 | dicyclopropylmethyl (Racemic, Preparation 27) | 1-methyl-pyrazol-5-yl | N-[1-(dicyclopropylmethyl)-2-[4-(3,5-dimethyl-1 pyrazol-4-yl)anilino]-2-oxo-ethyl]-2-methyl-pyrazole-3-carboxamide | 447.252 | 2.12 |
| 31 | dicyclopropylmethyl (Racemic, Preparation 27) | 1-isopropyl-pyrazol-5-yl | N-[1-(dicyclopropylmethyl)-2-[4-(3,5-dimethyl-1H-pyrazol-4-yl)anilino]-2-oxo-ethyl]-2-isopropyl-pyrazole-3-carboxamide | 475.283 | 2.25 |

-continued

| Ex. No. | R<sub>X</sub> | R<sub>Y</sub> | Name | Mass ion | LCMS retention time (min) |
|---|---|---|---|---|---|
| 32 | dicyclopropylmethyl, Enantiomer 1# | 1-isopropyl-pyrazol-5-yl | Enantiomer 1 of N-[1-(dicyclopropylmethyl)-2-[4-(3,5-dimethyl-1H-pyrazol-4-yl)anilino]-2-oxo-ethyl]-2-isopropyl-pyrazole-3-carboxamide (S)-Enantiomer | 475.283 | 2.25 |
| 33 | dicyclopropylmethyl, Enantiomer 2# | 1-isopropyl-pyrazol-5-yl | Enantiomer 2 of N-[1-(dicyclopropylmethyl)-2-[4-(3,5-dimethyl-1H-pyrazol-4-yl)anilino]-2-oxo-ethyl]-2-isopropyl-pyrazole-3-carboxamide (R)-Enantiomer | 475.283 | 2.25 |
| 34 | (4S)-chroman-4-yl, Preparation 35 | 1-methyl-pyrazol-5-yl | N-[(1S)-1-[(4S)-chroman-4-yl]-2-[4-(3,5-dimethyl-1H-pyrazol-4-yl)anilino]-2-oxo-ethyl]-2-methyl-pyrazole-3-carboxamide | 485.231 | 2.11 |
| 35 | di(cyclobutyl)methyl, Racemic | 1-ethyl-pyrazol-5-yl | N-[1-[di(cyclobutyl)methyl]-2-[4-(3,5-dimethyl-1H-pyrazol-4-yl)anilino]-2-oxo-ethyl]-2-ethyl-pyrazole-3-carboxamide | 489.299 | 2.42 |
| 36 | di(cyclobutyl)methyl, Enantiomer 1† | 1-ethyl-pyrazol-5-yl | Enantiomer 1 of N-[1-[di(cyclobutyl)methyl]-2-[4-(3,5-dimethyl-1H-pyrazol-4-yl)anilino]-2-oxo-ethyl]-2-ethyl-pyrazole-3-carboxamide (S) enantiomer | 489.299 | 2.42 |
| 37 | di(cyclobutyl)methyl, Enantiomer 2† | 1-ethyl-pyrazol-5-yl | Enantiomer 2 of N-[1-[di(cyclobutyl)methyl]-2-[4-(3,5-dimethyl-1H-pyrazol-4-yl)anilino]-2-oxo-ethyl]-2-ethyl-pyrazole-3-carboxamide (R) enantiomer | 489.299 | 2.42 |
| 38 | di(cyclobutyl)methyl, Racemic | 1-isopropyl-pyrazol-5-yl | N-[1-[di(cyclobutyl)methyl]-2-[4-(3,5-dimethyl-1H-pyrazol-4-yl)anilino]-2-oxo-ethyl]-2-isopropyl-pyrazole-3-carboxamide | 503.314 | 2.49 |
| 39 | di(cyclobutyl)methyl, Enantiomer 1† | 1-isopropyl-pyrazol-5-yl | Enantiomer 1 of N-[1-[di(cyclobutyl)methyl]-2-[4-(3,5-dimethyl-1H-pyrazol-4-yl)anilino]-2-oxo-ethyl]-2-isopropyl-pyrazole-3-carboxamide (S) enantiomer | 503.314 | 2.49 |
| 40 | di(cyclobutyl)methyl, Enantiomer 2† | 1-isopropyl-pyrazol-5-yl | Enantiomer 2 of N-[1-[di(cyclobutyl)methyl]-2-[4-(3,5-dimethyl-1H-pyrazol-4-yl)anilino]-2-oxo-ethyl]-2-isopropyl-pyrazole-3-carboxamide (R) enantiomer | 503.314 | 2.49 |

243

244

-continued

| Ex. No. | R_X | R_Y | Name | Mass ion | LCMS retention time (min) |
|---|---|---|---|---|---|
| 41 | 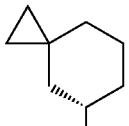<br>Preparation 45 | 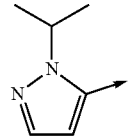 | N-[(1S)-2-[4-(3,5-dimethyl-1H-pyrazol-4-yl)anilino]-2-oxo-1-[(7S)-spiro[2.5]octan-7-yl]ethyl]-2-isopropyl-pyrazole-3-carboxamide | 489.299 | 2.36 |
| 42 |  | 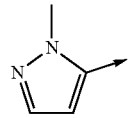 | N-[(1S)-1-[[4-(3,5-dimethyl-1H-pyrazol-4-yl)phenyl]carbamoyl]-2-methyl-propyl]-2-methyl-pyrazole-3-carboxamide; 2,2,2-trifluoroacetic acid | 395.22 | 1.96 |
| 43 | 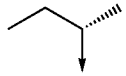 | 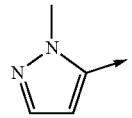 | N-[(1S,2S)-1-[[4-(3,5-dimethyl-1H-pyrazol-4-yl)phenyl]carbamoyl]-2-methyl-butyl]-2-methyl-pyrazole-3-carboxamide | 409.235 | 2.04 |
| 44 |  | 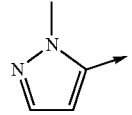 | N-[(1S)-1-benzyl-2[4-(3,5-dimethyl-1H-pyrazol-4-yl)anilino]-2-oxo-ethyl]-2-methyl-pyrazole-3-carboxamide | 443.22 | 2.06 |
| 45 | 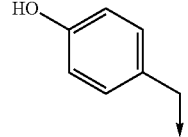 | 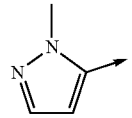 | N-[(1S)-2-[4-(3,5-dimethyl-1H-pyrazol-4-yl)anilino]-1-[(4-hydroxyphenyl)methyl]-2-oxo-ethyl]-2-methyl-pyrazole-3-carboxamide | 459.216 | 1.88 |
| 46 | 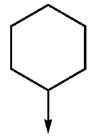 | 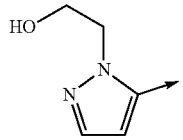 | N-[(1S)-1-cyclohexyl-2-[4-(3,5-dimethyl-1H-pyrazol-4-yl)anilino]-2-oxo-ethyl]-2-(2-hydroxyethyl)pyrazole-3-carboxamide | 465.262 | 2.03 |
| 47 | 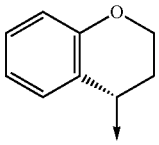<br>Preparation 35 | 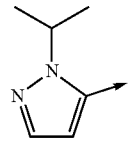 | N-[(1S)-1-[(4S)-chroman-4-yl]-2-[4-(3,5-dimethyl-1H-pyrazol-4-yl)anilino]-2-oxo-ethyl]-2-isopropyl-pyrazole-3-carboxamide | 513.263 | 2.24 |
| 48 | 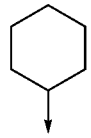 | 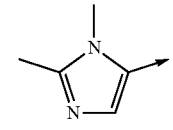 | N-[(1S)-1-cyclohexyl-2-[4-(3,5-dimethyl-1H-pyrazol-4-yl)anilino]-2-oxo-ethyl]-2,3-dimethyl-imidazole-4-carboxamide | 449.266 | 1.87 |
| 49 | 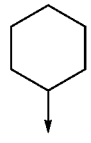 | 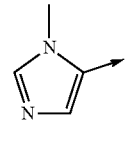 | N-[(1S)-1-cyclohexyl-2-[4-(3,5-dimethyl-1H-pyrazol-4-yl)anilino]-2-oxo-ethyl]-3-methyl-imidazole-4-carboxamide | 435.251 | 1.89 |
| 50 | 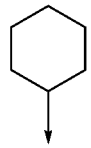 | 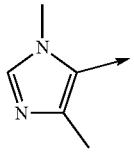 | N-[(1S)-1-cyclohexyl-2-[4-(3,5-dimethyl-1H-pyrazol-4-yl)anilino]-2-oxo-ethyl]-3,5-dimethyl-imidazole-4-carboxamide | 449.266 | 2.07 |

-continued

| Ex. No. | R_X | R_Y | Name | Mass ion | LCMS retention time (min) |
|---|---|---|---|---|---|
| 51 | cyclohexyl | 4-methylthiazol-5-yl methyl | (2S)-2-cyclohexyl-N-[4-(3,5-dimethyl-1H-pyrazol-4-yl)phenyl]-2-[[2-(4-methylthiazol-5-yl)acetyl]amino]acetamide | 466.228 | 2.07 |
| 52 | cyclohexyl | 2-methylthiazol-5-yl methyl | (2S)-2-cyclohexyl-N-[4-(3,5-dimethyl-1H-pyrazol-4-yl)phenyl]-2-[[2-(2-methylthiazol-5-yl)acetyl]amino]acetamide | 466.228 | 2.13 |
| 53 | cyclohexyl | 1-isopropyl-5-methyl-pyrazole | (2S)-2-cyclohexyl-N-[4-(3,5-dimethyl-1H-pyrazol-4-yl)phenyl]-2-[[2-(2-methylimidazol-1-yl)acetyl]amino]acetamide | 449.268 | 1.84 |
| 54 | cyclohexyl | 4-dimethylaminobenzyl | (2S)-2-cyclohexyl-2-[[2-(4-dimethylaminophenyl)acetyl]amino]-N-[4-(3,5-dimethyl-1H-pyrazol-4-yl)phenyl]acetamide | 488.303 | 2.13 |
| 55 | cyclohexyl | α,α-difluorobenzyl | N-[(1S)-1-cyclohexyl-2-[4-(3,5-dimethyl-1H-pyrazol-4-yl)anilino]-2-oxo-ethyl]-2,2-difluoro-2-phenyl-acetamide | 481.242 | 2.42 |
| 56 | cyclohexyl | 1,1-difluoropropyl | N-[(1S)-1-cyclohexyl-2-[4-(3,5-dimethyl-1H-pyrazol-4-yl)anilino]-2-oxo-ethyl]-2,2-difluoro-butanamide | 433.242 | 2.32 |
| 57 | cyclohexyl | 1-methylcyclopropyl | N-[(1S)-1-cyclohexyl-2-[4-(3,5-dimethyl-1H-pyrazol-4-yl)anilino]-2-oxo-ethyl]-1-methyl-cyclopropanecarboxamide | 409.261 | 2.25 |
| 58 | cyclohexyl | 3-methyl-isoxazol-4-yl | N-[(1S)-1-cyclohexyl-2-[4-(3,5-dimethyl-1H-pyrazol-4-yl)anilino]-2-oxo-ethyl]-3-methyl-isoxazole-4-carboxamide | 436.235 | 2.18 |
| 59 | cycloheptyl | 3-methyl-isoxazol-4-yl | N-[(1S)-1-cycloheptyl-2-[4-(3,5-dimethyl-1H pyrazol-4-yl)anilino]-2-oxo-ethyl]-3-methyl-isoxazole-4-carboxamide | 450.251 | 2.25 |

-continued

| Ex. No. | R$_X$ | R$_Y$ | Name | Mass ion | LCMS retention time (min) |
|---|---|---|---|---|---|
| 60 | cyclohexyl | 1-methyl-1H-1,2,3-triazol-4-yl | N-[(1S)-1-cyclohexyl-2-[4-(3,5-dimethyl-1H-pyrazol-4-yl)anilino]-2-oxo-ethyl]-3-methyl-triazole-4-carboxamide | 436.246 | 2.08 |
| 61 | cyclohexyl | 1-phenyl-1H-1,2,3-triazol-4-yl | N-[(1S)-1-cyclohexyl-2-[4-(3,5-dimethyl-1H-pyrazol-4-yl)anilino]-2-oxo-ethyl]-3-phenyl-triazole-4-carboxamide | 498.262 | 2.22 |
| 62 | cycloheptyl | 1-methyl-1H-1,2,3-triazol-4-yl | N-[(1S)-1-cycloheptyl-2-[4-(3,5-dimethyl-1H-pyrazol-4-yl)anilino]-2-oxo-ethyl]-3-methyl-triazole-4-carboxamide | 450.262 | 2.15 |
| 63 | cycloheptyl | 1-phenyl-1H-1,2,3-triazol-4-yl | N-[(1S)-1-cycloheptyl-2-[4-(3,5-dimethyl-1H-pyrazol-4-yl)anilino]-2-oxo-ethyl]-3-phenyl-triazole-4-carboxamide | 512.278 | 2.29 |
| 64 | cyclohexyl | 1H-pyrrolo[2,3-c]pyridin-3-yl | N-[(1S)-1-cyclohexyl-2-[4-(3,5-dimethyl-1H-pyrazol-4-yl)anilino]-2-oxo-ethyl]-1H-pyrrolo[2,3-c]pyridine-3-carboxamide | 471.25 | 1.88 |
| 65 | cyclohexyl | 1H-pyrrolo[2,3-b]pyridin-3-yl | N-[(1S)-1-cyclohexyl-2-[4-(3,5-dimethyl-1H-pyrazol-4-yl)anilino]-2-oxo-ethyl]-1H-pyrrolo[2,3-b]pyridine-3-carboxamide | 471.25 | 2.14 |
| 66 | cyclohexyl | 1-fluorocyclopropyl | N-[(1S)-1-cyclohexyl-2-[4-(3,5-dimethyl-1H-pyrazol-4-yl)anilino]-2-oxo-ethyl]-1-fluoro-cyclopropanecarboxamide | 413.235 | 2.29 |
| 67 | 4,4-difluorocyclohexyl (Preparation 9) | 1-fluorocyclopropyl | N-[(1S)-1-(4,4-difluorocyclohexyl)-2-[4-(3,5-dimethyl-1H-pyrazol-4-yl)anilino]-2-oxo-ethyl]-1-fluoro-cyclopropanecarboxamide | 449.217 | 2.16 |
| 68 | cyclohexyl | pyrazolo[1,5-a]pyridin-3-yl | N-[(1S)-1-cyclohexyl-2-[4-(3,5-dimethyl-1H-pyrazol-4-yl)anilino]-2-oxo-ethyl]pyrazolo[1,5-a]pyridine-3-carboxamide | 471.252 | 2.18 |

-continued

| Ex. No. | R_X | R_Y | Name | Mass ion | LCMS retention time (min) |
|---|---|---|---|---|---|
| 69 | 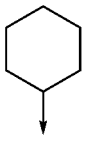 | 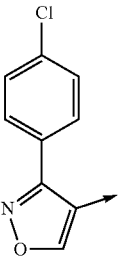 | 3-(4-chlorophenyl)-N-[(1S)-1-cyclohexyl-2-[4-(3,5-dimethyl-1H-pyrazol-4-yl)anilino]-2-oxo-ethyl]isoxazole-4-carboxamide | 532.213 | 2.56 |
| 70 | 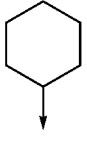 | 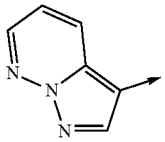 | N-[(1S)-1-cyclohexyl-2-[4-(3,5-dimethyl-1H-pyrazol-4-yl)anilino]-2-oxo-ethyl]pyrazolo[1,5-b]pyridazine-3-carboxamide | 472.247 | 2.12 |
| 71 | 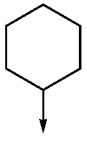 | 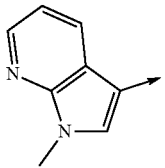 | N-[(1S)-1-cyclohexyl-2-[4-(3,5-dimethyl-1H-pyrazol-4-yl)anilino]-2-oxo-ethyl]-1-methyl-pyrrolo[2,3-b]pyridine-3-carboxamide | 485.3 | 0.65* |
| 72 | 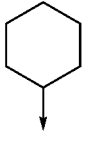 | 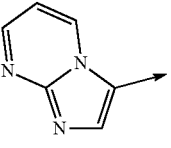 | N-[(1S)-1-cyclohexyl-2-[4-(3,5-dimethyl-1H-pyrazol-4-yl)anilino]-2-oxo-ethyl]imidazo[1,2-a]pyrimidine-3-carboxamide | 472.3 | 0.57* |
| 73 | 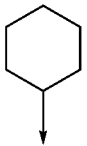 | 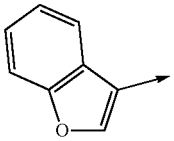 | N-[(1S)-1-cyclohexyl-2-[4-(3,5-dimethyl-1H-pyrazol-4-yl)anilino]-2-oxo-ethyl]benzofuran-3-carboxamide | 471.3 | 0.73* |
| 74 | 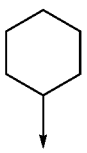 | 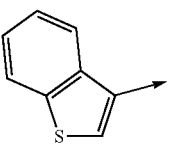 | N-[(1S)-1-cyclohexyl-2-[4-(3,5-dimethyl-1H-pyrazol-4-yl)anilino]-2-oxo-ethyl]benzothiophene-3-carboxamide | 487.2 | 0.75* |
| 75 | 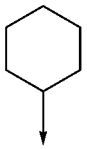 | 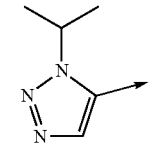 | N-[(1S)-1-cyclohexyl-2-[4-(3,5-dimethyl-1H-pyrazol-4-yl)anilino]-2-oxo-ethyl]-3-isopropyl-triazole-4-carboxamide | 464.279 | 2.19 |
| 102 | 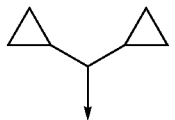  Preparation 52 | 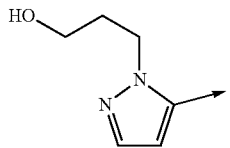  Preparation 65 | N-[(1S)-1-(dicyclopropylmethyl)-2-[4-(3,5-dimethyl-1H-pyrazol-4-yl)anilino]-2-oxo-ethyl]-2-(3-hydroxypropyl)pyrazole-3-carboxamide | 491.4 | 0.62* |

-continued

| Ex. No. | R_X | R_Y | Name | Mass ion | LCMS retention time (min) |
|---|---|---|---|---|---|
| 103 | 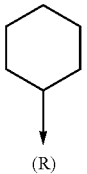 (R) | 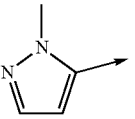 | N-[(1R)-1-cyclohexyl-2-[4-(3,5-dimethyl-1H-pyrazol-4-yl)anilino]-2-oxo-ethyl]-2-methyl-pyrazole-3-carboxamide | 435.251 | 2.16 |
| 104 | 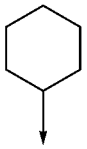 | 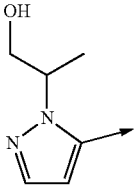 Preparation 46 | Diasteromer 1 of N-[(1S)-1-cyclohexyl-2-[4-(3,5-dimethyl-1H-pyrazol-4-yl)anilino]-2-oxo-ethyl]-2-(2-hydroxy-1-methyl-ethyl) pyrazole-3-carboxamide‡ | 479.273 | 2.06 |
| 105 | 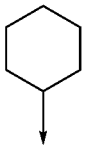 | 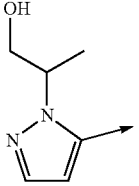 Preparation 46 | Diasteromer2 of N-[(1S)-1-cyclohexyl-2-[4-(3,5-dimethyl-1H-pyrazol-4-yl)anilino]-2-oxo-ethyl]-2-(2-hydroxy-1-methyl-ethyl) pyrazole-3-carboxamide‡ | 479.278 | 2.12 |
| 106 | 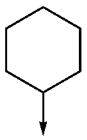 | 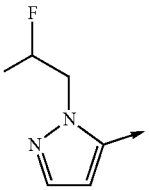 | N-[(1S)-1-cyclohexyl-2-[4-(3,5-dimethyl-1H-pyrazol-4-yl)anilino]-2-oxo-ethyl]-2-(2,2-difluoroethyl)pyrazole-3-carboxamide | 485.249 | 2.26 |
| 107 | 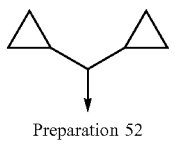 Preparation 52 | 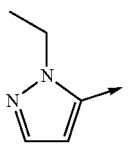 | N-[(1S)-1-(dicyclopropylmethyl)-2-[4-(3,5-dimethyl-1H-pyrazol-4-yl)anilino]-2-oxo-ethyl]-2-ethyl-pyrazole-3-carboxamide | 461.267 | 2.20 |
| 108 | 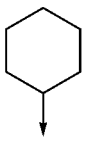 | 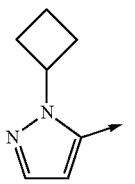 | 2-cyclobutyl-N-[(1S)-1-cyclohexyl-2-[4-(3,5-dimethyl-1H-pyrazol-4-yl)anilino]-2-oxo-ethyl]pyrazole-3-carboxamide | 475.282 | 2.36 |
| 109 | 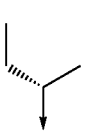 | 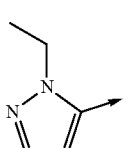 | N-[(1S,2S)-1-[[4-(3,5-dimethyl-1H-pyrazol-4-yl)phenyl]carbamoyl]-2-methyl-butyl]-2-ethyl-pyrazole-3-carboxamide | 423.249 | 2.13 |
| 110 |  | 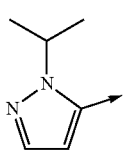 | N-[(1S,2S)-1-[4-(3,5-dimethyl-1H-pyrazol-4-yl)phenyl]carbamoyl]-2-methyl-butyl]-2-isopropyl-pyrazole-3-carboxamide | 437.266 | 2.20 |

-continued

| Ex. No. | R$_X$ | R$_Y$ | Name | Mass ion | LCMS retention time (min) |
|---|---|---|---|---|---|
| 111 | | | N-[(1R)-2-[4-(3,5-dimethyl-1H-pyrazol-4-yl)anilino]-2-oxo-1-spiro[2.5]octan-6-yl-ethyl]-2-isopropyl-pyrazole-3-carboxamide | 489.298 | 2.38 |
| 112 | | | N-[(1S)-2-[4-(3,5-dimethyl-1H-pyrazol-4-yl)anilino]-2-oxo-1-spiro[2.5]octan-6-yl-ethyl]-2-isopropyl-pyrazole-3-carboxamide | 489.296 | 2.38 |
| 113 | | | N-[(1S,2R)-1-[4-(3,5-dimethyl-1H-pyrazol-4-yl)phenyl]carbamoyl]-2-methyl-butyl]-2-methyl pyrazole-3-carboxamide | 409.235 | 2.07 |
| 114 | Preparation 52 | | 2-cyclobutyl-N-[(1S)-1-(dicyclopropylmethyl)-2-[4-(3,5-dimethyl-1H-pyrazol-4-yl)anilino]-2-oxo-ethyl]pyrazole-3-carboxamide | 487.282 | 2.33 |
| 115 | Preparation 52 | | N-[(1S)-1-(dicyclopropylmethyl)-2-[4-(3,5-dimethyl-1H-pyrazol-4-yl)anilino]-2-oxo-ethyl]-2-(2,2-difluoroethyl)pyrazole-3-carboxamide | 497.248 | 2.25 |
| 116 | Preparation 52 | | 2-cyclopropyl-N-[(1S)-1-(dicyclopropylmethyl)-2-[4-(3,5-dimethyl-1H-pyrazol-4-yl)anilino]-2-oxo-ethyl]pyrazole-3-carboxamide | 473.269 | 2.22 |
| 117 | Preparation 52 | | N-[(1S)-1-(dicyclopropylmethyl)-2-[4-(3,5-dimethyl-1H-pyrazol-4-yl)anilino]-2-oxo-ethyl]-2-methyl-pyrazole-3-carboxamide | 447.251 | 2.14 |
| 118 | | | N-[(1S)-1-[4-(3,5-dimethyl-1H-pyrazol-4-yl)phenyl]carbamoyl]-2-ethyl-butyl]-2-methyl-pyrazole-3-carboxamide | 423.251 | 2.14 |

-continued

| Ex. No. | R$_X$ | R$_Y$ | Name | Mass ion | LCMS retention time (min) |
|---|---|---|---|---|---|
| 119 | Preparation 52 | OH, Preparation 46 | Diastereomer 1 of N-[(1S) 1-(dicyclopropylmethyl)-2-[4-(3,5-dimethyl-1H-pyrazol-4-yl)anilino]-2-oxo-ethyl]-2-(2-hydroxy-1-methyl-ethyppyrazole-3-carboxamide‡ (S, S) diastereomer | 491.277 | 2.06 |
| 120 | Preparation 52 | OH, Preparation 46 | Diastereomer 2 of N-[(1S)-1-(dicyclopropylmethyl)-2-[4-(3,5-dimethyl-1H-pyrazol-4-yl)anilino]-2-oxo-ethyl]-2-(2-hydroxy-1-methyl-ethyppyrazole-3-carboxamide‡ (S, R) diastereomer | 491.277 | 2.10 |
| 121 |  |  | N-[(1S)-1-[4-(3,5-dimethyl-1H-pyrazol-4-yl)phenyl]carbamoyl]-2-ethyl-butyl]-2-isopropyl-pyrazole-3-carboxamide | 451.282 | 2.28 |
| 122 | Preparation 64 | OH | N-[(1S)-1-[di(cyclobutyl)methyl1-2-[4-(3,5-dimethyl-1H-pyrazol-4-yl)anilino]-2-oxo-ethyl]-2-(2-hydroxyethyl)pyrazole-3-carboxamide | 505.292 | 2.24 |
| 123 | Preparation 64 | OH, Preparation 46 | Diastereomer 1 of N-[(1S)-1-[di(cyclobutyl)methyl]-2-[4-(3,5-dimethyl-1H-pyrazol-4-yl)anilino]-2-oxo-ethyl]-2-(2-hydroxy-1-methyl-ethyl)pyrazole-3-carboxamide‡ | 519.309 | 2.26 |
| 124 | Preparation 64 | OH, Preparation 46 | Diastereomer 2 of N-[(1S)-1-[di(cyclobutyl)methyl]-2-[4-(3,5-dimethyl-1H-pyrazol-4-yl)anilino]-2-oxo-ethyl]-2-(2-hydroxy-1-methyl-ethyl)pyrazole-3-carboxamide‡ | 519.308 | 2.32 |
| 125 |  |  | Trans N-[(1S)-2-[4-(3,5-dimethyl-1H-pyrazol-4-yl)anilino]-1-(4-methylcyclohexyl)-2-oxo-ethyl]-2-methyl-pyrazole-3-carboxamide | 449.266 | 2.24 |

-continued

| Ex. No. | R_X | R_Y | Name | Mass ion | LCMS retention time (min) |
|---|---|---|---|---|---|
| 126 | trans 4-methylcyclohexyl | 1-ethyl-pyrazol-5-yl | Trans N-[(1S)-2-[4-(3,5-dimethyl-1H-pyrazol-4-yl)anilino]-1-(4-methylcyclohexyl)-2-oxo-ethyl]-2-ethyl-pyrazole-3-carboxamide | 463.283 | 2.31 |
| 127 | trans 4-methylcyclohexyl | 1-isopropyl-pyrazol-5-yl | Trans N-[(1S)-2-[4-(3,5-dimethyl-1H-pyrazol-4-yl)anilino]-1-(4-methylcyclohexyl)-2-oxo-ethyl]-2-isopropyl-pyrazole-3-carboxamide | 477.298 | 2.38 |
| 128 | dicyclopropylmethyl (Preparation 52) | 1-sec-butyl-pyrazol-5-yl | N-[(1S)-1-(dicyclopropylmethyl)-2-[4-(3,5-dimethyl-1H-pyrazol-4-yl)anilino]-2-oxo-ethyl]-2-sec-butyl-pyrazole-3-carboxamide | 489.298 | 2.33 |
| 129 | dicyclopropylmethyl (Preparation 52) | 1-(cyclopropylmethyl)-pyrazol-5-yl | 2-(cyclopropylmethyl)-N-[(1S)-1-(dicyclopropylmethyl)-2-[4-(3,5-dimethyl-1H-pyrazol-4-yl)anilino]-2-oxo-ethyl]pyrazole-3-carboxamide | 487.282 | 2.28 |
| 130 | dicyclopropylmethyl (Preparation 52) | 1-(3,3,3-trifluoropropyl)-pyrazol-5-yl | N-[(1S)-1-(dicyclopropylmethyl)-2-[4-(3,5-dimethyl-1H-pyrazol-4-yl)anilino]-2-oxo-ethyl]-2-(3,3,3-trifluoropropyl)pyrazole-3-carboxamide | 529.254 | 2.33 |
| 131 | dicyclopropylmethyl (Preparation 52) | 1-(2-dimethylaminoethyl)-pyrazol-5-yl | N-[(1S)-1-(dicyclopropylmethyl)-2-[4-(3,5-dimethyl-1H-pyrazol-4-yl)anilino]-2-oxo-ethyl]-2-(2-dimethylaminoethyl)pyrazole-3-carboxamide | 504.309 | 1.90 |
| 132 | dicyclopropylmethyl (Preparation 52) | 1-isobutyl-pyrazol-5-yl | N-[(1S)-1-(dicyclopropylmethyl)-2-[4-(3,5-dimethyl-1H-pyrazol-4-yl)anilino]-2-oxo-ethyl]-2-isobutyl-pyrazole-3-carboxamide | 489.298 | 2.33 |

-continued

| Ex. No. | R$_X$ | R$_Y$ | Name | Mass ion | LCMS retention time (min) |
|---|---|---|---|---|---|
| 133 | dicyclopropylmethyl (Preparation 52) | 1-propyl-pyrazol-5-yl (Prep.) | N-[(1S)-1-(dicyclopropylmethyl)-2-[4-(3,5-dimethyl-1H-pyrazol-4-yl)anilino]-2-oxo-ethyl]-2-propyl-pyrazole-3-carboxamide | 475.282 | 2.27 |
| 141 | (1S,3R,5S)-3,5-dimethylcyclohexyl (Preparation 190) | (1S)-2-hydroxy-1-methyl-ethyl pyrazolyl (Prep. 194) | N-[(1S)-1-[(3R,5S)-3,5-dimethylcyclohexyl]-2-[4-(3,5-dimethyl-1H-pyrazol-4-yl)anilino]-2-oxo-ethyl]-2-[(1S)-2-hydroxy-1-methyl-ethyl]pyrazole-3-carboxamide | 507 | 4.16 Method 5 Acquity BEH C18 column 0.05% FA in water with MeCN |
| 142 | cyclooctyl (Preparation 182) | 3-hydroxybutyl pyrazolyl (Prep. 202) | Diastereomer 1 of N-[1-cyclooctyl-2-[4-(3,5-dimethyl-1H-pyrazol-4-yl)anilino]-2-oxo-ethyl]-2-(3-hydroxybutyl)pyrazole-3-carboxamide§ | 521.324 | 2.27 |
| 143 | cyclooctyl (Preparation 182) | 3-hydroxybutyl pyrazolyl (Prep. 202) | Diastereomer 2 of N-[1-cyclooctyl-2-[4-(3,5-dimethyl-1H-pyrazol-4-yl)anilino]-2-oxo-ethyl]-2-(3-hydroxybutyl)pyrazole-3-carboxamide§ | 521.324 | 2.27 |
| 144 | cyclooctyl (Preparation 182) | 3-hydroxybutyl pyrazolyl (Prep. 202) | Diastereomer 3 of N-[1-cyclooctyl-2-[4-(3,5-dimethyl-1H-pyrazol-4-yl)anilino]-2-oxo-ethyl]-2-(3-hydroxybutyl)pyrazole-3-carboxamide§ | 521.324 | 2.27 |
| 145 | cyclooctyl (Preparation 182) | 3-hydroxybutyl pyrazolyl (Prep. 202) | Diastereomer 4 of N-[1-cyclooctyl-2-[4-(3,5-dimethyl-1H-pyrazol-4-yl)anilino]-2-oxo-ethyl]-2-(3-hydroxybutyl)pyrazole-3-carboxamide§ | 521.324 | 2.27 |
| 146 | (1S,3R,5S)-3,5-dimethylcyclohexyl (Preparation 190) | 2-methyl-pyrazol-3-yl | N-[(1S)-1-[(3R,5S)-3,5-dimethylcyclohexyl]-2-[4-(3,5-dimethyl-1H-pyrazol-4-yl)anilino]-2-oxo-ethyl]-2-methyl-pyrazole-3-carboxamide | 463.282 | 2.32 |

-continued

| Ex. No. | R_X | R_Y | Name | Mass ion | LCMS retention time (min) |
|---|---|---|---|---|---|
| 147 | Preparation 190 | | N-[(1S)-1-[(3R,5S)-3,5-dimethylcyclohexyl]-2-[4-(3,5-dimethyl-1H-pyrazol-4-yl)anilino]-2-oxo-ethyl]-2-methyl-pyrazole-3-carboxamide | 491.313 | 2.45 |
| 148 | | | N-[(1S)-2-[4-(3,5-dimethyl-1H-pyrazol-4-yl)anilino]-1-(4-methylcyclohexyl)-2-oxo-ethyl]-3-isopropyl-tnazole-4-carboxamide | 478.293 | 2.32 |
| 149 | | | N-[(1S)-2-[4-(3,5-dimethyl-1H-pyrazol-4-yl)anilino]-1-(4-methylcyclohexyl)-2-oxo-ethyl]-3-ethyl-triazole-4-carboxamide | 464.277 | 2.26 |
| 150 | Preparation 182 | Prep. 194 | Diastereomer 1 of N-[1-cyclooctyl-2-[4-(3,5-dimethyl-1H-pyrazol-4-yl)anilino]-2-oxo-ethyl]-2-[(1S)-2-hydroxy-1-methyl-ethyl]pyrazole-3-carboxamide§ | 507.308 | 2.29 |
| 151 | Preparation 182 | Prep. 194 | Diastereomer 1 of N-[1-cyclooctyl-2-[4-(3,5-dimethyl-1H-pyrazol-4-yl)anilino]-2-oxo-ethyl]-2-[(1S)-2-hydroxy-1-methyl-ethyl]pyrazole-3-carboxamide§ | 507.308 | 2.23 |
| 152 | Preparation 182 | | Enantiomer 1 of N-[1-cyclooctyl-2-[4-(3,5-dimethyl-1H-pyrazol-4-yl)anilino]-2-oxo-ethyl]-2-(1-methylethyl)pyrazole-3-carboxamide# | 491.313 | 2.47 |
| 153 | Preparation 182 | | Enantiomer 2 of N-[1-cyclooctyl-2-[4-(3,5-dimethyl-1H-pyrazol-4-yl)anilino]-2-oxo-ethyl]-2-(1-methylethyl)pyrazole-3-carboxamide# | 491.314 | 2.47 |

-continued

| Ex. No. | R<sub>X</sub> | R<sub>Y</sub> | Name | Mass ion | LCMS retention time (min) |
|---|---|---|---|---|---|
| 154 | 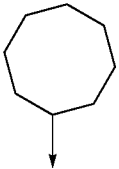 Preparation 182 | 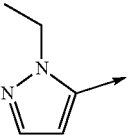 | Enantiomer 1 of N-[1-cyclooctyl-2-[4-(3,5-dimethyl-1H-pyrazol-4-yl)anilino]-2-oxo-ethyl]-2-ethyl-pyrazole-3-carboxamide# | 477.298 | 2.40 |
| 155 | 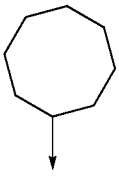 Preparation 182 | 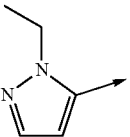 | Enantiomer 2 of N-[1-cyclooctyl-2-[4-(3,5-dimethyl-1H-pyrazol-4-yl)anilino]-2-oxo-ethyl]-2-ethyl-pyrazole-3-carboxamide# | 477.298 | 2.40 |
| 156 | 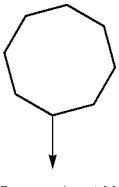 Preparation 182 | 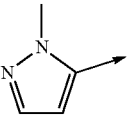 | Enantiomer 1 of N-[1-cyclooctyl-2-[4-(3,5-dimethyl-1H-pyrazol-4-yl)anilino]-2-oxo-ethyl]-2-methyl-pyrazole-3-carboxamide# | 463.282 | 2.33 |
| 157 | 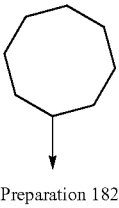 Preparation 182 | 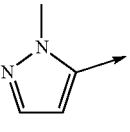 | Enantiomer 2 of N-[1-cyclooctyl-2-[4-(3,5-dimethyl-1H-pyrazol-4-yl)anilino]-2-oxo-ethyl]-2-methyl-pyrazole-3-carboxamide# | 463.282 | 2.33 |
| 158 | 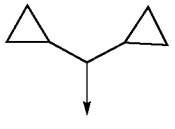 Preparation 52 | 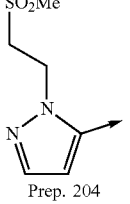 Prep. 204 | N-[(1S)-1-(dicyclopropylmethyl)-2-[4-(3,5-dimethyl-1H-pyrazol-4-yl)anilino]-2-oxo-ethyl]-2-(2-methylsulfonylethyl)pyrazole-3-carboxamide | 539.244 | 2.13 |
| 159 | 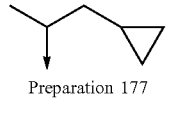 Preparation 177 | 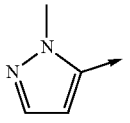 | Diastereomer 1 of N-[(1S)-3-cyclopropyl-1-[[4-(3,5-dimethyl-1H-pyrazol-4-yl)phenyl]carbamoyl]-2-methyl-propyl]-2-methyl-pyrazole-3-carboxamide§ | 435.251 | 2.18 |
| 160 | 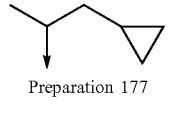 Preparation 177 | 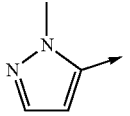 | Diastereomer 2 of N-[(1S)-3-cyclopropyl-1[[4-(3,5-dimethyl-1H-pyrazol-4-yl)phenyl]carbamoyl]-2-methyl-propyl]-2-methyl-pyrazole-3-carboxamide§ | 435.251 | 2.19 |

-continued

| Ex. No. | R$_X$ | R$_Y$ | Name | Mass ion | LCMS retention time (min) |
|---|---|---|---|---|---|
| 161 | dicyclopropylmethyl, Preparation 52 | 2-hydroxy-1-methylpropyl pyrazole, Prep. 206 | N-[(1S)-1-(dicyclopropylmethyl)-2-[4-(3,5-dimethyl-1H-pyrazol-4-yl)anilino]-2-oxo-ethyl]-2-[(1S,2S) and (1R,2R)-2-hydroxy-1-methyl-propyl]pyrazole-3-carboxamide | 505.293 | 2.14 |
| 162 | dicyclopropylmethyl, Preparation 52 | 2-isopropyl-1,2,4-triazole | N-[(1S)-1-(dicyclopropylmethyl)-2-[4-(3,5-dimethyl-1H-pyrazol-4-yl)anilino]-2-oxo-ethyl]-2-isopropyl-1,2,4-triazole-3-carboxamide | 476.277 | 2.36 |
| 163 | dicyclopropylmethyl, Preparation 52 | 2-methyl-1,2,4-triazole | N-[(1S)-1-(dicyclopropylmethyl)-2-[4-(3,5-dimethyl-1H-pyrazol-4-yl)anilino]-2-oxo-ethyl]-2-methyl-1,2,4-triazole-3-carboxamide | 448.246 | 2.19 |
| 164 | cyclobutyl, Preparation 169 | 2-hydroxymethyl pyrazole, Prep. 195 | Diastereomer 1 of N-[(1S)-2-cyclobutyl-[[4-(3,5-dimethyl-1H-pyrazol-4-yl)phenyl]carbamoyl]propyl]-2-[(1R)-2-hydroxy-1-methyl-ethyl]pyrazole-3-carboxamide§ | 479.277 | 2.16 |
| 165 | cyclobutyl, Preparation 169 | 2-hydroxymethyl pyrazole, Prep.195 | Diastereomer 2 of N-[(1S)-2-cyclobutyl-1-[[4-(3,5-dimethyl-1H-pyrazol-4-yl)phenyl]carbamoyl]propyl]-2-[(1R)-2-hydroxy-1-methyl-ethyl]pyrazole-3-carboxamide§ | 479.277 | 2.16 |
| 166 | di(cyclobutyl)methyl, Preparation 64 | 3-hydroxypropyl pyrazole, Prep. 65 | N-[(1S)-1-[di(cyclobutyl)methyl]-2-[4-(3,5-dimethyl-1H-pyrazol-4-yl)anilino]-2-oxo-ethyl]-2-(3-hydroxypropyl)pyrazole-3-carboxamide | 519.308 | 2.3 |
| 167 | dicyclopropylmethyl, Preparation 52 | phenyl | N-[(1S)-1-(dicyclopropylmethyl)-2-[4-(3,5-dimethyl-1H-pyrazol-4-yl)anilino]-2-oxo-ethyl]benzamide | 443.245 | 2.3 |
| 168 | dicyclopropylmethyl, Preparation 52 | tert-butyl | N-[(1S)-1-(dicyclopropylmethyl)-2-[4-(3,5-dimethyl-1H-pyrazol-4-yl)anilino]-2-oxo-ethyl]-2,2-dimethyl-propanamide | 423.276 | 2.31 |

-continued

| Ex. No. | R$_X$ | R$_Y$ | Name | Mass ion | LCMS retention time (min) |
|---|---|---|---|---|---|
| 169 | Preparation 52 | | N-[(1S)-1-(dicyclopropylmethyl)-2-[4-(3,5-dimethyl-1H-pyrazol-4-yl)anilino]-2-oxo-ethyl]cyclobutane carboxamide | 421.26 | 2.23 |
| 170 | Preparation 52 | | N-[(1S)-1-(dicyclopropylmethyl)-2-[4-(3,5-dimethyl-1H-pyrazol-4-yl)anilino]-2-oxo-ethyl]cyclopentane carboxamide | 435.276 | 2.31 |
| 171 | Preparation 52 | Prep. 217 | 2-(1-cyanoethyl)-N-[(1S)-1-(dicyclopropylmethyl)-2-[4-(3,5-dimethyl-1H-pyrazol-4-yl)anilino]-2-oxo-ethyl]pyrazole-3-carboxamide | 486.261 | 2.27 |
| 172 | Preparation 52 | Prep. 218 | 1-(1-cyanoethyl)-N-[(1S)-1-(dicyclopropylmethyl)-2-[4-(3,5-dimethyl-1H-pyrazol-4-yl)anilino]-2-oxo-ethyl]pyrazole-3-carboxamide | 486.262 | 2.21 |
| 173 | Preparation 169 | Prep. 194 | Diastereomer 1 of N-[(1S)-2-cyclobutyl-1-[[4-(3,5-dimethyl-1H-pyrazol-4-yl)phenyl]carbamoyl]propyl]-2-[(1S)-2-hydroxy-1-methyl-ethyl]pyrazole-3-carboxamide§ | 479.277 | 2.11 |
| 174 | Preparation 169 | Prep. 194 | Diastereomer 2 of N-[(1S)-2-cyclobutyl-1-[[4-(3,5-dimethyl-1H-pyrazol-4-yl)phenyl]carbamoyl]propyl]-2-[(1S)-2-hydroxy-1-methyl-ethyl]pyrazole-3-carboxamide§ | 479.277 | 2.1 |
| 175 | Preparation 168 | Prep. 46 | Diastereomer 1 of N-[(1S)-1-[[4-(3,5-dimethyl-1H-pyrazol-4-yl)phenyl]carbamoyl]-2,3,3-trimethyl-butyl]-2-[2-hydroxy-1-methyl-ethyl]pyrazole-3-carboxamide§ | 481.293 | 2.2 |
| 176 | Preparation 168 | Prep. 46 | Diastereomer 2 of N-[(1S)-1-[[4-(3,5-dimethyl-1H-pyrazol-4-yl)phenyl]carbamoyl]-2,3,3-trimethyl-butyl]-2-[2-hydroxy-1-methyl-ethyl]pyrazole-3-carboxamide§ | 481.292 | 2.2 |
| 177 | Preparation 168 | Prep. 46 | Diastereomer 3 of N-[(1S)-1-[[4-(3,5-dimethyl-1H-pyrazol-4-yl)phenyl]carbamoyl]-2,3,3-trimethyl-butyl]-2-[2-hydroxy-1-methyl-ethyl]pyrazole-3-carboxamide§ | 481.293 | 2.15 |

-continued

| Ex. No. | R$_X$ | R$_Y$ | Name | Mass ion | LCMS retention time (min) |
|---|---|---|---|---|---|
| 178 | Preparation 168 | Prep. 46 | Diastereomer 4 of N-[(1S)-1-[[4-(3,5-dimethyl-1H-pyrazol-4-yl)phenyl]carbamoyl]-2,3,3-trimethyl-butyl]-2-[2-hydroxy-1-methyl-ethyl]pyrazole-3-carboxamide§ | 481.293 | 2.11 |
| 179 | Preparation 52 | Prep. 215 | N-[(1S)-1-(dicyclopropylmethyl)-2-[4-(3,5-dimethyl-1H-pyrazol-4-yl)anilino]-2-oxo-ethyl]-2-(4,4,4-trifluoro-3-hydroxy-butyl)pyrazole-3-carboxamide | 559.265 | 2.28 |
| 180 | Preparation 89 | | N-[(1S)-1-[(7S)-6,6-difluorospiro[2.5]octan-7-yl]-2-[4-(3,5-dimethyl-1H-pyrazol-4-yl)anilino]-2-oxo-ethyl]-2-ethyl-pyrazole-3-carboxamide | 511.263 | 2.28 |
| 181 | Preparation 89 | | N-[(1S)-1-[(7S)-6,6-difluorospiro[2.5]octan-7-yl]-2-[4-(3,5-dimethyl-1H-pyrazol-4-yl)anilino]-2-oxo-ethyl]-2-isopropyl-pyrazole-3-carboxamide | 525.279 | 2.35 |
| 182 | Preparation 89 | | N-[(1S)-1-[(7S)-6,6-difluorospiro[2.5]octan-7-yl]-2-[4-(3,5-dimethyl-1H-pyrazol-4-yl)anilino]-2-oxo-ethyl]-2-isopropyl-pyrazole-3-carboxamide | 497.248 | 2.21 |
| 183 | Preparation 52 | | N-[(1S)-1-(dicyclopropylmethyl)-2-[4-(3,5-dimethyl-1H-pyrazol-4-yl)anilino]-2-oxo-ethyl]-2-(2-hydroxyethyl)pyrazole-3-carboxamide | 477.261 | 2.08 |
| 184 | Preparation 52 | | N-[(1S)-1-(dicyclopropylmethyl)-2-[4-(3,5-dimethyl-1H-pyrazol-4-yl)anilino]-2-oxo-ethyl]-2-(2,2,2-trifluoroethyl)pyrazole-3-carboxamide | 515.239 | 2.35 |

-continued

| Ex. No. | R$_X$ | R$_Y$ | Name | Mass ion | LCMS retention time (min) |
|---|---|---|---|---|---|
| 185 | Preparation 52 | Prep. 202 | N-[(1S)-1-(dicyclopropylmethyl)-2-[4-(3,5-dimethyl-1H-pyrazol-4-yl)anilino]-2-oxo-ethyl]-2-(3-hydroxybutyl)pyrazole-3-carboxamide | 505.292 | 2.16 |
| 186 | Preparation 52 | Prep. 209 | N-[(1S)-1-(dicyclopropylmethyl)-2-[4-(3,5-dimethyl-1H-pyrazol-4-yl)anilino]-2-oxo-ethyl]-2-(2,2-difluoropropyl)pyrazole-3-carboxamide | 511.263 | 2.28 |
| 187 | Preparation 176 | Prep. 46 | Diastereomer 1 of N-[(1S)-1-(2-adamantyl)-2-[4-(3,5-dimethyl-1H-pyrazol-4-yl)anilino]-2-oxo-ethyl]-2-(2-hydroxy-1-methyl-ethyl)pyrazole-3-carboxamide | 531.308 | 2.37 |
| 188 | Preparation 176 | Prep. 46 | Diastereomer 2 of N-[(1S)-1-(2-adamantyl)-2-[4-(3,5-dimethyl-1H-pyrazol-4-yl)anilino]-2-oxo-ethyl]-2-(2-hydroxy-1-methyl-ethyl)pyrazole-3-carboxamide | 531.308 | 2.3 |
| 189 | Preparation 52 | Prep. 199 | N-[(1S)-1-(dicyclopropylmethyl)-2-[4-(3,5-dimethyl-1H-pyrazol-4-yl)anilino]-2-oxo-ethyl]-2-(2,2-difluoro-1-methyl-ethyl)pyrazole-3-carboxamide | 511.263 | 2.35 |
| 190 | Preparation 169 | | Diastereomer 1 of N-[(1S)-2-cyclobutyl-1-[[4-(3,5-dimethyl-1H-pyrazol-4-yl)phenyl]carbamoyl]propyl]-2-isopropyl-pyrazole-3-carboxamide | 463.282 | 2.38 |
| 191 | Preparation 169 | | Diastereomer 2 of N-[(1S)-2-cyclobutyl-1-[[4-(3,5-dimethyl-1H-pyrazol-4-yl)phenyl]carbamoyl]propyl]-2-isopropyl-pyrazole-3-carboxamide | 463.282 | 2.38 |
| 192 | Preparation 169 | | Diastereomer 1 of N-[(1S)-2-cyclobutyl-1-[[4-(3,5-dimethyl-1H-pyrazol-4-yl)phenyl]carbamoyl]propyl]-2-ethyl-pyrazole-3-carboxamide | 449.267 | 2.3 |

-continued

| Ex. No. | R$_X$ | R$_Y$ | Name | Mass ion | LCMS retention time (min) |
|---|---|---|---|---|---|
| 193 | 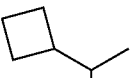<br>Preparation 169 | 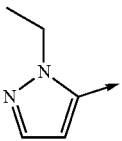 | Diastereomer 2 of N-[(1S)-2-cyclobutyl-1-[[4-(3,5-dimethyl-1H-pyrazol-4-yl)phenyl]carbamoyl]propyl]-2-ethyl-pyrazole-3-carboxamide | 449.267 | 2.3 |
| 194 | 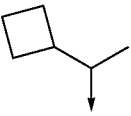<br>Preparation 169 | 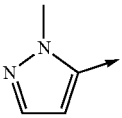 | Diastereomer 1 of N-[(1S)-2-cyclobutyl-1-[[4-(3,5-dimethyl-1H-pyrazol-4-yl)phenyl]carbamoyl]propyl]-2-methyl-pyrazole-3-carboxamide | 435.251 | 2.23 |
| 195 | 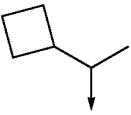<br>Preparation 169 | 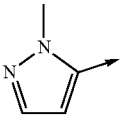 | Diastereomer 2 of N-[(1S)-2-cyclobutyl-1-[[4-(3,5-dimethyl-1H-pyrazol-4-yl)phenyl]carbamoyl]propyl]-2-methyl-pyrazole-3-carboxamide | 435.251 | 2.24 |
| 196 | 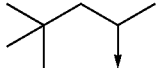<br>Preparation 175 | 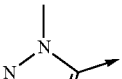 | N-[(1S)-1-[4-(3,5-dimethyl-1H-pyrazol-4-yl)phenyl]carbamoyl]-2,4,4-trimethyl-pentyl]-2 methyl-pyrazole-3-carboxamide | 451.282<br>Ratio of isomers 1:1 | 2.34 |
| 197 | 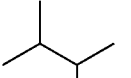<br>Preparation 172 | 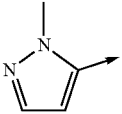 | N-[(1S)-1-[4-(3,5-dimethyl-1H-pyrazol-4-yl)phenyl]carbamoyl]-2,3-dimethyl-butyl]-2-methyl-pyrazole-3-carboxamide | 423.25 | 2.18 |
| 198 | 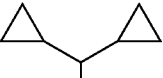<br>Preparation 52 | 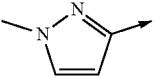 | N-[(1S)-1-(dicyclopropylmethyl)-2-[4-(3,5-dimethyl-1H-pyrazol-4-yl)anilino]-2-oxo-ethyl]-1-methyl-pyrazole-3-carboxamide | 447.25 | 2.17 |
| 199 | 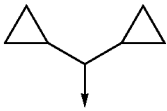<br>Preparation 52 | 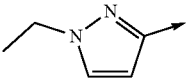 | N-[(1S)-1-(dicyclopropylmethyl)-2-[4-(3,5-dimethyl-1H-pyrazol-4-yl)anilino]-2-oxo-ethyl]-1-ethyl-pyrazole-3-carboxamide | 461.267 | 2.25 |
| 200 | 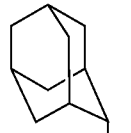<br>Preparation 176 | 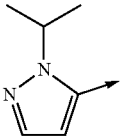 | N-[(1S)-1-(2-adamantyl)-2-[4-(3,5-dimethyl-1H-pyrazol-4-yl)anilino]-2-oxo-ethyl]-2-isopropyl-pyrazole-3-carboxamide | 515.313 | 2.52 |
| 201 | 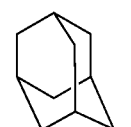<br>Preparation 176 | 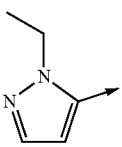 | N-[(1S)-1-(2-adamantyl)-2-[4-(3,5-dimethyl-1H-pyrazol-4-yl)anilino]-2-oxo-ethyl]-2-ethyl-pyrazole-3-carboxamide | 501.298 | 2.45 |

-continued

| Ex. No. | R_X | R_Y | Name | Mass ion | LCMS retention time (min) |
|---|---|---|---|---|---|
| 202 | Preparation 176 | | N-[(1S)-1-(2-adamantyl)-2-[4-(3,5-dimethyl-1H-pyrazol-4-yl)anilino]-2-oxo-ethyl]-2-methyl-pyrazole-3-carboxamide | 487.282 | 2.38 |
| 203 | | Prep. 202 | N-[(1S)-2-[4-(3,5-dimethyl-1H-pyrazol-4-yl)anilino]-1-(trans-4-methylcyclohexyl)-2-oxo-ethyl]-2-(3-hydroxybutyl)pyrazole-3-carboxamide | 507.309 | 2.23 |
| 204 | | Prep. 46 | Diastereomer 1 of N-[(1S)-2-[4-(3,5-dimethyl-1H-pyrazol-4-yl)anilino]-1-(trans-4-methylcyclohexyl)-2-oxo-ethyl]-2-(2-hydroxy-1-methyl-ethyl)pyrazole-3 carboxamide | 493.293 | 2.23 |
| 205 | | Prep. 46 | Diastereomer 2 of N-[(1S)-2-[4-(3,5-dimethyl-1H-pyrazol-4-yl)anilino]-1-(trans-4-methylcyclohexyl)-2-oxo-ethyl]-2-(2-hydroxy-1-methyl-ethyl)pyrazole-3 carboxamide | 493.293 | 2.17 |
| 206 | Preparation 52 | | N-[(1S)-1-(dicyclopropylmethyl)-2-[4-(3,5-dimethyl-1H-pyrazol-4-yl)anilino]-2-oxo-ethyl]-2-(2-methoxyethyl)pyrazole-3-carboxamide | 491.278 | 2.18 |
| 207 | Preparation 52 | | 2-(cyanomethyl)-N-[(1S)-1-(dicyclopropylmethyl)-2-[4-(3,5-dimethyl-1H-pyrazol-4-yl)anilino]-2-oxo-ethyl]pyrazole-3-carboxamide | 472.246 | 2.22 |
| 208 | | Prep. 65 | N-[(1S)-2-[4-(3,5-dimethyl-1H-pyrazol-4-yl)anilino]-1-(trans-4-methylcyclohexyl)-2-oxo-ethyl]-2-(3-hydroxypropyl)pyrazole-3-carboxamide | 493.293 | 2.18 |

-continued

| Ex. No. | R$_X$ | R$_Y$ | Name | Mass ion | LCMS retention time (min) |
|---|---|---|---|---|---|
| 209 | Preparation 90 | Prep. 65 | N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-(3-hydroxypropyl)pyrazole-3-carboxamide | 543.289 | 2.17 |
| 210 | Preparation 90 | Prep. 46 | Diastereomer 1 of N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-(2-hydroxy-1-methyl-ethyl)pyrazole-3-carboxamide | 543.289 | 2.17 |
| 211 | Preparation 90 | Prep. 46 | Diastereomer 2 of N-[(1S)-1-[(1S)-2,2-difluoro-5,5-dimethyl-cyclohexyl]-2-[4-(3,5-dimethyl-1H-pyrazol 4-yl)anilino]-2-oxo-ethyl]-2-(2-hydroxy-1-methyl-ethyl)pyrazole-3-carboxamide | 543.29 | 2.22 |
| 212 | Preparation 90 | | N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-isopropyl-pyrazole-3-carboxamide | 527.294 | 2.39 |
| 213 | Preparation 90 | | N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-ethyl-pyrazole-3-carboxamide | 513.28 | 2.32 |
| 214 | Preparation 90 | | N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-methyl-pyrazole-3-carboxamide | 499.263 | 2.25 |
| 215 | Preparation 52 | Prep. 213 | N-[(1S)-1-(dicyclopropylmethyl)-2-[4-(3,5-dimethyl-1H-pyrazol-4-yl)anilino]-2-oxo-ethyl]-2-(3,3-difluoropropyl)pyrazole-3-carboxamide | 511.263 | 2.3 |

| Ex. No. | R$_X$ | R$_Y$ | Name | Mass ion | LCMS retention time (min) |
|---|---|---|---|---|---|
| 216 | <br>Preparation 52 | 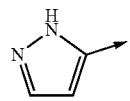 | N-[(1S)-1-(dicyclopropylmethyl)-2-[4-(3,5-dimethyl-1H-pyrazol-4-yl)anilino]-2-oxo-ethyl]-1H-pyrazole-5-carboxamide | 433.235 | 2.06 |
| 217 | 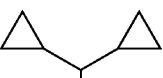<br>Preparation 52 | 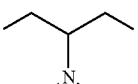<br>Prep. 200 | N-[(1S)-1-(dicyclopropylmethyl)-2-[4-(3,5-dimethyl-1H-pyrazol-4-yl)anilino]-2 oxo-ethyl]-2]-2-fluoro-1-(fluoromethyl)ethyl]pyrazole-3-carboxamide | 511.264 | 2.29 |
| 218 | 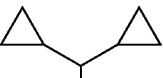<br>Preparation 52 | 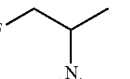<br>Prep. 199B | N-[(1S)-1-(dicyclopropylmethyl)-2-[4-(3,5-dimethyl-1H-pyrazol-4-yl)anilino]-2-oxo-ethyl]-2-(2-fluoro-methyl-ethyl)pyrazole-3-carboxamide | 493.273 | 2.27 |
| 219 | 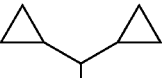<br>Preparation 52 | 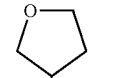<br>Prep. 198 | N-[(1S)-1-(dicyclopropylmethyl)-2-[4-(3,5-dimethyl-1H-pyrazol-4-yl)anilino]-2-oxo-ethyl]-2-tetrahydrofuran-3-yl-pyrazole-3-carboxamide | 503.277 | 2.19 |
| 220 | 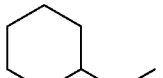<br>Preparation 171 | 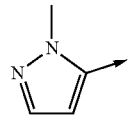 | N-[(1S)-2-cyclohexyl-1-[[4-(3,5-dimethyl-1H-pyrazol-4-yl)phenyl]carbamoyl]propyl]-2-methyl-pyrazole-3-carboxamide | 463.282 | 2.34 |
| 221 | 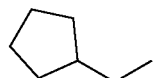<br>Preparation 170 | 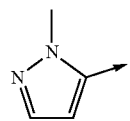 | N-[(1S)-2-cyclopentyl-1-[[4-(3,5-dimethyl-1H-pyrazol-4-yl)phenyl]carbamoyl]propyl]-2-methyl-pyrazole-3-carboxamide | 449.266 Ratio of isomers 1:2 | 2.27 |
| 222 | 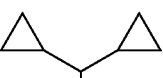<br>Preparation 52 | 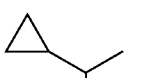<br>Prep. 197 | 2-(1-cyclopropylethyl)-N-[(1S)-1-(dicyclopropylmethyl)-2-[4-(3,5-dimethyl-1H-pyrazol-4-yl)anilino]-2-oxo-ethyl]pyrazole-3-carboxamide | 501.298 | 2.36 |
| 223 | 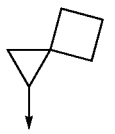<br>Preparation 173 | 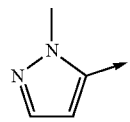 | N-[(1S)-2-[4-(3,5-dimethyl-1H-pyrazol-4-yl)anilino]-2-oxo-1-spiro[2.3]hexan-2-yl-ethyl]-2-methyl-pyrazole-3-carboxamide | 433.236 Ratio of isomers 2:3 | 2.13 |

-continued

| Ex. No. | $R_X$ | $R_Y$ | Name | Mass ion | LCMS retention time (min) |
|---|---|---|---|---|---|
| 224 | <br>Preparation 174 | 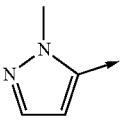 | N-[(1S)-1-(2,2-dimethylcyclopropyl)-2-[4-(3,5-dimethyl-1H-pyrazol-4-yl)anilino]-2-oxo-ethyl]-2-methyl-pyrazole-3-carboxamide | 421.234 Ratio of isomers 2:3 | 2.08 |
| 225 | 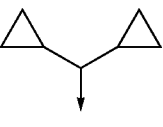<br>Preparation 52 | 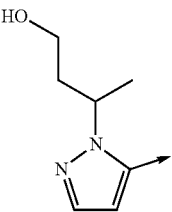<br>Prep. 202B | Diastereomer 1 of N-[(1S)-1-(dicyclopropylmethyl)-2-[4-(3,5-dimethyl-1H-pyrazol-4-yl)anilino]-2-oxo-ethyl]-2-(3-hydroxy-1-methyl-propyl)pyrazole-3-carboxamide | 505.294 | 2.15 |
| 226 | 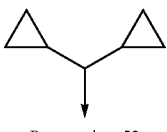<br>Preparation 52 | 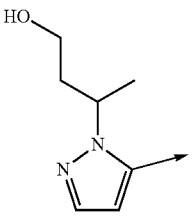 | Diastereomer 2 of N-[(1S)-1-(dicyclopropylmethyl)-2-[4-(3,5-dimethyl-1H-pyrazol-4-yl)anilino]-2-oxo-ethyl]-2-(3-hydroxy-1-methyl-propyl)pyrazole-3-carboxamide | 505.292 | 2.11 |
| 227 | 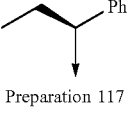<br>Preparation 117 | 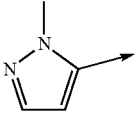 | Diastereomer 1 of N-[(2S)-1-[4-(3,5-dimethyl-1H-pyrazol-4-yl)phenyl]carbamoyl]-2-phenyl-butyl]-2-methyl-pyrazole-3-carboxamide** | 471.251 | 2.17 |
| 228 | 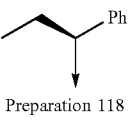<br>Preparation 118 | 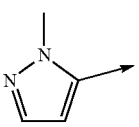 | Diastereomer 2 N-[(2S)-1-[4-(3,5-dimethyl-1H-pyrazol-4 yl)phenyl]carbamoyl]-2-phenyl-butyl]-2-methyl-pyrazole-3-carboxamide** | 471.251 | 2.22 |
| 229 | 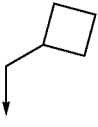 | 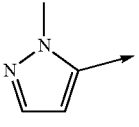 | N-[(1S)-1-(cyclobutylmethyl)-2-[4-(3,5-dimethyl-1H-pyrazol-4-yl)anilino]-2-oxo-ethyl]-2-methyl-pyrazole-3-carboxamide | 421.235 | 2.11 |
| 230 | 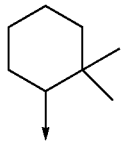<br>Preparation 152 | 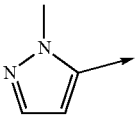 | N-[(1S)-1-(2,2-dimethylcyclohexyl)-2-[4-(3,5-dimethyl-1H-pyrazol-4-yl)anilino]-2-oxo-ethyl]-2-methyl-pyrazole-3-carboxamide | 463.282 | 2.32 |
| 231 | 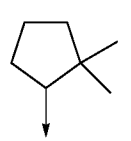<br>Preparation 153 | 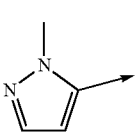 | N-[(1S)-1-(2,2-dimethylcyclopentyl)-2-[4-(3,5-dimethyl-1H-pyrazol-4-yl)anilino]-2-oxo-ethyl]-2-methyl-pyrazole-3-carboxamide | 449.266 | 2.22 |

-continued

| Ex. No. | $R_X$ | $R_Y$ | Name | Mass ion | LCMS retention time (min) |
|---|---|---|---|---|---|
| 232 | 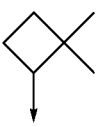<br>Preparation 154 | 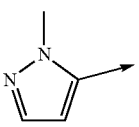 | N-[(1S)-1-(2,2-dimethylcyclobutyl)-2-[4-(3,5-dimethyl-1H-pyrazol-4-yl)anilino]-2-oxo-ethyl]-2-methyl-pyrazole-3-carboxamide | 435.25 Ratio of isomers 1:3 | 2.17 |
| 233 | 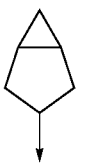<br>Preparation 155 | 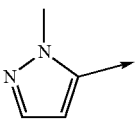 | N-[(1S)-1-[(1R,5S)-3-bicyclo[3.1.0]2-[4-(3,5-dimethyl-1H-pyrazol-4-yl)anilino]-2-oxo-ethyl]-2-methyl-pyrazole-3-carboxamide | 433.235 | 2.10 |
| 234 | 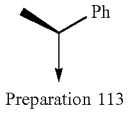<br>Preparation 113 | 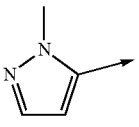 | Diastereomer 1 of N-[(2S)-1-[[4-(3,5-dimethyl-1H-pyrazol-4-yl)phenyl]carbamoyl]-2-phenyl-propyl]-2-methyl-pyrazole-3-carboxamide** | 457.235 | 2.14 |
| 235 | 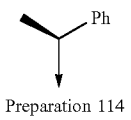<br>Preparation 114 | 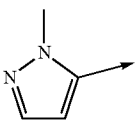 | Diastereomer 2 of N-[(2S)-1-[4-(3,5-dimethyl-1H-pyrazol-4-yl)phenyl]carbamoyl]-2-phenyl-propyl]-2-methyl-pyrazole-3-carboxamide** | 457.235 | 2.10 |
| 236 | 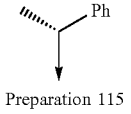<br>Preparation 115 | 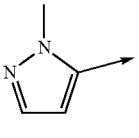 | Diastereomer 1 of N-[(2R)-1-[4-(3,5-dimethyl-1H-pyrazol-4-yl)phenyl]carbamoyl]-2 phenyl-propyl]-2-methyl-pyrazole-3-carboxamide** | 457.235 | 2.14 |
| 237 | 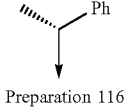<br>Preparation 116 | 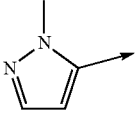 | Diastereomer 2 of N-[(2R)-1-[4-(3,5-dimethyl-1H-pyrazol-4-yl)phenyl]carbamoyl]-2-phenyl-propyl]-2-methyl-pyrazole-3-carboxamide** | 457.235 | 2.10 |
| 238 | 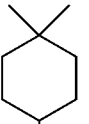<br>Preparation 156 | 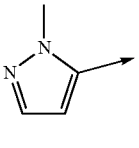 | N-[(1S)-1-(4,4-dimethylcyclohexyl)-2-[4-(3,5-dimethyl-1H-pyrazol-4-yl)anilino]-2-oxo-ethyl]-2-methyl-pyrazole-3-carboxamide | 463.282 | 2.30 |
| 239 | 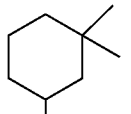<br>Preparation 157 | 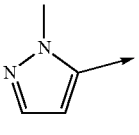 | N-[(1S)-1-(3,3-dimethylcyclohexyl)-2-[4-(3,5-dimethyl-1H-pyrazol-4-yl)anilino]-2-oxo-ethyl]-2-methyl-pyrazole-3-carboxamide | 463.282 Ratio of isomers 1:1 | 2.29 |
| 240 | 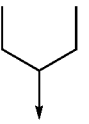 | 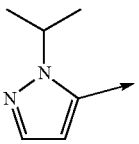 | N-[(1S)-1-[4-(3,5-dimethyl-1H-pyrazol-4-yl)phenyl]carbamoyl]-2-ethyl-butyl]-2-isopropyl-pyrazole-3-carboxamide | 451.282 | 2.28 |

-continued

| Ex. No. | R$_X$ | R$_Y$ | Name | Mass ion | LCMS retention time (min) |
|---|---|---|---|---|---|
| 241 | Preparation 45B | | N-[(1S)-2-[4-(3,5-dimethyl-1H-pyrazol-4-yl)anilino]-2-oxo-1-[(7R)-spiro[2.5]octan-7-yl]ethyl]-2-methyl-pyrazole-3-carboxamide‡‡ | 461.266 | 2.24 |
| 242 | | | N-[(1S)-1-[4-(3,5-dimethyl-1H-pyrazol-4-yl)phenyl]carbamoyl]-2-ethyl-butyl]-2-methyl-pyrazole-3-carboxamide | 423.251 | 2.14 |
| 243 | | | N-[(1S)-1-(cyclopropylmethyl)-2-[4-(3,5-dimethyl-1H-pyrazol-4-yl)anilino]-2-oxo-ethyl]-2-methyl-pyrazole-3-carboxamide | 407.22 | 2.00 |
| 244 | Preparation 151 | | N-[(1S)-1-[4-(3,5-dimethyl-1H-pyrazol-4-yl)phenyl]carbamoyl]-2-isopropyl-3-methyl-butyl]-2-methyl-pyrazole-3-carboxamide | 451.283 | 2.29 |
| 245 | Preparation 158 | | N-[(1S)-2-[4-(3,5-dimethyl-1H-pyrazol-4-yl)anilino]-2-oxo-1-(2,2,3,3-tetramethylcyclopropyl)ethyl]-2-methyl-pyrazole-3-carboxamide | 449.267 | 2.23 |
| 246 | Preparation 159 | | N-[(1S)-2-[4-(3,5-dimethyl-1H-pyrazol-4-yl)anilino]-1-[(1S,6R)-norcaran-7-yl]-2-oxo-ethyl]-2-methyl-pyrazole-3-carboxamide | 447.251 | 2.18 |
| 247 | Preparation 119 | | Diastereomer 1‡ of N-[(2-[4-(3,5-dimethyl-1H-pyrazol-4-yl)anilino]-1-[(1S)-4-fluoroindan-1-yl]-2-oxo-ethyl]-2-methyl-pyrazole-3-carboxamide** | 487.226 | 2.20 |
| 248 | Preparation 119 | | Diastereomer 2‡ of N-[(2-[4-(3,5-dimethyl-1H-pyrazol-4-yl)anilino]-1-[(1S)-4-fluoroindan-1-yl]-2-oxo-ethyl]-2-methyl-pyrazole-3-carboxamide** | 487.226 | 2.19 |

-continued

| Ex. No. | R_X | R_Y | Name | Mass ion | LCMS retention time (min) |
|---|---|---|---|---|---|
| 249 | Preparation 110 | | N-[(1S)-1-[(1S)-4,6-difluoroindan-1-yl]-2-[4-(3,5-dimethyl-1H-pyrazol-4-yl)anilino]-2-oxo-ethyl]-2-methyl-pyrazole-3-carboxamide (5:1 mixture of diastereomers) | 505.216 | 2.24 |
| 250 | Preparation 45B | | N-[(1S)-2-[4-(3,5-dimethyl-1H-pyrazol-4-yl)anilino]-2-oxo-1-[(7S)-spiro[2.5]octan-7-yl]ethyl]-2-methyl-pyrazole-3-carboxamide‡‡ | 461.267 | 2.25 |
| 251 | Preparation 85 | | N-[2-[4-(3,5-dimethyl-1H-pyrazol-4-yl)anilino]-1-(2-methylcyclopentyl)-2-oxo-ethyl]-2-isopropyl-pyrazole-3-carboxamide | 463.282 | 2.32 |
| 252 | Racemic Preparation 85 | | N-[2-[4-(3,5-dimethyl-1H-pyrazol-4-yl)anilino]-1-(2-methylcyclopentyl)-2-oxo-ethyl]-2-methyl-pyrazole-3-carboxamide | 435.251 | 2.18 |
| 253 | Preparation 162 | | N-[(1S)-1-[(4,4-difluorocyclohexyl)methyl]-2-[4-(3,5-dimethyl-1H-pyrazol-4-yl)anilino]-2-oxo-ethyl]-2-methyl-pyrazole-3-carboxamide | 485.248 | 2.14 |
| 254 | Preparation 163 | | N-[(1S)-1-(3-bicyclo[2.2.2]octanyl)-2-[4-(3,5-dimethyl-1H-pyrazol-4-yl)anilino]-2-oxo-ethyl]-2-methyl-pyrazole-3-carboxamide | 461.267 Ratio of isomers 2:3 | 2.25 |
| 255 | Preparation 109 | | N-[(1-[(1S)-5,7-difluorotetralin-1-yl]-2-[4-(3,5-dimethyl-1H-pyrazol-4-yl)anilino]-2-oxo-ethyl]-2-methyl-pyrazole-3-carboxamide (single diastereomer) | 519.232 | 2.30 |
| 256 | Preparation 120 | | N-[2-[4-(3,5-dimethyl-1H-pyrazol-4-yl)anilino]-1-[(1S)-5-fluorotetralin-1-yl]-2-oxo-ethyl]-2-methyl-pyrazole-3-carboxamide (single diastereomer)** | 501.242 | 2.26 |

-continued

| Ex. No. | R$_X$ | R$_Y$ | Name | Mass ion | LCMS retention time (min) |
|---|---|---|---|---|---|
| 257 | 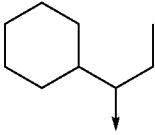<br>Preparation 160 | 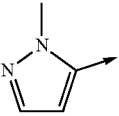 | Diastereomer 1 of N-[(1S)-2-cyclohexyl-1-[4-(3,5-dimethyl-1H-pyrazol-4-yl)phenyl]carbamoyl]butyl]-2-methyl-pyrazole-3-carboxamide | 477.298 | 2.39 |
| 258 | 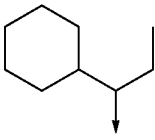<br>Preparation 161 | 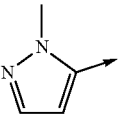 | Diastereomer 2 of N-[(1S)-2-cyclohexyl-1-[4-(3,5-dimethyl-1H-pyrazol-4-yl)phenyl]carbamoyl]butyl]-2-methyl-pyrazole-3-carboxamide | 477.298 | 2.39 |
| 259 | 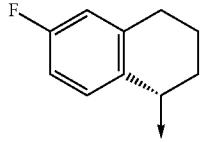<br>Preparation 97 | 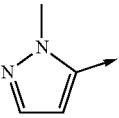 | Diastereomer 1 of N-[(2-[4-(3,5-dimethyl-1H-pyrazol-4-yl)anilino]-1[(1S)-6-fluorotetralin-1-yl]-2-oxo-ethyl]-2-methyl-pyrazole-3-carboxamide§ | 501.241 | 2.21 |
| 260 | 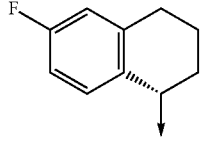<br>Preparation 97 | 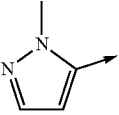 | Diastereomer 2 of N-[(2-[4-(3,5-dimethyl-1H-pyrazol-4-yl)anilino]-1-[(1S)-6-fluorotetralin-1-yl]-2-oxo-ethyl]-2-methyl-pyrazole-3-carboxamide§ | 501.242 | 2.26 |
| 261 | 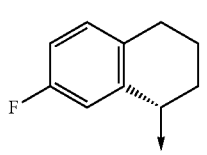<br>Preparation 98 | 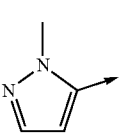 | N-[(2-[4-(3,5-dimethyl-1H-pyrazol-4-yl)anilino]-1-[(1S)-7-fluorotetralin-1-yl]-2-oxo-ethyl]-2-methyl-pyrazole-3-carboxamide (11:1 mixture of diastereomers) | 501.242 | 2.26 |
| 262 | 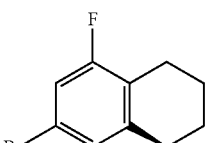<br>Preparation 106 | 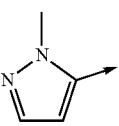 | N-[(1S)-1-[(1R)-7-bromo-5-fluoro-tetralin-1-yl]-2-[4-(3,5-dimethyl-1H-(pyrazol-4-yl)anilino]-2-oxo-ethyl]-2-methyl-pyrazole-3-carboxamide | 579.152 | 2.33 |
| 263 | 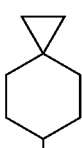<br>Preparation 69 | 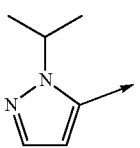 | N-[(1S)-2-[4-(3,5-dimethyl-1H-pyrazol-4-yl)anilino]-2-oxo-1-spiro[2.5]octan-6-yl-ethyl]-3-isopropyl-isoxazole-4-carboxamide† | 490.282 | 2.42 |
| 264 | 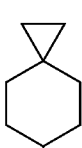<br>Preparation 69 | 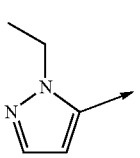 | N-[(1S)-2-[4-(3,5-dimethyl-1H-pyrazol-4-yl)anilino]-2-oxo-1-spiro[2.5]octan-6-yl-ethyl]-2-ethyl-pyrazole-3-carboxamide† | 475.283 | 2.31 |

-continued

| Ex. No. | R$_X$ | R$_Y$ | Name | Mass ion | LCMS retention time (min) |
|---|---|---|---|---|---|
| 265 | 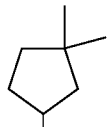<br>Preparation 84 | 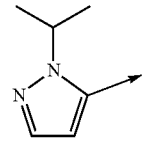 | N-[1-(3,3-dimethylcyclopentyl)-2-[4-(3,5-dimethyl-1H-pyrazol-4-yl)anilino]-2-oxo-ethyl]-2-isopropyl-pyrazole-3-carboxamide | 477.298 | 2.38 |
| 266 | 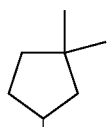<br>Preparation 84 | 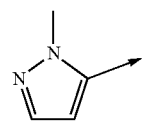 | N-[1-(3,3-dimethylcyclopentyl)-2-[4-(3,5-dimethyl-1H-pyrazol-4-yl)anilino]-2-oxo-ethyl]-2-methyl-pyrazole-3-carboxamide | 449.267 | 2.23 |
| 267 | 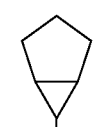<br>Preparation 159 | 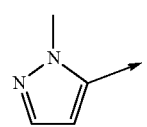 | N-[(1S)-1-[(1S,5R)-6-bicyclo[3.1.0]hexanyl]-2-[4-(3,5-dimethyl-1H-pyrazol-4-yl)anilino]-2-oxo-ethyl]-2-methyl-pyrazole-3-carboxamide | 433.235 | 2.10 |
| 268 | 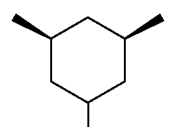<br>Preparation 165 | 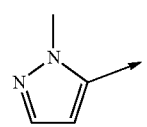 | N-[(1S)-1-[(3S,5R)-3,5-dimethylcyclohexyl]-2-[4-(3,5-dimethyl-1H-pyrazol-4-yl)anilino]-2-oxo-ethyl]-2-methyl-pyrazole-3-carboxamide | 463.282 Ratio of isomers 1:4 | 2.32 |
| 269 | 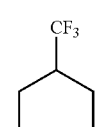<br>Preparation 166 | 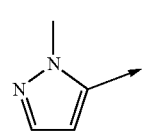 | N-[(1S)-2-[4-(3,5-dimethyl-1H-pyrazol-4-yl)anilino]-2-oxo-1-[4-(trifluoromethyl)cyclohexyl]ethyl]-2-methyl-pyrazole-3-carboxamide | 503.238 Ratio of isomers 1:4 | 2.22 |
| 270 | 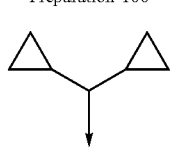<br>Preparation 52 | 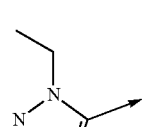 | N-[(1S)-1-(dicyclopropylmethyl)-2-[4-(3,5-dimethyl-1H-pyrazol-4-yl)anilino]-2-oxo-ethyl]-3-ethyl-triazole-4-carboxamide | 462.262 | 2.14 |
| 271 | 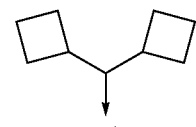<br>Preparation 64 | 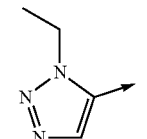 | N-[(1S)-1-[di(cyclobutyl)methyl]-2-[4-(3,5-dimethyl-1H-pyrazol-4-yl)anilino]-2-oxo-ethyl]-3-ethyl-triazole-4-carboxamide | 490.294 | 2.36 |
| 272 | 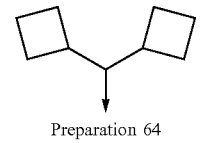<br>Preparation 64 | 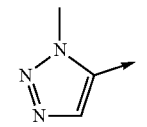 | N-[(1S)-1-[di(cyclobutyl)methyl]-2-[4-(3,5-dimethyl-1H-pyrazol-4-yl)anilino]-2-oxo-ethyl]-3-methyl-triazole-4-carboxamide | 476.278 | 2.30 |

-continued

| Ex. No. | R$_X$ | R$_Y$ | Name | Mass ion | LCMS retention time (min) |
|---|---|---|---|---|---|
| 273 | <br>Preparation 64 | 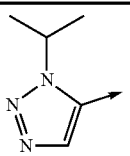 | N-[(1S)-1-[di(cyclobutyl)methyl]-2-[4-(3,5-dimethyl-1H-pyrazol-4-yl)anilino]-2-oxo-ethyl]-3-isopropyl-triazole-4-carboxamide | 504.311 | 2.42 |
| 274 | 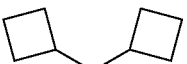<br>Preparation 64 | 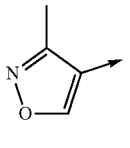 | N-[(1S)-1-[di(cyclobutyl)methyl]-2-[4-(3,5-dimethyl-1H-pyrazol-4-yl)anilino]-2-oxo-ethyl]-3-methyl-isoxazole-4-carboxamide | 476.267 | 2.40 |
| 275 | 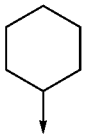 | 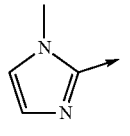 | N-[(1S)-1-cyclohexyl-2-[4-(3,5-dimethyl-1H-pyrazol-4-yl)anilino ]-2-oxo-ethyl]-1-methyl-imidazole-2-carboxamide | 435.251 | 2.18 |
| 276 | 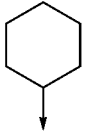 | 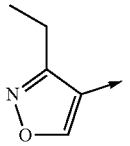 | N-[(1S)-1-cyclohexyl-2-[4-(3,5-dimethyl-1H-pyrazol-4-yl)anilino]-2-oxo-ethyl]-3-ethyl-isoxazole-4-carboxamide | 450.252 | 2.27 |
| 277 | 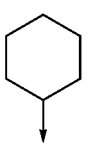 | 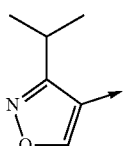 | N-[(1S)-1-cyclohexyl-2-[4-(3,5-dimethyl-1H-pyrazol-4-yl)anilino]-2-oxo-ethyl]-3-isopropyl-isoxazole-4-carboxamide | 464.267 | 2.34 |
| 278 | 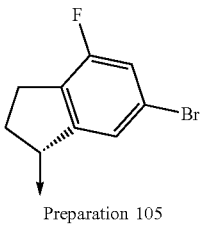<br>Preparation 105 | 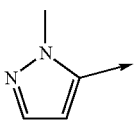 | N-[(1S)-1-[(1R)-6-bromo-4-fluoro-indan-1-yl]-2-[4-(3,5-dimethyl-1H-pyrazol-4-yl)anilino]-2-oxo-ethyl]-2-methyl-pyrazole-3-carboxamide | 565.137 | 2.30 |
| 279 | 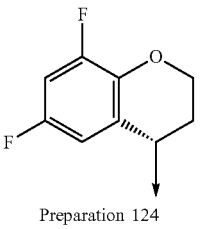<br>Preparation 124 | 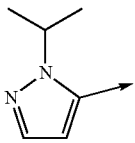 | N-[(1S)-1-[(4S)-6,8-difluorochroman-4-yl]-2-[4-(3,5-dimethyl-1H-pyrazol-4-yl)anilino]-2-oxo-ethyl]-2-isopropyl-pyrazole-3-carboxamide†† | 549.243 | 2.31 |
| 280 | 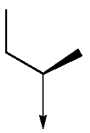 | 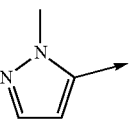 | N-[(1S,2R)-1-[4-(3,5-dimethyl-1H-pyrazol-4-yl)phenyl]carbamoyl]-2-methyl-butyl]-2-methyl-pyrazole-3-carboxamide | 409.235 | 2.07 |
| 281 | 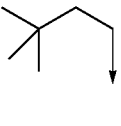 | 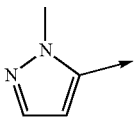 | N-[(1S)-1-[4-(3,5-dimethyl-1H-pyrazol-4-yl)phenyl]carbamoyl]-3,3-dimethyl-butyl]-2-methyl-pyrazole-3-carboxamide | 423.25 | 2.15 |

-continued

| Ex. No. | R_X | R_Y | Name | Mass ion | LCMS retention time (min) |
|---|---|---|---|---|---|
| 282 | 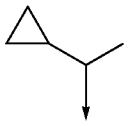<br>Preparation 69B | 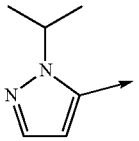 | Diastereomer 1 of N-[2-cyclopropyl-1-[4-(3,5-dimethyl-1H-pyrazol-4-yl)phenyl]carbamoyl]propyl]-2-isopropyl-pyrazole-3-carboxamide‡ | 449.266 | 2.22 |
| 283 | 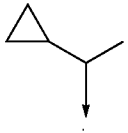<br>racemic<br>Preparation 69B | 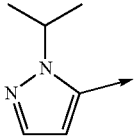 | Diastereomer 2 of N-[(1S,2S)-2-cyclopropyl-1-[4-(3,5-dimethyl-1H-pyrazol-4-yl)phenyl]carbamoyl]propyl-2-isopropyl-pyrazole-3-carboxamide‡ | 449.265 | 2.19 |
| 284 | 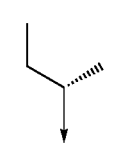 | 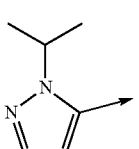 | N-[(1S,2S)-1-[4-(3,5-dimethyl-1H-pyrazol-4-yl)phenyl]carbamoyl]-2-methyl-butyl]-2-isopropyl-pyrazole-3-carboxamide | 437.266 | 2.20 |
| 285 | 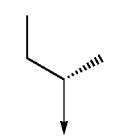 | 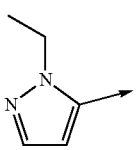 | N-[(1S,2S)-1-[4-(3,5-dimethyl-1H-pyrazol-4-yl)phenyl]carbamoyl]-2-methyl-butyl]-2-ethyl-pyrazole-3-carboxamide | 423.249 | 2.13 |
| 286 | 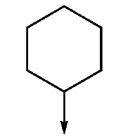 | 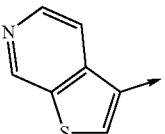 | N-[(1S)-1-cyclohexyl-2-[4-(3,5-dimethyl-1H-pyrazol-4-yl)anilino]-2-oxo-ethyl]thieno[2,3-c]pyridine-3-carboxamide | 488.213 | 2.05 |
| 287 | 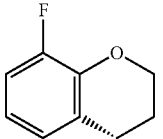<br>Preparation 121 | 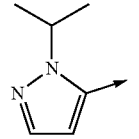 | N-[(1S)-2-[4-(3,5-dimethyl-1H-pyrazol-4-yl)anilino]-1-[(4S)-8-fluorochroman-4-yl]-2-oxo-ethyl]-2-isopropyl-pyrazole-3-carboxamide†† | 531.253 | 2.28 |
| 288 | 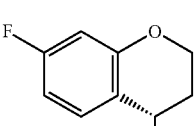<br>Preparation 122 | 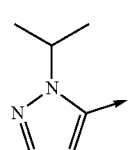 | N-[(1S)-2-[4-(3,5-dimethyl-1H-pyrazol-4-yl)anilino]-1-[(4S)-7-fluorochroman-4-yl]-2-oxo-ethyl]-2-isopropyl-pyrazole-3-carboxamide†† | 531.255 | 2.31 |
| 289 | 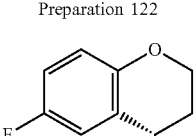<br>Preparation 123 | 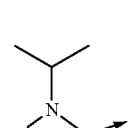 | N-[(1S)-2-[4-(3,5-dimethyl-1H-pyrazol-4-N yl)anilino]-1-[(4S)-6-fluorochroman-4-yl]-2-oxo-ethyl]-2-isopropyl-pyrazole-3-carboxamide†† | 531.254 | 2.29 |
| 290 | 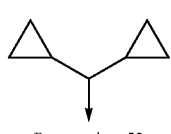<br>Preparation 52 | 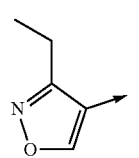 | N-[(1S)-1-(dicyclopropylmethyl)-2-[4-(3,5-dimethyl-1H-pyrazol-4-yl)anilino]-2-oxo-ethyl]-3-ethyl-isoxazole-4-carboxamide | 462.252 | 2.25 |

-continued

| Ex. No. | R_X | R_Y | Name | Mass ion | LCMS retention time (min) |
|---|---|---|---|---|---|
| 291 | Preparation 52 (dicyclopropylmethyl) | isopropyl-isoxazole | N-[(1S)-1-(dicyclopropylmethyl)-2-[4-(3,5-dimethyl-1H-pyrazol-4-yl)anilino]-2-oxo-ethyl]-3-isopropyl-isoxazole-4-carboxamide | 476.269 | 2.32 |
| 292 | Preparation 52 (dicyclopropylmethyl) | isopropyl-triazole | N-[(1S)-1-(dicyclopropylmethyl)-2-[4-(3,5-dimethyl-1H-pyrazol-4-yl)anilino]-2-oxo-ethyl]-3-isopropyl-triazole-4-carboxamide | 476.4 | 0.69* |
| 293 | cyclohexyl | imidazo[1,2-a]pyridine | N-[(1S)-1-cyclohexyl-2-[4-(3,5-dimethyl-1H-pyrazol-4-yl)anilino]-2-oxo-ethyl]imidazo[1,2-a]pyridine-3-carboxamide | 471.252 | 2.07 |
| 294 | bis(3,3-difluorocyclobutyl)methyl racemic Preparation 81 | isopropyl-pyrazole | N-[1-[bis(3,3-difluorocyclobutyl)methyl]-2-[4-(3,5-dimethyl-1H-pyrazol-4-yl)anilino]-2-oxo-ethyl]-2-isopropyl-pyrazole-3-carboxamide | 575.277 | 2.39 |
| 295 | bis(3,3-difluorocyclobutyl)methyl racemic Preparation 81 | methyl-pyrazole | N-[1-[bis(3,3-difluorocyclobutyl)methyl]-2-[4-(3,5-dimethyl-1H-pyrazol-4-yl)anilino]-2-oxo-ethyl]-2-isopropyl-pyrazole-3-carboxamide | 547.246 | 2.26 |
| 296 | cyclohexyl (R) amino acid | methyl-pyrazole | N-[(1R)-1-cyclohexyl-2-[4-(3,5-dimethyl-1H-pyrazol-4-yl)anilino]-2-oxo-ethyl]-2-methyl-pyrazole-3-carboxamide | 435.251 | 2.16 |
| 297 | benzyl (R) amino acid | methyl-pyrazole | N-[(1R)-1-benzyl-2-[4-(3,5-dimethyl-1H-pyrazol-4-yl)anilino]-2-oxo-ethyl]-2-methyl-pyrazole-3-carboxamide | 443.22 | 2.08 |
| 298 | isobutyl | methyl-pyrazole | N-[(1S)-1-[4-(3,5-dimethyl-1H-pyrazol-4-yl)phenyl]carbamoyl]-3-methyl-butyl]-2-methyl-pyrazole-3-carboxamide | 409.237 | 2.07 |

| Ex. No. | $R_X$ | $R_Y$ | Name | Mass ion | LCMS retention time (min) |
|---|---|---|---|---|---|
| 299 | ![structure] Preparation 146 | ![pyrazole] | Diastereomer 1 of N-[1-[cyclobutyl(phenyl)methyl]-2-[4-(3,5-dimethyl-1H-pyrazol-4-yl)anilino]-2-oxo-ethyl]-2-methyl-pyrazole-3-carboxamide§ | 497.268 | 2.26 |
| 300 | ![structure] Preparation 146 | ![pyrazole] | Diastereomer 2 of N-[1-[cyclobutyl(phenyl)methyl]-2-[4-(3,5-dimethyl-1H-pyrazol-4-yl)anilino]-2-oxo-ethyl]-2-methyl-pyrazole-3-carboxamide§ | 497.268 | 2.26 |

The enantiomers were separated by chiral SFC
†The enantiomers of the SEM protected precursors were separated by chiral SFC
‡The diastereomers were separated by preparative HPLC
*LCMS Method 3
▫Trans (2S)-2-(tert-butoxycarbonylamino)-2-(4-methylcyclohexyl)acetic acid was prepared according to the method in WO2018/229079
§The diastereomers were separated by chiral SFC.
**The aromatic bromide was removed according to the method of Example 375 prior to SEM deprotection according to the method of Example 1.
††The major (S,S) diastereomer was isolated by prep. HPLC.
‡‡The diastereomers of the SEM protected precursors were separated by chiral SFC.

Example 32—Method B—Single Enantiomer Synthesis

N-[(1S)-1-(Dicyclopropylmethyl)-2-[4-(3,5-dimethyl-1H-pyrazol-4-yl)anilino]-2-oxo-ethyl]-2-isopropyl-pyrazole-3-carboxamide

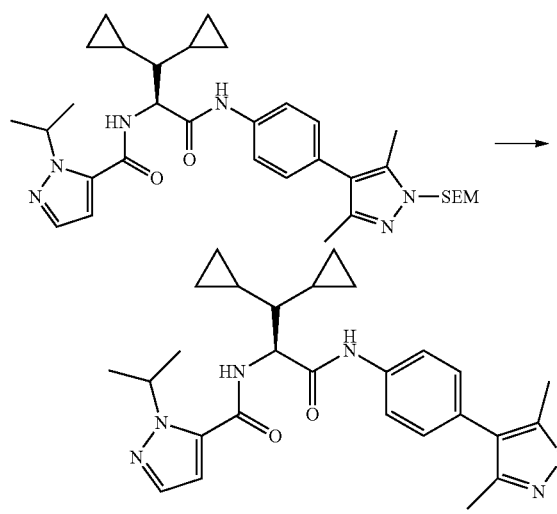

The compound of Preparation 60 (5.20 g, 8.60 mmol) was dissolved in chloroform (10 mL) and TFA (10 mL) and stirred at room temperature for 3 hours. The reaction mixture was evaporated and taken up in MeOH (25 mL) and water (20 mL). Conc. aqueous NH₃ was added slowly until the pH was 6-7. The mixture was concentrated in vacuo to remove MeOH and the crude solid product was filtered off, washed with water (20 mL) and dried in vacuo to give the crude product (4.1 g, 93% purity). Purification by column chromatography (silica, eluting with 3% EtOH in EtOAc) gave the title compound (2.36 g, 58%) as a white solid. 1H NMR (400 MHz, DMSO-d6) δ 12.23 (s, 1H), 10.18 (s, 1H), 8.43 (d, J=8.8 Hz, 1H), 7.69-7.62 (m, 2H), 7.50 (d, J=2.0 Hz, 1H), 7.27-7.20 (m, 2H), 6.93 (d, J=2.0 Hz, 1H), 5.42 (hept, J=6.6 Hz, 1H), 4.82 (t, J=8.2 Hz, 1H), 2.18 (s, 6H), 1.39 (d, J=6.6 Hz, 3H), 1.35 (d, J=6.6 Hz, 3H), 0.97-0.71 (m, 3H), 0.52-0.10 (m, 8H), LCMS (METHOD 3) (ES): m/z 475.5 [M+H]⁺, RT=0.73 min.

Example 32—Sulfate Salt

N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide Sulfuric Acid Salt A mixture of sulfuric acid (647 mg, 2.51 mmol, 5 mol/L) in isopropyl acetate (2 mL) was added to a stirring suspension of the compound of Example 32 (1.540 g, 3.245 mmol) in isopropyl acetate (10 mL) at 40° C. The acid mixture was washed in with further isopropyl acetate (7 mL). The mixture was stirred vigorously at 40° C. for 4 h. Briefly warmed further to 70° C. Reaction mixture became more homogenous albeit hazy. A seed crystal was added and the reaction mixture was stirred overnight at 40° C. A solid had crashed out on the bottom of flask. The sides of the flask were agitated, the speed of stirrer-bar rotation was increased and the mixture was left at 40° C. for 4 h. The colourless solid was collected by filtration, washing with 25 mL isopropyl acetate then dried under vacuum at 60° C. overnight to give the title compound (1.81 g, 99% yield). ICP-SFMS analysis showed a sulfur content of 40100 mg/kg, consistent with a 3:2 stoichiometry of N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide:sulfuric acid (calculated sulfur content 3.96%). 1H NMR (600 MHz, DMSO-d6) δ 10.23 (s, 1H), 8.44 (d, J=8.8 Hz, 1H), 7.80-7.60 (m, 2H), 7.50 (d, J=2.0 Hz, 1H), 7.39-7.19 (m, 2H), 6.93 (d, J=2.0 Hz, 1H), 5.41 (hept, J=6.6 Hz, 1H), 4.81 (t, J=8.3 Hz, 1H), 2.25 (s, 6H), 1.37 (dd, J=22.2, 6.6 Hz, 6H), 1.17 (d, J=6.3 Hz, 1H), 0.89 (dtd, J=13.4, 8.2, 5.3 Hz, 1H), 0.86-0.74 (m, 2H), 0.50-0.43 (m, 1H), 0.41-0.34 (m, 2H), 0.31 (qd, J=8.3, 4.7 Hz, 1H), 0.28-0.17 (m, 3H), 0.14 (dq, J=11.7, 6.9, 5.5 Hz, 1H). DSC: The obtained polymorph had a differential scanning calorimetry (DSC) curve comprising an endo thermo event with an onset at about 198° C. (±2° C.) (melting point) XRPD: In one embodiment the obtained polymorph has an XRPD pattern essentially similar to that shown in FIG. 1. In another embodiment the polymorph C of LEO 153339B is characterized by an XRPD pattern exhibiting one or more reflection peaks at approximately 2θ=8.8, 9.5, 10.3, 11.5, 18.5 and/or 22.0 (bold primary) (±0.1 degrees) respectively.

Example 32—Napadisylate Salt

N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide naphthalene-1,5-disulfonic acid salt A solution of 1,5-naphthalene-disulfonic acid tetrahydrate (676 mg, 1.88 mmol) in IPA (4 mL) was added to a solution of the compound of Example 32 (1.78 g, 3.75 mmol) in IPA (20 mL) at room temperature and the resultant mixture was stirred for 18 h. The reaction mixture was concentrated slowly under vacuum to leave ~5 mL solvent. The now opaque mixture was seeded and left at 40° C. for 6 h, then left to stand at room temperature overnight. The solid was collected and dried under reduced pressure at 40° C. for 4 h, to leave 2.33 g colourless solid, (quantitative yield). 1H NMR (600 MHz, DMSO-d6) δ 10.25 (s, 1H), 8.86 (d, J=8.5 Hz, 1H), 8.43 (d, J=8.8 Hz, 1H), 7.93 (d, J=7.0 Hz, 1H), 7.75-7.61 (m, 2H), 7.50 (d, J=1.9 Hz, 1H), 7.41 (dd, J=8.6, 7.0 Hz, 1H), 7.29 (d, J=8.5 Hz, 2H), 6.92 (d, J=2.0 Hz, 1H), 5.40 (hept, J=6.6 Hz, 1H), 4.80 (t, J=8.3 Hz, 1H), 2.27 (s, 6H), 1.36 (dd, J=21.6, 6.6 Hz, 6H), 0.89 (dtd, J=13.4, 8.4, 5.2 Hz, 1H), 0.85-0.73 (m, 2H), 0.50-0.42 (m, 1H), 0.37 (tt, J=9.2, 3.9 Hz, 2H), 0.31 (dtd, J=14.4, 8.6, 3.4 Hz, 1H), 0.27-0.17 (m, 3H), 0.13 (dq, J=11.7, 7.3, 5.7 Hz, 1H).

DSC: The obtained polymorph is a hydrate and has a differential scanning calorimetry (DSC) curve comprising an endo thermo event with an onset at about 131° C. (±2° C.) (melting point)

Figure 2:
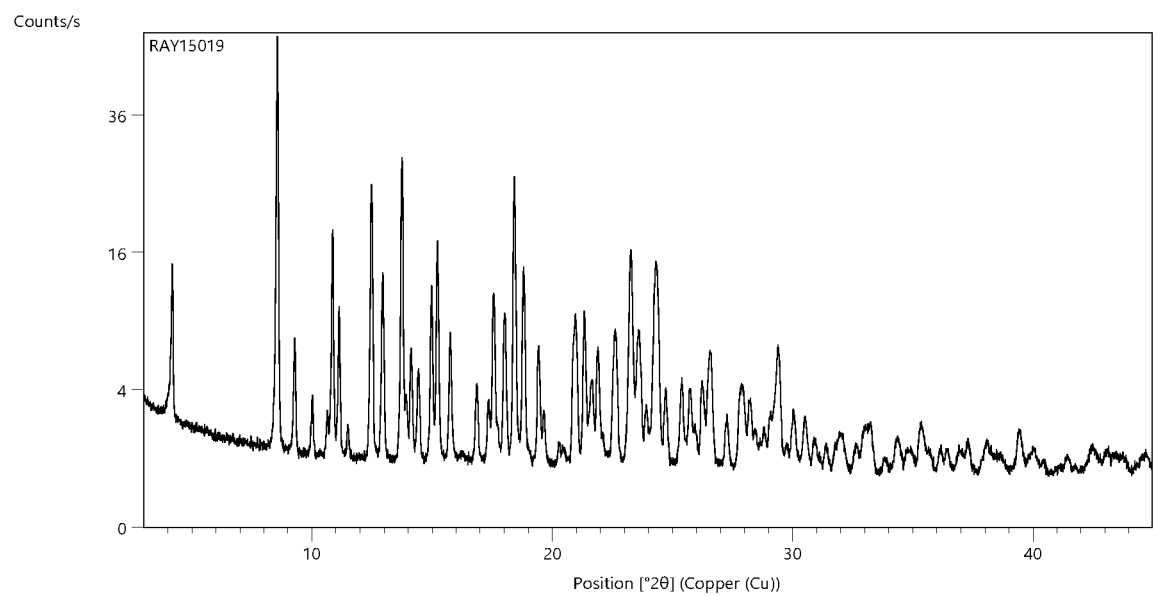

XRPD: In one embodiment the obtained polymorph has an XRPD pattern essentially similar to that shown in FIG. 2. In another embodiment the obtained polymorph is characterized by an XRPD pattern exhibiting one or more reflection peaks at approximately 2θ=4.2, 8.6, 9.3, 10.9, 12.5, 14.1, 14.4, 15.7, 18.5, 18.8, 21.0 and/or 21.3 (bold primary) (±0.1 degrees) respectively.

Example 119—Method B

N-[(1S)-1-(Dicyclopropylmethyl)-2-[4-(3,5-dimethyl-1H-pyrazol-4-yl)anilino]-2-oxo-ethyl]-2-[(1S)-2-hydroxy-1-methyl-ethyl]pyrazole-3-carboxamide

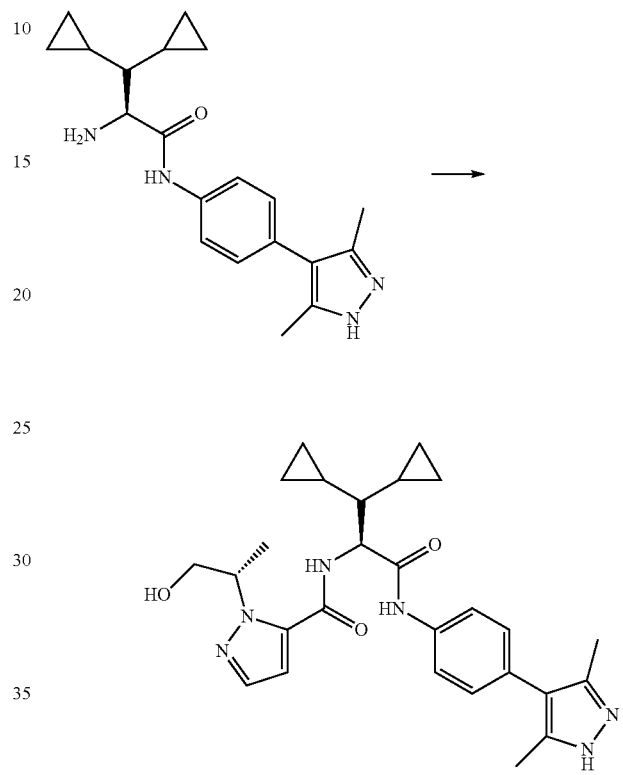

The amine of Preparation 273 (4.738 g, 14.0 mmol) was dissolved in DMF (20 mL) and the acid of Preparation 194 (2.38 g, 14.0 mmol) was added followed by DIPEA (9.74 mL, 7.23 g, 55.9 mmol) and HATU (5.85 g, 15.4 mmol). The mixture was stirred at room temperature for 2 hours then poured into water to give a white precipitate. The supernatant was decanted off and the residue was recrystallised from EtOAc to give the title compound (3.24 g, 47%) as a colourless solid. Evaporation of the mother liquor and purification by column chromatography (silica, eluting with DCM/MeOH, 100:0 to 95:5) gave further product (622 mg, 9%). 1H NMR (400 MHz, DMSO-d6) δ 12.25 (s, 1H), 10.17 (s, 1H), 8.43 (d, J=8.8 Hz, 1H), 7.69-7.60 (m, 2H), 7.51 (d, J=2.0 Hz, 1H), 7.27-7.19 (m, 2H), 6.92 (d, J=2.0 Hz, 1H), 5.31 (h, J=6.7 Hz, 1H), 4.88 (t, J=5.3 Hz, 1H), 4.85-4.76 (m, 1H), 3.72 (ddd, J=10.4, 7.1, 5.5 Hz, 1H), 3.60 (dt, J=10.8, 5.7 Hz, 1H), 2.18 (s, 6H), 1.33 (d, J=6.7 Hz, 3H), 1.04-0.70 (m, 3H), 0.55-0.43 (m, 1H), 0.43-0.11 (m, 7H); LCMS (METHOD 3) (ES): m/z 491.4 [M+H]+, RT=0.62 min.

Examples 482-484

Examples 482-484 were synthesised according to the method of Example 119—Method B, starting from the amine of Preparation 277 and using the appropriate carboxylic acid.

| Example No. | Structure | Name | Mass ion | LCMS retention time (min) |
|---|---|---|---|---|
| 482 | 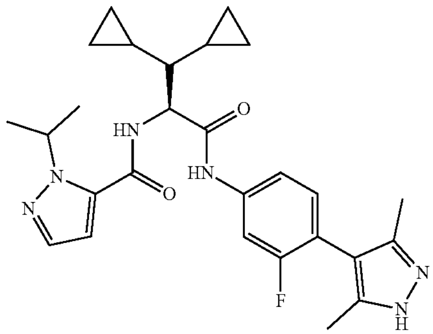 | N-[(1S)-1-(dicyclopropylmethyl)-2-[4-(3,5-dimethyl-1H-pyrazol-4-yl)-3-fluoro-anilino]-2-oxo-ethyl]-2-isopropyl-pyrazole-3-carboxamide | 493.273 | 2.34 |
| 483 | 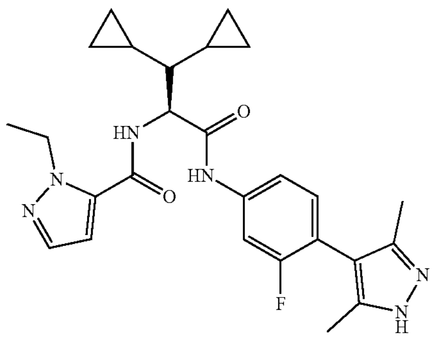 | N-[(1S)-1-(dicyclopropylmethyl)-2-[4-(3,5-dimethyl-1H-pyrazol-4-yl)-3-fluoro-anilino]-2-oxo-ethyl]-2-ethyl-pyrazole-3-carboxamide | 479.257 | 2.27 |
| 484 | 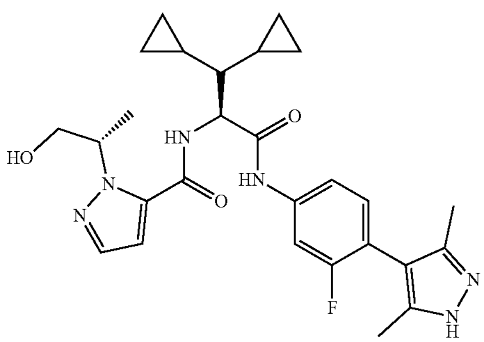 | N-[(1S)-1-(dicyclopropylmethyl)-2-[4-(3,5-dimethyl-1H-pyrazol-4-yl)-3-fluoro-anilino]-2-oxo-ethyl]-2-[(1S)-2-hydroxy-1-methyl-ethyl]pyrazole-3-carboxamide | 509.267 | 2.13 |

Examples 76-82 and 301-304

Examples 76-82 and 301-304 were synthesised according to the method of Example 1 starting from the indicated precursor.

An arrow denotes the point of attachment of the substituent $R_x$ to the parent molecule.

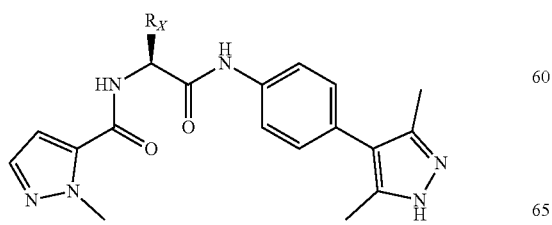

| Ex. No. | Rx | Precursor | Name | Mass ion | LCMS retention time (min) |
|---|---|---|---|---|---|
| 76 | indan-1-yl (1S) | Preparation 29 | N-[(1S)-2-[4-(3,5-dimethyl-1H-pyrazol-4-yl)anilino]-1-[(1R)-indan-1-yl]-2-oxo-ethyl]-2-methyl-pyrazole-3-carboxamide | 469.235 | 2.15 |
| 77 | 6-chloroindan-1-yl | Preparation 34 | N-[(1S)-1-[(1R)-6-chloroindan-1-yl]-2-[4-(3,5-dimethyl-1H-pyrazol-4-yl)anilino]-2-oxo-ethyl]-2-methyl-pyrazole-3-carboxamide | 503.197 | 2.22 |
| 78 | 6-cyanoindan-1-yl | Preparation 32 | N-[(1S)-1-[(1R)-6-cyanoindan-1-yl]-2-[4-(3,5-dimethyl-1H-pyrazol-4-yl)anilino]-2-oxo-ethyl]-2-methyl-pyrazole-3-carboxamide | 494.231 | 2.08 |
| 79 | (1S)-indan-1-yl | Preparation 30 | N-[(1S)-2-[4-(3,5-dimethyl-1H-pyrazol-4-yl)anilino]-1-[(1S)-indan-1-yl]-2-oxo-ethyl]-2-methyl-pyrazole-3-carboxamide | 469.236 | 2.16 |
| 80 | (1S)-6-cyanoindan-1-yl | Preparation 33 | N-[(1S)-1-[(1S)-6-cyanoindan-1-yl]-2-[4-(3,5-dimethyl-1H-pyrazol-4-yl)anilino]-2-oxo-ethyl]-2-methyl-pyrazole-3-carboxamide | 494.231 | 2.11 |
| 81 | (1S)-tetralin-1-yl | Preparation 28 | N-[(1S)-2-[4-(3,5-dimethyl-1H-pyrazol-4-yl)anilino]-2-oxo-1-[(1S)-tetralin-1-yl]ethyl]-2-methyl-pyrazole-3-carboxamide | 483.251 | 2.23 |
| 82 | (1S)-7-cyanotetralin-1-yl | Preparation 31 | N-[(1S)-1-[(1S)-7-cyanotetralin-1-yl]-2-[4-(3,5-dimethyl-1H-pyrazol-4-yl)anilino]-2-oxo-ethyl]-2-methyl-pyrazole-3-carboxamide | 508.246 | 2.16 |
| 301 | cyclopropyl(phenyl)methyl Diastereomer 1 | Preparation 131 | Diastereomer 1 of N-[1-[cyclopropyl(phenyl)methyl]-2-[4-(3,5-dimethyl-1H-pyrazol-4-yl)anilino]-2-oxo-ethyl]-2-methyl-pyrazole-3-carboxamide | 483.251 | 2.17 |
| 302 | cyclopropyl(phenyl)methyl Diastereomer 2 | Preparation 132 | Diastereomer 2 of N-[1-[cyclopropyl(phenyl)methyl]-2-[4-(3,5-dimethyl-1H-pyrazol-4-yl)anilino]-2-oxo-ethyl]-2-methyl-pyrazole-3-carboxamide | 483.251 | 2.17 |

-continued

| Ex. No. | R$_x$ | Precursor | Name | Mass ion | LCMS retention time (min) |
|---|---|---|---|---|---|
| 303 | Diastereomer 3 | Preparation 133 | Diastereomer 3 of N-[1-[cyclopropyl(phenyl)methyl]-2-[4-(3,5-dimethyl-1H-pyrazol-4-yl)anilino]-2-oxo-ethyl]-2-methyl-pyrazole-3-carboxamide | 483.251 | 2.17 |
| 304 | Diastereomer 4 | Preparation 134 | Diastereomer 4 of N-[1-[cyclopropyl(phenyl)methyl]-2-[4-(3,5-dimethyl-1H-pyrazol-4-yl)anilino]-2-oxo-ethyl]-2-methyl-pyrazole-3-carboxamide | 483.252 | 2.17 |

Example 83 tert-butyl N-[(1S)-1-cyclohexyl-2-[4-(3,5-dimethyl-imidazol-4-yl)anilino]-2-oxo-ethyl]carbamate

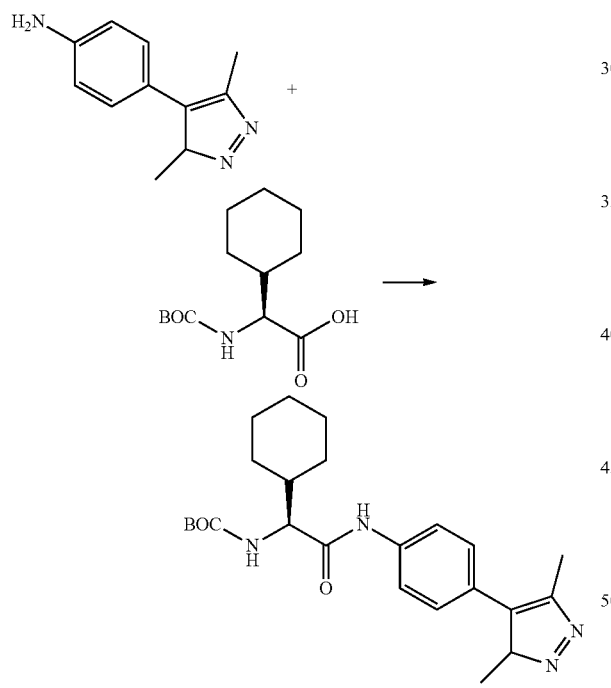

To a solution of (2S)-2-(tert-butoxycarbonylamino)-2-cyclohexyl-acetic acid (34 mg, 0.134 mmol) in DMF (0.5 mL) in a 4 mL vial was added DIPEA (0.117 mL, 0.67 mmol), followed by HATU (76 mg, 0.201 mmol) and 4-(3,5-dimethylimidazol-4-yl)aniline hydrochloride (30 mg, 0.134 mmol). The mixture was stirred at room temperature for 30 min. The crude reaction mixture was purified by basic reverse phase chromatography to give the title compound (25 mg, 44%) as a white solid. 1H NMR (300 MHz, DMSO-d6) δ 10.10 (s, 1H), 7.81-7.64 (m, 2H), 7.53 (s, 1H), 7.38-7.19 (m, 2H), 6.87 (d, J=8.4 Hz, 1H), 3.96 (t, J=8.1 Hz, 1H), 3.49 (s, 3H), 2.08 (s, 3H), 1.87-1.47 (m, 7H), 1.39 (s, 9H), 1.28-0.91 (m, 4H); LCMS (ES): m/z 427.271 [M+H]$^+$, RT=2.11 min.

Examples 84-89, 305 and 305B

Examples 84-89, 305 and 305B were synthesised according to the method of Example 83 starting from the appropriate Boc protected amino acid. An arrow denotes the point of attachment of the substituent R$_x$ to the parent molecule.

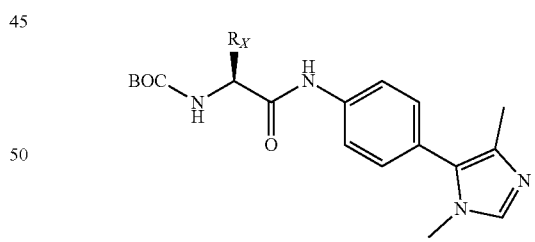

| Ex. No. | R$_x$ | Name | Mass ion | LCMS retention time (min) |
|---|---|---|---|---|
| 84 | Racemic Preparation 27 | tert-butyl N-[1-(dicyclopropylmethyl)-2-[4-(3,5-dimethylimidazol-4-yl)anilino]-2-oxo-ethyl]carbamate | 439.272 | 2.10 |

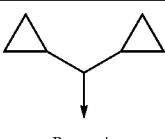

-continued

| Ex. No. | $R_x$ | Name | Mass ion | LCMS retention time (min) |
|---|---|---|---|---|
| 85 | 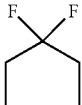 Enantiomer 1† | Enantiomer 1 of tert-butyl N-[1-(4,4-difluorocyclohexyl)-2-[4-(3,5-dimethylimidazol-4-yl)anilino]-2-oxo-ethyl]carbamate | 463.253 | 2.05 |
| 86 | 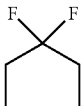 Enantiomer 2† | Enantiomer 2 of tert-butyl N-[1-(4,4-difluorocyclohexyl)-2-[4-(3,5-dimethylimidazol-4-yl)anilino]-2-oxo-ethyl]carbamate | 463.253 | 2.05 |
| 87 | 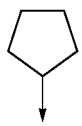 | tert-butyl N-[(1S)-1-cyclopentyl-2-[4-(3,5-dimethylimidazol-4-yl)anilino]-2-oxo-ethyl]carbamate | 413.256 | 2.04 |
| 88 | 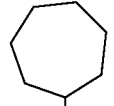 | tert-butyl N-[(1S)-1-cycloheptyl-2-[4-(3,5-dimethylimidazol-4-yl)anilino]-2-oxo-ethyl]carbamate | 441.287 | 2.19 |
| 89 | 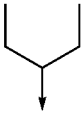 | tert-butyl N-[(1S)-1-[[4-(3,5-dimethylimidazol-4-yl)phenyl]carbamoyl]-2-ethyl-butyl]carbamate | 415.271 | 2.10 |
| 305 | 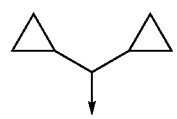 Preparation 52 | tert-butyl N-[(1S)-1-(dicyclopropylmethyl)-2-[4-(3,5-dimethylimidazol-4-yl)anilino]-2-oxo-ethyl]carbamate | 439.272 | 2.10 |
| 305 B |  | tert-butyl N-[(1S)-1-benzhydryl-2-[4-(3,5-dimethylimidazol-4-yl)anilino]-2-oxo-ethyl]carbamate | 511.8 | 0.71 Method 3 |

†The racemic amino acid was synthesised according to the methods of Preparation 7 and 8 but the crude amino acid was Boc protected rather than being converted to the nickel complex. The enantiomers of the final compound were separated by chiral SFC.

Examples 90-101 and 306-313

Examples 90-101 and 306-313 were synthesised according to the method of Example 83 starting from the appropriate Boc protected amino acid and coupling it with 4-(3-methylimidazol-4-yl)aniline. An arrow denotes the point of attachment of the substituent $R_x$ to the parent molecule.

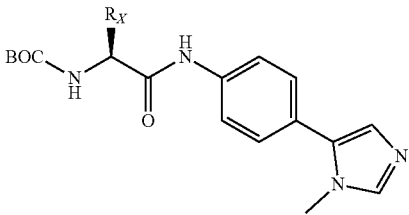

| Ex. No. | R$_x$ | Name | Mass ion | LCMS retention time (min) |
|---|---|---|---|---|
| 90 | (tetralin-Br, Preparation 21) | tert-butyl N-[(1S)-1-[(1R)-7-bromotetralin-1-yl]-2-[4-(3-methylimidazol-4-yl)anilino]-2-oxo-ethyl]carbamate | 539.3, 541.3 | 0.76 (Method 3) |
| 91 | isopropyl | tert-butyl N-[(1S)-2-methyl-1-[[4-(3-methylimidazol-4-yl)phenyl]carbamoyl]propyl]carbamate | 373.224 | 1.91 |
| 92 | cyclobutyl | tert-butyl N-[(1S)-1-cyclobutyl-2-[4-(3-methylimidazol-4-yl)anilino]-2-oxo-ethyl]carbamate | 385.224 | 1.94 |
| 93 | cyclohexylmethyl | tert-butyl N-[(1S)-1-(cyclohexylmethyl)-2-[4-(3-methylimidazol-4-yl)anilino]-2-oxo-ethyl]carbamate | 427.271 | 2.17 |
| 94 | sec-butyl variant | tert-butyl N-[(1S)-2-methyl-1-[[4-(3-methylimidazol-4-yl)phenyl]carbamoyl]butyl]carbamate | 387.24 | 1.99 |
| 95 | benzyl | tert-butyl N-[(1S)-1-benzyl-2-[4-(3-methylimidazol-4-yl)anilino]-2-oxo-ethyl]carbamate | 421.224 | 2.02 |
| 96 | isobutyl | tert-butyl N-[(1S)-3-methyl-1-[[4-(3-methylimidazol-4-yl)phenyl]carbamoyl]butyl]carbamate | 387.239 | 2.00 |
| 97 | 2-chlorobenzyl | tert-butyl N-[(1S)-1-[(2-chlorophenyl)methyl]-2-[4-(3-methylimidazol-4-yl)anilino]-2-oxo-ethyl]carbamate | 455.185 | 2.09 |
| 98 | cyclopentyl | tert-butyl N-[(1S)-1-cyclopentyl-2-[4-(3-methylimidazol-4-yl)anilino]-2-oxo-ethyl]carbamate | 399.239 | 2.00 |
| 99 | indan-2-yl | tert-butyl N-[(1S)-1-indan-2-yl-2-[4-(3-methylimidazol-4-yl)anilino]-2-oxo-ethyl]carbamate | 447.239 | 2.11 |

-continued

| Ex. No. | R_x | Name | Mass ion | LCMS retention time (min) |
|---|---|---|---|---|
| 100 | 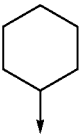 | tert-butyl N-[(1S)-1-cyclohexyl-2-[4-(3-methylimidazol-4-yl)anilino]-2-oxo-ethyl]carbamate | 413.255 | 2.08 |
| 101 | 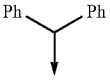 | tert-butyl N-[(1S)-1-benzhydryl-2-[4-(3-methylimidazol-4-yl)anilino]-2-oxo-ethyl]carbamate | 497.255 | 2.15 |
| 306 | 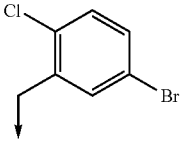 | tert-butyl N-[(1S)-1-[(5-bromo-2-chloro-phenyl)methyl]-2-[4-(3-methylimidazol-4-yl)anilino]-2-oxo-ethyl]carbamate | 533.3, 535.4 | 0.71 (Method 3) |
| 307 | 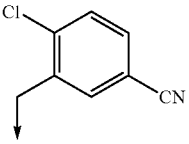 Preparation 75 | tert-butyl N-[(1S)-1-[(2-chloro-5-cyano-phenyl)methyl]-2-[4-(3-methylimidazol-4-yl)anilino]-2-oxo-ethyl]carbamate | 480.181 | 2.05 |
| 308 | 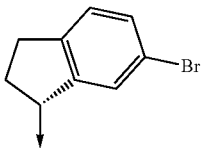 Preparation 14 | tert-butyl N-[(1S)-1-[(1R)-6-bromoindan-1-yl]-2-[4-(3-methylimidazol-4-yl)anilino]-2-oxo-ethyl]carbamate | 525.4, 527.4 | 0.69 (Method 3) |
| 309 | 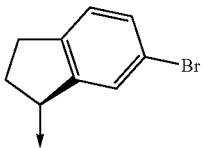 Preparation 17 | tert-butyl N-[(1S)-1-[(1S)-6-bromoindan-1-yl]-2-[4-(3-methylimidazol-4-yl)anilino]-2-oxo-ethyl]carbamate | 525.4, 527.4 | 0.72 (Method 3) |
| 310 | 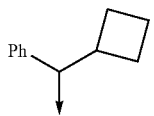 Preparation 146 | Diastereomer 1 of tert-butyl N-[1-[cyclobutyl(phenyl)methyl]-2-[4-(3-methylimidazol-4-yl)anilino]-2-oxo-ethyl]carbamate* | 475.271 | 2.22 |
| 311 | 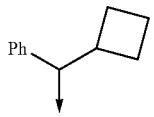 Preparation 146 | Diastereomer 2 of tert-butyl N-[1-[cyclobutyl(phenyl)methyl]-2-[4-(3-methylimidazol-4-yl)anilino]-2-oxo-ethyl]carbamate* | 475.271 | 2.22 |

| Ex. No. | R$_x$ | Name | Mass ion | LCMS retention time (min) |
|---|---|---|---|---|
| 312 | (cyclopentyl-cyclohexyl-methyl), Preparation 167 | Diastereomer 1 of tert-butyl N-[(1S)-1-[cyclohexyl-(cyclopentyl)methyl]-2-[4-(3-methylimidazol-4-yl)anilino]-2-oxo-ethyl]carbamate* | 495.335 | 2.49 |
| 313 | (cyclopentyl-cyclohexyl-methyl), Preparation 167 | Diastereomer 2 of tert-butyl N-[(1S)-1-[cyclohexyl-(cyclopentyl)methyl]-2-[4-(3-methylimidazol-4-yl)anilino]-2-oxo-ethyl]carbamate* | 495.335 | 2.49 |

*The 2 diastereomers were isolated by preparative chiral SFC.

Examples 314-317

Examples 314-317 were synthesised according to the method of Example 83 starting from the appropriate Boc protected amino acid and coupling it with 4-(4-methyl-1,2,4-triazol-3-yl)aniline. An arrow denotes the point of attachment of the substituent R$_x$ to the parent molecule.

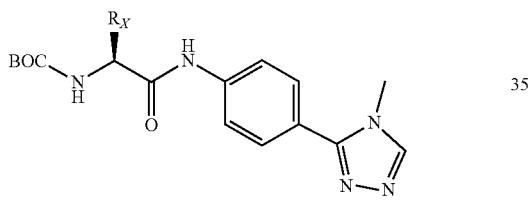

| Ex. No. | R$_x$ | Name | Mass ion | LCMS retention time (min) |
|---|---|---|---|---|
| 314 | cyclohexyl | tert-butyl N-[(1S)-1-cyclohexyl-2-[4-(4-methyl-1,2,4-triazol-3-yl)anilino]-2-oxo-ethyl]carbamate | 414.6 | 0.68 (Method 3) |
| 315 | cycloheptyl | tert-butyl N-[(1S)-1-cycloheptyl-2-[4-(4-methyl-1,2,4-triazol-3-yl)anilino]-2-oxo-ethyl]carbamate | 428.6 | 0.72 (Method 3) |
| 316 | Ph-CH-Ph | tert-butyl N-[(1S)-1-benzhydryl-2-[4-(4-methyl-1,2,4-triazol-3-yl)anilino]-2-oxo-ethyl]carbamate | 498.3 | 0.71 (Method 3) |

| Ex. No. | $R_x$ | Name | Mass ion | LCMS retention time (min) |
|---|---|---|---|---|
| 317 | 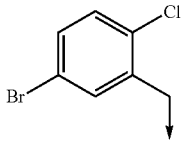 racemic | tert-butyl N-[1-[(5-bromo-2-chloro-phenyl)methyl]-2-[4-(4-methyl-1,2,4-triazol-3-yl)anilino]-2-oxo-ethyl]carbamate | 534.3, 536.3 | 0.73 (Method 3) |

Example 318

Tert-butyl N-[1-[(5-bromo-2-chloro-phenyl)methyl]-2-[4-(4-cyclopropyl-1,2,4-triazol-3-yl)anilino]-2-oxo-ethyl]carbamate

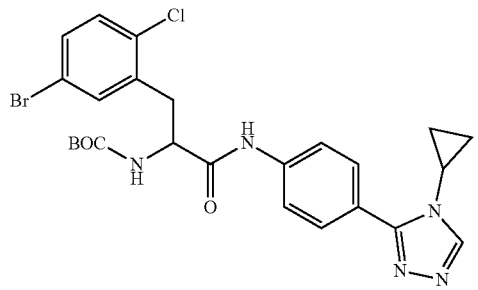 [SMILES: CC(C)(C)OC(=O)NC(Cc1cc(Br)ccc1Cl)C(=O)Nc1ccc(-c2nncn2C2CC2)cc1]

Example 318 was synthesised according to the method of Example 83 by coupling 3-(5-bromo-2-chloro-phenyl)-2-(tert-butoxycarbonylamino)propanoic acid with 4-(4-cyclopropyl-1,2,4-triazol-3-yl)aniline. LCMS (ES) (METHOD 3): m/z 560.2, 562.2 [M+H]$^+$; RT=0.79 min.

Examples 319-328

Examples 319-328 were synthesised according to the method of Preparation 3 from the appropriate aniline and the required Boc protected amino acid.

| Ex. No. | Starting materials | Structure | Name | Mass ion | LCMS RT (min) |
|---|---|---|---|---|---|
| 319 | 3-(5-bromo-2-chloro-phenyl)-2-(tert-butoxy-carbonylamino) propanoic acid, 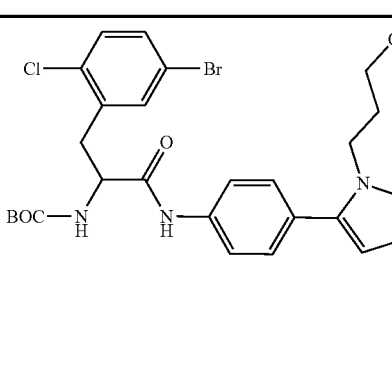 | 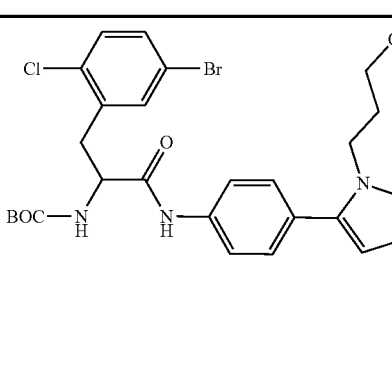 | tert-butyl N-[1-[(5-bromo-2-chloro-phenyl)methyl]-2-[4-[3-(3-hydroxypropyl)triazol-4-yl]anilino]-2-oxo-ethyl]carbamate | 578.3 580.3 | 0.77 (METHOD 3) |
| 320 | 3-(5-bromo-2-chloro-phenyl)-2-(tert-butoxy-carbonylamino) propanoic acid, 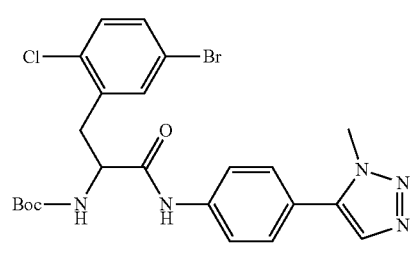 | 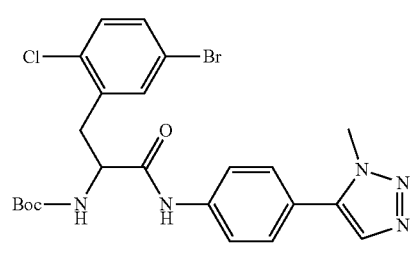 | tert-butyl N-[1-[(5-bromo-2-chloro-phenyl)methyl]-2-[4-(3-methyltriazol-4-yl)anilino]-2-oxo-ethyl]carbamate | 534.3 536.3 | 0.81 (METHOD 3) |

-continued

| Ex. No. | Starting materials | Structure | Name | Mass ion | LCMS RT (min) |
|---|---|---|---|---|---|
| 321 | 3-(5-bromo-2-chloro-phenyl)-2-(tert-butoxy-carbonylamino) propanoic acid, 4-(1,3,4-oxadiazol-2-yl)aniline | 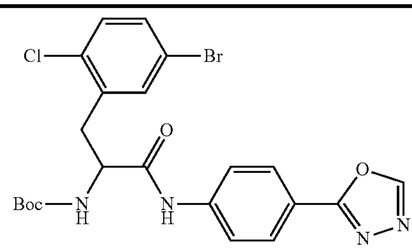 | tert-butyl N-[1-[(5-bromo-2-chloro-phenyl)methyl]-2-[4-(1,3,4-oxadiazol-2-yl)anilino]-2-oxo-ethyl]carbamate | 521.1 523.1 | 0.84 (METHOD 3) |
| 322 | Prep. 52, | 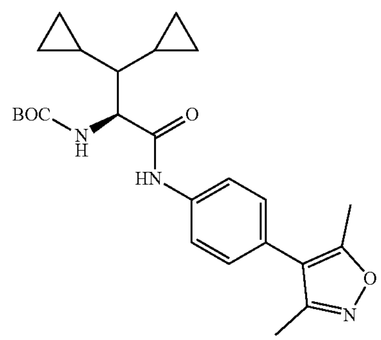 [SMILES: Cc1noc(C)c1-c1ccc(NC(=O)[C@@H](NC(=O)OC(C)(C)C)C(C2CC2)C2CC2)cc1] | tert-butyl (S)-(1,1-dicyclopropyl-3-((4-(3,5-dimethylisoxazol-4-yl)phenyl)amino)-3-oxopropan-2-yl)carbamate | 440 | 2.19 min (METHOD 5, ACQUITY UPLC BEH C18 column, 0.1% FA in water with MeCN) |
| 323 | Prep. 52, | 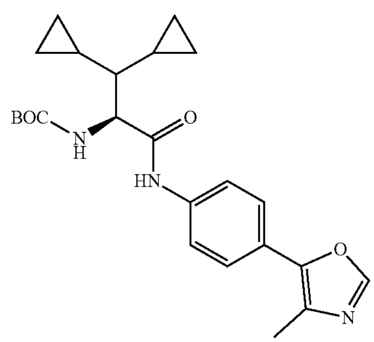 [SMILES: Cc1ncoc1-c1ccc(NC(=O)[C@@H](NC(=O)OC(C)(C)C)C(C2CC2)C2CC2)cc1] | tert-butyl (S)-(1,1-dicyclopropyl-3-((4-(4-methyloxazol-5-yl)phenyl)amino)-3-oxopropan-2-yl)carbamate | 426 | 2.16 min (METHOD 5, ACQUITY UPLC BEH C18 column, 0.1% FA in water with MeCN) |
| 324 | Prep. 52, Prep 255 | 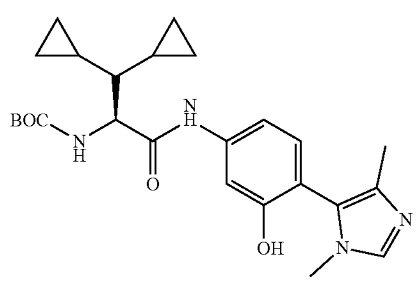 [SMILES: Cc1ncn(C)c1-c1ccc(NC(=O)[C@@H](NC(=O)OC(C)(C)C)C(C2CC2)C2CC2)cc1O] | tert-butyl N-[(1S)-1-(dicyclopropylmethyl)-2-[4-(3,5-dimethylimidazol-4-yl)-3-hydroxy-anilino]-2-oxo-ethyl]carbamate | 455.4 | 0.62 (METHOD 3) |
| 325 | Prep. 52, | 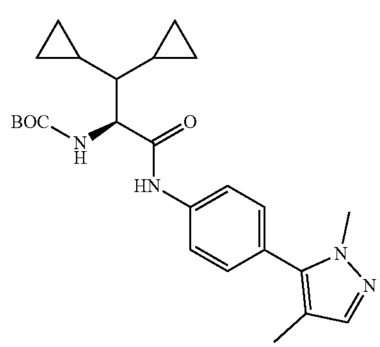 [SMILES: Cc1cnn(C)c1-c1ccc(NC(=O)[C@@H](NC(=O)OC(C)(C)C)C(C2CC2)C2CC2)cc1] | tert-butyl N-[(1S)-1-(dicyclopropylmethyl)-2-[4-(2,4-dimethylpyrazol-3-yl)anilino]-2-oxo-ethyl]carbamate | 439 | 2.78 min (METHOD 5) (ACQUITY UPLC BEH C18 column, 0.1% FA in water with MeCN). |

-continued

| Ex. No. | Starting materials | Structure | Name | Mass ion | LCMS RT (min) |
|---|---|---|---|---|---|
| 326 | Prep. 52, Prep 320 | 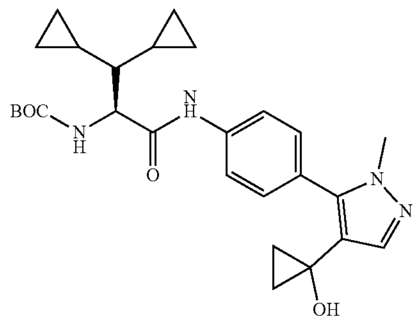 [SMILES: Cn1ncc(C2(O)CC2)c1-c1ccc(NC(=O)[C@@H](NC(=O)OC(C)(C)C)C(C2CC2)C2CC2)cc1] | tert-butyl N-[(1S)-1-(dicyclopropylmethyl)-2-[4-[4-(1-hydroxycyclopropyl)-2-methyl-pyrazol-3-yl]anilino]-2-oxo-ethyl]carbamate | 481 | 2.92 min (METHOD 5) (ACQUITY UPLC BEH C18 column, 0.1% FA in water with MeCN) |
| 327 | Prep. 52, | 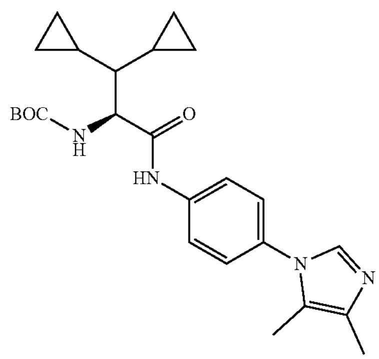 [SMILES: Cc1ncn(-c2ccc(NC(=O)[C@@H](NC(=O)OC(C)(C)C)C(C3CC3)C3CC3)cc2)c1C] | tert-butyl N-[(1S)-1-(dicyclopropylmethyl)-2-[4-(4,5-dimethylimidazol-1-yl)anilino]-2-oxo-ethyl]carbamate | 439 | 1.75 min (METHOD 5) (ACQUITY BEH C18 column, 0.1% FA in water with MeCN). |
| 328 | Prep. 52, | 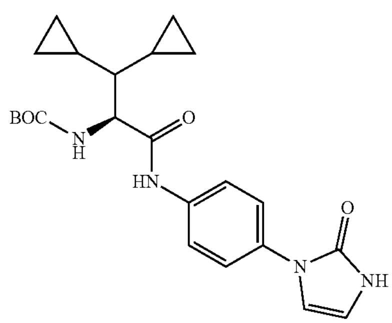 [SMILES: CC(C)(C)OC(=O)N[C@H](C(=O)Nc1ccc(-n2cc[nH]c2=O)cc1)C(C1CC1)C1CC1] | tert-butyl N-[(1S)-1-(dicyclopropylmethyl)-2-oxo-2-[4-(2-oxo-1H-imidazol-3-yl)anilino]ethyl]carbamate | 426 | 1.88 min (METHOD 5) (ACQUITY BEH C18 column, 0.05% FA in water with MeCN). |
| 329 | (2S)-2-(tert-butoxycarbonyl amino)-3,3-dicyclopropyl-propanoic acid, Prep. 337 | 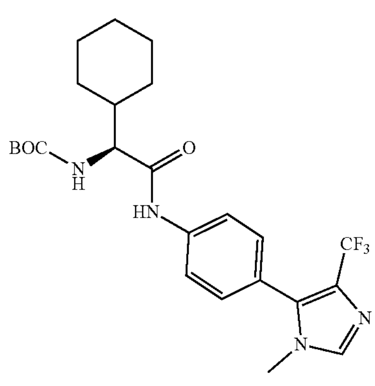 [SMILES: Cn1cnc(C(F)(F)F)c1-c1ccc(NC(=O)[C@@H](NC(=O)OC(C)(C)C)C2CCCCC2)cc1] | tert-butyl N-[(1S)-1-cyclohexyl-2-[4-[3-methyl-5-(trifluoromethyl)imidazol-4-yl]anilino]-2-oxo-ethyl]carbamate | 481.5 | 0.83 (METHOD 3) |

| Ex. No. | Starting materials | Structure | Name | Mass ion | LCMS RT (min) |
|---|---|---|---|---|---|
| 330 | (2S)-2-(tert-butoxycarbonyl amino)-3,3-dicyclopropyl-propanoic acid, Prep. 338 | 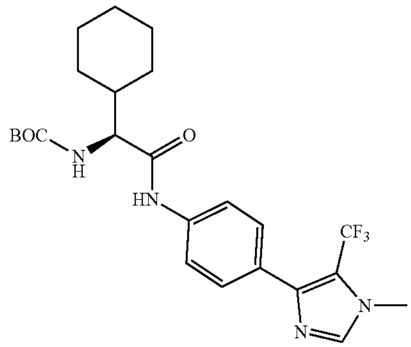 [SMILES: Cn1cnc(-c2ccc(NC(=O)[C@@H](NC(=O)OC(C)(C)C)C3CCCCC3)cc2)c1C(F)(F)F] | tert-butyl N-[(1S)-1-cyclohexyl-2-[4-[1-methyl-5-trifluoromethyl) imidazol-4-yl]anilino]-2-oxo-ethyl]carbamate | — | — |
| 331 | Prep. 21 | 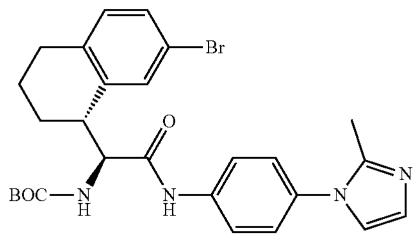 [SMILES: Cc1nccn1-c1ccc(NC(=O)[C@@H](NC(=O)OC(C)(C)C)[C@@H]2CCCc3ccc(Br)cc32)cc1] | tert-butyl N-[(1S)-1-[(1R)-7-bromotetralin-1-yl]-2-[4-(2-methylimidazol-1-yl)anilino]-2-oxo-ethyl]carbamate | 539.1 541.1 | 0.77 (METHOD 3) |

Examples 332-372

Examples 332-372 were synthesised according to the method of Preparation 5 from the indicated amine and the required carboxylic acid.

| Ex. No. | SM | Structure | Name | Mass ion | LCMS RT (min) |
|---|---|---|---|---|---|
| 332 | Prep 343 | 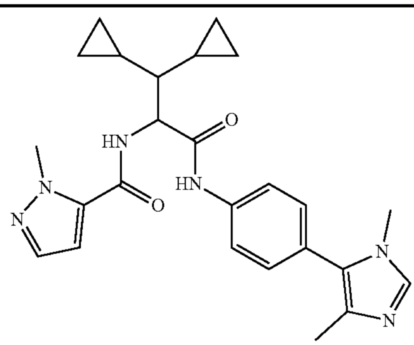 | N-[1-(dicyclopropylmethyl)-2-[4-(3,5-dimethylimidazol-4-yl)anilino]-2-oxo-ethyl]-2-methyl-pyrazole-3-carboxamide | 447.251 | 1.92 |
| 333 | Prep 341 | 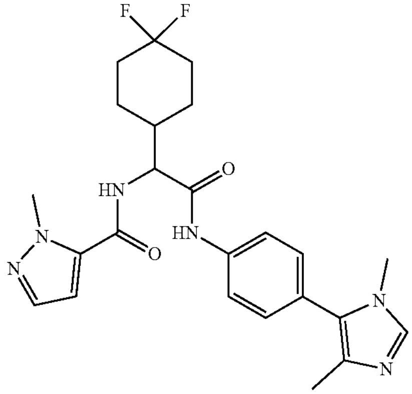 [SMILES: Cc1ncn(C)c1-c1ccc(NC(=O)C(NC(=O)c2ccnn2C)C2CCC(F)(F)CC2)cc1] | Enantiomer 1 of N-[1-(4,4-difluorocyclohexyl)-2-[4-(3,5-dimethylimidazol-4-yl)anilino]-2-oxo-ethyl]-2-methyl-pyrazole-3-carboxamide | 471.233 | 1.88 |

-continued

| Ex. No. | SM | Structure | Name | Mass ion | LCMS RT (min) |
|---|---|---|---|---|---|
| 334 | Prep 342 | 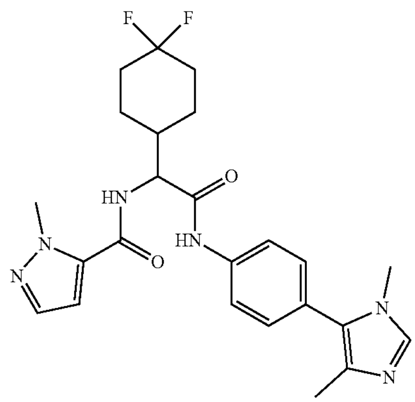 [SMILES: Cc1ncn(C)c1-c1ccc(NC(=O)C(NC(=O)c2ccnn2C)C2CCC(F)(F)CC2)cc1] | Enantiomer 2 of N-[1-(4,4-difluorocyclohexyl)-2-[4-(3,5-dimethylimidazol-4-yl)anilino]-2-oxo-ethyl]-2-methyl-pyrazole-3-carboxamide | 471.233 | 1.88 |
| 335 | Prep 345 | 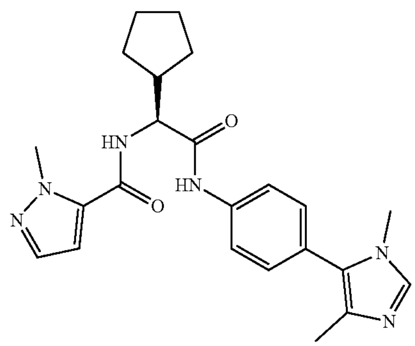 [SMILES: Cc1ncn(C)c1-c1ccc(NC(=O)[C@@H](NC(=O)c2ccnn2C)C2CCCC2)cc1] | N-[(1S)-1-cyclopentyl-2-[4-(3,5-dimethylimidazol-4-yl)anilino]-2-oxo-ethyl]-2-methyl-pyrazole-3-carboxamide | 421.235 | 1.87 |
| 336 | Prep 346 | 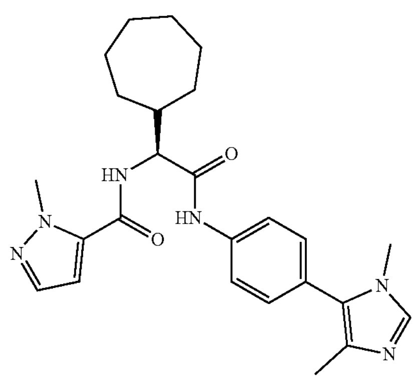 [SMILES: Cc1ncn(C)c1-c1ccc(NC(=O)[C@@H](NC(=O)c2ccnn2C)C2CCCCCC2)cc1] | N-[(1S)-1-cycloheptyl-2-[4-(3,5-dimethylimidazol-4-yl)anilino]-2-oxo-ethyl]-2-methyl-pyrazole-3-carboxamide | 449.267 | 2.00 |
| 337 | Prep 339 | 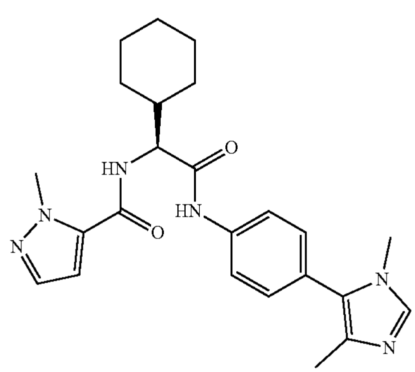 [SMILES: Cc1ncn(C)c1-c1ccc(NC(=O)[C@@H](NC(=O)c2ccnn2C)C2CCCCC2)cc1] | N-[(1S)-1-cyclohexyl-2-[4-(3,5-dimethylimidazol-4-yl)anilino]-2-oxo-ethyl]-2-methyl-pyrazole-3-carboxamide | 435.251 | 1.93 |

| Ex. No. | SM | Structure | Name | Mass ion | LCMS RT (min) |
|---|---|---|---|---|---|
| 338 | Prep 340 | 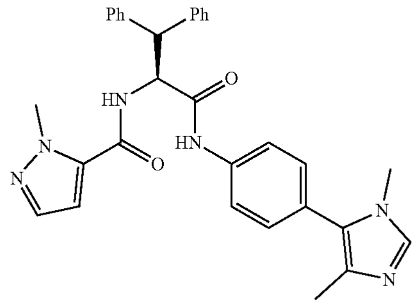 [SMILES: Cc1ncn(C)c1-c1ccc(NC(=O)[C@@H](NC(=O)c2ccnn2C)C(c2ccccc2)c2ccccc2)cc1] | N-[(1S)-1-benzhydryl-2-[4-(3,5-dimethylimidazol-4-yl)anilino]-2-oxo-ethyl]-2-methyl-pyrazole-3-carboxamide | 519.253 | 2.01 |
| 339 A | Prep 362 | 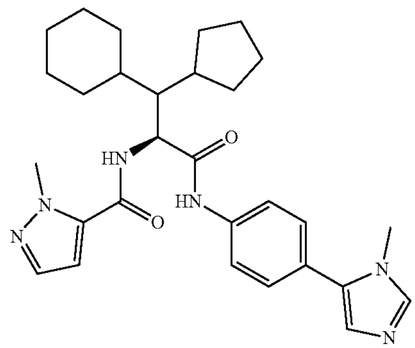 [SMILES: Cn1cncc1-c1ccc(NC(=O)[C@@H](NC(=O)c2ccnn2C)C(C2CCCCC2)C2CCCC2)cc1] | Diastereomer 1 of N-[1S)-1-[cyclohexyl-(cyclopentyl)methyl]-2-[4-(3-methylimidazol-4-yl)anilino]-2-oxo-ethyl]-2-methyl-pyrazole-3-carboxamide | 503.313 | 2.27 |
| 339 B | Prep 363 | 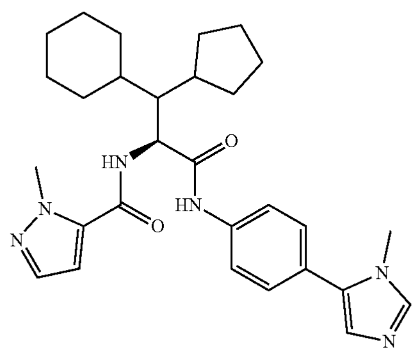 [SMILES: Cn1cncc1-c1ccc(NC(=O)[C@@H](NC(=O)c2ccnn2C)C(C2CCCCC2)C2CCCC2)cc1] | Diastereomer 2 of N-[1S)-1-[cyclohexyl-(cyclopentyl)methyl]-2-[4-(3-methylimidazol-4-yl)anilino]-2-oxo-ethyl]-2-methyl-pyrazole-3-carboxamide | 503.314 | 2.27 |
| 340 | Prep 352 | 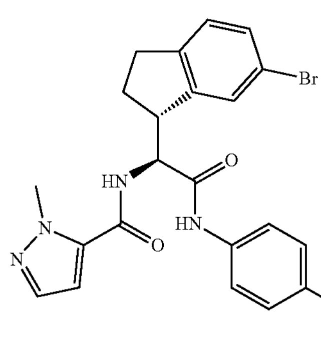 | N-[(1S)-1-[(1R)-6-bromoindan-1-yl]-2-[4-(3-methylimidazol-4-yl)anilino]-2-oxo-ethyl]-2-methyl-pyrazole-3-carboxamide | 533.131 | 1.99 |

| Ex. No. | SM | Structure | Name | Mass ion | LCMS RT (min) |
|---|---|---|---|---|---|
| 341 | Prep 353 | 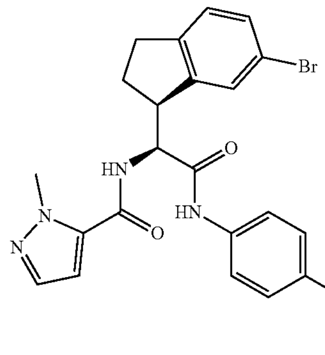 | N-[(1S)-1-[(1S)-6-bromoindan-1-yl]-2-[4-(3-methylimidazol-4-yl)anilino]-2-oxo-ethyl]-2-methyl-pyrazole-3-carboxamide | 533.131 | 2·03 |
| 342 | Prep 347 | 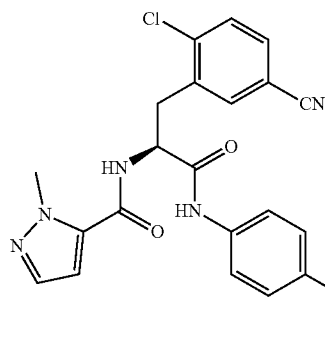 | N-[(1S)-1-[(2-chloro-5-cyano-phenyl)methyl]-2-[4-(3-methylimidazol-4-yl)anilino]-2-oxo-ethyl]-2-methyl-pyrazole-3-carboxamide | 488.161 | 1.88 |
| 343 | Prep 349 | 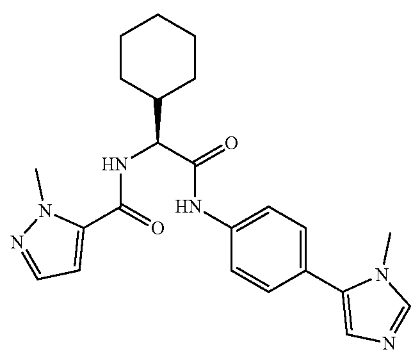 | N-[(1S)-1-cyclohexyl-2-[4-(3-methylimidazol-4-yl)anilino]-2-oxo-ethyl]-2-methyl-pyrazole-3-carboxamide | 421.234 | 1.91 |
| 344 | Prep 351 | 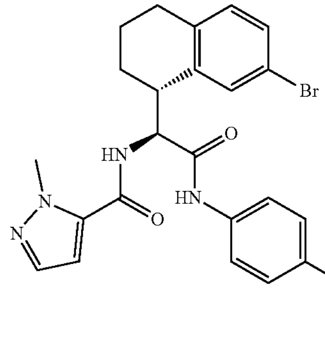 | N-[(1S)-1-[(1R)-7-bromotetralin-1-yl]-2-[4-(3-methylimidazol-4-yl)anilino]-2-oxo-ethyl]-2-methyl-pyrazole-3-carboxamide | 547.146 | 2.02 |

-continued

| Ex. No. | SM | Structure | Name | Mass ion | LCMS RT (min) |
|---|---|---|---|---|---|
| 345 | Prep 350 | 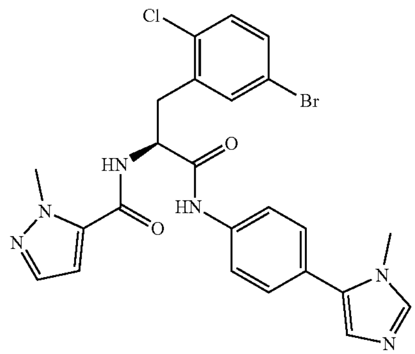 [SMILES: Cn1cncc1-c1ccc(NC(=O)[C@H](Cc2cc(Br)ccc2Cl)NC(=O)c2ccnn2C)cc1] | N-[(1S)-1-[(5-bromo-2-chloro-phenyl)methyl]-2-[4-(3-methylimidazol-4-yl)anilino]-2-oxo-ethyl]-2-methyl-pyrazole-3-carboxamide | 541.075 | 2.01 |
| 346 | Prep 348 | 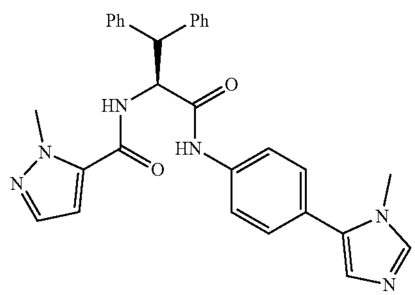 [SMILES: Cn1cncc1-c1ccc(NC(=O)[C@@H](NC(=O)c2ccnn2C)C(c2ccccc2)c2ccccc2)cc1] | N-[(1S)-1-benzhydryl-2-[4-(3-methylimidazol-4-yl)anilino]-2-oxo-ethyl]-2-methyl-pyrazole-3-carboxamide | 505.236 | 1.99 |
| 347 | Prep 348 | 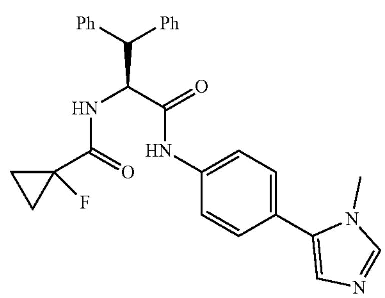 [SMILES: Cn1cncc1-c1ccc(NC(=O)[C@@H](NC(=O)C2(F)CC2)C(c2ccccc2)c2ccccc2)cc1] | N-[(1S)-1-benzhydryl-2-[4-(3-methylimidazol-4-yl)anilino]-2-oxo-ethyl]-1-fluoro-cyclopropanecarboxamide | 483.22 | 2.06 |
| 348 | Prep 354 | 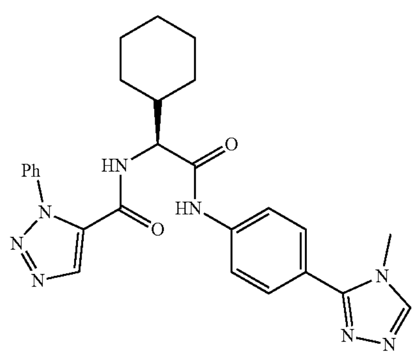 [SMILES: Cn1cnnc1-c1ccc(NC(=O)[C@@H](NC(=O)c2cnnn2-c2ccccc2)C2CCCCC2)cc1] | N-[(1S)-1-cyclohexyl-2-[4-(4-methyl-1,2,4-triazol-3-yl)anilino]-2-oxo-ethyl]-3-phenyl-triazole-4-carboxamide | 485.242 | 2.07 |

-continued

| Ex. No. | SM | Structure | Name | Mass ion | LCMS RT (min) |
|---|---|---|---|---|---|
| 349 | Prep 355 | 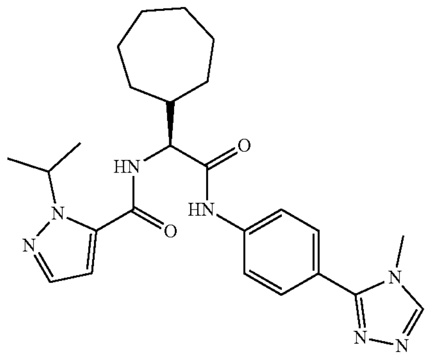 [SMILES: CC(C)n1nccc1C(=O)N[C@H](C(=O)Nc1ccc(-c2nncn2C)cc1)C1CCCCCC1] | N-[(1S)-1-cycloheptyl-2-[4-(4-methyl-1,2,4-triazol-3-yl)anilino]-2-oxo-ethyl]-2-isopropyl-pyrazole-3-carboxamide | 464.278 | 2.18 |
| 350 | Prep 355 | 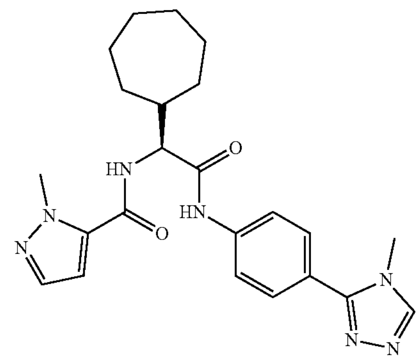 [SMILES: Cn1cnnc1-c1ccc(NC(=O)[C@@H](NC(=O)c2ccnn2C)C2CCCCCC2)cc1] | N-[(1S)-1-cycloheptyl-2-[4-(4-methyl-1,2,4-triazol-3-yl)anilino]-2-oxo-ethyl]-2-methyl-pyrazole-3-carboxamide | 436.246 | 2.05 |
| 351 | Prep 354 | 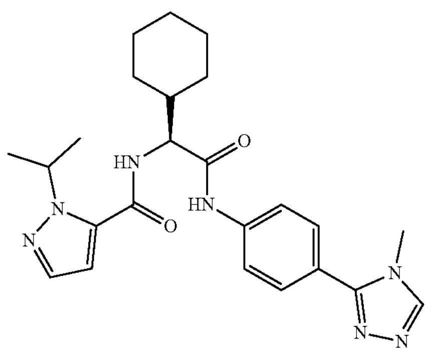 [SMILES: CC(C)n1nccc1C(=O)N[C@H](C(=O)Nc1ccc(-c2nncn2C)cc1)C1CCCCC1] | N-[(1S)-1-cyclohexyl-2-[4-(4-methyl-1,2,4-triazol-3-yl)anilino]-2-oxo-ethyl]-2-isopropyl-pyrazole-3-carboxamide | 450.262 | 2.10 |
| 352 | Prep 354 | 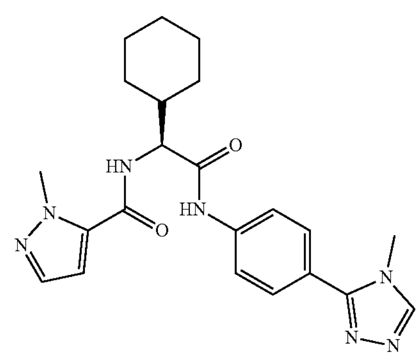 [SMILES: Cn1cnnc1-c1ccc(NC(=O)[C@@H](NC(=O)c2ccnn2C)C2CCCCC2)cc1] | N-[(1S)-1-cyclohexyl-2-[4-(4-methyl-1,2,4-triazol-3-yl)anilino]-2-oxo-ethyl]-2-methyl-pyrazole-3-carboxamide | 422.231 | 1.98 |

-continued

| Ex. No. | SM | Structure | Name | Mass ion | LCMS RT (min) |
|---|---|---|---|---|---|
| 353 | Prep 356 | 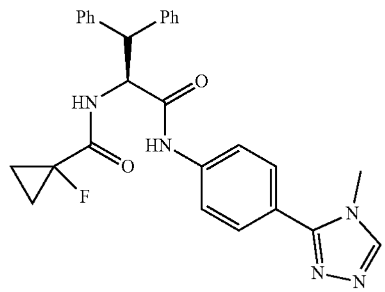 [SMILES: Cn1cnnc1-c1ccc(NC(=O)[C@@H](NC(=O)C2(F)CC2)C(c2ccccc2)c2ccccc2)cc1] | N-[(1S)-1-benzhydryl-2-[4-(4-methyl-1,2,4-triazol-3-yl)anilino]-2-oxo-ethyl]-1-fluoro-cyclopropanecarboxamide | 484.216 | 2.14 |
| 354 | Prep 356 | 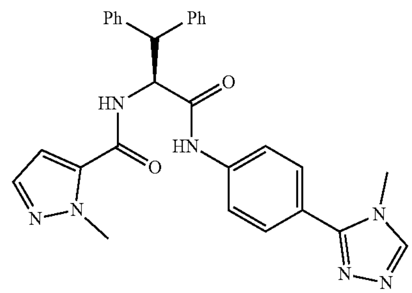 [SMILES: Cn1cnnc1-c1ccc(NC(=O)[C@@H](NC(=O)c2ccnn2C)C(c2ccccc2)c2ccccc2)cc1] | N-[(1S)-1-benzhydryl-2-[4-(4-methyl-1,2,4-triazol-3-yl)anilino]-2-oxo-ethyl]-2-methyl-pyrazole-3-carboxamide | 506.231 | 2.07 |
| 355 | Prep 358 | 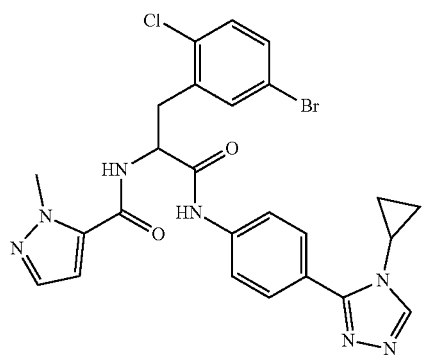 [SMILES: Cn1nccc1C(=O)NC(Cc1cc(Br)ccc1Cl)C(=O)Nc1ccc(-c2nncn2C2CC2)cc1] | N-[1-[(5-bromo-2-chloro-phenyl)methyl]-2-[4-(4-cyclopropyl-1,2,4-triazol-3-yl)anilino]-2-oxo-ethyl]-2-methyl-pyrazole-3-carboxamide | 568.2, 570.2 | 0.68 Method 3 |
| 356 | Prep 357 | 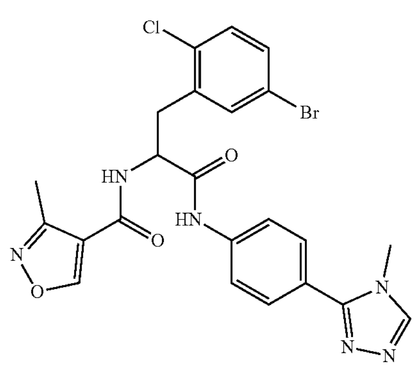 [SMILES: Cc1nocc1C(=O)NC(Cc1cc(Br)ccc1Cl)C(=O)Nc1ccc(-c2nncn2C)cc1] | N-[1-[(5-bromo-2-chloro-phenyl)methyl]-2-[4-(4-methyl-1,2,4-triazol-3-yl)anilino]-2-oxo-ethyl]-3-methyl-isoxazole-4-carboxamide | 543.3, 545.3 | 0.64 Method 3 |

-continued

| Ex. No. | SM | Structure | Name | Mass ion | LCMS RT (min) |
|---|---|---|---|---|---|
| 357 | Prep 357 | 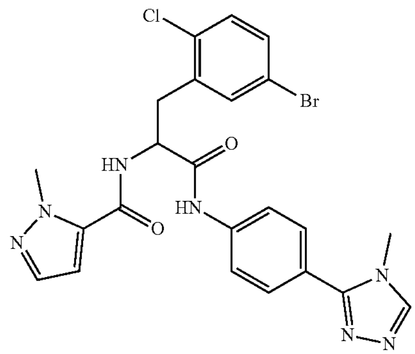 [SMILES: Cn1cnnc1-c1ccc(NC(=O)C(Cc2cc(Br)ccc2Cl)NC(=O)c2ccnn2C)cc1] | N-[1-[(5-bromo-2-chloro-phenyl)methyl]-2-[4-(4-methyl-1,2,4-triazol-3-yl)anilino]-2-oxo-ethyl]-2-methyl-pyrazole-3-carboxamide | 542.3, 544.3 | 0.62 Method 3 |
| 358 | Prep 335 | 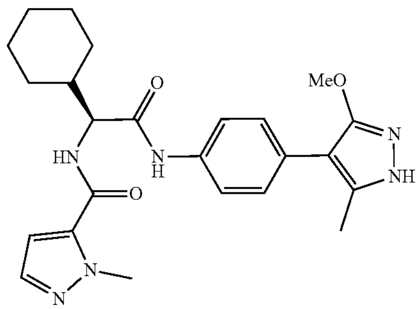 | N-[(1S)-1-cyclohexyl-2-[4-(5-methoxy-3-methyl-1H-pyrazol-4-yl)anilino]-2-oxo-ethyl]-2-methyl-pyrazole-3-carboxamide | 451.247 | 2.21 |
| 359 | Prep 336 | 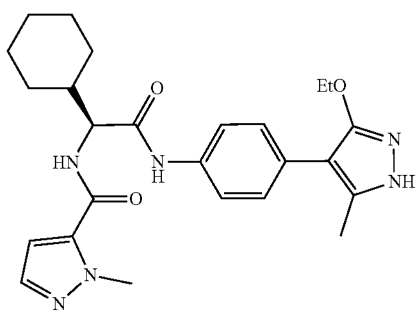 | N-[(1S)-1-cyclohexyl-2-[4-(5-ethoxy-3-methyl-1H-pyrazol-4-yl)anilino]-2-oxo-ethyl]-2-methyl-pyrazole-3-carboxamide | 465.263 | 2.27 |
| 360 | Prep 359 | 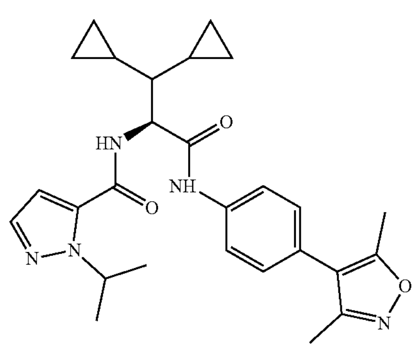 [SMILES: Cc1noc(C)c1-c1ccc(NC(=O)[C@@H](NC(=O)c2ccnn2C(C)C)C(C2CC2)C2CC2)cc1] | N-[(1S)-1-(dicyclopropylmethyl)-2-[4-(3,5-dimethylisoxazol-4-yl)anilino]-2-oxo-ethyl]-2-isopropyl-pyrazole-3-carboxamide | 476.266 | 2.49 |

| Ex. No. | SM | Structure | Name | Mass ion | LCMS RT (min) |
|---|---|---|---|---|---|
| 361 | Prep 360 | 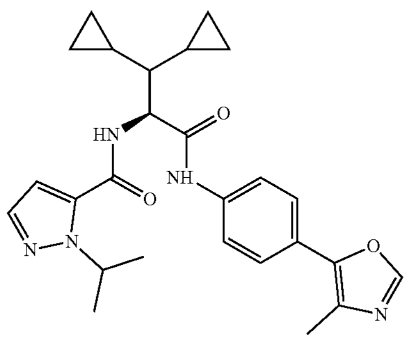 [SMILES: Cc1ncoc1-c1ccc(NC(=O)[C@@H](NC(=O)c2ccnn2C(C)C)C(C2CC2)C2CC2)cc1] | N-[(1S)-1-(dicyclopropylmethyl)-2-[4-(4-methyloxazol-5-yl)anilino]-2-oxo-ethyl]-2-isopropyl-pyrazole-3-carboxamide | 462.251 | 2.42 |
| 362 | Prep 361 | 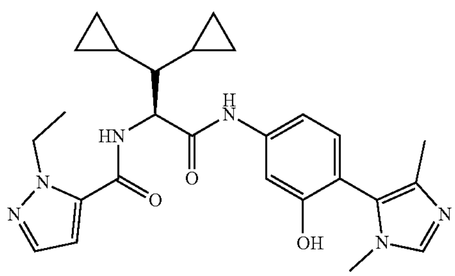 [SMILES: CCn1nccc1C(=O)N[C@H](C(=O)Nc1ccc(-c2c(C)ncn2C)c(O)c1)C(C1CC1)C1CC1] | N-[(1S)-1-(dicyclopropylmethyl)-2-[4-(3,5-dimethylimidazol-4-yl)-3-hydroxy-anilino]-2-oxo-ethyl]-2-ethyl-pyrazole-3-carboxamide | 477.261 | 1.94 |
| 363 | Prep 361 | 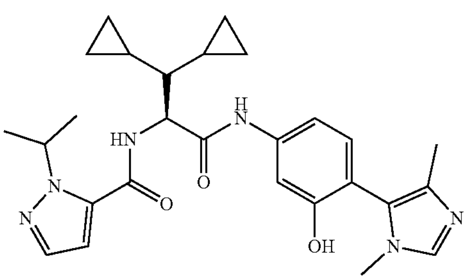 [SMILES: Cc1ncn(C)c1-c1ccc(NC(=O)[C@@H](NC(=O)c2ccnn2C(C)C)C(C2CC2)C2CC2)cc1O] | N-[(1S)-1-(dicyclopropylmethyl)-2-[4-(3,5-dimethylimidazol-4-yl)-3-hydroxy-anilino]-2-oxo-ethyl]-2-isopropyl-pyrazole-3-carboxamide | 491.277 | 1.99 |
| 364 | Prep 266 | 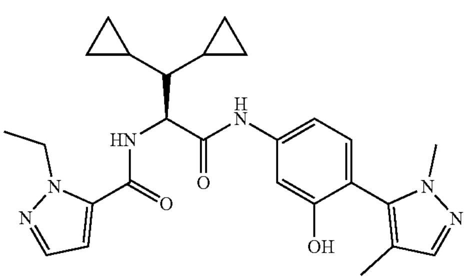 [SMILES: CCn1nccc1C(=O)N[C@H](C(=O)Nc1ccc(-c2c(C)cnn2C)c(O)c1)C(C1CC1)C1CC1] | N-[(1S)-1-(dicyclopropylmethyl)-2-[4-(2,4-dimethylpyrazol-3-yl)-3-hydroxy-anilino]-2-oxo-ethyl]-2-ethyl-pyrazole-3-carboxamide | 477.261 | 2.22 |
| 365 | Prep 266 | 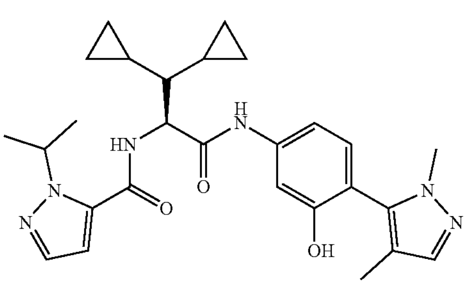 [SMILES: Cc1cnn(C)c1-c1ccc(NC(=O)[C@@H](NC(=O)c2ccnn2C(C)C)C(C2CC2)C2CC2)cc1O] | N-[(1S)-1-(dicyclopropylmethyl)-2-[4-(2,4-dimethylpyrazol-3-yl)-3-hydroxy-anilino]-2-oxo-ethyl]-2-isopropyl-pyrazole-3-carboxamide | 491.278 | 2.29 |

-continued

| Ex. No. | SM | Structure | Name | Mass ion | LCMS RT (min) |
|---|---|---|---|---|---|
| 366 | Prep 46, Prep 266 | 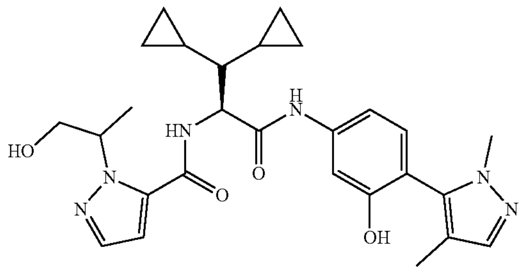 [SMILES: Cc1cnn(C)c1-c1ccc(NC(=O)[C@@H](NC(=O)c2ccnn2C(C)CO)C(C2CC2)C2CC2)cc1O] | N-[(1S)-1-(dicyclopropylmethyl)-2-[4-(2,4-dimethylpyrazol-3-yl)-3-hydroxy-anilino]-2-oxo-ethyl]-2-(2-hydroxy-1-methyl-ethyl)pyrazole-3-carboxamide | 507.273 | 2.11 |
| 367 | Prep 364 | 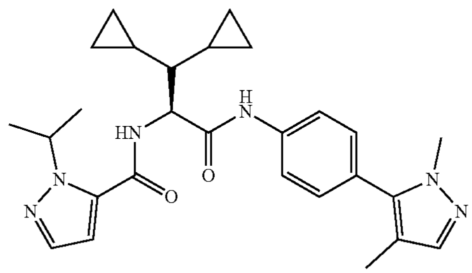 [SMILES: Cc1cnn(C)c1-c1ccc(NC(=O)[C@@H](NC(=O)c2ccnn2C(C)C)C(C2CC2)C2CC2)cc1] | N-[(1S)-1-(dicyclopropylmethyl)-2-[4-(2,4-dimethylpyrazol-3-yl)anilino]-2-oxo-ethyl]-2-isopropyl-pyrazole-3-carboxamide | 475.283 | 2.49 |
| 368 | Prep 365 | 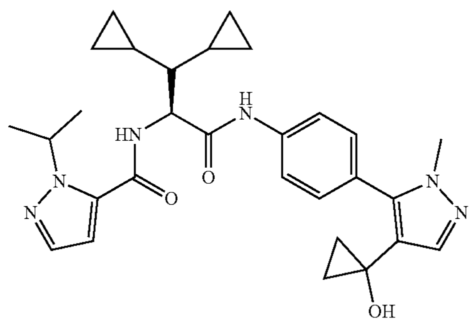 [SMILES: CC(C)n1nccc1C(=O)N[C@H](C(=O)Nc1ccc(-c2c(C3(O)CC3)cnn2C)cc1)C(C1CC1)C1CC1] | N-[(1S)-1-(dicyclopropylmethyl)-2-[4-[4-(1-hydroxycyclopropyl)-2-methyl-pyrazol-3-yl]anilino]-2-oxo-ethyl]-2-isopropyl-pyrazole-3-carboxamide | 517.293 | 2.28 |
| 369 | Prep 366 | 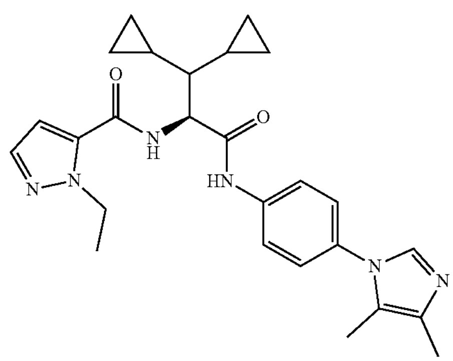 [SMILES: CCn1nccc1C(=O)N[C@H](C(=O)Nc1ccc(-n2cnc(C)c2C)cc1)C(C1CC1)C1CC1] | N-[(1S)-1-(dicyclopropylmethyl)-2-[4-(4,5-dimethylimidazol-1-yl)anilino]-2-oxo-ethyl]-2-ethyl-pyrazole-3-carboxamide | 461.266 | 2.02 |
| 370 | Prep 367 | 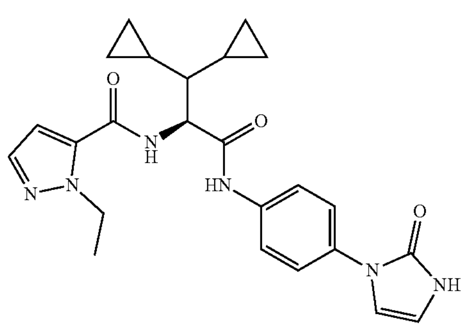 [SMILES: CCn1nccc1C(=O)N[C@H](C(=O)Nc1ccc(-n2cc[nH]c2=O)cc1)C(C1CC1)C1CC1] | N-[(1S)-1-(dicyclopropylmethyl)-2-[4-(4-methyl-2-oxo-1H-imidazol-3-yl)anilino]-2-oxo-ethyl]-2-ethyl-pyrazole-3-carboxamide | 463.246 | 2.13 |

| Ex. No. | SM | Structure | Name | Mass ion | LCMS RT (min) |
|---|---|---|---|---|---|
| 371 A | Prep 368 | 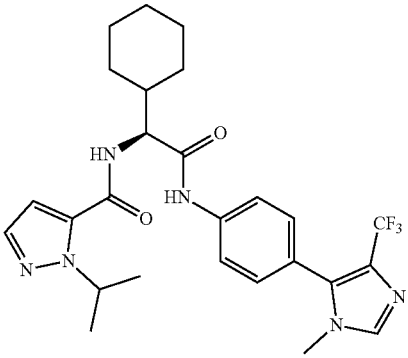 [SMILES: CC(C)n1nccc1C(=O)N[C@H](C(=O)Nc1ccc(-c2c(C(F)(F)F)ncn2C)cc1)C1CCCCC1] | N-[(1S)-1-cyclohexyl-2-[4-[3-methyl-5-(trifluoromethyl)imidazol-4-yl]anilino]-2-oxo-ethyl]-2-isopropyl-pyrazole-3-carboxamide | 517.254 | 2.42 |
| 371 B | Prep 369 | 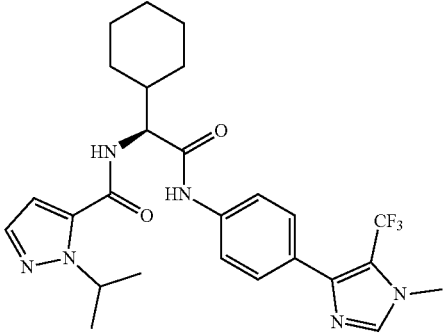 [SMILES: CC(C)n1nccc1C(=O)N[C@H](C(=O)Nc1ccc(-c2ncn(C)c2C(F)(F)F)cc1)C1CCCCC1] | N-[(1S)-1-cyclohexyl-2-[4-[1-methyl-5-(trifluoromethyl)imidazol-4-yl]anilino]-2-oxo-ethyl]-2-isopropyl-pyrazole-3-carboxamide | 517.254 | 2.45 |
| 372 | Prep 370 | 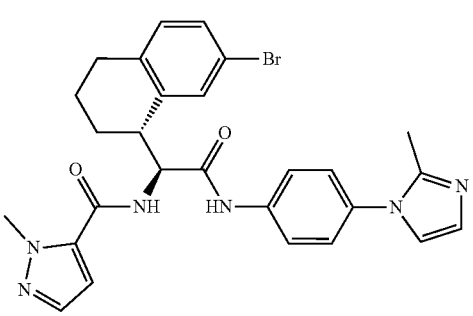 [SMILES: Cc1nccn1-c1ccc(NC(=O)[C@@H](NC(=O)c2ccnn2C)[C@@H]2CCCc3ccc(Br)cc32)cc1] | N-[(1S)-1-[(1R)-7-bromotetralin-1-yl]-2-[4-(2-methylimidazol-1-yl)anilino]-2-oxo-ethyl]-2-methyl-pyrazole-3-carboxamide | 547.3 549.3 | 0.66 Method 4 |

Example 373

N-(1,1-Bis(3-chlorophenyl)-3-((4-(1-methyl-1H-imidazol-5-yl)phenyl)amino)-3-oxopropan-2-yl)-1-methyl-1H-pyrazole-5-carboxamide

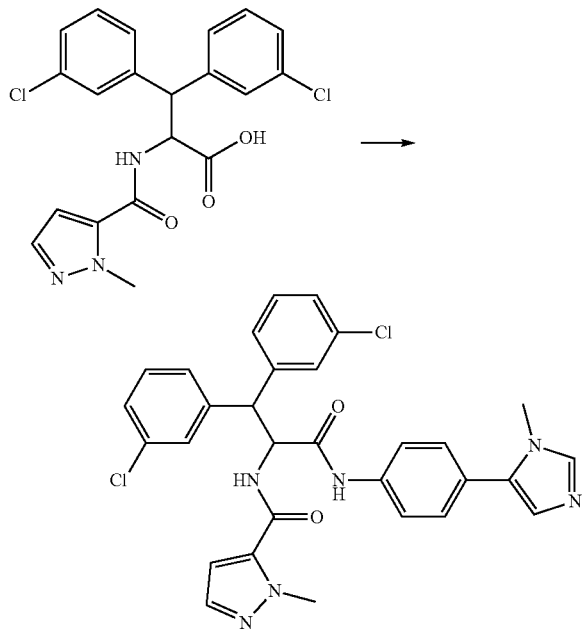

To a solution of the acid of Preparation 140 (1.0 g, 2.39 mmol) in DMF (20 mL) was added DIPEA (1.3 mL, 3.58 mmol) and T3P (12.6 g, 33.3 mmol, 50% solution in EtOAc) followed by 4-(1-methyl-1H-imidazol-5-yl)aniline (413 mg, 2.39 mmol) at 0° C. The resulting reaction mixture was stirred at room temperature for 16 hours then diluted with ice cold water (100 mL) and extracted with EtOAc (2×100 mL). The combined organic layers were washed with water (4×50 mL), brine (100 mL), dried over anhydrous $Na_2SO_4$ and concentrated under reduced pressure. The crude product was purified by prep. HPLC to give the title compound (400 mg, 29%) as an off white solid. The racemic mixture was separated by chiral SFC to give enantiomer 1 (30 mg) and enantiomer 2 (30 mg) as off white solids.

Preparative SFC Conditions: Column/dimensions: Chiralcel OD-H (30×250 mm), 5 μm; % $CO_2$: 60%; % Co solvent:40% (MeOH); Total Flow: 90.0 g/min; Back Pressure: 100.0 bar; UV: 214.0 nm.

Enantiomer 1: 1H NMR (400 MHz, DMSO-d6) δ 10.39 (s, 1H), 8.98-8.96 (d, J=8.8 Hz, 1H), 7.67 (s, 1H), 7.54 (s, 1H), 7.50-7.49 (m, 3H), 7.45-7.43 (d, J=7.6 Hz, 1H), 7.48-7.19 (m, 8H), 6.97 (s, 1H), 6.798-6.790 (d, J=3.6 Hz, 1H), 5.65-5.60 (dd, J=16.0 Hz, 8.0 Hz, 1H), 4.67-4.63 (d, J=11.6 Hz, 1H), 3.92 (s, 3H), 3.62 (s, 3H); LCMS (METHOD 5) (ESI): m/z: 573 [M+H$^+$]; RT=3.52 min; (ACQUITY UPLC BEH C18 column, 0.1% FA in water with MeCN); Chiral purity: 99% (RT: 1.30) Column: CHIRALCEL OD-3 (150× 4.6 mm) 3 μm; Co-solvent: 0.5% DEA in MeOH, Total flow: 3 g/min, % of co solvent: 40%, ABPR: 1500 Psi, Temperature: 30° C.

Enantiomer 2: 1H NMR (400 MHz, DMSO-d6) δ 10.39 (s, 1H), 8.98-8.96 (d, J=8.0 Hz, 1H), 7.69 (s, 1H), 7.54 (s, 1H), 7.50-7.48 (m, 3H), 7.45-7.43 (d, J=7.6 Hz, 1H), 7.39-7.19 (m, 8H), 6.99 (s, 1H), 6.785-6.779 (d, J=2.4 Hz, 1H), 5.65-5.60 (dd, J=16.0 Hz, 8.0 Hz, 1H), 4.66-4.64 (d, J=11.6 Hz, 1H), 3.92 (s, 3H), 3.63 (s, 3H); LCMS (METHOD 5) (ESI): m/z: 573 [M+H$^+$]; RT=3.54 min; (ACQUITY UPLC BEH C18 column, 0.1% FA in water with MeCN); Chiral purity: 98% (RT: 1.64) Column: CHIRALCEL OD-3 (150× 4.6 mm) 3 μm; Co-solvent: 0.5% DEA in Methanol, Total flow: 3 g/min, % of co solvent: 40%, ABPR: 1500 Psi, Temperature: 30° C.

Example 374

N-(1,1-Bis(3-Fluorophenyl)-3-((4-(1-methyl-1H-imidazol-5-yl)phenyl)amino)-3-oxopropan-2-yl)-1-methyl-1H-pyrazole-5-carboxamide

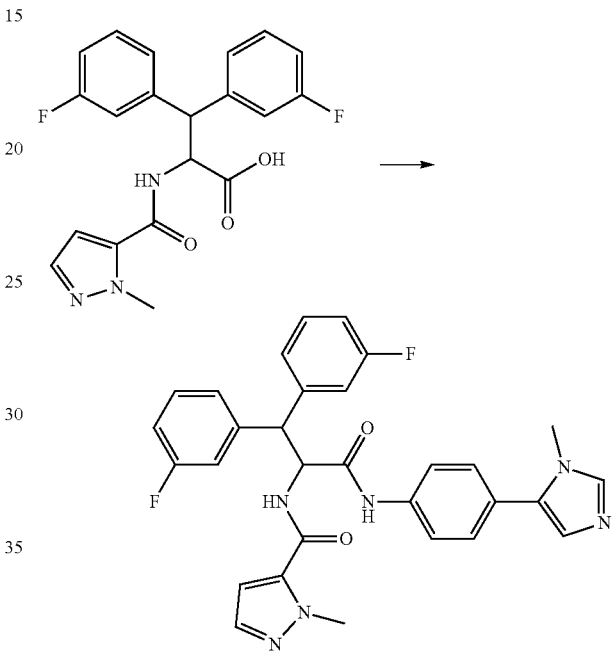

Example 374 was prepared according to the method of Example 373 from the acid of Preparation 141. This gave the title compound (400 mg, 50%) as an off white solid The racemic mixture was separated by chiral SFC to give enantiomer 1 (30 mg) and enantiomer 2 (30 mg) as off white solids.

Preparative SFC Conditions: Column/dimensions: Chiralcel OD-H (30×250 mm), 5 μm; % $CO_2$: 80%; % Co solvent:20% (MeOH); Total Flow: 90.0 g/min; UV:214.0 nm. Enantiomer 1: 1H NMR (400 MHz, DMSO-d6) δ 10.50 (br s, 1H), 8.98-8.96 (d, J=7.2 Hz, 1H), 7.58-7.56 (d, J=7.6 Hz, 2H), 7.47-7.45 (d, J=8.8 Hz, 2H), 7.40-7.39 (d, J=2.4 Hz, 1H), 7.37-7.23 (m, 8H), 7.03-6.95 (m, 2H), 6.79-6.79 (d, J=2.0 Hz, 1H), 5.64-5.59 (dd, J=8.8 Hz, 12.0 Hz, 1H), 4.70-4.67 (d, J=11.6 Hz, 1H), 3.92 (s, 3H), 3.76 (s, 3H); LCMS (METHOD 5) (ESI): m/z: 541 [M+H$^+$]; RT=1.82 min; (ACQUITY UPLC BEH C18 column, 0.1% FA in water with MeCN); Chiral purity: 99% (RT: 2.86) Column: CHIRALCEL OD-3 (150×4.6 mm) 3 μm; Co-solvent: MeOH, Total flow: 3 g/min, % of co solvent: 20%. Enantiomer 2: 1H NMR (400 MHz, DMSO-d6) δ 10.40 (br s, 1H), 8.98-8.96 (d, J=8.8 Hz, 1H), 7.59-7.56 (d, J=8.4 Hz, 2H), 7.48-7.46 (d, J=8.4 Hz, 2H), 7.40-7.39 (d, J=2.0 Hz, 1H), 7.37-7.23 (m, 8H), 7.01-6.96 (m, 2H), 6.79-6.87 (d, J=2.0 Hz, 1H), 5.61-5.59 (dd, J=8.4 Hz, 11.2 Hz, 1H), 4.70-4.67 (d, J=11.6 Hz, 1H), 3.92 (s, 3H), 3.76 (s, 3H); LCMS (METHOD 5) (ESI): m/z: 541 [M+H$^+$]; RT=1.83 min; (ACQUITY UPLC BEH C18 column, 0.1% FA in water with MeCN); Chiral purity: 99% (RT: 3.70) Column:

Example 375

2-Methyl-N-[(1S)-2-[4-(3-methylimidazol-4-yl)anilino]-2-oxo-1-[(1R)-tetralin-1-yl]ethyl]pyrazole-3-carboxamide

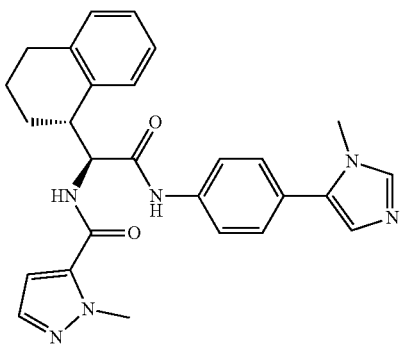 [SMILES: Cn1cncc1-c1ccc(NC(=O)[C@@H](NC(=O)c2ccnn2C)[C@@H]2CCCc3ccccc32)cc1]

A mixture of the bromide of Example 344 (15 mg, 0.0274 mmol) and 10% Pd on carbon (20 mg, 0.019 mmol) in MeOH (5 mL) was stirred at room temperature under hydrogen (1 atmosphere pressure) for 30 min. The catalyst was filtered off over Celite and washed several times with MeOH. The filtrate was concentrated in vacuo and the residue was purified by prep-HPLC (basic) to give the title compound (9 mg, 70%) as a white solid. 1H NMR (300 MHz, DMSO-d6) δ 10.05 (s, 1H), 8.59 (d, J=8.8 Hz, 1H), 7.65 (dd, J=1.2, 0.5 Hz, 1H), 7.62-7.54 (m, 2H), 7.44 (d, J=2.0 Hz, 1H), 7.43-7.36 (m, 2H), 7.17-6.89 (m, 6H), 5.07 (t, J=8.7 Hz, 1H), 3.97 (s, 3H), 3.65 (s, 3H), 3.45 (d, J=7.6 Hz, 1H), 2.96-2.81 (m, 1H), 2.79-2.63 (m, 1H), 1.97 (dd, J=23.5, 10.2 Hz, 2H), 1.68 (d, J=12.2 Hz, 2H).LCMS (METHOD 4) (ES): m/z 469.4 [M+H]$^+$, RT=0.60 min.

Examples 376-378

Examples 376-378 were synthesised according to the method of Example 375 from the indicated bromide.

| Ex. No. | Starting material | Structure | Name | Mass ion | LCMS RT (min) |
|---|---|---|---|---|---|
| 376 | Ex. 340 | 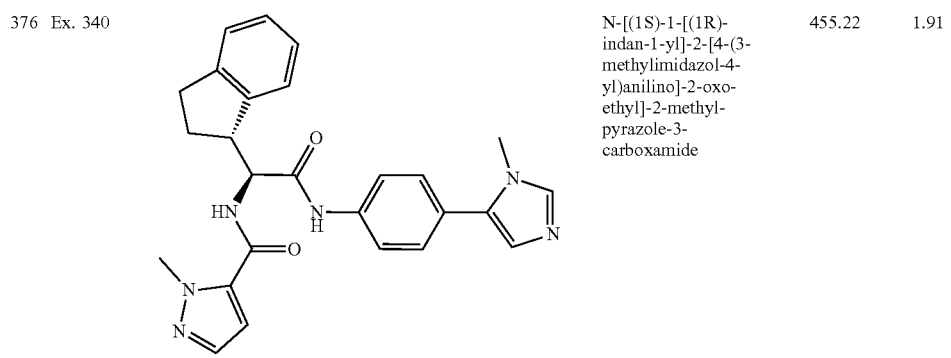 | N-[(1S)-1-[(1R)-indan-1-yl]-2-[4-(3-methylimidazol-4-yl)anilino]-2-oxo-ethyl]-2-methyl-pyrazole-3-carboxamide | 455.22 | 1.91 |
| 377 | Ex. 341 | 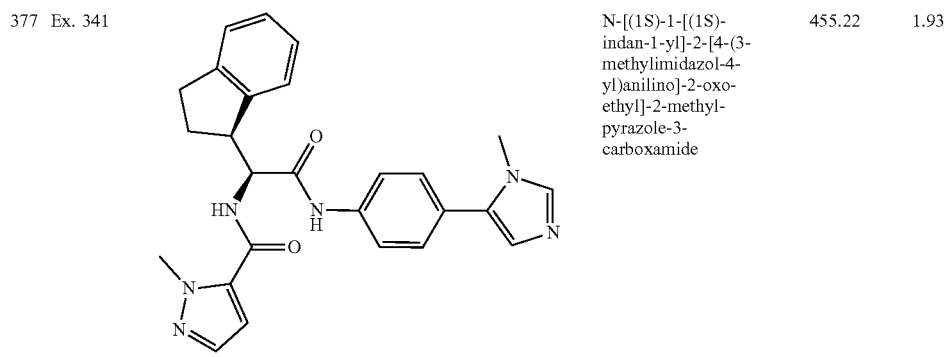 | N-[(1S)-1-[(1S)-indan-1-yl]-2-[4-(3-methylimidazol-4-yl)anilino]-2-oxo-ethyl]-2-methyl-pyrazole-3-carboxamide | 455.22 | 1.93 |

| Ex. No. | Starting material | Structure | Name | Mass ion | LCMS RT (min) |
|---|---|---|---|---|---|
| 378 | Ex. 372 | 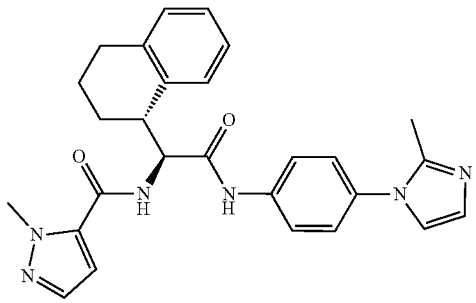 | 2-methyl-N-[(1S)-2-[4-(2-methylimidazol-1-yl)anilino]-2-oxo-1-[(1R)-tetralin-1-yl]ethyl]pyrazole-3-carboxamide | 469.233 | 1.95 |

Examples 379-388

Examples 379-388 were synthesised according to the method of Example 1 from the indicated SEM protected intermediate.

| Ex. No. | Starting material | Structure | Name | Mass ion | LCMS RT (min) |
|---|---|---|---|---|---|
| 379 | Prep. 326 | 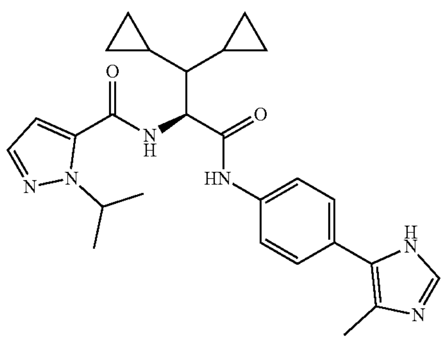 [SMILES: Cc1nc[nH]c1-c1ccc(NC(=O)[C@@H](NC(=O)c2ccnn2C(C)C)C(C2CC2)C2CC2)cc1] | N-[(1S)-1-(dicyclopropylmethyl)-2-[4-(4-methyl-1H-imidazol-5-yl)anilino]-2-oxo-ethyl]-2-isopropyl-pyrazole-3-carboxamide | 461.266 | 2.00 |
| 380 | Prep. 292 | 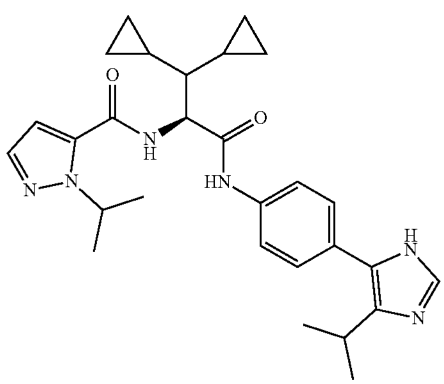 [SMILES: CC(C)c1nc[nH]c1-c1ccc(NC(=O)[C@@H](NC(=O)c2ccnn2C(C)C)C(C2CC2)C2CC2)cc1] | N-[(1S)-1-(dicyclopropylmethyl)-2-[4-(4-isopropyl-1H-imidazol-5-yl)anilino]-2-oxo-ethyl]-2-isopropyl-pyrazole-3-carboxamide | 489.297 | 2.08 |

-continued

| Ex. No. | Starting material | Structure | Name | Mass ion | LCMS RT (min) |
|---|---|---|---|---|---|
| 381 | Prep. 293 | 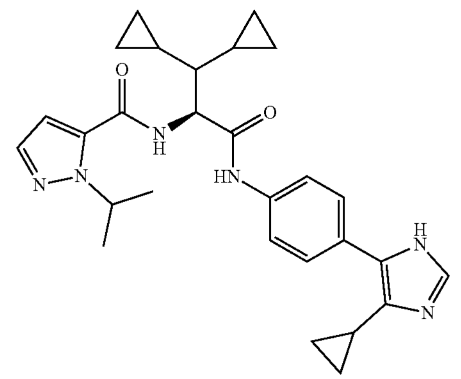 [SMILES: CC(C)n1nccc1C(=O)N[C@H](C(=O)Nc1ccc(-c2[nH]cnc2C2CC2)cc1)C(C1CC1)C1CC1] | N-[(1S)-2,2-dicyclopropyl-1-[[4-(4-cyclopropyl-1H-imidazol-5-yl)phenyl]carbamoyl]ethyl]-2-isopropyl-pyrazole-3-carboxamide | 487.282 | 2.05 |
| 382 | Prep. 294 | 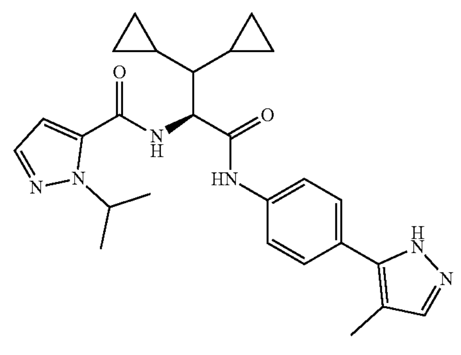 [SMILES: Cc1cn[nH]c1-c1ccc(NC(=O)[C@@H](NC(=O)c2ccnn2C(C)C)C(C2CC2)C2CC2)cc1] | N-[(1S)-1-(dicyclopropylmethyl)-2-[4-(4-methyl-1H-pyrazol-5-yl)anilino]-2-oxo-ethyl]-2-isopropyl-pyrazole-3-carboxamide | 461.266 | 2.32 |
| 383 | Prep. 295 | 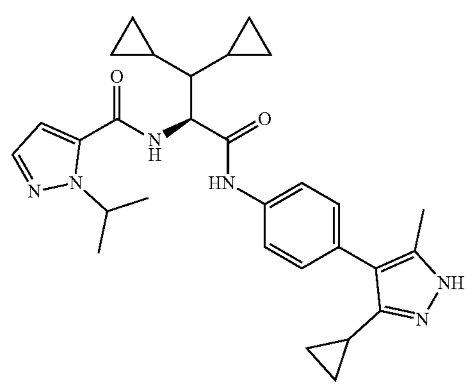 [SMILES: Cc1[nH]nc(C2CC2)c1-c1ccc(NC(=O)[C@@H](NC(=O)c2ccnn2C(C)C)C(C2CC2)C2CC2)cc1] | N-[(1S)-2,2-dicyclopropyl-1-[[4-(3-cyclopropyl-5-methyl-1H-pyrazol-4-yl)phenyl]carbamoyl]ethyl]-2-isopropyl-pyrazole-3-carboxamide | 501.298 | 2.41 |
| 384 | Prep. 323 | 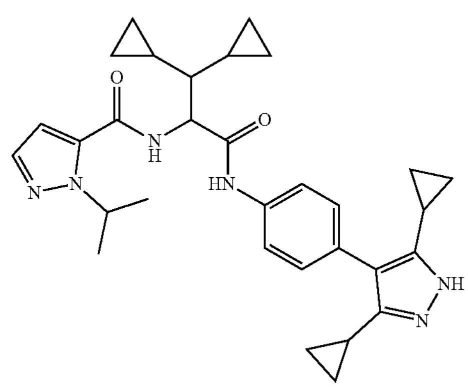 [SMILES: CC(C)n1nccc1C(=O)NC(C(=O)Nc1ccc(-c2c(C3CC3)n[nH]c2C2CC2)cc1)C(C1CC1)C1CC1] | Enantiomer 1 of N-[1-(dicyclopropylmethyl)-2-[4-(3,5-dicyclopropyl-1H-pyrazol-4-yl)anilino]-2-oxo-ethyl]-2-isopropyl-pyrazole-3-carboxamide* | 527.313 | 2.49 |

-continued

| Ex. No. | Starting material | Structure | Name | Mass ion | LCMS RT (min) |
|---|---|---|---|---|---|
| 385 | Prep. 323 | 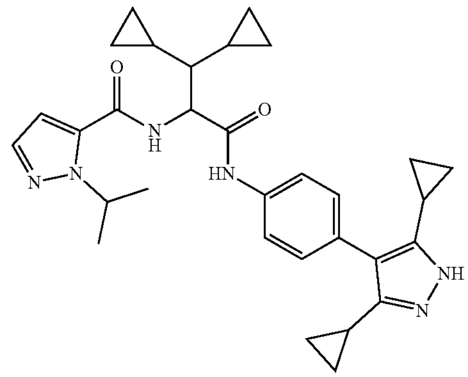 [SMILES: CC(C)n1nccc1C(=O)NC(C(=O)Nc1ccc(-c2c(C3CC3)n[nH]c2C2CC2)cc1)C(C1CC1)C1CC1] | Enantiomer 2 of N-[1-(dicyclopropylmethyl)-2-[4-(3,5-dicyclopropyl-1H-pyrazol-4-yl)anilino]-2-oxo-ethyl]-2-isopropyl-pyrazole-3-carboxamide* | 527.313 | 2.50 |
| 386 | Prep. 296 | 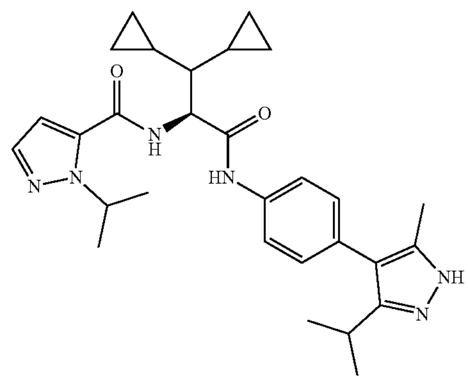 [SMILES: Cc1[nH]nc(C(C)C)c1-c1ccc(NC(=O)[C@@H](NC(=O)c2ccnn2C(C)C)C(C2CC2)C2CC2)cc1] | N-[(1S)-1-(dicyclopropylmethyl)-2-[4-(3-isopropyl-5-methyl-1H-pyrazol-4-yl)anilino]-2-oxo-ethyl]-2-isopropyl-pyrazole-3-carboxamide | 503.314 | 2.38 |
| 387 | Prep. 325 | 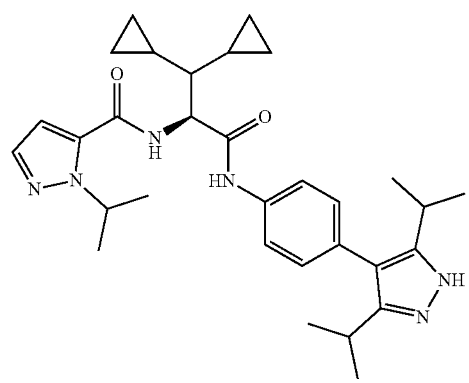 [SMILES: CC(C)c1n[nH]c(C(C)C)c1-c1ccc(NC(=O)[C@@H](NC(=O)c2ccnn2C(C)C)C(C2CC2)C2CC2)cc1] | N-[(1S)-1-(dicyclopropylmethyl)-2-[4-(3,5-diisopropyl-1H-pyrazol-4-yl)anilino]-2-oxo-ethyl]-2-isopropyl-pyrazole-3-carboxamide | 531.344 | 2.50 |
| 388 | Prep. 334 | 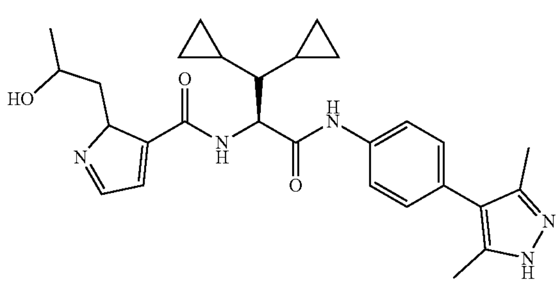 | N-[(1S)-1-(dicyclopropylmethyl)-2-[4-(3,5-dimethyl-1H-pyrazol-4-yl)anilino]-2-oxo-ethyl]-2-(2-hydroxypropyl)pyrazole-3-carboxamide | 491.277 | 2.1 |

*The compound was found to have racemised during synthesis and the 2 enantiomers were separated by chiral SFC.

Examples 389-399

Examples 389-399 were synthesised according to the methods of Preparation 3-5 and Example 1 from the indicated aniline, the Boc protected amino acid of Preparation 52 and the appropriate carboxylic acid.

| Ex. No. | Starting material | Structure | Name | Mass ion | LCMS RT (min) |
|---|---|---|---|---|---|
| 389 | Prep. 300, Prep. 194 | 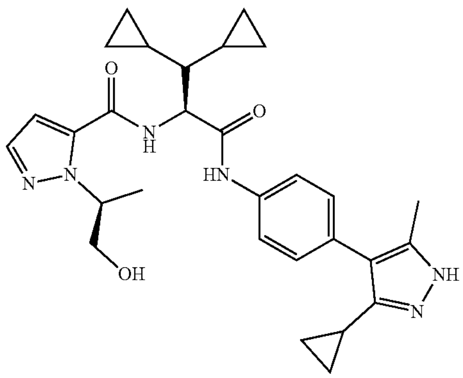 [SMILES: Cc1[nH]nc(C2CC2)c1-c1ccc(NC(=O)[C@@H](NC(=O)c2ccnn2[C@@H](C)CO)C(C2CC2)C2CC2)cc1] | N-[(1S)-2,2-dicyclopropyl-1-[[4-(3-cyclopropyl-5-methyl-1H-pyrazol-4-yl)phenyl]carbamoyl]ethyl]-2-[(1S)-2-hydroxy-1-methyl-ethyl]pyrazole-3-carboxamide | 517.293 | 2.17 |
| 390 | Prep. 300, Prep. 195 | 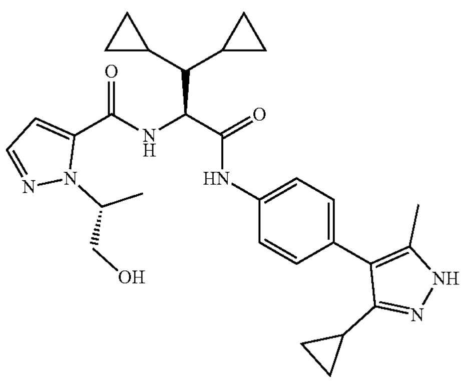 [SMILES: Cc1[nH]nc(C2CC2)c1-c1ccc(NC(=O)[C@@H](NC(=O)c2ccnn2[C@H](C)CO)C(C2CC2)C2CC2)cc1] | N-[(1S)-2,2-dicyclopropyl-1-[[4-(3-cyclopropyl-5-methyl-1H-pyrazol-4-yl)phenyl]carbamoyl]ethyl]-2-[(1R)-2-hydroxy-1-methyl-ethyl]pyrazole-3-carboxamide | 517.293 | 2.21 |
| 391 | Prep. 300 | 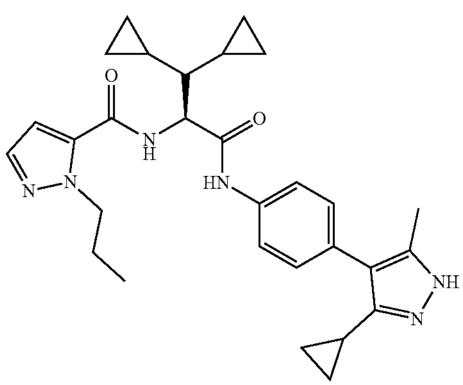 [SMILES: CCCn1nccc1C(=O)N[C@H](C(=O)Nc1ccc(-c2c(C3CC3)n[nH]c2C)cc1)C(C1CC1)C1CC1] | N-[(1S)-2,2-dicyclopropyl-1-[[4-(3-cyclopropyl-5-methyl-1H-pyrazol-4-yl)phenyl]carbamoyl]ethyl]-2-propyl-pyrazole-3-carboxamide | 501.298 | 2.40 |

-continued

| Ex. No. | Starting material | Structure | Name | Mass ion | LCMS RT (min) |
|---|---|---|---|---|---|
| 392 | Prep. 300 | 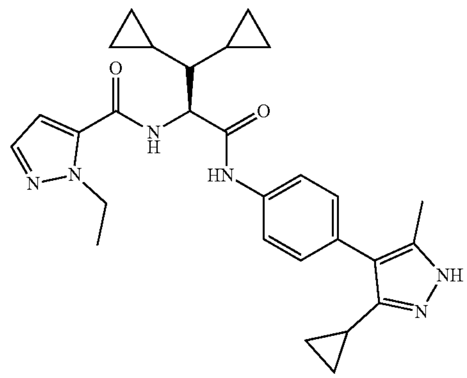 [SMILES: CCn1nccc1C(=O)N[C@H](C(=O)Nc1ccc(-c2c(C3CC3)n[nH]c2C)cc1)C(C1CC1)C1CC1] | N-[(1S)-2,2-dicyclopropyl-1-[[4-(3-cyclopropyl-5-methyl-1H-pyrazol-4-yl)phenyl]carbamoyl]ethyl]-2-ethyl-pyrazole-3-carboxamide | 487.283 | 2.33 |
| 393 | Prep. 312, Prep. 65 | 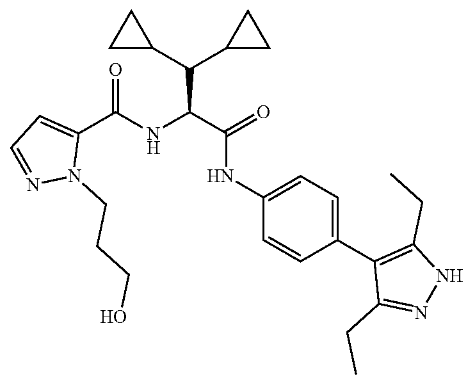 [SMILES: CCc1n[nH]c(CC)c1-c1ccc(NC(=O)[C@@H](NC(=O)c2ccnn2CCCO)C(C2CC2)C2CC2)cc1] | N-[(1S)-1-(dicyclopropylmethyl)-2-[4-(3,5-diethyl-1H-pyrazol-4-yl)anilino]-2-oxo-ethyl]-2-(3-hydroxypropyl)pyrazole-3-carboxamide | 519.309 | 2.19 |
| 394 | Prep. 312, Prep. 194 | 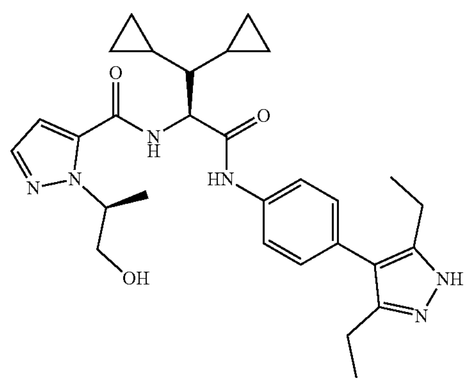 [SMILES: CCc1n[nH]c(CC)c1-c1ccc(NC(=O)[C@@H](NC(=O)c2ccnn2[C@@H](C)CO)C(C2CC2)C2CC2)cc1] | N-[(1S)-1-(dicyclopropylmethyl)-2-[4-(3,5-diethyl-1H-pyrazol-4-yl)anilino]-2-oxo-ethyl]-2-[(1S)-2-hydroxy-1-methyl-ethyl]pyrazole-3-carboxamide | 519.309 | 2.18 |
| 395 | Prep. 312, Prep. 195 | 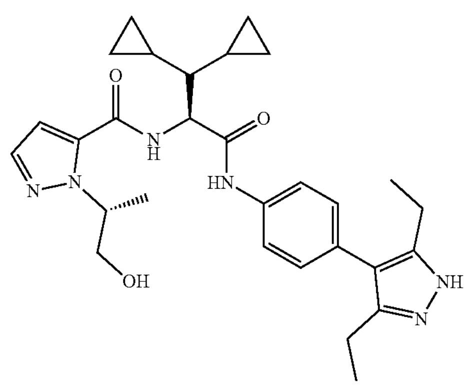 [SMILES: CCc1n[nH]c(CC)c1-c1ccc(NC(=O)[C@@H](NC(=O)c2ccnn2[C@H](C)CO)C(C2CC2)C2CC2)cc1] | N-[(1S)-1-(dicyclopropylmethyl)-2-[4-(3,5-diethyl-1H-pyrazol-4-yl)anilino]-2-oxo-ethyl]-2-[(1R)-2-hydroxy-1-methyl-ethyl]pyrazole-3-carboxamide | 519.308 | 2.23 |

-continued

| Ex. No. | Starting material | Structure | Name | Mass ion | LCMS RT (min) |
|---|---|---|---|---|---|
| 396 | Prep. 312 | 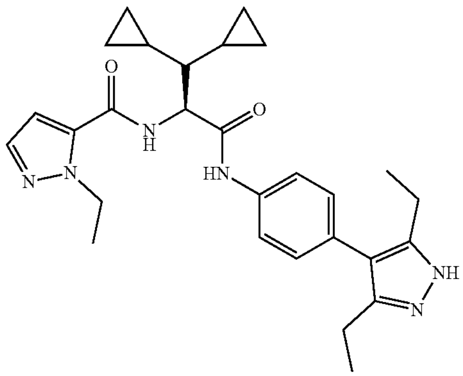 [SMILES: CCc1n[nH]c(CC)c1-c1ccc(NC(=O)[C@@H](NC(=O)c2ccnn2CC)C(C2CC2)C2CC2)cc1] | N-[(1S)-1-(dicyclopropylmethyl)-2-[4-(3,5-diethyl-1H-pyrazol-4-yl)anilino]-2-oxo-ethyl]-2-ethyl-pyrazole-3-carboxamide | 489.297 | 2.34 |
| 397 | Prep. 312 | 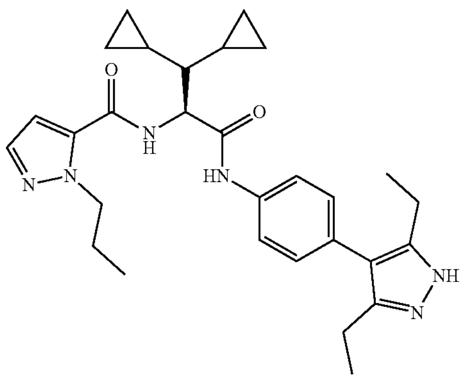 [SMILES: CCCn1nccc1C(=O)N[C@H](C(=O)Nc1ccc(-c2c(CC)n[nH]c2CC)cc1)C(C1CC1)C1CC1] | N-[(1S)-1-(dicyclopropylmethyl)-2-[4-(3,5-diethyl-1H-pyrazol-4-yl)anilino]-2-oxo-ethyl]-2-propyl-pyrazole-3-carboxamide | 503.314 | 2.43 |
| 398 | Prep. 312 | 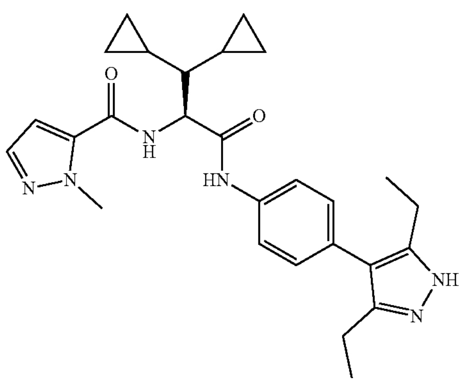 [SMILES: CCc1n[nH]c(CC)c1-c1ccc(NC(=O)[C@@H](NC(=O)c2ccnn2C)C(C2CC2)C2CC2)cc1] | N-[(1S)-1-(dicyclopropylmethyl)-2-[4-(3,5-diethyl-1H-pyrazol-4-yl)anilino]-2-oxo-ethyl]-2-methyl-pyrazole-3-carboxamide | 475.283 | 2.30 |
| 399 | Prep. 312 | 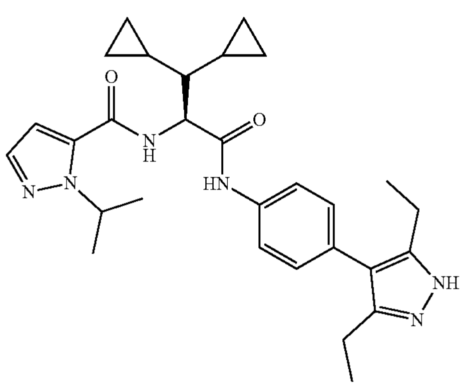 [SMILES: CCc1n[nH]c(CC)c1-c1ccc(NC(=O)[C@@H](NC(=O)c2ccnn2C(C)C)C(C2CC2)C2CC2)cc1] | N-[(1S)-1-(dicyclopropylmethyl)-2-[4-(3,5-diethyl-1H-pyrazol-4-yl)anilino]-2-oxo-ethyl]-2-isopropyl-pyrazole-3-carboxamide | 513.313 | 2.44 |

Example 400

N-[(1S)-1-Benzhydryl-2-[4-(3-methyl-1H-pyrazol-4-yl)anilino]-2-oxo-ethyl]-2-methyl-pyrazole-3-carboxamide

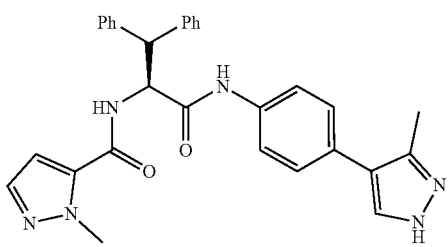 [SMILES: Cc1n[nH]cc1-c1ccc(NC(=O)[C@@H](NC(=O)c2ccnn2C)C(c2ccccc2)c2ccccc2)cc1]

The title compound was prepared according to the methods of Preparations 3-5 and Example 1 from the aniline of Preparation 272 and (2S)-2-(tert-butoxycarbonylamino)-3,3-diphenyl-propanoic acid. 1H NMR (300 MHz, DMSO-d6) δ 12.56 (br s, 1H), 10.21 (s, 1H), 8.85 (d, J=8.8 Hz, 1H), 7.80 (br s, 0.5H), 7.59 (br s, 0.5H), 7.52-7.38 (m, 6H), 7.37 (d, J=2.1 Hz, 1H), 7.33-7.18 (m, 6H), 7.18-7.07 (m, 2H), 6.77 (d, J=2.1 Hz, 1H), 5.63 (dd, J=11.7, 8.8 Hz, 1H), 4.63 (d, J=11.7 Hz, 1H), 3.91 (s, 3H), 2.31 (s, 3H); LCMS (ES): m/z 505.235 [M+H]+, RT=2.19 min.

Examples 401-409

Examples 401-409 were synthesised according to the method of Preparation 292 from the boronic ester of Preparation 281 and the appropriate heteroaromatic halide, which is either commercially available or synthesised as described in the indicated Preparation.

| Ex. No. | SM | Structure | Name | Mass ion | LCMS RT (min) |
|---|---|---|---|---|---|
| 401 | Prep. 283A | 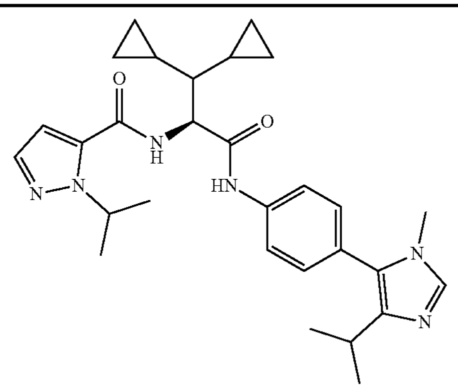 | N-[(1S)-1-(dicyclopropylmethyl)-2-[4-(5-isopropyl-3-methyl-imidazol-4-yl)anilino]-2-oxo-ethyl]-2-isopropyl-pyrazole-3-carboxamide | 503.314 | 2.10 |
| 402 | Prep. 285A | 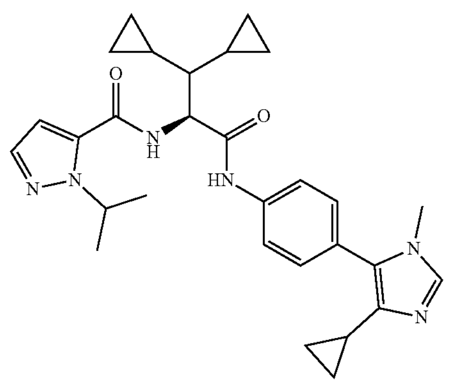 [SMILES: CC(C)n1nccc1C(=O)N[C@H](C(=O)Nc1ccc(-c2c(C3CC3)ncn2C)cc1)C(C1CC1)C1CC1] | N-[(1S)-2,2-dicyclopropyl-1-[[4-(5-cyclopropyl-3-methyl-imidazol-4-yl)phenyl]carbamoyl]ethyl]-2-isopropyl-pyrazole-3-carboxamide | 501.298 | 2.08 |
| 403 | | 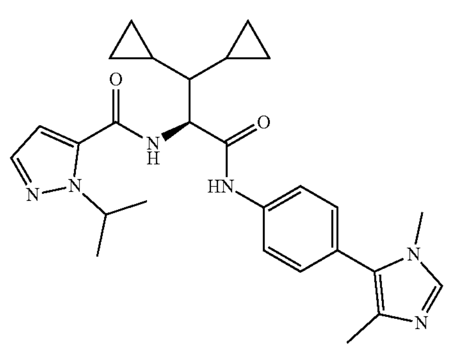 [SMILES: Cc1ncn(C)c1-c1ccc(NC(=O)[C@@H](NC(=O)c2ccnn2C(C)C)C(C2CC2)C2CC2)cc1] | N-[(1S)-1-(dicyclopropylmethyl)-2-[4-(3,5-dimethylimidazol-4-yl)anilino]-2-oxo-ethyl]-2-isopropyl-pyrazole-3-carboxamide | 475.282 | 2.02 |

| Ex. No. | SM | Structure | Name | Mass ion | LCMS RT (min) |
|---|---|---|---|---|---|
| 404 | 3-bromo-2-methylpyridine | 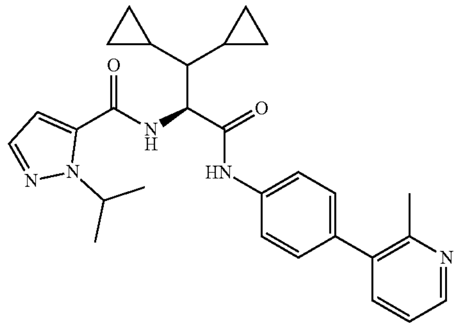 [SMILES: Cc1ncccc1-c1ccc(NC(=O)[C@@H](NC(=O)c2ccnn2C(C)C)C(C2CC2)C2CC2)cc1] | N-[(1S)-1-(dicyclopropylmethyl)-2-[4-(2-methyl-3-pyridyl)anilino]-2-oxo-ethyl]-2-isopropyl-pyrazole-3-carboxamide | 472.27 | 2.09 |
| 405 | 4-bromo-3-methylpyridine | 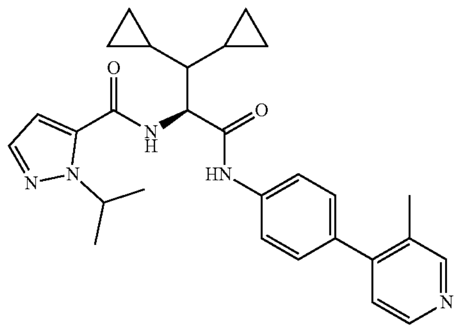 [SMILES: Cc1cnccc1-c1ccc(NC(=O)[C@@H](NC(=O)c2ccnn2C(C)C)C(C2CC2)C2CC2)cc1] | N-[(1S)-1-(dicyclopropylmethyl)-2-[4-(3-methyl-4-pyridyl)anilino]-2-oxo-ethyl]-2-isopropyl-pyrazole-3-carboxamide | 472.271 | 2.13 |
| 406 | Prep. 328 | 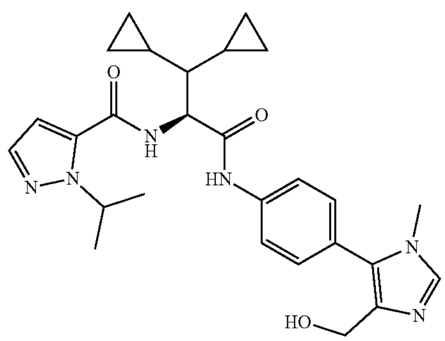 [SMILES: CC(C)n1nccc1C(=O)N[C@H](C(=O)Nc1ccc(-c2c(CO)ncn2C)cc1)C(C1CC1)C1CC1] | N-[(1S)-1-(dicyclopropylmethyl)-2-[4-[5-(hydroxymethyl)-3-methyl-imidazol-4-yl]anilino]-2-oxo-ethyl]-2-isopropyl-pyrazole-3-carboxamide | 491.277 | 1.98 |
| 407 | (3-bromo-2-pyridyl)methanol | 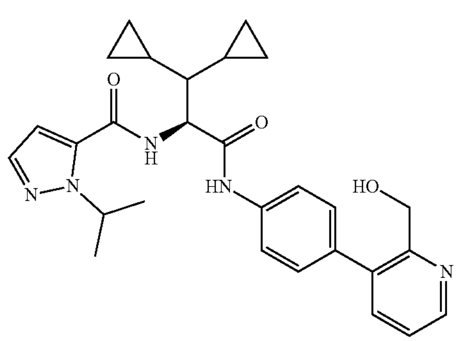 [SMILES: CC(C)n1nccc1C(=O)N[C@H](C(=O)Nc1ccc(-c2cccnc2CO)cc1)C(C1CC1)C1CC1] | N-[(1S)-1-(dicyclopropylmethyl)-2-[4-[2-(hydroxymethyl)-3-pyridyl]anilino]-2-oxo-ethyl]-2-isopropyl-pyrazole-3-carboxamide | 488.267 | 2.07 |

| Ex. No. | SM | Structure | Name | Mass ion | LCMS RT (min) |
|---|---|---|---|---|---|
| 408 | | 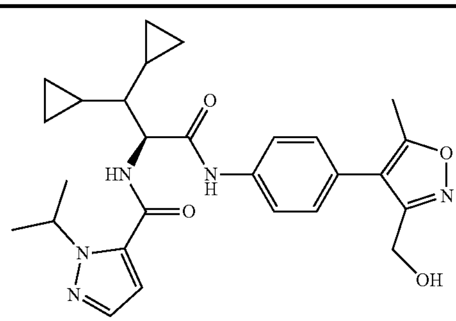 | N-[(1S)-1-(dicyclopropylmethyl)-2-[4-[3-(hydroxymethyl)-5-methyl-isoxazol-4-yl]anilino]-2-oxo-ethyl]-2-isopropyl-pyrazole-3-carboxamide | 492 | 2.71 Method 5 ACQUITY BEH C18 column, 0.05% FA in water with MeCN |
| 409 | | 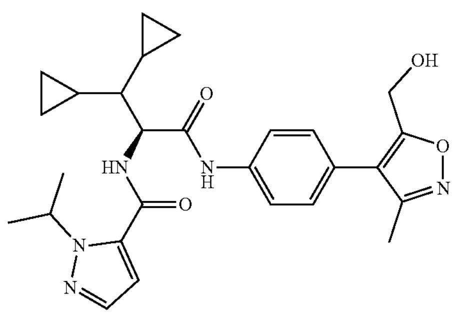 [SMILES: Cc1noc(CO)c1-c1ccc(NC(=O)[C@@H](NC(=O)c2ccnn2C(C)C)C(C2CC2)C2CC2)cc1] | N-[(1S)-1-(dicyclopropylmethyl)-2-[4-[5-(hydroxymethyl)-3-methyl-isoxazol-4-yl]anilino]-2-oxo-ethyl]-2-isopropyl-pyrazole-3-carboxamide | 492.261 | 2.29 |

Example 410

N-[(1S)-1-(Dicyclopropylmethyl)-2-[4-(3,5-dimethyl-1H-pyrazol-4-yl)-3-hydroxy-anilino]-2-oxo-ethyl]-2-isopropyl-pyrazole-3-carboxamide

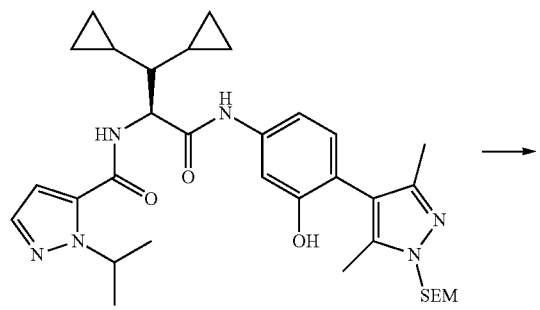

TFA (10 mL) was added to a solution of the compound of Preparation 261 (1.098 g, 1.77 mmol) in DCM (10 mL) at room temperature and the mixture was stirred for 2.5 hours. Thereafter the solvents were evaporated and purified by prep basic HPLC to give the title compound (323 mg, 29%) as a colourless solid. 1H NMR (600 MHz, DMSO-d6) δ 12.07 (s, 1H), 10.04 (s, 1H), 9.22 (s, 1H), 8.41 (d, J=8.8 Hz, 1H), 7.50 (d, J=2.0 Hz, 1H), 7.33 (d, J=2.0 Hz, 1H), 7.01 (dd, J=8.2, 2.1 Hz, 1H), 6.94 (d, J=8.2 Hz, 1H), 6.91 (d, J=2.0 Hz, 1H), 5.41 (hept, J=6.6 Hz, 1H), 4.80 (t, J=8.4 Hz, 1H), 2.04 (s, 6H), 1.39 (d, J=6.6 Hz, 3H), 1.35 (d, J=6.6 Hz, 3H), 0.95-0.85 (m, 1H), 0.85-0.71 (m, 2H), 0.53-0.43 (m, 1H), 0.43-0.34 (m, 2H), 0.35-0.12 (m, 5H); LCMS (ES): m/z 491.277 [M+H]+, RT=2.15 min.

Examples 411-417

Examples 411-417 were synthesised according to the methods of Preparations 259-261 and Example 410 staring from the aniline of Preparation 258 and using the appropriate Boc protected amino acid and carboxylic acid.

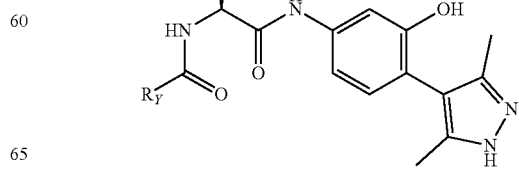

| Ex. No. | R$_X$ | R$_Y$ | Name | Mass ion | LCMS retention time (min) |
|---|---|---|---|---|---|
| 411 | Ph, Ph | | N-[(1S)-1-benzhydryl-2-[4-(3,5-dimethyl-1H-pyrazol-4-yl)-3-hydroxy-anilino]-2-oxo-ethyl]-2-methyl-pyrazole-3-carboxamide | 535.247 | 2.12 |
| 412 | cyclohexyl | | N-[(1S)-1-cyclohexyl-2-[4-(3,5-dimethyl-1H-pyrazol-4-yl)-3-hydroxy-anilino]-2-oxo-ethyl]-2-methyl-pyrazole-3-carboxamide | 451.246 | 2.02 |
| 413 Prep. 52 | dicyclopropylmethyl | | N-[(1S)-1-(dicyclopropylmethyl)-2-[4-(3,5-dimethyl-1H-pyrazol-4-yl)-3-hydroxy-anilino]-2-oxo-ethyl]-2-ethyl-pyrazole-3-carboxamide | 477.262 | 2.09 |
| 414 Prep. 52 | dicyclopropylmethyl | | N-[(1S)-1-(dicyclopropylmethyl)-2-[4-(3,5-dimethyl-1H-pyrazol-4-yl)-3-hydroxy-anilino]-2-oxo-ethyl]-2-methyl-pyrazole-3-carboxamide | 463.246 | 2.03 |
| 415 Prep. 52 | dicyclopropylmethyl | F-cyclopropyl | N-[(1S)-1-(dicyclopropylmethyl)-2-[4-(3,5-dimethyl-1H-pyrazol-4-yl)-3-hydroxy-anilino]-2-oxo-ethyl]-1-fluoro-cyclopropanecarboxamide | 441.23 | 2.12 |
| 416 | trans-4-methylcyclohexyl * | | N-[(1S)-2-[4-(3,5-dimethyl-1H-pyrazol-4-yl)-3-hydroxy-anilino]-1-(trans-4-methylcyclohexyl)-2-oxo-ethyl]-2-ethyl-pyrazole-3-carboxamide | 479.277 | 2.22 |
| 417 | trans-4-methylcyclohexyl * | | N-[(1S)-2-[4-(3,5-dimethyl-1H-pyrazol-4-yl)-3-hydroxy-anilino]-1-(trans-4-methylcyclohexyl)-2-oxo-ethyl]-2-isopropyl-pyrazole-3-carboxamide | 493.293 | 2.29 |

*Trans (2S)-2-(tert-butoxycarbonylamino)-2-(4-methylcyclohexyl)acetic acid was prepared according to the method in WO2018/229079

Example 418

N-[(1S)-1-(dicyclopropylmethyl)-2-[4-(3,5-diethyl-1H-pyrazol-4-yl)-3-hydroxy-anilino]-2-oxo-ethyl]-2-isopropyl-pyrazole-3-carboxamide

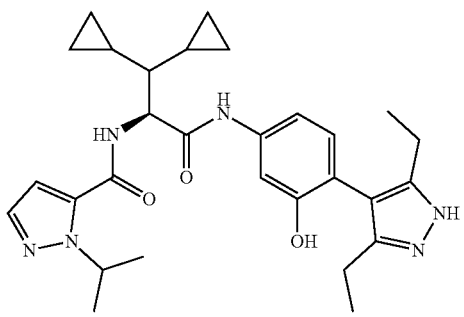 [SMILES: CCc1n[nH]c(CC)c1-c1ccc(NC(=O)[C@@H](NC(=O)c2ccnn2C(C)C)C(C2CC2)C2CC2)cc1O]

Example 418 was synthesised according to the methods of Preparations 259-261 and Example 410 staring from the aniline of Preparation 317 and using the Boc protected amino acid of Preparation 52 and 2-isopropylpyrazole-3-carboxylic acid. $^1$H NMR (400 MHz, DMSO-d$_6$) δ 12.10 (br s, 1H), 10.04 (s, 1H), 9.14 (s, 1H), 8.42 (d, J=8.8 Hz, 1H), 7.50 (d, J=2.0 Hz, 1H), 7.30 (d, =2.0 Hz, 1H), 7.05 (d, J=4.4 Hz, 1H), 6.99-6.91 (m, 2H), 5.41 (t, =6.8 Hz, 1H), 4.78 (t, J=2.41H), 2.49 (q, J=1.6 Hz, 4H), 1.40-1.34 (m, 6H), 1.05 (s, 2H), 1.01-0.93 (m, 6H), 0.78-0.738 (m, 3H), 0.395-0.154 (m, 6H). Chiral HPLC: 97%, RT: 2.40, Column: CHIRALPAK IC-3(4.6*150) mm, 3u, Co-Solvent: 0.5% of DEA in MeOH (20%), Column Temperature: 30° C., Flow: 3 g/min; LCMS (ES): m/z 519.308 [M+H]$^+$, RT=2.29 min.

Example 419

N-[(1S)-1-Cyclohexyl-2-[3-hydroxy-4-(3-methylimidazol-4-yl)anilino]-2-oxo-ethyl]-2-methyl-pyrazole-3-carboxamide

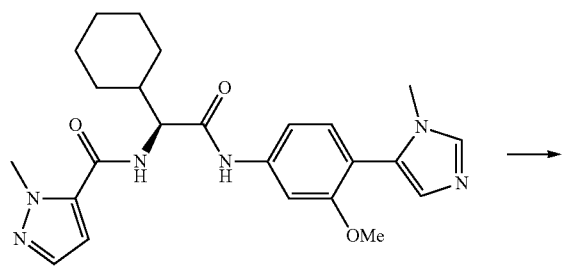

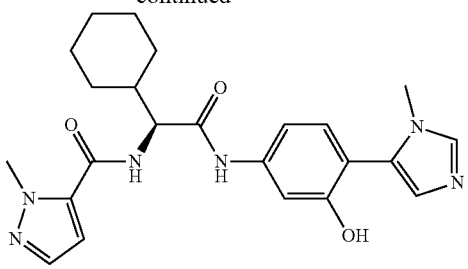

To an ice cold solution of the methoxy compound of Preparation 252 (60 mg, 0.133 mmol) in DCM (1 mL) was added BBr$_3$ (1M soln. in DCM, 1.33 mL, 1.33 mmol). The mixture was stirred at room temperature for 18 hours then quenched by pouring into ice cold MeOH (25 mL). The mixture was concentrated in vacuo then re-dissolved in MeOH (2 mL) and aqueous ammonia (0.5 mL). Purification by prep, basic HPLC gave the title compound (22.4 mg, 39%). 1H NMR (300 MHz, DMSO-d6) δ 10.19 (s, 1H), 9.81 (s, 1H), 8.47 (d, J=8.2 Hz, 1H), 7.61 (d, J=1.1 Hz, 1H), 7.46 (d, J=2.1 Hz, 1H), 7.44 (d, J=1.2 Hz, 1H), 7.09-7.04 (m, 3H), 6.79 (d, J=1.2 Hz, 1H), 4.41 (t, J=8.5 Hz, 1H), 4.03 (s, 3H), 3.49 (s, 3H), 1.96-1.79 (m, 2H), 1.79-1.67 (m, 2H), 1.67-1.53 (m, 2H), 1.35-0.94 (m, 5H); LCMS (ES): m/z 437.231 [M+H]$^+$, RT=1.90 min.

Example 420

Example 420 was synthesised according to the methods of Preparations 249-252 and Example 419 from the aniline of Preparation 248 and (2S)-2-(tert-butoxycarbonylamino)-3,3-diphenyl-propanoic acid.

| Example No. | Structure | Name | Mass ion | LCMS retention time (min) |
|---|---|---|---|---|
| 420 | (structure shown) | N-[(1S)-1-benzhydryl-2-[3-hydroxy-4-(3-methylimidazol-4-yl)anilino]-2-oxo-ethyl]-2-methyl-pyrazole-3-carboxamide | 521.231 | 1.97 |

Example 421

N-[(1S)-1-Benzhydryl-2-[3-hydroxy-4-(3-methyl-1H-pyrazol-4-yl)anilino]-2-oxo-ethyl]-2-methyl-pyrazole-3-carboxamide

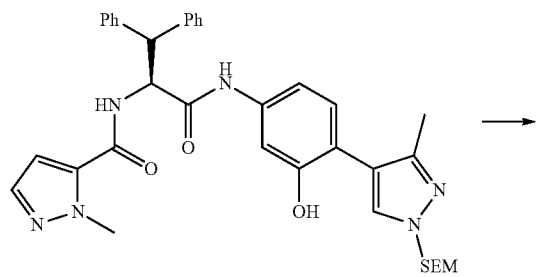

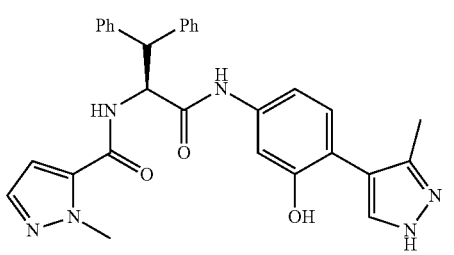

The compound of Preparation 271 was treated according to the method of Example 419 to give the title compound (16 mg, 42%). 1H NMR (300 MHz, DMSO-d6) δ 12.38 (s, 1H), 10.11 (s, 1H), 9.32 (s, 1H), 8.82 (d, J=8.7 Hz, 1H), 7.57-7.38 (m, 5H), 7.36 (d, J=2.0 Hz, 1H), 7.24 (q, J=7.8 Hz, 4H), 7.17-7.06 (m, 3H), 6.98 (d, J=8.3 Hz, 1H), 6.85 (dd, J=8.3, 2.0 Hz, 1H), 6.76 (d, J=2.1 Hz, 1H), 5.62 (dd, J=11.7, 8.7 Hz, 1H), 4.61 (d, J=11.7 Hz, 1H), 3.90 (s, 3H), 2.17 (s, 3H); LCMS (ES): m/z 521.231 [M+H]$^+$, RT=2.12 min.

Example 422

Cyclopropyl N-[(1S)-1-cyclohexyl-2-[3-hydroxy-4-(3-methylimidazol-4-yl)anilino]-2-oxo-ethyl]carbamate

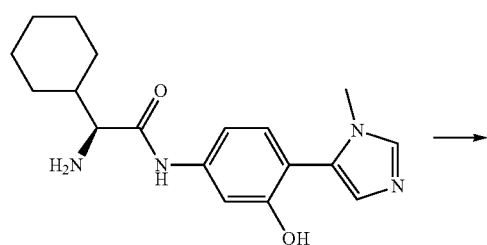

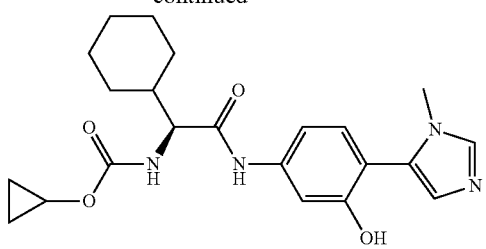

A mixture of cyclopropanol (2.3 mg, 0.040 mmol), bis(2,5-dioxopyrrolidin-1-yl) carbonate (10.3 mg, 0.040 mmol) and triethylamine (4.7 µL, 3.4 mg, 0.033 mmol) in acetonitrile (1 mL) was stirred at room temperature for 90 min. This was then added in portions (0.2 mL), 20 min between each addition, to a stirred solution of the amine of Preparation 251 (11 mg, 0.034 mmol) in DMF (1 mL). The crude mixture was purified by prep. acidic HPLC to give the title compound (6.1 mg, 44%). 1H NMR (300 MHz, DMSO-d6) δ 10.03 (s, 1H), 9.90 (s, 1H), 7.60 (s, 1H), 7.42 (d, J=1.6 Hz, 1H), 7.27 (d, J=8.6 Hz, 1H), 7.14-6.96 (m, 2H), 6.78 (s, 1H), 4.18-3.87 (m, 2H), 3.48 (s, 3H), 1.82-1.45 (m, 6H), 1.27-0.88 (m, 5H), 0.68-0.47 (m, 4H); LCMS (ES): m/z 413.219 [M+H]$^+$, RT=1.93 min.

Example 423

Cyclopropyl N-[(1S)-1-benzhydryl-2-[4-(3,5-dimethylimidazol-4-yl)anilino]-2-oxo-ethyl]carbamate

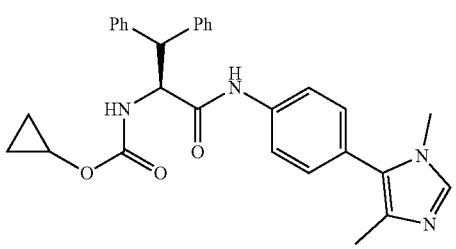 [SMILES: Cc1ncn(C)c1-c1ccc(NC(=O)[C@@H](NC(=O)OC2CC2)C(c2ccccc2)c2ccccc2)cc1]

Example 423 was prepared according to the method of Example 422 from the amine of Preparation 340. LCMS (ES): m/z 495.239 [M+H]$^+$, RT=2.08.

Examples 424 and 425

Examples 424 and 425 were synthesised according to the methods of Preparations 259-260, Example 422 and Example 1 starting from the aniline of Preparation 258 and using the appropriate Boc protected amino acid.

| Example No. | Structure | Name | Mass ion | LCMS retention time (min) |
|---|---|---|---|---|
| 424 | 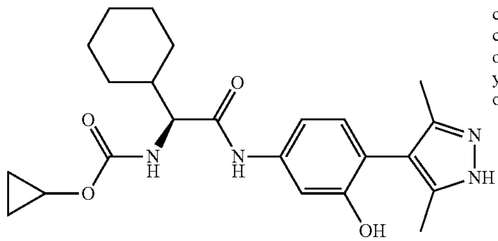 [SMILES: Cc1n[nH]c(C)c1-c1ccc(NC(=O)[C@@H](NC(=O)OC2CC2)C2CCCCC2)cc1O] | cyclopropyl N-[(1S)-1-cyclohexyl-2-[4-(3,5-dimethyl-1H-pyrazol-4-yl)-3-hydroxy-anilino]-2-oxo-ethyl]carbamate | 427.235 | 2.12 |
| 425 | 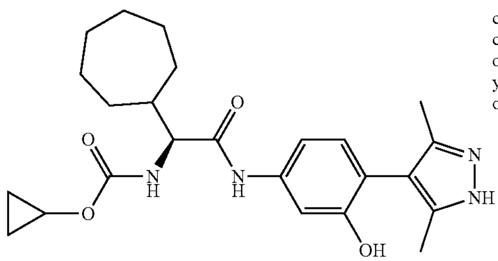 [SMILES: Cc1n[nH]c(C)c1-c1ccc(NC(=O)[C@@H](NC(=O)OC2CC2)C2CCCCCC2)cc1O] | cyclopropyl N-[(1S)-1-cycloheptyl-2-[4-(3,5-dimethyl-1H-pyrazol-4-yl)-3-hydroxy-anilino]-2-oxo-ethyl]carbamate | 441.250 | 2.16 |

Examples 426 and 427

Examples 426 and 427 were synthesised according to the methods of Preparations 3-4, Example 422 and Example 1 staring from the aniline of Preparation 2 and using the appropriate Boc protected amino acid.

| Example No. | Structure | Name | Mass ion | LCMS retention time (min) |
|---|---|---|---|---|
| 426 | 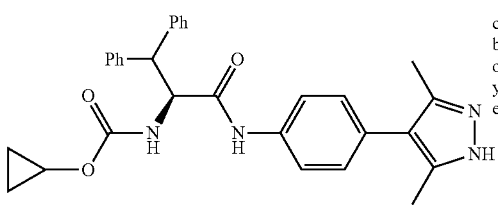 [SMILES: Cc1n[nH]c(C)c1-c1ccc(NC(=O)[C@@H](NC(=O)OC2CC2)C(c2ccccc2)c2ccccc2)cc1] | cyclopropyl N-[(1S)-1-benzhydryl-2-[4-(3,5-dimethyl-1H-pyrazol-4-yl)anilino]-2-oxo-ethyl]carbamate | 495.240 | 2.27 |
| 427 | 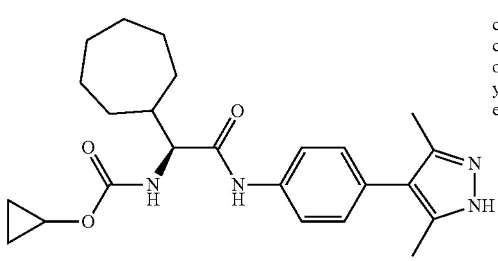 [SMILES: Cc1n[nH]c(C)c1-c1ccc(NC(=O)[C@@H](NC(=O)OC2CC2)C2CCCCCC2)cc1] | cyclopropyl N-[(1S)-1-cycloheptyl-2-[4-(3,5-dimethyl-1H-pyrazol-4-yl)anilino]-2-oxo-ethyl]carbamate | 425.255 | 2.30 |

Example 428

Cyclobutyl N-[(1S)-1-(dicyclopropylmethyl)-2-[4-(3,5-dimethyl-1H-pyrazol-4-yl)anilino]-2-oxo-ethyl]carbamate

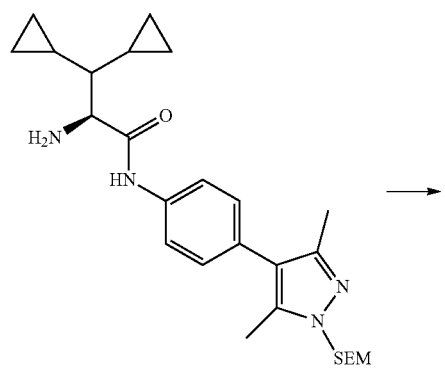

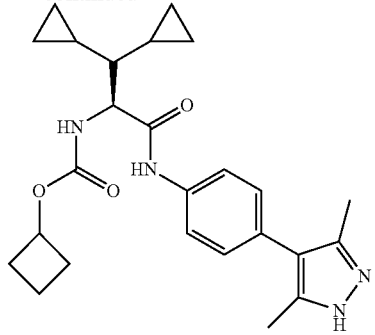

According to the method of Example 1 the compound of Preparation 374 was deprotected to give the title compound. 1H NMR (400 MHz, DMSO-d6) δ 9.70 (s, 1H), 7.60-7.28 (m, 2H), 7.09-6.99 (m, 2H), 6.94 (d, J=9.1 Hz, 1H), 4.66 (p, J=7.5 Hz, 1H), 4.13 (dd, J=9.1, 6.6 Hz, 1H), 2.11-2.02 (m, 2H), 2.00 (s, 6H), 1.87-1.72 (m, 2H), 1.62-1.46 (m, 1H), 1.44-1.28 (m, 1H), 0.75-0.64 (m, 1H), 0.63-0.51 (m, 1H), 0.46-0.35 (m, 1H), 0.33-–0.08 (m, 8H); LCMS (ES): m/z 437.255 [M+H]$^+$, RT=2.32 min.

Examples 429-431

Examples 429-431 were prepared according to the method of Example 1 starting from the indicated SEM protected intermediate.

| Example No. | Starting material | Structure | Name | Mass ion | LCMS retention time (min) |
|---|---|---|---|---|---|
| 429 | Prep. 371 | 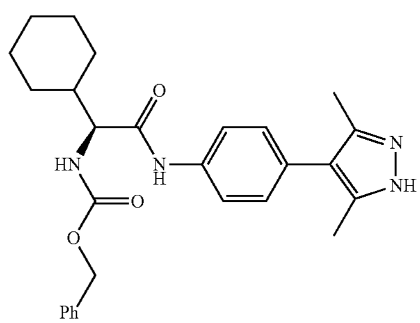 [SMILES: Cc1n[nH]c(C)c1-c1ccc(NC(=O)[C@@H](NC(=O)OCc2ccccc2)C2CCCCC2)cc1] | benzyl N-[(1S)-1-cyclohexyl-2-[4-(3,5-dimethyl-1H-pyrazol-4-yl)anilino]-2-oxo-ethyl]carbamate | 461.251 | 2.38 |
| 430 | Prep. 372 | 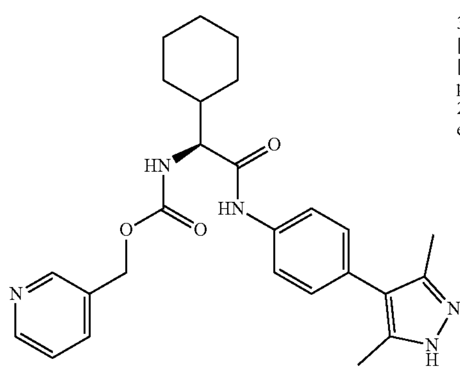 [SMILES: Cc1n[nH]c(C)c1-c1ccc(NC(=O)[C@@H](NC(=O)OCc2cccnc2)C2CCCCC2)cc1] | 3-pyridylmethyl N-[(1S)-1-cyclohexyl-2-[4-(3,5-dimethyl-1H-pyrazol-4-yl)anilino]-2-oxo-ethyl]carbamate | 462.251 | 2.01 |

| Example No. | Starting material | Structure | Name | Mass ion | LCMS retention time (min) |
|---|---|---|---|---|---|
| 43 | Prep. 373 | 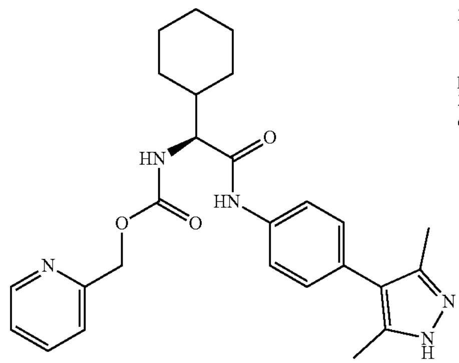 [SMILES: Cc1n[nH]c(C)c1-c1ccc(NC(=O)[C@@H](NC(=O)OCc2ccccn2)C2CCCCC2)cc1] | 2-pyridylmethyl N-[(1S)-1-cyclohexyl-2-[4-(3,5-dimethyl-1H-pyrazol-4-yl)anilino]-2-oxo-ethyl]carbamate | 462.251 | 2.11 |

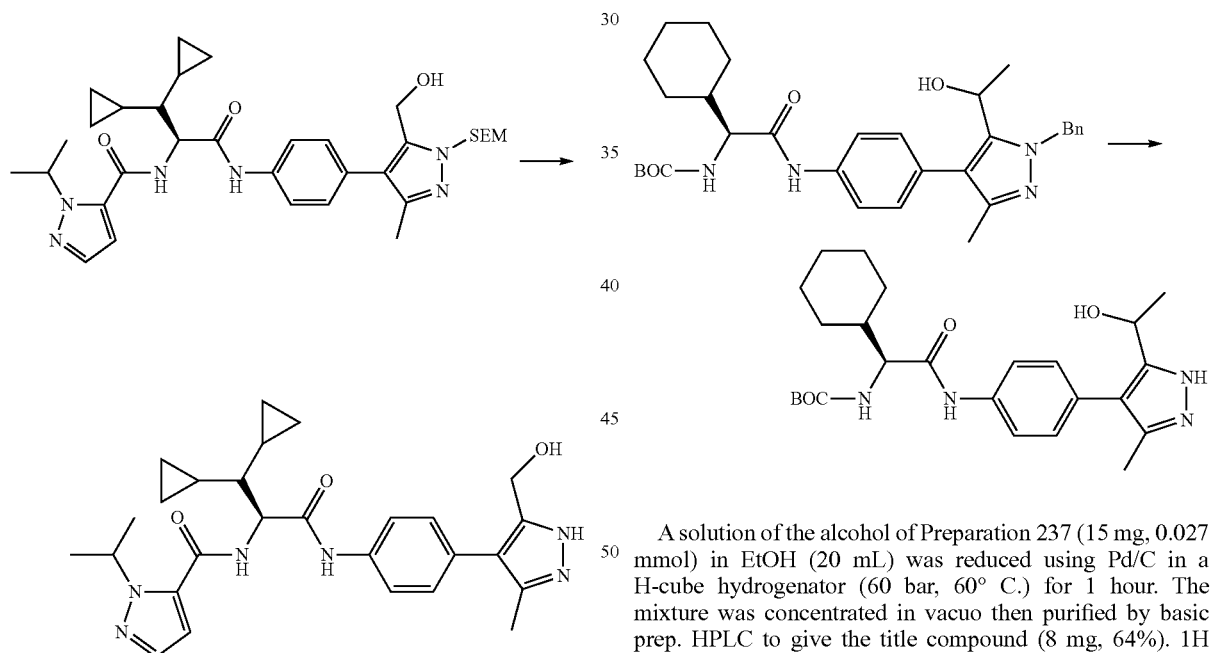

Example 432

N-[(1S)-1-(Dicyclopropylmethyl)-2-[4-[5-(hydroxymethyl)-3-methyl-1H-pyrazol-4-yl]anilino]-2-oxo-ethyl]-2-isopropyl-pyrazole-3-carboxamide The alcohol of Preparation 230 was deprotected according to the method of Example 1 to give the title compound (23 mg, 63%) after purification by basic prep. HPLC. 1H NMR (600 MHz, DMSO-d6) δ 12.45 (s, 1H), 10.18 (s, 1H), 8.43 (d, J=8.9 Hz, 1H), 7.67-7.60 (m, 2H), 7.50 (d, J=2.0 Hz, 1H), 7.44-7.28 (br m, 2H), 6.93 (d, J=2.0 Hz, 1H), 5.42 (hept, J=6.7 Hz, 1H), 5.20 and 4.93 (2×br s, 1H), 4.82 (t, J=8.3 Hz, 1H), 4.38 (br s, 2H), 2.23 (br s, 3H), 1.39 (d, J=6.6 Hz, 3H), 1.35 (d, J=6.6 Hz, 3H), 0.97-0.85 (m, 1H), 0.85-0.71 (m, 2H), 0.52-0.43 (m, 1H), 0.43-0.10 (m, 7H); LCMS (ES): m/z 491.276 [M+H]+, RT=2.19 min.

Example 433

Tert-butyl N-[(1S)-1-cyclohexyl-2-[4-[5-(1-hydroxyethyl)-3-methyl-1H-pyrazol-4-yl]anilino]-2-oxo-ethyl]carbamate A solution of the alcohol of Preparation 237 (15 mg, 0.027 mmol) in EtOH (20 mL) was reduced using Pd/C in a H-cube hydrogenator (60 bar, 60° C.) for 1 hour. The mixture was concentrated in vacuo then purified by basic prep. HPLC to give the title compound (8 mg, 64%). 1H NMR (600 MHz, DMSO-d6) δ 12.35 (s, 1H), 9.99 (s, 1H), 7.68-7.58 (m, 2H), 7.33-7.25 (m, 2H), 6.85 (d, J=8.6 Hz, 1H), 5.07 (s, 1H), 4.70 (q, J=6.5 Hz, 1H), 3.95 (t, J=8.3 Hz, 1H), 2.16 (s, 3H), 1.80-1.50 (m, 6H), 1.39 (s, 9H), 1.33 (d, J=6.6 Hz, 3H), 1.24-1.06 (m, 4H), 1.06-0.94 (m, 1H); LCMS (ES): m/z 457.282 [M+H]+, RT=2.27 min.

Examples 434-439

Examples 434-439 were synthesised by methods analogous to the synthesis of Example 433 starting from the alcohols of Preparation 231, 233 or 234, as required, and using the appropriate Boc protected amino acid.

| Example No. | Name | Mass ion | LCMS retention time (min) |
|---|---|---|---|
| 434 | tert-butyl N-[(1S)-1-benzhydryl-2-[4-[5-(1-hydroxyethyl)-3-methyl-1H-pyrazol-4-yl]anilino]-2-oxo-ethyl]carbamate | 541.282 | 2.31 |
| 435 | N-[(1S)-1-benzhydryl-2-[4-[5-(1-hydroxy-1-methyl-ethyl)-3-methyl-1H-pyrazol-4-yl]anilino]-2-oxo-ethyl]-2-methyl-pyrazole-3-carboxamide | 563.278 | 2.20 |
| 436 | tert-butyl N-[(1S)-1-cyclohexyl-2-[4-[5-(1-hydroxy-1-methyl-ethyl)-3-methyl-1H-pyrazol-4-yl]anilino]-2-oxo-ethyl]carbamate | 471.297 | 2.31 |
| 437 | tert-butyl N-[(1S)-1-benzhydryl-2-[4-[5-(hydroxymethyl)-3-methyl-1H-pyrazol-4-yl]anilino]-2-oxo-ethyl]carbamate | 527.266 | 2.29 |
| 438 | tert-butyl N-[(1S)-1-cyclohexyl-2-[4-[5-(hydroxymethyl)-3-methyl-1H-pyrazol-4-yl]anilino]-2-oxo-ethyl]carbamate | 443.266 | 2.23 |
| 439 | tert-butyl N-[(1S)-1-cycloheptyl-2-[4-[5-(hydroxymethyl)-3-methyl-1H-pyrazol-4-yl]anilino]-2-oxo-ethyl]carbamate | 457.281 | 2.31 |

Example 440

N-[(1S)-1-Cyclohexyl-2-[4-[5-(1-hydroxyethyl)-3-methyl-1H-pyrazol-4-yl]anilino]-2-oxo-ethyl]-2-methyl-pyrazole-3-carboxamide

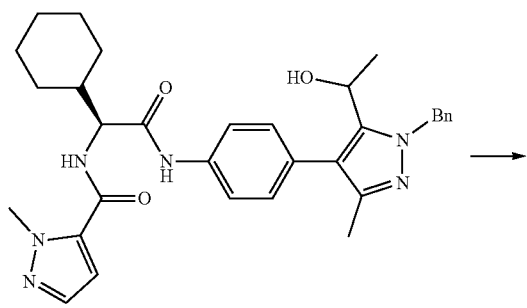

According to the method of Example 433 the compound of Preparation 239 was deprotected to give the title compound (11 mg, 58%). 1H NMR (600 MHz, DMSO-d6) δ 12.35 (br s, 1H), 10.23 (s, 1H), 8.50 (d, J=8.2 Hz, 1H), 7.71-7.61 (m, 2H), 7.46 (d, J=2.1 Hz, 1H), 7.35-7.28 (m, 2H), 7.07 (d, J=2.1 Hz, 1H), 5.08 (br s, 1H), 4.71 (q, J=6.6 Hz, 1H), 4.42 (t, J=8.6 Hz, 1H), 4.04 (s, 3H), 2.16 (s, 3H), 1.97-1.80 (m, 2H), 1.80-1.68 (m, 2H), 1.68-1.56 (m, 2H), 1.33 (d, J=6.6 Hz, 3H), 1.28-1.09 (m, 4H), 1.10-0.95 (m, 1H); LCMS (ES): m/z 465.262 [M+H]$^+$, RT=2.06 min.

Examples 441-447

Examples 441-447 were synthesised by methods analogous to the synthesis of Example 440 starting from the alcohols of Preparation 231, 233 or 234, using the appropriate Boc protected amino acid and the appropriate acid.

| Example No. | Structure | Name | Mass ion | LCMS retention time (min) |
|---|---|---|---|---|
| 441 | 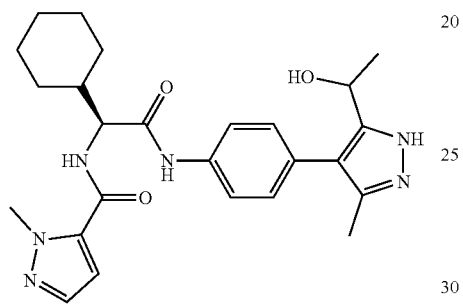 | N-[(1S)-1-cyclohexyl-2-[4-[5-(1-hydroxyethyl)-3-methyl-1H-pyrazol-4-yl]anilino]-2-oxo-ethyl]-1-fluoro-cyclopropanecarboxamide | 443.246 | 2.16 |
| 442 | 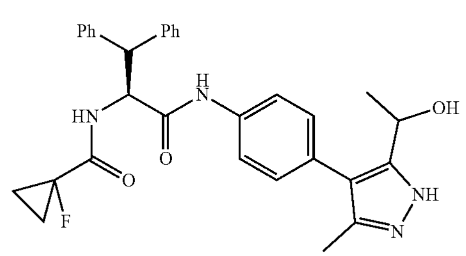 [SMILES: Cc1n[nH]c(C(C)O)c1-c1ccc(NC(=O)[C@@H](NC(=O)C2(F)CC2)C(c2ccccc2)c2ccccc2)cc1] | N-[(1S)-1-benzhydryl-2-[4-[5-(1-hydroxyethyl)-3-methyl-1H-pyrazol-4-yl]anilino]-2-oxo-ethyl]-1-fluoro-cyclopropanecarboxamide | 527.247 | 2.21 |

-continued

| Example No. | Structure | Name | Mass ion | LCMS retention time (min) |
|---|---|---|---|---|
| 443 | 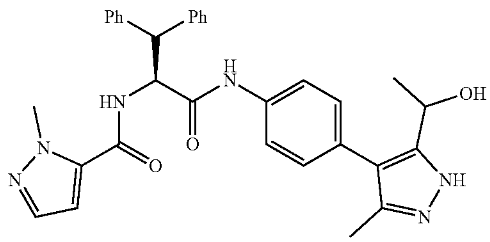 [SMILES: Cc1n[nH]c(C(C)O)c1-c1ccc(NC(=O)[C@@H](NC(=O)c2ccnn2C)C(c2ccccc2)c2ccccc2)cc1] | N-[(1S)-1-benzhydryl-2-[4-[5-(1-hydroxyethyl)-3-methyl-1H-pyrazol-4-yl]anilino]-2-oxo-ethyl]-2-methyl-pyrazole-3-carboxamide | 549.262 | 2.13 |
| 444 | 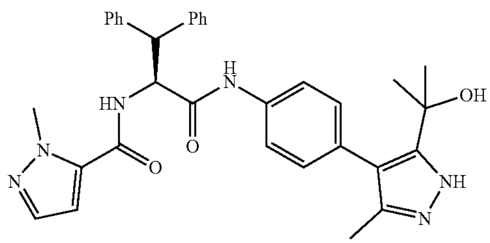 | N-[(1S)-1-benzhydryl-2-[4-[5-(1-hydroxy-1-methyl-ethyl)-3-methyl-1H-pyrazol-4-yl]anilino]-2-oxo-ethyl]-2-methyl-pyrazole-3-carboxamide | 563.278 | 2.20 |
| 445 | 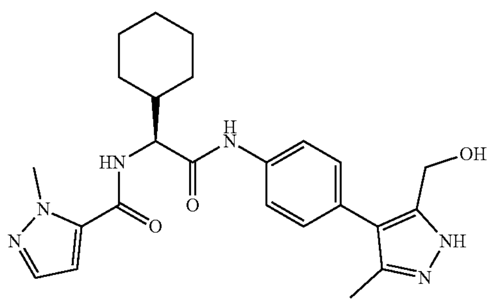 [SMILES: Cc1n[nH]c(CO)c1-c1ccc(NC(=O)[C@@H](NC(=O)c2ccnn2C)C2CCCCC2)cc1] | N-[(1S)-1-cyclohexyl-2-[4-[5-(hydroxymethyl)-3-methyl-1H-pyrazol-4-yl]anilino]-2-oxo-ethyl]-2-methyl-pyrazole-3-carboxamide | 451.245 | 2.04 |
| 446 | 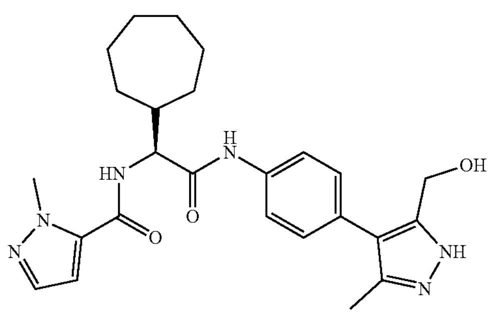 [SMILES: Cc1n[nH]c(CO)c1-c1ccc(NC(=O)[C@@H](NC(=O)c2ccnn2C)C2CCCCCC2)cc1] | N-[(1S)-1-cycloheptyl-2-[4-[5-(hydroxymethyl)-3-methyl-1H-pyrazol-4-yl]anilino]-2-oxo-ethyl]-2-methyl-pyrazole-3-carboxamide | 465.261 | 2.12 |
| 447 | 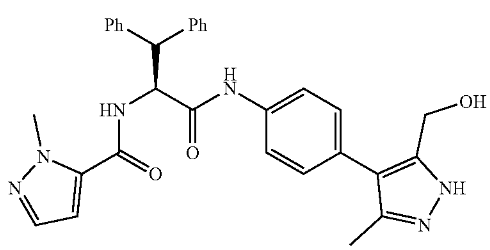 | N-[(1S)-1-benzhydryl-2-[4-[5-(hydroxymethyl)-3-methyl-1H-pyrazol-4-yl]anilino]-2-oxo-ethyl]-2-methyl-pyrazole-3-carboxamide | 535.246 | 2.11 |

Example 448

N-[(1S)-1-(Dicyclopropylmethyl)-2-[4-[5-(1-hydroxy-1-methyl-ethyl)-3-methyl-imidazol-4-yl]anilino]-2-oxo-ethyl]-2-isopropyl-pyrazole-3-carboxamide

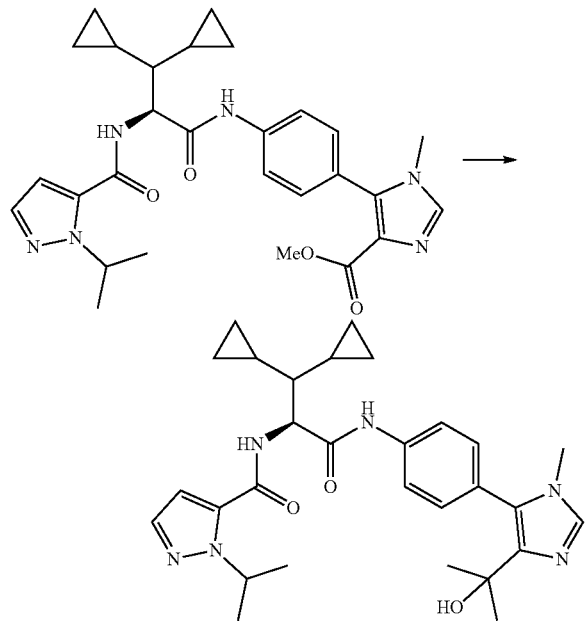

To a stirred solution of the ester of Preparation 332 (100 mg, 0.19 mmol) in THF (2 mL), methyl magnesium bromide (0.4 mL, 1.35 mmol, 3M in Di ethyl ether) was added at 0° C. The reaction mixture was stirred at room temperature for 16 h. The reaction mixture was quenched with sat. aq. NH₄Cl solution (30 mL). The aqueous layer was extracted with EtOAc (2×20 mL). The combined organic layer was dried over anhydrous Na₂SO₄ and concentrated under reduced pressure. The obtained crude residue was purified by prep. HPLC to afford the title compound as an off-white solid (9 mg, 9%). $^1$H NMR (400 MHz, DMSO-d$_6$) δ 10.33 (s, 1H), 8.51 (br d, J=8.82 Hz, 1H), 7.66 (d, J=8.58 Hz, 2H), 7.53 (s, 1H), 7.50 (d, J=1.91 Hz, 1H), 7.33 (d, J=8.58 Hz, 2H), 6.94 (d, J=1.91 Hz, 1H), 5.28-5.58 (m, 1H), 4.81 (br t, J=8.17 Hz, 1H), 4.37 (br s, 1H), 3.31 (s, 3H), 1.39 (d, J=6.56 Hz, 3H), 1.35 (d, J=6.68 Hz, 3H), 1.28 (s, 6H), 0.74-0.95 (m, 3H), 0.11-0.51 (m, 8H); LCMS (ES): m/z 519.308 [M+H]⁺, RT=2.06 min.; Chiral HPLC: Column: CHIRALCEL OD-3 (4.6*150 mm) 3 um Co-Solvent: 0.5% of DEA in MeOH (15%), Column Temperature: 30° C., Flow: 3 g/min, RT: 2.63 (95%).

Example 449

N-[(1S)-2-[4-(3-Amino-5-methyl-1H-pyrazol-4-yl)anilino]-1-cyclohexyl-2-oxo-ethyl]-2-methyl-pyrazole-3-carboxamide

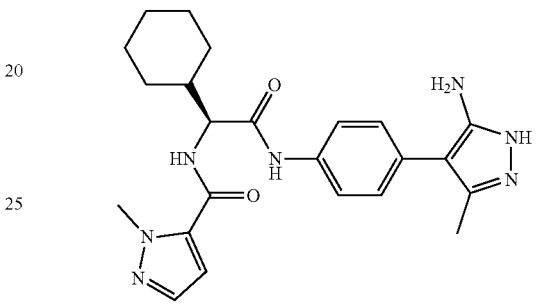

According to the methods of Preparations 3, 4 and 5 and Example 1 the aniline of Preparation 241 was converted to the title compound (23 mg). 1H NMR (300 MHz, DMSO-d6) δ 11.30 (s, 1H), 10.16 (s, 1H), 8.47 (d, J=8.2 Hz, 1H), 7.82-7.57 (m, 2H), 7.46 (d, J=2.1 Hz, 1H), 7.38-7.16 (m, 2H), 7.06 (d, J=2.1 Hz, 1H), 4.49-4.28 (m, 3H), 4.03 (s, 3H), 2.14 (s, 3H), 1.97-1.52 (m, 6H), 1.30-0.93 (m, 5H); LCMS (ES): m/z 436.246 [M+H]⁺, RT=1.97 min.

Examples 450-453

Examples 450-453 were synthesised by methods analogous to the synthesis of Example 449 starting from the aminopyrazoles of Preparation 241, 243 or 244, using the appropriate Boc protected amino acid and the appropriate pyrazole acid.

| Example No. | Structure | Name | Mass ion | LCMS retention time (min) |
|---|---|---|---|---|
| 450 | ![structure] | N-[(1S)-2-[4-(5-amino-3-methyl-1H-pyrazol-4-yl)anilino]-1-cycloheptyl-2-oxo-ethyl]-2-methyl-pyrazole-3-carboxamide | 450.262 | 2.05 |

-continued

| Example No. | Structure | Name | Mass ion | LCMS retention time (min) |
|---|---|---|---|---|
| 451 | 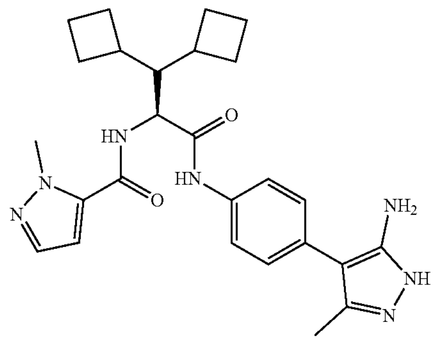 [SMILES: Cc1n[nH]c(N)c1-c1ccc(NC(=O)[C@@H](NC(=O)c2ccnn2C)C(C2CCC2)C2CCC2)cc1] | N-[(1S)-1-[[4-(3-amino-5-methyl-1H-pyrazol-4-yl)phenyl]carbamoyl]-2,2-di(cyclobutyl)ethyl]-2-methyl-pyrazole-3-carboxamide | 476.280 | 2.18 |
| 452 | 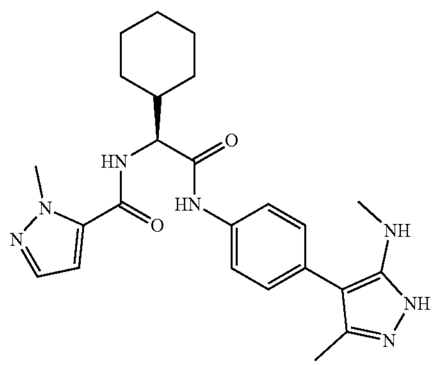 | N-[(1S)-1-cyclohexyl-2-[4-[5-methyl-3-(methylamino)-1H-pyrazol-4-yl]anilino]-2-oxo-ethyl]-2-methyl-pyrazole-3-carboxamide | 450.261 | 2.00 |
| 453 | 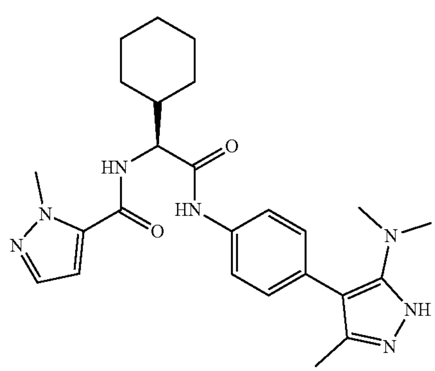 [SMILES: Cc1n[nH]c(N(C)C)c1-c1ccc(NC(=O)[C@@H](NC(=O)c2ccnn2C)C2CCCCC2)cc1] | N-[(1S)-1-cyclohexyl-2-[4-[3-(dimethylamino)-5-methyl-1H-pyrazol-4-yl]anilino]-2-oxo-ethyl]-2-methyl-pyrazole-3-carboxamide | 464.278 | 2.11 |

Example 454

Tert-butyl N-[(1S)-1-[(2-chlorophenyl)methyl]-2-[4-[4-(hydroxymethyl)triazol-1-yl]anilino]-2-oxo-ethyl] carbamate

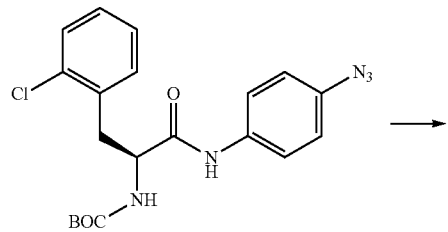

A mixture of the azide of Preparation 246 (20 mg, 0.048 mmol), propargyl alcohol (13 mg, 0.24 mmol) and CuI (2 mg, 0.01 mmol) in DMSO (0.5 mL) was heated at 95° C. for 1 hour. The mixture was filtered through silica gel (eluent: ethyl acetate) then purified by prep. reverse phase HPLC to give the title compound (15 mg, 66%). 1H NMR (600 MHz, DMSO-d6) δ 10.18 (s, 1H), 8.59 (s, 1H), 7.87-7.81 (m, 2H), 7.79-7.74 (m, 2H), 7.46-7.40 (m, 1H), 7.38-7.34 (m, 1H), 7.29-7.19 (m, 3H), 5.31 (s, 1H), 4.61 (s, 2H), 4.50-4.42 (m, 1H), 3.16 (dd, J=14.1, 6.0 Hz, 1H), 3.03 (dd, J=14.1, 8.9 Hz, 1H), 1.33 (s, 9H); LCMS (ES): m/z 472.173 [M+H]$^+$, RT=2.24 min.

Examples 455 and 456

Examples 455 and 456 were synthesised according to the method of Example 454 starting from the azide of Preparation 246 and using the appropriate alkyne.

| Example No. | Structure | Name | Mass ion | LCMS retention time (min) |
|---|---|---|---|---|
| 455 | 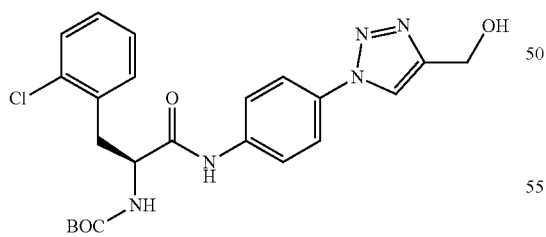 | tert-butyl N-[(1S)-1-[(2-chlorophenyl)methyl]-2-[4-[4-(2-hydroxyethyl)triazol-1-yl]anilino]-2-oxo-ethyl]carbamate | 486.196 | 2.25 |
| 456 | 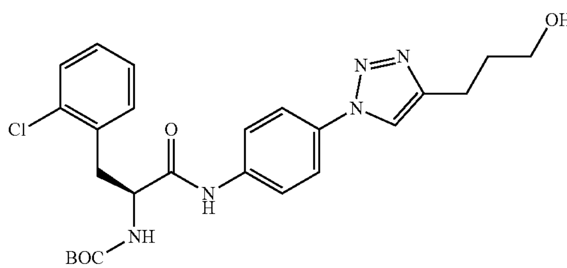 [SMILES: CC(C)(C)OC(=O)N[C@@H](Cc1ccccc1Cl)C(=O)Nc1ccc(-n2cc(CCCO)nn2)cc1] | tert-butyl N-[(1S)-1-[(2-chlorophenyl)methyl]-2-[4-[4-(3-hydroxypropyl)triazol-1-yl]anilino]-2-oxo-ethyl]carbamate | 500.209 | 2.17 |

Example 457

Tert-butyl N-[(1S)-1-[(2-chlorophenyl)methyl]-2-[4-[5-(2-hydroxyethyl)triazol-1-yl]anilino]-2-oxo-ethyl] carbamate

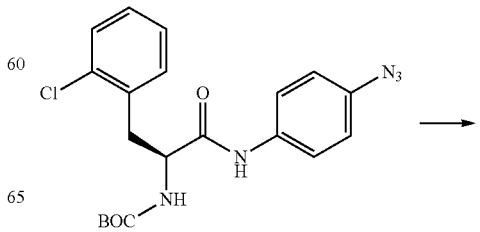

-continued

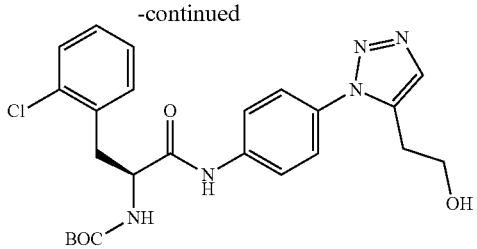

A mixture of the azide of Preparation 246 (20 mg, 0.048 mmol), but-3-yn-1-ol (17 mg, 0.24 mmol) and chlororuthenium;(1Z,5Z)-cycloocta-1,5-diene;1,2,3,4,5-pentamethyl-cyclopentane (8 mg, 0.01 mmol) in DMF (0.5 mL) was heated at 95° C. for 3 hours. The mixture was filtered through silica gel (eluent: ethyl acetate) then purified by prep, reverse phase HPLC to give the title compound (9 mg, 39%). 1H NMR (600 MHz, DMSO-d6) δ 10.24 (s, 1H), 7.82-7.77 (m, 2H), 7.73 (s, 1H), 7.53-7.47 (m, 2H), 7.46-7.40 (m, 1H), 7.39-7.35 (m, 1H), 7.29-7.21 (m, 3H), 4.83 (s, 1H), 4.55-4.38 (m, 1H), 3.65-3.52 (m, 2H), 3.16 (dd, J=14.2, 6.0 Hz, 1H), 3.04 (dd, J=14.2, 8.8 Hz, 1H), 2.79 (t, J=6.6 Hz, 2H), 1.34 (s, 9H); LCMS (ES): m/z 485.183 [M+H]$^+$, RT=2.23 min.

Example 458

Tert-butyl N-[(1S)-1-[(2-chlorophenyl)methyl]-2-[4-(5-isopentyltriazol-1-yl)anilino]-2-oxo-ethyl]carbamate

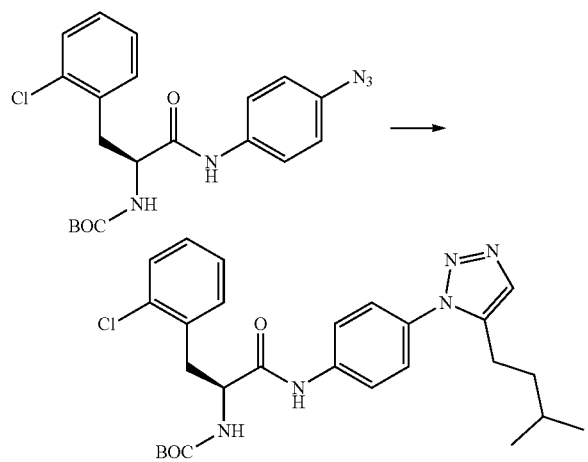

The title compound (7 mg, 28%) was prepared from the azide of Preparation 246 and 5-methylhex-1-yne according to the method of Example 457. LCMS (ES): m/z 512.243 [M+H]$^+$, RT=2.66 min.

Example 459

(2S)-2-cyclohexyl-N-[4-(3,5-dimethyl-1H-pyrazol-4-yl)phenyl]-2-[[3-hydroxypropyl(methyl)carbamoyl]amino]acetamide

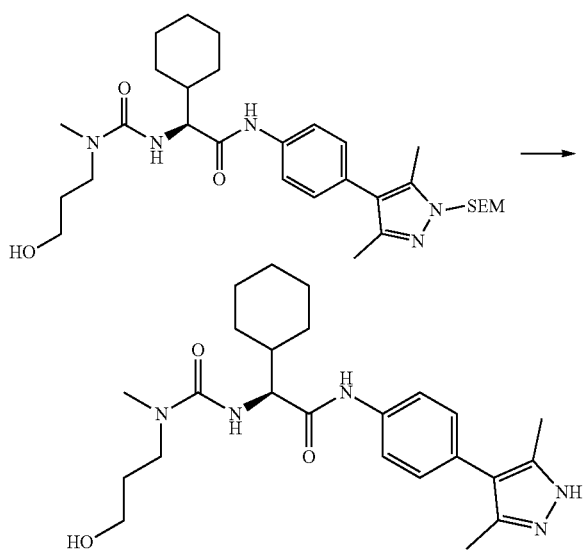

The compound of Preparation 221 was treated according to the method of Example 1 to give the title compound (10.9 mg, 10%) as an off white solid. $^1$H NMR (400 MHz, DMSO-d$_6$) δ 12.2 (br s, 1H), 10.01 (br s, 1H), 7.65-7.62 (d, J=8.8 Hz, 2H), 7.20-7.18 (d, J=8 Hz, 2H), 6.08-6.06 (d, J=8 Hz, 1H), 4.61-4.59 (t, J=6.8 Hz, 1H), 4.13-4.09 (t, J=8.4 Hz 1H), 3.42-3.40 (t, J=4 Hz 2H), 3.38-3.27 (m, 2H), 2.81 (s, 3H), 2.16 (s, 6H), 1.82-158 (m, 9H), 1.23-0.99 (m, 4H); LCMS (ES): m/z 442.281 [M+H]$^+$, RT=2.05 min.

Examples 460-478

Examples 460-478 were synthesised according to the methods of Preparation 220 and 221 and Example 459 starting from the compound of Preparation 4 using the appropriate amine.

| Example No. | Structure | Name | Mass ion | LCMS retention time (min) |
|---|---|---|---|---|
| 460 | ![structure] | Diastereomer 1 of N-[(1S)-1-cyclohexyl-2-[4-(3,5-dimethyl-1H-pyrazol-4-yl)anilino]-2-oxo-ethyl]-2-(3-hydroxypropyl)piperidine-1-carboxamide* | 496.328 | 2.20 |

-continued

| Example No. | Structure | Name | Mass ion | LCMS retention time (min) |
|---|---|---|---|---|
| 461 | 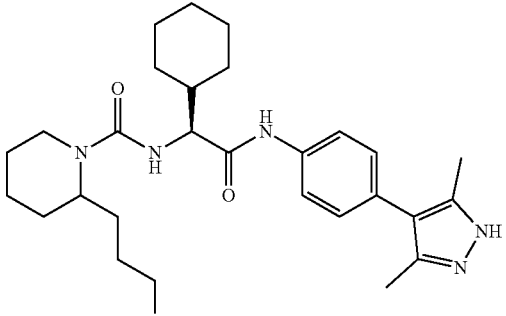 | Diastereomer 2 of N-[(1S)-1-cyclohexyl-2-[4-(3,5-dimethyl-1H-pyrazol-4-yl)anilino]-2-oxo-ethyl]-2-(3-hydroxypropyl)piperidine-1-carboxamide* | 496.329 | 2.18 |
| 462 | 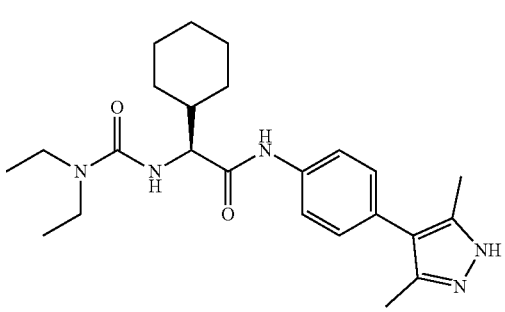 [SMILES: CCN(CC)C(=O)N[C@H](C(=O)Nc1ccc(-c2c(C)n[nH]c2C)cc1)C1CCCCC1] | (2S)-2-cyclohexyl-2-(diethylcarbamoylamino)-N-[4-(3,5-dimethyl-1H-pyrazol-4-yl)phenyl]acetamide | 426.287 | 2.28 |
| 463 | 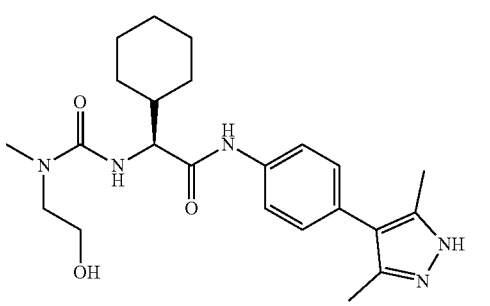 [SMILES: Cc1n[nH]c(C)c1-c1ccc(NC(=O)[C@@H](NC(=O)N(C)CCO)C2CCCCC2)cc1] | (2S)-2-cyclohexyl-N-[4-(3,5-dimethyl-1H-pyrazol-4-yl)phenyl]-2-[[2-hydroxyethyl(methyl)carbamoyl]amino]acetamide | 428.266 | 2.01 |
| 464 | 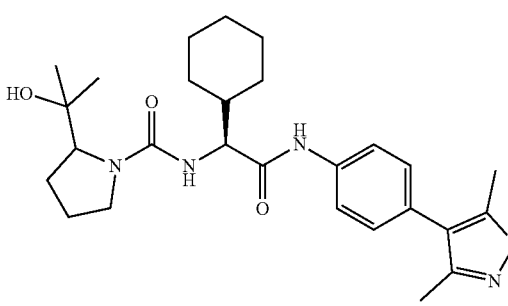 | Diastereomer 1 of N-[(1S)-1-cyclohexyl-2-[4-(3,5-dimethyl-1H-pyrazol-4-yl)anilino]-2-oxo-ethyl]-2-(1-hydroxy-1-methyl-ethyl)pyrrolidine-1-carboxamide* | 482.313 | 2.22 |
| 465 | 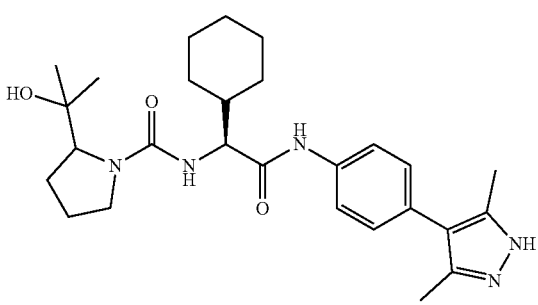 [SMILES: Cc1n[nH]c(C)c1-c1ccc(NC(=O)[C@@H](NC(=O)N2CCCC2C(C)(C)O)C2CCCCC2)cc1] | Diastereomer 2 of N-[(1S)-1-cyclohexyl-2-[4-(3,5-dimethyl-1H-pyrazol-4-yl)anilino]-2-oxo-ethyl]-2-(1-hydroxy-1-methyl-ethyl)pyrrolidine-1-carboxamide* | 482.313 | 2.25 |

-continued

| Example No. | Structure | Name | Mass ion | LCMS retention time (min) |
|---|---|---|---|---|
| 466 | 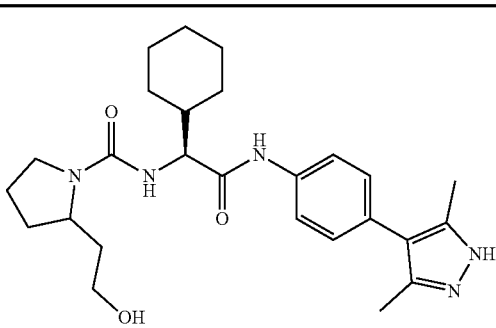 | Diastereomer 1 of N-[(1S)-1-cyclohexyl-2-[4-(3,5-dimethyl-1H-pyrazol-4-yl)anilino]-2-oxo-ethyl]-2-(2-hydroxyethyl)pyrrolidine-1-carboxamide* | 468.298 | 2.15 |
| 467 | 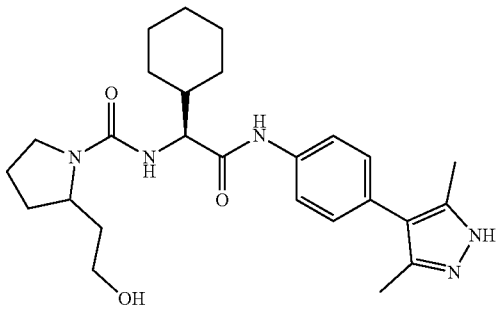 [SMILES: Cc1n[nH]c(C)c1-c1ccc(NC(=O)[C@@H](NC(=O)N2CCCC2CCO)C2CCCCC2)cc1] | Diastereomer 2 of N-[(1S)-1-cyclohexyl-2-[4-(3,5-dimethyl-1H-pyrazol-4-yl)anilino]-2-oxo-ethyl]-2-(2-hydroxyethyl)pyrrolidine-1-carboxamide* | 468.298 | 2.14 |
| 468 | 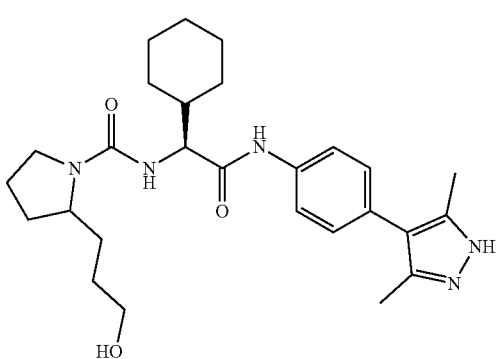 [SMILES: Cc1n[nH]c(C)c1-c1ccc(NC(=O)[C@@H](NC(=O)N2CCCC2CCCO)C2CCCCC2)cc1] | N-[(1S)-1-cyclohexyl-2-[4-(3,5-dimethyl-1H-pyrazol-4-yl)anilino]-2-oxo-ethyl]-2-(3-hydroxypropyl)-pyrrolidine-1-carboxamide | 482.313 | 2.14 |
| 469 | 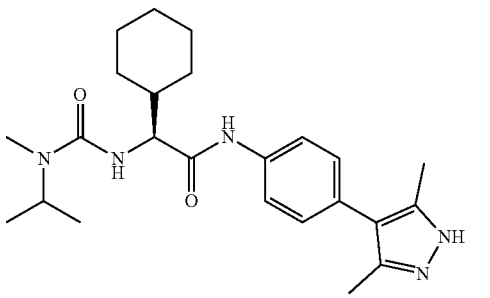 [SMILES: Cc1n[nH]c(C)c1-c1ccc(NC(=O)[C@@H](NC(=O)N(C)C(C)C)C2CCCCC2)cc1] | (2S)-2-cyclohexyl-N-[4-(3,5-dimethyl-1H-pyrazol-4-yl)phenyl]-2-[[isopropyl(methyl)carbamoyl]amino]acetamide | 426.286 | 2.26 |

-continued

| Example No. | Structure | Name | Mass ion | LCMS retention time (min) |
|---|---|---|---|---|
| 470 | 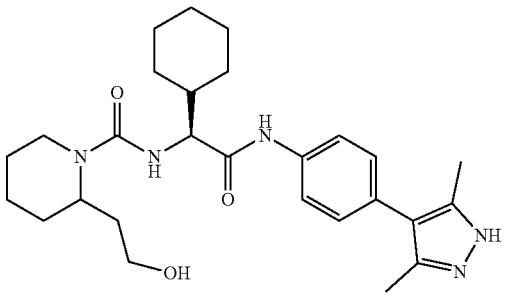 [SMILES: Cc1n[nH]c(C)c1-c1ccc(NC(=O)[C@@H](NC(=O)N2CCCCC2CCO)C2CCCCC2)cc1] | Diastereomer 1 of N-[(1S)-1-cyclohexyl-2-[4-(3,5-dimethyl-1H-pyrazol-4-yl)anilino]-2-oxo-ethyl]-2-(2-hydroxyethyl)piperidine-1-carboxamide* | 482.313 | 2.23 |
| 471 | 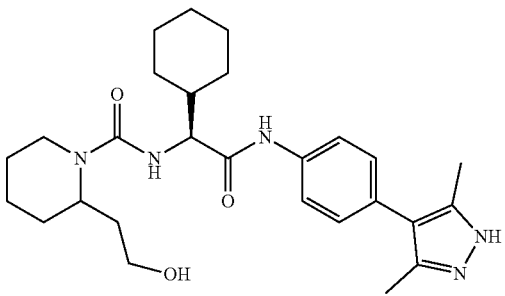 [SMILES: Cc1n[nH]c(C)c1-c1ccc(NC(=O)[C@@H](NC(=O)N2CCCCC2CCO)C2CCCCC2)cc1] | Diastereomer 2 of N-[(1S)-1-cyclohexyl-2-[4-(3,5-dimethyl-1H-pyrazol-4-yl)anilino]-2-oxo-ethyl]-2-(2-hydroxyethyl)piperidine-1-carboxamide* | 482.313 | 2.20 |
| 472 | 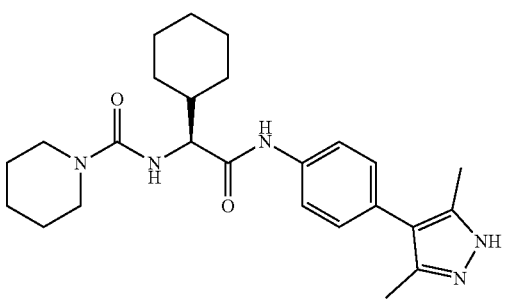 [SMILES: Cc1n[nH]c(C)c1-c1ccc(NC(=O)[C@@H](NC(=O)N2CCCCC2)C2CCCCC2)cc1] | N-[(1S)-1-cyclohexyl-2-[4-(3,5-dimethyl-1H-pyrazol-4-yl)anilino]-2-oxo-ethyl]piperidine-1-carboxamide | 438.287 | 2.30 |
| 473 | 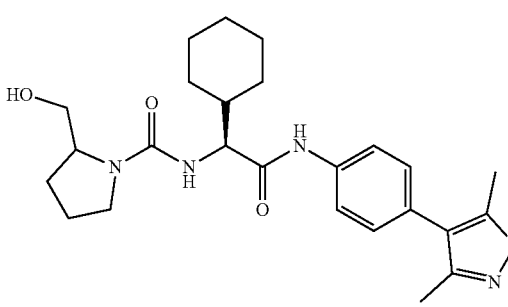 | Diastereomer 1 of N-[(1S)-1-cyclohexyl-2-[4-(3,5-dimethyl-1H-pyrazol-4-yl)anilino]-2-oxo-ethyl]-2-(hydroxymethyl)pyrrolidine-1-carboxamide* | 454.282 | 2.13 |
| 474 | 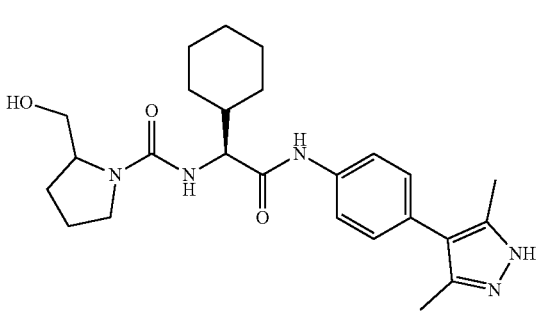 [SMILES: Cc1n[nH]c(C)c1-c1ccc(NC(=O)[C@@H](NC(=O)N2CCCC2CO)C2CCCCC2)cc1] | Diastereomer 2 of N-[(1S)-1-cyclohexyl-2-[4-(3,5-dimethyl-1H-pyrazol-4-yl)anilino]-2-oxo-ethyl]-2-(hydroxymethyl)pyrrolidine-1-carboxamide* | 454.282 | 2.09 |

-continued

| Example No. | Structure | Name | Mass ion | LCMS retention time (min) |
|---|---|---|---|---|
| 475 | 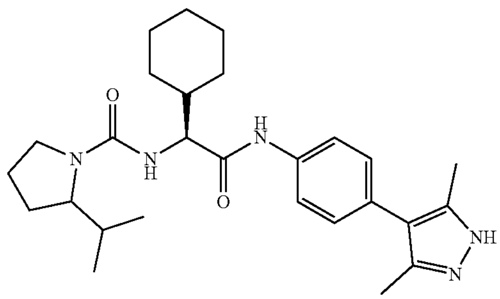 [SMILES: Cc1n[nH]c(C)c1-c1ccc(NC(=O)[C@@H](NC(=O)N2CCCC2C(C)C)C2CCCCC2)cc1] | N-[(1S)-1-cyclohexyl-2-[4-(3,5-dimethyl-1H-pyrazol-4-yl)anilino]-2-oxo-ethyl]-2-isopropyl-pyrrolidine-1-carboxamide | 466.318 | 2.44 |
| 476 | 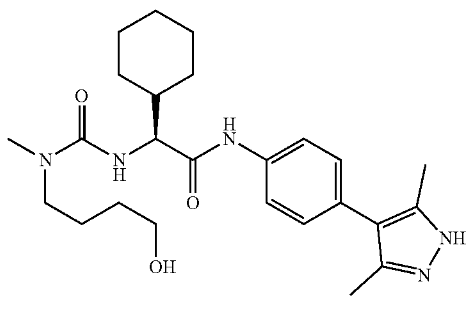 [SMILES: Cc1n[nH]c(C)c1-c1ccc(NC(=O)[C@@H](NC(=O)N(C)CCCCO)C2CCCCC2)cc1] | (2S)-2-cyclohexyl-N-[4-(3,5-dimethyl-1H-pyrazol-4-yl)phenyl]-2-[[4-hydroxybutyl(methyl)carbamoyl]amino]acetamide | 456.297 | 2.06 |
| 477 | 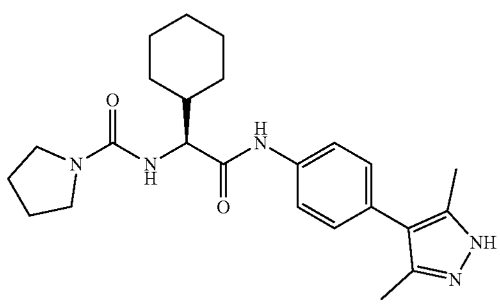 [SMILES: Cc1n[nH]c(C)c1-c1ccc(NC(=O)[C@@H](NC(=O)N2CCCC2)C2CCCCC2)cc1] | N-[(1S)-1-cyclohexyl-2-[4-(3,5-dimethyl-1H-pyrazol-4-yl)anilino]-2-oxo-ethyl]pyrrolidine-1-carboxamide | 424.271 | 2.20 |
| 478 | 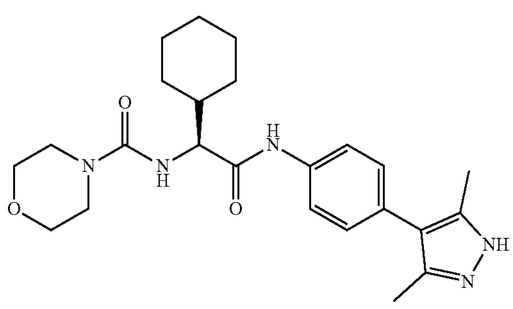 [SMILES: Cc1n[nH]c(C)c1-c1ccc(NC(=O)[C@@H](NC(=O)N2CCOCC2)C2CCCCC2)cc1] | N-[(1S)-1-cyclohexyl-2-[4-(3,5-dimethyl-1H-pyrazol-4-yl)anilino]-2-oxo-ethyl]morpholine-4-carboxamide | 440.266 | 2.09 |

*Racemic amine was used and the diastereomers were separated by chiral SFC

Example 479

4-hydroxy butyl N-[(1S)-1-(dicyclopropylmethyl)-2-[4-(3,5-dimethyl-1H-pyrazol-4-yl)anilino]-2-oxo-ethyl]carbamate

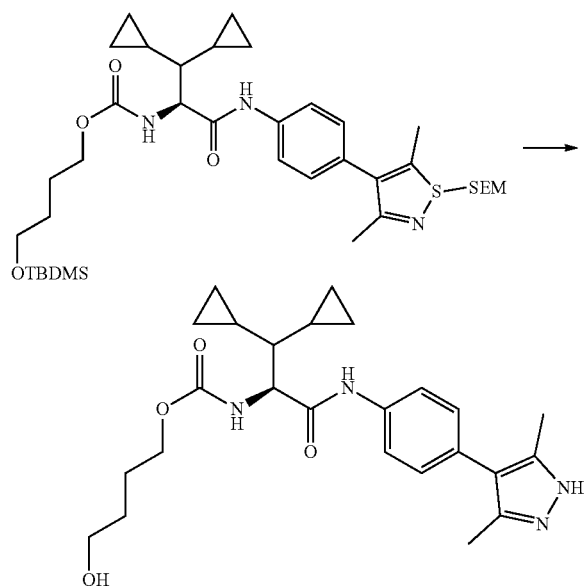

The compound of Preparation 377 (50 mg) was dissolved in DCM (0.5 mL). TFA (0.2 mL) was added at 0° C. The resulting reaction mixture was stirred at room temperature for 16 h. The reaction mixture was concentrated in vacuo to get the residue. This was diluted with cold water (10 mL) and pH adjusted to neutral with saturated aq. sodium hydrogen carbonate solution. This mixture was extracted with EtOAc (20 mL). The organic layer was dried over anhydrous sodium sulfate, filtered and concentrated in vacuo to get the residue. This residue was dissolved in a mixture of THF and water (2 mL, 1:1) and lithium hydroxide monohydrate (6 mg, 0.143 mmol) was added. The resulting reaction mixture was stirred at room temperature for 1 h then concentrated in vacuo to get the residue. This was diluted with cold water (10 mL) and pH adjusted to 4 with saturated aq. citric acid solution. The mixture was extracted with EtOAc (20 mL) and the organic layer was dried over anhydrous sodium sulfate, filtered, concentrated in vacuo to get the residue. This residue was purified by prep. HPLC to give the title compound (9 mg, 18% over 3 steps) as a white solid. 1H NMR (400 MHz, DMSO-d6) δ ppm: 12.2 (br s, 1H), 9.94 (s, 1H), 7.61 (d, J=8.4 Hz, 2H), 7.25 (d, J=8.8 Hz, 3H), 4.42 (t, J=5.2 Hz, 1H), 4.34 (m, 1H), 4.99-4.95 (t, J=6.8 Hz, 2H), 3.40 (m, 2H), 2.17 (s, 6H), 1.61-1.59 (m, 2H), 1.48-1.45 (m, 2H), 0.9 (m, 1H), 0.85 (m, 1H), 0.6 (m, 1H), 0.5-0.1 (m, 8H); LCMS (ES): m/z 455.265 [M+H]$^+$, RT=2.05 min. Chiral HPLC: Column: (R,R)WHELK-01 (4.6*150 mm) 3.5 um Co-Solvent: 0.5% of DEA in Methanol (40%), Column Temperature: 30° C., Flow: 3 g/min, RT: 1.28 (99%).

Examples 480 and 481

Examples 480 and 481 were synthesised by the same methods as Example 479 starting from the compound of Preparation 59 using the appropriate alcohol.

| Example No. | Structure | Name | Mass ion | LCMS retention time (min) |
|---|---|---|---|---|
| 480 | 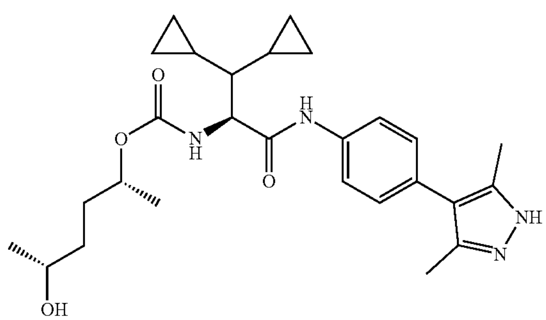 [SMILES: Cc1n[nH]c(C)c1-c1ccc(NC(=O)[C@@H](NC(=O)O[C@H](C)CC[C@@H](C)O)C(C2CC2)C2CC2)cc1] | [(1R,4R)-4-hydroxy-1-methyl-pentyl] N-[(1S)-1-(dicyclopropylmethyl)-2-[4-(3,5-dimethyl-1H-pyrazol-4-yl)anilino]-2-oxo-ethyl]carbamate | 480 | 4.45 ACQUITY BEH C18 column, 0.05% formic acid in water with MeCN |
| 481 | 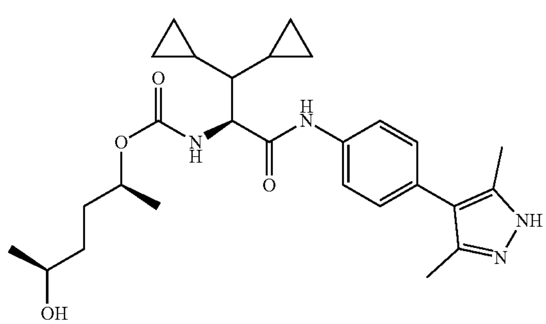 [SMILES: Cc1n[nH]c(C)c1-c1ccc(NC(=O)[C@@H](NC(=O)O[C@@H](C)CC[C@H](C)O)C(C2CC2)C2CC2)cc1] | [(1S,4S)-4-hydroxy-1-methyl-pentyl] N-[(1S)-1-(dicyclopropylmethyl)-2-[4-(3,5-dimethyl-1H-pyrazol-4-yl)anilino]-2-oxo-ethyl]carbamate | 483 | 4.5 ACQUITY BEH C18 column, 0.05% formic acid in water with MeCN |

Example 134

Disodium [4-[4-[[(2S)-3,3-dicyclopropyl-2-[(2-iso-propylpyrazole-3-carbonyl)amino]propanoyl]amino]phenyl]-3,5-dimethyl-pyrazol-1-yl]methyl phosphate

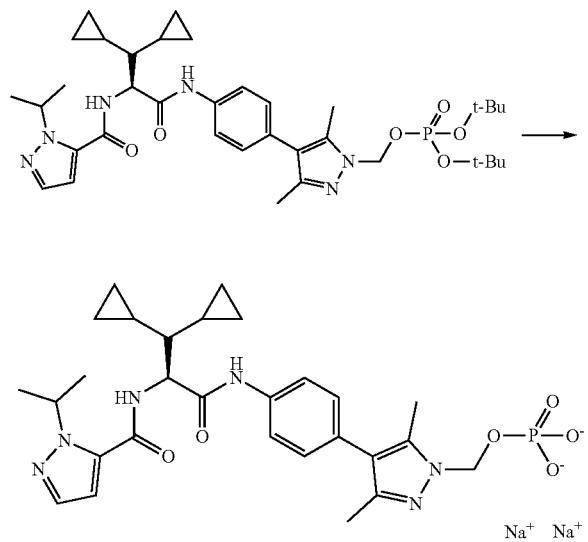

To a solution of the compound of Preparation 57 (2.05 g, 2.94 mmol) in anhydrous DCM (10 mL) was added TFA (2 mL) at 5° C. under argon. The solution was stirred at 5° C. for 20 minutes and then at room temperature for 1 hour. Toluene (20 mL) was added to the mixture, which was then concentrated in vacuo. The resulting gum was triturated with water (5×80 mL) until the pH was 3. Water (20 mL) was added to the residue followed by 1N NaOH (10 mL, 10 mmol) and the mixture was shaken for 10 minutes, ensuring the pH was >8. To the obtained mixture was added n-butanol (50 mL) and the mixture was concentrated in vacuo to approximately 40 mL. Further n-butanol (30 mL) was added and the mixture was concentrated in vacuo to approximately 30 mL. MeCN (30 mL) was added and the resulting fine precipitate was filtered. The filter cake was washed with MeCN (4×20 mL) and dried in vacuo, giving the title compound (1.38 g, 75%) as a white solid. 1H NMR (400 MHz, Deuterium Oxide) δ 7.42 (d, J=2.0 Hz, 1H), 7.37 (d, J=8.4 Hz, 2H), 7.19 (d, J=8.3 Hz, 2H), 6.59 (d, J=2.1 Hz, 1H), 5.44 (d, J=4.0 Hz, 2H), 4.92 (p, J=6.7 Hz, 1H), 4.68 (d, J=7.0 Hz, 1H), 2.17 (s, 3H), 2.02 (s, 3H), 1.25 (t, J=6.8 Hz, 6H), 0.77-0.58 (m, 3H), 0.45-0.22 (m, 4H), 0.20-0.09 (m, 3H), 0.04--0.05 (m, 1H); LCMS (METHOD 1) (ES): m/z 585.3 [M+H]+, RT=2.05 min.

Example 135

[4-[4-[[(2S)-3,3-Dicyclopropyl-2-[(2-isopropylpyrazole-3-carbonyl)amino]propanoyl]amino]phenyl]-3,5-dimethyl-pyrazol-1-yl]methyl dihydrogen phosphate

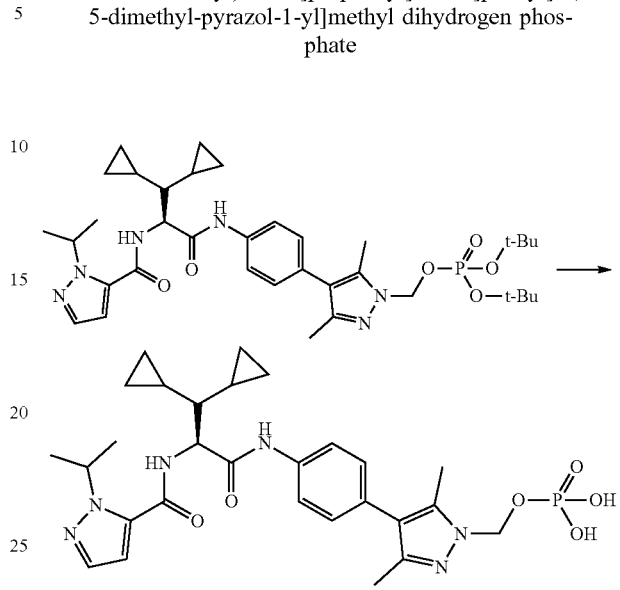

To a solution of the compound of Preparation 57 (620 mg, 0.89 mmol) in anhydrous DCM (10 mL) was added TFA (1 mL) at 5° C. under argon. The solution was stirred at 5° C. under argon for 2 hours. The reaction solution was concentrated in vacuo and the residue was basified with 1N NaOH (3 mL) until the pH was >8. To the obtained mixture was added 20 mL of MeCN. The precipitate was filtered, the residue was washed with MeCN (2×10 mL) and dried in vacuo, giving crude product as the disodium salt. The filtrate was concentrated in vacuo to give less pure crude product. Purification of all of the material by reverse phase HPLC (basic method) gave the title compound (277 mg, 50%) as a white solid after lyophilisation. 1H NMR (400 MHz, DMSO-d6) δ 10.24 (s, 1H), 8.45 (d, J=8.9 Hz, 1H), 7.66 (d, J=8.3 Hz, 2H), 7.49 (d, J=1.9 Hz, 1H), 7.25 (br, 2H), 7.18 (d, J=8.3 Hz, 2H), 6.94 (d, J=1.9 Hz, 1H), 5.56 (d, J=5.8 Hz, 2H), 5.43 (hept, J=6.5 Hz, 1H), 4.81 (t, J=7.7 Hz, 1H), 2.26 (s, 3H), 2.10 (s, 3H), 1.38 (d, J=6.6 Hz, 3H), 1.35 (d, J=6.6 Hz, 3H), 0.94-0.75 (m, 3H), 0.51-0.12 (m, 8H); LCMS (METHOD 1) (ES): m/z 585.3 [M+H]+, RT=2.05 min.

Example 136

Disodium [4-[4-[[(2S)-2-cyclohexyl-2-[(2-methylpyrazole-3-carbonyl)amino]acetyl]amino]phenyl]-3,5-dimethyl-pyrazol-1-yl]methyl phosphate

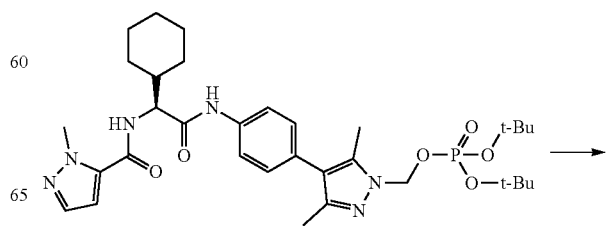

-continued

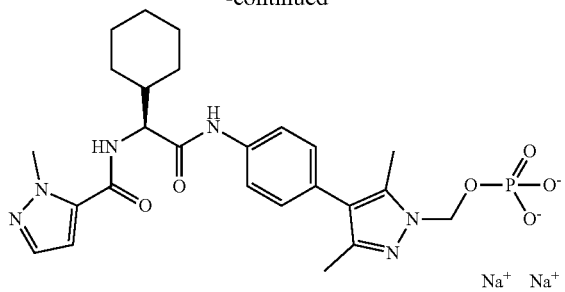

TFA (0.15 mL) was added to a solution of solution of the compound of Preparation 61 (100 mg, 0.15 mmol) in anhydrous DCM (1.5 mL) at 5° C. under argon. The solution was stirred at 5° C. for 3 hours and then concentrated in vacuo. The residue was basified with 1N NaOH (0.5 mL) to give a pH>8. To the obtained mixture was added MeCN (4 mL) and the resulting precipitate was filtered. The filter cake was washed with MeCN (2×4 mL) and dried in vacuo, to give the title compound (64 mg, 71%) as an off-white solid. 1H NMR 1H NMR (600 MHz, DMSO-d6) δ 10.47 (s, 1H), 8.74 (d, J=8.4 Hz, 1H), 7.77-7.62 (m, 2H), 7.44 (d, J=2.1 Hz, 1H), 7.22-7.05 (m, 3H), 5.53 (d, J=5.6 Hz, 2H), 4.40 (t, J=8.8 Hz, 1H), 4.04 (s, 3H), 2.25 (s, 3H), 2.09 (s, 3H), 1.99-1.80 (m, 2H), 1.78-1.65 (m, 2H), 1.65-1.56 (m, 2H), 1.32-1.09 (m, 5H); LCMS (METHOD 4) (ES): m/z 545.2 [M+H]$^+$, RT=0.44 min.

Example 137

[3,5-Dimethyl-4-[4-[[(2S)-2-[(2-methylpyrazole-3-carbonyl)amino]-3,3-diphenyl-propanoyl]amino]phenyl]pyrazol-1-yl]methyl dihydrogen phosphate

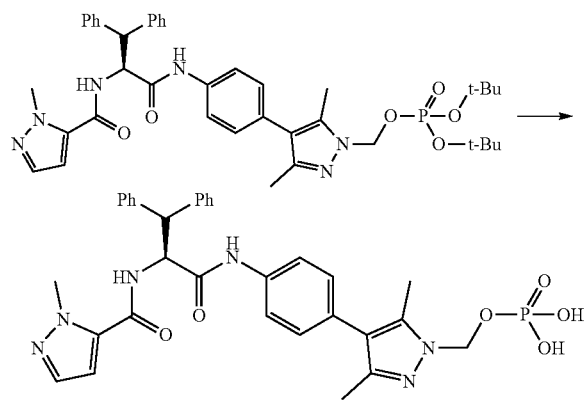

TFA (1 mL) was added to a solution of the compound of Preparation 62 (30 mg, 0.041 mmol) in DCM (1 mL) and the mixture was allowed to stand at room temperature for 30 minutes. The mixture was concentrated in vacuo, DMSO (1 mL) was added along with a few drops of aqueous NH$_3$. MeOH and water were added to the resulting cloudy suspension until a clear solution was obtained. Purification by reverse phase HPLC (basic method) gave the title compound (12 mg, 47%). 1H NMR (300 MHz, DMSO-d6) δ 10.46 (s, 1H), 9.02 (d, J=8.8 Hz, 1H), 7.55-7.41 (m, 6H), 7.35 (d, J=2.1 Hz, 1H), 7.32-7.00 (m, 10H), 6.80 (d, J=2.1 Hz, 1H), 5.76-5.46 (m, 3H), 4.72 (d, J=11.8 Hz, 1H), 3.90 (s, 3H), 2.22 (s, 3H), 2.06 (s, 3H); LCMS (METHOD 1) (ES): m/z 628.2 [M+H]$^+$, RT=1.99 min.

Example 482

Disodium [4-[4-[[(2S)-3,3-dicyclopropyl-2-[(2-ethylpyrazole-3-carbonyl)amino]propanoyl]amino]phenyl]-3,5-dimethyl-pyrazol-1-yl]methyl phosphate

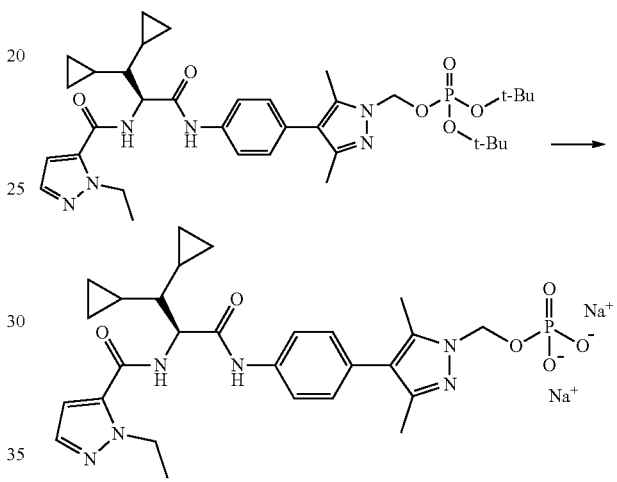

To a solution of the phosphate ester of Preparation 378 (9.5 g, 14 mmol) in DCM (100 mL) at 5° C. was added methanesulfonic acid (7 mL, 10.36 g, 108 mmol). The solution was stirred at 5° C. for 30 min then heptane (300 mL) was added causing precipitation of an oil. The supernatant was removed by decantation and water (150 mL) was added to the residue causing the crude product to precipitate. The mixture was filtered and the residue was washed with water (5×50 mL). The white solid was suspended in water (120 mL) and 1M NaOH was added dropwise to the stirred suspension to give pH 7-8. n-Butanol (100 mL) was added to give a two phase mixture and further 1M NaOH was added to the solution to keep the pH at 7-8. The total amount of 1M NaOH used was 30 mL (30 mmol). The two phases were separated and the organic phase was extracted once with water. To the combined aqueous phases was added n-butanol (100 mL). The mixture was concentrated in vacuo to ½ of the volume. To the residue was added MeCN (700 mL) and the resulting suspension was stirred at room temperature for 30 min and then filtered. The filter cake was washed with MeCN (3×75 mL) and dried in vacuo, to give the title compound (6.3 g, 74%) as a white solid. 1H NMR (400 MHz, Deuterium Oxide) δ 7.43-7.33 (m, 4H), 7.20 (d, J=8.2 Hz, 2H), 6.66 (d, J=2.1 Hz, 1H), 5.45 (d, J=4.6 Hz, 2H), 4.66 (d, J=6.9 Hz, 1H), 4.25 (q, J=7.2 Hz, 2H), 2.16 (s, 3H), 2.02 (s, 3H), 1.17 (t, J=7.2 Hz, 3H), 0.81-0.54 (m, 3H), 0.48-0.22 (m, 4H), 0.22-0.08 (m, 3H), 0.07--0.07 (m, 1H); LCMS (METHOD 3) (ES): m/z 571.4 [M+H]$^+$, RT=0.54 min.

Example 483

Disodium [4-[4-[[(2S)-3,3-dicyclopropyl-2-[[2-[(1S)-2-hydroxy-1-methyl-ethyl]pyrazole-3-carbonyl]amino]propanoyl]amino]phenyl]-3,5-dimethyl-pyrazol-1-yl]methyl phosphate

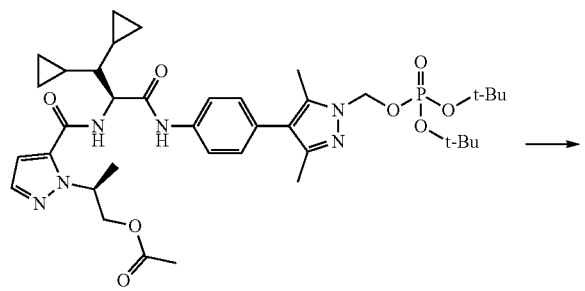

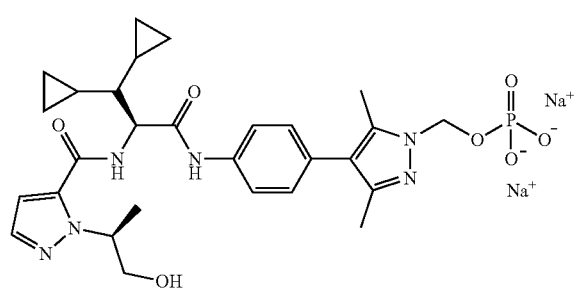

To a solution of the phosphate ester of Preparation 379 (3.50 g, 4.17 mmol) in DCM (42 mL) at 5° C. was added methanesulfonic acid (4.01 mg, 2.71 mL, 41.7 mmol). The solution was stirred at 5° C. for 20 min then heptane (140 mL) was added causing precipitation of an oil. The supernatant was removed by decantation and water (70 mL) was added to the residue causing the crude product to precipitate. The mixture was filtered and the residue was washed with water (35 mL×5). The white solid was suspended in water (20.9 mL) and 4M NaOH (2.61 mL, 10.4 mmol) was added dropwise to the stirred suspension to give pH 11. n-Butanol (15 mL) was added to give a slightly cloudy two phase mixture and this was stirred at room temperature for 5 hours. The pH dropped slowly with time and additional 4M NaOH was added to the solution to keep the pH at 11. The mixture was concentrated in vacuo to ⅔ of the original volume (water bath temp: 30° C., pressure: 8-10 mbar). To the two phase mixture was slowly added MeCN (200 mL) and the resulting suspension was stirred at room temperature for 30 min before being filtered. The filter cake was washed with MeCN (3×20 mL) and dried in vacuo, giving the title compound (2.42 g, 90%) as a white solid containing 3 mol % sodium mesylate and 20 mol % sodium acetate. 1H NMR (400 MHz, Deuterium Oxide) 57.46 (d, J=2.1 Hz, 1H), 7.41-7.29 (m, 2H), 7.28-7.14 (m, 2H), 6.64 (d, J=2.1 Hz, 1H), 5.43 (d, J=4.0 Hz, 2H), 5.03-4.84 (m, 1H), 4.64 (d, J=6.6 Hz, 1H), 3.74-3.53 (m, 2H), 2.16 (s, 3H), 2.02 (s, 3H), 1.23 (d, J=6.8 Hz, 3H), 0.79-0.57 (m, 3H), 0.48-0.21 (m, 4H), 0.21-0.05 (m, 3H), 0.05--0.08 (m, 1H); LCMS (METHOD 3) (ES): m/z 219.2 [M−H], RT=0.49 min.

Example 484

N-[(1S)-1-(Dicyclopropylmethyl)-2-[4-[1-(hydroxymethyl)-3,5-dimethyl-pyrazol-4-yl]anilino]-2-oxo-ethyl]-2-isopropyl-pyrazole-3-carboxamide

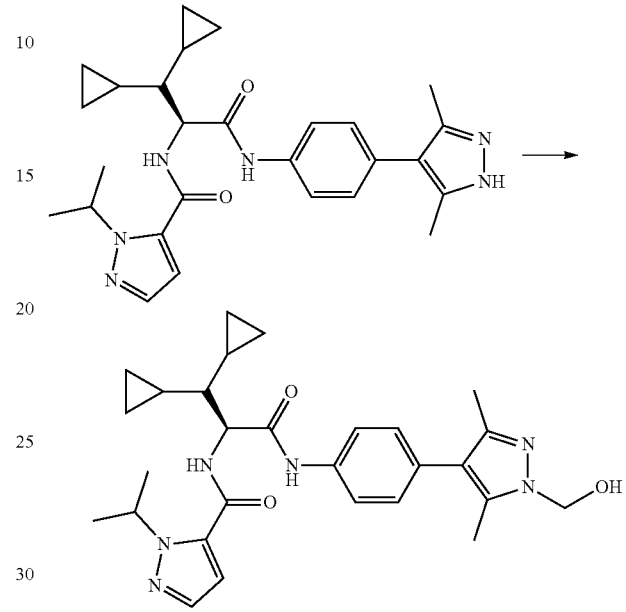

Sat. aq. formaldehyde (605, μL, 7.90 mmol) was added to the compound of Example 32 (1.25 g, 2.63 mmol) in EtOH (7 mL) under argon and the mixture was heated at 55° C. for 18 hours. After allowing the mixture to cool to room temperature the volatiles were removed in vacuo. The material was dried in a vacuum oven at 30° C. for 18 hours to give the title compound (1.29 g, 97%) as a colourless solid containing traces of the compound of Example 32. 1H NMR (600 MHz, DMSO-d6) δ 10.21 (s, 1H), 8.44 (d, J=8.7 Hz, 1H), 7.77-7.63 (m, 2H), 7.50 (d, J=2.0 Hz, 1H), 7.29-7.17 (m, 2H), 6.93 (d, J=2.0 Hz, 1H), 6.50 (t, J=7.4 Hz, 1H), 5.42 (hept, J=6.6 Hz, 1H), 5.31 (d, J=7.4 Hz, 2H), 4.82 (t, J=8.3 Hz, 1H), 2.26 (s, 3H), 2.14 (s, 3H), 1.39 (d, J=6.6 Hz, 3H), 1.35 (d, J=6.6 Hz, 3H), 0.95-0.86 (m, 1H), 0.86-0.72 (m, 2H), 0.52-0.43 (m, 1H), 0.43-0.11 (m, 7H).

Example 485

[4-[4-[[(2S)-3,3-dicyclopropyl-2-[(2-isopropylpyrazole-3-carbonyl)amino]propanoyl]-amino]phenyl]-3,5-dimethyl-pyrazol-1-yl]methyl (2S)-2-amino-3-methyl-butanoate

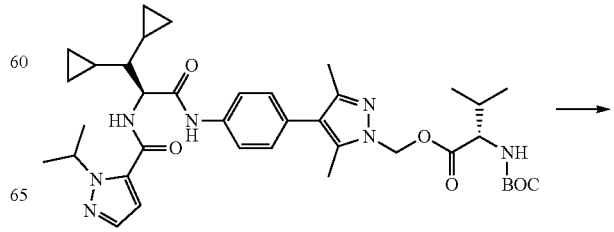

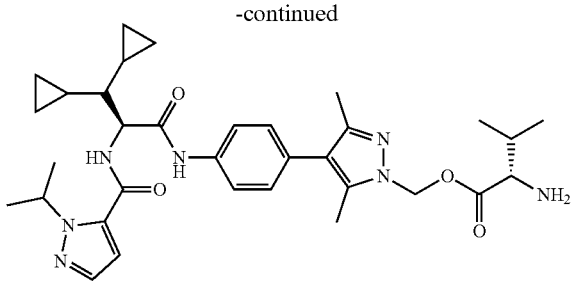

4M HCl in dioxane (1 mL, 4 mmol) was added to the compound of Preparation 380 (50 mg, 0.071 mmol) and the mixture was stirred at room temperature for 10 min. CH$_3$CN (5 mL) was added and the mixture was concentrated in vacuo. The residue was purified by acidic prep. HPLC to give the title compound (29 mg, 67%) as a colourless solid. 1H NMR (400 MHz, DMSO-d6) δ 10.24 (s, 1H), 8.45 (d, J=8.8 Hz, 1H), 7.78-7.63 (m, 2H), 7.50 (d, J=1.9 Hz, 1H), 7.33-7.16 (m, 2H), 6.93 (d, J=2.0 Hz, 1H), 6.03 (s, 2H), 5.42 (hept, J=6.6 Hz, 1H), 4.91-4.71 (m, 1H), 3.16 (d, J=5.3 Hz, 1H), 2.28 (s, 3H), 2.14 (s, 3H), 1.91-1.72 (m, 1H), 1.39 (d, J=6.6 Hz, 3H), 1.35 (d, J=6.6 Hz, 3H), 0.97-0.70 (m, 3H), 0.85 (d, J=6.8 Hz, 3H), 0.80 (d, J=6.8 Hz, 3H), 0.53-0.43 (m, 1H), 0.42-0.10 (m, 7H). LCMS (METHOD 3) (ES): m/z 604.6 [M+H]$^+$, RT=0.78 min.

Example 138: IL-8 Release Assay in Human Epithelial Keratinocytes Adult (HEKa)

Keratinocytes were seeded at 3500 cells/well in 384-well ViewPlates (Perkin Elmer) in Epilife medium (Thermo Fisher) containing human keratinocyte growth supplement (HKGS) without hydrocortisone and incubated in a humid incubator at 37° C. 5% CO$_2$, overnight. The following day growth medium was removed and 25 μl fresh Epilife medium added. 75 nL test compound in 100% DMSO was added into each well reserved for test compounds, by the use of acoustic pipetting. The remaining wells received an equal volume of DMSO only, as vehicle control, or terfenadine in DMSO, as a positive control for any cytotoxic compounds. Subsequently, another 25 μL Epilife medium was added to each well. Finally, wells containing test compounds and wells prepared to yield maximum stimulation received μL of 9 ng/mL recombinant, human embryonic kidney cell (HEK)-derived human IL-17AA+30 ng/mL human TNF-alpha, in Epilife medium. Wells prepared to define 100% inhibition of IL-17 effects received 25 μL of 30 ng/mL human TNF-alpha alone, in Epilife medium. Final concentrations were 3 ng/mL HEK-human IL-17AA+10 ng/mL human TNFalpha (maximum stimulation) and 10 ng/mL human TNFalpha alone (100% inhibition, Emax), respectively. Cells were incubated for 68-72 hours in the incubator. IL-8 released from the cells was measured by the use of a commercial homogenous time-resolved fluorescence (HTRF) assay (Cis-Bio). 2 μL cell culture supernatant was transferred to a 384-well Proxiplate. 5 μL HTRF reagent was added and the plates incubated sealed in the dark for 3-22 hours at room temperature. Time-resolved fluorescence was read at 665 vs 620 nm, with excitation at 320 nm, and IL-8 levels calculated as percent of controls. Reduction of the amount of secreted IL-8 indicates decreased IL-17 signaling. Concentration response curves were fitted by the use of a four-parameter logistic equation. Relative IC$_{50}$ and Emax were reported from curves showing acceptable fit (r$^2$>0.9). Cytotoxicity was measured in the cell-containing Viewplates following addition of 7 μL PrestoBlue (Thermo Fisher) and incubation for 2.5-3 hours at room temperature, by measuring fluorescence at 615 nm (excitation at 535 nm). Fluorescence was directly proportional to the amount of metabolic activity. Reduction of fluorescence signal indicated cytotoxicity.

Compounds of the present invention were tested in the IL-8 release assay in human epithelial keratinocytes. The results are summarized in Table 1.

Compounds having a Relative EC$_{50}$ of X; wherein X<100 nM; are indicated with *

Compounds having a Relative EC$_{50}$ of X; wherein 100 nM<X<1000 nM; are indicated with **

Compounds having a Relative EC$_{50}$ of X; wherein 1000 nM<X; are indicated with ***

TABLE 1

| Example No. | Rel EC$_{50}$ IL-8 release assay |
|---|---|
| 1 | ** |
| 2 | ** |
| 3 | * |
| 4 | ** |
| 5 | * |
| 6 | * |
| 7 | ** |
| 8 | *** |
| 9 | * |
| 10 | * |
| 11 | ** |
| 12 | * |
| 13 | * |
| 14 | *** |
| 15 | ** |
| 16 | ** |
| 17 | ** |
| 18 | ** |
| 19 | ** |
| 20 | ** |
| 21 | ** |
| 22 | ** |
| 23 | * |
| 24 | ** |
| 25 | *** |
| 26 | *** |
| 27 | ** |
| 28 | ** |
| 29 | ** |
| 30 | ** |
| 31 | * |
| 32 | * |
| 33 | *** |
| 34 | ** |
| 35 | * |
| 36 | * |
| 37 | ** |
| 38 | * |
| 39 | * |
| 40 | ** |
| 41 | * |
| 42 | *** |
| 43 | ** |
| 44 | *** |
| 45 | *** |
| 46 | ** |
| 47 | * |
| 48 | *** |
| 49 | *** |
| 50 | *** |
| 51 | *** |
| 52 | *** |
| 53 | *** |
| 54 | ** |
| 55 | ** |
| 56 | ** |

TABLE 1-continued

| Example No. | Rel EC$_{50}$ IL-8 release assay |
|---|---|
| 57 | ** |
| 58 | ** |
| 59 | * |
| 60 | ** |
| 61 | ** |
| 62 | ** |
| 63 | * |
| 64 | ** |
| 65 | *** |
| 66 | ** |
| 67 | *** |
| 68 | ** |
| 69 | *** |
| 70 | ** |
| 71 | ** |
| 72 | *** |
| 73 | ** |
| 74 | ** |
| 75 | ** |
| 76 | ** |
| 77 | ** |
| 78 | *** |
| 79 | * |
| 80 | ** |
| 81 | * |
| 82 | ** |
| 83 | ** |
| 84 | ** |
| 85 | *** |
| 86 | *** |
| 87 | *** |
| 88 | ** |
| 89 | *** |
| 90 | Not tested |
| 91 | *** |
| 92 | *** |
| 93 | *** |
| 94 | *** |
| 95 | *** |
| 96 | *** |
| 97 | *** |
| 98 | *** |
| 99 | *** |
| 100 | *** |
| 101 | *** |
| 102 | * |
| 103 | *** |
| 104 | ** |
| 105 | ** |
| 106 | * |
| 107 | * |
| 108 | * |
| 109 | ** |
| 110 | ** |
| 111 | *** |
| 112 | * |
| 113 | *** |
| 114 | * |
| 115 | * |
| 116 | * |
| 117 | * |
| 118 | ** |
| 119 | * |
| 120 | ** |
| 121 | ** |
| 122 | * |
| 123 | * |
| 124 | * |
| 125 | * |
| 126 | * |
| 127 | * |
| 128 | * |
| 129 | * |
| 130 | * |
| 131 | ** |
| 132 | * |
| 133 | * |
| 141 | * |
| 142 | ** |
| 143 | ** |
| 144 | * |
| 145 | * |
| 146 | * |
| 147 | * |
| 148 | * |
| 149 | ** |
| 150 | *** |
| 151 | * |
| 152 | * |
| 153 | ** |
| 154 | ** |
| 155 | * |
| 156 | * |
| 157 | *** |
| 158 | * |
| 159 | ** |
| 160 | ** |
| 161 | *** |
| 162 | ** |
| 163 | *** |
| 164 | ** |
| 165 | ** |
| 166 | * |
| 167 | ** |
| 168 | *** |
| 169 | *** |
| 170 | ** |
| 171 | *** |
| 172 | *** |
| 173 | * |
| 174 | ** |
| 175 | ** |
| 176 | ** |
| 177 | ** |
| 178 | * |
| 179 | * |
| 180 | * |
| 181 | * |
| 182 | * |
| 183 | ** |
| 184 | * |
| 185 | * |
| 186 | * |
| 187 | * |
| 188 | * |
| 189 | * |
| 190 | * |
| 191 | ** |
| 192 | * |
| 193 | ** |
| 194 | * |
| 195 | ** |
| 196 | * |
| 197 | ** |
| 198 | *** |
| 199 | *** |
| 200 | * |
| 201 | * |
| 202 | * |
| 203 | * |
| 204 | * |
| 205 | * |
| 206 | * |
| 207 | ** |
| 208 | * |
| 209 | * |
| 210 | * |
| 211 | * |
| 212 | * |
| 213 | * |
| 214 | * |
| 215 | * |
| 216 | ** |
| 217 | * |

TABLE 1-continued

| Example No. | Rel EC$_{50}$ IL-8 release assay |
|---|---|
| 218 | * |
| 219 | * |
| 220 | * |
| 221 | ** |
| 222 | * |
| 223 | *** |
| 224 | *** |
| 225 | * |
| 226 | * |
| 227 | *** |
| 228 | ** |
| 229 | *** |
| 230 | * |
| 231 | * |
| 232 | ** |
| 233 | ** |
| 234 | ** |
| 235 | *** |
| 236 | *** |
| 237 | *** |
| 238 | ** |
| 239 | * |
| 240 | ** |
| 241 | ** |
| 242 | ** |
| 243 | *** |
| 244 | * |
| 245 | ** |
| 246 | ** |
| 247 | * |
| 248 | *** |
| 249 | * |
| 250 | * |
| 251 | * |
| 252 | ** |
| 253 | *** |
| 254 | ** |
| 255 | * |
| 256 | * |
| 257 | * |
| 258 | * |
| 259 | *** |
| 260 | * |
| 261 | * |
| 262 | ** |
| 263 | ** |
| 264 | ** |
| 265 | ** |
| 266 | ** |
| 267 | *** |
| 268 | * |
| 269 | ** |
| 270 | ** |
| 271 | * |
| 272 | * |
| 273 | * |
| 274 | * |
| 275 | *** |
| 276 | * |
| 277 | * |
| 278 | ** |
| 279 | * |
| 280 | *** |
| 281 | ** |
| 282 | ** |
| 283 | ** |
| 284 | ** |
| 285 | ** |
| 286 | ** |
| 287 | * |
| 288 | * |
| 289 | * |
| 290 | * |
| 291 | * |
| 292 | * |
| 293 | ** |
| 294 | ** |
| 295 | ** |
| 296 | *** |
| 297 | *** |
| 298 | *** |
| 299 | * |
| 300 | *** |
| 301 | ** |
| 302 | *** |
| 303 | ** |
| 304 | *** |
| 305 | Not tested |
| 306 | Not tested |
| 307 | *** |
| 308 | Not tested |
| 309 | Not tested |
| 310 | *** |
| 311 | *** |
| 312 | *** |
| 313 | *** |
| 314 | Not tested |
| 315 | Not tested |
| 316 | Not tested |
| 317 | Not tested |
| 318 | Not tested |
| 319 | Not tested |
| 320 | Not tested |
| 321 | Not tested |
| 322 | Not tested |
| 323 | Not tested |
| 324 | Not tested |
| 325 | Not tested |
| 326 | Not tested |
| 327 | Not tested |
| 328 | Not tested |
| 329 | Not tested |
| 330 | Not tested |
| 331 | Not tested |
| 332 | ** |
| 333 | *** |
| 334 | *** |
| 335 | *** |
| 336 | ** |
| 337 | ** |
| 338 | ** |
| 339A | ** |
| 339B | ** |
| 340 | *** |
| 341 | ** |
| 342 | *** |
| 343 | *** |
| 344 | *** |
| 345 | ** |
| 346 | ** |
| 347 | ** |
| 348 | *** |
| 349 | ** |
| 350 | *** |
| 351 | ** |
| 352 | *** |
| 353 | *** |
| 354 | *** |
| 355 | Not tested |
| 356 | Not tested |
| 357 | Not tested |
| 358 | *** |
| 359 | ** |
| 360 | * |
| 361 | ** |
| 362 | ** |
| 363 | * |
| 364 | * |
| 365 | * |
| 366 | ** |
| 367 | * |
| 368 | ** |
| 369 | ** |
| 370 | *** |

TABLE 1-continued

| Example No. | Rel EC$_{50}$ IL-8 release assay |
|---|---|
| 371A | ** |
| 371B | *** |
| 372 | Not tested |
| 373A | ** |
| 373B | *** |
| 374A | *** |
| 374B | *** |
| 375 | *** |
| 376 | *** |
| 377 | ** |
| 378 | *** |
| 379 | *** |
| 380 | ** |
| 381 | ** |
| 382 | ** |
| 383 | * |
| 384 | ** |
| 385 | * |
| 386 | * |
| 387 | * |
| 388 | ** |
| 389 | * |
| 390 | * |
| 391 | * |
| 392 | * |
| 393 | * |
| 394 | * |
| 395 | * |
| 396 | * |
| 397 | * |
| 398 | * |
| 399 | * |
| 400 | ** |
| 401 | ** |
| 402 | ** |
| 403 | ** |
| 404 | ** |
| 405 | * |
| 406 | ** |
| 407 | ** |
| 408 | Not tested |
| 409 | ** |
| 410 | * |
| 411 | ** |
| 412 | * |
| 413 | * |
| 414 | * |
| 415 | ** |
| 416 | * |
| 417 | * |
| 418 | * |
| 419 | ** |
| 420 | ** |
| 421 | ** |
| 422 | *** |
| 423 | ** |
| 424 | ** |
| 425 | ** |
| 426 | ** |
| 427 | * |
| 428 | * |
| 429 | ** |
| 430 | ** |
| 431 | ** |
| 432 | * |
| 433 | *** |
| 434 | ** |
| 435 | ** |
| 436 | *** |
| 437 | ** |
| 438 | ** |
| 439 | ** |
| 440 | ** |
| 441 | *** |
| 442 | ** |
| 443 | ** |
| 444 | ** |
| 445 | ** |
| 446 | * |
| 447 | ** |
| 448 | ** |
| 449 | ** |
| 450 | ** |
| 451 | * |
| 452 | *** |
| 453 | ** |
| 454 | Not tested |
| 455 | Not tested |
| 456 | Not tested |
| 457 | Not tested |
| 458 | Not tested |
| 459 | *** |
| 460 | ** |
| 461 | *** |
| 462 | *** |
| 463 | *** |
| 464 | *** |
| 465 | *** |
| 466 | *** |
| 467 | *** |
| 468 | *** |
| 469 | ** |
| 470 | *** |
| 471 | *** |
| 472 | *** |
| 473 | *** |
| 474 | *** |
| 475 | *** |
| 476 | ** |
| 477 | *** |
| 478 | *** |
| 479 | ** |
| 480 | ** |
| 481 | *** |
| 482 | * |
| 483 | * |
| 484 | * |

Example 139. In Vivo Dosing of Compounds in Dog

Dog pharmacokinetics (PK) of Examples 32 and 135 were studied in male Beagles. On the day of dosing, the animals were fasted overnight. They had free access to drinking water, except in immediate connection with dosing, and were allowed to eat from 4 hrs after dosing and onwards. The dogs were weighed on the morning prior to dosing and the individual dose volumes were adjusted on a per kg body weight basis.

Oral dosing. The dogs were dosed PO by oral gavage. The test compounds were dosed as suspensions in 1% methyl cellulose solution (2.5 mL/kg). The stomach tube was then flushed with at least 15 mL water post-dose to ensure that all test formulation entered the stomach.

Intravenous dosing. The dogs were dosed i.v. via an in-dwelling catheter in venae *cephalica*. The dose volume was 1 mL/kg of a solution of Example 32 (0.3 mg/mL) in HPB (hydroxypropyl beta cyclodextrin)/PEG-4 (polyethylene glycol-4)/water (20:20:60). The dose was given as a short manual infusion over approximately 1 minute.

Study samples. Blood was sampled at 2, 5, 15 and 30 minutes, 1, 2, 4, 6, 8 and 24 hours (i.v.) and 5, 15 and 30 minutes, 1, 2, 4, 6, 8, 24 and 48 hours after start of PO dosing, from v. jugularis, and immediately transferred to an EDTA containing tube. Exactly 50 µL blood was immediately pipetted into a pre-labelled tube containing 100 µL distilled water, gently turned over to ensure complete mixing/haemolysis and frozen on dry ice. All blood samples were stored at −20° C. or lower prior to analysis. The compounds were quantified in blood by means of LC-MS/MS.

Standard PK parameters were calculated using non-compartmental analysis and Phoenix WinNonLin 6.4 (Certara, Princeton, N.J.).

Example 140. In Vivo Dosing of Compounds in Mouse

Mouse pharmacokinetics of Examples 32 and 135 were studied in female Balb/C mice. Animals were not fasted prior to the study and had access to water and certified rodent diet ad libitum during the study. The mice were weighed on the day of the study and the individual dose volumes were adjusted on a per kg body weight basis.

Oral dosing. The mice were dosed by oral gavage. Example 135 was dosed as a suspension in 1% methyl cellulose solution (10 mL/kg). Example 32 was dosed as a suspension in a formulation containing Betadex sulfobutyl ether sodium/PVP (polyvinyl pyrrolidone)/0.1% Citrate buffer pH 3 (20:5:75) (10 mL/kg).

Intravenous dosing. The mice were dosed i.v. via the tail vein. The dose volume was 2 mL/kg of a solution of Example 32 (0.2 mg/mL) in DMSO/ethanol/water/propylene glycol (PG) (2:8:50:40).

Study samples. Blood was collected (exactly 20 μL per time point) from the saphenous vein of each animal into $K_2$EDTA-coated capillaries. The capillaries were extracted with 100 μL MilliQ water with an internal standard. Blood samples were stored at −20° C. until analysis. The compounds were quantified in blood by means of LC-MS/MS.

Standard PK parameters were calculated using non-compartmental analysis in Phoenix WinNonLin 6.4 (Certara, Princeton, N.J.)

The bioavailabilty (F) was calculated using the equation below, where AUC is the area under the curve for the oral and i.v. dosing routes and D is the dose given i.v. or orally.

$$F=100\times(AUC_{po}\times D_{iv})/(AUC_{iv}\times D_{po})$$

The data in table 1 shows that the bioavailability of Example 32 is significantly higher when dosing the prodrug, Example 135, compared to dosing Example 32 itself.

TABLE 1

Bioavailability of Examples 32 and 135 in mouse and dog

| Species | Oral dose of Example 32 (mg/kg) | Bioavailability of Example 32 (%) | Oral dose of Example 135 (mg/kg) | Bioavailability of Example 32* (%) |
|---|---|---|---|---|
| Mouse | 50 | 26 | 50 | 77 |
| Dog | 1 | 23 | 1.8 | 78 |

*calculation based on the molar dose of Example 32 given i.v.

The following are further embodiments of the invention:

Embodiment 1. A compound according to formula (I)

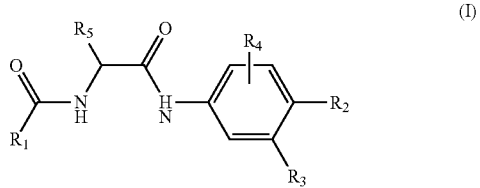

(I)

wherein $R_1$ is selected from the group consisting of 5- or 6-membered heteroaryl, 9- or 10-membered bicyclic heteroaryl, phenyl, $(C_1-C_6)$alkoxy, (C3-$C_7$)cycloalkoxy, $(C_1-C_6)$alkyl, phenyl-$(C_1-C_4)$alkyl, $(C_3-C_7)$cycloalkyl, 4-6-membered heterocycloalkyl and —$NR_cR_d$, wherein said 5- or 6-membered heteroaryl, 9- or 10-membered bicyclic heteroaryl, phenyl, $(C_1-C_6)$alkoxy, $(C_3-C_7)$cycloalkoxy, $(C_1-C_6)$alkyl, phenyl-$(C_1-C_4)$alkyl, $(C_3-C_7)$cycloalkyl and 4-6-membered heterocycloalkyl is optionally substituted with one or more substituents independently selected from $R_a$;

$R_a$ represents deuterium, halogen, hydroxy, —$NR_cR_d$, $(C_1-C_6)$alkyl, $(C_1-C_6)$alkylcarbonyl, $(C_3-C_7)$cycloalkyl, phenyl, 5- or 6-membered heteroaryl or 4-6-membered heterocycloalkyl, wherein said $(C_1-C_6)$alkyl, $(C_1-C_6)$alkylcarbonyl, $(C_3-C_7)$cycloalkyl, phenyl, 5- or 6-membered heteroaryl or 4-6-membered heterocycloalkyl is optionally substituted with one or more substituents independently selected from deuterium, halogen, hydroxy, cyano, $(C_1-C_4)$alkyl, $(C_3-C_7)$cycloalkyl, $(C_1-C_4)$alkoxy, —$SO_2$—$(C_1-C_4)$alkyl and —$NR_cR_d$;

$R_2$ is selected from the group consisting of 5- or 6-membered heteroaryl, wherein said 5- or 6-membered heteroaryl is optionally substituted with one or more substituents independently selected from $R_b$, wherein said 5- or 6-membered heteroaryl may optionally contain —CO— as a ring member and wherein when said 5 membered heteroaryl contains nitrogen as a ring atom said nitrogen may optionally be substituted with a substituent selected from $R_8$;

$R_b$ represents deuterium, halogen, cyano, hydroxy, —$NR_c R_d$, $(C_1-C_6)$alkyl, $(C_1-C_6)$alkoxy, $(C_1-C_6)$alkyl-CO—O—$(CH_2)_n$— or $(C_3-C_7)$cycloalkyl, wherein n is 1-4, and wherein said $(C_1-C_6)$alkyl, $(C_1-C_6)$alkoxy or $(C_3-C_7)$cycloalkyl is optionally substituted with one or more substituents independently selected from deuterium, halogen, cyano, hydroxy, —$NR_cR_d$ and $(C_1-C_4)$alkoxy;

$R_c$ and $R_d$ each independently are selected from the group consisting of hydrogen and $(C_1-C_6)$alkyl, or $R_c$ and $R_d$ together form pyrrolidinyl or piperidinyl, wherein said $(C_1-C_6)$alkyl, pyrrolidinyl or piperidinyl is optionally substituted with one or more substituents independently selected from halogen, cyano and hydroxy;

$R_8$ is selected from the group consisting of -L-PO(OH)$_2$ and —$CHR_gO$—$(CO\text{-}A\text{-}NR_h)_m$—$CO\text{-}A\text{-}NR_hR_i$, L is selected from the group consisting of a bond or —$CHR_gO$—, m is 0 or 1;

wherein each —CO-A-$NR_h$— independently represent an amino acid residue wherein the amino acid residue is selected from the natural amino acids either in D or L-form or as mixtures of the D and L form, and wherein said amino acid residue may be substituted on the α-amino group with a substituent $R_h$;

$R_g$, $R_h$, and $R_i$ are independently selected from hydrogen and $(C_1-C_6)$alkyl;

$R_3$ is selected from the group consisting of hydrogen, deuterium, hydroxy and halogen;

$R_4$ is selected from the group consisting of hydrogen, deuterium and halogen;

$R_5$ is selected from the group consisting of —$CHR_6R^7$, $(C_3-C_{10})$cycloalkyl and G, wherein said $(C_3-C_{10})$cycloalkyl and G are optionally substituted with one or more substituents independently selected from deuterium, halogen, cyano, hydroxy, $(C_1-C_4)$alkyl and halo$(C_1-C_4)$ alkyl;

G represents

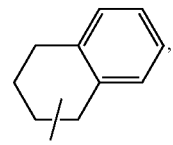
G₁,

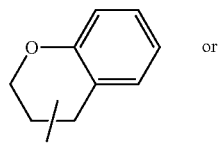
G₂ or

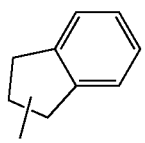
G₃

R₆ and R₇ each independently represents hydrogen, phenyl, ($C_1$-$C_6$)alkyl, or ($C_3$-$C_7$)cycloalkyl, wherein said phenyl, ($C_1$-$C_6$)alkyl or (C3-$C_7$)cycloalkyl is optionally substituted with one or more substituents independently selected from halogen, cyano, hydroxy and ($C_1$-$C_4$)alkyl; with the proviso that at least one of R₆ and R₇ are different from hydrogen;

or pharmaceutically acceptable salts, solvates, hydrates or prodrugs thereof.

Embodiment 2. A compound according to embodiment 1 above
wherein
R₁ is selected from the group consisting of 5- or 6-membered heteroaryl, 9- or 10-membered bicyclic heteroaryl, phenyl, ($C_1$-$C_6$)alkoxy, (C3-$C_7$)cycloalkoxy, ($C_1$-$C_6$)alkyl, phenyl-($C_1$-$C_4$)alkyl, ($C_3$-$C_7$)cycloalkyl, 4-6-membered heterocycloalkyl and —NR$_c$R$_d$, wherein said 5- or 6-membered heteroaryl, 9- or 10-membered bicyclic heteroaryl, phenyl, ($C_1$-$C_6$)alkoxy, ($C_3$-$C_7$)cycloalkoxy, ($C_1$-$C_6$)alkyl, phenyl-($C_1$-$C_4$)alkyl, ($C_3$-$C_7$)cycloalkyl and 4-6-membered heterocycloalkyl is optionally substituted with one or more substituents independently selected from R$_a$;

R$_a$ represents deuterium, halogen, hydroxy, —NR$_c$R$_d$, ($C_1$-$C_6$)alkyl, (C3-$C_7$)cycloalkyl, phenyl or 5- or 6-membered heteroaryl, wherein said ($C_1$-$C_6$)alkyl, ($C_3$-$C_7$)cycloalkyl, phenyl or 5- or 6-membered heteroaryl is optionally substituted with one or more substituents independently selected from deuterium, halogen, hydroxy, cyano, ($C_1$-$C_4$) alkyl, ($C_3$-$C_7$)cycloalkyl, ($C_1$-$C_4$)alkoxy and —NR$_c$R$_d$;

R₂ is selected from the group consisting of 5- or 6-membered heteroaryl, wherein said 5- or 6-membered heteroaryl is optionally substituted with one or more substituents independently selected from R$_b$ and wherein when said 5 membered heteroaryl contains nitrogen as a ring atom said nitrogen may optionally be substituted with a substituent selected from R$_g$;

R$_b$ represents deuterium, halogen, cyano, hydroxy, —NR$_c$R$_d$, ($C_1$-$C_6$)alkyl, ($C_1$-$C_6$)alkoxy or (C3-$C_7$)cycloalkyl, wherein said ($C_1$-$C_6$)alkyl, ($C_1$-$C_6$)alkoxy or ($C_3$-$C_7$)cycloalkyl is optionally substituted with one or more substituents independently selected from deuterium, halogen, hydroxy, —NR$_c$R$_d$ and ($C_1$-$C_4$)alkoxy;

R$_c$ and R$_d$ each independently are selected from the group consisting of hydrogen and ($C_1$-$C_4$) alkyl;

R₈ is selected from the group consisting of -L-PO(OH)₂,
L is selected from the group consisting of a bond or —CHR$_g$O—;

R$_g$ is selected from hydrogen and ($C_1$-$C_6$)alkyl;

R₃ is selected from the group consisting of hydrogen, deuterium, hydroxy and halogen;

R₄ is selected from the group consisting of hydrogen, deuterium and halogen;

R₅ is selected from the group consisting of —CHR₆R⁷, ($C_3$-$C_{10}$)cycloalkyl and G, wherein said ($C_3$-$C_{10}$)cycloalkyl and G are optionally substituted with one or more substituents independently selected from deuterium, halogen, cyano, hydroxy, ($C_1$-$C_4$)alkyl and halo($C_1$-$C_4$) alkyl;

G represents

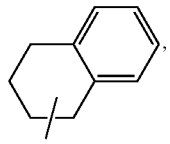
G₁,

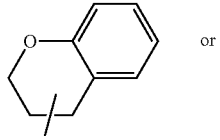
G₂ or

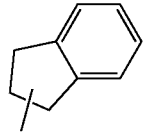
G₃

R₆ and R₇ each independently represents hydrogen, phenyl, ($C_1$-$C_4$)alkyl, or ($C_3$-$C_7$)cycloalkyl, wherein said phenyl, ($C_1$-$C_4$)alkyl or (C3-$C_7$)cycloalkyl is optionally substituted with one or more substituents independently selected from halogen, cyano, hydroxy and ($C_1$-$C_4$)alkyl; with the proviso that at least one of R₆ and R₇ are different from hydrogen; or pharmaceutically acceptable salts, solvates, hydrates or prodrugs thereof.

Embodiment 3. The compound according to embodiment 1 or embodiment 2 of general formula (Ia),

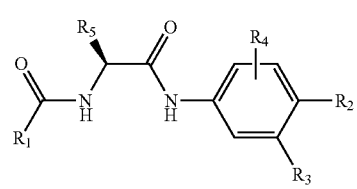
(Ia)

wherein R₁, R₂, R₃, R₄ and R₅ are as indicated in embodiment 1 or 2, or pharmaceutically acceptable salts, hydrates, solvates or prodrugs thereof.

Embodiment 4. The compound according to embodiment 1 or embodiment 2 of general formula (Ib),

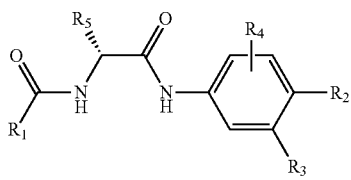

(Ib)

wherein $R_1$, $R_2$, $R_3$, $R_4$ and $R_5$ are as indicated in embodiment 1, or pharmaceutically acceptable salts, hydrates, solvates or prodrugs thereof.

Embodiment 5. The compound according to any one of the embodiments above wherein $R_1$ is selected from 5-membered heteroaryl, 9-membered bicyclic heteroaryl, $(C_3-C_7)$ cycloalkyl, 4-6-membered heterocycloalkyl, $(C_1-C_6)$alkyl and $(C_1-C_6)$alkoxy wherein said 5-membered heteroaryl, 9-membered bicyclic heteroaryl, $(C_3-C_7)$cycloalkyl, $(C_1-C_6)$ alkyl and $(C_1-C_6)$alkoxy is optionally substituted with one or more substituents independently selected from $R_a$.

Embodiment 6. The compound according to any one of the embodiments above wherein $R_1$ is selected from 5-membered heteroaryl, wherein said 5-membered heteroaryl is optionally substituted with one or more substituents independently selected from $R_a$.

Embodiment 7. The compound according to any one of the embodiments above, wherein $R_1$ is selected from pyrazolyl, imidazolyl, thiazolyl, isoxazolyl and triazolyl.

Embodiment 8. The compound according to any one of the embodiments above, wherein $R_1$ is selected from 9-membered bicyclic heteroaryl, wherein said 9-membered bicyclic heteroaryl is optionally substituted with one or more substituents independently selected from $R_a$.

Embodiment 9. The compound according to any one of the embodiments above, wherein $R_1$ is selected from pyrrolo[2,3-c]pyridinyl, pyrrolo[2,3-b]pyridinyl, pyrazolo[1,5-a]pyridinyl, pyrazolo[1,5-b]pyridazinyl, imidazo[1,2-a]pyrimidinyl, benzofuranyl and benzothiophenyl.

Embodiment 10. The compound according to any one of the embodiments above, wherein $R_1$ is selected from $(C_3-C_7)$cycloalkyl, wherein said $(C_3-C_7)$cycloalkyl is optionally substituted with one or more substituents independently selected from $R_a$.

Embodiment 11. The compound according to any one of the embodiments above, wherein $R_1$ is selected from cyclopropyl.

Embodiment 12. The compound according to any one of the embodiments above, wherein $R_1$ is selected from $(C_1-C_6)$alkyl, wherein said $(C_1-C_6)$alkyl is optionally substituted with one or more substituents independently selected from $R_a$.

Embodiment 13. The compound according to any one of the embodiments above, wherein $R_1$ is selected from methyl, ethyl and propyl, wherein said methyl, ethyl and propyl is optionally substituted with one or more substituents independently selected from $R_a$.

Embodiment 14. The compound according to any one of the embodiments above, wherein $R_1$ is selected from $(C_1-C_6)$alkoxy, wherein said $(C_1-C_6)$alkoxy is optionally substituted with one or more substituents independently selected from $R_a$.

Embodiment 15. The compound according to any one of the embodiments above, wherein $R_1$ is tert-butyloxy.

Embodiment 16. The compound according to any one of the embodiments above, wherein $R_a$ represents methyl, ethyl propyl, isopropyl, cyclopropyl, $-N(CH_3)_2$ or phenyl, wherein said methyl, ethyl propyl, isopropyl, cyclopropyl, $-N(CH_3)_2$ or phenyl, is optionally substituted with one or more substituents independently selected from fluoro, chloro and hydroxy.

Embodiment 17. The compound according to any one of the embodiments above, wherein $R_2$ is selected from pyrazolyl or imidazolyl, wherein said pyrazolyl or imidazolyl is optionally substituted with one or more substituents independently selected from $R_b$.

Embodiment 18. The compound according to any one of the embodiments above, wherein $R_2$ is selected from pyrazolyl or imidazolyl, wherein said pyrazolyl or imidazolyl is optionally substituted with one or more substituents independently selected from $(C_1-C_6)$alkyl.

Embodiment 19. The compound according to any one of the embodiments above, wherein $R_2$ is selected from the group consisting of 5-membered heteroaryl, wherein said 5-membered heteroaryl contain a nitrogen ring atom substituted with a substituent selected from $R_8$ and wherein the other ring atoms of said 5-membered heteroaryl is optionally substituted with one or more substituents independently selected from $R_b$.

Embodiment 20. The compound according to any one of the embodiments above, wherein $R_2$ is selected from pyrazolyl or imidazolyl, wherein said pyrazolyl or imidazolyl contain a nitrogen ring atom substituted with a substituent selected from $R_8$ and wherein the other ring atoms of said pyrazolyl or imidazolyl is optionally substituted with one or more substituents independently selected from $R_b$.

Embodiment 21. The compound according to any one of the embodiments above wherein $R_8$ is selected from the group consisting of $-L-PO(OH)_2$ and $-CHR_gO-(CO-A-NR_h)_m-CO-A-NR_hR_i$, L is selected from the group consisting of a bond or $-CHR_gO-$, m is 0 or 1;

wherein each $-CO-A-NR_h-$ independently represent an amino acid residue wherein the amino acid residue is selected from the natural amino acids either in D or L-form or as mixtures of the D and L form, and wherein said amino acid residue may be substituted on the α-amino group with a substituent $R_h$;

$R_g$, $R_h$, and $R_i$ are independently selected from hydrogen and $(C_1-C_6)$alkyl.

Embodiment 22. The compound according to embodiment 21 wherein $-CO-A-NR_h-$ represents an amino acid residue selected from $-CO-CH_2-NR_h-$,
$-CO-CH(CH_3)-NR_h-$,
$-CO-CH(CH_2OH)-NR_h-$,
$-CO-CH(CH_2SH)-NR_h-$,
$-CO-CH(CH(CH_3)(OH))-NR_h-$,
$-CO-CH(CH(CH_3)_2)-NR_h-$,
$-CO-CH(CH_2CH(CH_3)_2)-NR_h-$,
$-CO-CH(CH(CH_3)(CH_2CH_3))-NR_h-$,
$-CO-CH(CH_2CH_2-S-CH_3)-NR_h-$,
$-CO-CH(CH_2\text{-phenyl})-NR_h-$,
$-CO-CH(CH_2(4\text{-hydroxyphenyl}))-NR_h-$,
$-CO-CH(CH_2-COOH)-NR_h-$,
$-CO-CH(CH_2-CH_2-COOH)-NR_h-$,
$-CO-CH(CH_2-CH_2-CONH_2)-NR_h-$,
$-CO-CH(CH_2-CONH_2)-NR_h-$,
$-CO-CH((CH_2)_4-NH_2)-NR_h-$,
$-CO-CH((CH_2)-NH-C(NH)(NH_2))-NR_h-$, —CO—CH—(CH$_2$-(4-imidazolyl))—NR$_h$— and
—CO—CH—(CH$_2$-(3-indolyl))—NR$_h$.

Embodiment 23. The compound according to embodiment 21 wherein R$_8$ is —CH$_2$O—CO—CH(CH(CH$_3$)$_2$)—NH$_2$.

Embodiment 24. The compound according to any one of the embodiments above wherein R$_8$ is -L-PO(OH)$_2$.

Embodiment 25. The compound according to any one of the embodiments above wherein R$_8$ is —CH$_2$—PO(OH)$_2$.

Embodiment 26. The compound according to any one of the embodiments above, wherein R$_8$ is selected from —CHR$_6$R$^7$.

Embodiment 27. The compound according to any one of the embodiments above, wherein R$_8$ is selected from —CHR$_6$R$^7$, and wherein R$_6$ and R$^7$ each independently represents hydrogen, phenyl, cyclopropyl, cyclobutyl, cyclopentyl, cyclohexyl, methyl or ethyl, wherein said, phenyl, cyclopropyl, cyclobutyl, cyclopentyl, cyclohexyl, methyl or ethyl, is optionally substituted with one or more substituents independently selected from halogen, cyano, (C$_1$-C$_4$)alkyl; with the proviso that at least one of R$_6$ and R$_7$ are different from hydrogen.

Embodiment 28. The compound according to any one of the embodiments above, wherein R$_8$ is selected from (C$_3$-C$_{10}$)cycloalkyl, wherein said (C$_3$-C$_{10}$)cycloalkyl is optionally substituted with one or more substituents independently selected from deuterium, halogen, cyano, hydroxy, (C$_1$-C$_4$)alkyl and halo(C$_1$-C$_4$)alkyl.

Embodiment 29. The compound according to any one of the embodiments above, wherein R$_5$ is selected from cyclohexyl, cycloheptyl, cyclooctanyl, adamantyl, spiro[2.3]hexanyl, bicyclo[3,1,0]hexanyl, bicyclo[4,1,0]heptanyl and bicyclo[2,2,2]octanyl or spiro[2.5]octanyl, wherein said cyclohexyl, cycloheptyl, cyclooctanyl, adamantyl, spiro[2.3]hexanyl, bicyclo[3,1,0]hexanyl, bicyclo[4,1,0]heptanyl and bicyclo[2,2,2]octanyl or spiro[2.5]octanyl is optionally substituted with one or more substituents independently selected from deuterium, halogen, cyano, hydroxy, (C$_1$-C$_4$)alkyl and halo(C$_1$-C$_4$)alkyl.

Embodiment 30. The compound according to any one of the embodiments above, wherein R$_5$ is selected from G, wherein said G is optionally substituted with one or more substituents independently selected from deuterium, halogen, cyano, hydroxy, (C$_1$-C$_4$)alkyl and halo(C$_1$-C$_4$)alkyl and wherein G represents

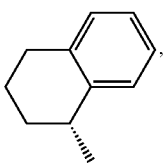

G$_1$

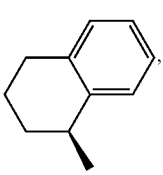

G$_2$ or

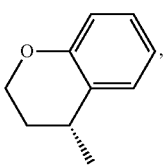

G$_3$

Embodiment 31. The compound according to any one of the embodiments above, wherein R$_5$ is selected from G, wherein G represents

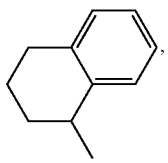

G$_{1a}$

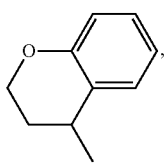

G$_{2a}$

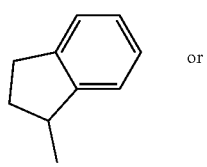

G$_{3a}$ or

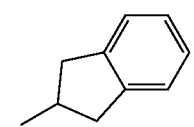

G$_{3b}$ wherein said G is optionally substituted with one or more substituents independently selected from deuterium, halogen, cyano, hydroxy, (C$_1$-C$_4$)alkyl and halo(C$_1$-C$_4$)alkyl.

Embodiment 32. The compound according to any one of the embodiments above, wherein R$_5$ is selected from G, wherein G represents G$_{1a'}$ G$_{1a''}$ G$_{2a'}$

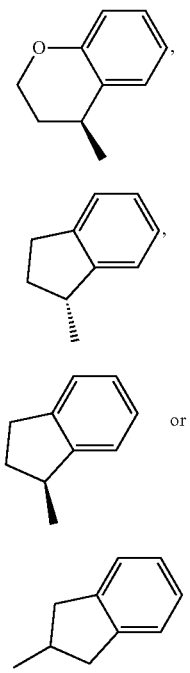

G2a″

G3a′

G3a″ or

G3b wherein said G is optionally substituted with one or more substituents independently selected from deuterium, halogen, cyano, hydroxy, $(C_1-C_4)$alkyl and halo$(C_1-C_4)$alkyl.

Embodiment 33. The compound according to any one of the embodiments 1-4 above, wherein $R_5$ is selected from —CHR$_6$R$_7$, and wherein $R_6$ and $R_7$ each independently represents hydrogen, phenyl, cyclopropyl, cyclobutyl, cyclopentyl, cyclohexyl, methyl or ethyl, wherein said phenyl, cyclopropyl, cyclobutyl, cyclopentyl, cyclohexyl, methyl or ethyl, is optionally substituted with one or more substituents independently selected from halogen, cyano, $(C_1-C_4)$alkyl; with the proviso that at least one of $R_6$ and $R_7$ are different from hydrogen;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl is optionally substituted with one or more substituents independently selected from $R_b$.

Embodiment 34. The compound according to any one of the embodiments 1-4 above, wherein $R_5$ is selected from —CHR$_6$R$_7$, and wherein $R_6$ and $R_7$ each independently represents phenyl, cyclopropyl, cyclobutyl, cyclopentyl and cyclohexyl;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl is optionally substituted with one or more substituents independently selected from $R_b$.

Embodiment 35. The compound according to any one of the embodiments 1-4 above, wherein $R_5$ is selected from —CHR$_6$R$^7$, and wherein $R_6$ and $R_7$ each independently represents hydrogen, methyl or ethyl, wherein said methyl or ethyl, is optionally substituted with one or more substituents independently selected from halogen, cyano, $(C_1-C_4)$alkyl; with the proviso that at least one of $R_6$ and $R_7$ are different from hydrogen;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl is optionally substituted with one or more substituents independently selected from $R_b$.

Embodiment 36. The compound according to any one of the embodiments 1-4 above, wherein $R_5$ is selected from $(C_3-C_{10})$cycloalkyl, wherein said $(C_3-C_{10})$cycloalkyl is optionally substituted with one or more substituents independently selected from deuterium, halogen, cyano, hydroxy, $(C_1-C_4)$alkyl and halo$(C_1-C_4)$alkyl;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl is optionally substituted with one or more substituents independently selected from $R_b$.

Embodiment 37. The compound according to any one of the embodiments 1-4 above, wherein $R_5$ is selected from cyclohexyl, cycloheptyl, cyclooctanyl, adamantyl, spiro[2.3]hexanyl, bicyclo[3,1,0]hexanyl, bicyclo[4,1,0]heptanyl and bicyclo[2,2,2]octanyl or spiro[2.5]octanyl, wherein said cyclohexyl, cycloheptyl, cyclooctanyl, adamantyl, spiro[2.3]hexanyl, bicyclo[3,1,0]hexanyl, bicyclo[4,1,0]heptanyl and bicyclo[2,2,2]octanyl or spiro[2.5]octanyl is optionally substituted with one or more substituents independently selected from deuterium, halogen, cyano, hydroxy, $(C_1-C_4)$alkyl and halo$(C_1-C_4)$alkyl;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl is optionally substituted with one or more substituents independently selected from $R_b$.

Embodiment 38. The compound according to any one of the embodiments 1-4 above, wherein $R_5$ is selected from G, wherein said G is optionally substituted with one or more substituents independently selected from deuterium, halogen, cyano, hydroxy, $(C_1-C_4)$alkyl and halo$(C_1-C_4)$alkyl and wherein G represents

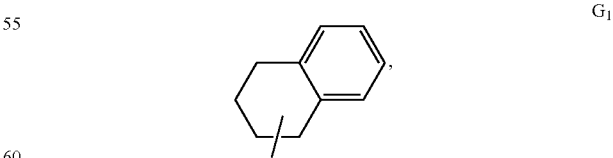

G1

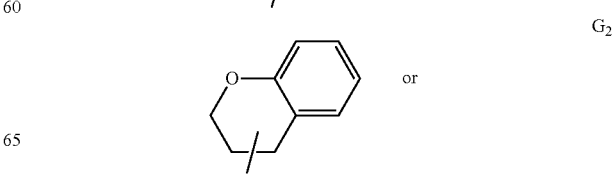

or

G2

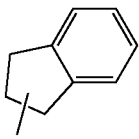 G₃ wherein said G is optionally substituted with one or more substituents independently selected from deuterium, halogen, cyano, hydroxy, (C₁-C₄)alkyl and halo(C₁-C₄)alkyl;

R₁ is pyrazolyl, wherein said pyrazolyl is optionally substituted with one or more substituents independently selected from R$_a$;

and wherein R₂ is selected from pyrazolyl or imidazolyl, wherein said pyrazolyl or imidazolyl is optionally substituted with one or more substituents independently selected from R$_b$.

Embodiment 39. The compound according to any one of the embodiments 1-4 above, wherein R₅ is selected from G, wherein G represents

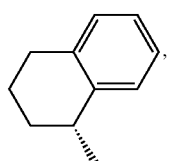 G₁ₐ′

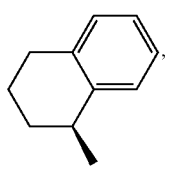 G₁ₐ″

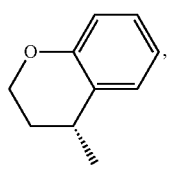 G₂ₐ′

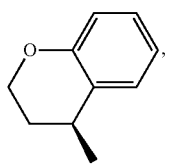 G₂ₐ″

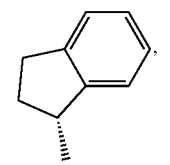 G₃ₐ′

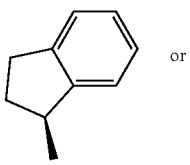 or G₃ₐ″

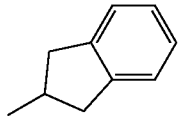 G₃ᵦ wherein said G is optionally substituted with one or more substituents independently selected from deuterium, halogen, cyano, hydroxy, (C₁-C₄)alkyl and halo(C₁-C₄)alkyl;

R₁ is pyrazolyl, wherein said pyrazolyl is optionally substituted with one or more substituents independently selected from R$_a$;

and wherein R₂ is selected from pyrazolyl or imidazolyl, wherein said pyrazolyl or imidazolyl is optionally substituted with one or more substituents independently selected from R$_b$.

Embodiment 40. The compound according to any one of the embodiments 33-39 above, wherein R₂ is selected from pyrazolyl or imidazolyl, wherein said pyrazolyl or imidazolyl is optionally substituted with one or more substituents independently selected from (C₁-C₆)alkyl.

Embodiment 41. The compound according to any one of the embodiments 33-39 above, wherein R₂ is selected from pyrazol-4-yl or imidazol-4-yl, wherein said pyrazol-4-yl or imidazole-4-yl is optionally substituted with one or more substituents independently selected from (C₁-C₆)alkyl.

Embodiment 42. The compound according to any one of the embodiments 33-39 above, wherein R₂ is pyrazol-4-yl, wherein said pyrazol-4-yl is optionally substituted with one or more substituents independently selected from (C₁-C₆)alkyl.

Embodiment 43. The compound according to any one of the embodiments 33-42 above, wherein R$_a$ represents methyl, ethyl propyl and isopropyl, wherein said methyl, ethyl propyl and isopropyl is optionally substituted with one or more substituents independently selected from fluoro, chloro, cyano, methoxy, hydroxy and cyclopropyl.

Embodiment 44. The compound according to embodiment 1 above, wherein the compound is selected from
N-[(1S)-1-cyclohexyl-2-[4-(3,5-dimethyl-1H-pyrazol-4-yl)anilino]-2-oxo-ethyl]-2-methyl-pyrazole-3-carboxamide,
N-[(1S)-1-benzhydryl-2-[4-(3,5-dimethyl-1H-pyrazol-4-yl)anilino]-2-oxo-ethyl]-2-methyl-pyrazole-3-carboxamide,
N-[(1S)-1-cycloheptyl-2-[4-(3,5-dimethyl-1H-pyrazol-4-yl)anilino]-2-oxo-ethyl]-2-methyl-pyrazole-3-carboxamide,
N-[(1S)-1-[(1R)-6-bromoindan-1-yl]-2-[4-(3,5-dimethyl-1H-pyrazol-4-yl)anilino]-2-oxo-ethyl]-2-methyl-pyrazole-3-carboxamide,
N-[(1S)-1-[(1S)-6-bromoindan-1-yl]-2-[4-(3,5-dimethyl-1H-pyrazol-4-yl)anilino]-2-oxo-ethyl]-2-methyl-pyrazole-3-carboxamide,
N-[(1S)-1-[(1S)-7-bromotetralin-1-yl]-2-[4-(3,5-dimethyl-1H-pyrazol-4-yl)anilino]-2-oxo-ethyl]-2-methyl-pyrazole-3-carboxamide,
N-[(1S)-1-[(1S)-3,3-difluorocycloheptyl]-2-[4-(3,5-dimethyl-1H-pyrazol-4-yl)anilino]-2-oxo-ethyl]-2-methyl-pyrazole-3-carboxamide,
2-tert-butyl-N-[(1S)-1-cyclohexyl-2-[4-(3,5-dimethyl-1H-pyrazol-4-yl)anilino]-2-oxo-ethyl]pyrazole-3-carboxamide,
N-[(1S)-1-cyclohexyl-2-[4-(3,5-dimethyl-1H-pyrazol-4-yl)anilino]-2-oxo-ethyl]-2-ethyl-pyrazole-3-carboxamide,
N-[(1S)-1-cyclohexyl-2-[4-(3,5-dimethyl-1H-pyrazol-4-yl)anilino]-2-oxo-ethyl]-2-isopropyl-pyrazole-3-carboxamide, N-[(1S)-1-(4,4-difluorocyclohexyl)-2-[4-(3,5-dimethyl-1H-pyrazol-4-yl)anilino]-2-oxo-ethyl]-2-methyl-pyrazole-3-carboxamide, N-[(1S)-1-(4,4-difluorocyclohexyl)-2-[4-(3,5-dimethyl-1H-pyrazol-4-yl)anilino]-2-oxo-ethyl]-2-isopropyl-pyrazole-3-carboxamide, N-[(1S)-1-di(cyclobutyl)methyl]-2-[4-(3,5-dimethyl-1H-pyrazol-4-yl)anilino]-2-oxo-ethyl]-2-methyl-pyrazole-3-carboxamide, N-[1-[[4-(3,5-dimethyl-1H-pyrazol-4-yl)phenyl]carbamoyl]-3,3,3-trifluoro-2-(trifluoromethyl)propyl]-2-methyl-pyrazole-3-carboxamide, N-[(1S)-1-(cyclohexylmethyl)-2-[4-(3,5-dimethyl-1H-pyrazol-4-yl)anilino]-2-oxo-ethyl]-2-methyl-pyrazole-3-carboxamide, N-[(1S)-1-(cyclohexylmethyl)-2-[4-(3,5-dimethyl-1H-pyrazol-4-yl)anilino]-2-oxo-ethyl]-2-ethyl-pyrazole-3-carboxamide, N-[(1S)-1-(cyclohexylmethyl)-2-[4-(3,5-dimethyl-1H-pyrazol-4-yl)anilino]-2-oxo-ethyl]-2-isopropyl-pyrazole-3-carboxamide, N-[(1S)-1-(4,4-difluorocyclohexyl)-2-[4-(3,5-dimethyl-1H-pyrazol-4-yl)anilino]-2-oxo-ethyl]-2-ethyl-pyrazole-3-carboxamide, N-[(1S)-1-[(1S)-3,3-difluorocyclohexyl]-2-[4-(3,5-dimethyl-1H-pyrazol-4-yl)anilino]-2-oxo-ethyl]-2-methyl-pyrazole-3-carboxamide, N-[2-[4-(3,5-dimethyl-1H-pyrazol-4-yl)anilino]-2-oxo-1-spiro[2.5]octan-6-yl-ethyl]-2-isopropyl-pyrazole-3-carboxamide, N-[2-[4-(3,5-dimethyl-1H-pyrazol-4-yl)anilino]-2-oxo-1-spiro[2.5]octan-6-yl-ethyl]-2-methyl-pyrazole-3-carboxamide, N-[(1S)-1-[(1S)-3,3-difluorocyclohexyl]-2-[4-(3,5-dimethyl-1H-pyrazol-4-yl)anilino]-2-oxo-ethyl]-2-ethyl-pyrazole-3-carboxamide, N-[(1S)-1-[(1S)-3,3-difluorocyclohexyl]-2-[4-(3,5-dimethyl-1H-pyrazol-4-yl)anilino]-2-oxo-ethyl]-2-isopropyl-pyrazole-3-carboxamide, N-[(1S)-1-[(2-chlorophenyl)methyl]-2-[4-(3,5-di methyl-1H-pyrazol-4-yl)anilino]-2-oxo-ethyl]-2-isopropyl-pyrazole-3-carboxamide, N-[(1S)-1-[(2-chlorophenyl)methyl]-2-[4-(3,5-di methyl-1H-pyrazol-4-yl)anilino]-2-oxo-ethyl]-2-methyl-pyrazole-3-carboxamide, N-[(1S)-1-[(4R)-chroman-4-yl]-2-[4-(3,5-dimethyl-1H-pyrazol-4-yl)anilino]-2-oxo-ethyl]-2-methyl-pyrazole-3-carboxamide, N-[(1S)-1-cyclohexyl-2-[4-(3,5-di methyl-1H-pyrazol-4-yl)anilino]-2-oxo-ethyl]-2-cyclopropyl-pyrazole-3-carboxamide, N-[(1S)-1-cyclohexyl-2-[4-(3,5-dimethyl-1H-pyrazol-4-yl)anilino]-2-oxo-ethyl]-2-(difluoromethyl)pyrazole-3-carboxamide, N-[(1S)-1-cyclohexyl-2-[4-(3,5-di methyl-1H-pyrazol-4-yl)anilino]-2-oxo-ethyl]-2-(2,2,2-trifluoroethyl)pyrazole-3-carboxamide, N-[1-(dicyclopropylmethyl)-2-[4-(3,5-dimethyl-1H-pyrazol-4-yl)anilino]-2-oxo-ethyl]-2-methyl-pyrazole-3-carboxamide, N-[1-(dicyclopropylmethyl)-2-[4-(3,5-dimethyl-1H-pyrazol-4-yl)anilino]-2-oxo-ethyl]-2-isopropyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide, N-[(1R)-1-(dicyclopropylmethyl)-2-[4-(3,5-dimethyl-1H-pyrazol-4-yl)anilino]-2-oxo-ethyl]-2-isopropyl-pyrazole-3-carboxamide, N-[(1S)-1-[(4S)-chroman-4-yl]-2-[4-(3,5-dimethyl-1H-pyrazol-4-yl)anilino]-2-oxo-ethyl]-2-methyl-pyrazole-3-carboxamide, N-[1-[di(cyclobutyl)methyl]-2-[4-(3,5-dimethyl-1H-pyrazol-4-yl)anilino]-2-oxo-ethyl]-2-ethyl-pyrazole-3-carboxamide, N-[(1S)-1-[di(cyclobutyl)methyl]-2-[4-(3,5-dimethyl-1H-pyrazol-4-yl)anilino]-2-oxo-ethyl]-2-ethyl-pyrazole-3-carboxamide, N-[(1R)-1-[di(cyclobutyl)methyl]-2-[4-(3,5-dimethyl-1H-pyrazol-4-yl)anilino]-2-oxo-ethyl]-2-ethyl-pyrazole-3-carboxamide, N-[1-[di(cyclobutyl)methyl]-2-[4-(3,5-dimethyl-1H-pyrazol-4-yl)anilino]-2-oxo-ethyl]-2-isopropyl-pyrazole-3-carboxamide, N-[(1S)-1-[di(cyclobutyl)methyl]-2-[4-(3,5-dimethyl-1H-pyrazol-4-yl)anilino]-2-oxo-ethyl]-2-isopropyl-pyrazole-3-carboxamide, N-[(1R)-1-[di(cyclobutyl)methyl]-2-[4-(3,5-dimethyl-1H-pyrazol-4-yl)anilino]-2-oxo-ethyl]-2-isopropyl-pyrazole-3-carboxamide, N-[(1S)-2-[4-(3,5-dimethyl-1H-pyrazol-4-yl)anilino]-2-oxo-1-[(7S)-spiro[2.5]octan-7-yl]ethyl]-2-isopropyl-pyrazole-3-carboxamide, N-[(1S)-1-[[4-(3,5-dimethyl-1H-pyrazol-4-yl)phenyl]carbamoyl]-2-methyl-propyl]-2-methyl-pyrazole-3-carboxamide; 2,2,2-trifluoroacetic acid, N-[(1S,2S)-1-[[4-(3,5-dimethyl-1H-pyrazol-4-yl)phenyl]carbamoyl]-2-methyl-butyl]-2-methyl-pyrazole-3-carboxamide, N-[(1S)-1-benzyl-2-[4-(3,5-dimethyl-1H-pyrazol-4-yl)anilino]-2-oxo-ethyl]-2-methyl-pyrazole-3-carboxamide, N-[(1S)-2-[4-(3,5-dimethyl-1H-pyrazol-4-yl)anilino]-1-[(4-hydroxyphenyl)methyl]-2-oxo-ethyl]-2-methyl-pyrazole-3-carboxamide, N-[(1S)-1-cyclohexyl-2-[4-(3,5-dimethyl-1H-pyrazol-4-yl)anilino]-2-oxo-ethyl]-2-(2-hydroxyethyl)pyrazole-3-carboxamide, N-[(1S)-1-[(4S)-chroman-4-yl]-2-[4-(3,5-di methyl-1H-pyrazol-4-yl)anilino]-2-oxo-ethyl]-2-isopropyl-pyrazole-3-carboxamide, N-[(1S)-1-cyclohexyl-2-[4-(3,5-dimethyl-1H-pyrazol-4-yl)anilino]-2-oxo-ethyl]-2,3-dimethyl-imidazole-4-carboxamide, N-[(1S)-1-cyclohexyl-2-[4-(3,5-dimethyl-1H-pyrazol-4-yl)anilino]-2-oxo-ethyl]-3-methyl-imidazole-4-carboxamide, N-[(1S)-1-cyclohexyl-2-[4-(3,5-dimethyl-1H-pyrazol-4-yl)anilino]-2-oxo-ethyl]-3,5-dimethyl-imidazole-4-carboxamide, (2S)-2-cyclohexyl-N-[4-(3,5-dimethyl-1H-pyrazol-4-yl)phenyl]-2-[[2-(4-methylthiazol-5-yl)acetyl]amino]acetamide, (2S)-2-cyclohexyl-N-[4-(3,5-di methyl-1H-pyrazol-4-yl)phenyl]-2-[[2-(2-methylthiazol-5-yl)acetyl]amino]acetamide, (2S)-2-cyclohexyl-N-[4-(3,5-di methyl-1H-pyrazol-4-yl)phenyl]-2-[[2-(2-methylimidazol-1-yl)acetyl]amino]acetamide, (2S)-2-cyclohexyl-2-[[2-(4-dimethylaminophenyl)acetyl]amino]-N-[4-(3,5-dimethyl-1H-pyrazol-4-yl)phenyl]acetamide, N-[(1S)-1-cyclohexyl-2-[4-(3,5-dimethyl-1H-pyrazol-4-yl)anilino]-2-oxo-ethyl]-2,2-difluoro-2-phenyl-acetamide, N-[(1S) -1-cyclohexyl-2-[4-(3,5-dimethyl-1H-pyrazol-4-yl)anilino]-2-oxo-ethyl]-2,2-difluoro-butanamide, N-[(1S)-1-cyclohexyl-2-[4-(3,5-dimethyl-1H-pyrazol-4-yl)anilino]-2-oxo-ethyl]-1-methyl-cyclopropanecarboxamide, N-[(1S)-1-cyclohexyl-2-[4-(3,5-dimethyl-1H-pyrazol-4-yl)anilino]-2-oxo-ethyl]-3-methyl-isoxazole-4-carboxamide, N-[(1S)-1-cycloheptyl-2-[4-(3,5-dimethyl-1H-pyrazol-4-yl)anilino]-2-oxo-ethyl]-3-methyl-isoxazole-4-carboxamide, N-[(1S)-1-cyclohexyl-2-[4-(3,5-dimethyl-1H-pyrazol-4-yl)anilino]-2-oxo-ethyl]-3-methyl-triazole-4-carboxamide, N-[(1S)-1-cyclohexyl-2-[4-(3,5-dimethyl-1H-pyrazol-4-yl)anilino]-2-oxo-ethyl]-3-phenyl-triazole-4-carboxamide, N-[(1S)-1-cycloheptyl-2-[4-(3,5-dimethyl-1H-pyrazol-4-yl)anilino]-2-oxo-ethyl]-3-methyl-triazole-4-carboxamide, N-[(1S)-1-cycloheptyl-2-[4-(3,5-dimethyl-1H-pyrazol-4-yl)anilino]-2-oxo-ethyl]-3-phenyl-triazole-4-carboxamide, N-[(1S)-1-cyclohexyl-2-[4-(3,5-dimethyl-1H-pyrazol-4-yl)anilino]-2-oxo-ethyl]-1H-pyrrolo[2,3-c]pyridine-3-carboxamide, N-[(1S)-1-cyclohexyl-2-[4-(3,5-dimethyl-1H-pyrazol-4-yl)anilino]-2-oxo-ethyl]-1H-pyrrolo[2,3-b]pyridine-3-carboxamide, N-[(1S)-1-cyclohexyl-2-[4-(3,5-dimethyl-1H-pyrazol-4-yl)anilino]-2-oxo-ethyl]-1-fluoro-cyclopropanecarboxamide, N-[(1S)-1-(4,4-difluorocyclohexyl)-2-[4-(3,5-dimethyl-1H-pyrazol-4-yl)anilino]-2-oxo-ethyl]-1-fluoro-cyclopropanecarboxamide, N-[(1S)-1-cyclohexyl-2-[4-(3,5-dimethyl-1H-pyrazol-4-yl)anilino]-2-oxo-ethyl]pyrazolo[1,5-a]pyridine-3-carboxamide, 3-(4-chlorophenyl)-N-[(1S)-1-cyclohexyl-2-[4-(3,5-dimethyl-1H-pyrazol-4-yl)anilino]-2-oxo-ethyl]isoxazole-4-carboxamide, N-[(1S)-1-cyclohexyl-2-[4-(3,5-dimethyl-1H-pyrazol-4-yl)anilino]-2-oxo-ethyl]pyrazolo[1,5-b]pyridazine-3-carboxamide, N-[(1S)-1-cyclohexyl-2-[4-(3,5-dimethyl-1H-pyrazol-4-yl)anilino]-2-oxo-ethyl]-1-methyl-pyrrolo[2,3-b]pyridine-3-carboxamide, N-[(1S)-1-cyclohexyl-2-[4-(3,5-dimethyl-1H-pyrazol-4-yl)anilino]-2-oxo-ethyl]imidazo[1,2-a]pyrimidine-3-carboxamide, N-[(1S)-1-cyclohexyl-2-[4-(3,5-di methyl-1H-pyrazol-4-yl)anilino]-2-oxo-ethyl]benzofuran-3-carboxamide, N-[(1S)-1-cyclohexyl-2-[4-(3,5-di methyl-1H-pyrazol-4-yl)anilino]-2-oxo-ethyl]benzothiophene-3-carboxamide, N-[(1S)-1-cyclohexyl-2-[4-(3,5-dimethyl-1H-pyrazol-4-yl)anilino]-2-oxo-ethyl]-3-isopropyl-triazole-4-carboxamide, N-[(1S)-2-[4-(3,5-dimethyl-1H-pyrazol-4-yl)anilino]-1-[(1R)-indan-1-yl]-2-oxo-ethyl]-2-methyl-pyrazole-3-carboxamide, N-[(1S)-1-[(1R)-6-chloroindan-1-yl]-2-[4-(3,5-dimethyl-1H-pyrazol-4-yl)anilino]-2-oxo-ethyl]-2-methyl-pyrazole-3-carboxamide, N-[(1S)-1-[(1R)-6-cyanoindan-1-yl]-2-[4-(3,5-di methyl-1H-pyrazol-4-yl)anilino]-2-oxo-ethyl]-2-methyl-pyrazole-3-carboxamide, N-[(1S)-2-[4-(3,5-dimethyl-1H-pyrazol-4-yl)anilino]-1-[(1S)-indan-1-yl]-2-oxo-ethyl]-2-methyl-pyrazole-3-carboxamide, N-[(1S)-1-[(1S)-6-cyanoindan-1-yl]-2-[4-(3,5-dimethyl-1H-pyrazol-4-yl)anilino]-2-oxo-ethyl]-2-methyl-pyrazole-3-carboxamide, N-[(1S)-2-[4-(3,5-dimethyl-1H-pyrazol-4-yl)anilino]-2-oxo-1-[(1S)-tetralin-1-yl]ethyl]-2-methyl-pyrazole-3-carboxamide, N-[(1S)-1-[(1S)-7-cyanotetralin-1-yl]-2-[4-(3,5-dimethyl-1H-pyrazol-4-yl)anilino]-2-oxo-ethyl]-2-methyl-pyrazole-3-carboxamide, tert-butyl N-[(1S)-1-cyclohexyl-2-[4-(3,5-dimethylimidazol-4-yl)anilino]-2-oxo-ethyl]carbamate, tert-butyl N-[1-(dicyclopropylmethyl)-2-[4-(3,5-dimethylimidazol-4-yl)anilino]-2-oxo-ethyl]carbamate, tert-butyl N-[1-(4,4-difluorocyclohexyl)-2-[4-(3,5-dimethylimidazol-4-yl)anilino]-2-oxo-ethyl]carbamate, tert-butyl N-[(1S)-1-cyclopentyl-2-[4-(3,5-dimethylimidazol-4-yl)anilino]-2-oxo-ethyl]carbamate, tert-butyl N-[(1S)-1-cycloheptyl-2-[4-(3,5-dimethylimidazol-4-yl)anilino]-2-oxo-ethyl]carbamate, tert-butyl N-[(1S)-1-[[4-(3,5-dimethylimidazol-4-yl)phenyl]carbamoyl]-2-ethyl-butyl]carbamate, tert-butyl N-[(1S)-1-[(1R)-7-bromotetralin-1-yl]-2-[4-(3-methylimidazol-4-yl)anilino]-2-oxo-ethyl]carbamate, tert-butyl N-[(1S)-2-methyl-1-[[4-(3-methylimidazol-4-yl)phenyl]carbamoyl]propyl]carbamate, tert-butyl N-[(1S)-1-cyclobutyl-2-[4-(3-methylimidazol-4-yl)anilino]-2-oxo-ethyl]carbamate, tert-butyl N-[(1S)-1-(cyclohexylmethyl)-2-[4-(3-methylimidazol-4-yl)anilino]-2-oxo-ethyl]carbamate, tert-butyl N-[(1S)-2-methyl-1-[[4-(3-methylimidazol-4-yl)phenyl]carbamoyl]butyl]carbamate, tert-butyl N-[(1S)-1-benzyl-2-[4-(3-methylimidazol-4-yl)anilino]-2-oxo-ethyl]carbamate, tert-butyl N-[(1S)-3-methyl-1-[[4-(3-methylimidazol-4-yl)phenyl]carbamoyl]butyl]carbamate, tert-butyl N-[(1S)-1-[(2-chlorophenyl)methyl]-2-[4-(3-methylimidazol-4-yl)anilino]-2-oxo-ethyl]carbamate, tert-butyl N-[(1S)-1-cyclopentyl-2-[4-(3-methylimidazol-4-yl)anilino]-2-oxo-ethyl]carbamate, tert-butyl N-[(1S)-1-indan-2-yl-2-[4-(3-methylimidazol-4-yl)anilino]-2-oxo-ethyl]carbamate, tert-butyl N-[(1S)-1-cyclohexyl-2-[4-(3-methylimidazol-4-yl)anilino]-2-oxo-ethyl]carbamate, tert-butyl N-[(1S)-1-benzhydryl-2-[4-(3-methylimidazol-4-yl)anilino]-2-oxo-ethyl]carbamate, N-[(1S)-1-(dicyclopropylmethyl)-2-[4-(3,5-dimethyl-1H-pyrazol-4-yl)anilino]-2-oxo-ethyl]-2-(3-hydroxypropyl)pyrazole-3-carboxamide, N-[(1R)-1-cyclohexyl-2-[4-(3,5-dimethyl-1H-pyrazol-4-yl)anilino]-2-oxo-ethyl]-2-methyl-pyrazole-3-carboxamide, N-[(1S)-1-cyclohexyl-2-[4-(3,5-dimethyl-1H-pyrazol-4-yl)anilino]-2-oxo-ethyl]-2-(2-hydroxy-1-methyl-ethyl)pyrazole-3-carboxamide, N-[(1S)-1-cyclohexyl-2-[4-(3,5-dimethyl-1H-pyrazol-4-yl)anilino]-2-oxo-ethyl]-2-(2,2-difluoroethyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-ethyl-pyrazole-3-carboxamide, 2-cyclobutyl-N-[(1S)-1-cyclohexyl-2-[4-(3,5-dimethyl-1H-pyrazol-4-yl)anilino]-2-oxo-ethyl]pyrazole-3-carboxamide, N-[(1S,2S)-1-[[4-(3,5-dimethyl-1H-pyrazol-4-yl)phenyl]carbamoyl]-2-methyl-butyl]-2-ethyl-pyrazole-3-carboxamide, N-[(1S,2S)-1-[[4-(3,5-dimethyl-1H-pyrazol-4-yl)phenyl]carbamoyl]-2-methyl-butyl]-2-isopropyl-pyrazole-3-carboxamide, N-[(1R)-2-[4-(3,5-dimethyl-1H-pyrazol-4-yl)anilino]-2-oxo-1-spiro[2.5]octan-6-yl-ethyl]-2-isopropyl-pyrazole-3-carboxamide, N-[(1S)-2-[4-(3,5-dimethyl-1H-pyrazol-4-yl)anilino]-2-oxo-1-spiro[2.5]octan-6-yl-ethyl]-2-isopropyl-pyrazole-3-carboxamide, N-[(1S,2R)-1-[[4-(3,5-dimethyl-1H-pyrazol-4-yl)phenyl]carbamoyl]-2-methyl-butyl]-2-methyl-pyrazole-3-carboxamide, 2-cyclobutyl-N-[(1S)-1-(dicyclopropylmethyl)-2-[4-(3,5-dimethyl-1H-pyrazol-4-yl)anilino]-2-oxo-ethyl]pyrazole-3-carboxamide, N-[(1S)-1-(dicyclopropylmethyl)-2-[4-(3,5-dimethyl-1H-pyrazol-4-yl)anilino]-2-oxo-ethyl]-2-(2,2-difluoroethyl)pyrazole-3-carboxamide, 2-cyclopropyl-N-[(1S)-1-(dicyclopropylmethyl)-2-[4-(3,5-dimethyl-1H-pyrazol-4-yl)anilino]-2-oxo-ethyl]pyrazole-3-carboxamide, N-[(1S)-1-(dicyclopropylmethyl)-2-[4-(3,5-dimethyl-1H-pyrazol-4-yl)anilino]-2-oxo-ethyl]-2-methyl-pyrazole-3-carboxamide, N-[(1S)-1-[[4-(3,5-dimethyl-1H-pyrazol-4-yl)phenyl]carbamoyl]-2-ethyl-butyl]-2-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-[(1S)-2-hydroxy-1-methyl-ethyl]pyrazole-3-carboxamide, N-[(1S)-1-(dicyclopropylmethyl)-2-[4-(3,5-dimethyl-1H-pyrazol-4-yl)anilino]-2-oxo-ethyl]-2-[(1R)-2-hydroxy-1-methyl-ethyl]pyrazole-3-carboxamide, N-[(1S)-1-[[4-(3,5-dimethyl-1H-pyrazol-4-yl)phenyl]carbamoyl]-2-ethyl-butyl]-2-isopropyl-pyrazole-3-carboxamide, N-[(1S)-1-[di(cyclobutyl)methyl]-2-[4-(3,5-dimethyl-1H-pyrazol-4-yl)anilino]-2-oxo-ethyl]-2-(2-hydroxyethyl)pyrazole-3-carboxamide, N-[(1S)-1-[di(cyclobutyl)methyl]-2-[4-(3,5-dimethyl-1H-pyrazol-4-yl)anilino]-2-oxo-ethyl]-2-(2-hydroxy-1-methyl-ethyl)pyrazole-3-carboxamide, N-[(1 S)-2-[4-(3,5-dimethyl-1H-pyrazol-4-yl)anilino]-1-(4-methylcyclohexyl)-2-oxo-ethyl]-2-methyl-pyrazole-3-carboxamide, N-[(1S)-2-[4-(3,5-dimethyl-1H-pyrazol-4-yl)anilino]-1-(4-methylcyclohexyl)-2-oxo-ethyl]-2-ethyl-pyrazole-3-carboxamide, N-[(1 S)-2-[4-(3,5-dimethyl-1H-pyrazol-4-yl)anilino]-1-(4-methylcyclohexyl)-2-oxo-ethyl]-2-isopropyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-sec-butyl-pyrazole-3-carboxamide, 2-(cyclopropyl methyl)-N-[(1S)-1-(dicyclopropylmethyl)-2-[4-(3,5-dimethyl-1H-pyrazol-4-yl)anilino]-2-oxo-ethyl]pyrazole-3-carboxamide, N-[(1S)-1-(dicyclopropylmethyl)-2-[4-(3,5-dimethyl-1H-pyrazol-4-yl)anilino]-2-oxo-ethyl]-2-(3,3,3-trifluoropropyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-(2-dimethylaminoethyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-isobutyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-propyl-pyrazole-3-carboxamide, N-[(1S)-1-[(3R,5S)-3,5-dimethylcyclohexyl]-2-[4-(3,5-dimethyl-1H-pyrazol-4-yl)anilino]-2-oxo-ethyl]-2-[(1S)-2-hydroxy-1-methyl-ethyl]pyrazole-3-carboxamide, N-[1-cyclooctyl-2-[4-(3,5-dimethyl-1H-pyrazol-4-yl)anilino]-2-oxo-ethyl]-2-(3-hydroxybutyl)pyrazole-3-carboxamide, N-[(1S)-1-[(3R,5S)-3,5-dimethylcyclohexyl]-2-[4-(3,5-dimethyl-1H-pyrazol-4-yl)anilino]-2-oxo-ethyl]-2-methyl-pyrazole-3-carboxamide, N-[(1S)-1-[(3R,5S)-3,5-dimethylcyclohexyl]-2-[4-(3,5-dimethyl-1H-pyrazol-4-yl)anilino]-2-oxo-ethyl]-2-isopropyl-pyrazole-3-carboxamide, N-[(1 S)-2-[4-(3,5-dimethyl-1H-pyrazol-4-yl)anilino]-1-(4-methylcyclohexyl)-2-oxo-ethyl]-3-isopropyl-triazole-4-carboxamide, N-[(1S)-2-[4-(3,5-dimethyl-1H-pyrazol-4-yl)anilino]-1-(4-methylcyclohexyl)-2-oxo-ethyl]-3-ethyl-triazole-4-carboxamide, N-[1-cyclooctyl-2-[4-(3,5-dimethyl-1H-pyrazol-4-yl)anilino]-2-oxo-ethyl]-2-[(1S)-2-hydroxy-1-methyl-ethyl]pyrazole-3-carboxamide, N-[1-cyclooctyl-2-[4-(3,5-dimethyl-1H-pyrazol-4-yl)anilino]-2-oxo-ethyl]-2-(1-methylethyl)pyrazole-3-carboxamide, N-[1-cyclooctyl-2-[4-(3,5-dimethyl-1H-pyrazol-4-yl)anilino]-2-oxo-ethyl]-2-ethyl-pyrazole-3-carboxamide, N-[1-cyclooctyl-2-[4-(3,5-dimethyl-1H-pyrazol-4-yl)anilino]-2-oxo-ethyl]-2-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-(2-methylsulfonylethyl)pyrazole-3-carboxamide, N-[(1S)-3-cyclopropyl-1-[[4-(3,5-dimethyl-1H-pyrazol-4-yl)phenyl]carbamoyl]-2-methyl-propyl]-2-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-[(1S,2S) and (1R,2R)-2-hydroxy-1-methyl-propyl]pyrazole-3-carboxamide, N-[(1S)-1-(dicyclopropylmethyl)-2-[4-(3,5-dimethyl-1H-pyrazol-4-yl)anilino]-2-oxo-ethyl]-2-isopropyl-1,2,4-triazole-3-carboxamide, N-[(1S)-1-(dicyclopropylmethyl)-2-[4-(3,5-dimethyl-1H-pyrazol-4-yl)anilino]-2-oxo-ethyl]-2-methyl-1,2,4-triazole-3-carboxamide, N-[(1S)-2-cyclobutyl-1-[[4-(3,5-dimethyl-1H-pyrazol-4-yl)phenyl]carbamoyl]propyl]-2-[(1R)-2-hydroxy-1-methyl-ethyl]pyrazole-3-carboxamide, N-[(1S)-1-[di(cyclobutyl)methyl]-2-[4-(3,5-dimethyl-1H-pyrazol-4-yl)anilino]-2-oxo-ethyl]-2-(3-hydroxypropyl)pyrazole-3-carboxamide, N-[(1S)-1-(dicyclopropylmethyl)-2-[4-(3,5-dimethyl-1H-pyrazol-4-yl)anilino]-2-oxo-ethyl]benzamide, N-[(1S)-1-(dicyclopropylmethyl)-2-[4-(3,5-dimethyl-1H-pyrazol-4-yl)anilino]-2-oxo-ethyl]-2,2-dimethyl-propanamide, N-[(1S)-1-(dicyclopropylmethyl)-2-[4-(3,5-dimethyl-1H-pyrazol-4-yl)anilino]-2-oxo-ethyl]cyclobutanecarboxamide, N-[(1S)-1-(dicyclopropylmethyl)-2-[4-(3,5-dimethyl-1H-pyrazol-4-yl)anilino]-2-oxo-ethyl]cyclopentanecarboxamide, 2-(1-cyanoethyl)-N-[(1S)-1-(dicyclopropylmethyl)-2-[4-(3,5-dimethyl-1H-pyrazol-4-yl)anilino]-2-oxo-ethyl]pyrazole-3-carboxamide, 1-(1-cyanoethyl)-N-[(1S)-1-(dicyclopropylmethyl)-2-[4-(3,5-dimethyl-1H-pyrazol-4-yl)anilino]-2-oxo-ethyl]pyrazole-3-carboxamide, N-[(1S)-2-cyclobutyl-1-[[4-(3,5-dimethyl-1H-pyrazol-4-yl)phenyl]carbamoyl]propyl]-2-[(1S)-2-hydroxy-1-methyl-ethyl]pyrazole-3-carboxamide, N-[(1S)-1-[[4-(3,5-dimethyl-1H-pyrazol-4-yl)phenyl]carbamoyl]-2,3,3-trimethyl-butyl]-2-[2-hydroxy-1-methyl-ethyl]pyrazole-3-carboxamide, N-[(1S)-1-(dicyclopropylmethyl)-2-[4-(3,5-dimethyl-1H-pyrazol-4-yl)anilino]-2-oxo-ethyl]-2-(4,4,4-trifluoro-3-hydroxy-butyl)pyrazole-3-carboxamide, N-[(1S)-1-[(7S)-6,6-difluorospiro[2.5]octan-7-yl]-2-[4-(3,5-dimethyl-1H-pyrazol-4-yl)anilino]-2-oxo-ethyl]-2-ethyl-pyrazole-3-carboxamide, N-[(1S)-1-[(7S)-6,6-difluorospiro[2.5]octan-7-yl]-2-[4-(3,5-dimethyl-1H-pyrazol-4-yl)anilino]-2-oxo-ethyl]-2-isopropyl-pyrazole-3-carboxamide, N-[(1S)-1-[(7S)-6,6-difluorospiro[2.5]octan-7-yl]-2-[4-(3,5-dimethyl-1H-pyrazol-4-yl)anilino]-2-oxo-ethyl]-2-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-(2-hydroxyethyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-(2,2,2-trifluoroethyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-(3-hydroxybutyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-(2,2-difluoropropyl)pyrazole-3-carboxamide, N-[(1S)-1-(2-adamantyl)-2-[4-(3,5-dimethyl-1H-pyrazol-4-yl)anilino]-2-oxo-ethyl]-2-(2-hydroxy-1-methyl-ethyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-(2,2-difluoro-1-methyl-ethyl)pyrazole-3-carboxamide, N-[(1S)-2-cyclobutyl-1-[[4-(3,5-dimethyl-1H-pyrazol-4-yl)phenyl]carbamoyl]propyl]-2-isopropyl-pyrazole-3-carboxamide, N-[(1S)-2-cyclobutyl-1-[[4-(3,5-dimethyl-1H-pyrazol-4-yl)phenyl]carbamoyl]propyl]-2-ethyl-pyrazole-3-carboxamide, N-[(1S)-2-cyclobutyl-1-[[4-(3,5-dimethyl-1H-pyrazol-4-yl)phenyl]carbamoyl]propyl]-2-methyl-pyrazole-3-carboxamide, N-[(1S)-1-[[4-(3,5-dimethyl-1H-pyrazol-4-yl)phenyl]carbamoyl]-2,4,4-trimethyl-pentyl]-2-methyl-pyrazole-3-carboxamide, N-[(1S)-1-[[4-(3,5-dimethyl-1H-pyrazol-4-yl)phenyl]carbamoyl]-2,3-dimethyl-butyl]-2-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-1-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-1-ethyl-pyrazole-3-carboxamide, N-[(1S)-1-(2-adamantyl)-2-[4-(3,5-dimethyl-1H-pyrazol-4-yl)anilino]-2-oxo-ethyl]-2-isopropyl-pyrazole-3-carboxamide, N-[(1S)-1-(2-adamantyl)-2-[4-(3,5-dimethyl-1H-pyrazol-4-yl)anilino]-2-oxo-ethyl]-2-ethyl-pyrazole-3-carboxamide, N-[(1S)-1-(2-adamantyl)-2-[4-(3,5-dimethyl-1H-pyrazol-4-yl)anilino]-2-oxo-ethyl]-2-methyl-pyrazole-3-carboxamide, N-[(1 S)-2-[4-(3,5-dimethyl-1H-pyrazol-4-yl)anilino]-1-(4-methylcyclohexyl)-2-oxo-ethyl]-2-(3-hydroxybutyl)pyrazole-3-carboxamide, N-[(1 S)-2-[4-(3,5-dimethyl-1H-pyrazol-4-yl)anilino]-1-(trans-4-methylcyclohexyl)-2-oxo-ethyl]-2-(2-hydroxy-1-methyl-ethyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-(2-methoxyethyl)pyrazole-3-carboxamide, 2-(cyanomethyl)-N-[(1S)-1-(dicyclopropylmethyl)-2-[4-(3,5-dimethyl-1H-pyrazol-4-yl)anilino]-2-oxo-ethyl]pyrazole-3-carboxamide, N-[(1S)-2-[4-(3,5-dimethyl-1H-pyrazol-4-yl)anilino]-1-(4-methylcyclohexyl)-2-oxo-ethyl]-2-(3-hydroxypropyl)pyrazole-3-carboxamide, N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-(3-hydroxypropyl)pyrazole-3-carboxamide, N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-(2-hydroxy-1-methyl-ethyl) pyrazole-3-carboxamide, N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-isopropyl-pyrazole-3-carboxamide, N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-ethyl-pyrazole-3-carboxamide, N-[(1S)-1-[(1S)-2,2-difluoro-5,5-dimethyl-cyclohexyl]-2-[4-(3,5-dimethyl-1H-pyrazol-4-yl)anilino]-2-oxo-ethyl]-2-(2-ethyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-(3,3-difluoropropyl)pyrazole-3-carboxamide, N-[(1S)-1-(dicyclopropylmethyl)-2-[4-(3,5-dimethyl-1H-pyrazol-4-yl)anilino]-2-oxo-ethyl]-1H-pyrazole-5-carboxamide, N-[(1S)-1-(dicyclopropylmethyl)-2-[4-(3,5-dimethyl-1H-pyrazol-4-yl)anilino]-2-oxo-ethyl]-2-[2-fluoro-1-(fluoromethyl)ethyl]pyrazole-3-carboxamide, N-[(1S)-1-(dicyclopropylmethyl)-2-[4-(3,5-dimethyl-1H-pyrazol-4-yl)anilino]-2-oxo-ethyl]-2-(2-fluoro-1-methyl-ethyl)pyrazole-3-carboxamide, N-[(1S)-1-(dicyclopropylmethyl)-2-[4-(3,5-dimethyl-1H-pyrazol-4-yl)anilino]-2-oxo-ethyl]-2-tetrahydrofuran-3-yl-pyrazole-3-carboxamide, N-[(1S)-2-cyclohexyl-1-[[4-(3,5-dimethyl-1H-pyrazol-4-yl)phenyl]carbamoyl]propyl]-2-methyl-pyrazole-3-carboxamide, N-[(1S)-2-cyclopentyl-1-[[4-(3,5-dimethyl-1H-pyrazol-4-yl)phenyl]carbamoyl]propyl]-2-methyl-pyrazole-3-carboxamide, 2-(1-cyclopropylethyl)-N-[(1S)-1-(dicyclopropylmethyl)-2-[4-(3,5-dimethyl-1H-pyrazol-4-yl)anilino]-2-oxo-ethyl] pyrazole-3-carboxamide, N-[(1S)-2-[4-(3,5-dimethyl-1H-pyrazol-4-yl)anilino]-2-oxo-1-spiro[2.3]hexan-2-yl-ethyl]-2-methyl-pyrazole-3-carboxamide, N-[(1S)-1-(2,2-dimethylcyclopropyl)-2-[4-(3,5-dimethyl-1H-pyrazol-4-yl)anilino]-2-oxo-ethyl]-2-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-(3-hydroxy-1-methyl-propyl)pyrazole-3-carboxamide, N-[(2S)-1-[[4-(3,5-dimethyl-1H-pyrazol-4-yl)phenyl]carbamoyl]-2-phenyl-butyl]-2-methyl-pyrazole-3-carboxamide, N-[(1S)-1-(cyclobutylmethyl)-2-[4-(3,5-dimethyl-1H-pyrazol-4-yl)anilino]-2-oxo-ethyl]-2-methyl-pyrazole-3-carboxamide, N-[(1S)-1-(2,2-dimethylcyclohexyl)-2-[4-(3,5-dimethyl-1H-pyrazol-4-yl)anilino]-2-oxo-ethyl]-2-methyl-pyrazole-3-carboxamide, N-[(1S)-1-(2,2-dimethylcyclopentyl)-2-[4-(3,5-dimethyl-1H-pyrazol-4-yl)anilino]-2-oxo-ethyl]-2-methyl-pyrazole-3-carboxamide, N-[(1S)-1-(2,2-dimethylcyclobutyl)-2-[4-(3,5-dimethyl-1H-pyrazol-4-yl)anilino]-2-oxo-ethyl]-2-methyl-pyrazole-3-carboxamide, N-[(1S)-1-[(1R,5S)-3-bicyclo[3.1.0]hexanyl]-2-[4-(3,5-dimethyl-1H-pyrazol-4-yl)anilino]-2-oxo-ethyl]-2-methyl-pyrazole-3-carboxamide, N-[(2S)-1-[[4-(3,5-dimethyl-1H-pyrazol-4-yl)phenyl]carbamoyl]-2-phenyl-propyl]-2-methyl-pyrazole-3-carboxamide, N-[(2R)-1-[[4-(3,5-dimethyl-1H-pyrazol-4-yl)phenyl]carbamoyl]-2-phenyl-propyl]-2-methyl-pyrazole-3-carboxamide, N-[(1S)-1-(4,4-dimethylcyclohexyl)-2-[4-(3,5-dimethyl-1H-pyrazol-4-yl)anilino]-2-oxo-ethyl]-2-methyl-pyrazole-3-carboxamide, N-[(1S)-1-(3,3-dimethylcyclohexyl)-2-[4-(3,5-dimethyl-1H-pyrazol-4-yl)anilino]-2-oxo-ethyl]-2-methyl-pyrazole-3-carboxamide, N-[(1S)-1-[[4-(3,5-dimethyl-1H-pyrazol-4-yl)phenyl]carbamoyl]-2-ethyl-butyl]-2-isopropyl-pyrazole-3-carboxamide, N-[(1S)-2-[4-(3,5-dimethyl-1H-pyrazol-4-yl)anilino]-2-oxo-1-[(7R)-spiro[2.5]octan-7-yl]ethyl]-2-methyl-pyrazole-3-carboxamide, N-[(1S)-1-[[4-(3,5-dimethyl-1H-pyrazol-4-yl)phenyl]carbamoyl]-2-ethyl-butyl]-2-methyl-pyrazole-3-carboxamide, N-[(1S)-1-(cyclopropylmethyl)-2-[4-(3,5-di methyl-1H-pyrazol-4-yl)anilino]-2-oxo-ethyl]-2-methyl-pyrazole-3-carboxamide, N-[(1S)-1-[[4-(3,5-dimethyl-1H-pyrazol-4-yl)phenyl]carbamoyl]-2-isopropyl-3-methyl-butyl]-2-methyl-pyrazole-3-carboxamide, N-[(1S)-2-[4-(3,5-dimethyl-1H-pyrazol-4-yl)anilino]-2-oxo-1-(2,2,3,3-tetramethylcyclopropyl)ethyl]-2-methyl-pyrazole-3-carboxamide, N-[(1 S)-2-[4-(3,5-dimethyl-1H-pyrazol-4-yl)anilino]-1-norcaran-7-yl-2-oxo-ethyl]-2-methyl-pyrazole-3-carboxamide, N-[(1S)-2-[4-(3,5-dimethyl-1H-pyrazol-4-yl)anilino]-1-[(1S)-4-fluoroindan-1-yl]-2-oxo-ethyl]-2-methyl-pyrazole-3-carboxamide, N-[(1R)-2-[4-(3,5-dimethyl-1H-pyrazol-4-yl)anilino]-1-[(1S)-4-fluoroindan-1-yl]-2-oxo-ethyl]-2-methyl-pyrazole-3-carboxamide, N-[(1S)-1-[(1S)-4,6-difluoroindan-1-yl]-2-[4-(3,5-dimethyl-1H-pyrazol-4-yl)anilino]-2-oxo-ethyl]-2-methyl-pyrazole-3-carboxamide, N-[(1S)-2-[4-(3,5-dimethyl-1H-pyrazol-4-yl)anilino]-2-oxo-1-[(7S)-spiro[2.5]octan-7-yl]ethyl]-2-methyl-pyrazole-3-carboxamide, N-[2-[4-(3,5-dimethyl-1H-pyrazol-4-yl)anilino]-1-(2-methylcyclopentyl)-2-oxo-ethyl]-2-isopropyl-pyrazole-3-carboxamide, N-[2-[4-(3,5-dimethyl-1H-pyrazol-4-yl)anilino]-1-(2-methylcyclopentyl)-2-oxo-ethyl]-2-methyl-pyrazole-3-carboxamide, N-[(1S)-1-[(4,4-difluorocyclohexyl)methyl]-2-[4-(3,5-dimethyl-1H-pyrazol-4-yl)anilino]-2-oxo-ethyl]-2-methyl-pyrazole-3-carboxamide, N-[(1S)-1-(3-bicyclo[2.2.2]octanyl)-2-[4-(3,5-dimethyl-1H-pyrazol-4-yl)anilino]-2-oxo-ethyl]-2-methyl-pyrazole-3-carboxamide, N-[(1S)-1-[(1S)-5,7-difluorotetralin-1-yl]-2-[4-(3,5-dimethyl-1H-pyrazol-4-yl)anilino]-2-oxo-ethyl]-2-methyl-pyrazole-3-carboxamide, N-[(1S)-2-[4-(3,5-dimethyl-1H-pyrazol-4-yl)anilino]-1-[(1S)-5-fluorotetralin-1-yl]-2-oxo-ethyl]-2-methyl-pyrazole-3-carboxamide, N-[(1S)-2-cyclohexyl-1-[[4-(3,5-dimethyl-1H-pyrazol-4-yl)phenyl]carbamoyl]butyl]-2-methyl-pyrazole-3-carboxamide, N-[(1R)-2-[4-(3,5-dimethyl-1H-pyrazol-4-yl)anilino]-1-[(1S)-6-fluorotetralin-1-yl]-2-oxo-ethyl]-2-methyl-pyrazole-3-carboxamide, N-[(1S)-2-[4-(3,5-dimethyl-1H-pyrazol-4-yl)anilino]-1-[(1S)-6-fluorotetralin-1-yl]-2-oxo-ethyl]-2-methyl-pyrazole-3-carboxamide, N-[(1S)-2-[4-(3,5-dimethyl-1H-pyrazol-4-yl)anilino]-1-[(1S)-7-fluorotetralin-1-yl]-2-oxo-ethyl]-2-methyl-pyrazole-3-carboxamide; 2,2,2-trifluoroacetic acid, N-[(1S)-1-[(1R)-7-bromo-5-fluoro-tetralin-1-yl]-2-[4-(3,5-di methyl-1H-pyrazol-4-yl)anilino]-2-oxo-ethyl]-2-methyl-pyrazole-3-carboxamide; 2,2,2-trifluoroacetic acid, N-[(1S)-2-[4-(3,5-dimethyl-1H-pyrazol-4-yl)anilino]-2-oxo-1-spiro[2.5]octan-6-yl-ethyl]-3-isopropyl-isoxazole-4-carboxamide, N-[(1S)-2-[4-(3,5-dimethyl-1H-pyrazol-4-yl)anilino]-2-oxo-1-spiro[2.5]octan-6-yl-ethyl]-2-ethyl-pyrazole-3-carboxamide, N-[1-(3,3-dimethylcyclopentyl)-2-[4-(3,5-dimethyl-1H-pyrazol-4-yl)anilino]-2-oxo-ethyl]-2-isopropyl-pyrazole-3-carboxamide, N-[1-(3,3-dimethylcyclopentyl)-2-[4-(3,5-dimethyl-1H-pyrazol-4-yl)anilino]-2-oxo-ethyl]-2-methyl-pyrazole-3-carboxamide, N-[(1S)-1-(6-bicyclo[3.1.0]hexanyl)-2-[4-(3,5-dimethyl-1H-pyrazol-4-yl)anilino]-2-oxo-ethyl]-2-methyl-pyrazole-3-carboxamide.

N-[(1S)-1-[(3S,5R)-3,5-dimethylcyclohexyl]-2-[4-(3,5-dimethyl-1H-pyrazol-4-yl)anilino]-2-oxo-ethyl]-2-methyl-pyrazole-3-carboxamide, N-[(1S)-2-[4-(3,5-dimethyl-1H-pyrazol-4-yl)anilino]-2-oxo-1-[4-(trifluoromethyl)cyclohexyl]ethyl]-2-methyl-pyrazole-3-carboxamide, N-[(1S)-1-(dicyclopropylmethyl)-2-[4-(3,5-dimethyl-1H-pyrazol-4-yl)anilino]-2-oxo-ethyl]-3-ethyl-triazole-4-carboxamide, N-[(1S)-1-[di(cyclobutyl)methyl]-2-[4-(3,5-dimethyl-1H-pyrazol-4-yl)anilino]-2-oxo-ethyl]-3-ethyl-triazole-4-carboxamide, N-[(1S)-1-[di(cyclobutyl)methyl]-2-[4-(3,5-dimethyl-1H-pyrazol-4-yl)anilino]-2-oxo-ethyl]-3-methyl-triazole-4-carboxamide, N-[(1S)-1-[di(cyclobutyl)methyl]-2-[4-(3,5-dimethyl-1H-pyrazol-4-yl)anilino]-2-oxo-ethyl]-3-isopropyl-triazole-4-carboxamide, N-[(1S)-1-[di(cyclobutyl)methyl]-2-[4-(3,5-dimethyl-1H-pyrazol-4-yl)anilino]-2-oxo-ethyl]-3-methyl-isoxazole-4-carboxamide, N-[(1S)-1-cyclohexyl-2-[4-(3,5-dimethyl-1H-pyrazol-4-yl)anilino]-2-oxo-ethyl]-1-methyl-imidazole-2-carboxamide, N-[(1S)-1-cyclohexyl-2-[4-(3,5-dimethyl-1H-pyrazol-4-yl)anilino]-2-oxo-ethyl]-3-ethyl-isoxazole-4-carboxamide, N-[(1S)-1-cyclohexyl-2-[4-(3,5-dimethyl-1H-pyrazol-4-yl)anilino]-2-oxo-ethyl]-3-isopropyl-isoxazole-4-carboxamide, N-[(1S)-1-[(1R)-6-bromo-4-fluoro-indan-1-yl]-2-[4-(3,5-dimethyl-1H-pyrazol-4-yl)anilino]-2-oxo-ethyl]-2-methyl-pyrazole-3-carboxamide, N-[(1S)-1-[(4S)-6,8-difluorochroman-4-yl]-2-[4-(3,5-dimethyl-1H-pyrazol-4-yl)anilino]-2-oxo-ethyl]-2-isopropyl-pyrazole-3-carboxamide, N-[(1S,2R)-1-[[4-(3,5-dimethyl-1H-pyrazol-4-yl)phenyl]carbamoyl]-2-methyl-butyl]-2-methyl-pyrazole-3-carboxamide, N-[(1S)-1-[[4-(3,5-dimethyl-1H-pyrazol-4-yl)phenyl]carbamoyl]-3,3-dimethyl-butyl]-2-methyl-pyrazole-3-carboxamide, N-[(1S,2R)-2-cyclopropyl-1-[[4-(3,5-dimethyl-1H-pyrazol-4-yl)phenyl]carbamoyl]propyl]-2-isopropyl-pyrazole-3-carboxamide, N-[(1S,2S)-2-cyclopropyl-1-[[4-(3,5-dimethyl-1H-pyrazol-4-yl)phenyl]carbamoyl]propyl]-2-isopropyl-pyrazole-3-carboxamide, N-[(1S,2S)-1-[[4-(3,5-dimethyl-1H-pyrazol-4-yl)phenyl]carbamoyl]-2-methyl-butyl]-2-isopropyl-pyrazole-3-carboxamide, N-[(1S,2S)-1-[[4-(3,5-dimethyl-1H-pyrazol-4-yl)phenyl]carbamoyl]-2-methyl-butyl]-2-ethyl-pyrazole-3-carboxamide, N-[(1S)-1-cyclohexyl-2-[4-(3,5-dimethyl-1H-pyrazol-4-yl)anilino]-2-oxo-ethyl]thieno[2,3-c]pyridine-3-carboxamide, N-[(1S)-2-[4-(3,5-dimethyl-1H-pyrazol-4-yl)anilino]-1-[(4S)-8-fluorochroman-4-yl]-2-oxo-ethyl]-2-isopropyl-pyrazole-3-carboxamide, N-[(1S)-2-[4-(3,5-dimethyl-1H-pyrazol-4-yl)anilino]-1-[(4S)-7-fluorochroman-4-yl]-2-oxo-ethyl]-2-isopropyl-pyrazole-3-carboxamide, N-[(1S)-2-[4-(3,5-dimethyl-1H-pyrazol-4-yl)anilino]-1-[(4S)-6-fluorochroman-4-yl]-2-oxo-ethyl]-2-isopropyl-pyrazole-3-carboxamide, N-[(1S)-1-(dicyclopropylmethyl)-2-[4-(3,5-dimethyl-1H-pyrazol-4-yl)anilino]-2-oxo-ethyl]-3-ethyl-isoxazole-4-carboxamide.

N-[(1S)-1-(dicyclopropylmethyl)-2-[4-(3,5-dimethyl-1H-pyrazol-4-yl)anilino]-2-oxo-ethyl]-3-isopropyl-isoxazole-4-carboxamide, N-[(1S)-1-(dicyclopropylmethyl)-2-[4-(3,5-dimethyl-1H-pyrazol-4-yl)anilino]-2-oxo-ethyl]-3-isopropyl-triazole-4-carboxamide, N-[(1S)-1-cyclohexyl-2-[4-(3,5-dimethyl-1H-pyrazol-4-yl)anilino]-2-oxo-ethyl]imidazo[1,2-a]pyridine-3-carboxamide, N-[1-[bis(3,3-difluorocyclobutyl)methyl]-2-[4-(3,5-dimethyl-1H-pyrazol-4-yl)anilino]-2-oxo-ethyl]-2-isopropyl-pyrazole-3-carboxamide, N-[1-[bis(3,3-difluorocyclobutyl)methyl]-2-[4-(3,5-dimethyl-1H-pyrazol-4-yl)anilino]-2-oxo-ethyl]-2-methyl-pyrazole-3-carboxamide, N-[(1R)-1-cyclohexyl-2-[4-(3,5-dimethyl-1H-pyrazol-4-yl)anilino]-2-oxo-ethyl]-2-methyl-pyrazole-3-carboxamide, N-[(1R)-1-benzyl-2-[4-(3,5-dimethyl-1H-pyrazol-4-yl)anilino]-2-oxo-ethyl]-2-methyl-pyrazole-3-carboxamide, N-[(1S)-1-[[4-(3,5-dimethyl-1H-pyrazol-4-yl)phenyl]carbamoyl]-3-methyl-butyl]-2-methyl-pyrazole-3-carboxamide, N-[1-[cyclobutyl(phenyl)methyl]-2-[4-(3,5-dimethyl-1H-pyrazol-4-yl)anilino]-2-oxo-ethyl]-2-methyl-pyrazole-3-carboxamide, N-[1-[cyclopropyl(phenyl)methyl]-2-[4-(3,5-dimethyl-1H-pyrazol-4-yl)anilino]-2-oxo-ethyl]-2-methyl-pyrazole-3-carboxamide, tert-butyl N-[(1S)-1-(dicyclopropylmethyl)-2-[4-(3,5-dimethylimidazol-4-yl)anilino]-2-oxo-ethyl]carbamate, tert-butyl N-[1-[(5-bromo-2-chloro-phenyl)methyl]-2-[4-(3-methylimidazol-4-yl)anilino]-2-oxo-ethyl]carbamate, tert-butyl N-[(1S)-1-[(2-chloro-5-cyano-phenyl)methyl]-2-[4-(3-methylimidazol-4-yl)anilino]-2-oxo-ethyl]carbamate, tert-butyl N-[(1S)-1-[(1R)-6-bromoindan-1-yl]-2-[4-(3-methylimidazol-4-yl)anilino]-2-oxo-ethyl]carbamate, tert-butyl N-[(1S)-1-[(1S)-6-bromoindan-1-yl]-2-[4-(3-methylimidazol-4-yl)anilino]-2-oxo-ethyl]carbamate, tert-butyl N-[1-[cyclobutyl(phenyl)methyl]-2-[4-(3-methylimidazol-4-yl)anilino]-2-oxo-ethyl]carbamate, tert-butyl N-[(1S)-1-[cyclohexyl-(cyclopentyl)methyl]-2-[4-(3-methylimidazol-4-yl)anilino]-2-oxo-ethyl]carbamate, tert-butyl N-[(1S)-1-cyclohexyl-2-[4-(4-methyl-1,2,4-triazol-3-yl)anilino]-2-oxo-ethyl]carbamate, tert-butyl N-[(1S)-1-cycloheptyl-2-[4-(4-methyl-1,2,4-triazol-3-yl)anilino]-2-oxo-ethyl]carbamate, tert-butyl N-[(1S)-1-benzhydryl-2-[4-(4-methyl-1,2,4-triazol-3-yl)anilino]-2-oxo-ethyl]carbamate, tert-butyl N-[1-[(5-bromo-2-chloro-phenyl)methyl]-2-[4-(4-methyl-1,2,4-triazol-3-yl)anilino]-2-oxo-ethyl]carbamate, tert-butyl N-[1-[(5-bromo-2-chloro-phenyl)methyl]-2-[4-(4-cyclopropyl-1,2,4-triazol-3-yl)anilino]-2-oxo-ethyl]carbamate, tert-butyl N-[1-[(5-bromo-2-chloro-phenyl)methyl]-2-[4-[3-(3-hydroxypropyl)triazol-4-yl]anilino]-2-oxo-ethyl]carbamate, tert-butyl N-[1-[(5-bromo-2-chloro-phenyl)methyl]-2-[4-(3-methyltriazol-4-yl)anilino]-2-oxo-ethyl]carbamate, tert-butyl N-[1-[(5-bromo-2-chloro-phenyl)methyl]-2-[4-(1,3,4-oxadiazol-2-yl)anilino]-2-oxo-ethyl]carbamate, tert-butyl (S)-(1,1-dicyclopropyl-3-((4-(3,5-dimethylisoxazol-4-yl)phenyl)amino)-3-oxopropan-2-yl)carbamate, tert-butyl (S)-(1,1-dicyclopropyl-3-((4-(4-methyloxazol-5-yl)phenyl)amino)-3-oxopropan-2-yl)carbamate, tert-butyl N-[1-(dicyclopropylmethyl)-2-[4-(3,5-dimethylimidazol-4-yl)-3-hydroxy-anilino]-2-oxo-ethyl]carbamate, tert-butyl N-[(1S)-1-(dicyclopropylmethyl)-2-[4-(2,4-dimethylpyrazol-3-yl)anilino]-2-oxo-ethyl]carbamate, tert-butyl N-[(1S)-1-(dicyclopropylmethyl)-2-[4-[4-(1-hydroxycyclopropyl)-2-methyl-pyrazol-3-yl]anilino]-2-oxo-ethyl]carbamate, tert-butyl N-[(1S)-1-(dicyclopropylmethyl)-2-[4-(4,5-dimethylimidazol-1-yl)anilino]-2-oxo-ethyl]carbamate, tert-butyl N-[(1S)-1-(dicyclopropylmethyl)-2-oxo-2-[4-(2-oxo-1H-imidazol-3-yl)anilino]ethyl]carbamate, tert-butyl N-[(1S)-1-cyclohexyl-2-[4-[3-methyl-5-(trifluoromethyl)imidazol-4-yl]anilino]-2-oxo-ethyl]carbamate, tert-butyl N-[(1S)-1-cyclohexyl-2-[4-[1-methyl-5-(trifluoromethyl)imidazol-4-yl]anilino]-2-oxo-ethyl]carbamate, tert-butyl N-[(1S)-1-[(1R)-7-bromotetralin-1-yl]-2-[4-(2-methylimidazol-1-yl)anilino]-2-oxo-ethyl]carbamate, N-[1-(dicyclopropylmethyl)-2-[4-(3,5-dimethylimidazol-4-yl)anilino]-2-oxo-ethyl]-2-methyl-pyrazole-3-carboxamide,
N-[1-(4,4-difluorocyclohexyl)-2-[4-(3,5-dimethylimidazol-4-yl)anilino]-2-oxo-ethyl]-2-methyl-pyrazole-3-carboxamide,
N-[(1S)-1-cyclopentyl-2-[4-(3,5-dimethylimidazol-4-yl)anilino]-2-oxo-ethyl]-2-methyl-pyrazole-3-carboxamide,
N-[(1S)-1-cycloheptyl-2-[4-(3,5-dimethylimidazol-4-yl)anilino]-2-oxo-ethyl]-2-methyl-pyrazole-3-carboxamide,
N-[(1S)-1-cyclohexyl-2-[4-(3,5-dimethylimidazol-4-yl)anilino]-2-oxo-ethyl]-2-methyl-pyrazole-3-carboxamide,
N-[(1S)-1-benzhydryl-2-[4-(3,5-dimethylimidazol-4-yl)anilino]-2-oxo-ethyl]-2-methyl-pyrazole-3-carboxamide,
N-[(1S)-1-[(1R)-6-bromoindan-1-yl]-2-[4-(3-methylimidazol-4-yl)anilino]-2-oxo-ethyl]-2-methyl-pyrazole-3-carboxamide,
N-[(1S)-1-[(1S)-6-bromoindan-1-yl]-2-[4-(3-methylimidazol-4-yl)anilino]-2-oxo-ethyl]-2-methyl-pyrazole-3-carboxamide,
N-[(1S)-1-[(2-chloro-5-cyano-phenyl)methyl]-2-[4-(3-methylimidazol-4-yl)anilino]-2-oxo-ethyl]-2-methyl-pyrazole-3-carboxamide,
N-[(1S)-1-cyclohexyl-2-[4-(3-methylimidazol-4-yl)anilino]-2-oxo-ethyl]-2-methyl-pyrazole-3-carboxamide,
N-[(1S)-1-[(1R)-7-bromotetralin-1-yl]-2-[4-(3-methylimidazol-4-yl)anilino]-2-oxo-ethyl]-2-methyl-pyrazole-3-carboxamide,
N-[(1S)-1-[(5-bromo-2-chloro-phenyl)methyl]-2-[4-(3-methylimidazol-4-yl)anilino]-2-oxo-ethyl]-2-methyl-pyrazole-3-carboxamide,
N-[(1S)-1-benzhydryl-2-[4-(3-methylimidazol-4-yl)anilino]-2-oxo-ethyl]-2-methyl-pyrazole-3-carboxamide,
N-[(1S)-1-benzhydryl-2-[4-(3-methylimidazol-4-yl)anilino]-2-oxo-ethyl]-1-fluoro-cyclopropanecarboxamide,
N-[(1S)-1-cyclohexyl-2-[4-(4-methyl-1,2,4-triazol-3-yl)anilino]-2-oxo-ethyl]-3-phenyl-triazole-4-carboxamide,
N-[(1S)-1-cycloheptyl-2-[4-(4-methyl-1,2,4-triazol-3-yl)anilino]-2-oxo-ethyl]-2-isopropyl-pyrazole-3-carboxamide,
N-[(1S)-1-cycloheptyl-2-[4-(4-methyl-1,2,4-triazol-3-yl)anilino]-2-oxo-ethyl]-2-methyl-pyrazole-3-carboxamide,
N-[(1S)-1-cyclohexyl-2-[4-(4-methyl-1,2,4-triazol-3-yl)anilino]-2-oxo-ethyl]-2-isopropyl-pyrazole-3-carboxamide,
N-[(1S)-1-cyclohexyl-2-[4-(4-methyl-1,2,4-triazol-3-yl)anilino]-2-oxo-ethyl]-2-methyl-pyrazole-3-carboxamide,
N-[(1S)-1-benzhydryl-2-[4-(4-methyl-1,2,4-triazol-3-yl)anilino]-2-oxo-ethyl]-1-fluoro-cyclopropanecarboxamide,
N-[(1S)-1-benzhydryl-2-[4-(4-methyl-1,2,4-triazol-3-yl)anilino]-2-oxo-ethyl]-2-methyl-pyrazole-3-carboxamide,
N-[1-[(5-bromo-2-chloro-phenyl)methyl]-2-[4-(4-cyclopropyl-1,2,4-triazol-3-yl)anilino]-2-oxo-ethyl]-2-methyl-pyrazole-3-carboxamide,
N-[1-[(5-bromo-2-chloro-phenyl)methyl]-2-[4-(4-(4-methyl-1,2,4-triazol-3-yl)anilino]-2-oxo-ethyl]-3-methyl-isoxazole-4-carboxamide,
N-[1-[(5-bromo-2-chloro-phenyl)methyl]-2-[4-(4-(4-methyl-1,2,4-triazol-3-yl)anilino]-2-oxo-ethyl]-2-methyl-pyrazole-3-carboxamide,
N-[(1S)-1-cyclohexyl-2-[4-(5-methoxy-3-methyl-1H-pyrazol-4-yl)anilino]-2-oxo-ethyl]-2-methyl-pyrazole-3-carboxamide,
N-[(1S)-1-cyclohexyl-2-[4-(5-ethoxy-3-methyl-1H-pyrazol-4-yl)anilino]-2-oxo-ethyl]-2-methyl-pyrazole-3-carboxamide,
N-[(1S)-1-(dicyclopropylmethyl)-2-[4-(3,5-dimethylisoxazol-4-yl)anilino]-2-oxo-ethyl]-2-isopropyl-pyrazole-3-carboxamide,
N-[(1S)-1-(dicyclopropylmethyl)-2-[4-(4-methyloxazol-5-yl)anilino]-2-oxo-ethyl]-2-isopropyl-pyrazole-3-carboxamide,
N-[(1S)-1-(dicyclopropylmethyl)-2-[4-(3,5-dimethylimidazol-4-yl)-3-hydroxy-anilino]-2-oxo-ethyl]-2-ethyl-pyrazole-3-carboxamide,
N-[(1S)-1-(dicyclopropylmethyl)-2-[4-(3,5-dimethylimidazol-4-yl)-3-hydroxy-anilino]-2-oxo-ethyl]-2-isopropyl-pyrazole-3-carboxamide,
N-[(1S)-1-(dicyclopropylmethyl)-2-[4-(2,4-dimethylpyrazol-3-yl)-3-hydroxy-anilino]-2-oxo-ethyl]-2-ethyl-pyrazole-3-carboxamide,
N-[(1S)-1-(dicyclopropylmethyl)-2-[4-(2,4-dimethylpyrazol-3-yl)-3-hydroxy-anilino]-2-oxo-ethyl]-2-isopropyl-pyrazole-3-carboxamide,
N-[(1S)-1-(dicyclopropylmethyl)-2-[4-(2,4-dimethylpyrazol-3-yl)-3-hydroxy-anilino]-2-oxo-ethyl]-2-(2-hydroxy-1-methyl-ethyl)pyrazole-3-carboxamide,
N-[(1S)-1-(dicyclopropylmethyl)-2-[4-(2,4-dimethylpyrazol-3-yl)anilino]-2-oxo-ethyl]-2-isopropyl-pyrazole-3-carboxamide,
N-[(1S)-1-(dicyclopropylmethyl)-2-[4-[4-(1-hydroxycyclopropyl)-2-methyl-pyrazol-3-yl]anilino]-2-oxo-ethyl]-2-isopropyl-pyrazole-3-carboxamide,
N-[(1S)-1-(dicyclopropylmethyl)-2-[4-(4,5-dimethylimidazol-1-yl)anilino]-2-oxo-ethyl]-2-ethyl-pyrazole-3-carboxamide,
N-[(1S)-1-(dicyclopropylmethyl)-2-oxo-2-[4-(2-oxo-1H-imidazol-3-yl)anilino]ethyl]-2-ethyl-pyrazole-3-carboxamide,
N-[(1S)-1-[(1R)-7-bromotetralin-1-yl]-2-[4-(2-methylimidazol-1-yl)anilino]-2-oxo-ethyl]-2-methyl-pyrazole-3-carboxamide,
2-methyl-N-[(1S)-2-[4-(3-methylimidazol-4-yl)anilino]-2-oxo-1-[(1R)-tetralin-1-yl]ethyl]pyrazole-3-carboxamide,
N-[(1S)-1-[(1R)-indan-1-yl]-2-[4-(3-methylimidazol-4-yl)anilino]-2-oxo-ethyl]-2-methyl-pyrazole-3-carboxamide,
N-[(1S)-1-[(1S)-indan-1-yl]-2-[4-(3-methylimidazol-4-yl)anilino]-2-oxo-ethyl]-2-methyl-pyrazole-3-carboxamide,
2-methyl-N-[(1S)-2-[4-(2-methylimidazol-1-yl)anilino]-2-oxo-1-[(1R)-tetralin-1-yl]ethyl]pyrazole-3-carboxamide,
N-[(1S)-1-(dicyclopropylmethyl)-2-[4-(4-methyl-1H-imidazol-5-yl)anilino]-2-oxo-ethyl]-2-isopropyl-pyrazole-3-carboxamide,
N-[(1S)-1-(dicyclopropylmethyl)-2-[4-(4-isopropyl-1H-imidazol-5-yl)anilino]-2-oxo-ethyl]-2-isopropyl-pyrazole-3-carboxamide,
N-[(1S)-2,2-dicyclopropyl-1-[[4-(4-cyclopropyl-1H-imidazol-5-yl)phenyl]carbamoyl]ethyl]-2-isopropyl-pyrazole-3-carboxamide,
N-[(1S)-1-(dicyclopropylmethyl)-2-[4-(4-methyl-1H-pyrazol-5-yl)anilino]-2-oxo-ethyl]-2-isopropyl-pyrazole-3-carboxamide,
N-[(1S)-2,2-dicyclopropyl-1-[[4-(3-cyclopropyl-5-methyl-1H-pyrazol-4-yl)phenyl]carbamoyl]ethyl]-2-isopropyl-pyrazole-3-carboxamide,
N-[1-(dicyclopropylmethyl)-2-[4-(3,5-dicyclopropyl-1H-pyrazol-4-yl)anilino]-2-oxo-ethyl]-2-isopropyl-pyrazole-3-carboxamide,
N-[(1S)-1-(dicyclopropylmethyl)-2-[4-(3-isopropyl-5-methyl-1H-pyrazol-4-yl)anilino]-2-oxo-ethyl]-2-isopropyl-pyrazole-3-carboxamide,
N-[(1S)-1-(dicyclopropylmethyl)-2-[4-(3,5-diisopropyl-1H-pyrazol-4-yl)anilino]-2-oxo-ethyl]-2-isopropyl-pyrazole-3-carboxamide, N-[(1S)-1-(dicyclopropylmethyl)-2-[4-(3,5-dimethyl-1H-pyrazol-4-yl)anilino]-2-oxo-ethyl]-2-(2-hydroxypropyl)pyrazole-3-carboxamide, N-[(1S)-2,2-dicyclopropyl-1-[[4-(3-cyclopropyl-5-methyl-1H-pyrazol-4-yl)phenyl]carbamoyl]ethyl]-2-[(1S)-2-hydroxy-1-methyl-ethyl]pyrazole-3-carboxamide, N-[(1S)-2,2-dicyclopropyl-1-[[4-(3-cyclopropyl-5-methyl-1H-pyrazol-4-yl)phenyl]carbamoyl]ethyl]-2-[(1R)-2-hydroxy-1-methyl-ethyl]pyrazole-3-carboxamide, N-[(1S)-2,2-dicyclopropyl-1-[[4-(3-cyclopropyl-5-methyl-1H-pyrazol-4-yl)phenyl]carbamoyl]ethyl]-2-propyl-pyrazole-3-carboxamide, N-[(1S)-2,2-dicyclopropyl-1-[[4-(3-cyclopropyl-5-methyl-1H-pyrazol-4-yl)phenyl]carbamoyl]ethyl]-2-ethyl-pyrazole-3-carboxamide, N-[(1S)-1-(dicyclopropylmethyl)-2-[4-(3,5-diethyl-1H-pyrazol-4-yl)anilino]-2-oxo-ethyl]-2-(3-hydroxypropyl)pyrazole-3-carboxamide, N-[(1S)-1-(dicyclopropylmethyl)-2-[4-(3,5-diethyl-1H-pyrazol-4-yl)anilino]-2-oxo-ethyl]-2-[(1S)-2-hydroxy-1-methyl-ethyl]pyrazole-3-carboxamide, N-[(1S)-1-(dicyclopropylmethyl)-2-[4-(3,5-diethyl-1H-pyrazol-4-yl)anilino]-2-oxo-ethyl]-2-[(1R)-2-hydroxy-1-methyl-ethyl]pyrazole-3-carboxamide, N-[(1S)-1-(dicyclopropylmethyl)-2-[4-(3,5-diethyl-1H-pyrazol-4-yl)anilino]-2-oxo-ethyl]-2-ethyl-pyrazole-3-carboxamide, N-[(1S)-1-(dicyclopropylmethyl)-2-[4-(3,5-diethyl-1H-pyrazol-4-yl)anilino]-2-oxo-ethyl]-2-propyl-pyrazole-3-carboxamide, N-[(1S)-1-(dicyclopropylmethyl)-2-[4-(3,5-diethyl-1H-pyrazol-4-yl)anilino]-2-oxo-ethyl]-2-methyl-pyrazole-3-carboxamide, N-[(1S)-1-(dicyclopropylmethyl)-2-[4-(3,5-diethyl-1H-pyrazol-4-yl)anilino]-2-oxo-ethyl]-2-isopropyl-pyrazole-3-carboxamide, N-[(1S)-1-benzhydryl-2-[4-(3-methyl-1H-pyrazol-4-yl)anilino]-2-oxo-ethyl]-2-methyl-pyrazole-3-carboxamide, N-[(1S)-1-(dicyclopropylmethyl)-2-[4-(5-isopropyl-3-methyl-imidazol-4-yl)anilino]-2-oxo-ethyl]-2-isopropyl-pyrazole-3-carboxamide, N-[(1S)-2,2-dicyclopropyl-1-[[4-(5-cyclopropyl-3-methyl-imidazol-4-yl)phenyl]carbamoyl]ethyl]-2-isopropyl-pyrazole-3-carboxamide, N-[(1S)-1-(dicyclopropylmethyl)-2-[4-(3,5-dimethylimidazol-4-yl)anilino]-2-oxo-ethyl]-2-isopropyl-pyrazole-3-carboxamide, N-[(1S)-1-(dicyclopropylmethyl)-2-[4-(2-methyl-3-pyridyl)anilino]-2-oxo-ethyl]-2-isopropyl-pyrazole-3-carboxamide, N-[(1S)-1-(dicyclopropylmethyl)-2-[4-(3-methyl-4-pyridyl)anilino]-2-oxo-ethyl]-2-isopropyl-pyrazole-3-carboxamide, N-[(1S)-1-(dicyclopropylmethyl)-2-[4-[5-(hydroxymethyl)-3-methyl-imidazol-4-yl]anilino]-2-oxo-ethyl]-2-isopropyl-pyrazole-3-carboxamide, N-[(1S)-1-(dicyclopropylmethyl)-2-[4-[2-(hydroxymethyl)-3-pyridyl]anilino]-2-oxo-ethyl]-2-isopropyl-pyrazole-3-carboxamide, N-[(1S)-1-(dicyclopropylmethyl)-2-[4-[3-(hydroxymethyl)-5-methyl-isoxazol-4-yl]anilino]-2-oxo-ethyl]-2-isopropyl-pyrazole-3-carboxamide, N-[(1S)-1-(dicyclopropylmethyl)-2-[4-[5-(hydroxymethyl)-3-methyl-isoxazol-4-yl]anilino]-2-oxo-ethyl]-2-isopropyl-pyrazole-3-carboxamide, N-[(1S)-1-(dicyclopropylmethyl)-2-[4-(3,5-dimethyl-1H-pyrazol-4-yl)-3-hydroxy-anilino]-2-oxo-ethyl]-2-isopropyl-pyrazole-3-carboxamide, N-[(1S)-1-benzhydryl-2-[4-(3,5-dimethyl-1H-pyrazol-4-yl)-3-hydroxy-anilino]-2-oxo-ethyl]-2-methyl-pyrazole-3-carboxamide, N-[(1S)-1-cyclohexyl-2-[4-(3,5-dimethyl-1H-pyrazol-4-yl)-3-hydroxy-anilino]-2-oxo-ethyl]-2-methyl-pyrazole-3-carboxamide, N-[(1S)-1-(dicyclopropylmethyl)-2-[4-(3,5-dimethyl-1H-pyrazol-4-yl)-3-hydroxy-anilino]-2-oxo-ethyl]-2-ethyl-pyrazole-3-carboxamide, N-[(1S)-1-(dicyclopropylmethyl)-2-[4-(3,5-dimethyl-1H-pyrazol-4-yl)-3-hydroxy-anilino]-2-oxo-ethyl]-2-methyl-pyrazole-3-carboxamide, N-[(1S)-1-(dicyclopropylmethyl)-2-[4-(3,5-dimethyl-1H-pyrazol-4-yl)-3-hydroxy-anilino]-2-oxo-ethyl]-1-fluoro-cyclopropanecarboxamide, N-[(1S)-2-[4-(3,5-dimethyl-1H-pyrazol-4-yl)-3-hydroxy-anilino]-1-(4-methylcyclohexyl)-2-oxo-ethyl]-2-ethyl-pyrazole-3-carboxamide, N-[(1S)-2-[4-(3,5-dimethyl-1H-pyrazol-4-yl)-3-hydroxy-anilino]-1-(4-methylcyclohexyl)-2-oxo-ethyl]-2-isopropyl-pyrazole-3-carboxamide, N-[(1S)-1-(dicyclopropylmethyl)-2-[4-(3,5-diethyl-1H-pyrazol-4-yl)-3-hydroxy-anilino]-2-oxo-ethyl]-2-isopropyl-pyrazole-3-carboxamide, N-[(1S)-1-cyclohexyl-2-[3-hydroxy-4-(3-methylimidazol-4-yl)anilino]-2-oxo-ethyl]-2-methyl-pyrazole-3-carboxamide, N-[(1S)-1-benzhydryl-2-[3-hydroxy-4-(3-methylimidazol-4-yl)anilino]-2-oxo-ethyl]-2-methyl-pyrazole-3-carboxamide, N-[(1S)-1-benzhydryl-2-[3-hydroxy-4-(3-methyl-1H-pyrazol-4-yl)anilino]-2-oxo-ethyl]-2-methyl-pyrazole-3-carboxamide, cyclopropyl N-[(1S)-1-cyclohexyl-2-[3-hydroxy-4-(3-methylimidazol-4-yl)anilino]-2-oxo-ethyl]carbamate, cyclopropyl N-[(1S)-1-benzhydryl-2-[4-(3,5-dimethylimidazol-4-yl)anilino]-2-oxo-ethyl]carbamate, cyclopropyl N-[(1S)-1-cyclohexyl-2-[4-(3,5-dimethyl-1H-pyrazol-4-yl)-3-hydroxy-anilino]-2-oxo-ethyl]carbamate, cyclopropyl N-[(1S)-1-cycloheptyl-2-[4-(3,5-dimethyl-1H-pyrazol-4-yl)-3-hydroxy-anilino]-2-oxo-ethyl]carbamate, cyclopropyl N-[(1S)-1-benzhydryl-2-[4-(3,5-dimethyl-1H-pyrazol-4-yl)anilino]-2-oxo-ethyl]carbamate, cyclopropyl N-[(1S)-1-cycloheptyl-2-[4-(3,5-dimethyl-1H-pyrazol-4-yl)anilino]-2-oxo-ethyl]carbamate, cyclobutyl N-[(1S)-1-(dicyclopropylmethyl)-2-[4-(3,5-dimethyl-1H-pyrazol-4-yl)anilino]-2-oxo-ethyl]carbamate, benzyl N-[(1S)-1-cyclohexyl-2-[4-(3,5-dimethyl-1H-pyrazol-4-yl)anilino]-2-oxo-ethyl]carbamate, 3-pyridylmethyl N-[(1S)-1-cyclohexyl-2-[4-(3,5-dimethyl-1H-pyrazol-4-yl)anilino]-2-oxo-ethyl]carbamate, 2-pyridylmethyl N-[(1S)-1-cyclohexyl-2-[4-(3,5-dimethyl-1H-pyrazol-4-yl)anilino]-2-oxo-ethyl]carbamate, N-[(1S)-1-(dicyclopropylmethyl)-2-[4-[5-(hydroxymethyl)-3-methyl-1H-pyrazol-4-yl]anilino]-2-oxo-ethyl]-2-isopropyl-pyrazole-3-carboxamide, tert-butyl N-[(1S)-1-cyclohexyl-2-[4-[5-(1-hydroxyethyl)-3-methyl-1H-pyrazol-4-yl]anilino]-2-oxo-ethyl]carbamate, tert-butyl N-[(1S)-1-benzhydryl-2-[4-[5-(1-hydroxyethyl)-3-methyl-1H-pyrazol-4-yl]anilino]-2-oxo-ethyl]carbamate, tert-butyl N-[(1S)-1-benzhydryl-2-[4-[5-(1-hydroxy-1-methyl-ethyl)-3-methyl-1H-pyrazol-4-yl]anilino]-2-oxo-ethyl]carbamate,
tert-butyl N-[(1S)-1-cyclohexyl-2-[4-[5-(1-hydroxy-1-methyl-ethyl)-3-methyl-1H-pyrazol-4-yl]anilino]-2-oxo-ethyl]carbamate,
tert-butyl N-[(1S)-1-benzhydryl-2-[4-[5-(hydroxymethyl)-3-methyl-1H-pyrazol-4-yl]anilino]-2-oxo-ethyl]carbamate,
tert-butyl N-[(1S)-1-cyclohexyl-2-[4-[5-(hydroxymethyl)-3-methyl-1H-pyrazol-4-yl]anilino]-2-oxo-ethyl]carbamate,
tert-butyl N-[(1S)-1-cycloheptyl-2-[4-[5-(hydroxymethyl)-3-methyl-1H-pyrazol-4-yl]anilino]-2-oxo-ethyl]carbamate,
N-[(1S)-1-cyclohexyl-2-[4-[5-(1-hydroxyethyl)-3-methyl-1H-pyrazol-4-yl]anilino]-2-oxo-ethyl]-2-methyl-pyrazole-3-carboxamide,
N-[(1S)-1-cyclohexyl-2-[4-[5-(1-hydroxyethyl)-3-methyl-1H-pyrazol-4-yl]anilino]-2-oxo-ethyl]-1-fluoro-cyclopropanecarboxamide,
N-[(1S)-1-benzhydryl-2-[4-[5-(1-hydroxyethyl)-3-methyl-1H-pyrazol-4-yl]anilino]-2-oxo-ethyl]-1-fluoro-cyclopropanecarboxamide,
N-[(1S)-1-benzhydryl-2-[4-[5-(1-hydroxyethyl)-3-methyl-1H-pyrazol-4-yl]anilino]-2-oxo-ethyl]-2-methyl-pyrazole-3-carboxamide,
N-[(1S)-1-benzhydryl-2-[4-[5-(1-hydroxy-1-methyl-ethyl)-3-methyl-1H-pyrazol-4-yl]anilino]-2-oxo-ethyl]-2-methyl-pyrazole-3-carboxamide,
N-[(1S)-1-cyclohexyl-2-[4-[5-(hydroxymethyl)-3-methyl-1H-pyrazol-4-yl]anilino]-2-oxo-ethyl]-2-methyl-pyrazole-3-carboxamide,
N-[(1S)-1-cycloheptyl-2-[4-[5-(hydroxymethyl)-3-methyl-1H-pyrazol-4-yl]anilino]-2-oxo-ethyl]-2-methyl-pyrazole-3-carboxamide,
N-[(1S)-1-benzhydryl-2-[4-[5-(hydroxymethyl)-3-methyl-1H-pyrazol-4-yl]anilino]-2-oxo-ethyl]-2-methyl-pyrazole-3-carboxamide,
N-[(1S)-1-(dicyclopropylmethyl)-2-[4-[5-(1-hydroxy-1-methyl-ethyl)-3-methyl-imidazol-4-yl]anilino]-2-oxo-ethyl]-2-isopropyl-pyrazole-3-carboxamide,
N-[(1S)-2-[4-(3-amino-5-methyl-1H-pyrazol-4-yl)anilino]-1-cyclohexyl-2-oxo-ethyl]-2-methyl-pyrazole-3-carboxamide,
N-[(1S)-2-[4-(5-amino-3-methyl-1H-pyrazol-4-yl)anilino]-1-cycloheptyl-2-oxo-ethyl]-2-methyl-pyrazole-3-carboxamide,
N-[(1S)-1-[[4-(3-amino-5-methyl-1H-pyrazol-4-yl)phenyl]carbamoyl]-2,2-di(cyclobutyl)ethyl]-2-methyl-pyrazole-3-carboxamide hydrochloride,
N-[(1S)-1-cyclohexyl-2-[4-[5-methyl-3-(methylamino)-1H-pyrazol-4-yl]anilino]-2-oxo-ethyl]-2-methyl-pyrazole-3-carboxamide,
N-[(1S)-1-cyclohexyl-2-[4-[3-(dimethylamino)-5-methyl-1H-pyrazol-4-yl]anilino]-2-oxo-ethyl]-2-methyl-pyrazole-3-carboxamide,
tert-butyl N-[(1S)-1-[(2-chlorophenyl)methyl]-2-[4-[4-(hydroxymethyl)triazol-1-yl]anilino]-2-oxo-ethyl]carbamate,
tert-butyl N-[(1S)-1-[(2-chlorophenyl)methyl]-2-[4-[4-(2-hydroxyethyl)triazol-1-yl]anilino]-2-oxo-ethyl]carbamate,
tert-butyl N-[(1S)-1-[(2-chlorophenyl)methyl]-2-[4-[4-(3-hydroxypropyl)triazol-1-yl]anilino]-2-oxo-ethyl]carbamate,
tert-butyl N-[(1S)-1-[(2-chlorophenyl)methyl]-2-[4-[5-(2-hydroxyethyl)triazol-1-yl]anilino]-2-oxo-ethyl]carbamate,
tert-butyl N-[(1S)-1-[(2-chlorophenyl)methyl]-2-[4-(5-isopentyltriazol-1-yl)anilino]-2-oxo-ethyl]carbamate,
(2S)-2-cyclohexyl-N-[4-(3,5-dimethyl-1H-pyrazol-4-yl)phenyl]-2-[[3-hydroxypropyl(methyl)carbamoyl]amino]acetamide,
N-[(1S)-1-cyclohexyl-2-[4-(3,5-dimethyl-1H-pyrazol-4-yl)anilino]-2-oxo-ethyl]-2-(3-hydroxypropyl)piperidine-1-carboxamide,
(2S)-2-cyclohexyl-2-(diethylcarbamoylamino)-N-[4-(3,5-dimethyl-1H-pyrazol-4-yl)phenyl]acetamide,
(2S)-2-cyclohexyl-N-[4-(3,5-dimethyl-1H-pyrazol-4-yl)phenyl]-2-[[2-hydroxyethyl(methyl)carbamoyl]amino]acetamide,
N-[(1S)-1-cyclohexyl-2-[4-(3,5-dimethyl-1H-pyrazol-4-yl)anilino]-2-oxo-ethyl]-2-(1-hydroxy-1-methyl-ethyl) pyrrolidine-1-carboxamide,
N-[(1S)-1-cyclohexyl-2-[4-(3,5-dimethyl-1H-pyrazol-4-yl)anilino]-2-oxo-ethyl]-2-(2-hydroxyethyl) pyrrolidine-1-carboxamide,
N-[(1S)-1-cyclohexyl-2-[4-(3,5-dimethyl-1H-pyrazol-4-yl)anilino]-2-oxo-ethyl]-2-(3-hydroxypropyl)pyrrolidine-1-carboxamide,
(2S)-2-cyclohexyl-N-[4-(3,5-dimethyl-1H-pyrazol-4-yl)phenyl]-2-[[isopropyl(methyl)carbamoyl]amino]acetamide,
N-[(1S)-1-cyclohexyl-2-[4-(3,5-dimethyl-1H-pyrazol-4-yl)anilino]-2-oxo-ethyl]-2-(2-hydroxyethyl)piperidine-1-carboxamide,
N-[(1S)-1-cyclohexyl-2-[4-(3,5-dimethyl-1H-pyrazol-4-yl)anilino]-2-oxo-ethyl]piperidine-1-carboxamide,
N-[(1S)-1-cyclohexyl-2-[4-(3,5-dimethyl-1H-pyrazol-4-yl)anilino]-2-oxo-ethyl]-2-(hydroxymethyl)pyrrolidine-1-carboxamide,
N-[(1S)-1-cyclohexyl-2-[4-(3,5-dimethyl-1H-pyrazol-4-yl)anilino]-2-oxo-ethyl]-2-isopropyl-pyrrolidine-1-carboxamide,
(2S)-2-cyclohexyl-N-[4-(3,5-dimethyl-1H-pyrazol-4-yl)phenyl]-2-[[4-hydroxybutyl(methyl)carbamoyl]amino]acetamide,
N-[(1S)-1-cyclohexyl-2-[4-(3,5-dimethyl-1H-pyrazol-4-yl)anilino]-2-oxo-ethyl]pyrrolidine-1-carboxamide,
N-[(1S)-1-cyclohexyl-2-[4-(3,5-dimethyl-1H-pyrazol-4-yl)anilino]-2-oxo-ethyl]morpholine-4-carboxamide,
4-hydroxy butyl N-[(1S)-1-(dicyclopropylmethyl)-2-[4-(3,5-dimethyl-1H-pyrazol-4-yl)anilino]-2-oxo-ethyl]carbamate,
[(1R,4R)-4-hydroxy-1-methyl-pentyl] N-[(1S)-1-(dicyclopropylmethyl)-2-[4-(3,5-dimethyl-1H-pyrazol-4-yl)anilino]-2-oxo-ethyl]carbamate,
[(1S,4S)-4-hydroxy-1-methyl-pentyl] N-[(1S)-1-(dicyclopropylmethyl)-2-[4-(3,5-dimethyl-1H-pyrazol-4-yl)anilino]-2-oxo-ethyl]carbamate,
N-[(1S)-1-(dicyclopropylmethyl)-2-[4-[1-(hydroxymethyl)-3,5-dimethyl-pyrazol-4-yl]anilino]-2-oxo-ethyl]-2-isopropyl-pyrazole-3-carboxamide,
N-[1S)-1-[cyclohexyl-(cyclopentyl)methyl]-2-[4-(3-methylimidazol-4-yl)anilino]-2-oxo-ethyl]-2-methyl-pyrazole-3-carboxamide,
N-[(1S)-1-cyclohexyl-2-[4-[3-methyl-5-(trifluoromethyl)imidazol-4-yl]anilino]-2-oxo-ethyl]-2-isopropyl-pyrazole-3-carboxamide,
N-[(1S)-1-cyclohexyl-2-[4-[1-methyl-5-(trifluoromethyl)imidazol-4-yl]anilino]-2-oxo-ethyl]-2-isopropyl-pyrazole-3-carboxamide, N-(1,1-Bis(3-chlorophenyl)-3-((4-(1-methyl-1H-imidazol-5-yl)phenyl)amino)-3-oxopropan-2-yl)-1-methyl-1H-pyrazole-5-carboxamide,
N-(1,1-Bis(3-Fluorophenyl)-3-((4-(1-methyl-1H-imidazol-5-yl)phenyl)amino)-3-oxopropan-2-yl)-1-methyl-1H-pyrazole-5-carboxamide
N-[(1S)-1-(dicyclopropylmethyl)-2-[4-(3,5-dimethyl-1H-pyrazol-4-yl)-3-fluoro-anilino]-2-oxo-ethyl]-2-isopropyl-pyrazole-3-carboxamide,
N-[(1S)-1-(dicyclopropylmethyl)-2-[4-(3,5-dimethyl-1H-pyrazol-4-yl)-3-fluoro-anilino]-2-oxo-ethyl]-2-ethyl-pyrazole-3-carboxamide and
N-[(1S)-1-(dicyclopropylmethyl)-2-[4-(3,5-dimethyl-1H-pyrazol-4-yl)-3-fluoro-anilino]-2-oxo-ethyl]-2-[(1S)-2-hydroxy-1-methyl-ethyl]pyrazole-3-carboxamide,
or pharmaceutically acceptable salts, hydrates, solvates or prodrugs thereof.

Embodiment 45. The compound according to embodiment 1 above, wherein said compound is N-[(1S)-1-cyclohexyl-2-[4-(3,5-dimethyl-1H-pyrazol-4-yl)anilino]-2-oxo-ethyl]-2-methyl-pyrazole-3-carboxamide, or pharmaceutically acceptable salts, hydrates, solvates or prodrugs thereof.

Embodiment 46. The compound according to embodiment 1 above, wherein said compound is N-[(1S)-1-(4,4-difluorocyclohexyl)-2-[4-(3,5-dimethyl-1H-pyrazol-4-yl)anilino]-2-oxo-ethyl]-2-isopropyl-pyrazole-3-carboxamide, or pharmaceutically acceptable salts, hydrates, solvates or prodrugs thereof.

Embodiment 47. The compound according to embodiment 1 above, wherein said compound is N-[(1S)-1-[di(cyclobutyl)methyl]-2-[4-(3,5-dimethyl-1H-pyrazol-4-yl)anilino]-2-oxo-ethyl]-2-methyl-pyrazole-3-carboxamide, or pharmaceutically acceptable salts, hydrates, solvates or prodrugs thereof.

Embodiment 48. The compound according to embodiments above 1, wherein said compound is N-[1-(dicyclopropylmethyl)-2-[4-(3,5-dimethyl-1H-pyrazol-4-yl)anilino]-2-oxo-ethyl]-2-isopropyl-pyrazole-3-carboxamide, or pharmaceutically acceptable salts, hydrates, solvates or prodrugs thereof.

Embodiment 49. The compound according to embodiment 1 above, wherein said compound is N-[(1S)-(dicyclopropylmethyl)-2-[4-(3,5-dimethyl-1H-pyrazol-4-yl)anilino]-2-oxo-ethyl]-2-isopropyl-pyrazole-3-carboxamide, or pharmaceutically acceptable salts, hydrates, solvates or prodrugs thereof.

Embodiment 50. The compound according to embodiment 1 above wherein said compound is N-[(1S)-1-(dicyclopropylmethyl)-2-[4-(3,5-dimethyl-1H-pyrazol-4-yl)anilino]-2-oxo-ethyl]-2-ethyl-pyrazole-3-carboxamide, or pharmaceutically acceptable salts, hydrates, solvates or prodrugs thereof.

Embodiment 51. The compound according to embodiment 1 above wherein said compound is N-[(1S)-1-(dicyclopropylmethyl)-2-[4-(3,5-dimethyl-1H-pyrazol-4-yl)anilino]-2-oxo-ethyl]-2-(2-hydroxy-1-methyl-ethyl)pyrazole-3-carboxamide, or pharmaceutically acceptable salts, hydrates, solvates or prodrugs thereof.

Embodiment 52. The compound according to embodiment 1 above wherein said compound is N-[(1S)-1-(dicyclopropylmethyl)-2-[4-(3,5-dimethyl-1H-pyrazol-4-yl)anilino]-2-oxo-ethyl]-2-(3-hydroxypropyl)pyrazole-3-carboxamide, or pharmaceutically acceptable salts, hydrates, solvates or prodrugs thereof.

Embodiment 53. The compound according to embodiment 1 above wherein said compound is N-[(1S)-1-(dicyclopropylmethyl)-2-[4-(3,5-dimethyl-1H-pyrazol-4-yl)anilino]-2-oxo-ethyl]-2-propyl-pyrazole-3-carboxamide, or pharmaceutically acceptable salts, hydrates, solvates or prodrugs thereof.

Embodiment 54. The compound according to embodiment 1 above wherein said compound is N-[(1S)-1-(dicyclopropylmethyl)-2-[4-(3,5-dimethyl-1H-pyrazol-4-yl)anilino]-2-oxo-ethyl]-2-(3,3,3-trifluoropropyl)pyrazole-3-carboxamide, or pharmaceutically acceptable salts, hydrates, solvates or prodrugs thereof.

Embodiment 55. The compound according to embodiment 1 above wherein said compound is trans N-[(1S)-2-[4-(3,5-dimethyl-1H-pyrazol-4-yl)anilino]-1-(4-methylcyclohexyl)-2-oxo-ethyl]-2-ethyl-pyrazole-3-carboxamide, or pharmaceutically acceptable salts, hydrates, solvates or prodrugs thereof.

Embodiment 56. The compound according to embodiment 1 above wherein said compound is trans N-[(1S)-2-[4-(3,5-dimethyl-1H-pyrazol-4-yl)anilino]-1-(4-methylcyclohexyl)-2-oxo-ethyl]-2-methyl-pyrazole-3-carboxamide, or pharmaceutically acceptable salts, hydrates, solvates or prodrugs thereof.

Embodiment 57. The compound according to embodiment 1 above, wherein said compound is N-[(1S)-1-cyclohexyl-2-[4-(3,5-dimethyl-1H-pyrazol-4-yl)anilino]-2-oxo-ethyl]-3-isopropyl-triazole-4-carboxamide, or pharmaceutically acceptable salts, hydrates, solvates or prodrugs thereof.

Embodiment 58. The compound according to embodiment 1 above, wherein said compound is N-[(1S)-2-[4-(3,5-dimethyl-1H-pyrazol-4-yl)anilino]-1-[(1S)-indan-1-yl]-2-oxo-ethyl]-2-methyl-pyrazole-3-carboxamide, or pharmaceutically acceptable salts, hydrates, solvates or prodrugs thereof.

Embodiment 59. The compound according to embodiment 1 above, wherein said compound is N-[(1S)-2-[4-(3,5-dimethyl-1H-pyrazol-4-yl)anilino]-2-oxo-1-[(1S)-tetralin-1-yl]ethyl]-2-methyl-pyrazole-3-carboxamide, or pharmaceutically acceptable salts, hydrates, solvates or prodrugs thereof.

Embodiment 60. The compound according to any one of embodiments 1-4 above, wherein
$R_5$ is selected from —$CHR_6R_7$, and wherein $R_6$ and $R_7$ each independently represents hydrogen, phenyl, cyclopropyl, cyclobutyl, cyclopentyl, cyclohexyl, methyl or ethyl, wherein said, phenyl, cyclopropyl, cyclobutyl, cyclopentyl, cyclohexyl, methyl or ethyl, is optionally substituted with one or more substituents independently selected from halogen, cyano, ($C_1$-$C_4$)alkyl; with the proviso that at least one of $R_6$ and $R_7$ are different from hydrogen;
$R_1$ is pyrazolyl, wherein said pyrazolyl is optionally substituted with one or more substituents independently selected from $R_a$;
and wherein $R_2$ is selected from pyrazolyl or imidazolyl, wherein said pyrazolyl or imidazolyl contain a nitrogen ring atom substituted with a substituent selected from $R_8$ and wherein the other ring atoms of said imidazolyl or pyrazolyl is optionally substituted with one or more substituents independently selected from $R_b$.

Embodiment 61. The compound according to any one of the embodiments 1-4 above, wherein
$R_5$ is selected from —$CHR_6R_7$, and wherein $R_6$ and $R_7$ each independently represents phenyl, cyclopropyl, cyclobutyl, cyclopentyl and cyclohexyl;
$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl contain a nitrogen ring atom substituted with a substituent selected from $R_8$ and wherein the other ring atoms of said imidazolyl or pyrazolyl is optionally substituted with one or more substituents independently selected from $R_b$.

Embodiment 62. The compound according to any one of the embodiments 1-4 above, wherein $R_5$ is selected from —$CHR_6R_7$, and wherein $R_6$ and $R_7$ each independently represents hydrogen, methyl or ethyl, wherein said methyl or ethyl, is optionally substituted with one or more substituents independently selected from halogen, cyano, $(C_1-C_4)$alkyl; with the proviso that at least one of $R_6$ and $R_7$ are different from hydrogen;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl contain a nitrogen ring atom substituted with a substituent selected from $R_8$ and wherein the other ring atoms of said imidazolyl or pyrazolyl is optionally substituted with one or more substituents independently selected from $R_b$.

Embodiment 63. The compound according to any one of the embodiments 1-4 above, wherein $R_5$ is selected from $(C_3-C_{10})$cycloalkyl, wherein said $(C_3-C_{10})$cycloalkyl is optionally substituted with one or more substituents independently selected from deuterium, halogen, cyano, hydroxy, $(C_1-C_4)$alkyl and halo$(C_1-C_4)$alkyl;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl contain a nitrogen ring atom substituted with a substituent selected from $R_8$ and wherein said pyrazolyl or imidazolyl is optionally further substituted with one or more substituents independently selected from $R_b$.

Embodiment 64. The compound according to any one of the embodiments 1-4 above, wherein $R_5$ is selected from cyclohexyl, cycloheptyl, cyclooctanyl, adamantyl, spiro[2.3]hexanyl, bicyclo[3,1,0]hexanyl, bicyclo[4,1,0]heptanyl and bicyclo[2,2,2]octanyl or spiro[2.5]octanyl, wherein said cyclohexyl, cycloheptyl, cyclooctanyl, adamantyl, spiro[2.3]hexanyl, bicyclo[3,1,0]hexanyl, bicyclo[4,1,0]heptanyl and bicyclo[2,2,2]octanyl or spiro[2.5]octanyl is optionally substituted with one or more substituents independently selected from deuterium, halogen, cyano, hydroxy, $(C_1-C_4)$alkyl and halo$(C_1-C_4)$alkyl;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl contain a nitrogen ring atom substituted with a substituent selected from $R_8$ and wherein the other ring atoms of said imidazolyl or pyrazolyl is optionally substituted with one or more substituents independently selected from $R_b$.

Embodiment 65. The compound according to any one of the embodiments 1-4 above, wherein $R_5$ is selected from G, wherein said G is optionally substituted with one or more substituents independently selected from deuterium, halogen, cyano, hydroxy, $(C_1-C_4)$alkyl and halo$(C_1-C_4)$alkyl and wherein G represents

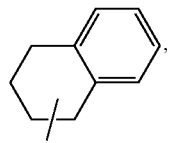  $G_1$

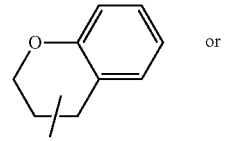  $G_2$ or

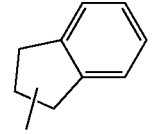  $G_3$ wherein said G is optionally substituted with one or more substituents independently selected from deuterium, halogen, cyano, hydroxy, $(C_1-C_4)$alkyl and halo$(C_1-C_4)$alkyl;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl contain a nitrogen ring atom substituted with a substituent selected from $R_8$ and wherein the other ring atoms of said imidazolyl or pyrazolyl is optionally substituted with one or more substituents independently selected from $R_b$.

Embodiment 66. The compound according to any one of the embodiments 1-4 above, wherein $R_5$ is selected from G, wherein G represents

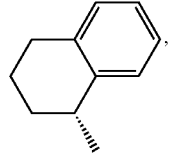  $G_{1a'}$

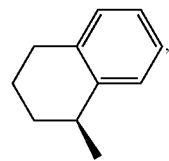  $G_{1a''}$

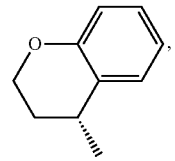  $G_{2a'}$

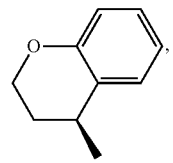  $G_{2a''}$

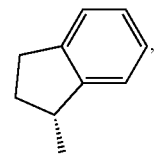
G3a′

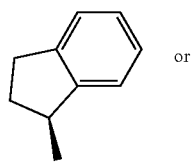
or
G3a″

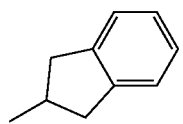
G3b wherein said G is optionally substituted with one or more substituents independently selected from deuterium, halogen, cyano, hydroxy, $(C_1-C_4)$alkyl and halo$(C_1-C_4)$alkyl;

$R_1$ is pyrazolyl, wherein said pyrazolyl is optionally substituted with one or more substituents independently selected from $R_a$;

and wherein $R_2$ is selected from pyrazolyl or imidazolyl, wherein said pyrazolyl or imidazolyl contain a nitrogen ring atom substituted with a substituent selected from $R_8$ and wherein the other ring atoms of said imidazolyl or pyrazolyl is optionally substituted with one or more substituents independently selected from $R_b$.

Embodiment 67. The compound according to any one of the embodiments 60-66 above, wherein $R_2$ is selected from pyrazolyl or imidazolyl, wherein said pyrazolyl or imidazolyl contain a nitrogen ring atom substituted with a substituent selected from $R_8$ and wherein the other ring atoms of said imidazolyl or pyrazolyl is optionally substituted with one or more substituents independently selected from $(C_1-C_6)$alkyl.

Embodiment 68. The compound according to any one of the embodiments 60-67 above, wherein $R_2$ is selected from pyrazol-4-yl or imidazole-4-yl, wherein said pyrazol-4-yl or imidazole-4-yl contain a nitrogen ring atom substituted with a substituent selected from $R_8$ and wherein the other ring atoms of said imidazole-4-yl or pyrazol-4-yl is optionally substituted with one or more substituents independently selected from $(C_1-C_6)$alkyl.

Embodiment 69. The compound according to any one of the embodiments 60-67 above, wherein $R_2$ is pyrazol-4-yl, wherein said pyrazol-4-yl contain a nitrogen ring atom substituted with a substituent selected from $R_8$ and wherein the other ring atoms of said pyrazol-4-yl is optionally substituted with one or more substituents independently selected from $(C_1-C_6)$alkyl.

Embodiment 70. The compound according to any one of claims 60-69 above wherein $R_8$ is selected from the group consisting of -L-PO(OH)$_2$ and
—CHR$_g$O—(CO-A-NR$_h$)$_m$—CO-A-NR$_h$R$_i$,
L is selected from the group consisting of a bond or —CHR$_g$O—,
m is 0 or 1;

wherein each —CO-A-NR$_h$— independently represent an amino acid residue wherein the amino acid residue is selected from the natural amino acids either in D or L-form or as mixtures of the D and L form, wherein said amino acid residue may be substituted on the α-amino group with a substituent R$_h$;

R$_g$, R$_h$, and R$_i$ are independently selected from hydrogen and $(C_1-C_6)$alkyl.

Embodiment 71. The compound according to embodiment 60 wherein —CO-A-NR$_h$— represents an amino acid residue selected from
—CO—CH$_2$—NR$_h$—,
—CO—CH(CH$_3$)—NR$_h$—,
—CO—CH(CH$_2$OH)—NR$_h$—,
—CO—CH(CH$_2$SH)—NR$_h$—,
—CO—CH(CH(CH$_3$)(OH))—NR$_h$—,
—CO—CH(CH(CH$_3$)$_2$)—NR$_h$—,
—CO—CH(CH$_2$CH(CH$_3$)$_2$)—NR$_h$—,
—CO—CH(CH(CH$_3$)(CH$_2$CH$_3$))—NR$_h$—,
—CO—CH(CH$_2$CH$_2$—S—CH$_3$)—NR$_h$—,
—CO—CH(CH$_2$-phenyl)—NR$_h$—,
—CO—CH(CH$_2$(4-hydroxyphenyl)—NR$_h$—,
—CO—CH(CH$_2$—COOH)—NR$_h$—,
—CO—CH(CH$_2$—CH$_2$—COOH)—NR$_h$—,
—CO—CH(CH$_2$—CH$_2$—CONH$_2$)—NR$_h$—,
—CO—CH(CH$_2$—CONH$_2$)—NR$_h$—,
—CO—CH((CH$_2$)$_4$—NH$_2$)—NR$_h$—,
—CO—CH((CH$_2$)$_3$—NH—C(NH)(NH$_2$))—NR$_h$—,
—CO—CH—(CH$_2$-(4-imidazolyl))—NR$_h$— and
—CO—CH—(CH$_2$-(3-indolyl))—NR$_h$.

Embodiment 72. The compound according to embodiment 70 wherein R$_8$ is —CH$_2$O—CO—CH(CH(CH$_3$)$_2$)—NH$_2$.

Embodiment 73. The compound according to embodiment 70 wherein R$_8$ is —CH$_2$—PO(OH)$_2$.

Embodiment 74. The compound according to any one of the embodiments 60-73 above, wherein R$_a$ represents methyl, ethyl propyl, isopropyl, cyclopropyl, —N(CH$_3$)$_2$ or phenyl, wherein said methyl, ethyl propyl, isopropyl, cyclopropyl, —N(CH$_3$)$_2$ or phenyl, is optionally substituted with one or more substituents independently selected from fluoro, chloro, cyano, hydroxy, methoxy and cyclopropyl.

Embodiment 75. A compound according to embodiment 1 above selected from
[4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl dihydrogen phosphate,
[4-[4-[[(2S)-2-cyclohexyl-2-[(2-methylpyrazole-3-carbonyl)amino]acetyl]amino]phenyl]-3,5-dimethyl-pyrazol-1-yl]methyl dihydrogen phosphate,
[3,5-Dimethyl-4-[4-[[(2S)-2-[(2-methylpyrazole-3-carbonyl)amino]-3,3-diphenyl-propanoyl]amino]phenyl]pyrazol-1-yl]methyl dihydrogen phosphate,
[4-[4-[[(2S)-3,3-dicyclopropyl-2-[(2-ethylpyrazole-3-carbonyl)amino]propanoyl]amino]phenyl]-3,5-dimethyl-pyrazol-1-yl]methyl dihydrogen phosphate and
[4-[4-[[(2S)-3,3-dicyclopropyl-2-[[2-(2-hydroxy-1-methyl-ethyl)pyrazole-3-carbonyl]amino]propanoyl]amino]phenyl]-3,5-dimethyl-pyrazol-1-yl]methyl dihydrogen phosphate
or pharmaceutically acceptable salts, hydrates or solvates thereof.

Embodiment 76. A compound according to embodiment 1 above wherein said compound is disodium [4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl phosphate or hydrates or solvates thereof.

Embodiment 77. A compound according to embodiment 1 above wherein said compound is [4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl dihydrogen phosphate, or pharmaceutically acceptable salts, hydrates or solvates thereof.

Embodiment 78. A compound according to embodiment 1 above wherein said compound is [4-[4-[[(2S)-2-cyclohexyl-2-[(2-methylpyrazole-3-carbonyl)amino]acetyl]amino]phenyl]-3,5-dimethyl-pyrazol-1-yl]methyl dihydrogen phosphate, or pharmaceutically acceptable salts, hydrates or solvates thereof.

Embodiment 79. A compound according to embodiment 1 above wherein said compound is [3,5-Dimethyl-4-[4-[[(2S)-2-[(2-methylpyrazole-3-carbonyl)amino]-3,3-diphenyl-propanoyl]amino]phenyl]pyrazol-1-yl]methyl dihydrogen phosphate, or pharmaceutically acceptable salts, hydrates or solvates thereof.

Embodiment 80. A compound according embodiment 1 above wherein said compound is [4-[4-[[(2S)-3,3-dicyclopropyl-2-[(2-ethylpyrazole-3-carbonyl)amino]propanoyl]amino]phenyl]-3,5-dimethyl-pyrazol-1-yl]methyl dihydrogen phosphate, or pharmaceutically acceptable salts, hydrates or solvates thereof.

Embodiment 81. A compound according embodiment 1 above wherein said compound is [4-[4-[[(2S)-3,3-dicyclopropyl-2-[[2-(2-hydroxy-1-methyl-ethyl)pyrazole-3-carbonyl]amino]propanoyl]amino]phenyl]-3,5-dimethyl-pyrazol-1-yl]methyl dihydrogen phosphate, or pharmaceutically acceptable salts, hydrates or solvates thereof.

Embodiment 82. A compound according to embodiment 1 above wherein said compound is disodium [4-[4-[[(2S)-2-cyclohexyl-2-[(2-methylpyrazole-3-carbonyl)amino]acetyl]amino]phenyl]-3,5-dimethyl-pyrazol-1-yl]methyl dihydrogen phosphate, or hydrates or solvates thereof.

Embodiment 83. A compound according to embodiment 1 above wherein said compound is 5 [4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl (2S)-2-amino-3-methyl-butanoate or pharmaceutically acceptable salts, hydrates or solvates thereof.

Embodiment 84. A compound according to embodiment 1 above wherein said compound is disodium [4-[4-[[(2S)-3,3-dicyclopropyl-2-[(2-ethylpyrazole-3-carbonyl)amino]propanoyl]amino]phenyl]-3,5-dimethyl-pyrazol-1-yl]methyl phosphate, or hydrates or solvates thereof.

Embodiment 85. A compound according to embodiment 1 above wherein said compound is disodium [4-[4-[[(2S)-3,3-dicyclopropyl-2-[[2-[(1S)-2-hydroxy-1-methyl-ethyl]pyrazole-3-carbonyl]amino]propanoyl]amino]phenyl]-3,5-dimethyl-pyrazol-1-yl]methyl phosphate, or hydrates or solvates thereof.

Embodiment 86. A compound according to embodiment 1 above wherein said compound is N-[(1S)-1-(dicyclopropylmethyl)-2-[4-(3,5-dimethyl-1H-pyrazol-4-yl)-3-fluoro-anilino]-2-oxo-ethyl]-2-isopropyl-pyrazole-3-carboxamide or pharmaceutically acceptable salts, hydrates or solvates thereof.

Embodiment 87. A compound according to embodiment 1 above wherein said compound is N-[(1S)-1-(dicyclopropylmethyl)-2-[4-(3,5-dimethyl-1H-pyrazol-4-yl)-3-fluoro-anilino]-2-oxo-ethyl]-2-ethyl-pyrazole-3-carboxamide or pharmaceutically acceptable salts, hydrates or solvates thereof.

Embodiment 88. A compound according to embodiment 1 above wherein said compound is N-[(1S)-1-(dicyclopropylmethyl)-2-[4-(3,5-dimethyl-1H-pyrazol-4-yl)-3-fluoro-anilino]-2-[(1S)-2-hydroxy-1-methyl-ethyl]pyrazole-3-carboxamide or pharmaceutically acceptable salts, hydrates or solvates thereof.

Embodiment 89. A compound according to embodiment 1 above wherein said compound is N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide sulfuric acid salt.

Embodiment 90. A compound according to embodiment 1 above wherein said compound is N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide naphthalene-1,5-disulfonic acid salt.

The invention claimed is:
1. A compound according to formula (I)

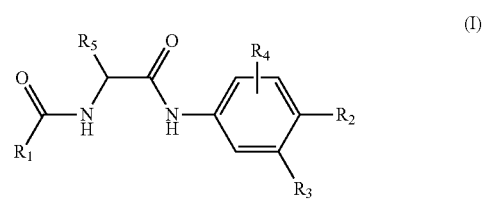

wherein:
$R_1$ is selected from the group consisting of 5- or 6-membered heteroaryl, 9- or 10-membered bicyclic heteroaryl, phenyl, ($C_1$-$C_6$)alkoxy, ($C_3$-$C_7$)cycloalkoxy, ($C_1$-$C_6$)alkyl, phenyl-($C_1$-$C_4$)alkyl, ($C_3$-$C_7$)cycloalkyl, 4-6-membered heterocycloalkyl, and —$NR_cR_d$, wherein the 5- or 6-membered heteroaryl, 9- or 10-membered bicyclic heteroaryl, phenyl, ($C_1$-$C_6$)alkoxy, ($C_3$-$C_7$)cycloalkoxy, ($C_1$-$C_6$)alkyl, phenyl-($C_1$-$C_4$)alkyl, ($C_3$-$C_7$)cycloalkyl, and 4-6-membered heterocycloalkyl is optionally substituted with one or more substituents independently selected from $R_a$;

$R_a$ is selected from the group consisting of deuterium, halogen, hydroxy, —$NR_cR_d$, ($C_1$-$C_6$)alkyl, ($C_1$-$C_6$)alkylcarbonyl, ($C_3$-$C_7$)cycloalkyl, phenyl, 5- or 6-membered heteroaryl, and 4-6-membered heterocycloalkyl, wherein the ($C_1$-$C_6$)alkyl, ($C_1$-$C_6$)alkylcarbonyl, ($C_3$-$C_7$)cycloalkyl, phenyl, 5- or 6-membered heteroaryl, or 4-6-membered heterocycloalkyl is optionally substituted with one or more substituents independently selected from deuterium, halogen, hydroxy, cyano, ($C_1$-$C_4$)alkyl, ($C_3$-$C_7$)cycloalkyl, ($C_1$-$C_4$)alkoxy, —$SO_2$—($C_1$-$C_4$)alkyl, and —$NR_cR_d$;

$R_2$ is a 5- or 6-membered heteroaryl, wherein the 5- or 6-membered heteroaryl is optionally substituted with one or more substituents independently selected from $R_b$, wherein the 5- or 6-membered heteroaryl may optionally contain —CO— as a ring member, and wherein when the 5 membered heteroaryl contains nitrogen as a ring atom that may optionally be substituted with a substituent selected from $R_g$;

$R_b$ represents is selected from the group consisting of deuterium, halogen, cyano, hydroxy, —$NR_cR_d$, ($C_1$-$C_6$)alkyl, ($C_1$-$C_6$)alkoxy, ($C_1$-$C_6$)alkyl-CO—O—($CH_2$)$_n$—, and ($C_3$-$C_7$)cycloalkyl, wherein n is 1-4, and wherein the ($C_1$-$C_6$)alkyl, ($C_1$-$C_6$)alkoxy, or ($C_3$-$C_7$)cycloalkyl is optionally substituted with one or more substituents independently selected from deuterium, halogen, cyano, hydroxy, —$NR_cR_d$, and ($C_1$-$C_4$)alkoxy;

$R_c$ and $R_d$ each independently are hydrogen or ($C_1$-$C_6$)alkyl, or $R_c$ and $R_d$ together form pyrrolidinyl or piperidinyl, wherein the ($C_1$-$C_6$)alkyl, pyrrolidinyl, or piperidinyl is optionally substituted with one or more substituents independently selected from halogen, cyano, and hydroxy;

$R_8$ is -L-PO(OH)$_2$ or —CHR$_g$O—(CO-A-NR$_h$)$_m$—CO-A-NR$_h$R$_i$;

L is a bond or —CHR$_g$O—;

m is 0 or 1;

each —CO-A-NR$_h$— independently is a natural D-form amino acid residue, a natural L-form amino acid, or a mixture thereof, wherein the amino acid residue may optionally be substituted on the α-amino group with a substituent R$_h$;

$R_g$, $R_h$, and $R_i$ each independently are hydrogen or (C$_1$-C$_6$)alkyl;

$R_3$ is selected from the group consisting of hydrogen, deuterium, hydroxy, and halogen;

$R_4$ is selected from the group consisting of hydrogen, deuterium, and halogen;

$R_5$ is selected from the group consisting of —CHR$_6$R$_7$, (C$_3$-C$_{10}$)cycloalkyl, and G, wherein the (C$_3$-C$_{10}$)cycloalkyl and G are optionally substituted with one or more substituents independently selected from deuterium, halogen, cyano, hydroxy, (C$_1$-C$_4$)alkyl, and halo(C$_1$-C$_4$)alkyl;

G is selected from the group consisting of G1, G2, and G3

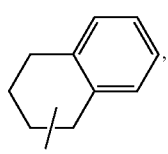 G$_1$

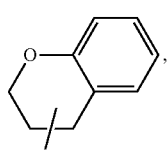 G$_2$

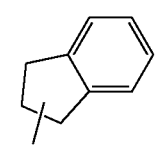 G$_3$ $R_6$ and $R_7$ each independently are selected from the group consisting of hydrogen, phenyl, (C$_1$-C$_6$)alkyl, and (C$_3$-C$_7$)cycloalkyl, wherein the phenyl, (C$_1$-C$_6$)alkyl, or (C$_3$-C$_7$)cycloalkyl is optionally substituted with one or more substituents independently selected from halogen, cyano, hydroxy, and (C$_1$-C$_4$)alkyl, with the proviso that at least one of $R_6$ and $R_7$ are different from hydrogen;

provided that when $R_5$ is (C$_2$-C$_4$)alkyl, cyclopentyl, cyclohexylmethyl, benzyl, or substituted benzyl, $R^1$ is selected from the group consisting of pyrazolyl, imidazolyl, thiazolyl, isoxazolyl, and triazolyl, wherein the pyrazolyl, imidazolyl, thiazolyl, isoxazolyl, or triazolyl is optionally substituted with one or more substituents independently selected from R$_a$;

or a pharmaceutically acceptable salt, hydrate, or solvate thereof.

2. The compound according to claim 1 having the formula (Ia)

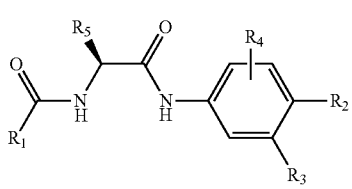 (Ia)

or a pharmaceutically acceptable salt, hydrate, or solvate thereof.

3. The compound according to claim 2, wherein $R_5$ is selected from the group consisting of cyclohexyl, cycloheptyl, cyclooctanyl, adamantyl, spiro[2.3]hexanyl, bicyclo[3,1,0]hexanyl, bicyclo[4,1,0]heptanyl, bicyclo[2,2,2]octanyl, and spiro[2.5]octanyl; wherein the cyclohexyl, cycloheptyl, cyclooctanyl, adamantyl, spiro[2.3]hexanyl, bicyclo[3,1,0]hexanyl, bicyclo[4,1,0]heptanyl, bicyclo[2,2,2]octanyl or spiro[2.5]octanyl is optionally substituted with one or more substituents independently selected from deuterium, halogen, cyano, hydroxy, (C$_1$-C$_4$)alkyl, and halo(C$_1$-C$_4$)alkyl.

4. The compound according to claim 3, wherein $R_1$ is selected from the group consisting of 5-membered heteroaryl, 9-membered bicyclic heteroaryl, (C$_3$-C$_7$)cycloalkyl, 4-6-membered heterocycloalkyl, (C$_1$-C$_6$)alkyl, and (C$_1$-C$_6$)alkoxy; wherein the 5-membered heteroaryl, 9-membered bicyclic heteroaryl, (C$_3$-C$_7$)cycloalkyl, 4-6-membered heterocycloalkyl, (C$_1$-C$_6$)alkyl, and (C$_1$-C$_6$)alkoxy is optionally substituted with one or more substituents independently selected from R$_a$.

5. The compound according to claim 4, wherein $R_1$ is selected from the group consisting of pyrazolyl, imidazolyl, thiazolyl, isoxazolyl, and triazolyl and $R_1$ is optionally substituted with one or more substituents independently selected from R$_a$.

6. The compound according to claim 5, wherein $R_2$ is a 5-membered heteroaryl, and the 5-membered heteroaryl is optionally substituted with one or more substituents independently selected from R$_b$.

7. The compound according to claim 6, wherein $R_2$ is a pyrazolyl or imidazolyl, and the pyrazolyl or imidazolyl is optionally substituted with one or more substituents independently selected from R$_b$.

8. The compound according to claim 7, wherein $R_2$ is pyrazol-4-yl or imidazole-4-yl, and the pyrazol-4-yl or imidazol-4-yl is optionally substituted with (C$_1$-C$_6$)alkyl.

9. The compound according to claim 5, wherein $R_2$ is a 5-membered heteroaryl that contains a nitrogen ring atom substituted by a substituent selected from R$_8$, and the other ring atoms of the 5-membered heteroaryl are each optionally substituted with one or more substituents independently selected from R$_b$.

10. The compound according to claim 9, wherein $R_2$ is pyrazolyl or imidazolyl, wherein the pyrazolyl or imidazolyl contains a nitrogen ring atom substituted by a substituent selected from R$_8$, and the other ring atoms of the 5-membered heteroaryl are each optionally substituted with one or more substituents independently selected from R$_b$.

11. The compound according to claim 10, wherein $R_2$ is pyrazol-4-yl or imidazole-4-yl, wherein the pyrazol-4-yl or imidazol-4-yl contains a nitrogen ring atom substituted by a substituent selected from R$_8$, and the other ring atoms of the pyrazol-4-yl or imidazole-4-yl are each optionally substituted with (C$_1$-C$_6$)alkyl.

12. The compound according to claim 11, wherein $R_8$ is -L-PO(OH)$_2$ or —CHR$_g$O—(CO-A-NR$_h$)$_m$—CO-A-NR$_h$R$_i$; wherein:

L is a bond or —CHR$_g$O—, m is 0 or 1; and

—CO-A-NR$_h$— is an amino acid residue selected from the group consisting of:
(i) —CO—CH$_2$—NR$_h$—,
(ii) —CO—CH(CH$_3$)—NR$_h$—,
(iii) —CO—CH(CH$_2$OH)—NR$_h$—,
(iv) —CO—CH(CH$_2$SH)—NR$_h$—,
(v) —CO—CH(CH(CH$_3$)(OH))—NR$_h$—,
(vi) —CO—CH(CH(CH$_3$)$_2$)—NR$_h$—,
(vii) —CO—CH(CH$_2$CH(CH$_3$)$_2$)—NR$_h$—,
(viii) —CO—CH(CH(CH$_3$)(CH$_2$CH$_3$))—NR$_h$—,
(ix) —CO—CH(CH$_2$CH$_2$—S—CH$_3$)—NR$_h$—,
(x) —CO—CH(CH$_2$-phenyl)—NR$_h$—,
(xi) —CO—CH(CH$_2$(4-hydroxyphenyl))—NR$_h$—,
(xii) —CO—CH(CH$_2$—COOH)—NR$_h$—,
(xiii) —CO—CH(CH$_2$—CH$_2$—COOH)—NR$_h$—,
(xiv) —CO—CH(CH$_2$—CH$_2$—CONH$_2$)—NR$_h$—,
(xv) —CO—CH(CH$_2$—CONH$_2$)—NR$_h$—,
(xvi) —CO—CH((CH$_2$)$_4$—NH$_2$)—NR$_h$—,
(xvii) —CO—CH((CH$_2$)$_3$—NH—C(NH)(NH$_2$))—NR$_h$—,
(xviii) —CO—CH—(CH$_2$-(4-imidazolyl))—NR$_h$— and
(xix) —CO—CH—(CH$_2$-(3-indolyl))—NR$_h$;

and $R_g$, $R_h$, and $R_i$ each independently are hydrogen or (C$_1$-C$_6$)alkyl.

13. The compound according to claim 12, wherein $R_8$ is —CH$_2$—PO(OH)$_2$.

14. The compound according to claim 2, wherein $R_5$ is selected from the group consisting of $G_{1a}$, $G_{2a}$, $G_{3a}$, and $G_{3b}$:

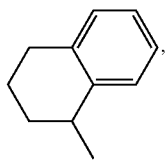
$G_{1a}$

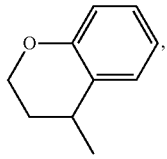
$G_{2a}$

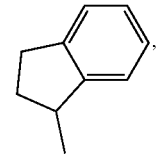
$G_{3a}$

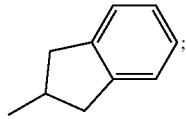
$G_{3b}$ wherein $G_{1a}$, $G_{2a}$, $G_{3a}$, or $G_{3b}$ is optionally substituted with one or more substituents independently selected from the group consisting of deuterium, halogen, cyano, hydroxy, (C$_1$-C$_4$)alkyl, and halo(C$_1$-C$_4$)alkyl.

15. The compound according to claim 14, wherein $R_1$ is selected from the group consisting of 5-membered heteroaryl, 9-membered bicyclic heteroaryl, (C$_3$-C$_7$)cycloalkyl, 4-6-membered heterocycloalkyl, (C$_1$-C$_6$)alkyl, and (C$_1$-C$_6$)alkoxy; wherein the 5-membered heteroaryl, 9-membered bicyclic heteroaryl, (C$_3$-C$_7$)cycloalkyl, 4-6-membered heterocycloalkyl, (C$_1$-C$_6$)alkyl and (C$_1$-C$_6$)alkoxy is optionally substituted with one or more substituents independently selected from $R_a$.

16. The compound according to claim 15, wherein $R_1$ is selected from the group consisting of pyrazolyl, imidazolyl, thiazolyl, isoxazolyl, and triazolyl and $R_1$ is optionally substituted with one or more substituents independently selected from $R_a$.

17. The compound according to claim 16, wherein $R_2$ is a 5-membered heteroaryl, and the 5-membered heteroaryl is optionally substituted with one or more substituents independently selected from $R_b$.

18. The compound according to claim 17, wherein $R_2$ is a pyrazolyl or imidazolyl, and the pyrazolyl or imidazolyl is optionally substituted with one or more substituents independently selected from $R_b$.

19. The compound according to claim 18, wherein $R_2$ is pyrazol-4-yl or imidazole-4-yl, and the pyrazol-4-yl or imidazol-4-yl is optionally substituted with (C$_1$-C$_6$)alkyl.

20. The compound according to claim 16, wherein $R_2$ is a 5-membered heteroaryl; that contains a nitrogen ring atom substituted by a substituent selected from $R_8$ and the other ring atoms of the 5-membered heteroaryl are each optionally substituted with one or more substituents independently selected from $R_b$.

21. The compound according to claim 20, wherein $R_2$ is pyrazolyl or imidazolyl, wherein the pyrazolyl or imidazolyl contains a nitrogen ring atom substituted by a substituent selected from $R_8$ and the other ring atoms of the 5-membered heteroaryl are each optionally substituted with one or more substituents independently selected from $R_b$.

22. The compound according to claim 21, wherein $R_2$ is pyrazol-4-yl or imidazole-4-yl, wherein the pyrazol-4-yl or imidazol-4-yl contains a nitrogen ring atom substituted by a substituent selected from $R_8$ and the other ring atoms of the pyrazol-4-yl or imidazole-4-yl are each optionally substituted with (C$_1$-C$_6$)alkyl.

23. The compound according to claim 22, wherein $R_8$ is -L-PO(OH)$_2$ or —CHR$_g$O—(CO-A-NR$_h$)$_m$—CO-A-NR$_h$R$_i$; wherein:

L is a bond or —CHR$_g$O—, m is 0 or 1; and

—CO-A-NR$_h$— is an amino acid residue selected from the group consisting of:
(i) —CO—CH$_2$—NR$_h$—,
(ii) —CO—CH(CH$_3$)—NR$_h$—,
(iii) —CO—CH(CH$_2$OH)—NR$_h$—,
(iv) —CO—CH(CH$_2$SH)—NR$_h$—,
(v) —CO—CH(CH(CH$_3$)(OH))—NR$_h$—,
(vi) —CO—CH(CH(CH$_3$)$_2$)—NR$_h$—,
(vii) —CO—CH(CH$_2$CH(CH$_3$)$_2$)—NR$_h$—,
(viii) —CO—CH(CH(CH$_3$)(CH$_2$CH$_3$))—NR$_h$—,
(ix) —CO—CH(CH$_2$CH$_2$—S—CH$_3$)—NR$_h$—,
(x) —CO—CH(CH$_2$-phenyl)—NR$_h$—,
(xi) —CO—CH(CH$_2$(4-hydroxyphenyl))—NR$_h$—,
(xii) —CO—CH(CH$_2$—COOH)—NR$_h$—,
(xiii) —CO—CH(CH$_2$—CH$_2$—COOH)—NR$_h$—,
(xiv) —CO—CH(CH$_2$—CH$_2$—CONH$_2$)—NR$_h$—,
(xv) —CO—CH(CH$_2$—CONH$_2$)—NR$_h$—, (xvi) —CO—CH((CH$_2$)$_4$—NH$_2$)—NR$_h$—,
(xvii) —CO—CH((CH$_2$)$_3$—NH—C(NH)(NH$_2$))—NR$_h$—,
(xviii) —CO—CH—(CH$_2$-(4-imidazolyl))—NR$_h$— and
(xix) —CO—CH—(CH$_2$-(3-indolyl))—NR$_h$;
and R$_g$, R$_h$, and R$_i$ each independently are hydrogen or (C$_1$-C$_6$)alkyl.

24. The compound according to claim 23, wherein R$_8$ is —CH$_2$—PO(OH)$_2$.

25. The compound according to claim 2, wherein R$_5$ is —CHR$_6$R$_7$; wherein R$_6$ and R$_7$ each independently are selected from the group consisting of hydrogen, phenyl, cyclopropyl, cyclobutyl, cyclopentyl, cyclohexyl, methyl, and ethyl; and wherein the phenyl, cyclopropyl, cyclobutyl, cyclopentyl, cyclohexyl, methyl, or ethyl, is optionally substituted with one or more substituents independently selected from halogen, cyano, and (C$_1$-C$_4$)alkyl; with the proviso that at least one of R$_6$ and R$_7$ are different from hydrogen.

26. The compound according to claim 25, wherein R$_1$ is selected from the group consisting of 5-membered heteroaryl, 9-membered bicyclic heteroaryl, (C3-C$_7$)cycloalkyl, 4-6-membered heterocycloalkyl, (C$_1$-C$_6$)alkyl and (C$_1$-C$_6$)alkoxy; wherein the 5-membered heteroaryl, 9-membered bicyclic heteroaryl, (C$_3$-C$_7$)cycloalkyl, 4-6-membered heterocycloalkyl, (C$_1$-C$_6$)alkyl and (C$_1$-C$_6$)alkoxy is optionally substituted with one or more substituents independently selected from R$_a$.

27. The compound according to claim 26, wherein R$_1$ is selected from the group consisting of pyrazolyl, imidazolyl, thiazolyl, isoxazolyl, and triazolyl and R$_1$ is optionally substituted with one or more substituents independently selected from R$_a$.

28. The compound according to claim 26, wherein R$_2$ is a 5-membered heteroaryl, and the 5-membered heteroaryl is optionally substituted with one or more substituents independently selected from R$_b$.

29. The compound according to claim 28, wherein R$_2$ is a pyrazolyl or imidazolyl, and the pyrazolyl or imidazolyl is optionally substituted with one or more substituents independently selected from R$_b$.

30. The compound according to claim 29, wherein R$_2$ is pyrazol-4-yl or imidazole-4-yl, and the pyrazol-4-yl or imidazol-4-yl is optionally substituted with one or more substituents independently selected from (C$_1$-C$_6$)alkyl.

31. The compound according to claim 27, wherein R$_2$ is a 5-membered heteroaryl that contains a nitrogen ring atom substituted by a substituent selected from R$_8$ and the other ring atoms of the 5-membered heteroaryl are each optionally substituted with one or more substituents independently selected from R$_b$.

32. The compound according to claim 31, wherein R$_2$ is pyrazolyl or imidazolyl, wherein the pyrazolyl or imidazolyl contains a nitrogen ring atom substituted by a substituent selected from R$_8$, and the other ring atoms of the 5-membered heteroaryl are each optionally substituted with one or more substituents independently selected from R$_b$.

33. The compound according to claim 32, wherein R$_2$ is pyrazol-4-yl or imidazole-4-yl; wherein the pyrazol-4-yl or imidazol-4-yl contains a nitrogen ring atom substituted by a substituent selected from R$_8$ and the other ring atoms of the pyrazol-4-yl or imidazole-4-yl are each optionally substituted with (C$_1$-C$_6$)alkyl.

34. The compound according to claim 33, wherein R$_8$ is -L-PO(OH)$_2$ or —CHR$_g$O—(CO-A-NR$_h$)$_m$—CO-A-NR$_h$R$_i$; wherein:
L is a bond or —CHR$_g$O—,
m is 0 or 1; and
—CO-A-NR$_h$— is an amino acid residue selected from the group consisting of:
(i) —CO—CH$_2$—NR$_h$—,
(ii) —CO—CH(CH$_3$)—NR$_h$—,
(iii) —CO—CH(CH$_2$OH)—NR$_h$—,
(iv) —CO—CH(CH$_2$SH)—NR$_h$—,
(v) —CO—CH(CH(CH$_3$)(OH))—NR$_h$—,
(vi) —CO—CH(CH(CH$_3$)$_2$)—NR$_h$—,
(vii) —CO—CH(CH$_2$CH(CH$_3$)$_2$)—NR$_h$—,
(viii) —CO—CH(CH(CH$_3$)(CH$_2$CH$_3$))—NR$_h$—,
(ix) —CO—CH(CH$_2$CH$_2$—S—CH$_3$)—NR$_h$—,
(x) —CO—CH(CH$_2$-phenyl)—NR$_h$—,
(xi) —CO—CH(CH$_2$(4-hydroxyphenyl)—NR$_h$—,
(xii) —CO—CH(CH$_2$—COOH)—NR$_h$—,
(xiii) —CO—CH(CH$_2$—CH$_2$—COOH)—NR$_h$—,
(xiv) —CO—CH(CH$_2$—CH$_2$—CONH$_2$)—NR$_h$—,
(xv) —CO—CH(CH$_2$—CONH$_2$)—NR$_h$—,
(xvi) —CO—CH((CH$_2$)$_4$—NH$_2$)—NR$_h$—,
(xvii) —CO—CH((CH$_2$)$_3$—NH—C(NH)(NH$_2$))—NR$_h$—,
(xviii) —CO—CH—(CH$_2$-(4-imidazolyl))—NR$_h$— and
(xix) —CO—CH—(CH$_2$-(3-indolyl))—NR$_h$;
and R$_g$, R$_h$, and R$_i$ each independently are hydrogen or (C$_1$-C6)alkyl.

35. The compound according to claim 34, wherein R$_8$ is —CH$_2$—PO(OH)$_2$.

36. The compound according to claim 2, wherein R$_5$ is —CHR$_6$R$_7$; wherein R$_6$ and R$_7$ are each independently (C$_3$-C$_7$)cycloalkyl; and wherein (C$_3$-C$_7$)cycloalkyl is optionally substituted with one or more substituents independently selected from halogen, cyano, hydroxy, and (C$_1$-C$_4$)alkyl.

37. The compound according to claim 36, wherein R$_1$ is selected from the group consisting of 5-membered heteroaryl, 9-membered bicyclic heteroaryl, (C$_3$-C$_7$)cycloalkyl, 4-6-membered heterocycloalkyl, (C$_1$-C$_6$)alkyl, and (C$_1$-C$_6$)alkoxy; wherein the 5-membered heteroaryl, 9-membered bicyclic heteroaryl, (C$_3$-C$_7$)cycloalkyl, 4-6-membered heterocycloalkyl, (C$_1$-C$_6$)alkyl and (C$_1$-C$_6$)alkoxy is optionally substituted with one or more substituents independently selected from R$_a$.

38. The compound according to claim 37, wherein R$_1$ is selected from the group consisting of pyrazolyl, imidazolyl, thiazolyl, isoxazolyl, and triazolyl and R$_1$ is optionally substituted with one or more substituents independently selected from R$_a$.

39. The compound according to claim 38, wherein R$_2$ is a 5-membered heteroaryl, and the 5-membered heteroaryl is optionally substituted with one or more substituents independently selected from R$_b$.

40. The compound according to claim 39, wherein R$_2$ is a pyrazolyl or imidazolyl, and the pyrazolyl or imidazolyl is optionally substituted with one or more substituents independently selected from R$_b$.

41. The compound according to claim 40, wherein R$_2$ is pyrazol-4-yl or imidazole-4-yl, and the pyrazol-4-yl or imidazol-4-yl is optionally substituted with (C$_1$-C$_6$)alkyl.

42. The compound according to claim 38, wherein R$_2$ is a 5-membered heteroaryl that contains a nitrogen ring atom substituted by a substituent selected from R$_8$ and the other ring atoms of the 5-membered heteroaryl are each optionally substituted with one or more substituents independently selected from $R_b$.

43. The compound according to claim 42, wherein $R_2$ is pyrazolyl or imidazolyl that contains a nitrogen ring atom substituted by a substituent selected from $R_8$ and the other ring atoms of the 5-membered heteroaryl are each optionally substituted with one or more substituents independently selected from $R_b$.

44. The compound according to claim 43, wherein $R_2$ is pyrazol-4-yl or imidazole-4-yl; wherein the pyrazol-4-yl or imidazol-4-yl contain a nitrogen ring atom substituted by a substituent selected from $R_8$ and the other ring atoms of the pyrazol-4-yl or imidazole-4-yl are each optionally substituted with $(C_1-C_6)$alkyl.

45. The compound according to claim 44, wherein $R_8$ is -L-PO(OH)$_2$ or —CHR$_g$O—(CO-A-NR$_h$)$_m$—CO-A-NR$_h$R$_i$;
    wherein:
    L is a bond or —CHR$_g$O—,
    m is 0 or 1; and
    —CO-A-NR$_h$— is an amino acid residue selected from the group consisting of:
    (i) —CO—CH$_2$—NR$_h$—,
    (ii) —CO—CH(CH$_3$)—NR$_h$—,
    (iii) —CO—CH(CH$_2$OH)—NR$_h$—,
    (iv) —CO—CH(CH$_2$SH)—NR$_h$—,
    (v) —CO—CH(CH(CH$_3$)(OH))—NR$_h$—,
    (vi) —CO—CH(CH(CH$_3$)$_2$)—NR$_h$—,
    (vii) —CO—CH(CH$_2$CH(CH$_3$)$_2$)—NR$_h$—,
    (viii) —CO—CH(CH(CH$_3$)(CH$_2$CH$_3$))—NR$_h$—,
    (ix) —CO—CH(CH$_2$CH$_2$—S—CH$_3$)—NR$_h$—,
    (x) —CO—CH(CH$_2$-phenyl)—NR$_h$—,
    (xi) —CO—CH(CH$_2$(4-hydroxyphenyl)—NR$_h$—,
    (xii) —CO—CH(CH$_2$—COOH)—NR$_h$—,
    (xiii) —CO—CH(CH$_2$—CH$_2$—COOH)—NR$_h$—,
    (xiv) —CO—CH(CH$_2$—CH$_2$—CONH$_2$)—NR$_h$—,
    (xv) —CO—CH(CH$_2$—CONH$_2$)—NR$_h$—,
    (xvi) —CO—CH((CH$_2$)$_4$—NH$_2$)—NR$_h$—,
    (xvii) —CO—CH((CH$_2$)$_3$—NH—C(NH)(NH$_2$))—NR$_h$—,
    (xviii) —CO—CH—(CH$_2$-(4-imidazolyl))—NR$_h$— and
    (xix) —CO—CH—(CH$_2$-(3-indolyl))—NR$_h$;
    and $R_g$, $R_h$, and $R_i$ each independently are hydrogen or $(C_1-C_6)$alkyl.

46. The compound according to claim 45, wherein $R_8$ is —CH$_2$—PO(OH)$_2$.

47. A compound according to claim 1, wherein the compound is:
    N-[(1 S)-1-(dicyclopropylmethyl)-2-[4-(3,5-dimethyl-1H-pyrazol-4-yl)anilino]-2-oxo-ethyl]-2-isopropyl-pyrazole-3-carboxamide
    or a pharmaceutically acceptable salt, hydrate, or solvate thereof.

48. A compound according to claim 1 selected from:
    (i) [4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl dihydrogen phosphate,
    (ii) [4-[4-[[(2S)-2-cyclohexyl-2-[(2-methylpyrazole-3-carbonyl)amino]acetyl]amino]phenyl]-3,5-dimethyl-pyrazol-1-yl]methyl phosphate,
    (iii) [3,5-Dimethyl-4-[4-[[(2S)-2-[(2-methylpyrazole-3-carbonyl)amino]-3,3-diphenyl-propanoyl]amino]phenyl]pyrazol-1-yl]methyl dihydrogen phosphate,
    (iv) [4-[4-[[(2S)-3,3-dicyclopropyl-2-[(2-ethylpyrazole-3-carbonyl)amino]propanoyl]amino]phenyl]-3,5-dimethyl-pyrazol-1-yl]methyl dihydrogen phosphate,
    (v) [4-[4-[[(2S)-3,3-dicyclopropyl-2-[[2-(2-hydroxy-1-methyl-ethyl)pyrazole-3-carbonyl]amino]propanoyl]amino]phenyl]-3,5-dimethyl-pyrazol-1-yl]methyl dihydrogen phosphate, and
    (vi) [4-[4-[[(2S)-3,3-dicyclopropyl-2-[(2-isopropylpyrazole-3-carbonyl)amino]propanoyl]amino]phenyl]-3,5-dimethyl-pyrazol-1-yl]methyl (2S)-2-amino-3-methyl-butanoate,
    or a pharmaceutically acceptable salt, hydrate, or solvate thereof.

49. A compound according to claim 1, wherein the compound is N-[(1 S)-1-(dicyclopropylmethyl)-2-[4-(3,5-dimethyl-1H-pyrazol-4-yl)anilino]-2-oxo-ethyl]-2-isopropyl-pyrazole-3-carboxamide sulfuric acid salt.

50. A compound according to claim 1, wherein the compound is N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide naphthalene-1,5-disulfonic acid salt.

51. A pharmaceutical composition comprising a compound according to claim 1 and one or more pharmaceutically acceptable vehicles, excipients, or carriers.

52. The pharmaceutical composition according to claim 51, further comprising one or more other therapeutically active compounds.

53. A method of treating a disease, disorder, or condition responsive to modulation of IL-17 comprising administering to a subject in need thereof a therapeutically effective amount of a compound according to claim 1.

54. A method of treatment according to claim 53, wherein the disease, disorder or condition is an autoimmune disease.

55. A method of treatment according to claim 53, wherein the disease, disorder or condition is psoriasis, ankylosing spondylitis, spondyloarthritis, or psoriatic arthritis.

56. A compound according to claim 1, wherein the compound is N-[(1S)-1-(dicyclopropylmethyl)-2-[4-(3,5-dimethyl-1H-pyrazol-4-yl)anilino]-2-oxo-ethyl]-2-ethyl-pyrazole-3-carboxamide or a pharmaceutically acceptable salt, hydrate, or solvate thereof.

57. A compound according to claim 1, wherein the compound is N-[(1S)-1-(dicyclopropylmethyl)-2-[4-(3,5-dimethyl-1H-pyrazol-4-yl)anilino]-2-oxo-ethyl]-2-[(1S)-2-hydroxy-1-methyl-ethyl]pyrazole-3-carboxamide or a pharmaceutically acceptable salt, hydrate, or solvate thereof.

58. A compound according to claim 1, wherein the compound is N-[(1S)-1-(dicyclopropylmethyl)-2-[4-(3,5-dimethyl-1H-pyrazol-4-yl)anilino]-2-oxo-ethyl]-2-(3-hydroxypropyl)pyrazole-3-carboxamide or a pharmaceutically acceptable salt, hydrate, or solvate thereof.

59. A compound according to claim 1, wherein the compound is N-[(1S)-1-(dicyclopropylmethyl)-2-[4-(3,5-dimethyl-1H-pyrazol-4-yl)anilino]-2-oxo-ethyl]-2-propyl-pyrazole-3-carboxamide or a pharmaceutically acceptable salt, hydrate, or solvate thereof.

60. A compound according to claim 1, wherein the compound is N-[(1S)-1-(dicyclopropylmethyl)-2-[4-(3,5-dimethyl-1H-pyrazol-4-yl)-3-fluoro-anilino]-2-oxo-ethyl]-2-isopropyl-pyrazole-3-carboxamide or a pharmaceutically acceptable salt, hydrate, or solvate thereof.

61. A compound according to claim 1, wherein the compound is N-[(1S)-1-(dicyclopropylmethyl)-)-2-[4-(3,5-dimethyl-1H-pyrazol-4-yl)-3-fluoro-anilino]-2-oxo-ethyl]-2-ethyl-pyrazole-3-carboxamide or a pharmaceutically acceptable salt, hydrate, or solvate thereof.

62. A compound according to claim 1, wherein the compound is N-[(1S)-1-(dicyclopropylmethyl)-2[4-(3,5-dimethyl-1H-pyrazol-4-yl)-3-fluoro-anilino]-2-oxo-ethyl]-2-

[(1S)-2-hydroxy-1-methyl-ethyl]pyrazole-3-carboxamide or a pharmaceutically acceptable salt, hydrate, or solvate thereof.

63. A compound according to claim 1, wherein the compound is N-[(1S)-1-(dicyclopropylmethyl)-2-[4-(3,5-dimethyl-1H-pyrazol-4-yl)anilino]-2-oxo-ethyl]-2-(4,4,4-trifluoro-3-hydroxy-butyl)pyrazole-3-carboxamide or a pharmaceutically acceptable salt, hydrate, or solvate thereof.

64. A compound according to claim 1, wherein the compound is N-[(1S)-1-[di(cyclobutyl)methyl]-2-[4-(3,5-dimethyl-1H-pyrazol-4-yl)anilino]-2-oxo-ethyl]-2-(3-hydroxypropyl)pyrazole-3-carboxamide or a pharmaceutically acceptable salt, hydrate, or solvate thereof.

65. A compound according to claim 1, wherein the compound is trans N-[(1S)-2-[4-(3,5-dimethyl-1H-pyrazol-4-yl)anilino]-1-(4-methylcyclohexyl)-2-oxo-ethyl]-2-ethyl-pyrazole-3-carboxamide or a pharmaceutically acceptable salt, hydrate, or solvate thereof.

66. A compound according to claim 1, wherein the compound is trans N-[(1S)-2-[4-(3,5-dimethyl-1H-pyrazol-4-yl)anilino]-1-(4-methylcyclohexyl)-2-oxo-ethyl]-2-isopropyl-pyrazole-3-carboxamide or a pharmaceutically acceptable salt, hydrate, or solvate thereof.

67. A compound according to claim 1, wherein the compound is N-[(1S)-1-(Dicyclopropylmethyl)-2-[4-[5-(hydroxymethyl)-3-methyl-1H-pyrazol-4-yl]anilino]-2-oxo-ethyl]-2-isopropyl-pyrazole-3-carboxamide or a pharmaceutically acceptable salt, hydrate, or solvate thereof.

68. A compound according to claim 1, wherein the compound is N-[(1S)-2-[4-(3,5-dimethyl-1H-pyrazol-4-yl)-3-hydroxy-anilino]-1-(trans-4-methylcyclo-hexyl)-2-oxo-ethyl]-2-isopropyl-pyrazole-3-carboxamide or a pharmaceutically acceptable salt, hydrate, or solvate thereof.

69. A compound according to claim 1, wherein the compound is N-[(1S)-1-(dicyclopropylmethyl)-2-[4-(3,5-dimethyl-1H-pyrazol-4-yl) -3-hydroxy-anilino]-2-oxo-ethyl]-2-isopropyl-pyrazole-3-carboxamide or a pharmaceutically acceptable salt, hydrate, or solvate thereof.

70. A compound according to claim 1, wherein the compound is N-[(1S)-2,2-dicyclopropyl-1-[[4-(3-cyclopropyl-5-methyl-1H-pyrazol-4-yl) phenyl]carbamoyl]ethyl]-2-isopropyl-pyrazole-3-carboxamide or a pharmaceutically acceptable salt, hydrate, or solvate thereof.

71. A compound according to claim 1, wherein the compound is N-[(1S)-1-(dicyclopropylmethyl)-2-[4-(3,5-diethyl-1H-pyrazol-4yl)anilino]-2-oxo-ethyl]-2-[(1S)-2-hydroxy-1-methyl-ethyl]pyrazole-3-carboxamide or a pharmaceutically acceptable salt, hydrate, or solvate thereof.

72. A compound according to claim 1, wherein the compound is N-[(1S)-1-[di(cyclobutyl)methyl]-2-[4-(3,5-dimethyl-1H-pyrazol-4-yl)anilino]-2-oxo-ethyl]-2-(2-hydroxy-1-methyl-ethyl)pyrazole-3-carboxamide or a pharmaceutically acceptable salt, hydrate, or solvate thereof.

73. A compound according to claim 1, wherein the compound is N-[1-cyclooctyl-2-[4-(3,5-dimethyl-1H-pyrazol-4-yl)anilino]-2-oxo-ethyl]-2-(3-hydroxybutyl)pyrazole-3-carboxamide or a pharmaceutically acceptable salt, hydrate, or solvate thereof.

\* \* \* \* \*

UNITED STATES PATENT AND TRADEMARK OFFICE
CERTIFICATE OF CORRECTION

| | | |
|---|---|---|
| PATENT NO. | : 11,377,425 B1 | Page 1 of 1 |
| APPLICATION NO. | : 16/765143 | |
| DATED | : July 5, 2022 | |
| INVENTOR(S) | : Kevin Neil Dack et al. | |

It is certified that error appears in the above-identified patent and that said Letters Patent is hereby corrected as shown below:

On the Title Page

Item (30) Foreign Application Priority Data, "18214002" should read as --18214002.0--.

Item (30) Foreign Application Priority Data, "19187352" should read as --19187352.0--.

In the Claims

Claim 1, Column 456, Line 56, "represents is" should read as --is--.

Claim 35, Column 462, Line 31, "($C_1$-C6)" should read as --($C_1$-$C_6$)--.

Claim 47, Column 463, Lines 51-53, "N-[(1 S)-1-(dicyclopropylmethyl)-2-[4-(3,5-dimethyl-1H-pyrazol-4-yl)anilino]-2-oxo-ethyl]-2-isopropyl-pyrazole-3-carboxamide" should read as --N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide--.

Claim 49, Column 464, Lines 12-14, "N-[(1 S)-1-(dicyclopropylmethyl)-2-[4-(3,5-dimethyl-1H-pyrazol-4-yl)anilino]-2-oxo-ethyl]-2-isopropyl-pyrazole-3-carboxamide" should read as --N-[(1S)-1-(dicyclopropylmethyl)-2-[4-(3,5-dimethyl-1H-pyrazol-4-yl)anilino]-2-oxo-ethyl]-2-isopropyl-pyrazole-3-carboxamide--.

Claim 69, Column 466, Lines 5-7, "N-[(1S)-1-(dicyclopropylmethyl)-2-[4-(3,5-dimethyl-1H-pyrazol-4-yl) -3-hydroxy-anilino]-2-oxo-ethyl]-2-isopropyl-pyrazole-3-carboxamide" should read as --N-[(1S)-1-(dicyclopropylmethyl)-2-[4-(3,5-dimethyl-1H-pyrazol-4-yl)-3-hydroxy-anilino]-2-oxo-ethyl]-2-isopropyl-pyrazole-3-carboxamide--.

Signed and Sealed this
Twenty-fourth Day of January, 2023

Katherine Kelly Vidal
*Director of the United States Patent and Trademark Office*